(12) United States Patent
Vinegar et al.

(10) Patent No.: US 7,986,869 B2
(45) Date of Patent: Jul. 26, 2011

(54) VARYING PROPERTIES ALONG LENGTHS OF TEMPERATURE LIMITED HEATERS

(75) Inventors: Harold J. Vinegar, Bellaire, TX (US); Xueying Xie, Houston, TX (US); David Scott Miller, Katy, TX (US); Jean Charles Ginestra, Richmond, TX (US)

(73) Assignee: Shell Oil Company, Houston, TX (US)

( * ) Notice: Subject to any disclaimer, the term of this patent is extended or adjusted under 35 U.S.C. 154(b) by 1471 days.

(21) Appl. No.: 11/409,562

(22) Filed: Apr. 21, 2006

(65) Prior Publication Data

US 2007/0045268 A1    Mar. 1, 2007

Related U.S. Application Data

(60) Provisional application No. 60/674,081, filed on Apr. 22, 2005, provisional application No. 60/729,763, filed on Oct. 24, 2005.

(51) Int. Cl.
*H05B 3/02* (2006.01)

(52) U.S. Cl. .................. 392/301; 29/860; 166/302

(58) Field of Classification Search .................. None
See application file for complete search history.

(56) References Cited

U.S. PATENT DOCUMENTS

| | | | |
|---|---|---|---|
| 48,994 A | 7/1865 | Parry | |
| 94,813 A | 9/1885 | Dickey | |
| 326,439 A | 9/1885 | McEachen | |
| 0,345,586 A | 7/1886 | Hall | |
| 760,304 A | 5/1904 | Butler | |
| 1,269,747 A | * 6/1918 | Rogers | |
| 1,342,741 A | 6/1920 | Day | |
| 1,457,479 A | 6/1923 | Wolcott | |
| 1,510,655 A | 6/1924 | Clark | |
| 1,634,236 A | 6/1927 | Ranney | |
| 1,646,599 A | 10/1927 | Schaefer | |
| 1,666,488 A | 4/1928 | Crawshaw | |
| 1,681,523 A | 8/1928 | Downey et al. | |
| 1,913,395 A | 6/1933 | Karrick | |
| 2,244,255 A | 6/1941 | Looman | |
| 2,244,256 A | 6/1941 | Looman | |
| 2,319,702 A | 5/1943 | Moon | |
| 2,365,591 A | 12/1944 | Ranney | |
| 2,390,770 A | 12/1945 | Barton et al. | |

(Continued)

FOREIGN PATENT DOCUMENTS

CA    899987    5/1972

(Continued)

OTHER PUBLICATIONS

U.S. Patent and Trademark Office, "Office Communication," for U.S. Appl. No. 11/788,858 mailed Apr. 23, 2009.

(Continued)

*Primary Examiner* — Thor S Campbell

(57) ABSTRACT

A system for heating a subsurface formation is described. The system includes an elongated heater in an opening in the formation. The elongated heater includes two or more portions along the length of the heater that have different power outputs. At least one portion of the elongated heater includes at least one temperature limited portion with at least one selected temperature at which the portion provides a reduced heat output. The heater is configured to provide heat to the formation with the different power outputs. The heater is configured so that the heater heats one or more portions of the formation at one or more selected heating rates.

16 Claims, 127 Drawing Sheets

U.S. PATENT DOCUMENTS

| | | | |
|---|---|---|---|
| 2,423,674 A | 7/1947 | Agren | |
| 2,444,755 A | 7/1948 | Steffen | |
| 2,466,945 A | 4/1949 | Greene | |
| 2,472,445 A | 6/1949 | Sprong | |
| 2,481,051 A | 9/1949 | Uren | |
| 2,484,063 A | 10/1949 | Ackley | |
| 2,497,868 A | 2/1951 | Dalin | |
| 2,548,360 A | 4/1951 | Germain | |
| 2,593,477 A | 4/1952 | Newman et al. | |
| 2,595,979 A | 5/1952 | Pevere et al. | |
| 2,630,306 A | 3/1953 | Evans | |
| 2,630,307 A | 3/1953 | Martin | |
| 2,634,961 A | 4/1953 | Ljungstrom | |
| 2,642,943 A | 6/1953 | Smith et al. | |
| 2,670,802 A | 3/1954 | Ackley | |
| 2,685,930 A | 8/1954 | Albaugh | |
| 2,695,163 A | 11/1954 | Pearce et al. | |
| 2,703,621 A | 3/1955 | Ford | |
| 2,714,930 A | 8/1955 | Carpenter | |
| 2,732,195 A | 1/1956 | Ljungstrom | |
| 2,734,579 A | 2/1956 | Elkins | |
| 2,743,906 A | 5/1956 | Coyle | |
| 2,757,739 A | 8/1956 | Douglas et al. | |
| 2,771,954 A | 11/1956 | Jenks et al. | |
| 2,777,679 A | 1/1957 | Ljungstrom | |
| 2,780,449 A | 2/1957 | Fisher et al. | |
| 2,780,450 A | 2/1957 | Ljungstrom | |
| 2,786,660 A | 3/1957 | Alleman | |
| 2,789,805 A | 4/1957 | Ljungstrom | |
| 2,793,696 A | 5/1957 | Morse | |
| 2,794,504 A | 6/1957 | Carpenter | |
| 2,801,089 A | 7/1957 | Scott, Jr. | |
| 2,803,305 A | 8/1957 | Behning et al. | |
| 2,804,149 A | 8/1957 | Kile | |
| 2,819,761 A | 1/1958 | Popham et al. | |
| 2,825,408 A | 3/1958 | Watson | |
| 2,841,375 A | 7/1958 | Salomonsson | |
| 2,857,002 A | 10/1958 | Pevere et al. | |
| 2,862,558 A | 12/1958 | Dixon | |
| 2,890,754 A | 6/1959 | Hoffstrom et al. | |
| 2,890,755 A | 6/1959 | Eurenius et al. | |
| 2,902,270 A | 9/1959 | Salomonsson et al. | |
| 2,906,337 A | 9/1959 | Henning | |
| 2,906,340 A | 9/1959 | Herzog | |
| 2,914,309 A | 11/1959 | Salomonsson | |
| 2,923,535 A | 2/1960 | Ljungstrom | |
| 2,932,352 A | 4/1960 | Stegemeier | |
| 2,939,689 A | 6/1960 | Ljungstrom | |
| 2,942,223 A | 6/1960 | Lennox et al. | |
| 2,954,826 A | 10/1960 | Sievers | |
| 2,958,519 A | 11/1960 | Hurley | |
| 2,969,226 A | 1/1961 | Huntington | |
| 2,970,826 A | 2/1961 | Woodruff | |
| 2,974,937 A | 3/1961 | Kiel | |
| 2,991,046 A * | 7/1961 | Yahn | |
| 2,994,376 A | 8/1961 | Crawford et al. | |
| 2,997,105 A | 8/1961 | Campion et al. | |
| 2,998,457 A | 8/1961 | Paulsen | |
| 3,004,601 A | 10/1961 | Bodine | |
| 3,004,603 A | 10/1961 | Rogers et al. | |
| 3,007,521 A | 11/1961 | Trantham et al. | |
| 3,010,513 A | 11/1961 | Gerner | |
| 3,010,516 A | 11/1961 | Schleicher | |
| 3,016,053 A | 1/1962 | Medovick | |
| 3,017,168 A | 1/1962 | Carr | |
| 3,026,940 A | 3/1962 | Spitz | |
| 3,032,102 A | 5/1962 | Parker | |
| 3,036,632 A | 5/1962 | Koch et al. | |
| 3,044,545 A | 7/1962 | Tooke | |
| 3,048,221 A | 8/1962 | Tek | |
| 3,050,123 A | 8/1962 | Scott | |
| 3,057,404 A | 10/1962 | Berstrom | |
| 3,058,730 A | 10/1962 | Bays | |
| 3,061,009 A | 10/1962 | Shirley | |
| 3,062,282 A | 11/1962 | Schleicher | |
| 3,095,031 A | 6/1963 | Eurenius et al. | |
| 3,097,690 A | 7/1963 | Terwilliger et al. | |
| 3,105,545 A | 10/1963 | Prats et al. | |
| 3,106,244 A | 10/1963 | Parker | |
| 3,110,345 A | 11/1963 | Reed et al. | |
| 3,113,619 A | 12/1963 | Reichle | |
| 3,113,620 A | 12/1963 | Hemminger | |
| 3,113,623 A | 12/1963 | Krueger | |
| 3,114,417 A | 12/1963 | McCarthy | |
| 3,116,792 A | 1/1964 | Purre | |
| 3,120,264 A | 2/1964 | Barron | |
| 3,127,935 A | 4/1964 | Poettmann et al. | |
| 3,127,936 A | 4/1964 | Eurenius | |
| 3,131,763 A | 5/1964 | Kunetka et al. | |
| 3,132,692 A | 5/1964 | Marx et al. | |
| 3,137,347 A | 6/1964 | Parker | |
| 3,138,203 A | 6/1964 | Weiss et al. | |
| 3,139,928 A | 7/1964 | Broussard | |
| 3,142,336 A | 7/1964 | Doscher | |
| 3,149,670 A | 9/1964 | Grant | |
| 3,149,672 A | 9/1964 | Orkiszewsko et al. | |
| 3,150,715 A | 9/1964 | Dietz | |
| 3,163,745 A | 12/1964 | Boston | |
| 3,164,207 A | 1/1965 | Thessen et al. | |
| 3,165,154 A | 1/1965 | Santourian | |
| 3,170,842 A | 2/1965 | Kehler | |
| 3,181,613 A | 5/1965 | Krueger | |
| 3,182,721 A | 5/1965 | Hardy | |
| 3,183,675 A | 5/1965 | Schroeder | |
| 3,191,679 A | 6/1965 | Miller | |
| 3,205,942 A | 9/1965 | Sandberg | |
| 3,205,944 A | 9/1965 | Walton | |
| 3,205,946 A | 9/1965 | Prats et al. | |
| 3,207,220 A | 9/1965 | Williams | |
| 3,208,531 A | 9/1965 | Tamplen | |
| 3,209,825 A | 10/1965 | Alexander et al. | |
| 3,221,811 A | 12/1965 | Prats | |
| 3,233,668 A | 2/1966 | Hamilton et al. | |
| 3,237,689 A | 3/1966 | Justheim | |
| 3,241,611 A | 3/1966 | Dougan | |
| 3,246,695 A | 4/1966 | Robinson | |
| 3,250,327 A | 5/1966 | Crider | |
| 3,262,741 A | 7/1966 | Edmonds et al. | |
| 3,267,680 A | 8/1966 | Schlumberger | |
| 3,272,261 A | 9/1966 | Morse | |
| 3,273,640 A | 9/1966 | Huntington | |
| 3,275,076 A | 9/1966 | Sharp | |
| 3,278,234 A | 10/1966 | Helvenston et al. | |
| 3,284,281 A | 11/1966 | Thomas | |
| 3,285,335 A | 11/1966 | Reistle, Jr. | |
| 3,288,648 A | 11/1966 | Jones | |
| 3,294,167 A | 12/1966 | Vogel | |
| 3,302,707 A | 2/1967 | Slusser | |
| 3,316,344 A | 4/1967 | Kidd et al. | |
| 3,316,962 A | 5/1967 | Lange | |
| 3,332,480 A | 7/1967 | Parrish | |
| 3,338,306 A * | 8/1967 | Cook | |
| 3,342,258 A | 9/1967 | Prats | |
| 3,342,267 A | 9/1967 | Cotter et al. | |
| 3,349,845 A | 10/1967 | Holbert et al. | |
| 3,352,355 A * | 11/1967 | Putman | |
| 3,358,756 A | 12/1967 | Vogel | |
| 3,362,751 A | 1/1968 | Tinlin | |
| 3,372,754 A | 3/1968 | McDonald | |
| 3,379,248 A * | 4/1968 | Strange | |
| 3,380,913 A * | 4/1968 | Henderson | |
| 3,386,508 A | 6/1968 | Bielstein et al. | |
| 3,389,975 A | 6/1968 | Van Nostrand | |
| 3,399,623 A | 9/1968 | Creed | |
| 3,410,977 A | 11/1968 | Ando | |
| 3,434,541 A | 3/1969 | Cook et al. | |
| 3,455,383 A | 7/1969 | Prats et al. | |
| 3,465,819 A * | 9/1969 | Dixon | |
| 3,477,058 A | 11/1969 | Vedder et al. | |
| 3,485,300 A | 12/1969 | Engle | |
| 3,492,463 A | 1/1970 | Wringer et al. | |
| 3,501,201 A | 3/1970 | Closmann et al. | |
| 3,502,372 A | 3/1970 | Prats | |
| 3,513,913 A | 5/1970 | Bruist | |
| 3,515,837 A | 6/1970 | Ando | |
| 3,528,501 A * | 9/1970 | Parker | |
| 3,529,682 A | 9/1970 | Coyne et al. | |

| | | | | | | |
|---|---|---|---|---|---|---|
| 3,537,528 A * | 11/1970 | Herce et al. | | 4,076,761 A | 2/1978 | Chang et al. |
| 3,542,131 A * | 11/1970 | Walton et al. | | 4,083,604 A | 4/1978 | Bohn et al. |
| 3,547,192 A | 12/1970 | Claridge et al. | | 4,084,637 A | 4/1978 | Todd |
| 3,547,193 A * | 12/1970 | Gill | | 4,087,130 A | 5/1978 | Garrett |
| 3,554,285 A | 1/1971 | Meldau | | 4,089,372 A | 5/1978 | Terry |
| 3,562,401 A * | 2/1971 | Long | | 4,089,373 A | 5/1978 | Reynolds et al. |
| 3,565,171 A * | 2/1971 | Closmann | | 4,089,374 A | 5/1978 | Terry |
| 3,572,838 A | 3/1971 | Templeton | | 4,091,869 A | 5/1978 | Hoyer |
| 3,578,080 A * | 5/1971 | Closmann | | 4,093,025 A | 6/1978 | Terry |
| 3,580,987 A | 5/1971 | Priaroggia | | 4,093,026 A | 6/1978 | Ridley |
| 3,593,789 A | 7/1971 | Prats | | 4,096,163 A | 6/1978 | Chang et al. |
| 3,595,082 A * | 7/1971 | Miller et al. | | 4,099,567 A | 7/1978 | Terry |
| 3,599,714 A * | 8/1971 | Messman et al. | | 4,114,688 A | 9/1978 | Terry |
| 3,605,890 A * | 9/1971 | Holm | | 4,119,349 A | 10/1978 | Albulescu et al. |
| 3,614,387 A | 10/1971 | Wrob et al. | | 4,125,159 A | 11/1978 | Vann |
| 3,614,986 A | 10/1971 | Gill | | 4,130,575 A | 12/1978 | Jorn |
| 3,618,663 A | 11/1971 | Needham | | 4,133,825 A | 1/1979 | Stroud et al. |
| 3,629,551 A | 12/1971 | Ando | | 4,138,442 A | 2/1979 | Chang et al. |
| 3,661,423 A * | 5/1972 | Garret | | 4,140,180 A | 2/1979 | Bridges et al. |
| 3,675,715 A * | 7/1972 | Speller, Jr. | | 4,140,181 A | 2/1979 | Ridley et al. |
| 3,679,812 A * | 7/1972 | Owens | | 4,144,935 A | 3/1979 | Bridges et al. |
| 3,680,633 A * | 8/1972 | Bennett | | 4,148,359 A | 4/1979 | Laumbach et al. |
| 3,700,280 A | 10/1972 | Papadopoulos et al. | | 4,158,467 A | 6/1979 | Larson et al. |
| 3,757,860 A * | 9/1973 | Pritchett | | 4,169,506 A | 10/1979 | Berry |
| 3,759,328 A | 9/1973 | Ueber et al. | | 4,183,405 A | 1/1980 | Magnie |
| 3,759,574 A | 9/1973 | Beard | | 4,184,548 A | 1/1980 | Ginsburgh et al. |
| 3,761,599 A | 9/1973 | Beatty | | 4,185,692 A | 1/1980 | Terry |
| 3,766,982 A * | 10/1973 | Justheim | | 4,186,801 A | 2/1980 | Madgavkar et al. |
| 3,770,398 A * | 11/1973 | Abraham et al. | | 4,193,451 A | 3/1980 | Dauphine |
| 3,779,602 A | 12/1973 | Beard et al. | | 4,197,911 A | 4/1980 | Anada |
| 3,794,113 A | 2/1974 | Strange et al. | | 4,199,024 A | 4/1980 | Rose et al. |
| 3,794,116 A * | 2/1974 | Higgins | | 4,199,025 A | 4/1980 | Carpenter |
| 3,804,169 A | 4/1974 | Closmann | | 4,228,853 A | 10/1980 | Harvey et al. |
| 3,804,172 A | 4/1974 | Closmann et al. | | 4,228,854 A | 10/1980 | Sacuta |
| 3,809,159 A * | 5/1974 | Young et al. | | 4,232,902 A | 11/1980 | Cuevas |
| 3,853,185 A | 12/1974 | Dahl et al. | | 4,243,101 A | 1/1981 | Grupping |
| 3,881,551 A | 5/1975 | Terry et al. | | 4,250,230 A | 2/1981 | Terry |
| 3,882,941 A * | 5/1975 | Pelofsky | | 4,250,962 A | 2/1981 | Madgavkar et al. |
| 3,893,918 A | 7/1975 | Favret, Jr. | | 4,252,191 A | 2/1981 | Pusch et al. |
| 3,894,769 A | 7/1975 | Tham et al. | | 4,256,945 A | 3/1981 | Carter et al. |
| 3,907,045 A | 9/1975 | Dahl et al. | | 4,265,307 A | 5/1981 | Elkins |
| 3,922,148 A | 11/1975 | Child | | 4,273,188 A | 6/1981 | Vogel et al. |
| 3,924,680 A | 12/1975 | Terry | | 4,274,487 A | 6/1981 | Hollingsworth et al. |
| 3,933,447 A | 1/1976 | Pasini, III et al. | | 4,277,416 A | 7/1981 | Grant |
| 3,941,421 A | 3/1976 | Burton, III et al. | | 4,280,046 A | 7/1981 | Shimotori et al. |
| 3,947,683 A | 3/1976 | Schultz et al. | | 4,282,587 A | 8/1981 | Silverman |
| 3,948,319 A | 4/1976 | Pritchett | | RE30,738 E | 9/1981 | Bridges et al. |
| 3,948,755 A | 4/1976 | McCollum et al. | | 4,289,354 A | 9/1981 | Zakiewicz |
| 3,950,029 A | 4/1976 | Timmins | | 4,290,650 A | 9/1981 | Thompson |
| 3,952,802 A | 4/1976 | Terry | | 4,299,086 A | 11/1981 | Madgavkar et al. |
| 3,954,140 A | 5/1976 | Hendrick | | 4,299,285 A | 11/1981 | Tsai et al. |
| 3,973,628 A | 8/1976 | Colgate | | 4,303,126 A | 12/1981 | Blevins |
| 3,986,349 A | 10/1976 | Egan | | 4,305,463 A | 12/1981 | Zakiewicz |
| 3,986,556 A | 10/1976 | Haynes | | 4,306,621 A | 12/1981 | Boyd et al. |
| 3,986,557 A | 10/1976 | Striegler et al. | | 4,311,340 A | 1/1982 | Lyons et al. |
| 3,987,851 A | 10/1976 | Tham | | 4,324,292 A | 4/1982 | Jacobs et al. |
| 3,993,132 A | 11/1976 | Cram et al. | | 4,344,483 A | 8/1982 | Fisher et al. |
| 3,994,340 A | 11/1976 | Anderson et al. | | 4,353,418 A | 10/1982 | Hoekstra et al. |
| 3,994,341 A | 11/1976 | Anderson et al. | | 4,359,687 A | 11/1982 | Vinegar et al. |
| 3,999,607 A | 12/1976 | Pennington et al. | | 4,363,361 A | 12/1982 | Madgavkar et al. |
| 4,005,752 A | 2/1977 | Cha | | 4,366,668 A | 1/1983 | Madgavkar et al. |
| 4,006,778 A | 2/1977 | Redford et al. | | 4,378,048 A | 3/1983 | Madgavkar et al. |
| 4,008,762 A | 2/1977 | Fisher et al. | | 4,380,930 A | 4/1983 | Podhrasky et al. |
| 4,010,800 A | 3/1977 | Terry | | 4,381,641 A | 5/1983 | Madgavkar et al. |
| 4,016,239 A | 4/1977 | Fenton | | 4,382,469 A | 5/1983 | Bell et al. |
| 4,017,319 A | 4/1977 | Greskovich et al. | | 4,384,613 A | 5/1983 | Owen et al. |
| 4,018,280 A | 4/1977 | Daviduk et al. | | 4,384,614 A | 5/1983 | Justheim |
| 4,019,575 A | 4/1977 | Pisio et al. | | 4,385,661 A | 5/1983 | Fox |
| 4,026,357 A | 5/1977 | Redford | | 4,390,067 A | 6/1983 | Willman |
| 4,029,360 A | 6/1977 | French | | 4,390,973 A | 6/1983 | Rietsch |
| 4,031,956 A | 6/1977 | Terry | | 4,396,062 A | 8/1983 | Iskander |
| 4,037,655 A | 7/1977 | Carpenter | | 4,397,732 A | 8/1983 | Hoover et al. |
| 4,037,658 A | 7/1977 | Anderson | | 4,398,151 A | 8/1983 | Vinegar et al. |
| 4,042,026 A | 8/1977 | Pusch et al. | | 4,399,866 A | 8/1983 | Dearth |
| 4,043,393 A | 8/1977 | Fisher et al. | | 4,401,099 A | 8/1983 | Collier |
| 4,048,637 A | 9/1977 | Jacomini | | 4,401,162 A | 8/1983 | Osborne |
| 4,049,053 A | 9/1977 | Fisher et al. | | 4,401,163 A | 8/1983 | Elkins |
| 4,057,293 A | 11/1977 | Garrett | | 4,407,973 A | 10/1983 | van Dijk et al. |
| 4,067,390 A | 1/1978 | Camacho et al. | | 4,409,090 A | 10/1983 | Hanson et al. |

| Patent No. | Type | Date | Inventor(s) |
|---|---|---|---|
| 4,410,042 | A | 10/1983 | Shu |
| 4,412,124 | A | 10/1983 | Kobayashi |
| 4,412,585 | A | 11/1983 | Bouck |
| 4,417,782 | A | 11/1983 | Clarke et al. |
| 4,418,752 | A | 12/1983 | Boyer et al. |
| 4,423,311 | A | 12/1983 | Varney, Sr. |
| 4,425,967 | A | 1/1984 | Hoekstra |
| 4,428,700 | A | 1/1984 | Lennemann |
| 4,429,745 | A | 2/1984 | Cook |
| 4,437,519 | A | 3/1984 | Cha et al. |
| 4,440,224 | A | 4/1984 | Kreinin et al. |
| 4,441,985 | A | 4/1984 | Burchfield et al. |
| 4,442,896 | A | 4/1984 | Reale et al. |
| 4,444,255 | A | 4/1984 | Geoffrey et al. |
| 4,444,258 | A | 4/1984 | Kalmar |
| 4,445,574 | A | 5/1984 | Vann |
| 4,446,917 | A | 5/1984 | Todd |
| 4,452,491 | A | 6/1984 | Seglin et al. |
| 4,455,215 | A | 6/1984 | Jarrott et al. |
| 4,456,065 | A | 6/1984 | Heim et al. |
| 4,457,365 | A | 7/1984 | Kasevich et al. |
| 4,457,374 | A | 7/1984 | Hoekstra et al. |
| 4,458,757 | A | 7/1984 | Bock et al. |
| 4,458,767 | A | 7/1984 | Hoehn, Jr. |
| 4,460,044 | A | 7/1984 | Porter |
| 4,474,238 | A | 10/1984 | Gentry et al. |
| 4,479,541 | A | 10/1984 | Wang |
| 4,485,868 | A | 12/1984 | Sresty et al. |
| 4,485,869 | A | 12/1984 | Sresty et al. |
| 4,487,257 | A | 12/1984 | Dauphine |
| 4,489,782 | A | 12/1984 | Perkins |
| 4,491,179 | A | 1/1985 | Pirson et al. |
| 4,498,531 | A | 2/1985 | Vrolyk |
| 4,498,535 | A | 2/1985 | Bridges |
| 4,499,209 | A | 2/1985 | Hoek et al. |
| 4,501,326 | A | 2/1985 | Edmunds |
| 4,501,445 | A | 2/1985 | Gregoli |
| 4,513,816 | A | 4/1985 | Hubert |
| 4,518,548 | A | 5/1985 | Yarbrough |
| 4,524,826 | A | 6/1985 | Savage |
| 4,524,827 | A | 6/1985 | Bridges et al. |
| 4,530,401 | A | 7/1985 | Hartman et al. |
| 4,537,252 | A | 8/1985 | Puri |
| 4,538,682 | A | 9/1985 | McManus et al. |
| 4,540,882 | A | 9/1985 | Vinegar et al. |
| 4,542,648 | A | 9/1985 | Vinegar et al. |
| 4,545,435 | A | 10/1985 | Bridges et al. |
| 4,549,073 | A | 10/1985 | Tamura et al. |
| 4,549,396 | A | 10/1985 | Garwood et al. |
| 4,552,214 | A | 11/1985 | Forgac et al. |
| 4,570,715 | A | 2/1986 | Van Meurs et al. |
| 4,571,491 | A | 2/1986 | Vinegar et al. |
| 4,572,229 | A | 2/1986 | Mueller et al. |
| 4,572,299 | A | 2/1986 | Van Egmond et al. |
| 4,573,530 | A | 3/1986 | Audeh et al. |
| 4,576,231 | A | 3/1986 | Dowling et al. |
| 4,577,503 | A | 3/1986 | Imaino et al. |
| 4,577,690 | A | 3/1986 | Medlin |
| 4,577,691 | A | 3/1986 | Huang et al. |
| 4,583,046 | A | 4/1986 | Vinegar et al. |
| 4,583,242 | A | 4/1986 | Vinegar et al. |
| 4,585,066 | A | 4/1986 | Moore et al. |
| 4,592,423 | A | 6/1986 | Savage et al. |
| 4,597,441 | A | 7/1986 | Ware et al. |
| 4,597,444 | A | 7/1986 | Hutchinson |
| 4,598,392 | A | 7/1986 | Pann |
| 4,598,770 | A | 7/1986 | Shu et al. |
| 4,598,772 | A | 7/1986 | Holmes |
| 4,605,489 | A | 8/1986 | Madgavkar |
| 4,605,680 | A | 8/1986 | Beuther et al. |
| 4,608,818 | A | 9/1986 | Goebel et al. |
| 4,609,041 | A * | 9/1986 | Magda |
| 4,613,754 | A | 9/1986 | Vinegar et al. |
| 4,616,705 | A | 10/1986 | Stegemeier et al. |
| 4,623,401 | A | 11/1986 | Derbyshire et al. |
| 4,623,444 | A | 11/1986 | Che et al. |
| 4,626,665 | A | 12/1986 | Fort, III |
| 4,635,197 | A | 1/1987 | Vinegar et al. |
| 4,637,464 | A | 1/1987 | Forgac et al. |
| 4,639,712 | A | 1/1987 | Kobayashi et al. |
| 4,640,352 | A | 2/1987 | Van Meurs et al. |
| 4,640,353 | A | 2/1987 | Schuh |
| 4,644,283 | A | 2/1987 | Vinegar et al. |
| 4,645,906 | A | 2/1987 | Yagnik et al. |
| 4,651,825 | A | 3/1987 | Wilson |
| 4,658,215 | A | 4/1987 | Vinegar et al. |
| 4,662,437 | A | 5/1987 | Renfro et al. |
| 4,662,438 | A | 5/1987 | Taflove et al. |
| 4,662,439 | A | 5/1987 | Puri |
| 4,662,443 | A | 5/1987 | Puri et al. |
| 4,663,711 | A | 5/1987 | Vinegar et al. |
| 4,669,542 | A | 6/1987 | Venkatesan |
| 4,671,102 | A | 6/1987 | Vinegar et al. |
| 4,682,652 | A | 7/1987 | Huang et al. |
| 4,691,771 | A | 9/1987 | Ware et al. |
| 4,694,907 | A | 9/1987 | Stahl et al. |
| 4,695,713 | A | 9/1987 | Krumme |
| 4,698,149 | A | 10/1987 | Mitchell |
| 4,698,583 | A | 10/1987 | Sandberg |
| 4,701,587 | A | 10/1987 | Carter et al. |
| 4,704,514 | A | 11/1987 | Van Edmond et al. |
| 4,706,751 | A | 11/1987 | Gondouin |
| 4,716,960 | A | 1/1988 | Eastlund et al. |
| 4,717,814 | A | 1/1988 | Krumme |
| 4,719,423 | A | 1/1988 | Vinegar et al. |
| 4,728,892 | A | 3/1988 | Vinegar et al. |
| 4,730,162 | A | 3/1988 | Vinegar et al. |
| 4,733,057 | A | 3/1988 | Stanzel et al. |
| 4,734,115 | A | 3/1988 | Howard et al. |
| 4,743,854 | A | 5/1988 | Vinegar et al. |
| 4,744,245 | A | 5/1988 | White |
| 4,752,673 | A | 6/1988 | Krumme |
| 4,756,367 | A | 7/1988 | Puri et al. |
| 4,762,425 | A | 8/1988 | Shakkottai et al. |
| 4,766,958 | A | 8/1988 | Faecke |
| 4,769,602 | A | 9/1988 | Vinegar et al. |
| 4,769,606 | A | 9/1988 | Vinegar et al. |
| 4,772,634 | A | 9/1988 | Farooque |
| 4,776,638 | A | 10/1988 | Hahn |
| 4,785,163 | A | 11/1988 | Sandberg |
| 4,787,452 | A | 11/1988 | Jennings, Jr. |
| 4,793,409 | A | 12/1988 | Bridges et al. |
| 4,794,226 | A | 12/1988 | Derbyshire |
| 4,808,925 | A | 2/1989 | Baird |
| 4,814,587 | A | 3/1989 | Carter |
| 4,817,711 | A | 4/1989 | Jeambey |
| 4,818,370 | A | 4/1989 | Gregoli et al. |
| 4,821,798 | A | 4/1989 | Bridges et al. |
| 4,823,890 | A | 4/1989 | Lang |
| 4,827,761 | A | 5/1989 | Vinegar et al. |
| 4,828,031 | A | 5/1989 | Davis |
| 4,848,460 | A | 7/1989 | Johnson, Jr. et al. |
| 4,848,924 | A | 7/1989 | Nuspl et al. |
| 4,849,611 | A | 7/1989 | Whitney et al. |
| 4,852,648 | A | 8/1989 | Akkerman et al. |
| 4,856,341 | A | 8/1989 | Vinegar et al. |
| 4,856,587 | A | 8/1989 | Nielson |
| 4,860,544 | A | 8/1989 | Krieg et al. |
| 4,866,983 | A | 9/1989 | Vinegar et al. |
| 4,884,455 | A | 12/1989 | Vinegar et al. |
| 4,885,080 | A | 12/1989 | Brown et al. |
| 4,886,118 | A | 12/1989 | Van Meurs et al. |
| 4,893,504 | A | 1/1990 | O'Meara, Jr. et al. |
| 4,895,206 | A | 1/1990 | Price |
| 4,912,971 | A | 4/1990 | Jeambey |
| 4,913,065 | A | 4/1990 | Hemsath |
| 4,926,941 | A | 5/1990 | Glandt et al. |
| 4,927,857 | A | 5/1990 | McShea, III et al. |
| 4,928,765 | A | 5/1990 | Nielson |
| 4,974,425 | A | 12/1990 | Krieg et al. |
| 4,982,786 | A | 1/1991 | Jennings, Jr. |
| 4,983,319 | A | 1/1991 | Gregoli et al. |
| 4,984,594 | A | 1/1991 | Vinegar et al. |
| 4,985,313 | A | 1/1991 | Penneck et al. |
| 4,987,368 | A | 1/1991 | Vinegar |
| 4,994,093 | A | 2/1991 | Wetzel et al. |
| 5,008,085 | A | 4/1991 | Bain et al. |
| 5,011,329 | A | 4/1991 | Nelson et al. |

| | | |
|---|---|---|
| 5,020,596 A | 6/1991 | Hemsath |
| 5,027,896 A | 7/1991 | Anderson |
| 5,040,601 A | 8/1991 | Karlsson et al. |
| 5,042,579 A | 8/1991 | Glandt et al. |
| 5,046,559 A | 9/1991 | Glandt |
| 5,050,386 A | 9/1991 | Krieg et al. |
| 5,054,551 A | 10/1991 | Duerksen |
| 5,059,303 A | 10/1991 | Taylor et al. |
| 5,060,287 A | 10/1991 | Van Egmond |
| 5,060,726 A | 10/1991 | Glandt et al. |
| 5,064,006 A | 11/1991 | Waters et al. |
| 5,065,501 A | 11/1991 | Henschen et al. |
| 5,065,818 A | 11/1991 | Van Egmond |
| 5,066,852 A | 11/1991 | Willbanks |
| 5,073,625 A | 12/1991 | Derbyshire |
| 5,082,054 A | 1/1992 | Kiamanesh |
| 5,082,055 A | 1/1992 | Hemsath |
| 5,085,276 A | 2/1992 | Rivas et al. |
| 5,097,903 A | 3/1992 | Wilensky |
| 5,099,918 A | 3/1992 | Bridges et al. |
| 5,103,920 A | 4/1992 | Patton |
| 5,126,037 A | 6/1992 | Showalter |
| 5,133,406 A | 7/1992 | Puri |
| 5,145,003 A | 9/1992 | Duerksen |
| 5,152,341 A | 10/1992 | Kasevich |
| 5,168,927 A | 12/1992 | Stegemeier et al. |
| 5,182,427 A | 1/1993 | McGaffigan |
| 5,182,792 A | 1/1993 | Goncalves |
| 5,189,283 A | 2/1993 | Carl, Jr. et al. |
| 5,190,405 A | 3/1993 | Vinegar et al. |
| 5,201,219 A | 4/1993 | Bandurski et al. |
| 5,207,273 A | 5/1993 | Cates et al. |
| 5,209,987 A | 5/1993 | Penneck et al. |
| 5,211,230 A | 5/1993 | Ostapovich et al. |
| 5,217,076 A | 6/1993 | Masek |
| 5,226,961 A | 7/1993 | Nahm et al. |
| 5,229,583 A | 7/1993 | van Egmond et al. |
| 5,236,039 A | 8/1993 | Edelstein et al. |
| 5,255,742 A | 10/1993 | Mikus |
| 5,261,490 A | 11/1993 | Ebinuma |
| 5,285,846 A | 2/1994 | Mohn |
| 5,289,882 A | 3/1994 | Moore |
| 5,295,763 A | 3/1994 | Stenborg et al. |
| 5,297,626 A | 3/1994 | Vinegar et al. |
| 5,305,239 A | 4/1994 | Kinra |
| 5,305,829 A | 4/1994 | Kumar |
| 5,306,640 A | 4/1994 | Vinegar et al. |
| 5,316,664 A | 5/1994 | Gregoli et al. |
| 5,318,116 A | 6/1994 | Vinegar et al. |
| 5,332,036 A | 7/1994 | Shirley et al. |
| 5,339,897 A | 8/1994 | Leaute |
| 5,339,904 A | 8/1994 | Jennings et al. |
| 5,340,467 A | 8/1994 | Gregoli et al. |
| 5,349,859 A | 9/1994 | Kleppe |
| 5,360,067 A | 11/1994 | Meo, III |
| 5,363,094 A | 11/1994 | Staron et al. |
| 5,366,012 A | 11/1994 | Lohbeck |
| 5,377,756 A | 1/1995 | Northrop et al. |
| 5,388,640 A | 2/1995 | Puri et al. |
| 5,388,641 A | 2/1995 | Yee et al. |
| 5,388,642 A | 2/1995 | Puri et al. |
| 5,388,643 A | 2/1995 | Yee et al. |
| 5,388,645 A | 2/1995 | Puri et al. |
| 5,391,291 A | 2/1995 | Winquist et al. |
| 5,392,854 A | 2/1995 | Vinegar et al. |
| 5,404,952 A | 4/1995 | Vinegar et al. |
| 5,409,071 A | 4/1995 | Wellington et al. |
| 5,411,086 A | 5/1995 | Burcham et al. |
| 5,411,089 A | 5/1995 | Vinegar et al. |
| 5,411,104 A | 5/1995 | Stanley |
| 5,415,231 A | 5/1995 | Northrop et al. |
| 5,431,224 A | 7/1995 | Laali |
| 5,433,271 A | 7/1995 | Vinegar et al. |
| 5,435,666 A | 7/1995 | Hassett et al. |
| 5,437,506 A | 8/1995 | Gray |
| 5,439,054 A | 8/1995 | Chaback et al. |
| 5,454,666 A | 10/1995 | Chaback et al. |
| 5,456,315 A | 10/1995 | Kisman et al. |
| 5,497,087 A | 3/1996 | Vinegar et al. |
| 5,498,960 A | 3/1996 | Vinegar et al. |
| 5,512,732 A | 4/1996 | Yagnik et al. |
| 5,517,593 A | 5/1996 | Nenniger et al. |
| 5,525,322 A | 6/1996 | Willms |
| 5,541,517 A | 7/1996 | Hartmann et al. |
| 5,545,803 A | 8/1996 | Heath et al. |
| 5,553,189 A | 9/1996 | Stegemeier et al. |
| 5,554,453 A | 9/1996 | Steinfeld et al. |
| 5,566,755 A | 10/1996 | Seidle et al. |
| 5,571,403 A | 11/1996 | Scott et al. |
| 5,579,575 A | 12/1996 | Lamome et al. |
| 5,619,611 A | 4/1997 | Loschen et al. |
| 5,621,844 A | 4/1997 | Bridges |
| 5,621,845 A | 4/1997 | Bridges et al. |
| 5,624,188 A | 4/1997 | West |
| 5,632,336 A | 5/1997 | Notz et al. |
| 5,652,389 A | 7/1997 | Schaps et al. |
| 5,656,239 A | 8/1997 | Stegemeier et al. |
| 5,713,415 A | 2/1998 | Bridges |
| 5,751,895 A | 5/1998 | Bridges |
| 5,759,022 A | 6/1998 | Koppang et al. |
| 5,760,307 A | 6/1998 | Latimer et al. |
| 5,769,569 A | 6/1998 | Hosseini |
| 5,777,229 A | 7/1998 | Geier et al. |
| 5,782,301 A | 7/1998 | Neuroth et al. |
| 5,823,256 A | 10/1998 | Moore |
| 5,826,655 A | 10/1998 | Snow et al. |
| 5,828,797 A | 10/1998 | Minott et al. |
| 5,854,472 A | 12/1998 | Wildi |
| 5,861,137 A | 1/1999 | Edlund |
| 5,862,858 A | 1/1999 | Wellington et al. |
| 5,868,202 A | 2/1999 | Hsu |
| 5,899,269 A | 5/1999 | Wellington et al. |
| 5,899,958 A | 5/1999 | Dowell et al. |
| 5,911,898 A | 6/1999 | Jacobs et al. |
| 5,926,437 A | 7/1999 | Ortiz |
| 5,935,421 A | 8/1999 | Brons et al. |
| 5,968,349 A | 10/1999 | Duyvesteyn et al. |
| 5,984,010 A | 11/1999 | Elias et al. |
| 5,984,582 A | 11/1999 | Schwert |
| 5,985,138 A | 11/1999 | Humphreys |
| 5,997,214 A | 12/1999 | de Rouffignac et al. |
| 6,015,015 A | 1/2000 | Luft et al. |
| 6,016,867 A | 1/2000 | Gregoli et al. |
| 6,016,868 A | 1/2000 | Gregoli et al. |
| 6,019,172 A | 2/2000 | Wellington et al. |
| 6,023,554 A | 2/2000 | Vinegar et al. |
| 6,026,914 A | 2/2000 | Adams et al. |
| 6,035,701 A | 3/2000 | Lowry et al. |
| 6,039,121 A * | 3/2000 | Kisman |
| 6,056,057 A | 5/2000 | Vinegar et al. |
| 6,078,868 A | 6/2000 | Dubinsky |
| 6,079,499 A | 6/2000 | Mikus et al. |
| 6,084,826 A | 7/2000 | Leggett, III |
| 6,085,512 A | 7/2000 | Agee et al. |
| 6,088,294 A | 7/2000 | Leggett, III et al. |
| 6,094,048 A | 7/2000 | Vinegar et al. |
| 6,102,122 A | 8/2000 | de Rouffignac |
| 6,102,137 A | 8/2000 | Ward et al. |
| 6,102,622 A | 8/2000 | Vinegar et al. |
| 6,110,358 A | 8/2000 | Aldous et al. |
| 6,112,808 A | 9/2000 | Isted |
| 6,152,987 A | 11/2000 | Ma et al. |
| 6,155,117 A | 12/2000 | Stevens et al. |
| 6,172,124 B1 | 1/2001 | Wolflick et al. |
| 6,173,775 B1 | 1/2001 | Elias et al. |
| 6,192,748 B1 | 2/2001 | Miller |
| 6,193,010 B1 | 2/2001 | Minto |
| 6,196,350 B1 | 3/2001 | Minto |
| 6,257,334 B1 | 7/2001 | Cyr et al. |
| 6,269,310 B1 | 7/2001 | Washbourne |
| 6,288,372 B1 | 9/2001 | Sandberg et al. |
| 6,313,431 B1 | 11/2001 | Schneider et al. |
| 6,328,104 B1 | 12/2001 | Graue |
| 6,353,706 B1 | 3/2002 | Bridges |
| 6,354,373 B1 | 3/2002 | Vercaemer et al. |
| 6,357,526 B1 | 3/2002 | Abdel-Halim et al. |
| 6,388,947 B1 | 5/2002 | Washbourne et al. |
| 6,412,559 B1 | 7/2002 | Gunter et al. |

| | | | |
|---|---|---|---|
| 6,422,318 B1 | 7/2002 | Rider | |
| 6,427,124 B1 | 7/2002 | Dubinsky et al. | |
| 6,467,543 B1 | 10/2002 | Talwani et al. | |
| 6,485,232 B1 | 11/2002 | Vinegar et al. | |
| 6,499,536 B1 | 12/2002 | Ellingsen | |
| 6,540,018 B1 | 4/2003 | Vinegar | |
| 6,581,684 B2 | 6/2003 | Wellington et al. | |
| 6,584,406 B1 | 6/2003 | Harmon et al. | |
| 6,585,046 B2 * | 7/2003 | Neuroth et al. | |
| 6,588,266 B2 | 7/2003 | Tubel et al. | |
| 6,588,503 B2 | 7/2003 | Karanikas et al. | |
| 6,588,504 B2 | 7/2003 | Wellington et al. | |
| 6,591,906 B2 | 7/2003 | Wellington et al. | |
| 6,591,907 B2 | 7/2003 | Zhang et al. | |
| 6,607,033 B2 | 8/2003 | Wellington et al. | |
| 6,609,570 B2 | 8/2003 | Wellington et al. | |
| 6,609,761 B1 | 8/2003 | Ramey et al. | |
| 6,679,332 B2 | 1/2004 | Vinegar et al. | |
| 6,684,948 B1 | 2/2004 | Savage | |
| 6,688,387 B1 | 2/2004 | Wellington et al. | |
| 6,698,515 B2 | 3/2004 | Karanikas et al. | |
| 6,702,016 B2 | 3/2004 | de Rouffignac et al. | |
| 6,708,758 B2 | 3/2004 | de Rouffignac et al. | |
| 6,712,135 B2 | 3/2004 | Wellington et al. | |
| 6,712,136 B2 | 3/2004 | de Rouffignac et al. | |
| 6,712,137 B2 | 3/2004 | Vinegar et al. | |
| 6,715,546 B2 | 4/2004 | Vinegar et al. | |
| 6,715,547 B2 | 4/2004 | Vinegar et al. | |
| 6,715,548 B2 | 4/2004 | Wellington et al. | |
| 6,715,549 B2 | 4/2004 | Wellington et al. | |
| 6,715,550 B2 | 4/2004 | Vinegar et al. | |
| 6,719,047 B2 | 4/2004 | Fowler et al. | |
| 6,722,429 B2 | 4/2004 | de Rouffignac et al. | |
| 6,722,430 B2 | 4/2004 | Vinegar et al. | |
| 6,722,431 B2 | 4/2004 | Karanikas et al. | |
| 6,725,920 B2 | 4/2004 | Zhang et al. | |
| 6,725,921 B2 | 4/2004 | de Rouffignac et al. | |
| 6,725,928 B2 | 4/2004 | Vinegar et al. | |
| 6,729,395 B2 | 5/2004 | Shahin, Jr. et al. | |
| 6,729,396 B2 | 5/2004 | Vinegar et al. | |
| 6,729,397 B2 | 5/2004 | Zhang et al. | |
| 6,729,401 B2 | 5/2004 | Vinegar et al. | |
| 6,732,794 B2 | 5/2004 | Wellington et al. | |
| 6,732,795 B2 | 5/2004 | de Rouffignac et al. | |
| 6,732,796 B2 | 5/2004 | Vinegar et al. | |
| 6,736,215 B2 | 5/2004 | Maher et al. | |
| 6,739,393 B2 | 5/2004 | Vinegar et al. | |
| 6,739,394 B2 | 5/2004 | Vinegar et al. | |
| 6,742,587 B2 | 6/2004 | Vinegar et al. | |
| 6,742,588 B2 | 6/2004 | Wellington et al. | |
| 6,742,589 B2 | 6/2004 | Berchenko et al. | |
| 6,742,593 B2 | 6/2004 | Vinegar et al. | |
| 6,745,831 B2 | 6/2004 | de Rouffignac et al. | |
| 6,745,832 B2 | 6/2004 | Wellington et al. | |
| 6,745,837 B2 | 6/2004 | Wellington et al. | |
| 6,749,021 B2 | 6/2004 | Vinegar et al. | |
| 6,752,210 B2 | 6/2004 | de Rouffignac et al. | |
| 6,758,268 B2 | 7/2004 | Vinegar et al. | |
| 6,761,216 B2 | 7/2004 | Vinegar et al. | |
| 6,763,886 B2 | 7/2004 | Schoeling et al. | |
| 6,769,483 B2 | 8/2004 | de Rouffignac et al. | |
| 6,769,485 B2 | 8/2004 | Vinegar et al. | |
| 6,782,947 B2 | 8/2004 | de Rouffignac et al. | |
| 6,789,625 B2 | 9/2004 | de Rouffignac et al. | |
| 6,805,194 B2 | 10/2004 | Davidson et al. | |
| 6,805,195 B2 | 10/2004 | Vinegar et al. | |
| 6,820,688 B2 | 11/2004 | Vinegar et al. | |
| 6,854,534 B2 | 2/2005 | Livingstone | |
| 6,866,097 B2 | 3/2005 | Vinegar et al. | |
| 6,871,707 B2 | 3/2005 | Karanikas et al. | |
| 6,877,554 B2 | 4/2005 | Stegemeier et al. | |
| 6,877,555 B2 | 4/2005 | Karanikas et al. | |
| 6,880,633 B2 | 4/2005 | Wellington et al. | |
| 6,880,635 B2 | 4/2005 | Vinegar et al. | |
| 6,889,769 B2 | 5/2005 | Wellington et al. | |
| 6,896,053 B2 | 5/2005 | Berchenko et al. | |
| 6,902,003 B2 | 6/2005 | Maher et al. | |
| 6,902,004 B2 | 6/2005 | de Rouffignac et al. | |
| 6,910,536 B2 | 6/2005 | Wellington et al. | |
| 6,913,078 B2 | 7/2005 | Shahin, Jr. et al. | |
| 6,913,079 B2 | 7/2005 | Tubel | |
| 6,915,850 B2 | 7/2005 | Vinegar et al. | |
| 6,918,442 B2 | 7/2005 | Wellington et al. | |
| 6,918,443 B2 | 7/2005 | Wellington et al. | |
| 6,918,444 B2 | 7/2005 | Passey | |
| 6,923,257 B2 | 8/2005 | Wellington et al. | |
| 6,923,258 B2 | 8/2005 | Wellington et al. | |
| 6,929,067 B2 | 8/2005 | Vinegar et al. | |
| 6,932,155 B2 | 8/2005 | Vinegar et al. | |
| 6,948,562 B2 | 9/2005 | Wellington et al. | |
| 6,948,563 B2 | 9/2005 | Wellington et al. | |
| 6,951,247 B2 | 10/2005 | de Rouffignac et al. | |
| 6,953,087 B2 | 10/2005 | de Rouffignac et al. | |
| 6,958,704 B2 | 10/2005 | Vinegar et al. | |
| 6,959,761 B2 | 11/2005 | Berchenko et al. | |
| 6,964,300 B2 | 11/2005 | Vinegar et al. | |
| 6,966,372 B2 | 11/2005 | Wellington et al. | |
| 6,966,374 B2 | 11/2005 | Vinegar et al. | |
| 6,969,123 B2 | 11/2005 | Vinegar et al. | |
| 6,973,967 B2 * | 12/2005 | Stegemeier et al. | |
| 6,981,548 B2 | 1/2006 | Wellington et al. | |
| 6,981,553 B2 | 1/2006 | Stegemeier et al. | |
| 6,991,032 B2 | 1/2006 | Berchenko et al. | |
| 6,991,045 B2 | 1/2006 | Vinegar et al. | |
| 6,994,160 B2 | 2/2006 | Wellington et al. | |
| 6,994,168 B2 | 2/2006 | Wellington et al. | |
| 6,994,169 B2 | 2/2006 | Zhang et al. | |
| 6,997,255 B2 | 2/2006 | Wellington et al. | |
| 6,997,518 B2 | 2/2006 | Vinegar et al. | |
| 7,004,247 B2 | 2/2006 | Cole et al. | |
| 7,004,251 B2 | 2/2006 | Ward et al. | |
| 7,011,154 B2 | 3/2006 | Maher et al. | |
| 7,032,660 B2 | 4/2006 | Vinegar et al. | |
| 7,036,583 B2 | 5/2006 | de Rouffignac et al. | |
| 7,040,397 B2 | 5/2006 | de Rouffignac et al. | |
| 7,040,398 B2 | 5/2006 | Wellington et al. | |
| 7,040,399 B2 | 5/2006 | Wellington et al. | |
| 7,040,400 B2 | 5/2006 | de Rouffignac et al. | |
| 7,048,051 B2 | 5/2006 | McQueen | |
| 7,051,807 B2 | 5/2006 | Vinegar et al. | |
| 7,051,808 B1 | 5/2006 | Vinegar et al. | |
| 7,055,600 B2 | 6/2006 | Messier et al. | |
| 7,063,145 B2 | 6/2006 | Veenstra et al. | |
| 7,066,254 B2 | 6/2006 | Vinegar et al. | |
| 7,066,257 B2 | 6/2006 | Wellington et al. | |
| 7,073,578 B2 | 7/2006 | Vinegar et al. | |
| 7,077,198 B2 | 7/2006 | Vinegar et al. | |
| 7,077,199 B2 | 7/2006 | Vinegar et al. | |
| 7,086,465 B2 | 8/2006 | Wellington et al. | |
| 7,086,468 B2 | 8/2006 | de Rouffignac et al. | |
| 7,090,013 B2 * | 8/2006 | Wellington et al. | |
| 7,096,941 B2 | 8/2006 | de Rouffignac et al. | |
| 7,096,942 B1 | 8/2006 | de Rouffignac et al. | |
| 7,096,953 B2 | 8/2006 | de Rouffignac et al. | |
| 7,100,994 B2 | 9/2006 | Vinegar et al. | |
| 7,104,319 B2 | 9/2006 | Vinegar et al. | |
| 7,114,566 B2 | 10/2006 | Vinegar et al. | |
| 7,121,341 B2 | 10/2006 | Vinegar et al. | |
| 7,121,342 B2 | 10/2006 | Vinegar et al. | |
| 7,124,584 B1 | 10/2006 | Wetzel et al. | |
| 7,128,153 B2 | 10/2006 | Vinegar et al. | |
| 7,147,057 B2 | 12/2006 | Steele et al. | |
| 7,147,059 B2 | 12/2006 | Hirsch et al. | |
| 7,156,176 B2 | 1/2007 | Vinegar et al. | |
| 7,165,615 B2 | 1/2007 | Vinegar et al. | |
| 7,170,424 B2 | 1/2007 | Vinegar et al. | |
| 7,204,327 B2 | 4/2007 | Livingstone | |
| 7,219,734 B2 * | 5/2007 | Bai et al. | |
| 3,051,235 A1 | 6/2007 | Banks | |
| 7,225,866 B2 | 6/2007 | Berchenko et al. | |
| 7,337,841 B2 | 3/2008 | Ravi | |
| 7,353,872 B2 | 4/2008 | Sandberg et al. | |
| 7,370,704 B2 | 5/2008 | Harris | |
| 7,383,877 B2 | 6/2008 | Vinegar et al. | |
| 7,424,915 B2 | 9/2008 | Vinegar et al. | |
| 7,431,076 B2 | 10/2008 | Sandberg et al. | |
| 7,435,037 B2 | 10/2008 | McKinzie, II | |
| 7,461,691 B2 | 12/2008 | Vinegar et al. | |

| Patent/Pub No. | Date | Inventor |
|---|---|---|
| 7,481,274 B2 | 1/2009 | Vinegar et al. |
| 7,490,665 B2 | 2/2009 | Sandberg et al. |
| 7,500,528 B2 | 3/2009 | McKinzie et al. |
| 7,510,000 B2 | 3/2009 | Sanz et al. |
| 7,527,094 B2 | 5/2009 | McKinzie et al. |
| 7,533,719 B2 | 5/2009 | Hinson et al. |
| 7,540,324 B2 | 6/2009 | de Rouffignac et al. |
| 7,549,470 B2 | 6/2009 | Vinegar et al. |
| 7,556,095 B2 | 7/2009 | Vinegar |
| 7,556,096 B2 | 7/2009 | Vinegar et al. |
| 7,559,367 B2 | 7/2009 | Vinegar et al. |
| 7,559,368 B2 | 7/2009 | Vinegar |
| 7,562,706 B2 | 7/2009 | Li et al. |
| 7,562,707 B2 | 7/2009 | Miller |
| 7,575,052 B2 | 8/2009 | Sandberg et al. |
| 7,575,053 B2 | 8/2009 | Vinegar et al. |
| 7,581,589 B2 | 9/2009 | Roes et al. |
| 7,584,789 B2 | 9/2009 | Mo et al. |
| 7,591,310 B2 | 9/2009 | Minderhoud et al. |
| 7,597,147 B2 | 10/2009 | Vitek et al. |
| 7,604,052 B2 | 10/2009 | Roes et al. |
| 7,610,962 B2 | 11/2009 | Fowler |
| 7,631,689 B2 | 12/2009 | Vinegar et al. |
| 7,631,690 B2 | 12/2009 | Vinegar et al. |
| 7,635,023 B2 | 12/2009 | Goldberg et al. |
| 7,635,024 B2 | 12/2009 | Karanikas et al. |
| 7,635,025 B2 | 12/2009 | Vinegar et al. |
| 7,640,980 B2 | 1/2010 | Vinegar et al. |
| 7,644,765 B2 | 1/2010 | Stegemeier et al. |
| 7,673,681 B2 | 3/2010 | Vinegar et al. |
| 7,677,310 B2 | 3/2010 | Vinegar et al. |
| 7,681,647 B2 | 3/2010 | Mudunuri et al. |
| 7,683,296 B2 | 3/2010 | Brady et al. |
| 7,703,513 B2 | 4/2010 | Vinegar et al. |
| 7,717,171 B2 | 5/2010 | Stegemeier et al. |
| 7,730,945 B2 | 6/2010 | Pieterson et al. |
| 7,730,946 B2 | 6/2010 | Vinegar et al. |
| 7,730,947 B2 | 6/2010 | Stegemeier et al. |
| 7,735,935 B2 | 6/2010 | Vinegar et al. |
| 2001/0049342 A1 | 12/2001 | Passey et al. |
| 2002/0027001 A1 | 3/2002 | Wellington et al. |
| 2002/0028070 A1 | 3/2002 | Holen |
| 2002/0033253 A1 | 3/2002 | de Rouffignac et al. |
| 2002/0035307 A1 | 3/2002 | Vinegar et al. |
| 2002/0036085 A1 | 3/2002 | Bass et al. |
| 2002/0036089 A1 | 3/2002 | Vinegar et al. |
| 2002/0038069 A1 | 3/2002 | Wellington et al. |
| 2002/0038709 A1 | 4/2002 | Wellington et al. |
| 2002/0040779 A1 | 4/2002 | Wellington et al. |
| 2002/0040780 A1 | 4/2002 | Wellington et al. |
| 2002/0040781 A1 | 4/2002 | Keedy et al. |
| 2002/0049360 A1 | 4/2002 | Wellington et al. |
| 2002/0053431 A1 | 5/2002 | Wellington et al. |
| 2002/0076212 A1 | 6/2002 | Zhang et al. |
| 2002/0112890 A1 | 8/2002 | Wentworth et al. |
| 2002/0112987 A1 | 8/2002 | Hou et al. |
| 2002/0153141 A1 | 10/2002 | Hartman et al. |
| 2003/0029617 A1 | 2/2003 | Brown et al. |
| 2003/0038734 A1 | 2/2003 | Hirsch et al. |
| 2003/0066642 A1 | 4/2003 | Wellington et al. |
| 2003/0075318 A1 | 4/2003 | Keedy et al. |
| 2003/0079877 A1 | 5/2003 | Wellington et al. |
| 2003/0085034 A1 | 5/2003 | Wellington et al. |
| 2003/0131989 A1* | 7/2003 | Zakiewicz |
| 2003/0146002 A1 | 8/2003 | Vinegar et al. |
| 2003/0157380 A1 | 8/2003 | Assarabowski et al. |
| 2003/0196789 A1 | 10/2003 | Wellington et al. |
| 2003/0196810 A1 | 10/2003 | Vinegar et al. |
| 2003/0201098 A1 | 10/2003 | Karanikas et al. |
| 2004/0020642 A1 | 2/2004 | Vinegar et al. |
| 2004/0035582 A1 | 2/2004 | Zupanick |
| 2004/0079553 A1 | 4/2004 | Livingstone |
| 2004/0140096 A1 | 7/2004 | Sandberg et al. |
| 2004/0144540 A1 | 7/2004 | Sandberg et al. |
| 2004/0144541 A1 | 7/2004 | Picha et al. |
| 2004/0145969 A1 | 7/2004 | Bai et al. |
| 2004/0146288 A1 | 7/2004 | Vinegar et al. |
| 2005/0006097 A1 | 1/2005 | Sandberg et al. |
| 2005/0269077 A1 | 12/2005 | Sandberg |
| 2005/0269088 A1 | 12/2005 | Vinegar et al. |
| 2005/0269089 A1 | 12/2005 | Sandberg et al. |
| 2005/0269090 A1 | 12/2005 | Vinegar et al. |
| 2005/0269091 A1 | 12/2005 | Pastor-Sanz et al. |
| 2005/0269092 A1 | 12/2005 | Vinegar et al. |
| 2005/0269093 A1 | 12/2005 | Sandberg et al. |
| 2005/0269094 A1 | 12/2005 | Harris |
| 2005/0269095 A1 | 12/2005 | Fairbanks |
| 2005/0269313 A1 | 12/2005 | Vinegar et al. |
| 2006/0005968 A1 | 1/2006 | Vinegar et al. |
| 2006/0213657 A1 | 9/2006 | Berchenko et al. |
| 2006/0289536 A1 | 12/2006 | Vinegar et al. |
| 2007/0045265 A1 | 3/2007 | McKinzie et al. |
| 2007/0045266 A1 | 3/2007 | Sandberg et al. |
| 2007/0045267 A1 | 3/2007 | Vinegar et al. |
| 2007/0045268 A1 | 3/2007 | Vinegar et al. |
| 2007/0095536 A1 | 5/2007 | Vinegar et al. |
| 2007/0095537 A1 | 5/2007 | Vinegar et al. |
| 2007/0108200 A1 | 5/2007 | McKinzie et al. |
| 2007/0108201 A1 | 5/2007 | Vinegar et al. |
| 2007/0119098 A1 | 5/2007 | Diaz et al. |
| 2007/0131411 A1 | 6/2007 | Vinegar et al. |
| 2007/0131415 A1 | 6/2007 | Vinegar et al. |
| 2007/0133959 A1 | 6/2007 | Vinegar et al. |
| 2007/0133960 A1 | 6/2007 | Vinegar et al. |
| 2007/0221377 A1 | 9/2007 | Vinegar et al. |
| 2008/0006410 A1 | 1/2008 | Looney et al. |
| 2008/0017370 A1 | 1/2008 | Vinegar et al. |
| 2008/0017380 A1 | 1/2008 | Vinegar et al. |
| 2008/0035347 A1 | 2/2008 | Brady et al. |
| 2008/0035348 A1 | 2/2008 | Vitec et al. |
| 2008/0035705 A1 | 2/2008 | Menotti et al. |
| 2008/0038144 A1 | 2/2008 | Maziasz et al. |
| 2008/0128134 A1 | 6/2008 | Mudunuri et al. |
| 2008/0135244 A1 | 6/2008 | Miller et al. |
| 2008/0135253 A1 | 6/2008 | Vinegar et al. |
| 2008/0135254 A1 | 6/2008 | Vinegar et al. |
| 2008/0142216 A1 | 6/2008 | Vinegar et al. |
| 2008/0142217 A1 | 6/2008 | Pieterson et al. |
| 2008/0173442 A1 | 7/2008 | Vinegar et al. |
| 2008/0173444 A1 | 7/2008 | Stone et al. |
| 2008/0173449 A1 | 7/2008 | Fowler |
| 2008/0174115 A1 | 7/2008 | Lambirth |
| 2008/0185147 A1 | 8/2008 | Vinegar et al. |
| 2008/0217003 A1 | 9/2008 | Kuhlman et al. |
| 2008/0217004 A1 | 9/2008 | de Rouffignac et al. |
| 2008/0217015 A1 | 9/2008 | Vinegar et al. |
| 2008/0217016 A1 | 9/2008 | Stegemeier et al. |
| 2008/0217321 A1 | 9/2008 | Vinegar et al. |
| 2008/0236831 A1 | 10/2008 | Hsu et al. |
| 2008/0277113 A1 | 11/2008 | Stegemeier et al. |
| 2008/0283246 A1 | 11/2008 | Karanikas et al. |
| 2009/0014180 A1 | 1/2009 | Stegemeier et al. |
| 2009/0014181 A1 | 1/2009 | Vinegar et al. |
| 2009/0071652 A1 | 3/2009 | Vinegar et al. |
| 2009/0078461 A1 | 3/2009 | Mansure et al. |
| 2009/0084547 A1 | 4/2009 | Farmayan et al. |
| 2009/0090158 A1 | 4/2009 | Davidson et al. |
| 2009/0090509 A1 | 4/2009 | Vinegar et al. |
| 2009/0095476 A1 | 4/2009 | Nguyen et al. |
| 2009/0095477 A1 | 4/2009 | Nguyen et al. |
| 2009/0095478 A1 | 4/2009 | Karanikas et al. |
| 2009/0095479 A1 | 4/2009 | Karanikas et al. |
| 2009/0095480 A1 | 4/2009 | Vinegar et al. |
| 2009/0101346 A1 | 4/2009 | Vinegar et al. |
| 2009/0120646 A1 | 5/2009 | Kim et al. |
| 2009/0126929 A1 | 5/2009 | Vinegar |
| 2009/0189617 A1 | 7/2009 | Burns et al. |
| 2009/0194269 A1 | 8/2009 | Vinegar |
| 2009/0194282 A1 | 8/2009 | Beer et al. |
| 2009/0194286 A1 | 8/2009 | Mason |
| 2009/0194287 A1 | 8/2009 | Nguyen et al. |
| 2009/0194329 A1 | 8/2009 | Guimerans et al. |
| 2009/0194333 A1 | 8/2009 | MacDonald |
| 2009/0194524 A1 | 8/2009 | Kim et al. |
| 2009/0200022 A1 | 8/2009 | Bravo et al. |
| 2009/0200023 A1 | 8/2009 | Costello et al. |
| 2009/0200025 A1 | 8/2009 | Bravo et al. |
| 2009/0200031 A1 | 8/2009 | Miller |

| | | | |
|---|---|---|---|
| 2009/0200290 | A1 | 8/2009 | Cardinal et al. |
| 2009/0200854 | A1 | 8/2009 | Vinegar |
| 2009/0260823 | A1 | 10/2009 | Prince-Wright et al. |
| 2009/0260824 | A1 | 10/2009 | Burns et al. |
| 2009/0272526 | A1 | 11/2009 | Burns et al. |
| 2009/0272533 | A1 | 11/2009 | Burns et al. |
| 2009/0272535 | A1 | 11/2009 | Burns et al. |
| 2009/0272536 | A1 | 11/2009 | Burns et al. |
| 2009/0272578 | A1 | 11/2009 | MacDonald |
| 2009/0301724 | A1 | 12/2009 | Roes et al. |
| 2009/0321417 | A1 | 12/2009 | Burns et al. |
| 2010/0089584 | A1 | 4/2010 | Burns |

FOREIGN PATENT DOCUMENTS

| | | |
|---|---|---|
| CA | 1165361 | 4/1984 |
| CA | 1168283 | 5/1984 |
| CA | 1196594 | 11/1985 |
| CA | 1253555 | 5/1989 |
| CA | 1288043 | 8/1991 |
| CA | 2015460 | 10/1991 |
| EP | 107927 | 5/1984 |
| EP | 0130671 | 1/1985 |
| EP | 0940558 | 9/1999 |
| GB | 156396 | 1/1921 |
| GB | 1204405 | 9/1970 |
| JP | 2000340350 | 12/2000 |
| SE | 121737 | 3/1948 |
| SE | 123136 | 3/1948 |
| SE | 123137 | 11/1948 |
| SE | 123138 | 11/1948 |
| SE | 126674 | 11/1949 |
| WO | 9506093 | 3/1995 |
| WO | 97/01017 | 1/1997 |
| WO | 97/23924 | 7/1997 |
| WO | 9901640 | 1/1999 |
| WO | 00/19061 | 4/2000 |
| WO | 2005010320 | 2/2005 |
| WO | 2007098370 | 8/2007 |

OTHER PUBLICATIONS

U.S. Patent and Trademark Office, "Office Communication," for U.S. Appl. No. 11/788,860 mailed Feb. 23, 2009.
U.S. Patent and Trademark Office, "Office Communication," for U.S. Appl. No. 10/693,820 mailed May 28, 2009.
U.S. Patent and Trademark Office, "Office Communication," for U.S. Appl. No. 10/693,700 mailed May 28, 2009.
U.S. Patent and Trademark Office, "Office Communication," for U.S. Appl. No. 10/693,840 mailed May 28, 2009.
U.S. Patent and Trademark Office, "Office Communication," for U.S. Appl. No. 11/112,881 mailed May 28, 2009.
U.S. Patent and Trademark Office, "Office Communication," for U.S. Appl. No. 11/584,801 mailed Oct. 27, 2009.
U.S. Patent and Trademark Office, "Office Communication," for U.S. Appl. No. 11/409,523 mailed Feb. 2, 2010.
U.S. Patent and Trademark Office, "Office Communication," for U.S. Appl. No. 10/693,700 mailed Jan. 8, 2008; 7 pages.
U.S. Patent and Trademark Office, "Office Communication," for U.S. Appl. No. 11/854,801 mailed Jan. 11, 2008; 7 pages.
U.S. Patent and Trademark Office, "Office Communication," for U.S. Appl. No. 10/693,840 mailed Jan. 8, 2008; 11 pages.
U.S. Patent and Trademark Office, "Office Communication," for U.S. Appl. No. 10/693,820 mailed Jan. 8, 2008; 8 pages.
U.S. Patent and Trademark Office, "Office Communication," for U.S. Appl. No. 10/693,820 mailed Jan. 8, 2008; 8 pages.
U.S. Patent and Trademark Office, "Office Communication," for U.S. Appl. No. 10/693,820 mailed Jan. 8, 2008; 8 pages.
U.S. Patent and Trademark Office, "Office Communication," for U.S. Appl. No. 11/113,353 mailed Jan. 11, 2008.
T35. SSAB report, "Cost for Mining," 1959-1979; 13 pages. (Swedish).
T36. SSAB report, "Cost Comparison of Mining and Processing of Shale and Dolomite Using Various Production Alternatives", 1960; 64 pages. (Swedish).
T37. SSAB report, "Assessment of Future Mining Alternatives of Shale and Dolomite," 1962; 59 pages. (Swedish).

T40. SAAB report, "Swedish Geological Survey Report, Plan to Delineate Oil shale Resource in Narkes Area (near Kvarntorp)," 1941; 13 pages. (Swedish).
T41. SAAB report, "Recovery Efficiency," 1941; 61 pages. (Swedish).
T42. SAAB report, "Geologic Work Conducted to Assess Possibility of Expanding Shale Mining Area in Kvarntorp; Drilling Results, Seismic Results," 1942; 79 pages. (Swedish).
T43. SSAB report, "Ojematinigar vid Norrtorp," 1941; 141 pages. (Swedish).
T44. SSAB report, "Inhopplingschema, Norrtorp II 20/3/-17/8," 1945; 50 pages. (Swedish).
T45. SSAB report, "Secondary Recovery after LINS," 1945; 81 pages. (Swedish).
T46. SSAB report, "Maps and Diagrams, Geology," 1947; 137 pages. (Swedish).
T47. SSAB report, "Styrehseprotoholl," 1943; 10 pages. (Swedish).
T48. SSAB report, "Early Shale Retorting Trials" 1951-1952; 134 pages. (Swedish).
T49. SSAB report, "Analysis of Lujunstrom Oil and its Use as Liquid Fuel," Thesis by E. Pals, 1949; 83 pages. (Swedish).
T50. SSAB report, "Environmental Sulphur and Effect on Vegetation," 1951; 50 pages. (Swedish).
T51. SSAB report, "Tar Sands." vol. 135 1953; 20 pages. (Swedish, pp. 12-15 English translation).
T52. SSAB report, "Assessment of Skanes Area (Southern Sweden) Shales as Fuel Source," 1954; 54 pages. (Swedish).
T53. SSAB report, "From as Utre Dn Text Geology Reserves," 1960; 93 pages. (Swedish).
T54. SSAB report, "Kvarntorps-Environmental Area Assessment," 1981; 50 pages. (Swedish).
T27. SAAB, "Santa Cruz, California, Field Test of the Lins Method for the Recovery of Oil from Sand-Figures," 1955 vol. 2; 146 pages.
T28. "Santa Cruz, California, Field Test of the Lins Method for the Recovery of Oil from Sand-Memorandum re: tests," 1955 vol. 3; 256 pages.
T29. Helander, "Santa Cruz, California, Field Test of Carbon Steel Burner Casings for the Lins Method of Oil Recovery," 1959; 38 pages.
T30. Helander et al., Santa Cruz, California, "Field Test of Fluidized Bed Burners for the Lins Method of Oil Recovery," 1959; 86 pages.
T31. SSAB report, "Bradford Residual Oil, Athabasa Ft. McMurray," 1951; 207 pages.
T32. "Lins Burner Test Results-English," 1959-1960; 148 pages.
T33. SSAB "Annual Reports, SSAB Laboratory, Address Annually Issues-Shale and Ash, Oil, Gas, Waste Water, Analytical," 1953-1954, 166 pages. (Swedish).
T34. SSAB report, "Financial Matter, Swedish taxes, etc.," 1960-1961; 37 pages. (Swedish).
T26. SAAB, "Santa Cruz, California, Field Test of the Lins Method for the Recovery of Oil from Sand," 1955 vol. 1; 141 pages.
T24. Gejrot et al., "The Shale Oil Industry in Sweden," Carlo Colombo Publishers-Rome, Proceedings of the Fourth World Petroleum Congress, 1955; 8 pages.
T23. SAAB report, "The Swedish Shale Oil Industry," 1948; 8 pages.
T25. Hedback, T. J., "The Swedish Shale as Raw Material for Production of Power, Oil and Gas," XIth Sectional Meeting World power Conference, 1957; 9 pages.
A230. Bosch et al., "Evaluation of Downhole Electric Impedance Heating Systems for Paraffin Control in Oil Wells;" Industry Applications Society 37th Annual Petroleum and Chemical Industry Conference; The Institute of Electrical and Electronics Engineers Inc., Sep. 1990, pp. 223-227.
A231. Eastlund et al., "New System Stops Paraffin Build-up," Petroleum Engineer, Jan. 1989, (3 pages).
A241. Ljungström, "The Shale Oil Question, Old and New Viewpoints," A Lecture in the Engineering Science Academy, Feb. 23, 1950, published in Teknisk Trdskrift, Jan. 1951 p. 33-40.
A242. "Underground Shale Oil Pyrolysis According to the Ljungström Method," Svenska Skifferolje Aktiebolaget (Swedish Shale Oil Corp.), IVA, vol. 24, 1953, No. 3, pp. 118-123.
A246. Yen et al., "Oil Shale," Developments in Petroleum Science 5, 1976, pp. 187-189, 197-198.

A249. Tissot et al., "Geochemistry and Pyrolysis of Oil Shales," Geochemistry and Chemistry of Oil Shales, American Chemical Society, 1983, pp. 1-11.
A293. Bissell et al, "Shale Oil Cracking Kinetics and Diagnostics," November 1983; 27 pages.
A311. Cummins et al. Thermal Degradation of Green River Kerogen at 150° to 350 °C. Rate of Production Formation, 1972; 18 pages.
A314. Lewis et al., "Oil Shale Retorting Processes: A Technical Overview," Mar. 1984; 18 pages.
A316. Piwinskii et al., "The Permittivity and Electrical Conductivity of Oil Shale," Apr. 28, 1975; 12 pages.
A319. Reynolds et al. "Analysis of Oil Shale and Petroleum Source Rock Pyrolysis by Triple Quadrupole Mass Spectrometry: Comparisons of Gas Evolution at the Heating Rate of 10 °C./Min.," Oct. 1990; 57 pages.
A325. Sandholtz et al., "Operating Laboratory Oil Shale Retorts in an In-Situ Mode," Aug. 1977; 16 pages.
A337. Wise et al., "A Laboratory Study of Green River Oil Shale Retorting Under Pressure in a Nitrogen Atmosphere," Sep. 1976; 24 pages.
A351. Berchenko et al., "In Situ Measurement of Some Thermoporoelastic Parameters of a Granite," Poromechanics, A Tribute to Maurice Biot, 1998, pp. 545-550.
A352. The VertiTrak System Brochure, Baker Hughes, INT-01-1307A4, 2001; 8 pages.
AA19. Bosch et al. "Evaluation of Downhole Electric Impedance Heating Systems for Paraffin Control in Oil Wells," IEEE Transactions on Industrial Applications, 1991, vol. 28; pp. 190-194.
AA20. McGee et al. "Electrical Heating with Horizontal Wells, The Heat Transfer Problem, " International Conference on Horizontal Well Technology, Calgary, Alberta Canada, 1996; 14 pages.
AA21. "IEEE Recommended Practice for Electrical Impedance, Induction, and Skin Effect Heating of Pipelines and Vessels," IEEE Std. 844-200, 2000; 6 pages.
T02. Burnham, "Oil Shale Retorting Dependence of timing and composition on temperature and heating rate," Jan. 27, 1995; 23 pages.
T04. Campbell, et al., "Kinetics of oil generation from Colorado Oil Shale" IPC Business Press, Fuel, 1978; 3 pages.
T07. Hill et al., "The Characteristics of a Low Temperature in situ Shale Oil," American Institute of Mining, Metallurgical & Petroleum Engineers, 1967; pp. 75-90.
T11. Hill et al. "Direct Production of Low Pour Point High Gravity Shale Oil," I&EC Product Research and Development, 1967, vol. 6; pp. 52-59.
T13. SSAB report, "A Brief Description of the Ljungstrom Method for Shale Oil Production," 1950; 12 pages.
T14. Salomonsson, SSAB report, "The Lungström In Situ-Method for Shale Oil Recovery," 1950; 28 pages.
T15. "Swedish shale oil-Production method in Sweden," Organisation for European Economic Co-operation, 1952; 70 pages.
T16. SSAB report, "Kvarn Torp," 1958; 36 pages.
T17. SSAB report, "Kvarn Torp," 1951; 35 pages.
T19. Vogel et al. "An Analog Computer for Studying Heat Transfrer during a Thermal Recovery Process," AIME Petroleum Transactions, 1955; pp. 205-212.
T20. "Skiferolja Genom Uppvarmning AV Skifferberget," Faxin Department och Namder, 1941; 3 pages.
T22. Ronnby, E. "Kvarntorp—Sveriges Storsta skifferoljeindustri," 1943; 9 pages.
U.S. Patent and Trademark Office, "Office Communication," for U.S. Appl. No. 11/113,353 mailed Jul. 25, 2008.
U.S. Patent and Trademark Office, "Office Communication," for U.S. Appl. No. 11/409,565 mailed Dec. 2, 2008.
PCT "International Search Report and Written Opinion" for International Application No. PCT/US08/79709, mailed, Dec. 12, 2008; 7 pages.
U. S. Patent and Trademark Office, "Office Communication," for U.S. Appl. No. 10/693,820 mailed Jul. 27, 2007; 9 pages.
U. S. Patent and Trademark Office, "Office Communication," for U.S. Appl. No. 10/693,700 mailed Jul. 27, 2007; 8 pages.
U. S. Patent and Trademark Office, "Office Communication," for U.S. Appl. No. 10/693,840 mailed Jul. 27, 2007; 13 pages.
U. S. Patent and Trademark Office, "Office Communication," for U.S. Appl. No. 11/112,863 mailed Aug. 20, 2007; 8 pages.
U.S. Patent and Trademark Office, "Office Communication," for U.S. Appl. No. 10/693,744 mailed Jan. 4, 2006; 14 pages.
U.S. Patent and Trademark Office, "Office Communication," for U.S. Appl. No. 10/693,840 mailed Jan. 12, 2006; 27 pages.
U.S. Patent and Trademark Office, "Office Communication," for U.S. Appl. No. 10/693,744 mailed Jul. 18, 2006.
U.S. Patent and Trademark Office, "Office Communication," for U.S. Appl. No. 11/112,714 mailed May 21, 2007; 14 pages.
U.S. Patent and Trademark Office, "Office Communication," for U.S. Appl. No. 11/112,855 mailed Jul. 20, 2007; 4 pages.
U.S. Patent and Trademark Office, "Office Communication," for U.S. Appl. No. 09/841,193 mailed Mar. 24, 2003; 18 pages.
U.S. Patent and Trademark Office, "Office Communication," for U.S. Appl. No. 10/693,816 mailed Aug. 24, 2005; 14 pages.
U.S. Patent and Trademark Office, "Office Communication," for U.S. Appl. No. 10/693,700 mailed Aug. 25, 2005; 14 pages.
U.S. Patent and Trademark Office, "Office Communication," for U.S. Appl. No. 10/693,819 mailed Sep. 22, 2005; 7 pages.
U.S. Patent and Trademark Office, "Office Communication," for U.S. Appl. No. 10/279,288 mailed Oct. 7, 2005; 13 pages.
U.S. Patent and Trademark Office, "Office Communication," for U.S. Appl. No. 10/279,288 mailed Mar. 16, 2006; 5 pages.
U.S. Patent and Trademark Office, "Office Communication," for U.S. Appl. No. 11/112,881 mailed Apr. 28, 2006; 12 pages.
U.S. Patent and Trademark Office, "Office Communication," for U.S. Appl. No. 10/693,700 mailed Aug. 25, 2006.
U.S. Patent and Trademark Office, "Office Communication," for U.S. Appl. No. 10/693,840 mailed Sep. 15, 2006.
U.S. Patent and Trademark Office, "Office Communication," for U.S. Appl. No. 11/112,881 mailed Dec. 6, 2006; 12 pages.
U.S. Patent and Trademark Office, "Office Communication," for U.S. Appl. No. 11/112,881 mailed May 18, 2007; 8 pages.
U.S. Patent and Trademark Office, "Office Communication," for U.S. Appl. No. 11/112,713 mailed Aug. 20, 2007; 6 pages.
Co-pending U.S. Appl. No. 11/585,302 entitled "Temperature Limited Heater With a Conduit Substantially Electrically Isolated From the Formation" filed Oct. 20, 2006.
Co-pending U.S. Appl. No. 11/584,805 entitled "Varying Heating in Dawsonite Zones in Hydrocarbon Containing Formations" filed Oct. 20, 2006.
Co-pending U.S. Appl. No. 11/788,860 entitled "Adjusting Alloy Compositions for Selected Properties in Temperature Limited Heaters" filed Apr. 20, 2007.
Co-pending U.S. Appl. No. 11/788,869 entitled "Joint Used for Coupling Long Heaters" filed Apr. 20, 2007.
Co-pending U.S. Appl. No. 11/788,826 entitled "Welding Shield for Coupling Heaters" filed Apr. 20, 2007.
Co-pending U.S. Appl. No. 11/788,863 entitled "Temperature Limited Heaters Using Phase Transformation of Ferromagnetic Material" filed Apr. 20, 2007.
Co-pending U.S. Appl. No. 11/788,859 entitled "Time Sequenced Heating of Multiple Layers in a Hydrocarbon Containing Formation" filed Apr. 20, 2007.
Co-pending U.S. Appl. No. 11/788,871 entitled "Non-Ferromagnetic Overburden Casing" filed Apr. 20, 2007.
Co-pending U.S. Appl. No. 11/788,858 entitled "High Strength Alloys" filed Apr. 20, 2007.
U.S. Patent and Trademark Office, "Office Communication," for U.S. Appl. No. 11/112,881 mailed Dec. 13, 2007; 8 pages.
PCT "International Search Report and Written Opinion" for International Application No. PCT/US07/09741, mailed, Aug. 28, 2008; 12 pages.
PCT "International Search Report and Written Opinion" for International Application No. PCT/US07/22376, mailed, Aug. 22, 2008; 10 pages.
U.S. Patent and Trademark Office, "Office Communication," for U.S. Appl. No. 11/112,881 mailed Oct. 1, 2008.
U.S. Patent and Trademark Office, "Office Communication," for U.S. Appl. No. 11/409,556 mailed Sep. 17, 2008.
U.S. Patent and Trademark Office, "Office Communication," for U.S. Appl. No. 11/585,302 mailed Sep. 11, 2008.

U.S. Patent and Trademark Office, "Office Communication," for U.S. Appl. No. 11/788,863 mailed Sep. 17, 2008.

U.S. Patent and Trademark Office, "Office Communication," for U.S. Appl. No. 11/788,871 mailed Oct. 1, 2008.

Moreno, James B., Sandia National Laboratories, "Methods and Energy Sources for Heating Subsurface Geological Formations, Task 1: Heat Delivery Systems," Nov. 20, 2002, pp. 1-166.

U.S. Patent and Trademark Office, "Office Communication," for U.S. Appl. No. 11/113,353 mailed Jul. 25, 2008.

U.S. Patent and Trademark Office, "Office Communication," for U.S. Appl. No. 11/584,427 mailed Jul. 24, 2008.

U.S. Patent and Trademark Office, "Office Communication," for U.S. Appl. No. 11/788,870 mailed Jul. 23, 2008.

U.S. Patent and Trademark Office, "Office Communication," for U.S. Appl. No. 10/693,816 mailed Aug. 5, 2008.

U.S. Patent and Trademark Office, "Office Communication," for U.S. Appl. No. 11/584,801 mailed Aug. 11, 2008.

PCT "International Search Report and Written Opinion" for International Application No. PCT/US06/40971, mailed Jul. 23, 2008; 9 pages.

PCT "International Search Report and Written Opinion" for International Application No. PCT/US06/15142, mailed, Jul. 21, 2008; 10 pages.

U.S. Patent and Trademark Office, "Office Communication," for U.S. Appl. No. 10/693,820 mailed Aug. 18, 2008; 8 pages.

U.S. Patent and Trademark Office, "Office Communication," for U.S. Appl. No. 10/693,700 mailed Aug. 18, 2008; 7 pages.

U.S. Patent and Trademark Office, "Office Communication," for U.S. Appl. No. 10/693,840 mailed Aug. 18, 2008.

Euroasian Patent Office "Notification" for co-pending Eurasian Application No. 2007002299/27 mailed Jun. 17, 2008; 4 pages.

PCT "International Search Report and Written Opinion" for International Application No. PCT/US08/60743, mailed, Aug. 18, 2008; 7 pages.

PCT "International Search Report and Written Opinion" for International Application No. PCT/US08/60740, mailed, Aug. 19, 2008; 7 pages.

U.S. Patent and Trademark Office, "Office Communication," for U.S. Appl. No. 11/409,566 mailed Mar. 17, 2008.

PCT "International Search Report and Written Opinion" for International Application No. PCT/US07/67062, mailed, May 15, 200.

SR36. PCT "International Search Report and Written Opinion" for International Application No. PCT/US2005013889 mailed Jul. 25, 2005; 5 pages.

SR41. PCT "International Search Report and Written Opinion" for International Application No. PCT/US2005013923 mailed Jul. 25, 2005; 7 pages.

SR42. PCT "International Search Report and Written Opinion" for International Application No. PCT/US2006/014776, 13 pages.

SR43. PCT "International Search Report and Written Opinion" for International Application No. PCT/US2006/015101, 13 pages.

SR44. PCT "International Search Report and Written Opinion" for International Application No. PCT/US2006/015105, 12 pages.

SR45. PCT "International Search Report and Written Opinion" for International Application No. PCT/US2006/015106, mailed Aug. 7, 2006; 9 pages.

SR48. PCT "International Search Report and Written Opinion" for International Application No. PCT/US2006/015106, mailed Aug. 7, 2006; 9 pages.

SR50. PCT "International Serach Report and Written Opinion" for International Application No. PCT/US2006/015084, mailed Sep. 6, 2006; 8 pages.

SR51. PCT "International Serach Report and Written Opinion" for International Application No. PCT/US2006/015166, mailed Aug. 30, 2006; 6 pages.

SR53. PCT "International Search Report and Written Opinion" for International Application No. PCT/US2006/041122 mailed Mar. 9, 2007; 6 pages.

U.S. Patent and Trademark Office, Office Communication for U.S. Appl. No. 11/409,525 mailed Feb. 23, 2010.

U.S. Patent and Trademark Office, Office Communication for U.S. Appl. No. 11/409,558 mailed Mar. 9, 2010.

U.S. Patent and Trademark Office, Office Communication for U.S. Appl. No. 11/409,565 mailed Mar. 5, 2010.

U.S. Patent and Trademark Office, "Office Communication," for U.S. Appl. No. 12/106,060 mailed Apr. 27, 2010.

U.S. Patent and Trademark Office, "Office Communication," for U.S. Appl. No. 12/106,139 mailed Jul. 21, 2010.

* cited by examiner

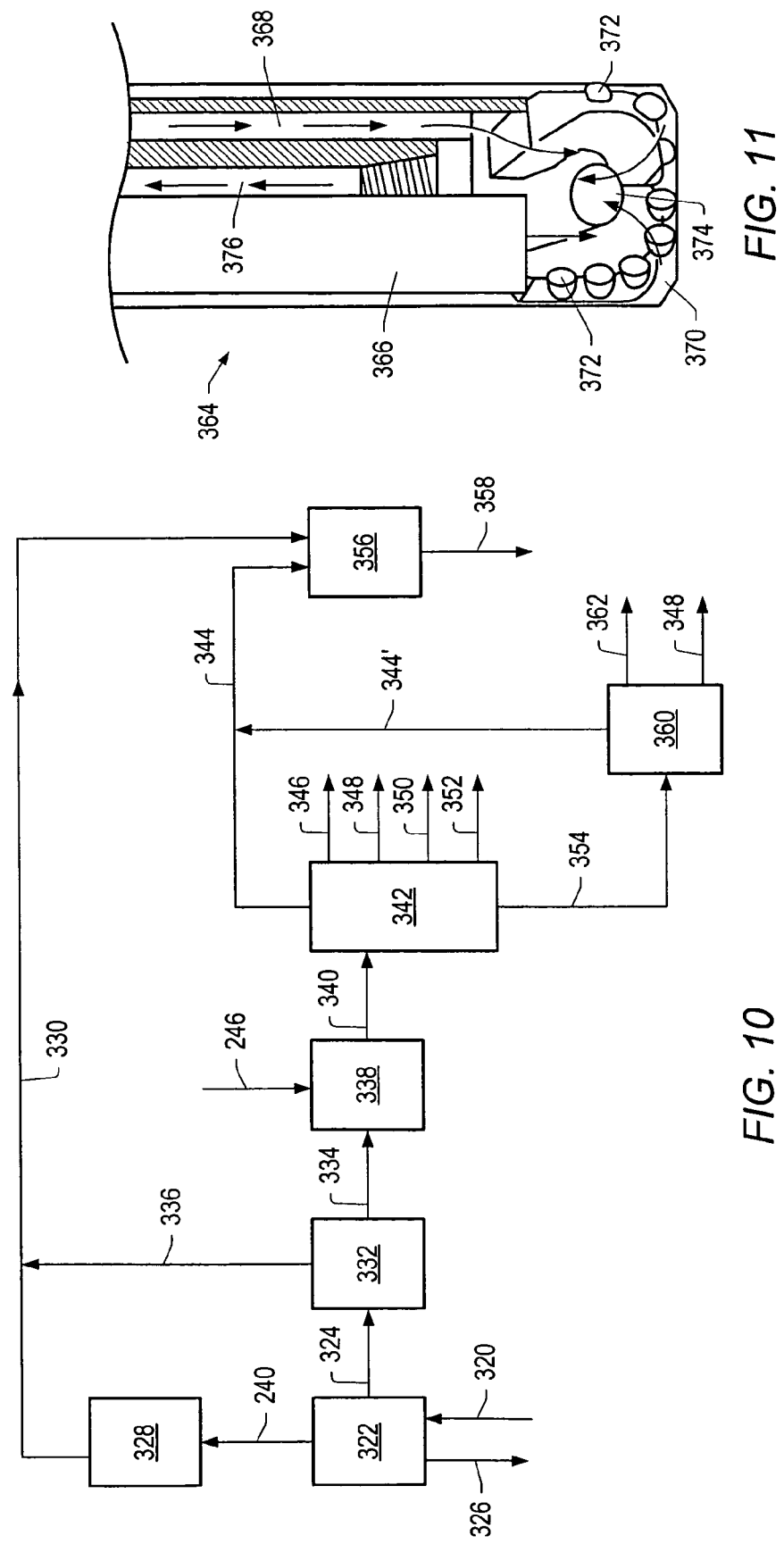

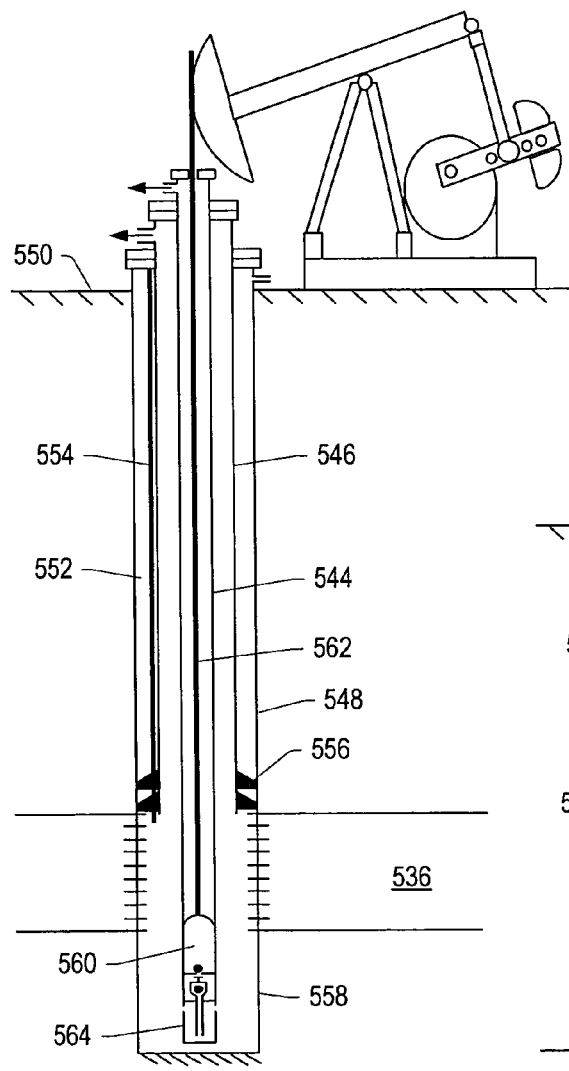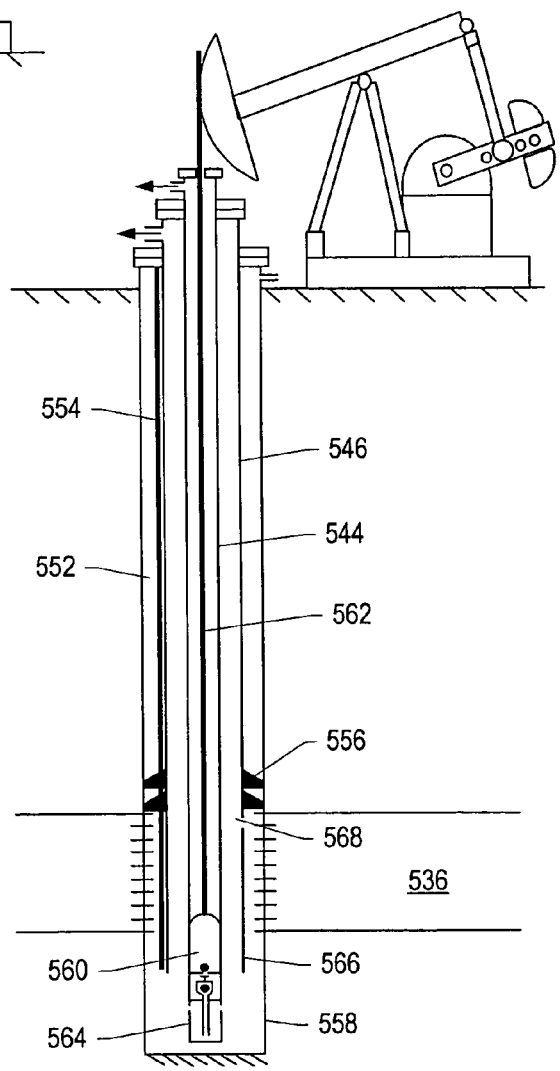
FIG. 29
FIG. 30

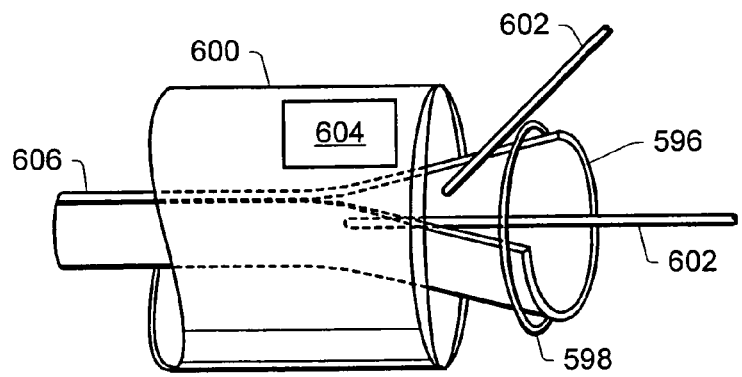
FIG. 39
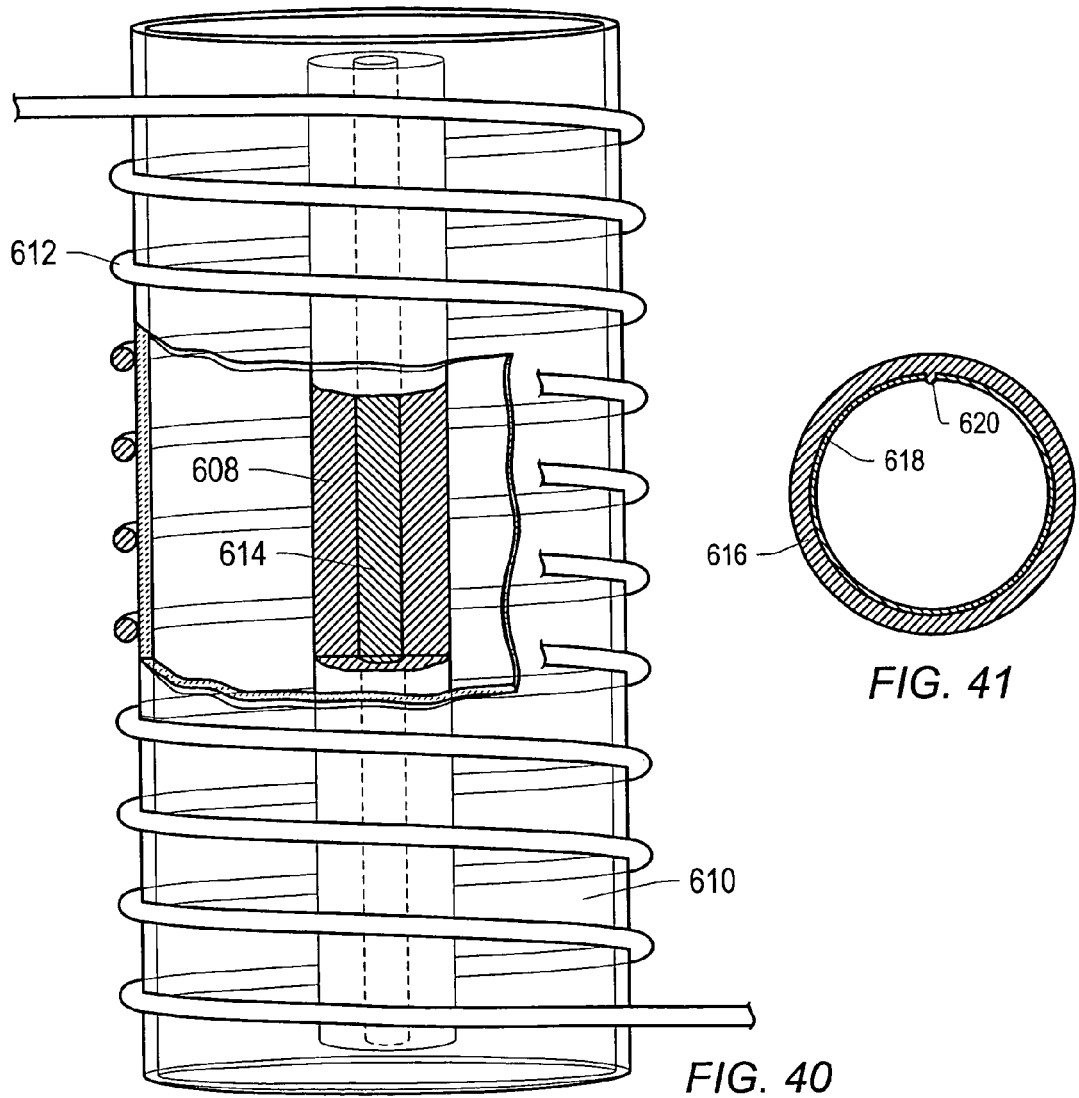
FIG. 41
FIG. 40

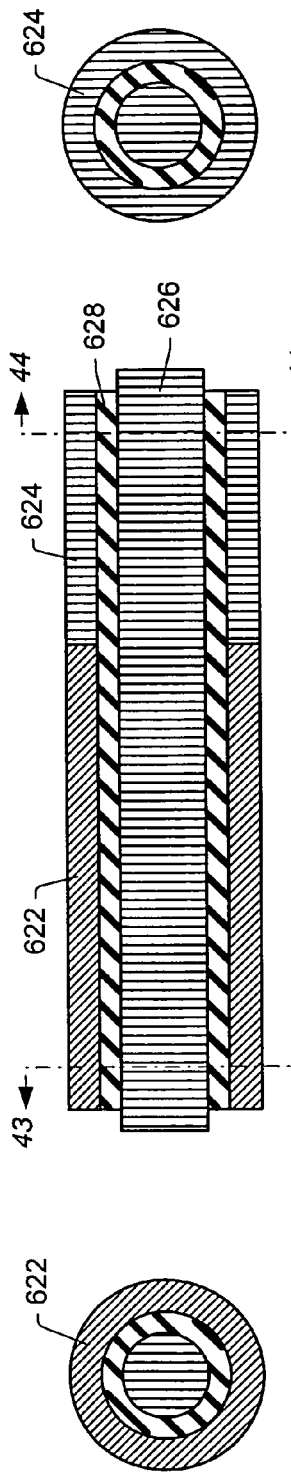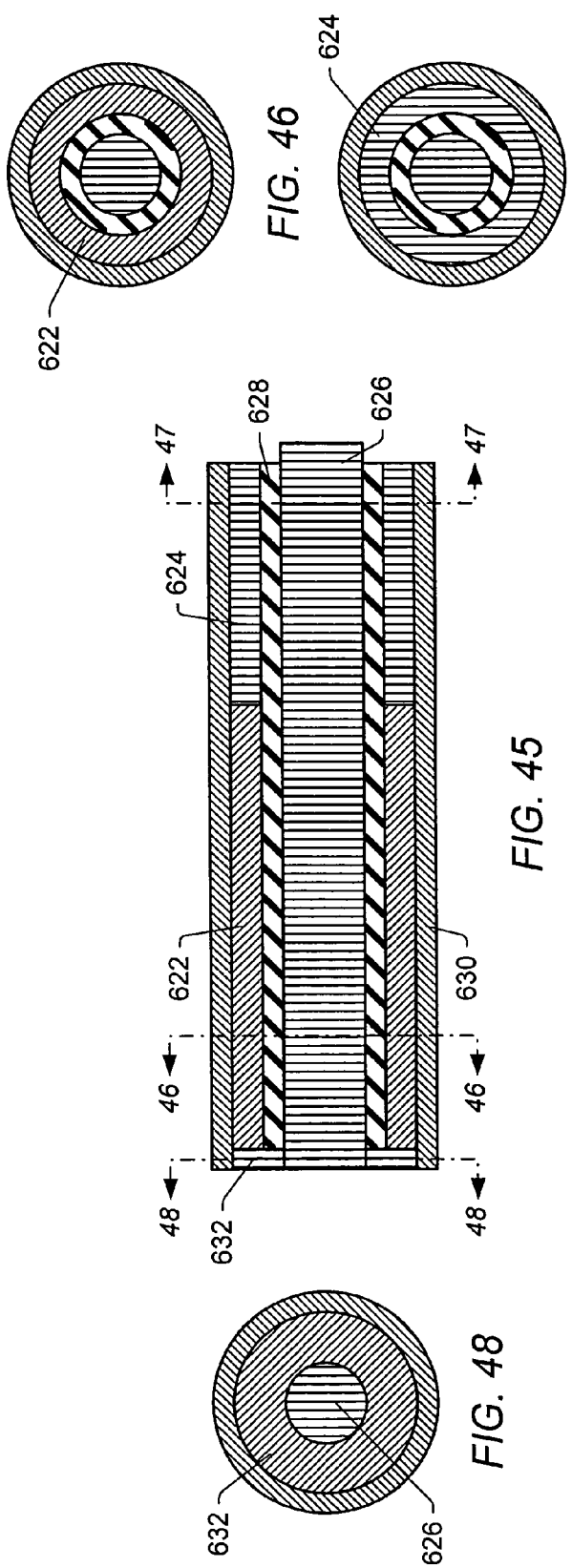

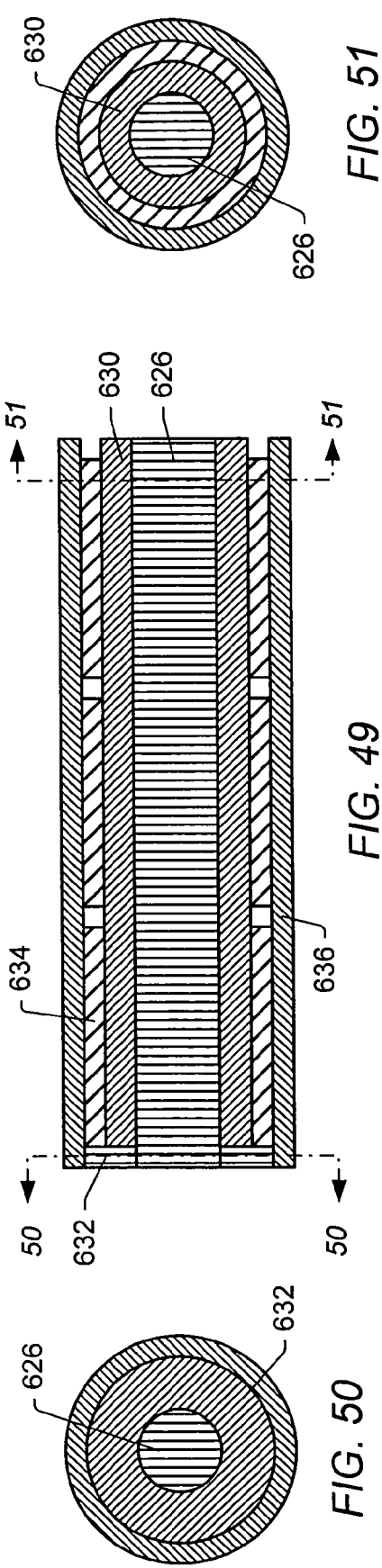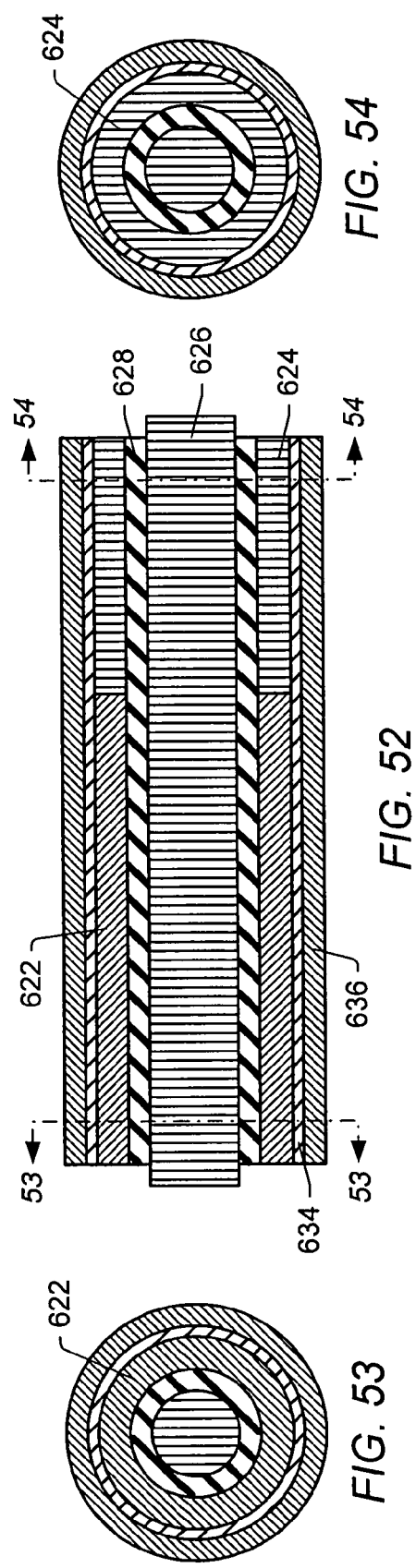

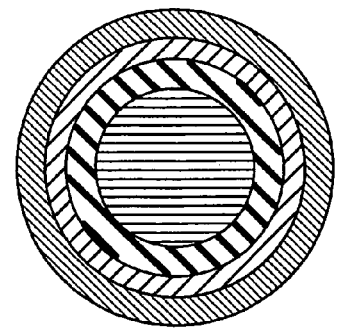
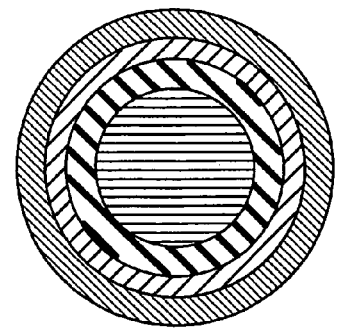
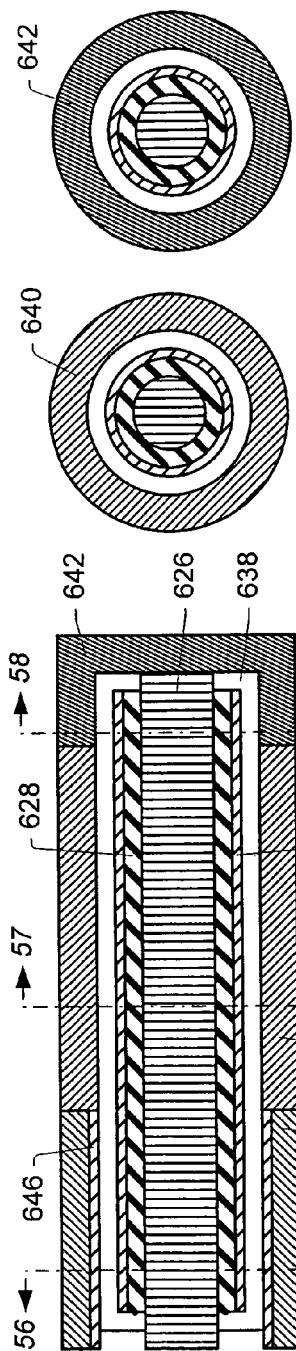
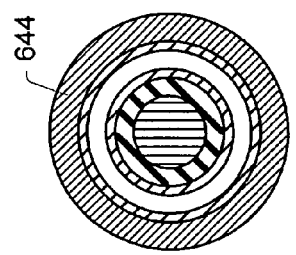
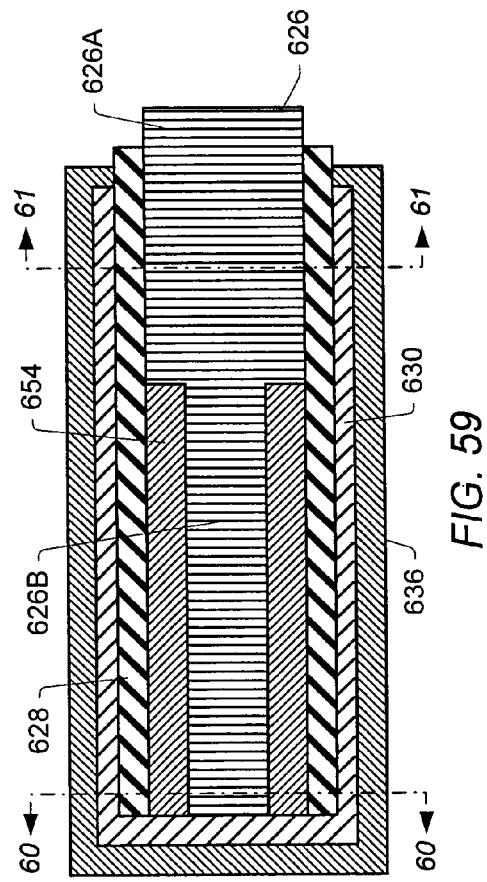
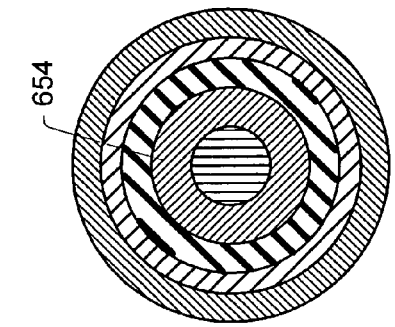

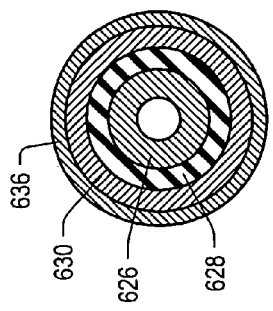
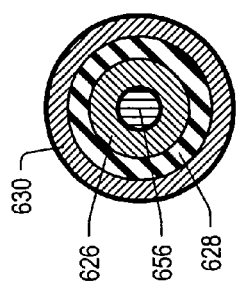
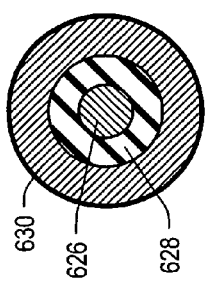
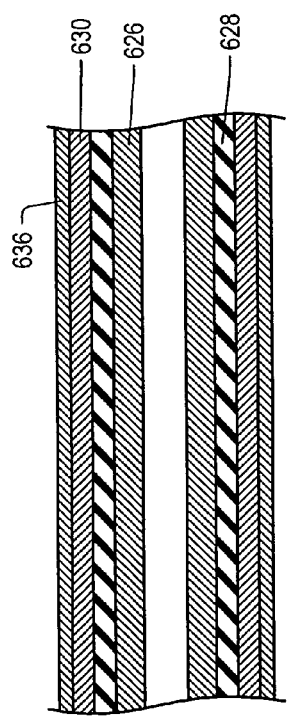
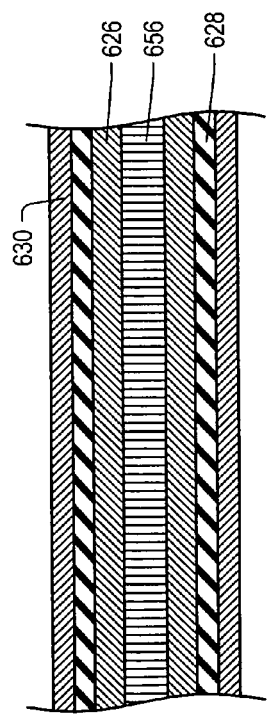
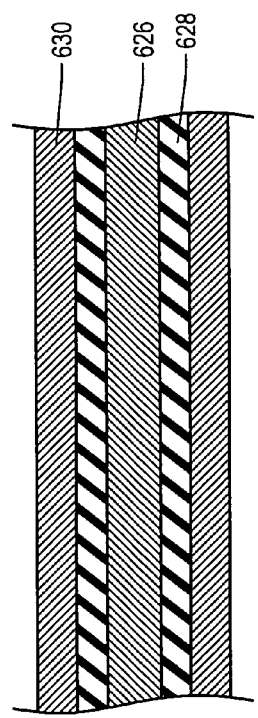

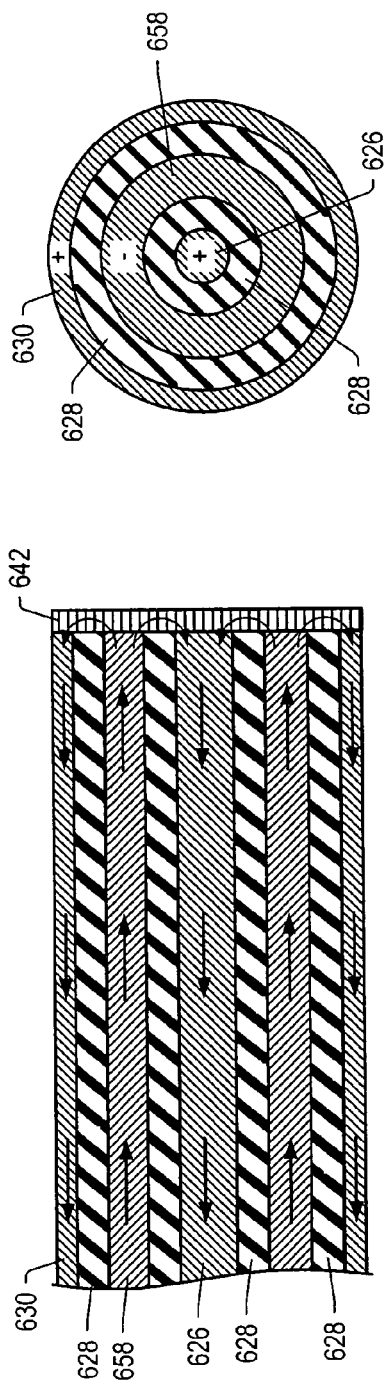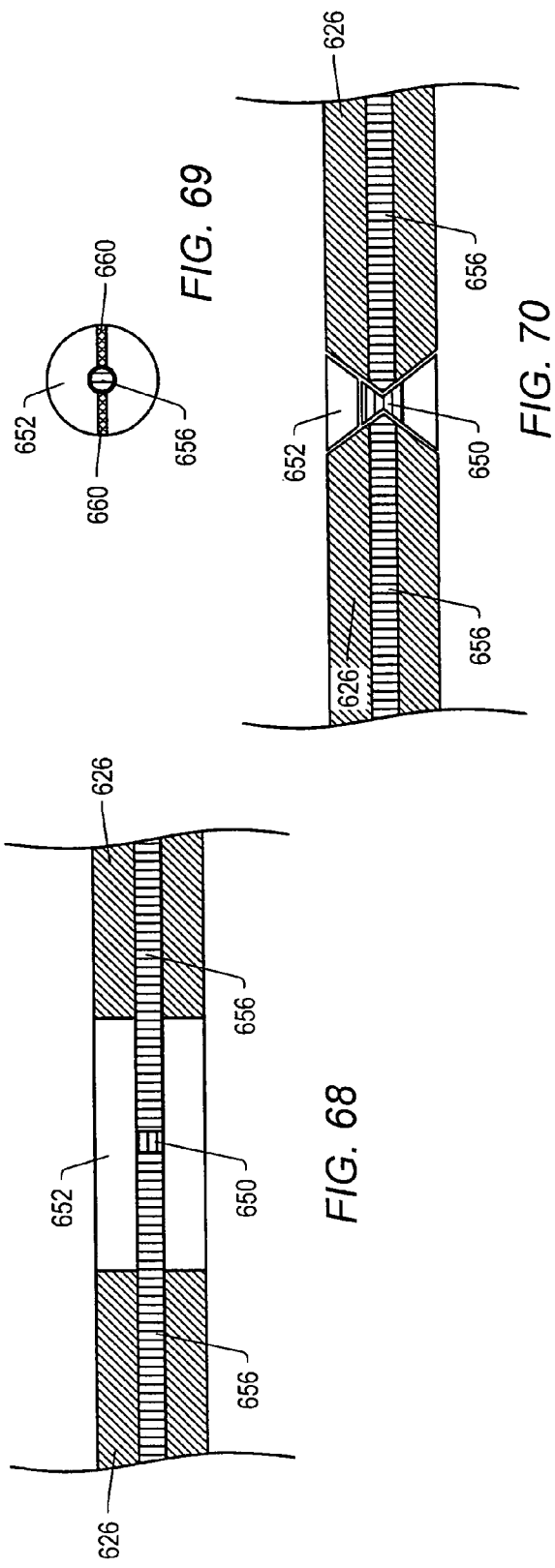
FIG. 67B
FIG. 69
FIG. 70
FIG. 67A
FIG. 68

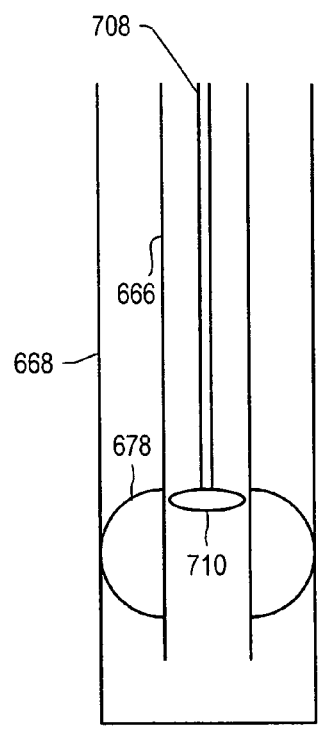
*FIG. 79*
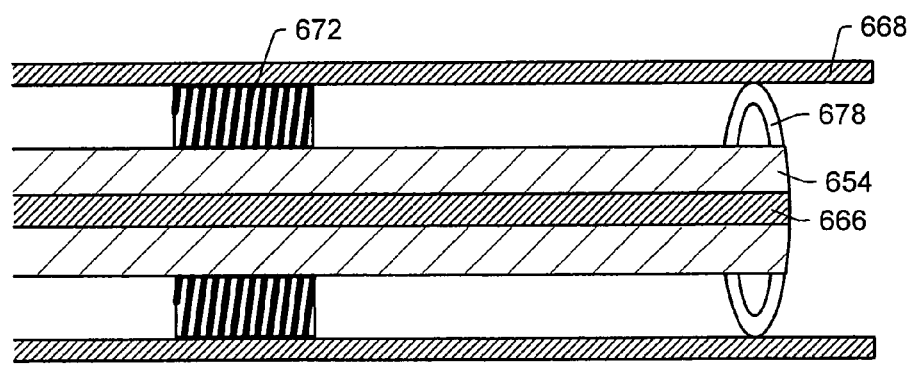
*FIG. 80*
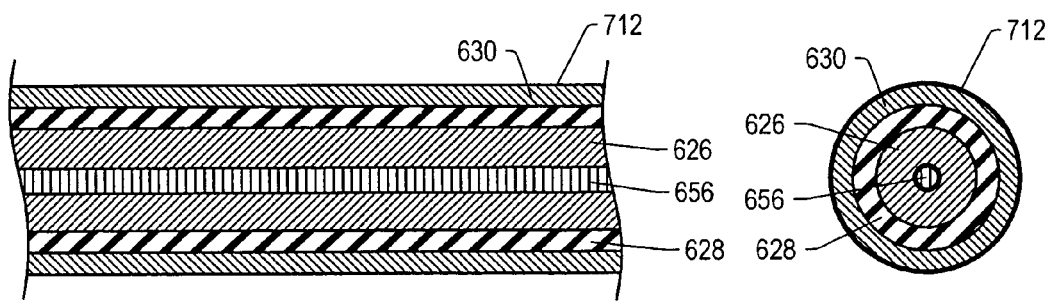
*FIG. 81A*  *FIG. 81B*

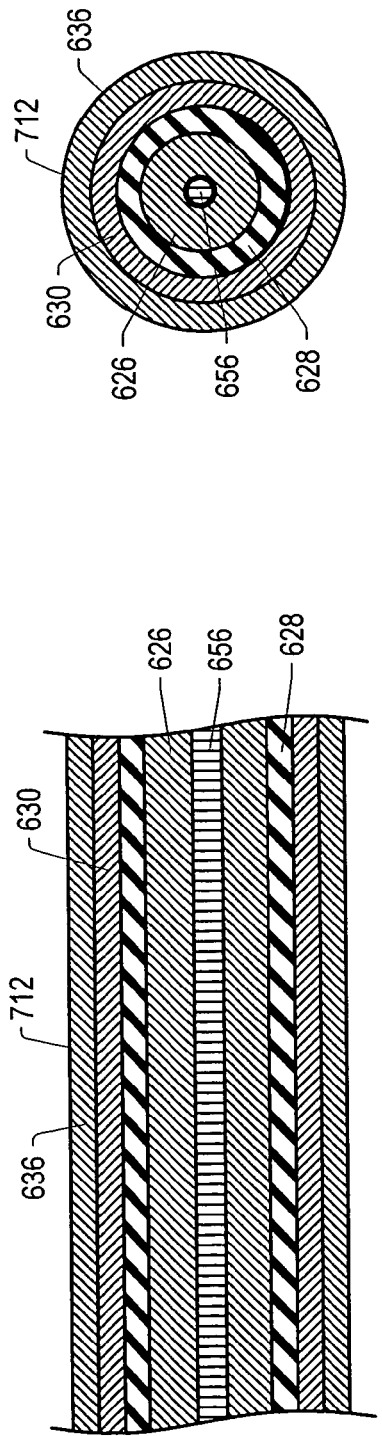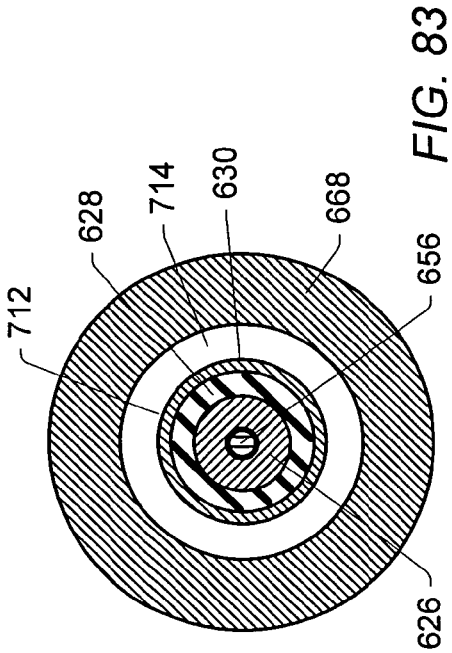

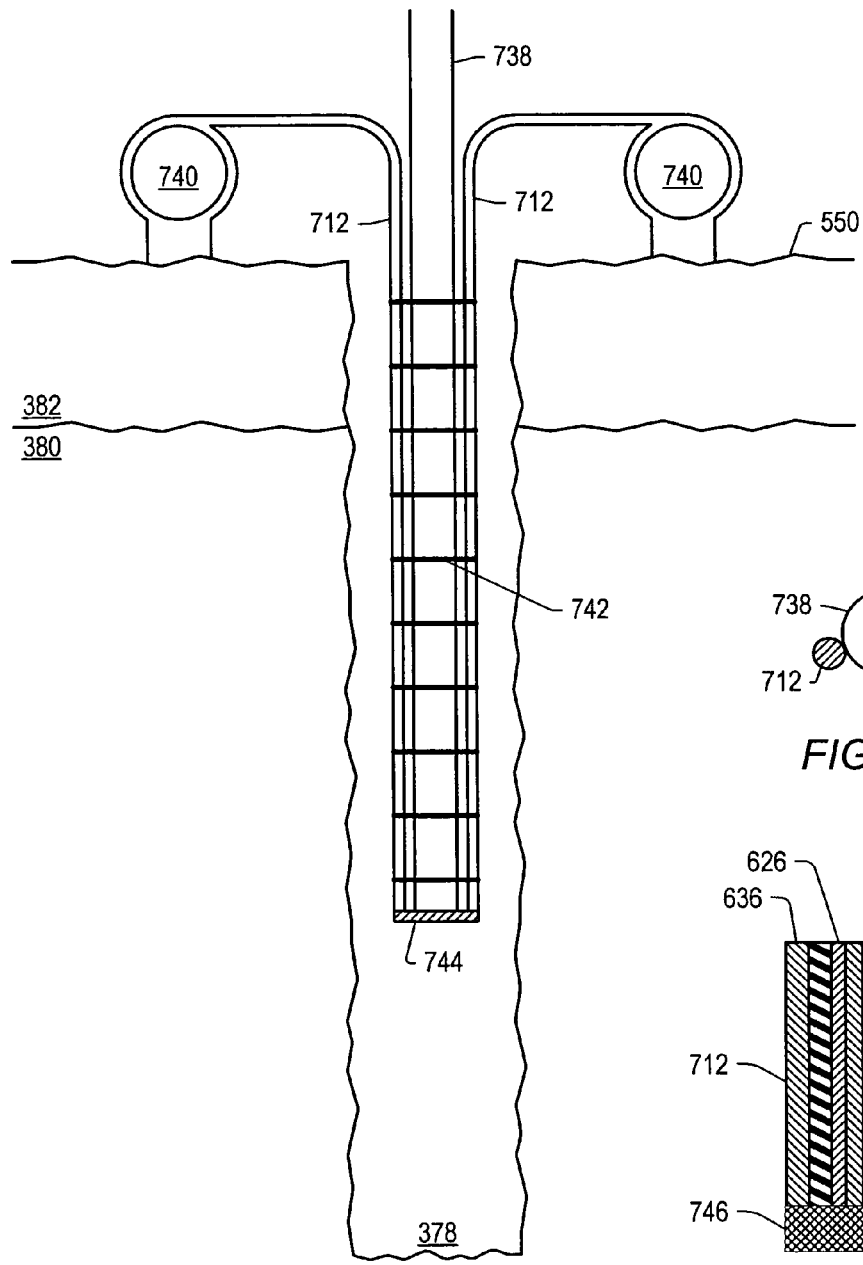
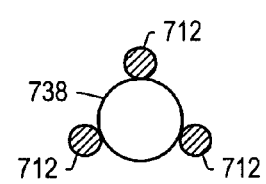
FIG. 97B
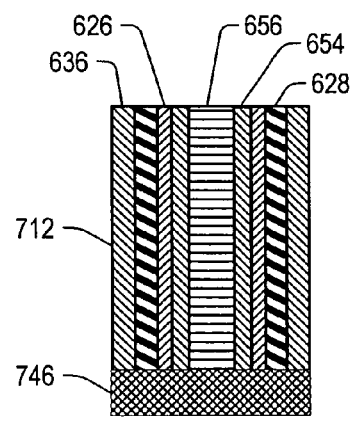
FIG. 97A FIG. 97C

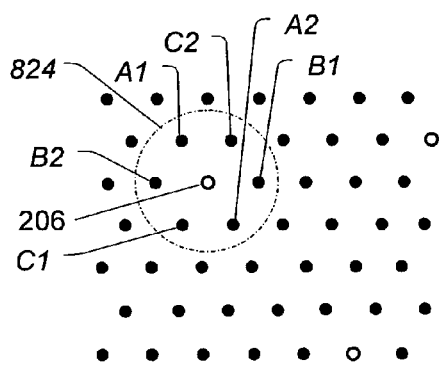
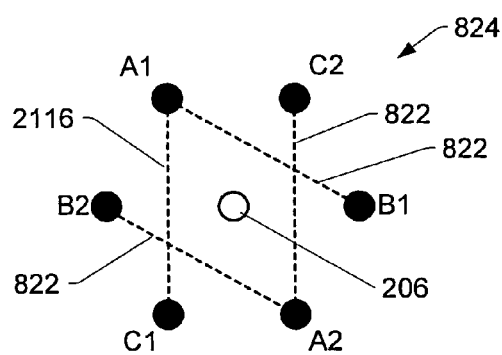
FIG. 128        FIG. 129
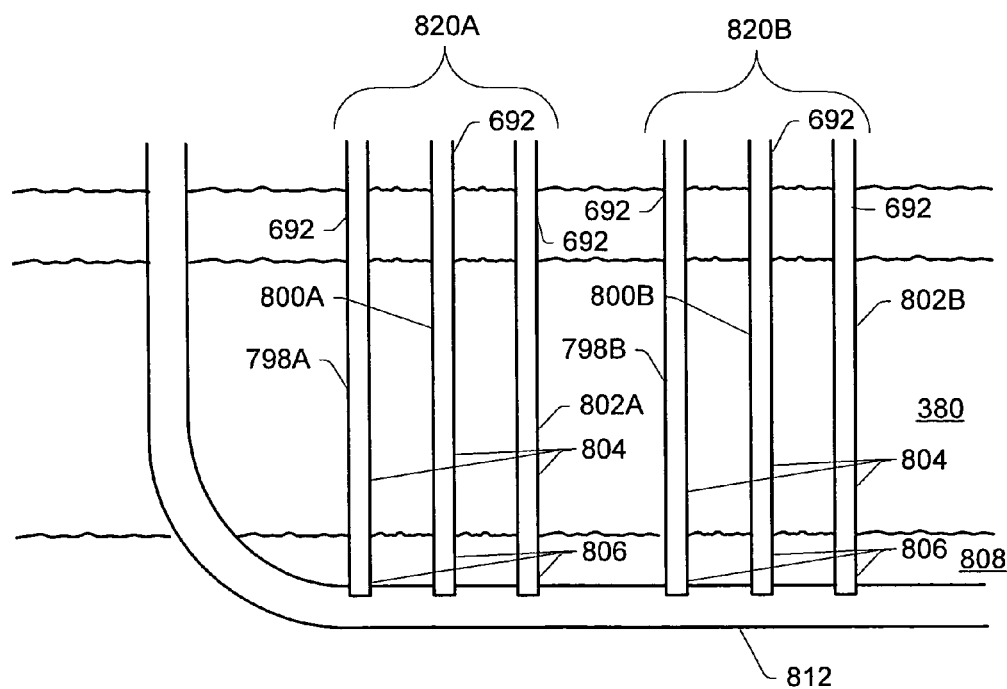
FIG. 130

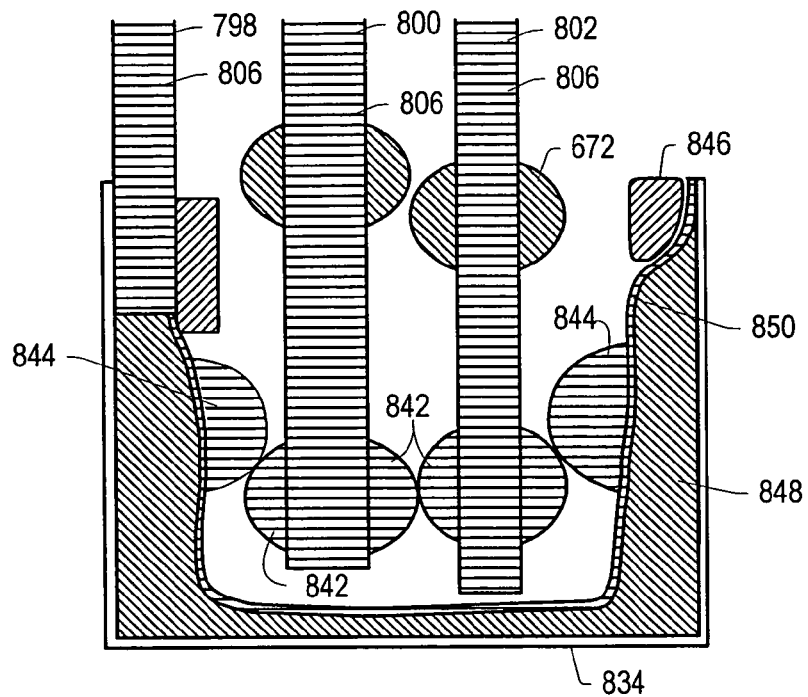
FIG. 135
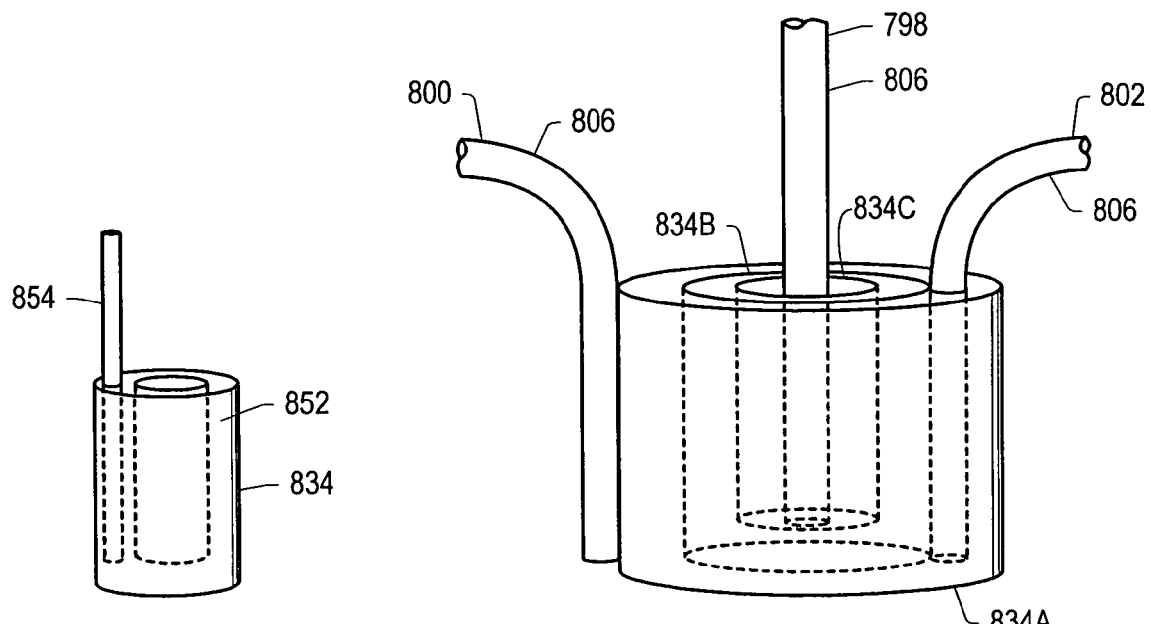
FIG. 136
FIG. 137

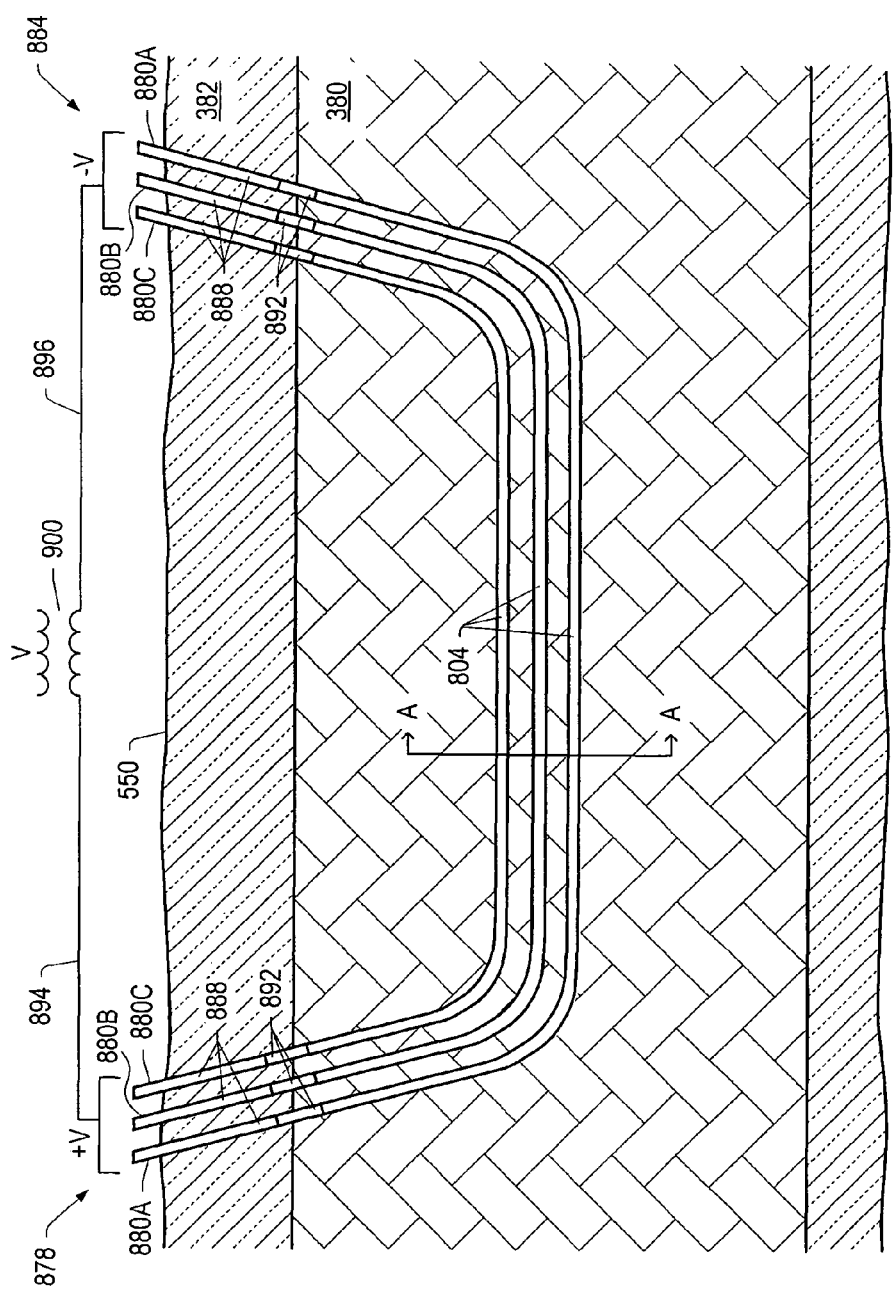
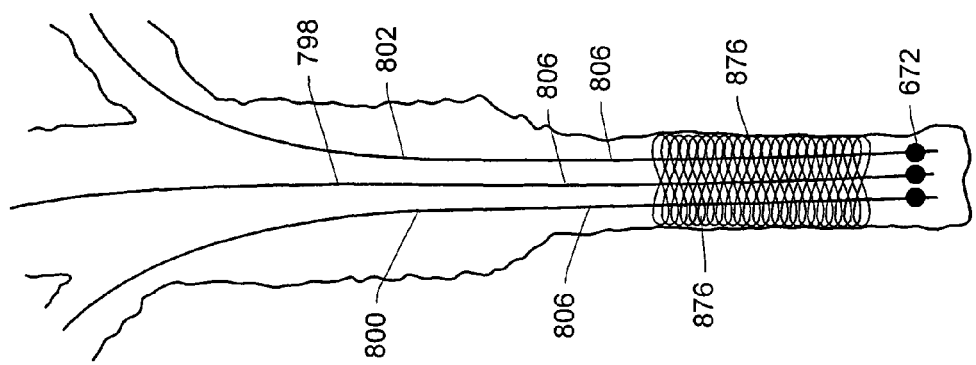
FIG. 145
FIG. 144

VARYING PROPERTIES ALONG LENGTHS OF TEMPERATURE LIMITED HEATERS

PRIORITY CLAIM

This patent application claims priority to U.S. Provisional Patent No. 60/674,081 entitled "SYSTEMS AND PROCESSES FOR USE IN TREATING SUBSURFACE FORMATIONS" to Vinegar et al. filed on Apr. 22, 2005, and to U.S. Provisional Patent No. 60/729,763 entitled "SYSTEMS AND PROCESSES FOR USE IN TREATING SUBSURFACE FORMATIONS" to Vinegar et al. filed on Oct. 24, 2005.

GOVERNMENT INTEREST

The Government may have certain rights in this invention pursuant to Agreement No. ERD-05-2516 between UT-Battelle, LLC, operating under prime contract No. DE-AC05-00OR22725 for the US Department of Energy and Shell Exploration and Production Company.

RELATED PATENTS

This patent application incorporates by reference in its entirety each of U.S. Pat. No. 6,688,387 to Wellington et al.; U.S. Pat. No. 6,698,515 to Karanikas et al.; U.S. Pat. No. 6,880,633 to Wellington et al.; and U.S. Pat. No. 6,782,947 to de Rouffignac et al. This patent application incorporates by reference in its entirety each of U.S. Patent Application Publication Nos. 2003-0102126 to Sumnu-Dindoruk et al.; 2003-0205378 to Wellington et al.; 2004-0146288 to Vinegar et al.; 2005-0051327 to Vinegar et al.; and 2005-0269313 to Vinegar et al. This patent application incorporates by reference in its entirety U.S. patent application Ser. No. 11/112,881 to Vinegar et al.

BACKGROUND

1. Field of the Invention

The present invention relates generally to methods and systems for heating and producing hydrocarbons, hydrogen, and/or other products from various subsurface formations such as hydrocarbon containing formations. Embodiments relate to conductor materials and thicknesses for temperature limited heaters used to treat subsurface formations.

2. Description of Related Art

Hydrocarbons obtained from subterranean formations are often used as energy resources, as feedstocks, and as consumer products. Concerns over depletion of available hydrocarbon resources and concerns over declining overall quality of produced hydrocarbons have led to development of processes for more efficient recovery, processing and/or use of available hydrocarbon resources. In situ processes may be used to remove hydrocarbon materials from subterranean formations. Chemical and/or physical properties of hydrocarbon material in a subterranean formation may need to be changed to allow hydrocarbon material to be more easily removed from the subterranean formation. The chemical and physical changes may include in situ reactions that produce removable fluids, composition changes, solubility changes, density changes, phase changes, and/or viscosity changes of the hydrocarbon material in the formation. A fluid may be, but is not limited to, a gas, a liquid, an emulsion, a slurry, and/or a stream of solid particles that has flow characteristics similar to liquid flow.

Heaters may be placed in wellbores to heat a formation during an in situ process. Examples of in situ processes utilizing downhole heaters are illustrated in U.S. Pat. No. 2,634,961 to Ljungstrom; U.S. Pat. No. 2,732,195 to Ljungstrom; U.S. Pat. No. 2,780,450 to Ljungstrom; U.S. Pat. No. 2,789,805 to Ljungstrom; U.S. Pat. No. 2,923,535 to Ljungstrom; and U.S. Pat. No. 4,886,118 to Van Meurs et al., each of which is incorporated by reference as if fully set forth herein Application of heat to oil shale formations is described in U.S. Pat. No. 2,923,535 to Ljungstrom and U.S. Pat. No. 4,886,118 to Van Meurs et al. Heat may be applied to the oil shale formation to pyrolyze kerogen in the oil shale formation. The heat may also fracture the formation to increase permeability of the formation. The increased permeability may allow formation fluid to travel to a production well where the fluid is removed from the oil shale formation. In some processes disclosed by Ljungstrom, for example, an oxygen containing gaseous medium is introduced to a permeable stratum, preferably while still hot from a preheating step, to initiate combustion.

A heat source may be used to heat a subterranean formation. Electric heaters may be used to heat the subterranean formation by radiation and/or conduction. An electric heater may resistively heat an element. U.S. Pat. No. 2,548,360 to Germain, which is incorporated by reference as if fully set forth herein, describes an electric heating element placed in a viscous oil in a wellbore. The heater element heats and thins the oil to allow the oil to be pumped from the wellbore. U.S. Pat. No. 4,716,960 to Eastlund et al., which is incorporated by reference as if fully set forth herein, describes electrically heating tubing of a petroleum well by passing a relatively low voltage current through the tubing to prevent formation of solids. U.S. Pat. No. 5,065,818 to Van Egmond, which is incorporated by reference as if fully set forth herein describes an electric heating element that is cemented into a well borehole without a casing surrounding the heating element.

U.S. Pat. No. 6,023,554 to Vinegar et al., which is incorporated by reference as if fully set forth herein, describes an electric heating element that is positioned in a casing. The heating element generates radiant energy that heats the casing. A granular solid fill material may be placed between the casing and the formation. The casing may conductively heat the fill material, which in turn conductively heats the formation.

SUMMARY

Embodiments described herein generally relate to systems, methods, and heaters for treating a subsurface formation. Embodiments described herein also generally relate to heaters that have novel components therein. Such heaters can be obtained by using the systems and methods described herein.

In some embodiments, the invention provides a system for heating a subsurface formation, including: an elongated heater in an opening in the formation, wherein the elongated heater includes two or more portions along the length of the heater that have different power outputs, at least one portion of the elongated heater including at least one temperature limited portion with at least one selected temperature at which the portion provides a reduced heat output; and the heater being configured to provide heat to the formation with the different power outputs, and being configured so that the heater heats one or more portions of the formation at one or more selected heating rates.

In some embodiments, the invention provides a method for heating a subsurface formation, including: applying an electrical current to an elongated heater such that the heater provides an electrically resistive heat output, wherein the elongated heater includes two or more portions along the length of the heater that have different power outputs, at least one portion of the elongated heater including at least one temperature limited portion with at least one selected temperature at which the portion provides a reduced heat output; providing heat to the formation with the different power outputs so that the heater heats one or more portions of the formation at one or more selected heating rates; and allowing the heat to transfer to a section of the formation.

In certain embodiments, the invention provides one or more systems, methods, and/or heaters. In some embodiments, the systems, methods, and/or heaters are used for treating a subsurface formation.

In further embodiments, features from specific embodiments may be combined with features from other embodiments. For example, features from one embodiment may be combined with features from any of the other embodiments.

In further embodiments, treating a subsurface formation is performed using any of the methods, systems, or heaters described herein.

In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings in which:

FIG. 10 depicts a schematic representation of an embodiment of a system for treating the mixture produced from the in situ conversion process.

FIG. 11 depicts a schematic drawing of an embodiment of a reverse-circulating polycrystalline diamond compact drill bit design.

FIG. 29 depicts an embodiment of a dual concentric rod pump system with a 2-phase separator.

FIG. 30 depicts an embodiment of a dual concentric rod pump system with a gas/vapor shroud and sump.

FIG. 39 depicts an embodiment of a device for longitudinal welding of a tubular using ERW.

FIG. 40 depicts an embodiment of an apparatus for forming a composite conductor, with a portion of the apparatus shown in cross section.

FIG. 41 depicts a cross-sectional representation of an embodiment of an inner conductor and an outer conductor formed by a tube-in-tube milling process.

FIGS. 42, 43, and 44 depict cross-sectional representations of an embodiment of a temperature limited heater with an outer conductor having a ferromagnetic section and a non-ferromagnetic section.

FIGS. 45, 46, 47, and 48 depict cross-sectional representations of an embodiment of a temperature limited heater with an outer conductor having a ferromagnetic section and a non-ferromagnetic section placed inside a sheath.

FIGS. 49, 50, and 51 depict cross-sectional representations of an embodiment of a temperature limited heater with a ferromagnetic outer conductor.

FIGS. 52, 53, and 54 depict cross-sectional representations of an embodiment of a temperature limited heater with an outer conductor.

FIGS. 55, 56, 57, and 58 depict cross-sectional representations of an embodiment of a temperature limited heater.

FIGS. 59, 60, and 61 depict cross-sectional representations of an embodiment of a temperature limited heater with an overburden section and a heating section.

FIGS. 62A and 62B depict cross-sectional representations of an embodiment of a temperature limited heater.

FIGS. 63A and 63B depict cross-sectional representations of an embodiment of a temperature limited heater.

FIGS. 64A and 64B depict cross-sectional representations of an embodiment of a temperature limited heater.

FIGS. 67A and 67B depict cross-sectional representations of an embodiment of a temperature limited heater.

FIG. 68 depicts an embodiment of a coupled section of a composite electrical conductor.

FIG. 69 depicts an end view of an embodiment of a coupled section of a composite electrical conductor.

FIG. 70 depicts an embodiment for coupling together sections of a composite electrical conductor.

FIG. 79 depicts an embodiment of a fiber optic cable sleeve in a conductor-in-conduit heater.

FIG. 80 depicts an embodiment of a conductor-in-conduit temperature limited heater.

FIG. 81A and FIG. 81B depict an embodiment of an insulated conductor heater.

FIG. 82A and FIG. 82B depict an embodiment of an insulated conductor heater.

FIG. 83 depicts an embodiment of an insulated conductor located inside a conduit.

FIGS. 97A and 97B depict an embodiment for installing heaters in a wellbore.

FIG. 97C depicts an embodiment of an insulated conductor with the sheath shorted to the conductors.

FIG. 128 depicts a top view representation of an embodiment of a plurality of triads of three-phase heaters in a hexagonal pattern.

FIG. 129 depicts a top view representation of an embodiment of a hexagon from FIG. 128.

FIG. 130 depicts an embodiment of triads of heaters coupled to a horizontal bus bar.

FIG. 135 depicts an embodiment of a container for coupling contacting elements with bulbs on the contacting elements.

FIG. 136 depicts an alternative embodiment for a container.

FIG. 137 depicts an alternative embodiment for coupling contacting elements of three legs of a heater.

FIG. 140 depicts a side view representation of another alternative embodiment for coupling contacting elements using temperature limited heating elements.

FIG. 141 depicts a side view representation of an alternative embodiment for coupling contacting elements of three legs of a heater.

FIG. 142 depicts a top view representation of the alternative embodiment for coupling contacting elements of three legs of a heater depicted in FIG. 141.

FIG. 143 depicts an embodiment of a contacting element with a brush contactor.

FIG. 144 depicts an embodiment for coupling contacting elements with brush contactors.

FIG. 145 depicts a side-view representation of an embodiment of substantially u-shaped heaters.

FIG. 146 depicts a representational top view of an embodiment of a surface pattern of heaters depicted in FIG. 145.

FIG. 147 depicts a cross-sectional representation of substantially u-shaped heaters in a hydrocarbon layer.

FIG. 148 depicts a side view representation of an embodiment of substantially vertical heaters coupled to a substantially horizontal wellbore.

FIG. 149 depicts an embodiment of a substantially u-shaped heater that electrically isolates itself from the formation.

FIGS. 150A and 150B depict an embodiment for using substantially u-shaped wellbores to time sequence heat two layers in a hydrocarbon containing formation.

FIG. 151 depicts an embodiment of a temperature limited heater with current return through the formation.

Figure 152:
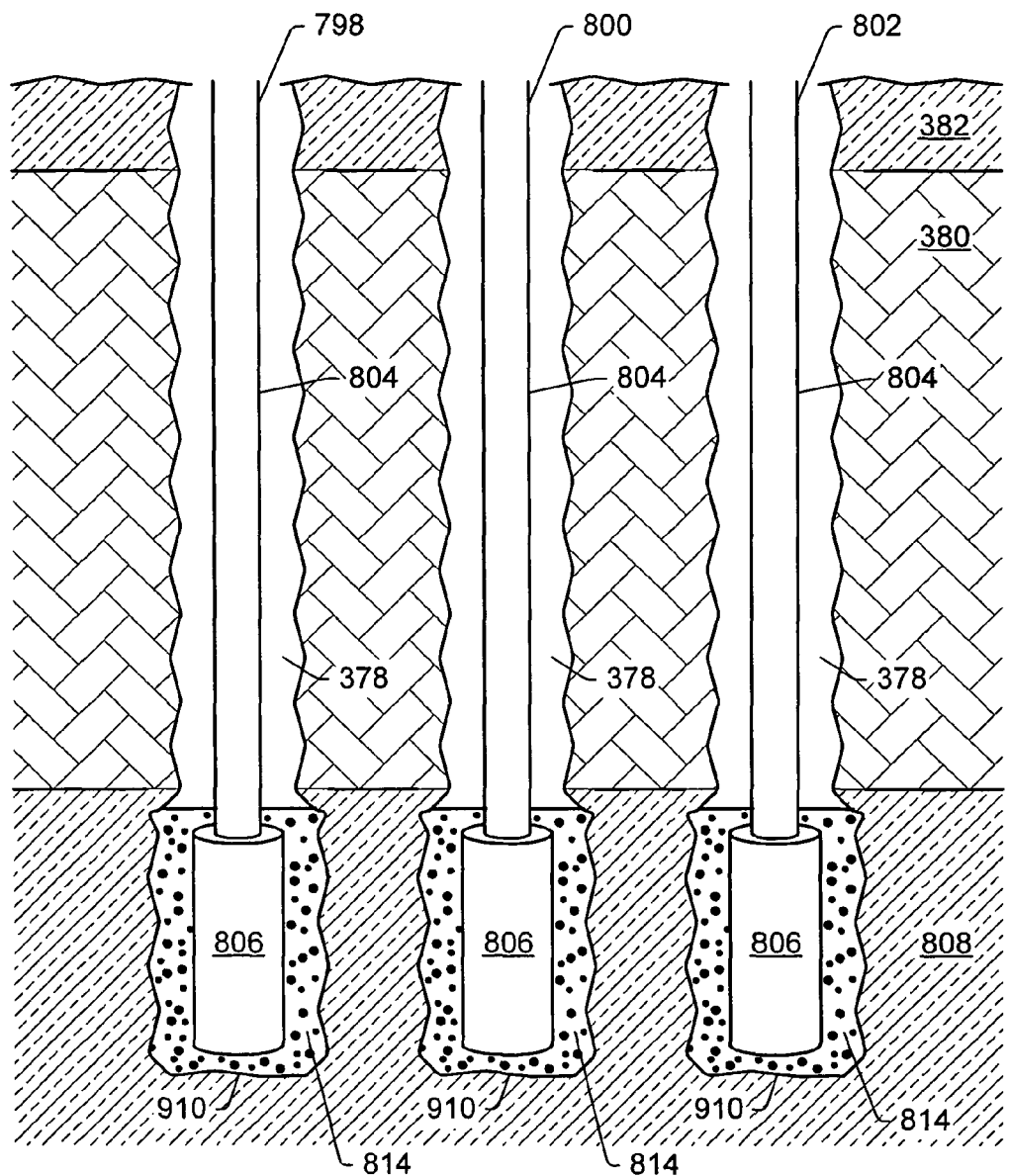

FIG. 152 depicts a representation of an embodiment of a three-phase temperature limited heater with current connection through the formation.

Figure 153:
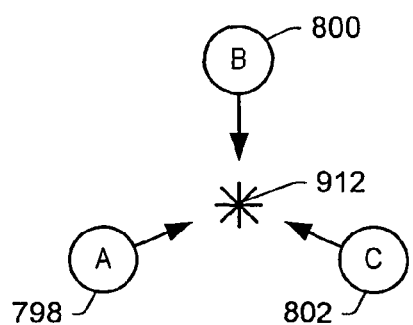

FIG. 153 depicts an aerial view of the embodiment shown in FIG. 152.

Figure 154:
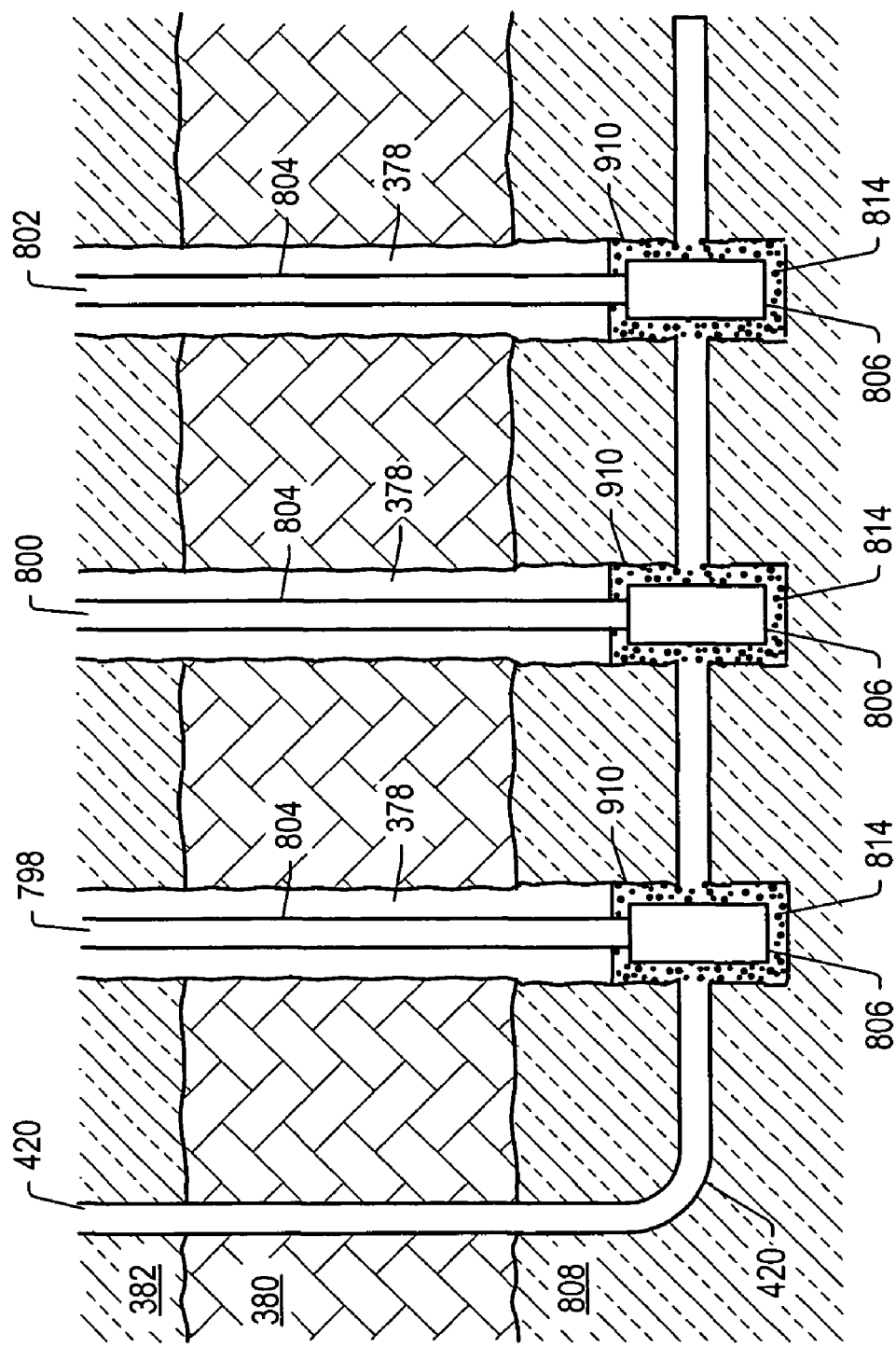

FIG. 154 depicts an embodiment of three temperature limited heaters electrically coupled to a horizontal wellbore in the formation.

Figure 155:
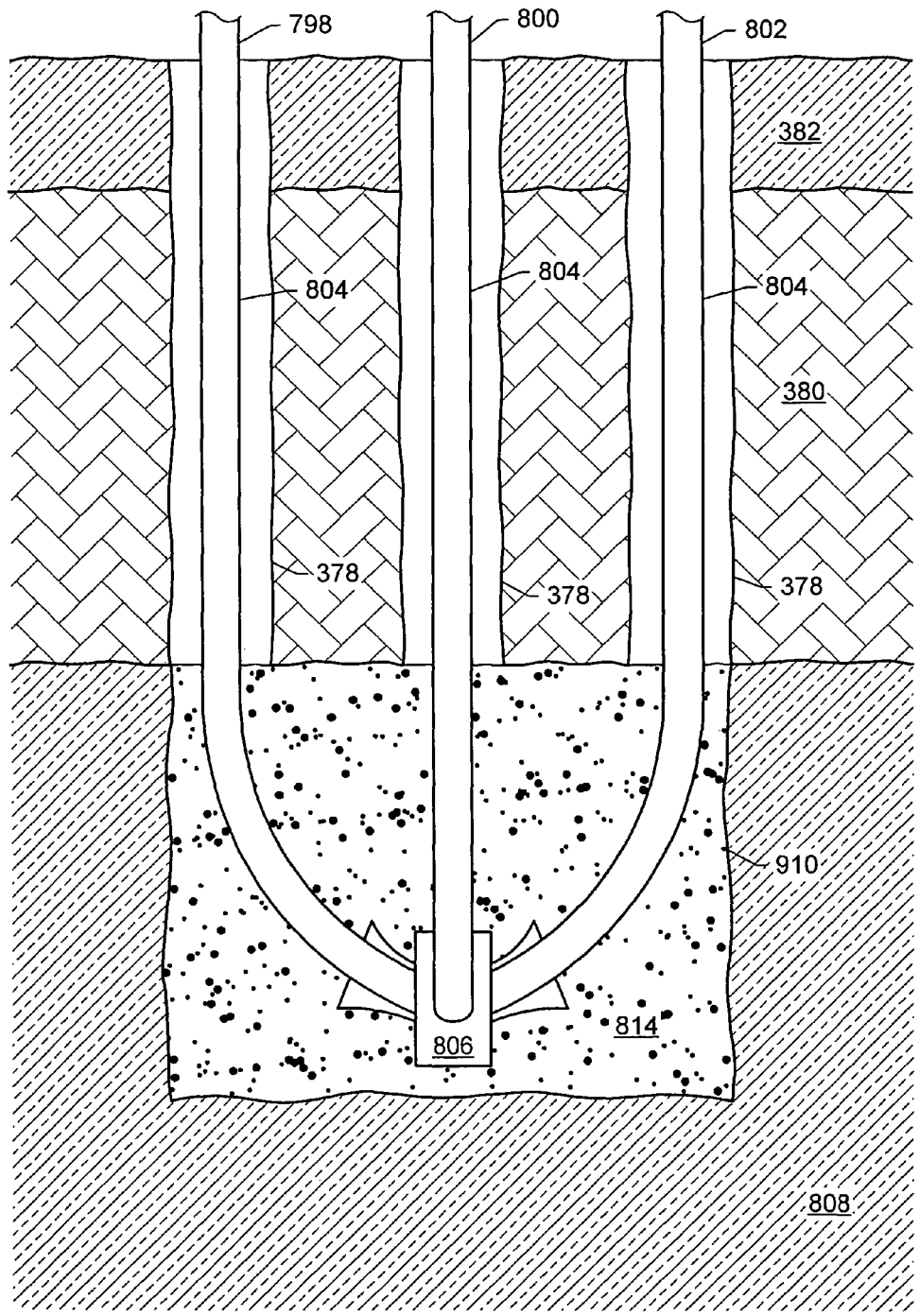

FIG. 155 depicts a representation of an embodiment of a three-phase temperature limited heater with a common current connection through the formation.

Figure 156:
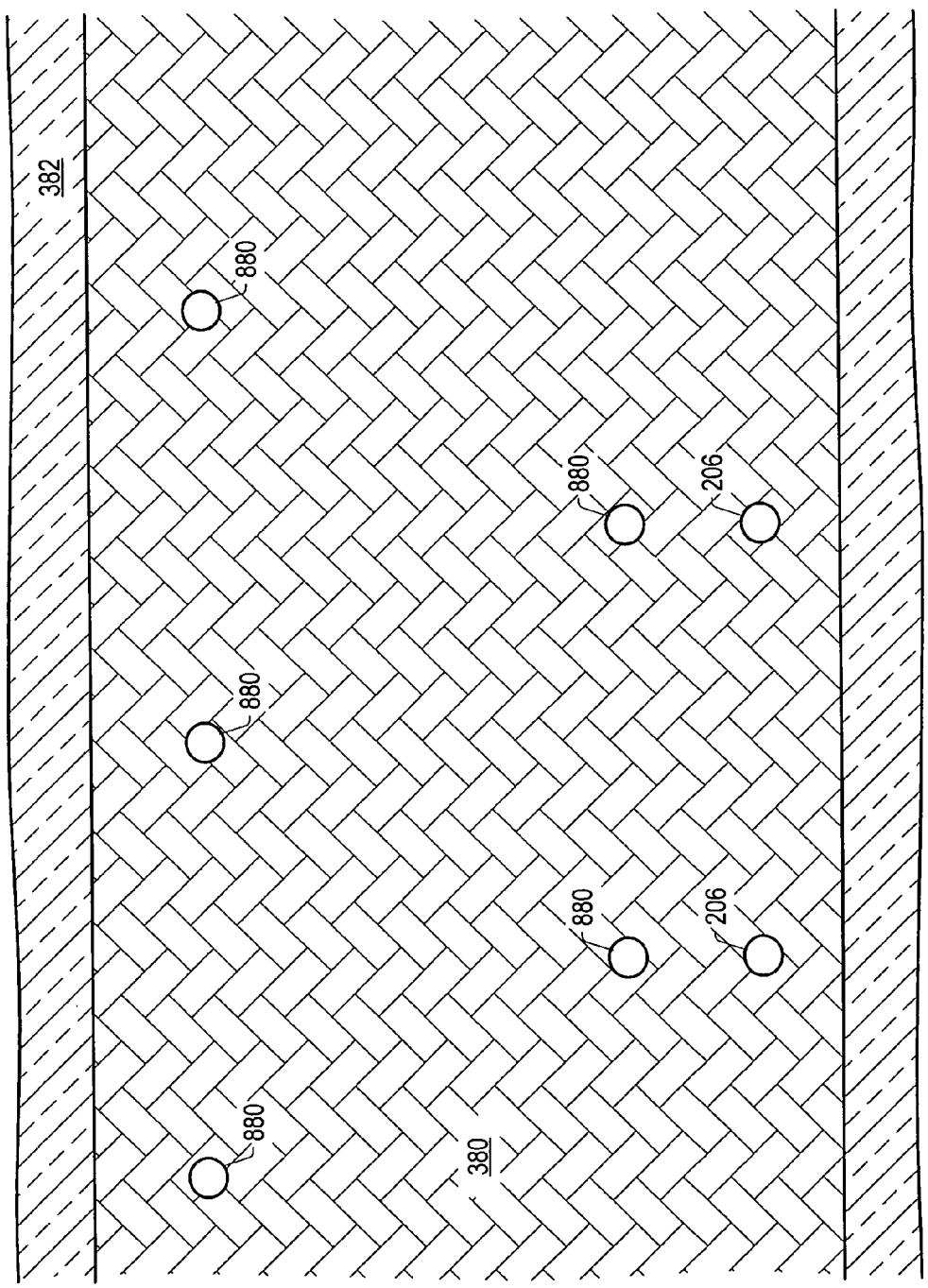

FIG. 156 depicts a side view representation of an embodiment for producing mobilized fluids from a tar sands formation.

Figure 157:
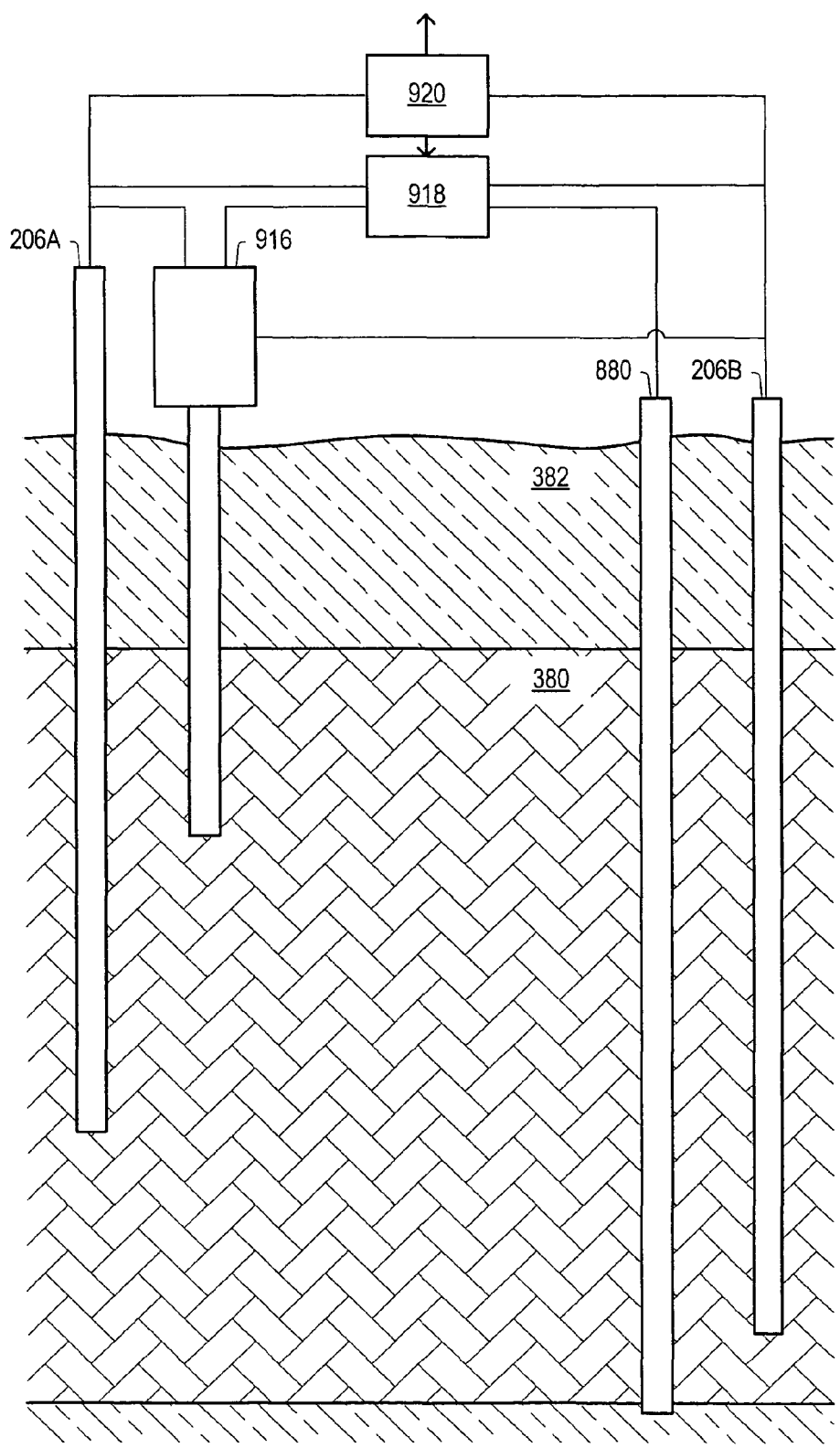

FIG. 157 depicts a representation of an embodiment for producing hydrocarbons from a tar sands formation.

Figure 158:
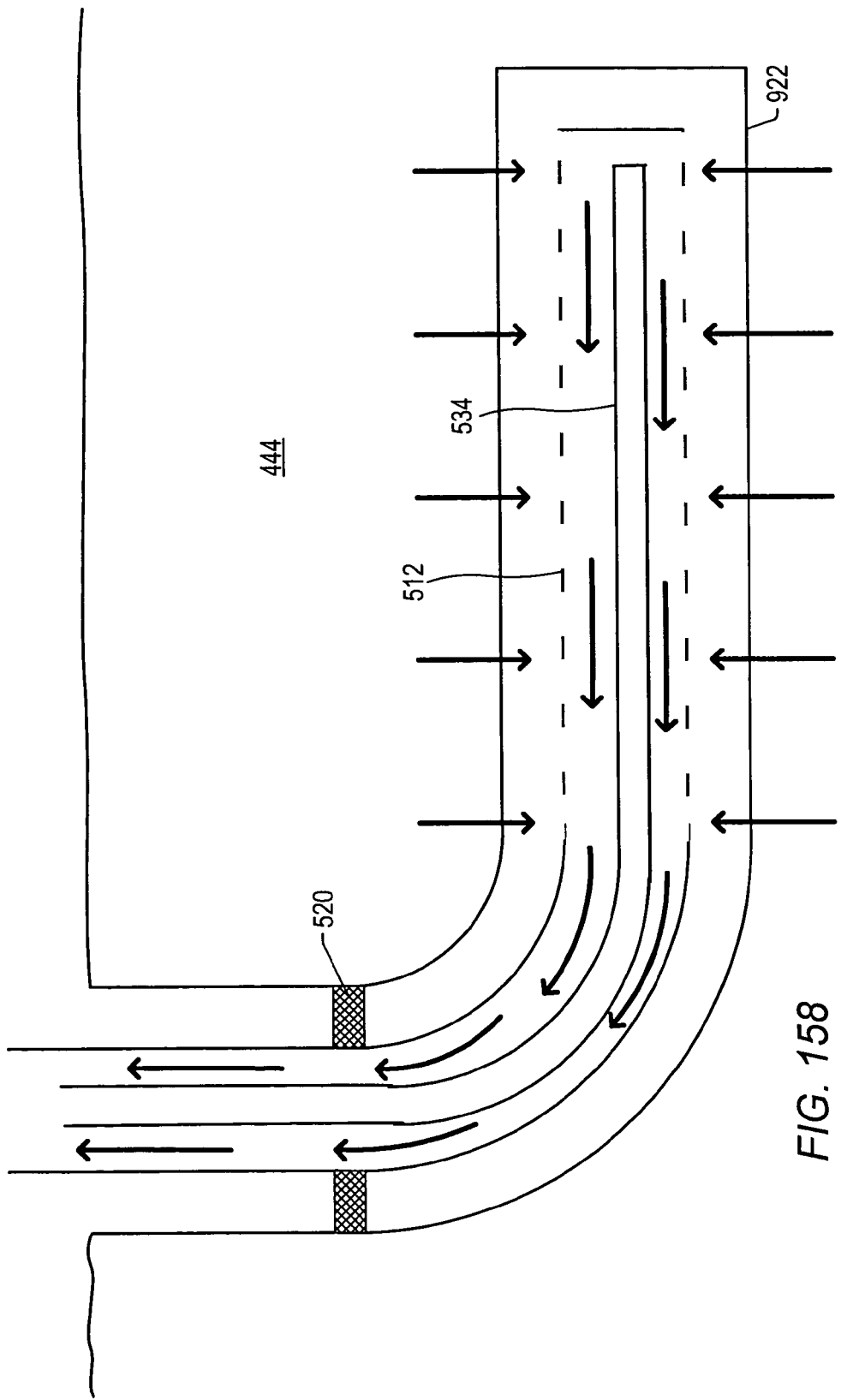

FIG. 158 depicts an embodiment for heating and producing from a formation with a temperature limited heater in a production wellbore.

Figure 159:
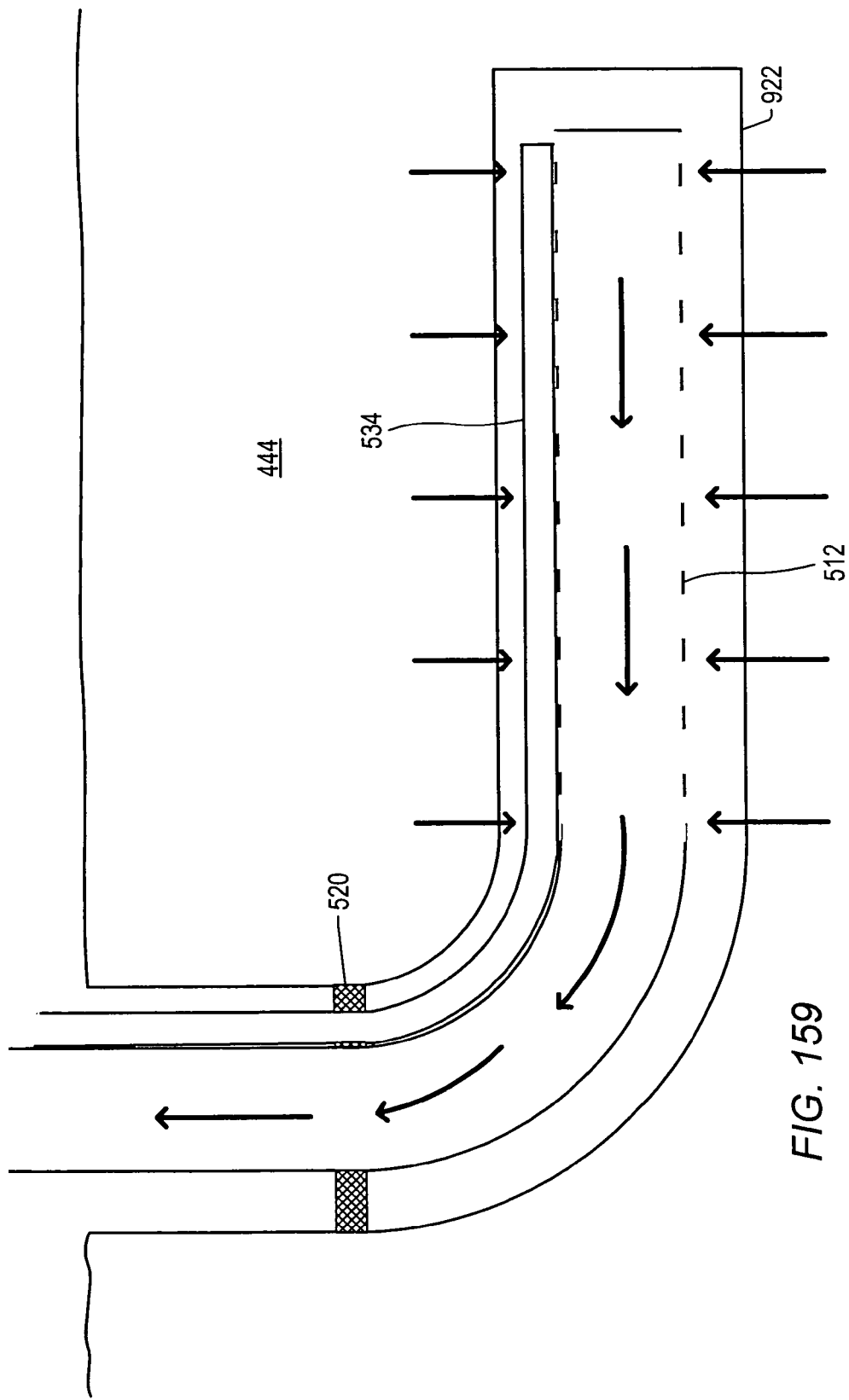

FIG. 159 depicts an embodiment for heating and producing from a formation with a temperature limited heater and a production wellbore.

Figure 160:
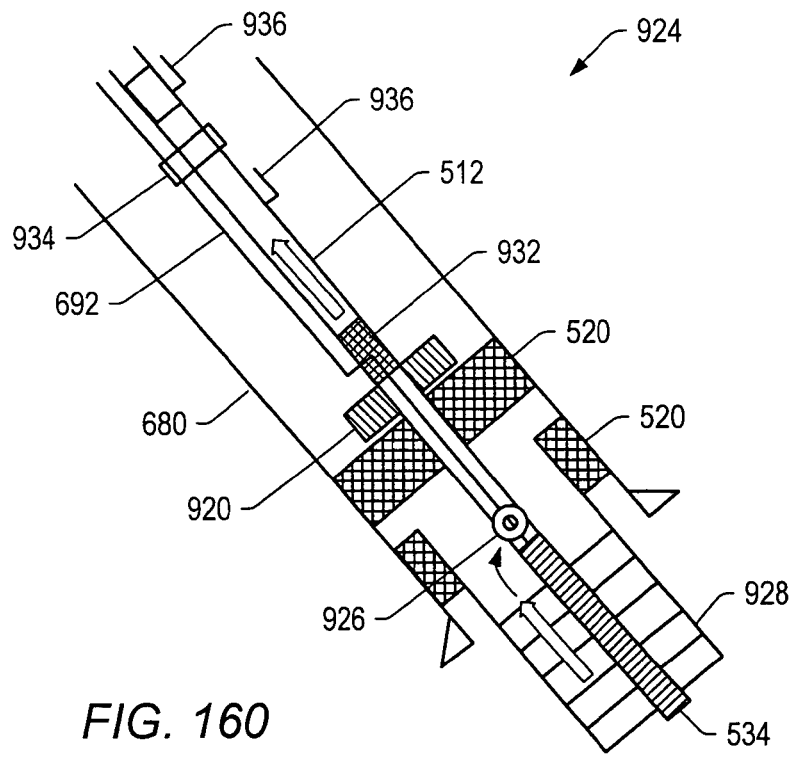

FIG. 160 depicts an embodiment of a heating/production assembly that may be located in a wellbore for gas lifting.

Figure 161:
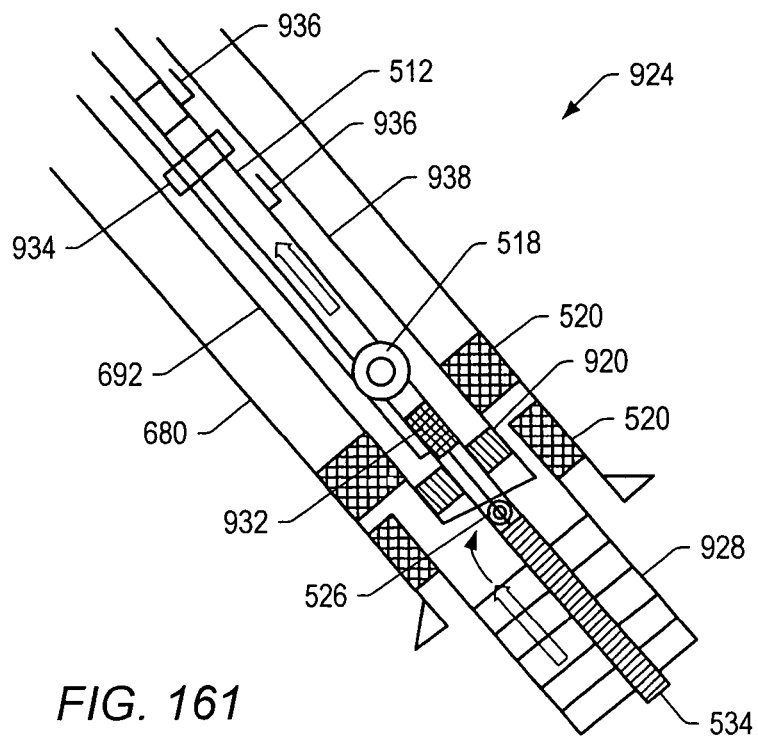

FIG. 161 depicts an embodiment of a heating/production assembly that may be located in a wellbore for gas lifting.

Figure 162:
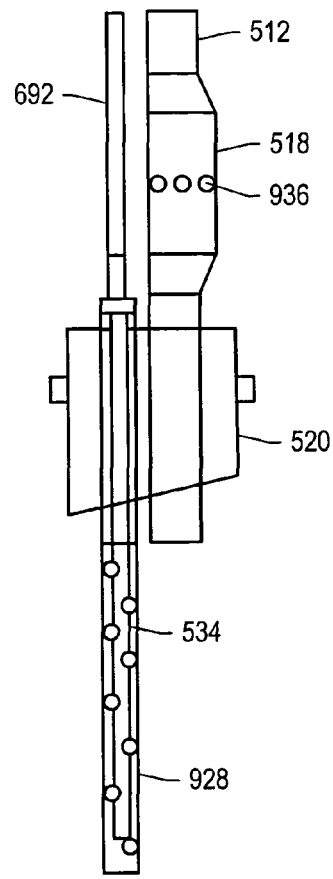

FIG. 162 depicts another embodiment of a heating/production assembly that may be located in a wellbore for gas lifting.

Figure 163:
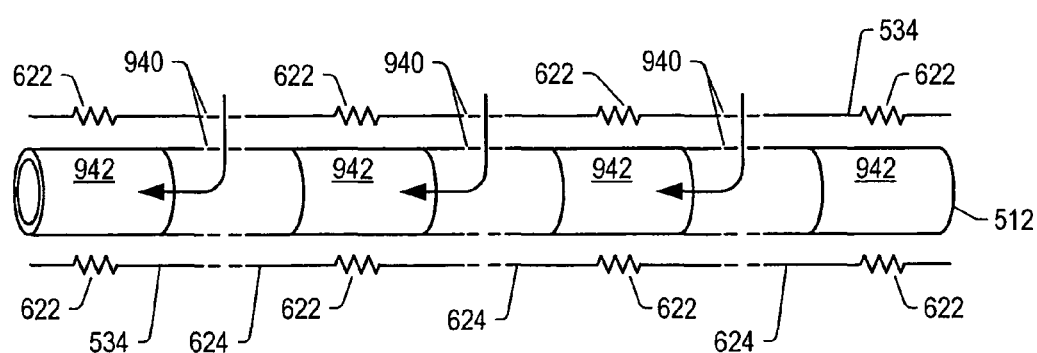

FIG. 163 depicts an embodiment of a production conduit and a heater.

Figure 164:
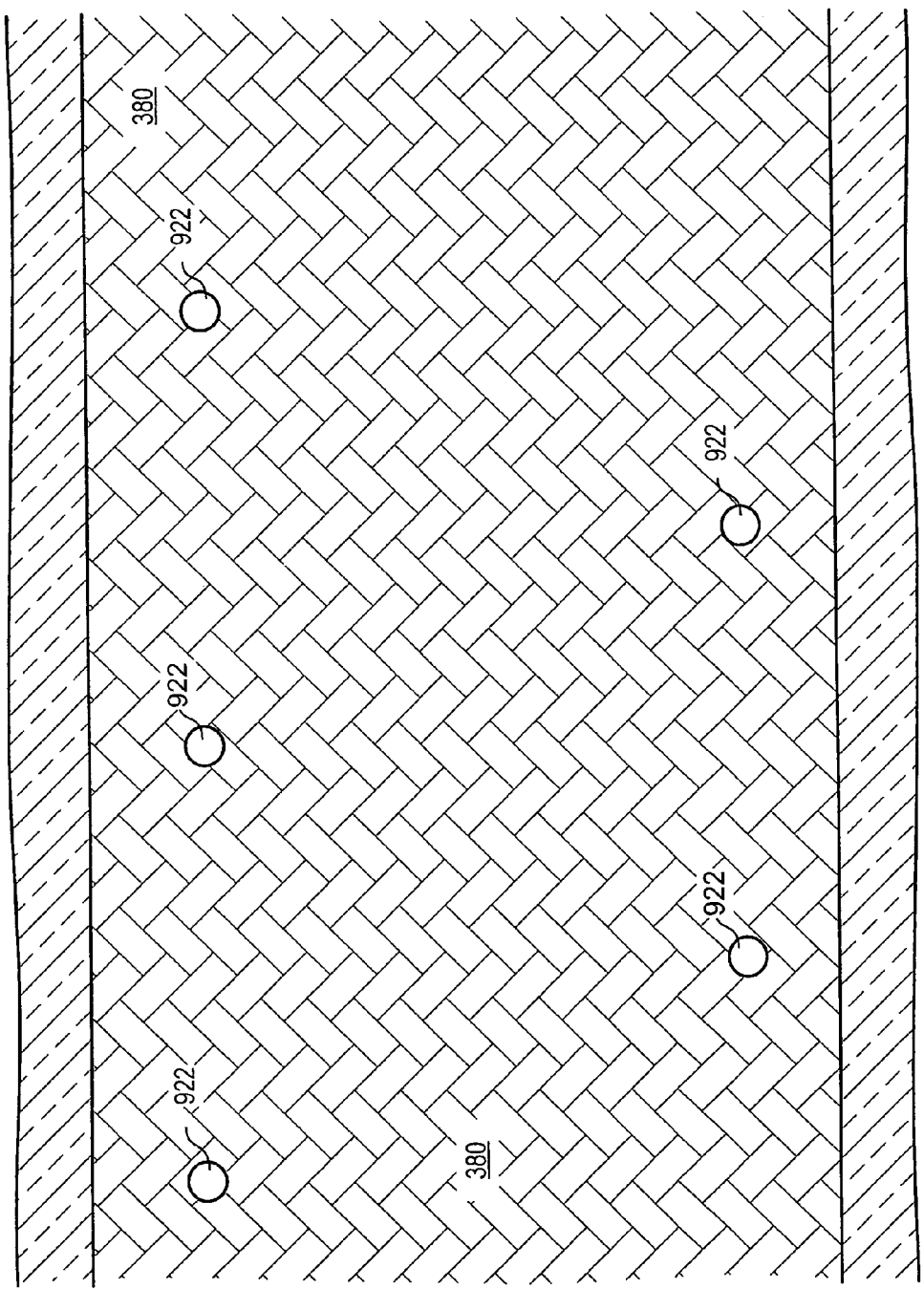

FIG. 164 depicts an embodiment for treating a formation.

Figure 165:
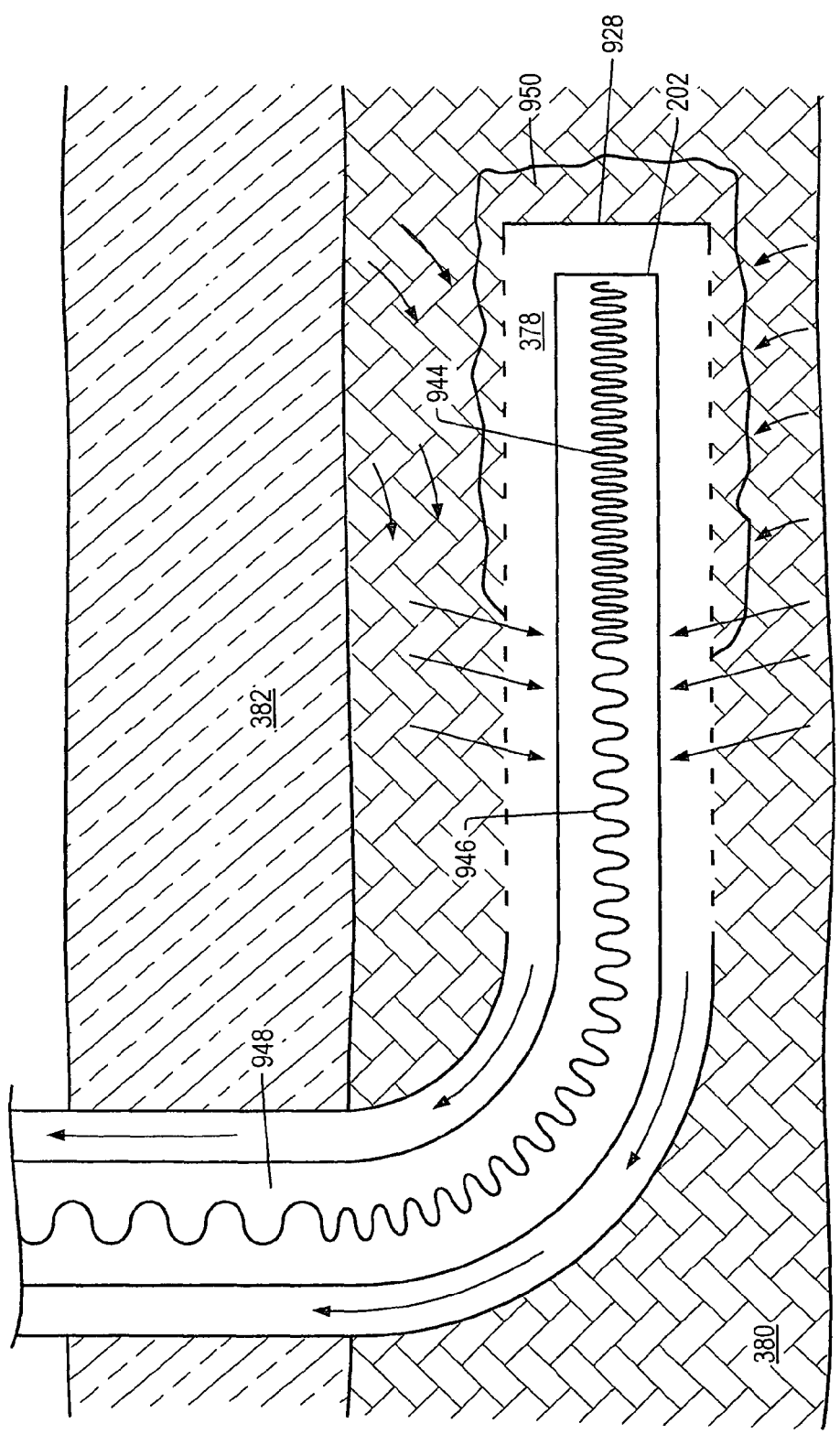

FIG. 165 depicts an embodiment of a heater well with selective heating.

Figure 166:
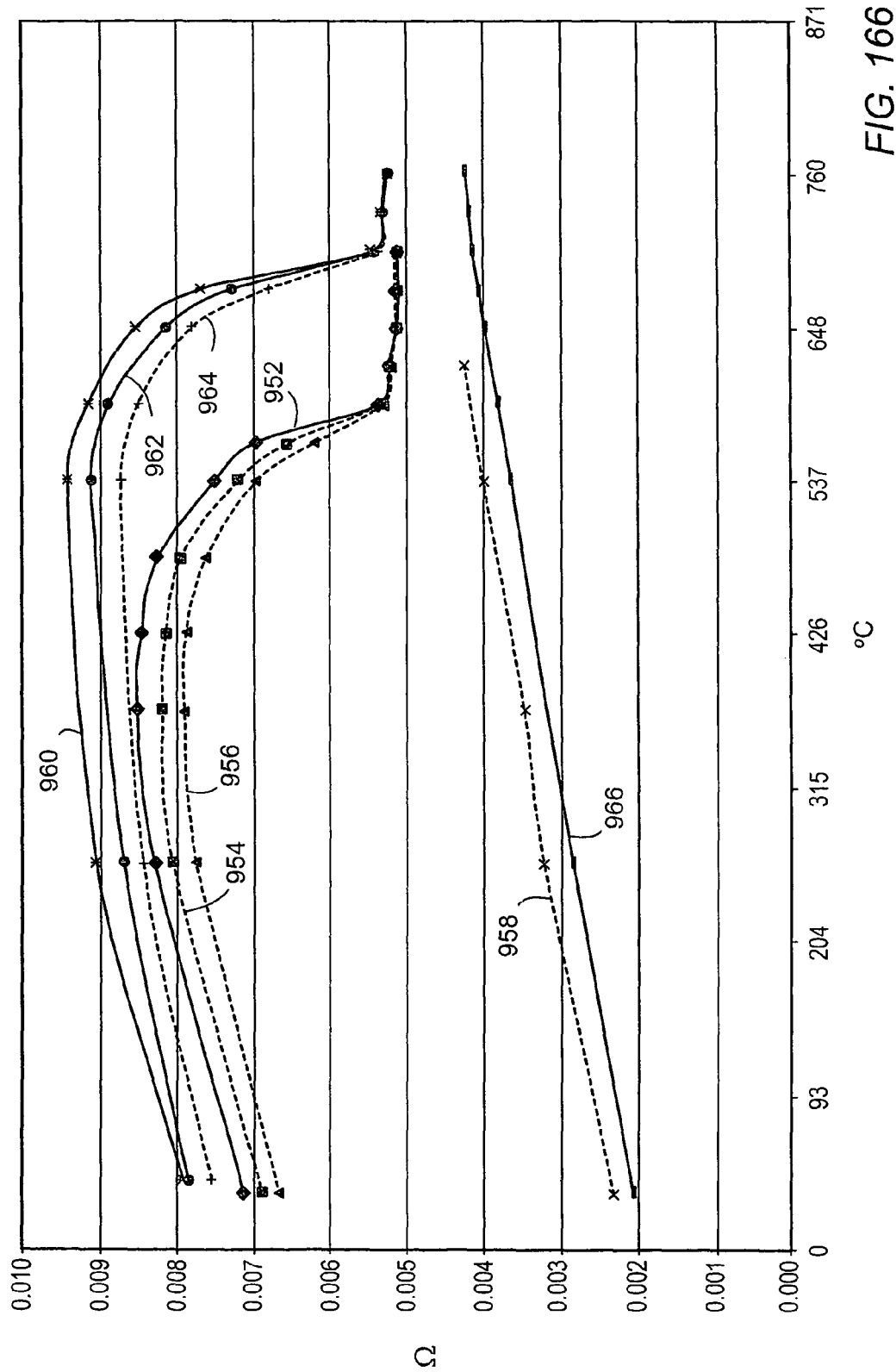

FIG. 166 depicts electrical resistance versus temperature at various applied electrical currents for a 446 stainless steel rod.

Figure 167:
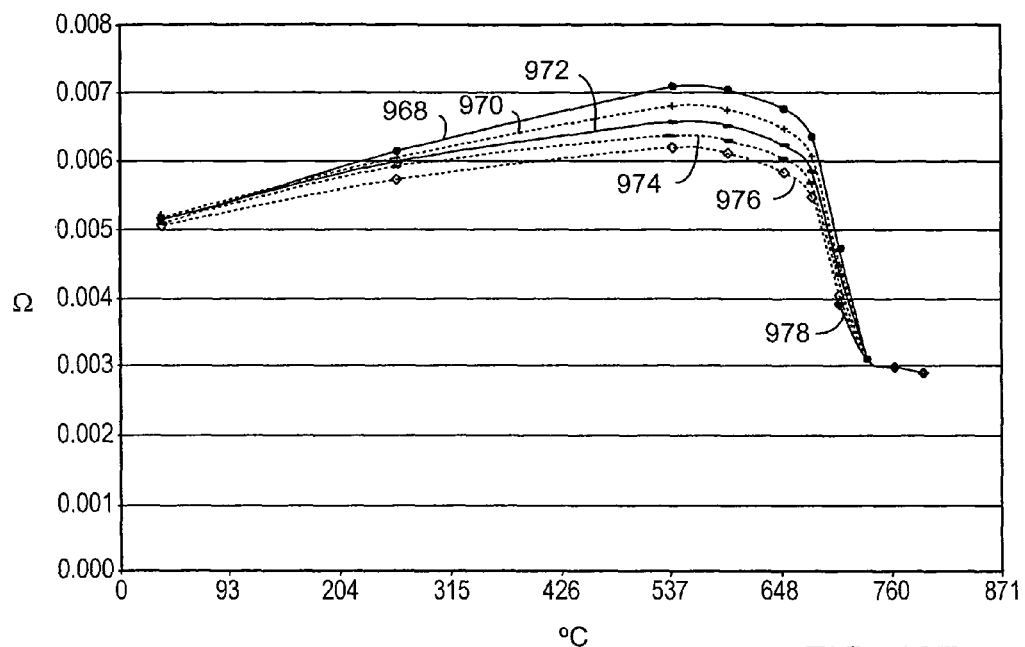

FIG. 167 shows resistance profiles as a function of temperature at various applied electrical currents for a copper rod contained in a conduit of Sumitomo HCM12A.

Figure 168:
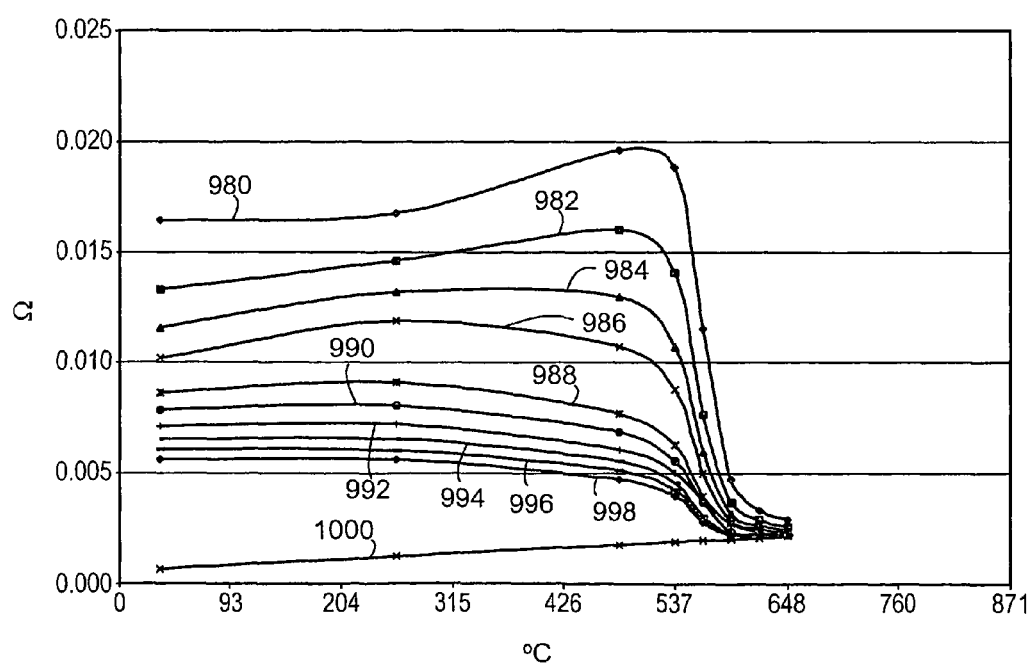

FIG. 168 depicts electrical resistance versus temperature at various applied electrical currents for a temperature limited heater.

Figure 169:
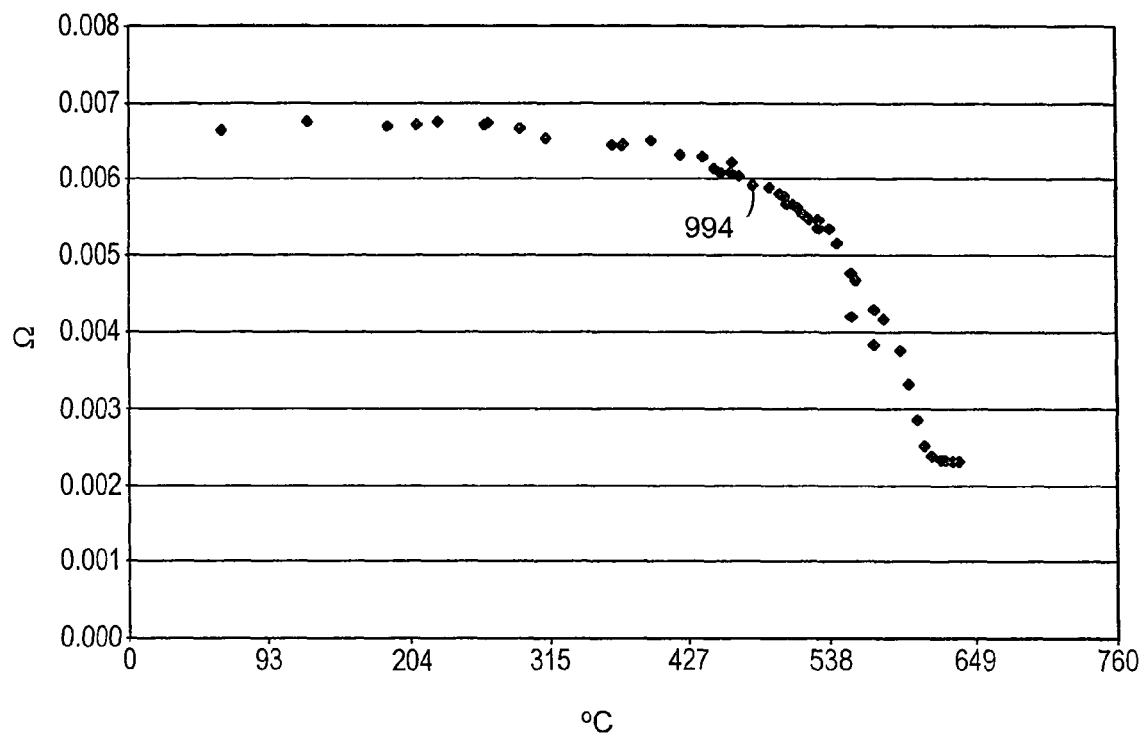

FIG. 169 depicts raw data for a temperature limited heater.

Figure 170:
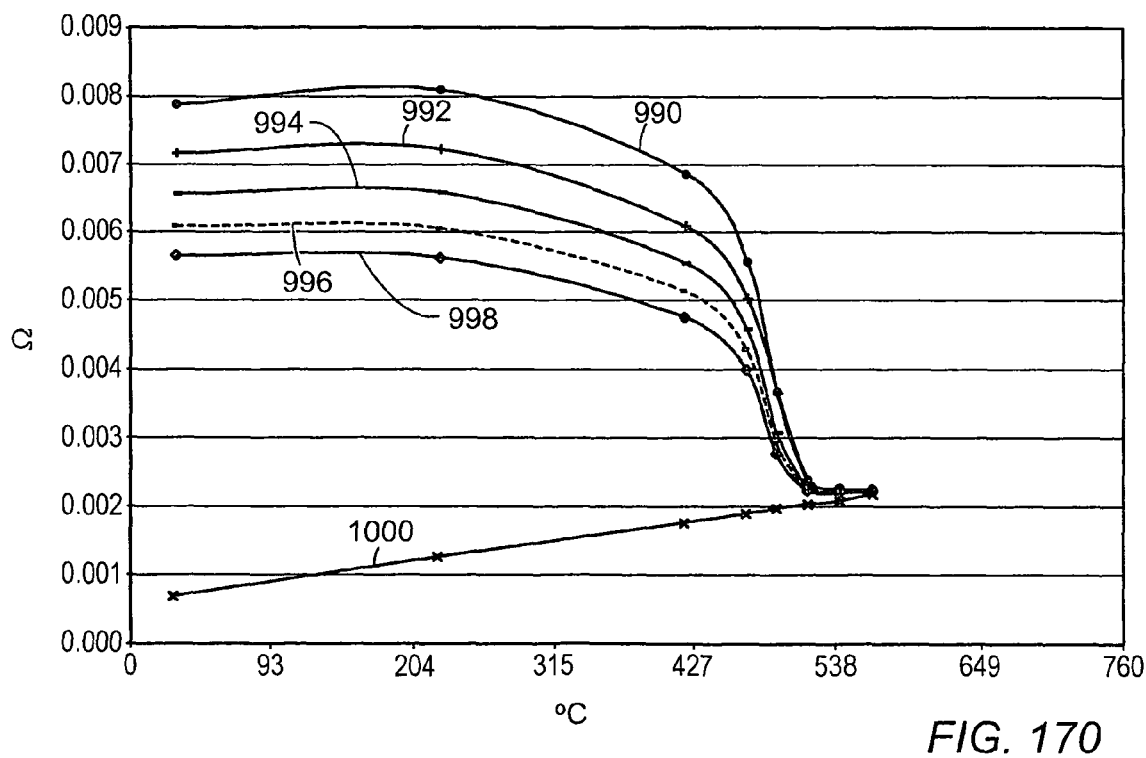

FIG. 170 depicts electrical resistance versus temperature at various applied electrical currents for a temperature limited heater.

Figure 171:
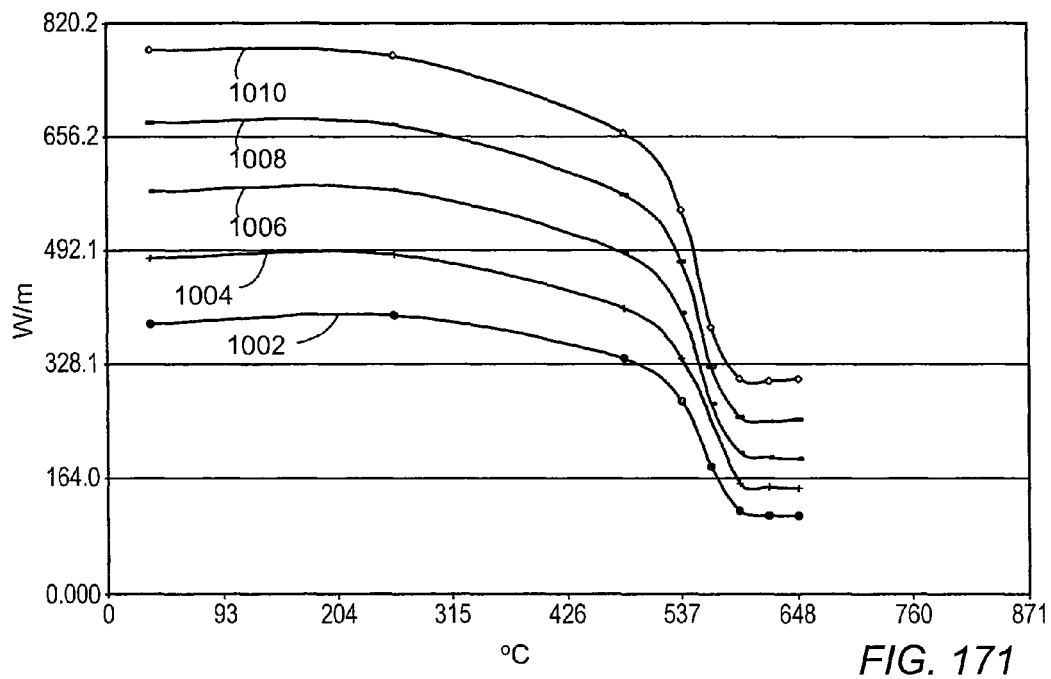

FIG. 171 depicts power versus temperature at various applied electrical currents for a temperature limited heater.

Figure 172:
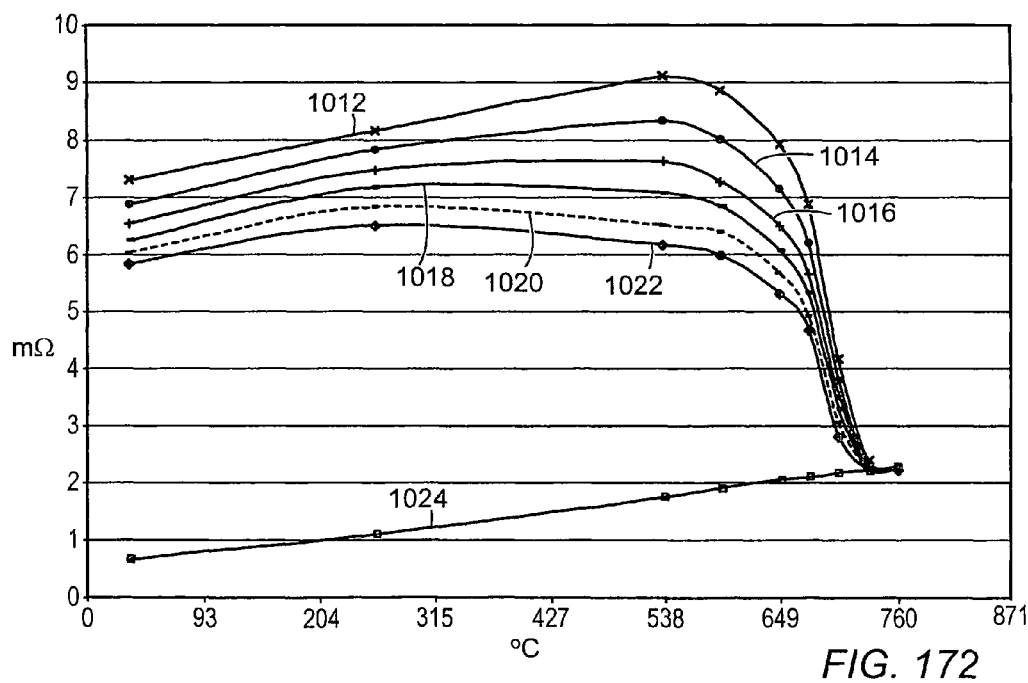

FIG. 172 depicts electrical resistance versus temperature at various applied electrical currents for a temperature limited heater.

Figure 173:
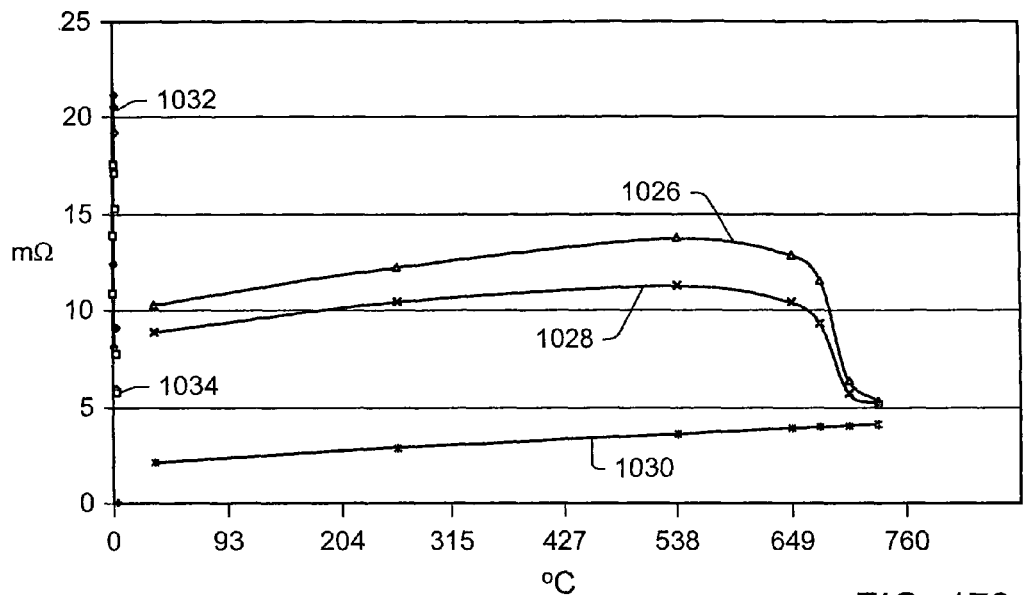

FIG. 173 depicts data of electrical resistance versus temperature for a solid 2.54 cm diameter, 1.8 m long 410 stainless steel rod at various applied electrical currents.

Figure 174:
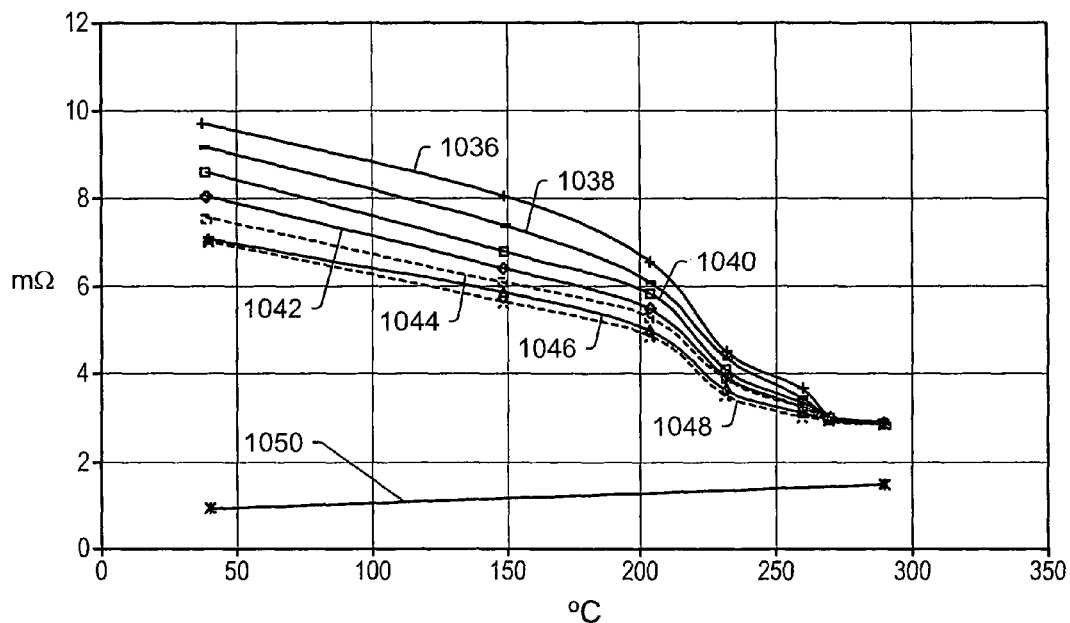

FIG. 174 depicts data of electrical resistance versus temperature for a composite 1.9 cm, 1.8 m long alloy 42-6 rod with a copper core (the rod has an outside diameter to copper diameter ratio of 2:1) at various applied electrical currents.

Figure 175:
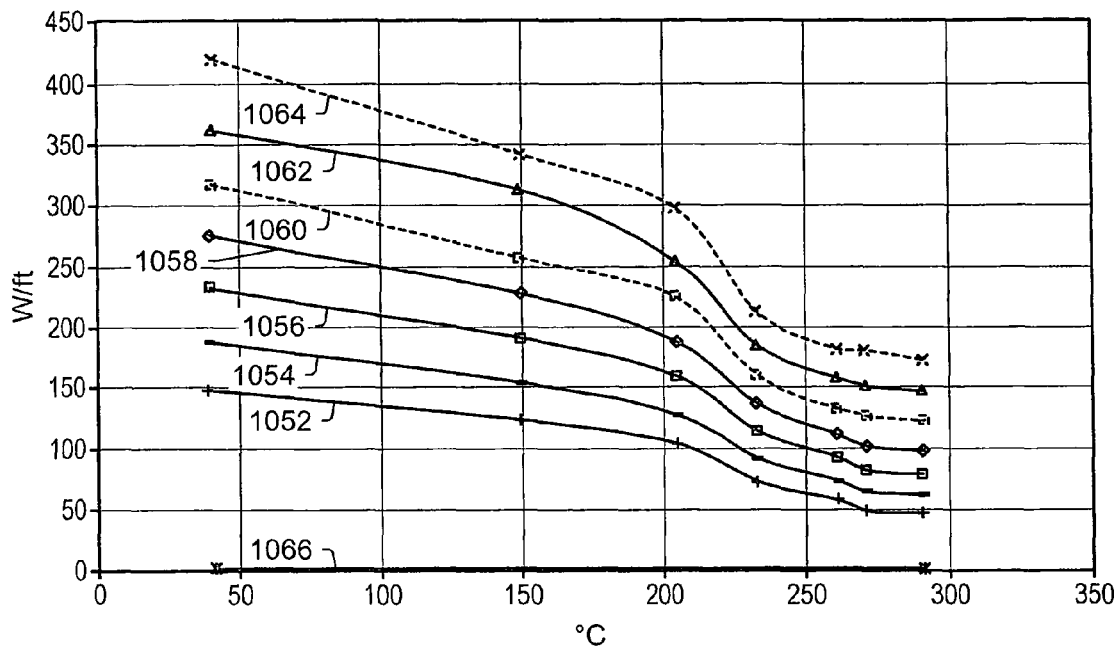

FIG. 175 depicts data of power output versus temperature for a composite 1.9 cm, 1.8 m long alloy 42-6 rod with a copper core (the rod has an outside diameter to copper diameter ratio of 2:1) at various applied electrical currents.

Figure 176:
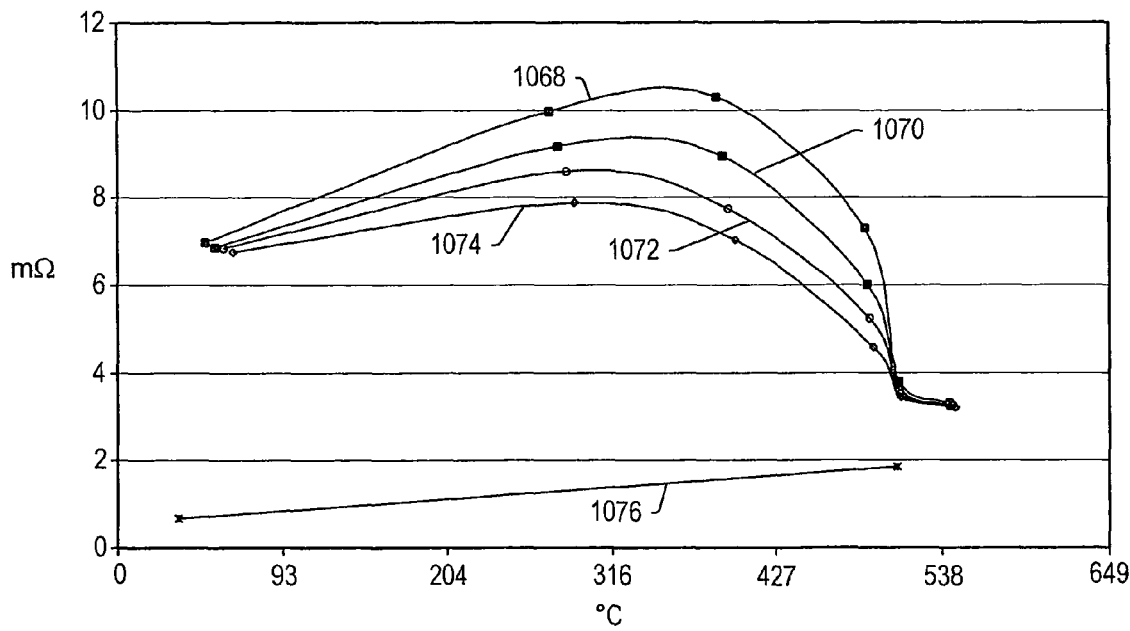

FIG. 176 depicts data of electrical resistance versus temperature for a composite 0.75" diameter, 6 foot long Alloy 52 rod with a 0.375" diameter copper core at various applied electrical currents.

Figure 177:
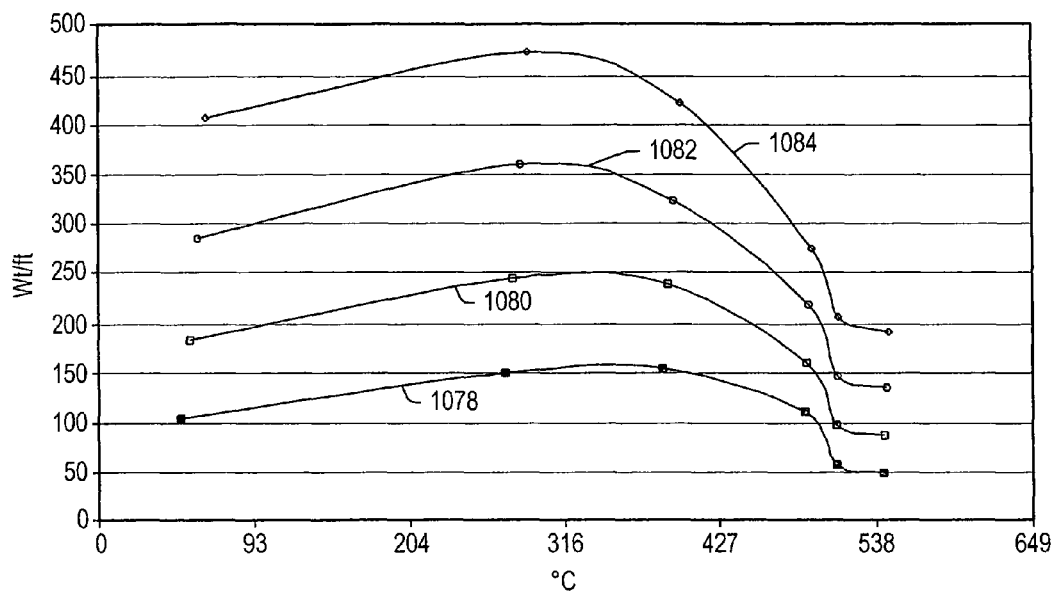

FIG. 177 depicts data of power output versus temperature for a composite 1.75" diameter, 6 foot long Alloy 52 rod with a 0.375" diameter copper core at various applied electrical currents.

Figure 178:
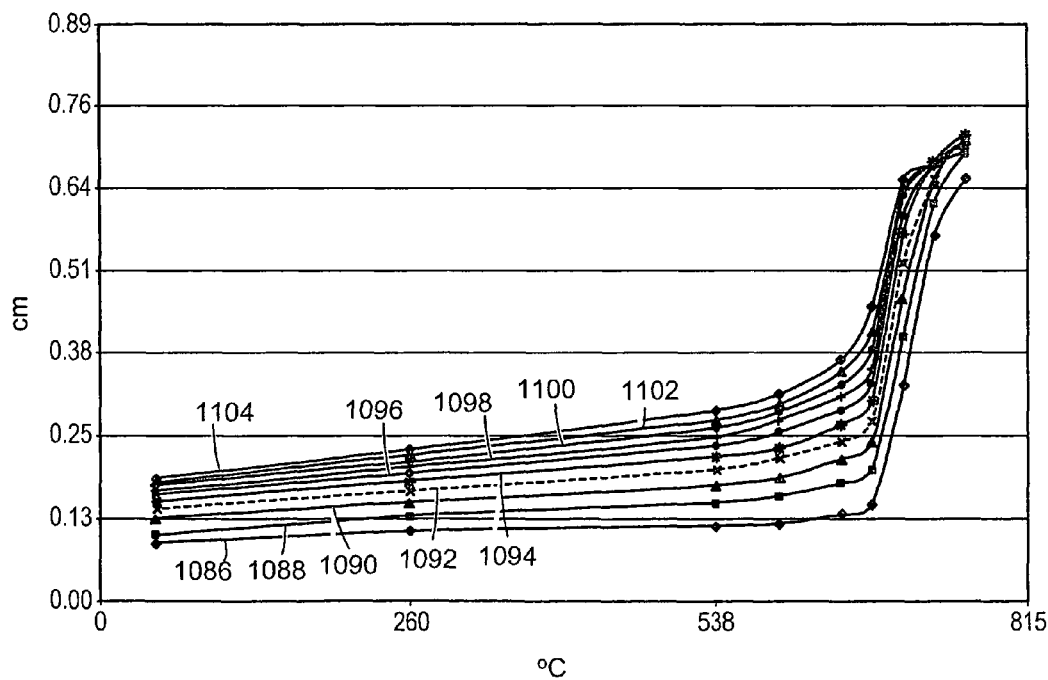

FIG. 178 depicts data for values of skin depth versus temperature for a solid 2.54 cm diameter, 1.8 m long 410 stainless steel rod at various applied AC electrical currents.

Figure 179:
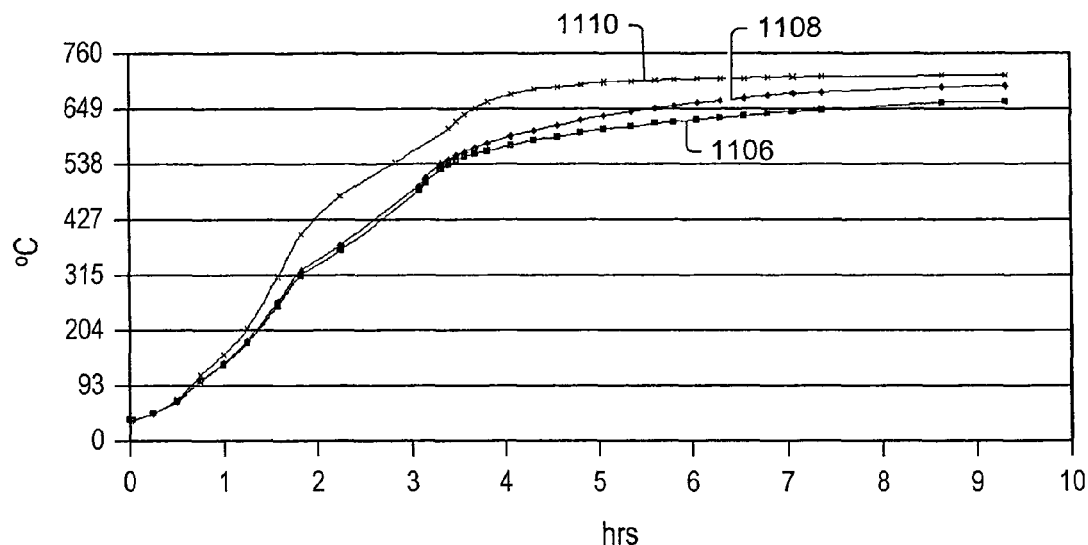

FIG. 179 depicts temperature versus time for a temperature limited heater.

Figure 180:
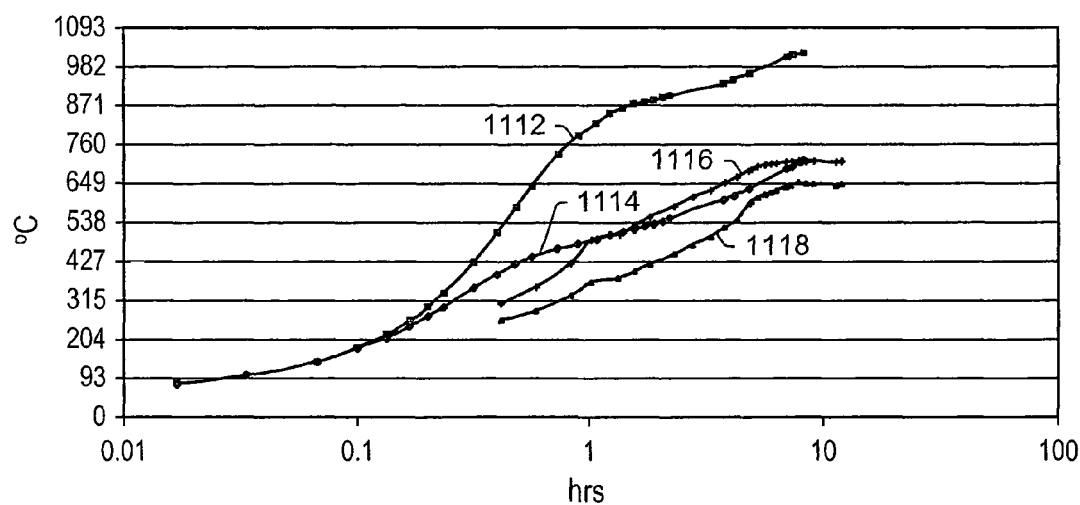

FIG. 180 depicts temperature versus log time data for a 2.5 cm solid 410 stainless steel rod and a 2.5 cm solid 304 stainless steel rod.

Figure 181:
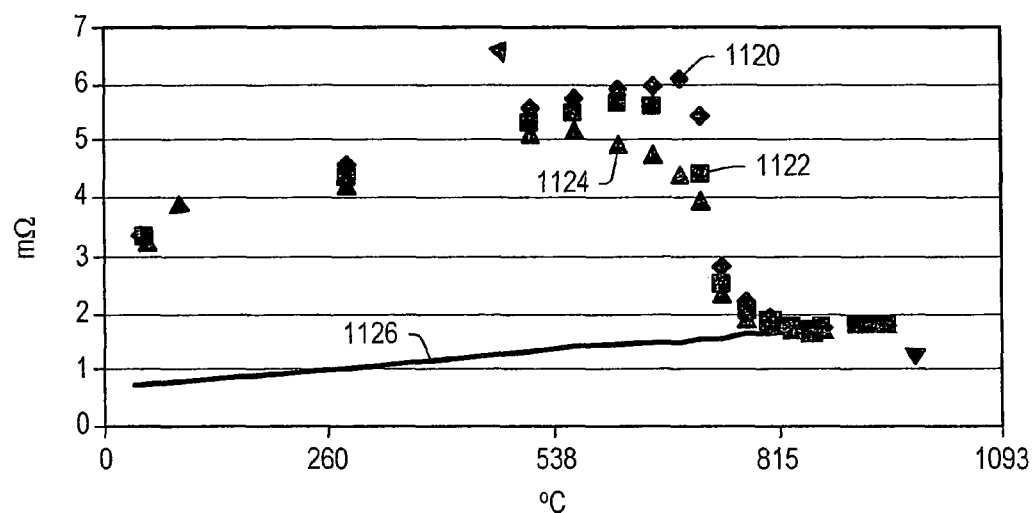

FIG. 181 depicts experimentally measured resistance versus temperature at several currents for a temperature limited heater with a copper core, a carbon steel ferromagnetic conductor, and a stainless steel 347H stainless steel support member.

Figure 182:
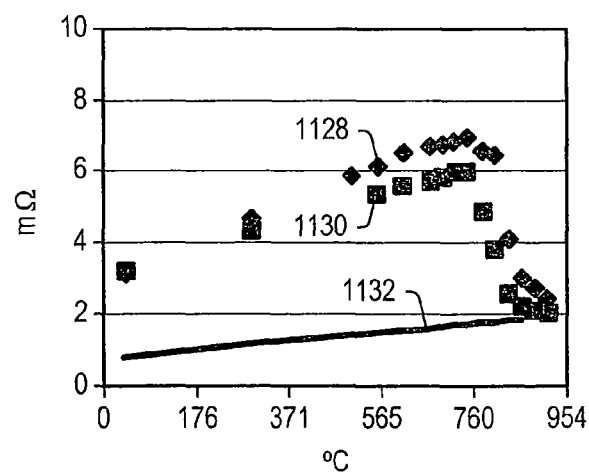

FIG. 182 depicts experimentally measured resistance versus temperature at several currents for a temperature limited heater with a copper core, an iron-cobalt ferromagnetic conductor, and a stainless steel 347H stainless steel support member.

Figure 183:
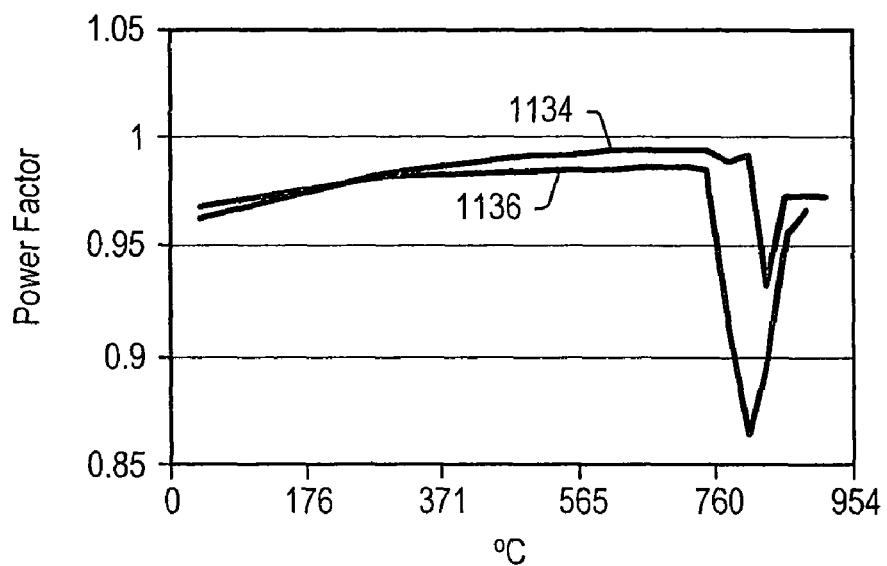

FIG. 183 depicts experimentally measured power factor versus temperature at two AC currents for a temperature limited heater with a copper core, a carbon steel ferromagnetic conductor, and a 347H stainless steel support member.

Figure 184:
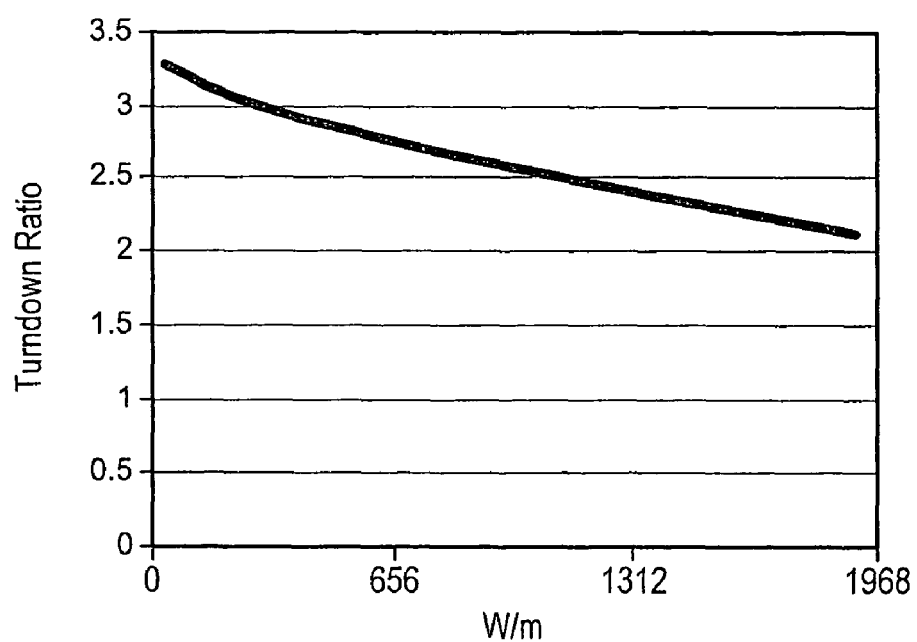

FIG. 184 depicts experimentally measured turndown ratio versus maximum power delivered for a temperature limited heater with a copper core, a carbon steel ferromagnetic conductor, and a 347H stainless steel support member.

Figure 185:
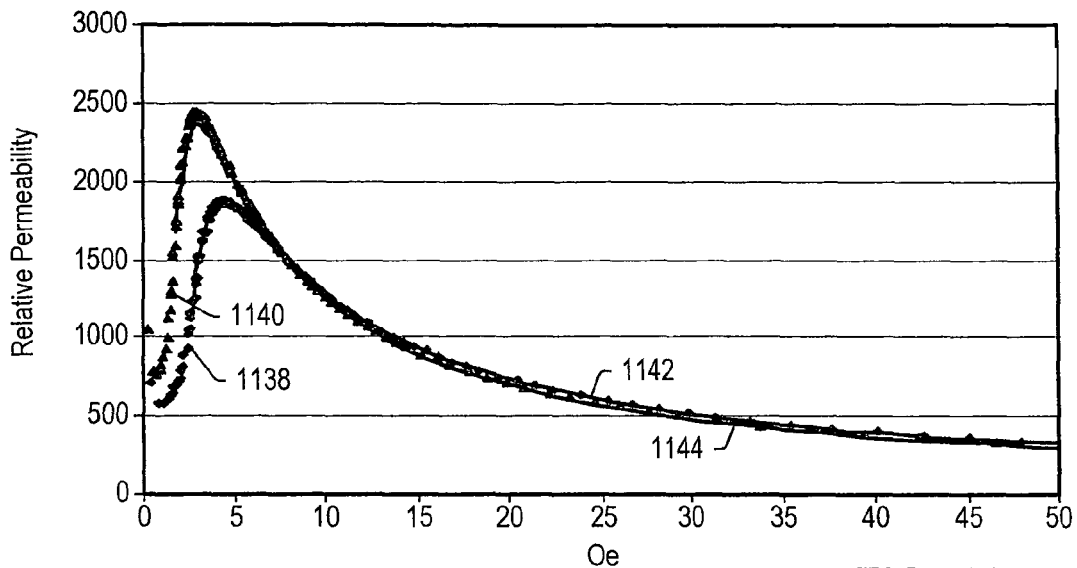

FIG. 185 depicts examples of relative magnetic permeability versus magnetic field for both the found correlations and raw data for carbon steel.

Figure 186:
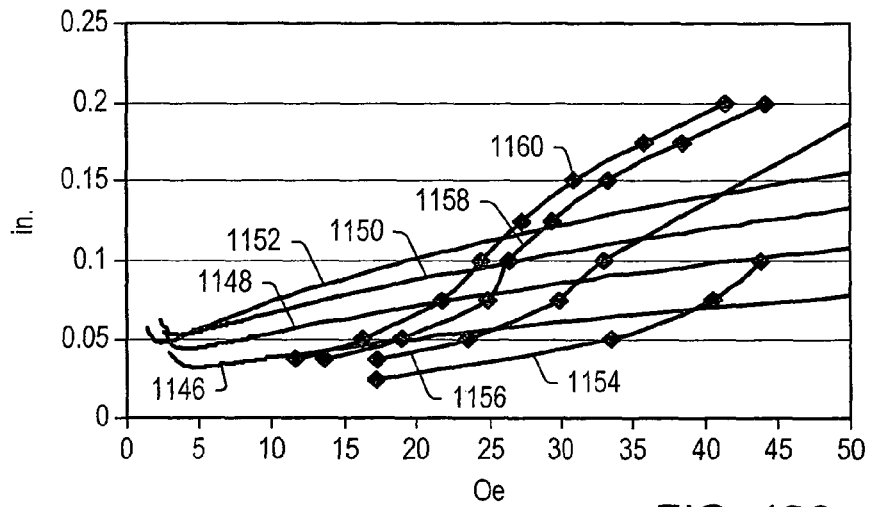

FIG. 186 shows the resulting plots of skin depth versus magnetic field for four temperatures and 400 A current.

Figure 187:
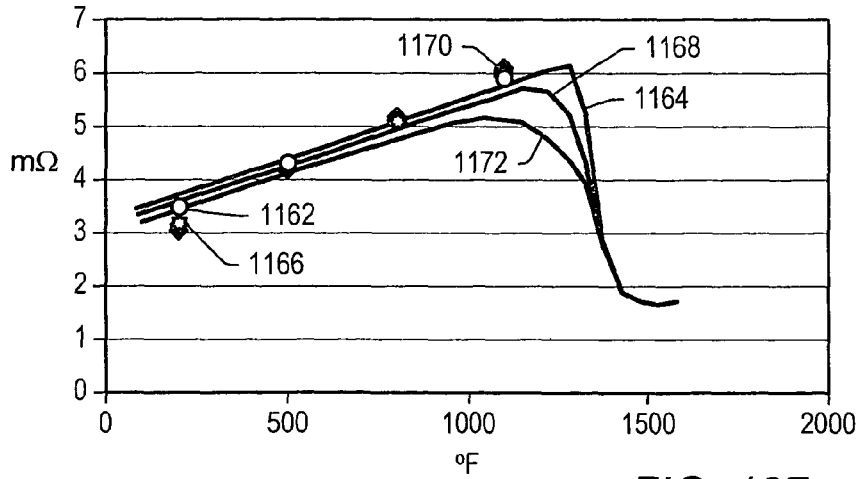

FIG. 187 shows a comparison between the experimental and numerical (calculated) results for currents of 300 A, 400 A, and 500 A.

Figure 188:
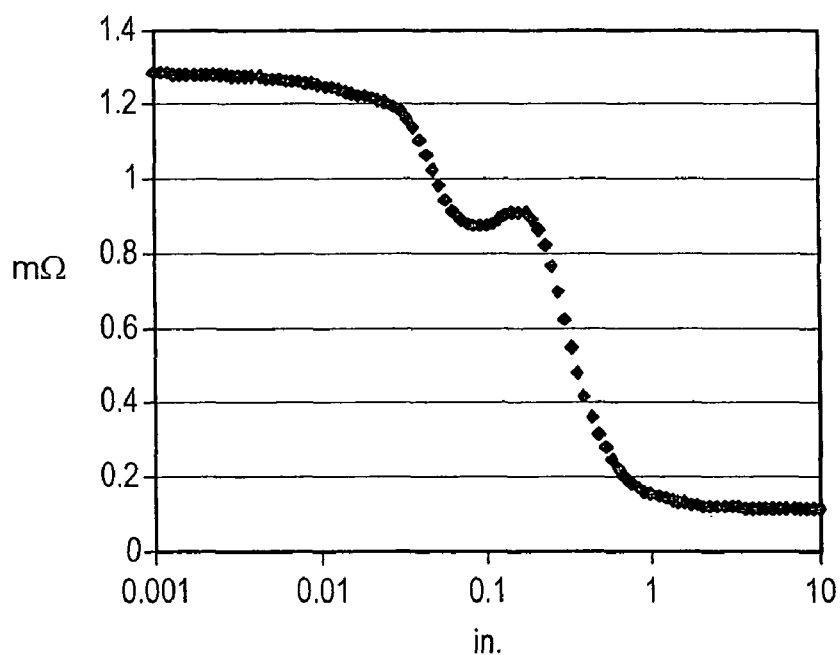

FIG. 188 shows the AC resistance per foot of the heater element as a function of skin depth at 1100° F. calculated from the theoretical model.

Figure 189:
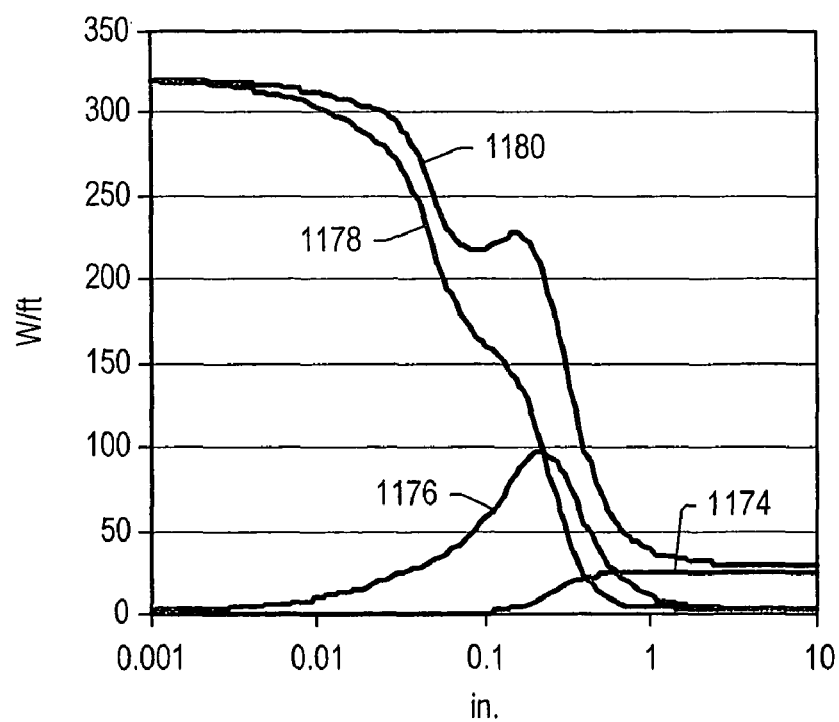

FIG. 189 depicts the power generated per unit length in each heater component versus skin depth for a temperature limited heater.

FIGS. 190 A-C compare the results of theoretical calculations with experimental data for resistance versus temperature in a temperature limited heater.

Figure 191:
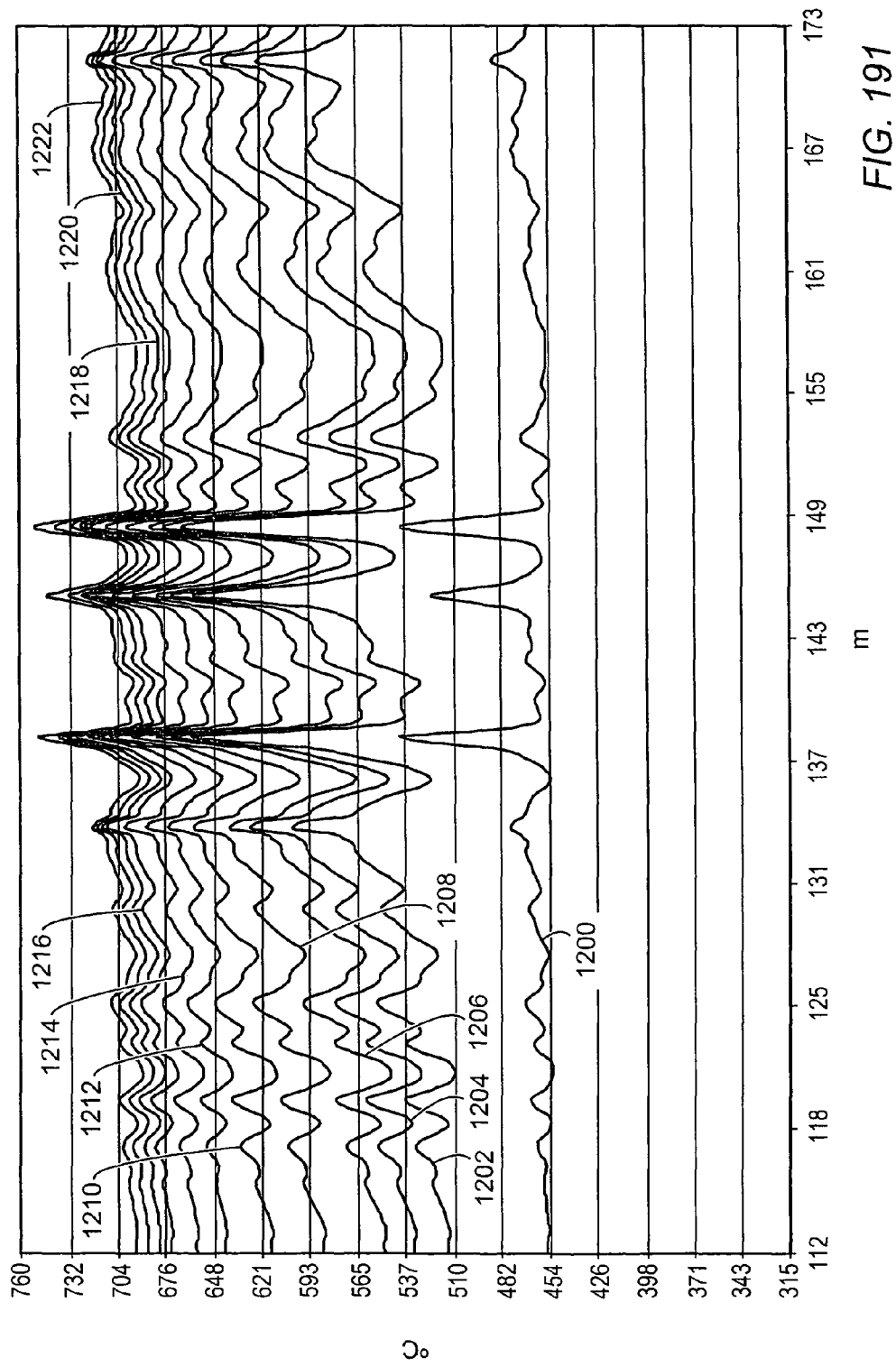

FIG. 191 displays temperature of the center conductor of a conductor-in-conduit heater as a function of formation depth for a Curie temperature heater with a turndown ratio of 2:1.

Figure 192:
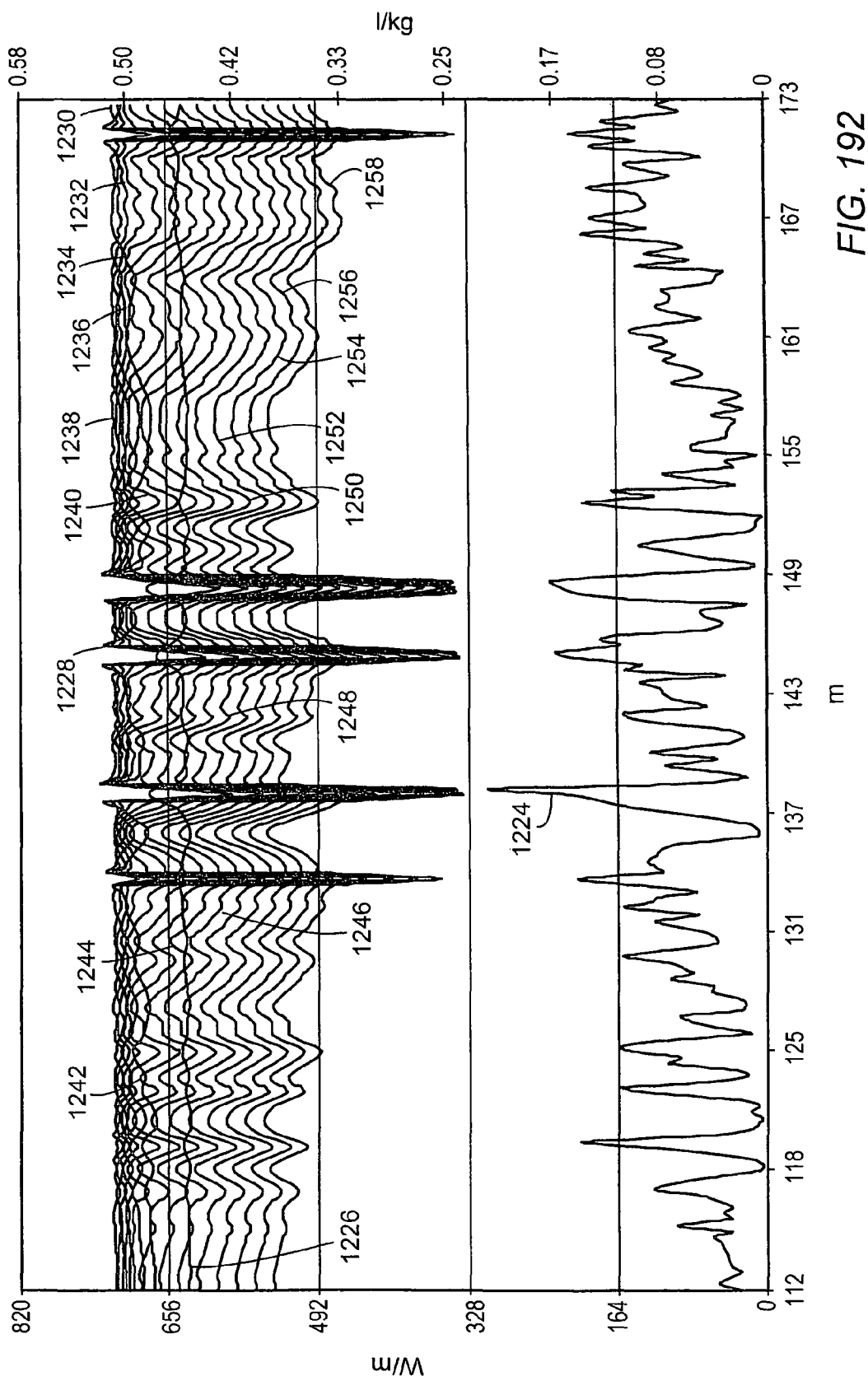

FIG. 192 displays heater heat flux through a formation for a turndown ratio of 2:1 along with the oil shale richness profile.

Figure 193:
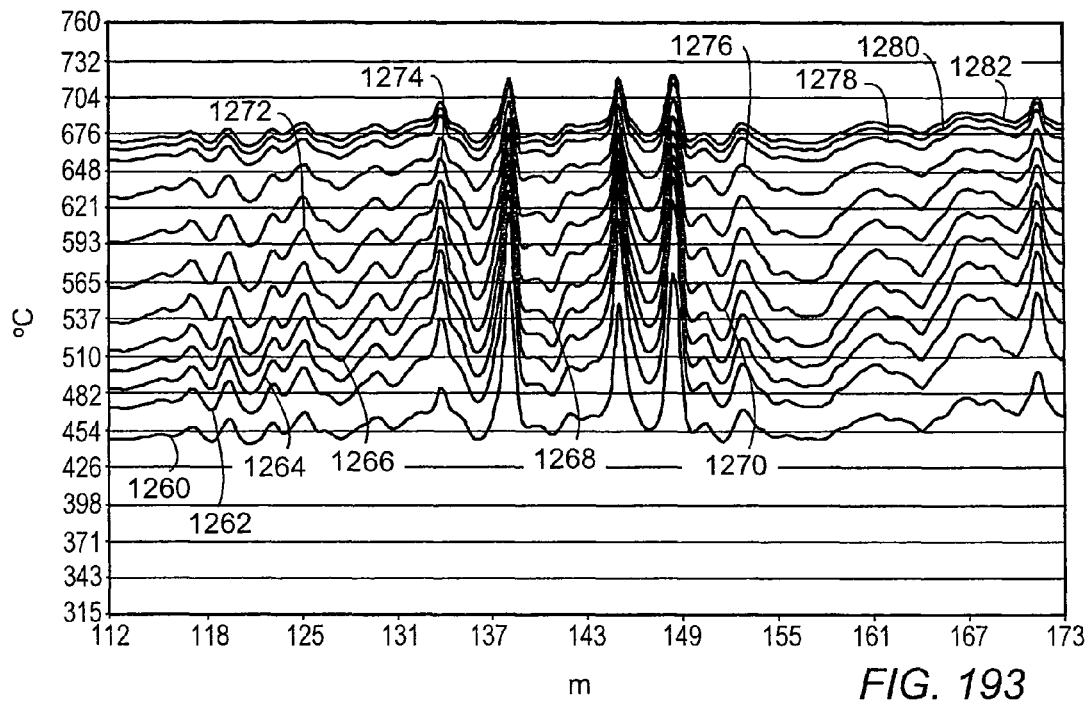

FIG. 193 displays heater temperature as a function of formation depth for a turndown ratio of 3:1.

Figure 194:
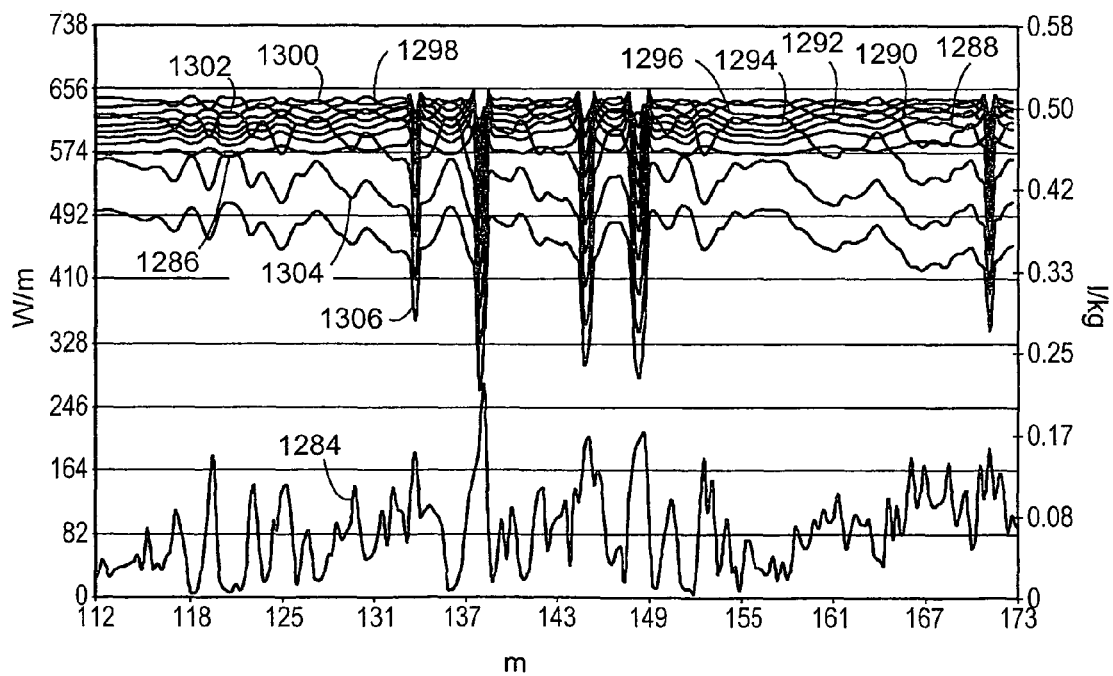

FIG. 194 displays heater heat flux through a formation for a turndown ratio of 3:1 along with the oil shale richness profile.

Figure 195:
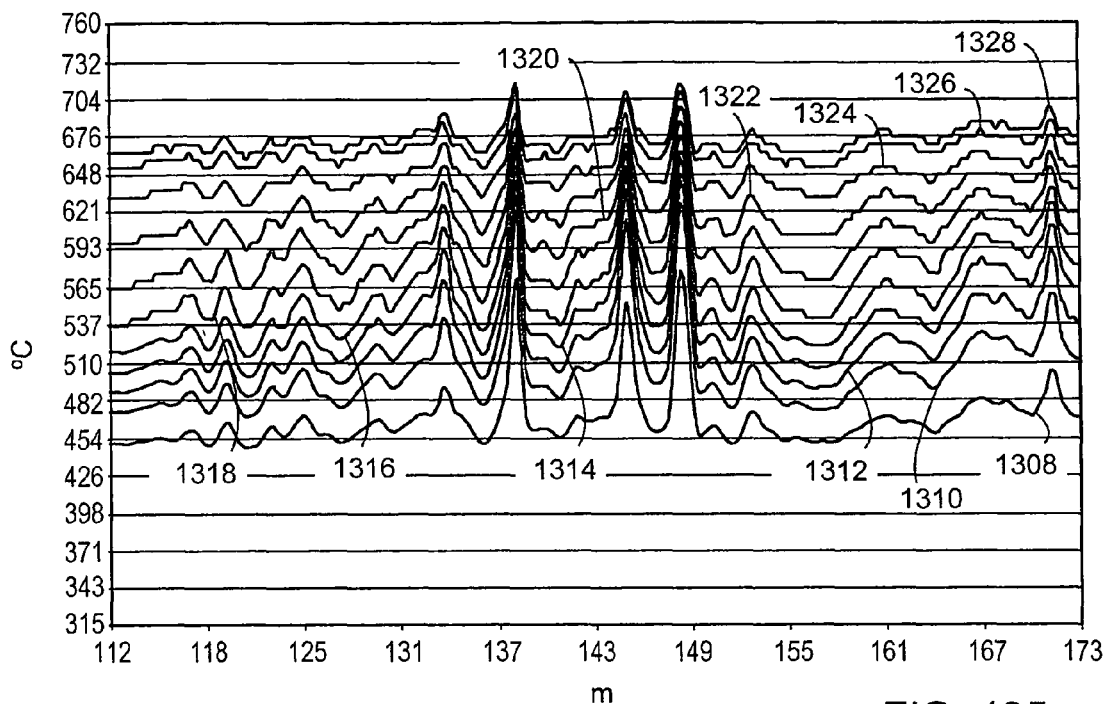

FIG. 195 displays heater temperature as a function of formation depth for a turndown ratio of 4:1.

Figure 196:
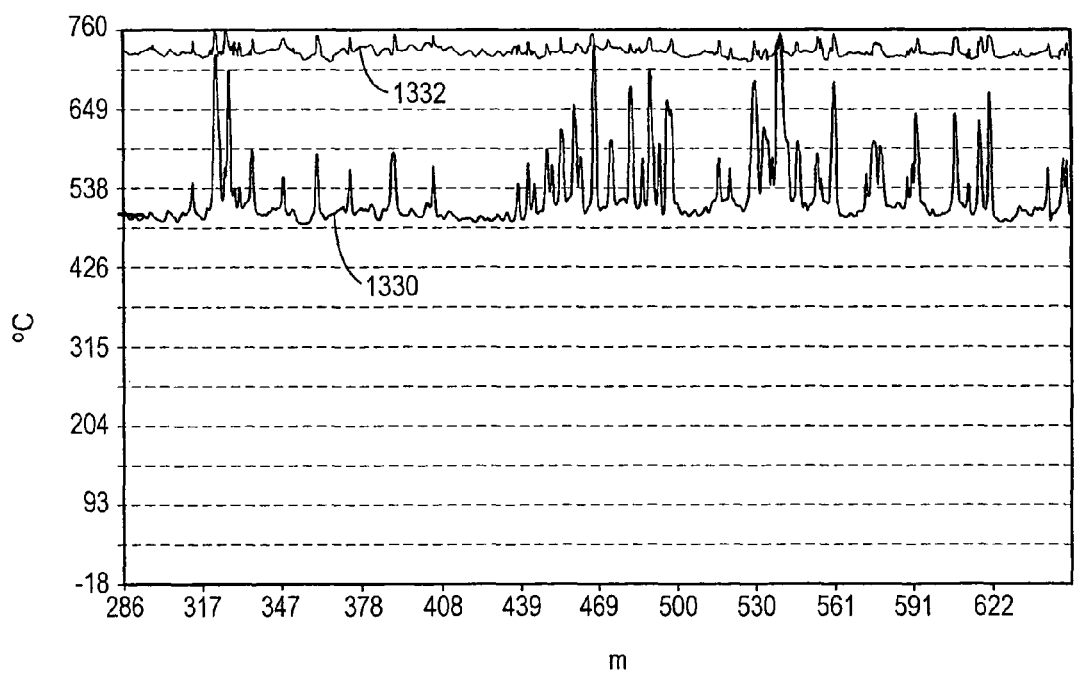

FIG. 196 depicts heater temperature versus depth for heaters used in a simulation for heating oil shale.

Figure 197:
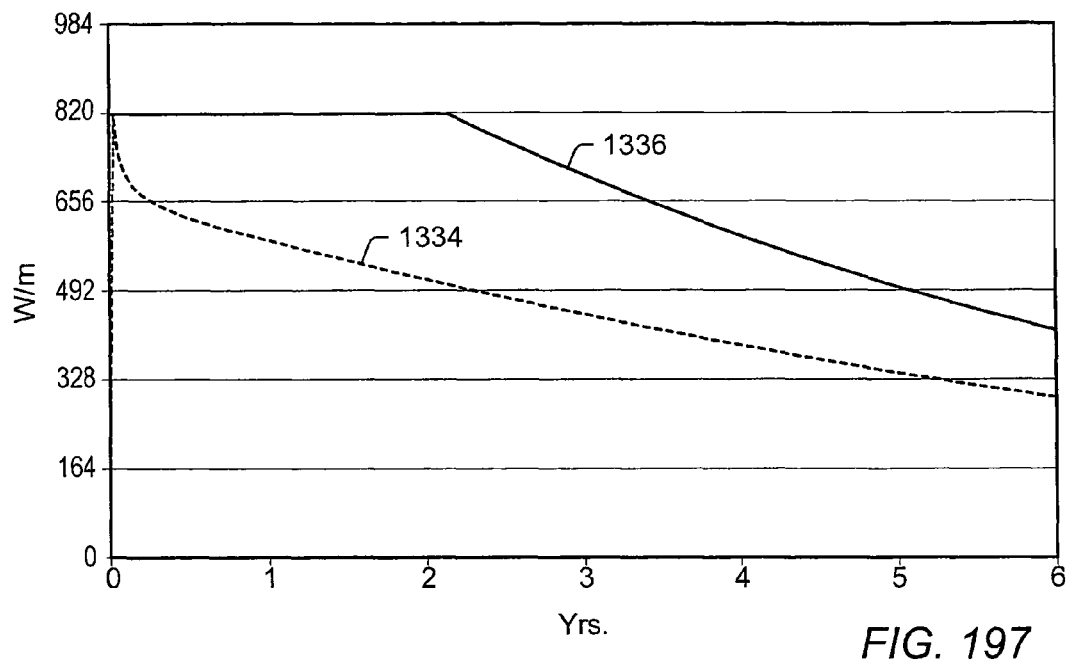

FIG. 197 depicts heater heat flux versus time for heaters used in a simulation for heating oil shale.

Figure 198:
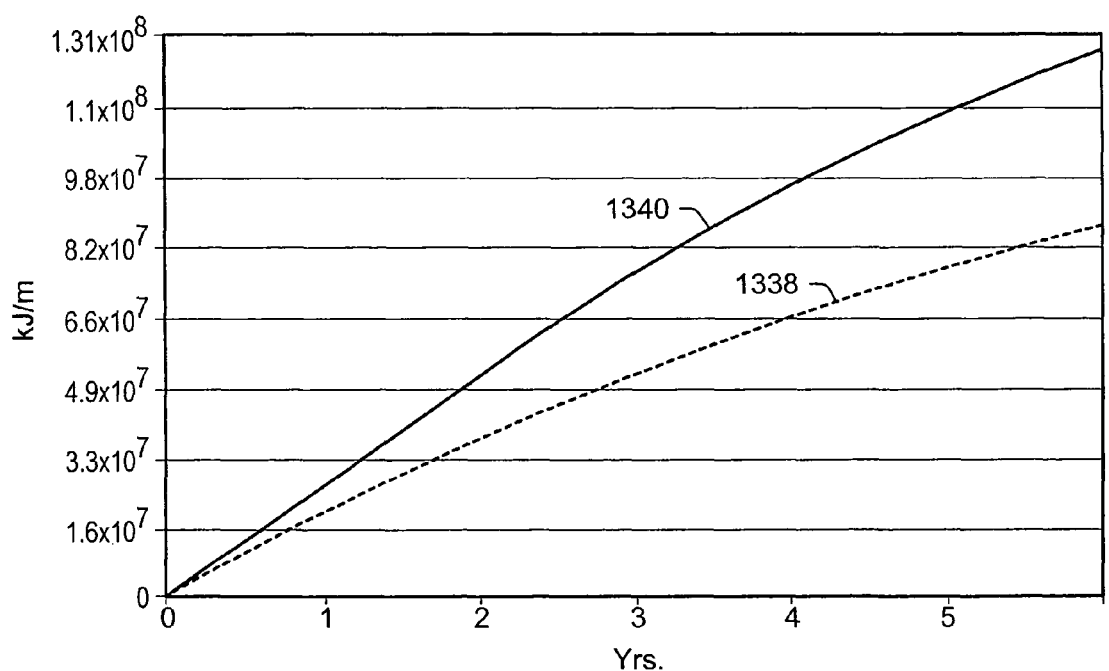

FIG. 198 depicts accumulated heat input versus time in a simulation for heating oil shale.

Figure 199:
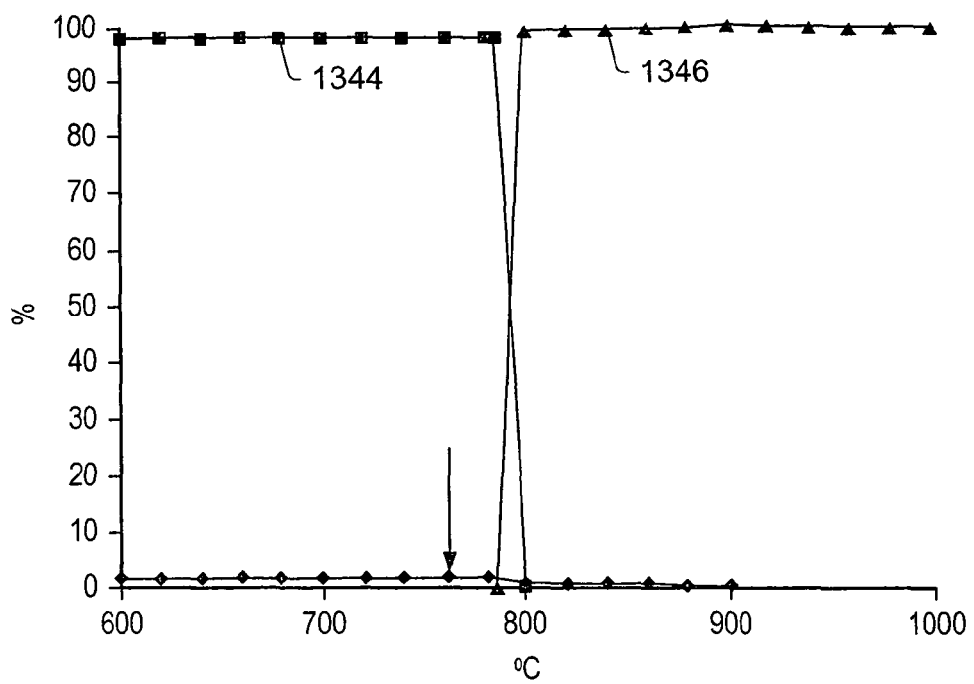

FIG. 199 depicts experimental calculations of weight percentages of ferrite and austenite phases versus temperature for iron alloy TC3.

Figure 200:
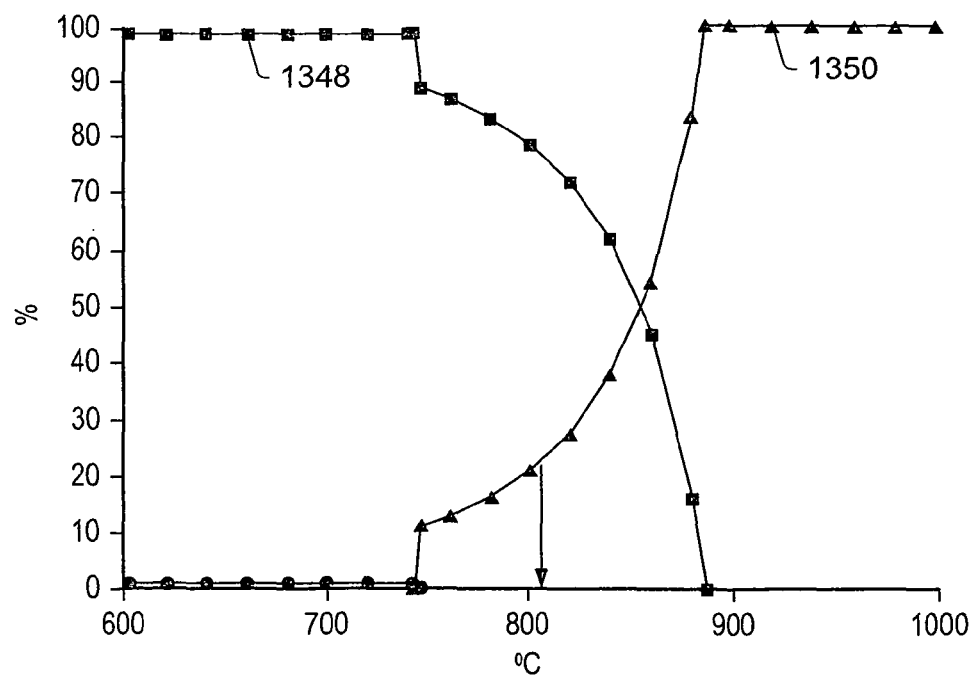

FIG. 200 depicts experimental calculations of weight percentages of ferrite and austenite phases versus temperature for iron alloy FM-4.

Figure 201:
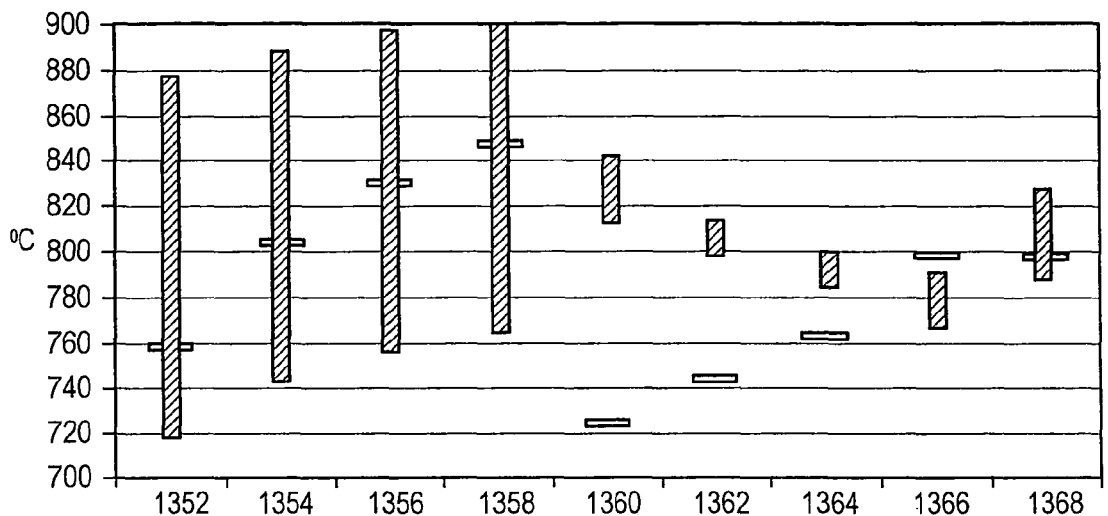

FIG. 201 depicts the Curie temperature and phase transformation temperature range for several iron alloys.

Figure 202:
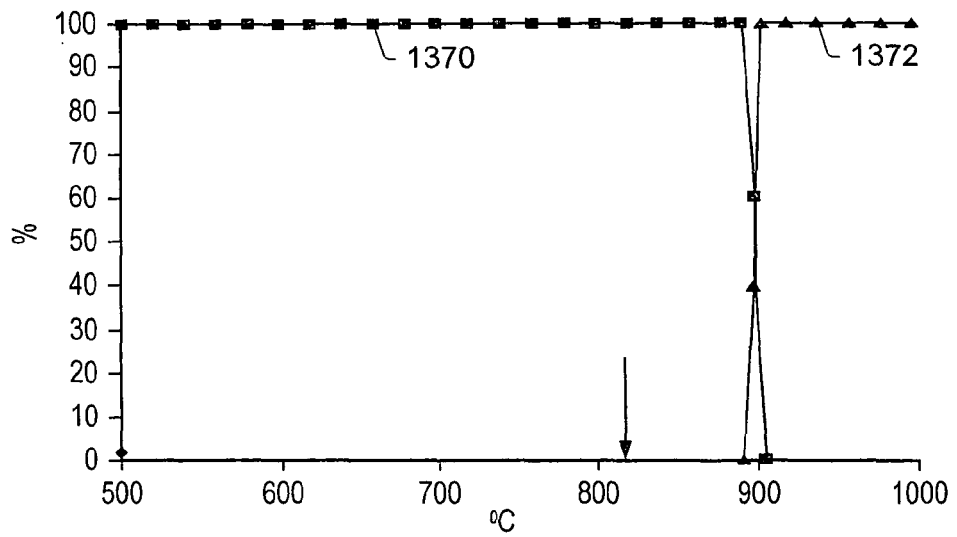

FIG. 202 depicts experimental calculations of weight percentages of ferrite and austenite phases versus temperature for an iron-cobalt alloy with 5.63% by weight cobalt and 0.4% by weight manganese.

Figure 203:
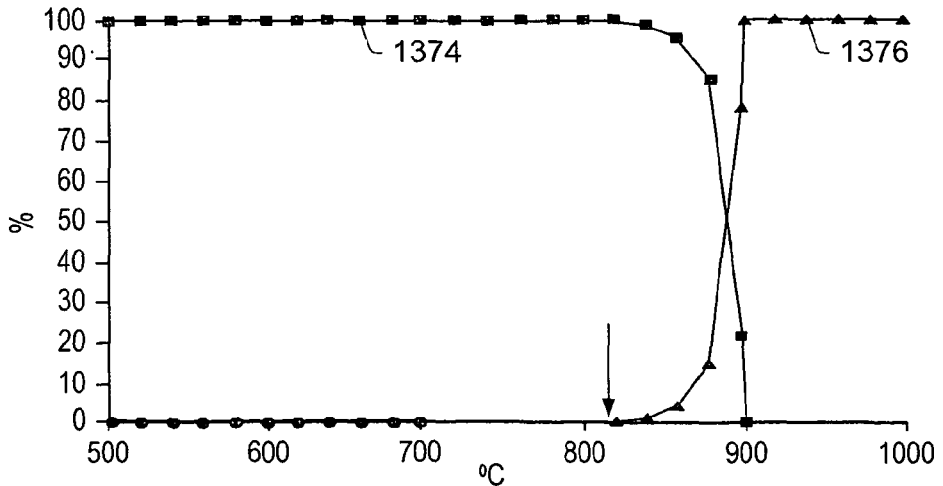

FIG. 203 depicts experimental calculations of weight percentages of ferrite and austenite phases versus temperature for an iron-cobalt alloy with 5.63% by weight cobalt, 0.4% by weight manganese, and 0.01% carbon.

Figure 204:
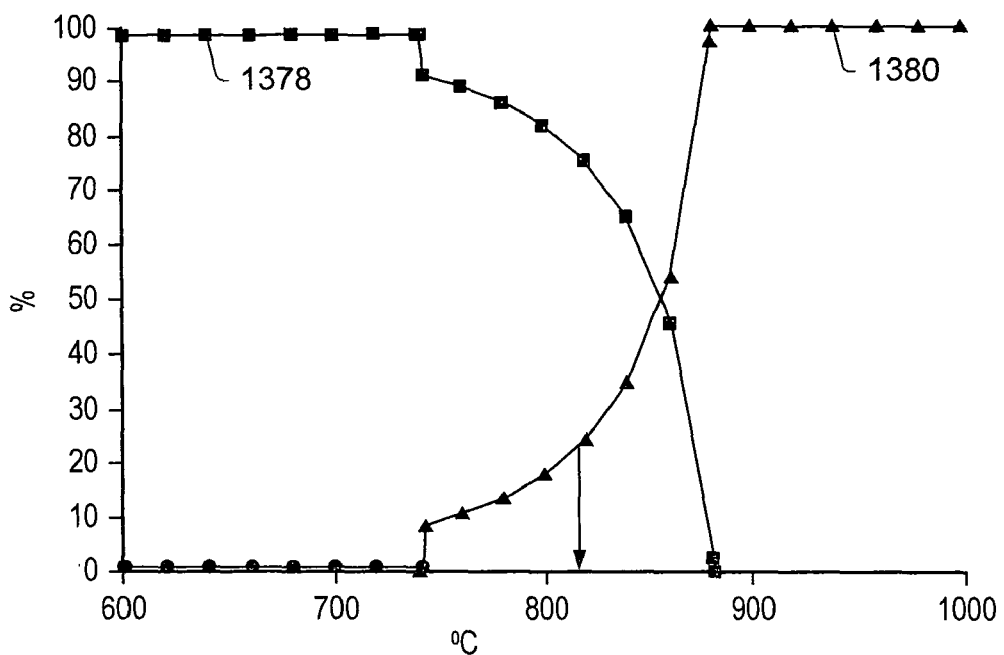

FIG. 204 depicts experimental calculations of weight percentages of ferrite and austenite phases versus temperature for an iron-cobalt alloy with 5.63% by weight cobalt, 0.4% by weight manganese, and 0.085% carbon.

Figure 205:
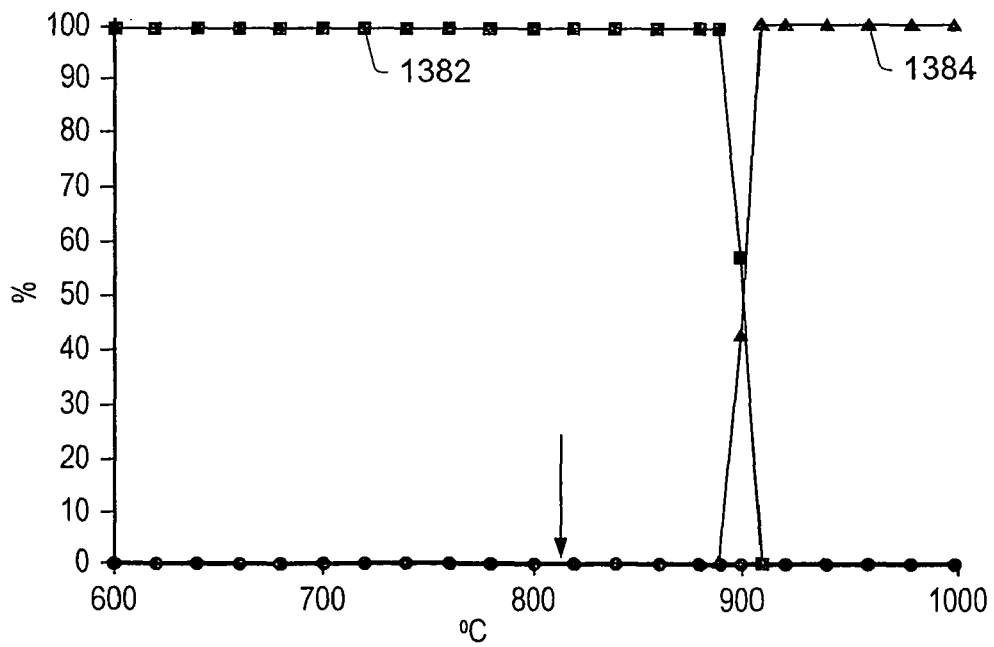

FIG. 205 depicts experimental calculations of weight percentages of ferrite and austenite phases versus temperature for an iron-cobalt alloy with 5.63% by weight cobalt, 0.4% by weight manganese, 0.085% carbon, and 0.4% titanium.

Figure 206:
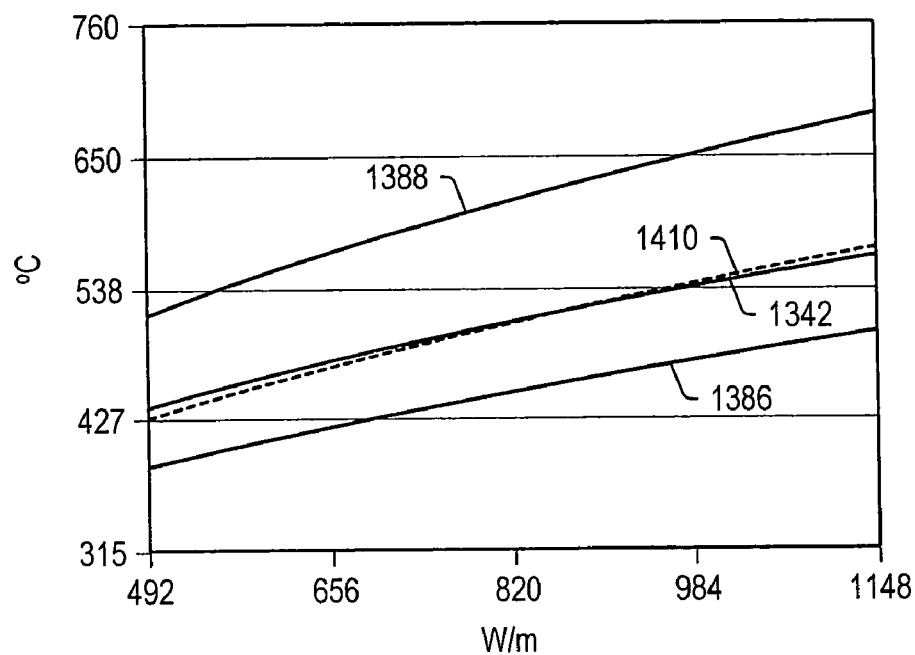

FIG. 206 shows heater rod temperature as a function of the power generated within a rod.

Figure 207:
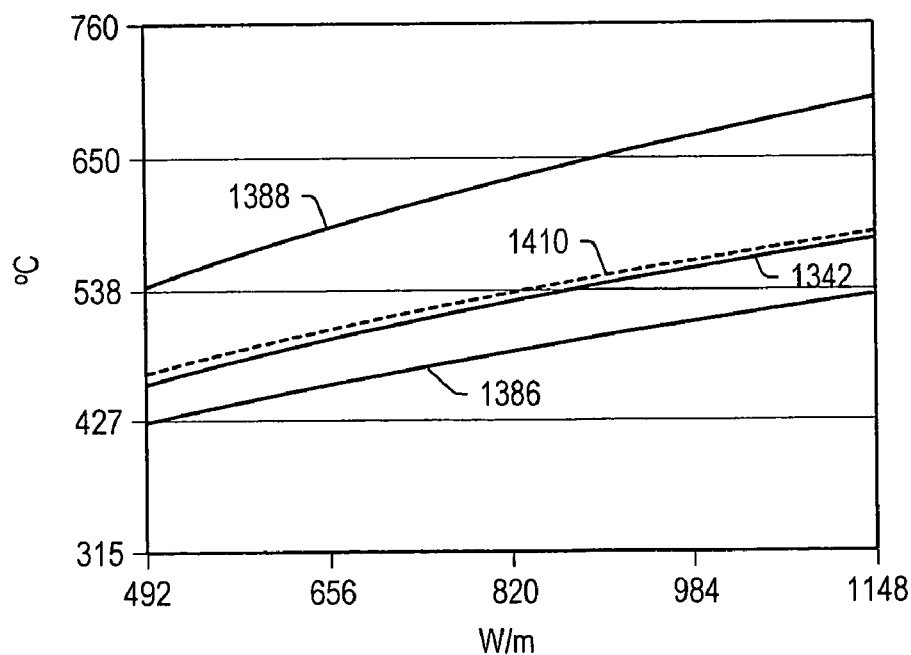

FIG. 207 shows heater rod temperature as a function of the power generated within a rod.

Figure 208:
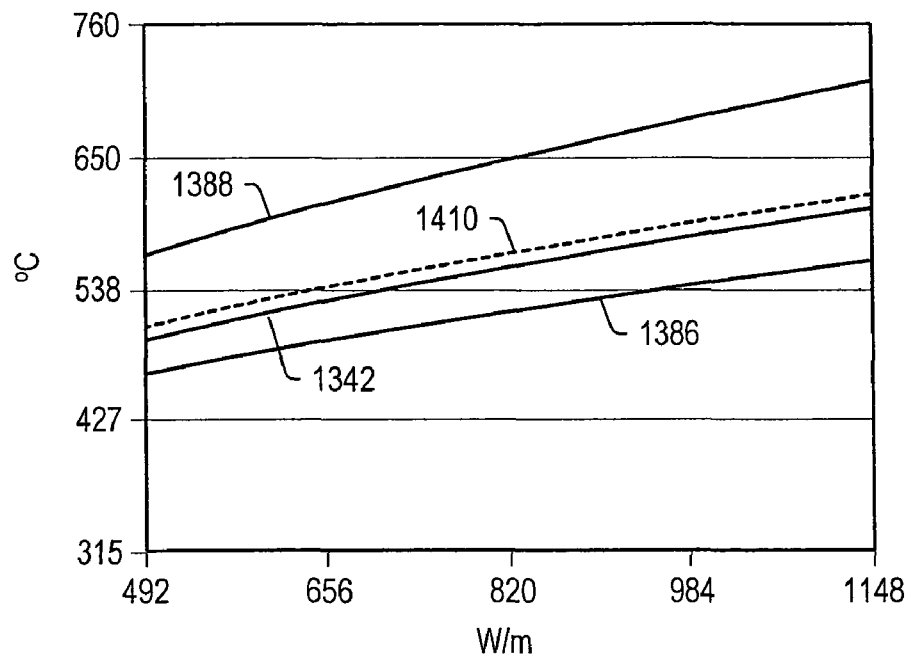

FIG. 208 shows heater rod temperature as a function of the power generated within a rod.

Figure 209:
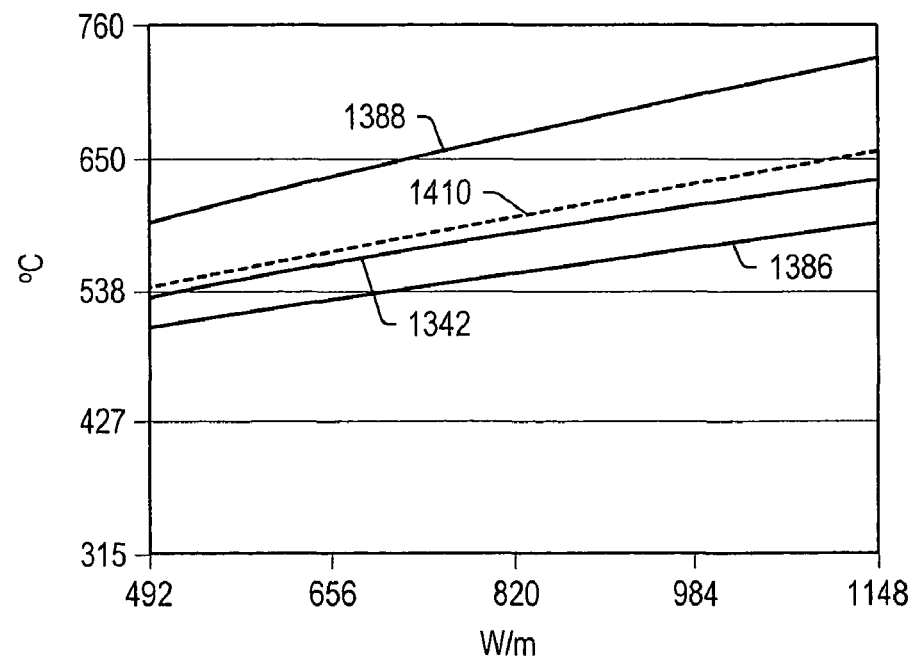

FIG. 209 shows heater rod temperature as a function of the power generated within a rod.

Figure 210:
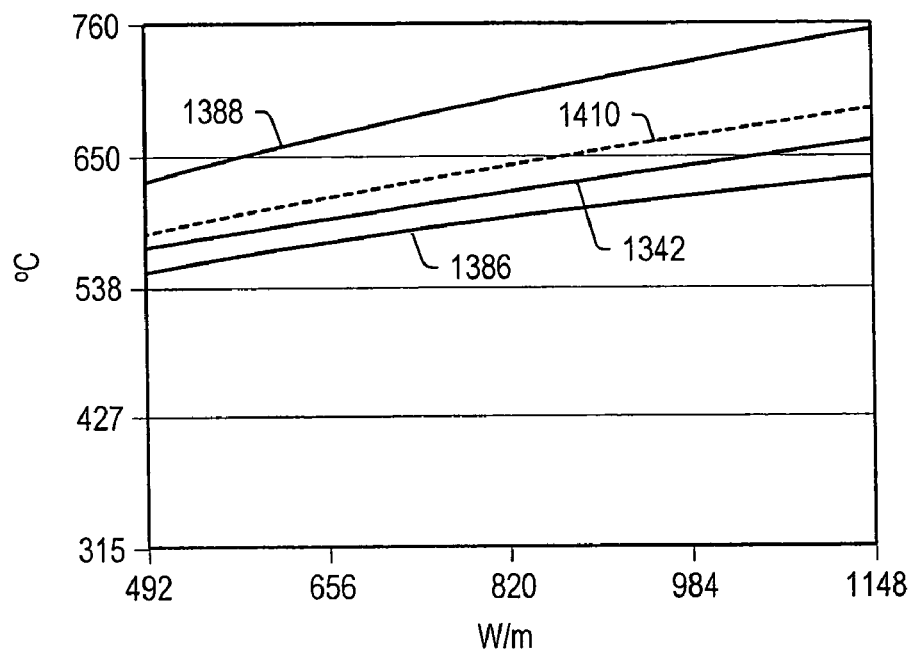

FIG. 210 shows heater rod temperature as a function of the power generated within a rod.

Figure 211:
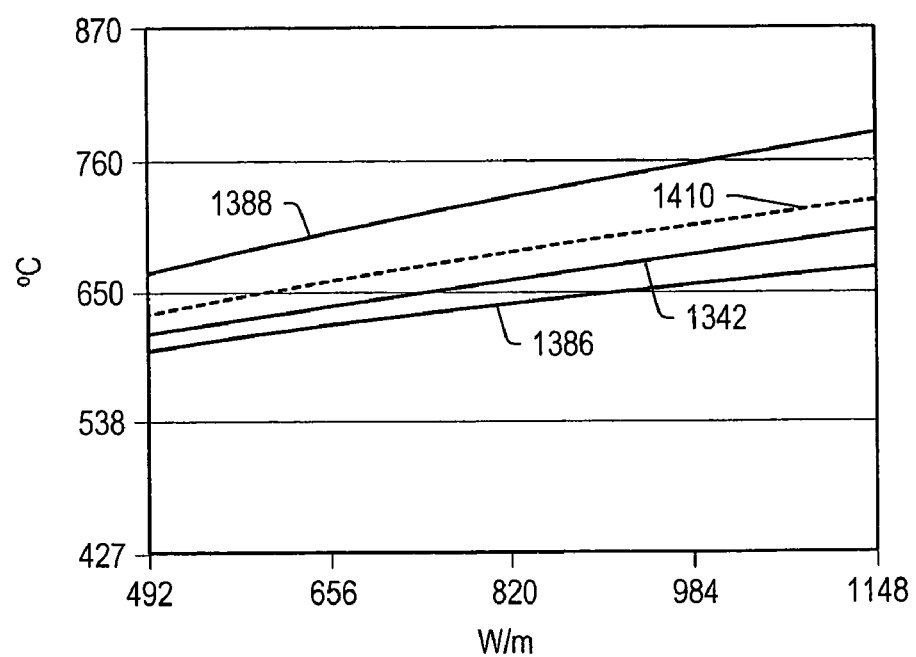

FIG. 211 shows heater rod temperature as a function of the power generated within a rod.

Figure 212:
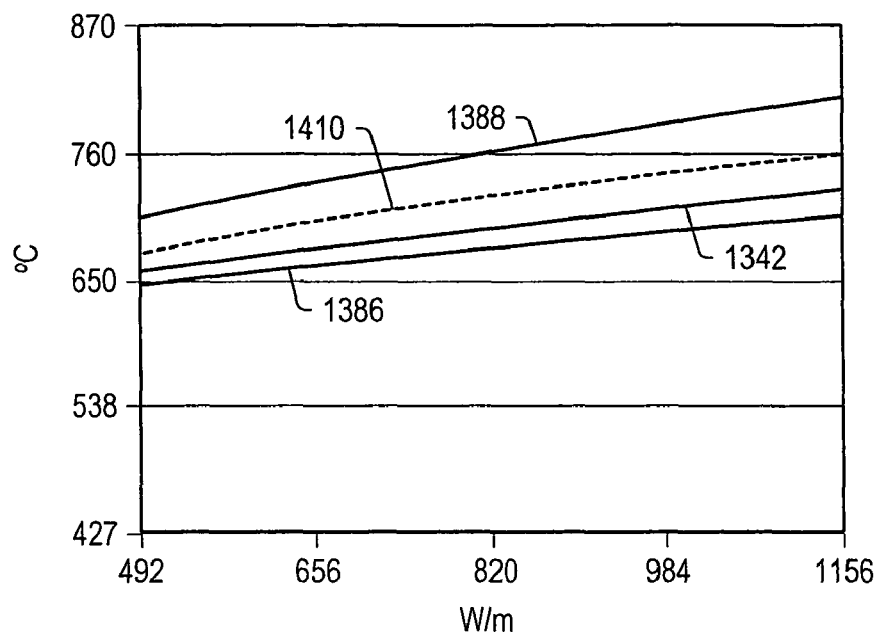

FIG. 212 shows heater rod temperature as a function of the power generated within a rod.

Figure 213:
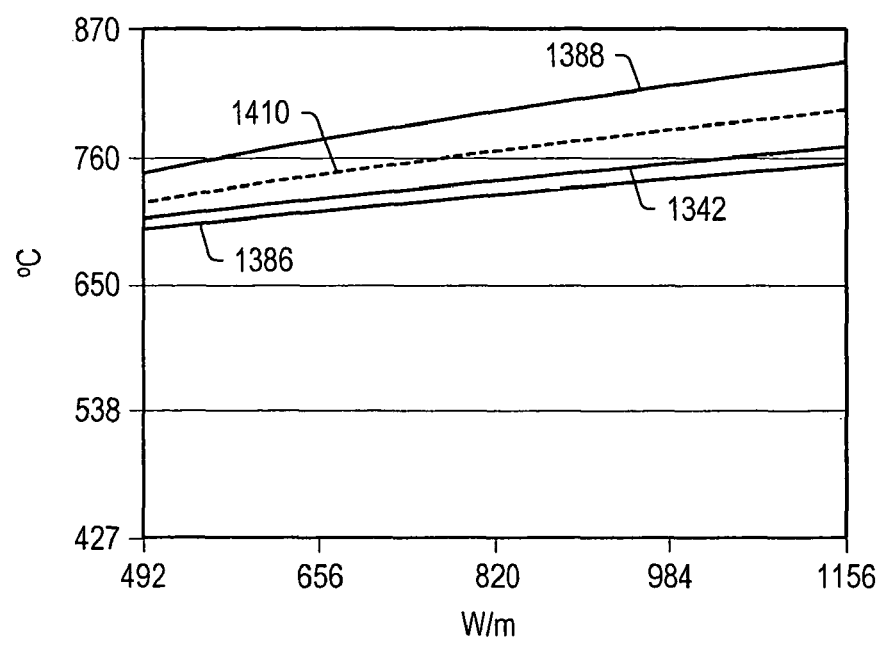

FIG. 213 shows heater rod temperature as a function of the power generated within a rod.

Figure 214:
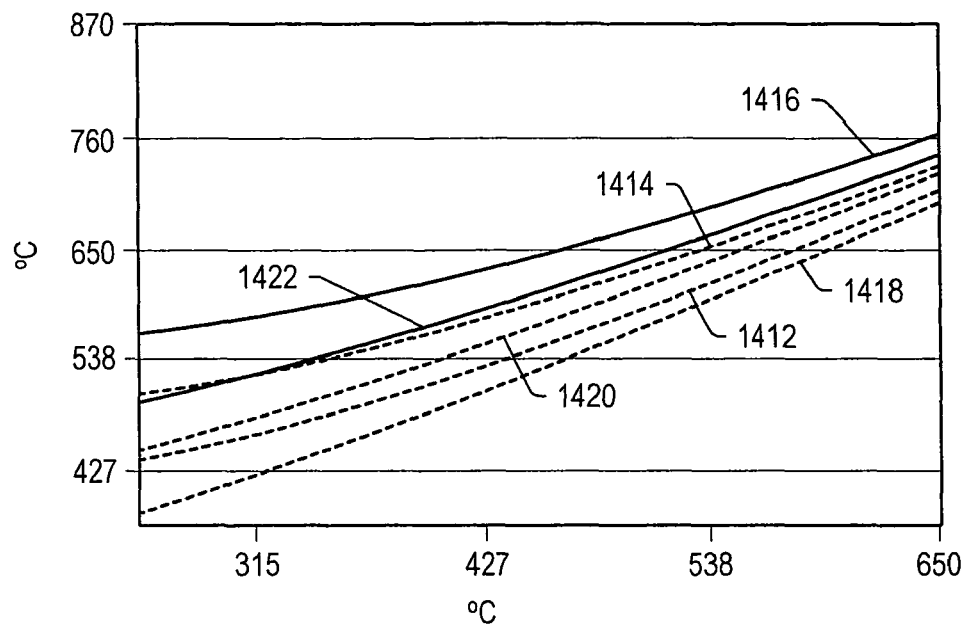

FIG. 214 shows a plot of center heater rod temperature versus conduit temperature for various heater powers with air or helium in the annulus.

Figure 215:
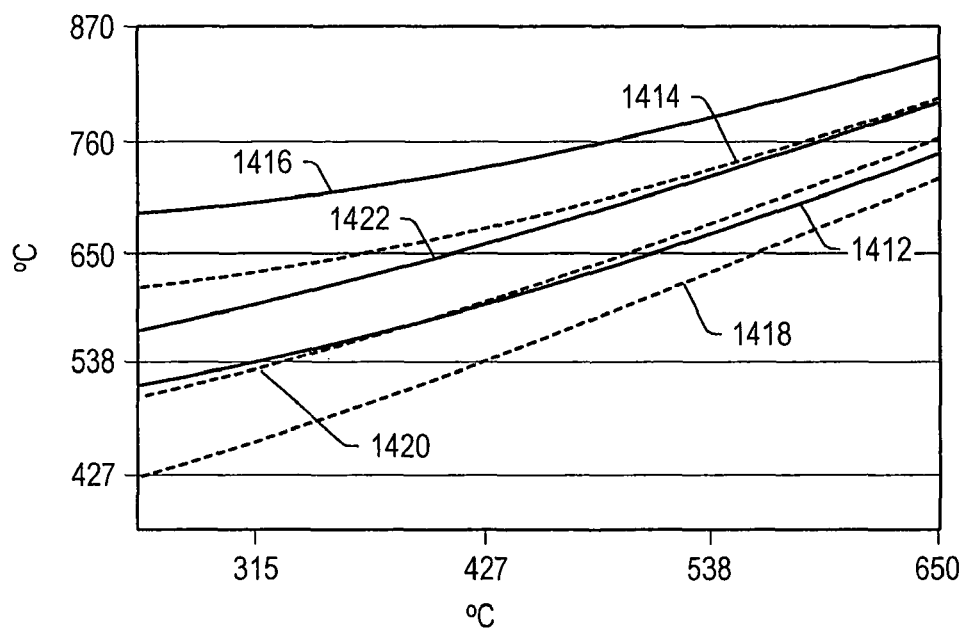

FIG. 215 shows a plot of center heater rod temperature versus conduit temperature for various heater powers with air or helium in the annulus.

Figure 216:
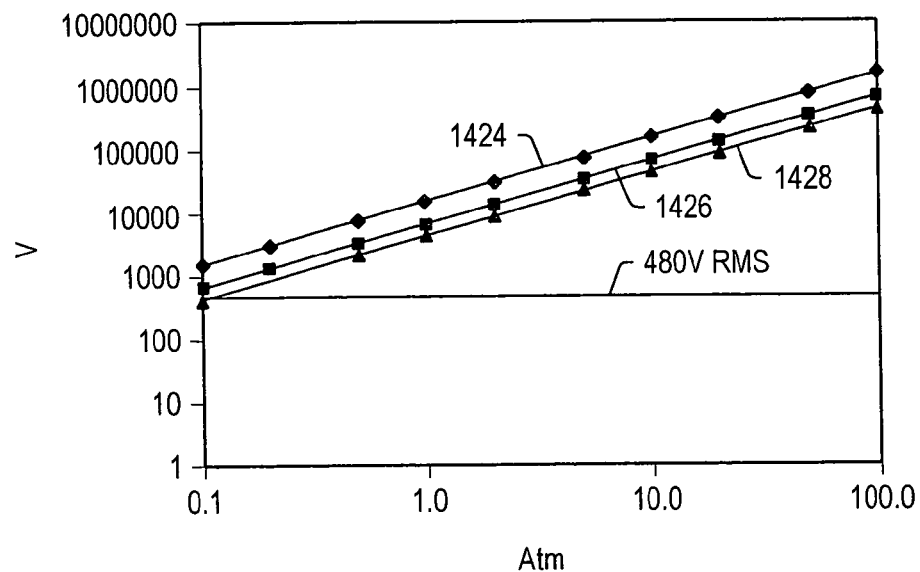

FIG. 216 depicts spark gap breakdown voltages versus pressure at different temperatures for a conductor-in-conduit heater with air in the annulus.

Figure 217:
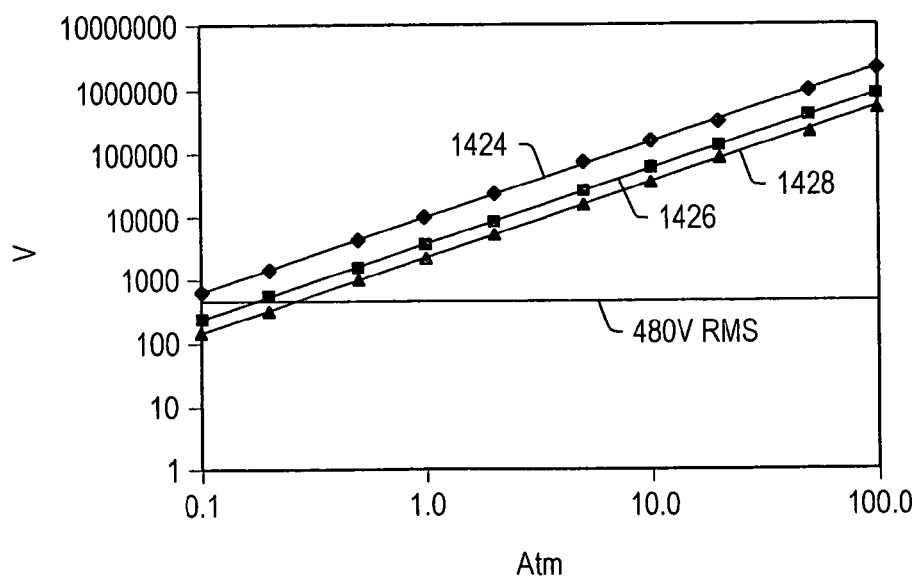

FIG. 217 depicts spark gap breakdown voltages versus pressure at different temperatures for a conductor-in-conduit heater with helium in the annulus.

Figure 218:
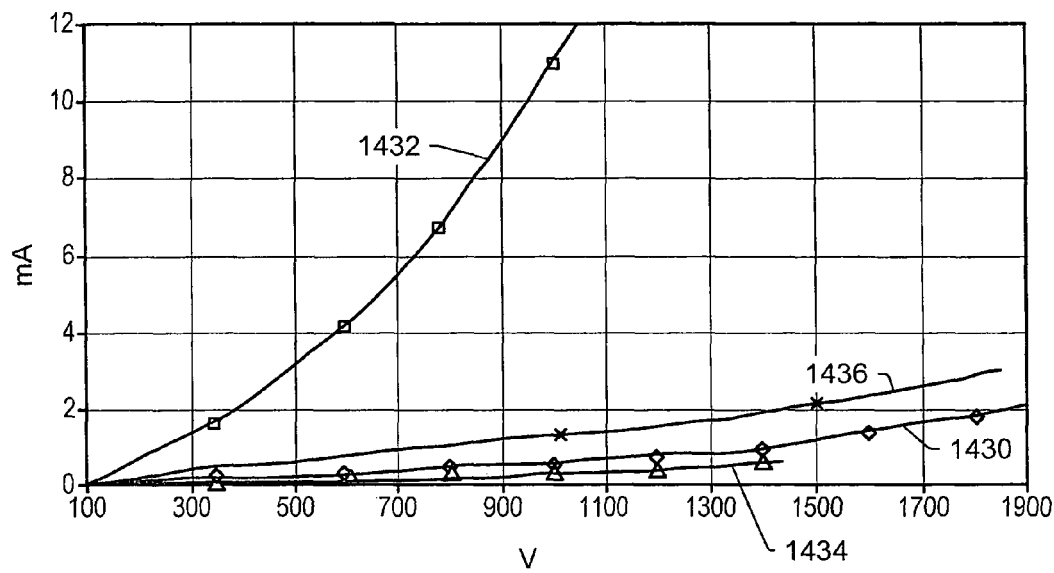

FIG. 218 depicts data of leakage current measurements versus voltage for alumina and silicon nitride centralizers at selected temperatures.

Figure 219:
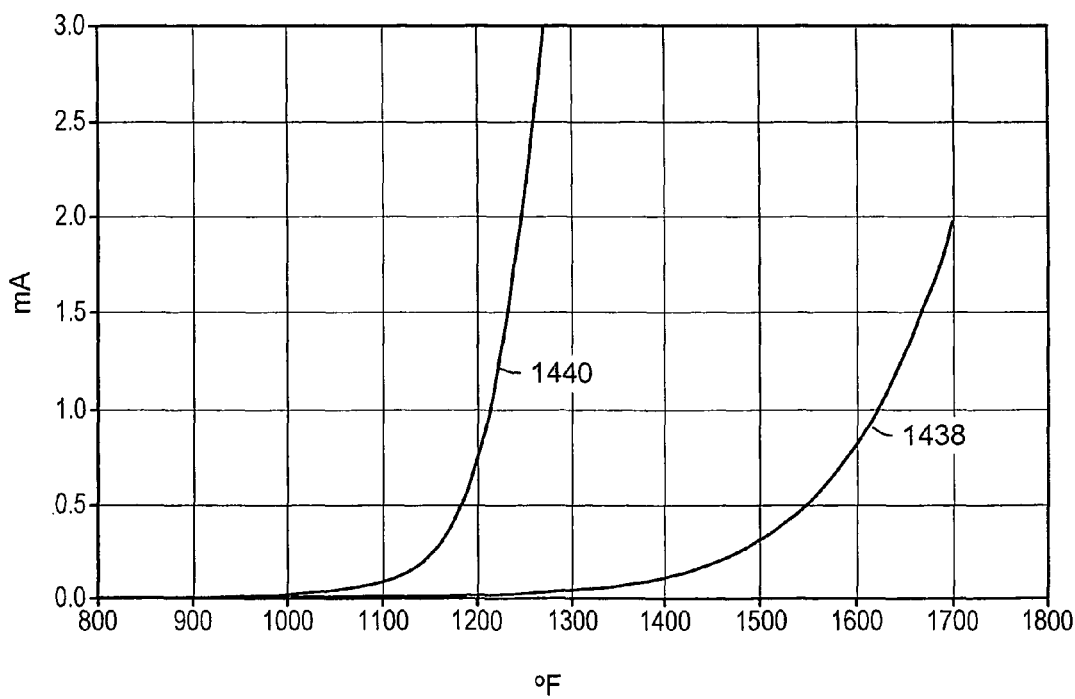

FIG. 219 depicts leakage current measurements versus temperature for two different types of silicon nitride.

Figure 220:
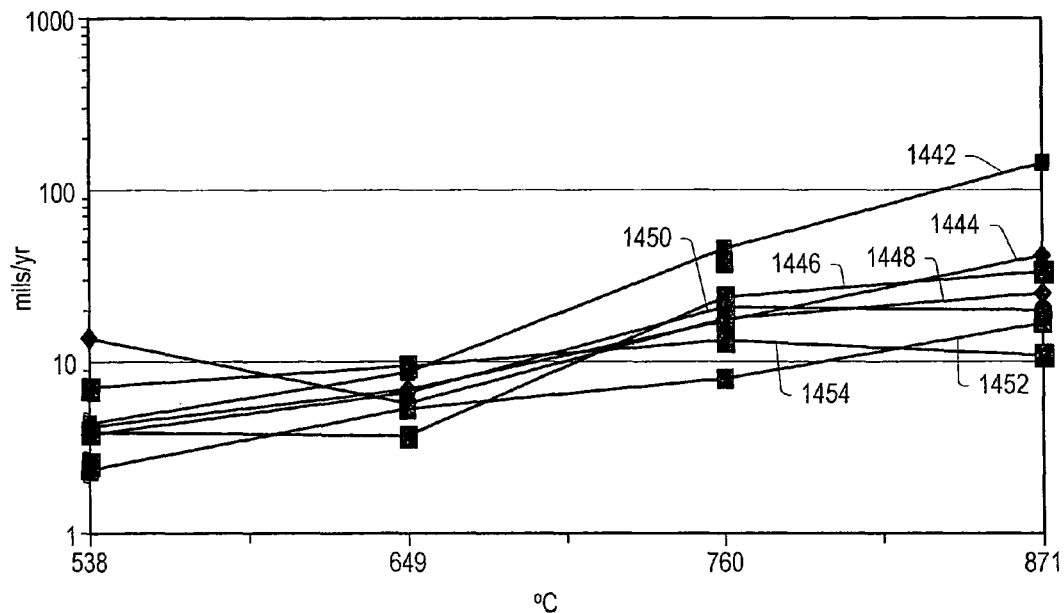

FIG. 220 depicts projected corrosion rates over a one-year period for several metals in a sulfidation atmosphere.

Figure 221:
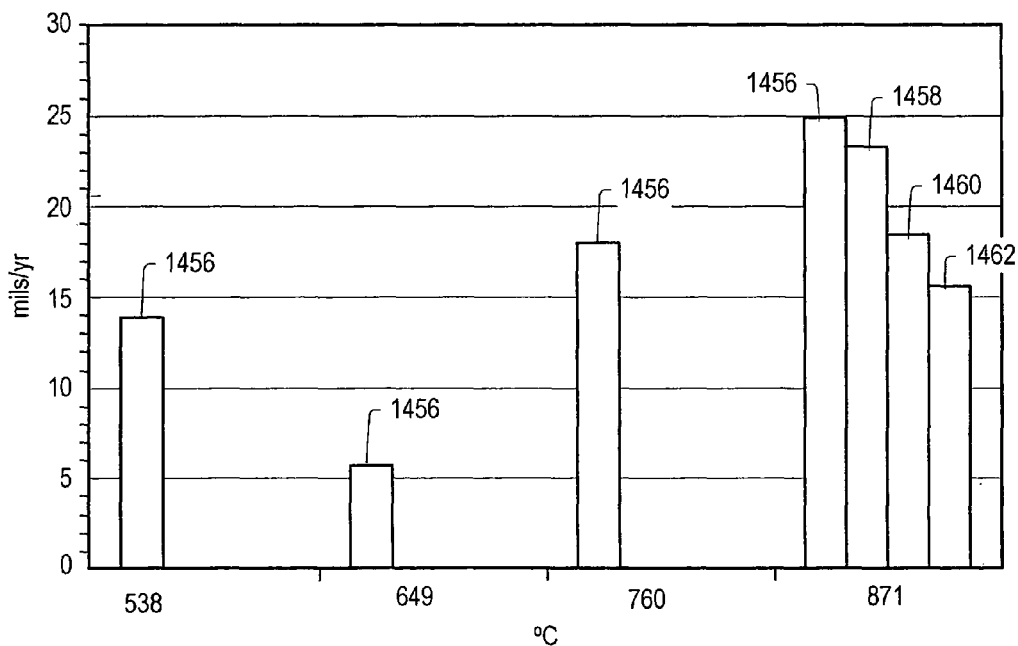

FIG. 221 depicts projected corrosion rates over a one-year period for 410 stainless steel and 410 stainless steel containing various amounts of cobalt in a sulfidation atmosphere.

Figure 222:
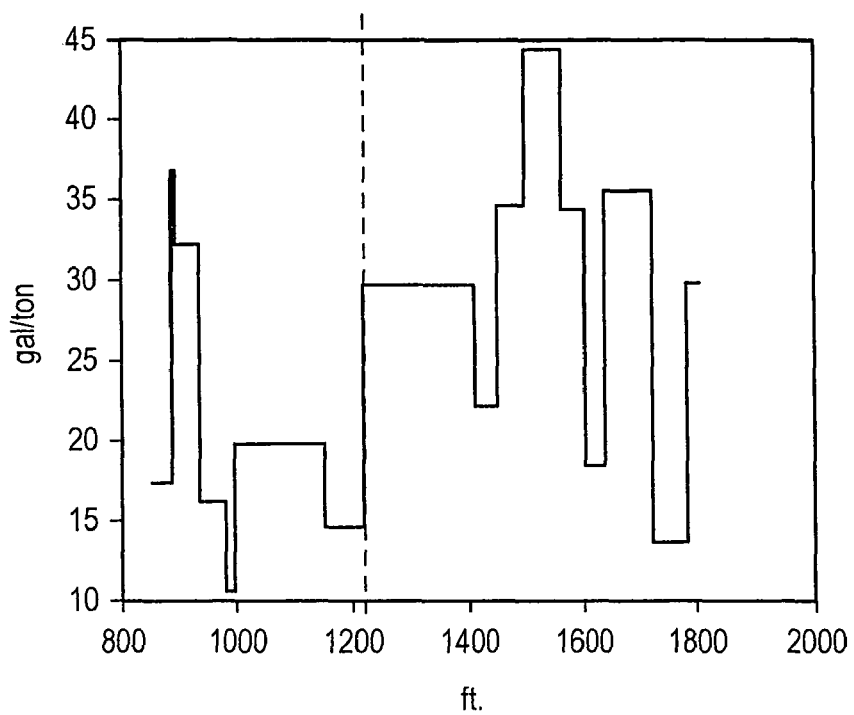

FIG. 222 depicts an example of richness of an oil shale formation (gal/ton) versus depth (ft).

Figure 223:
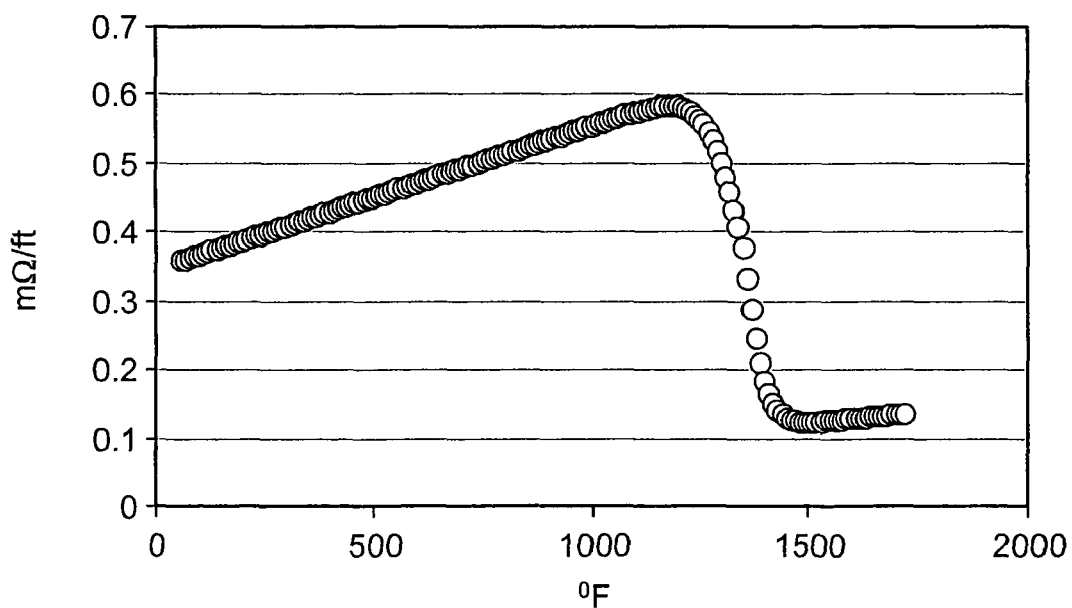

FIG. 223 depicts resistance per foot (mΩ/ft) versus temperature (° F.) profile of a first example of a heater.

Figure 224:
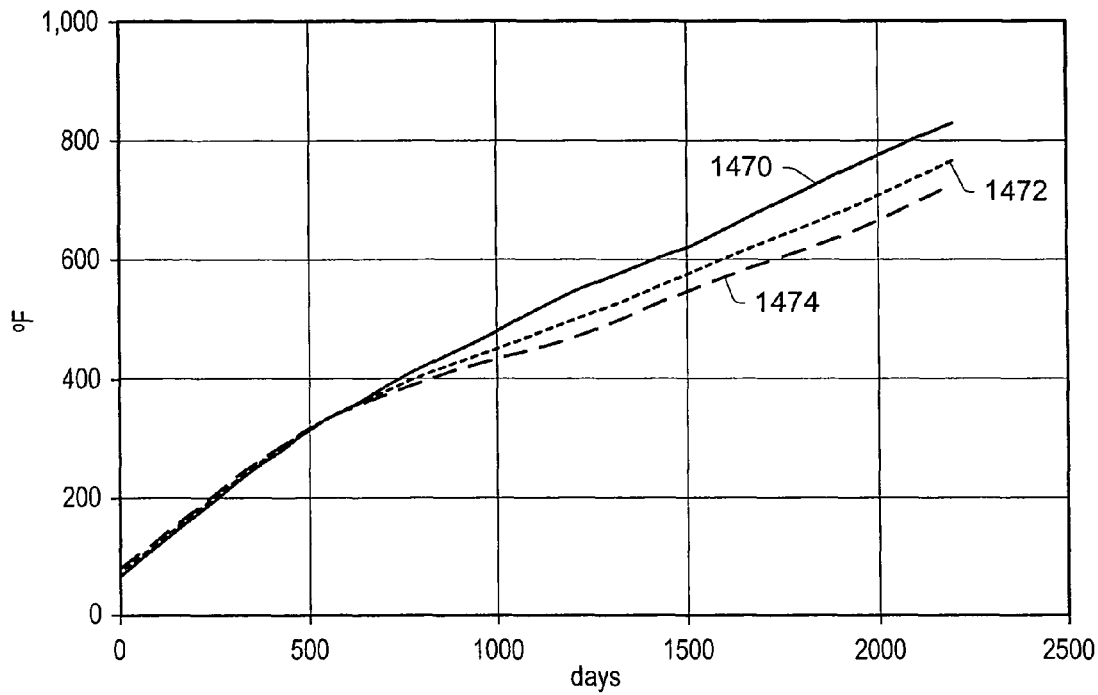

FIG. 224 depicts average temperature in the formation (° F.) versus time (days) as determined by the simulation for the first example.

Figure 225:
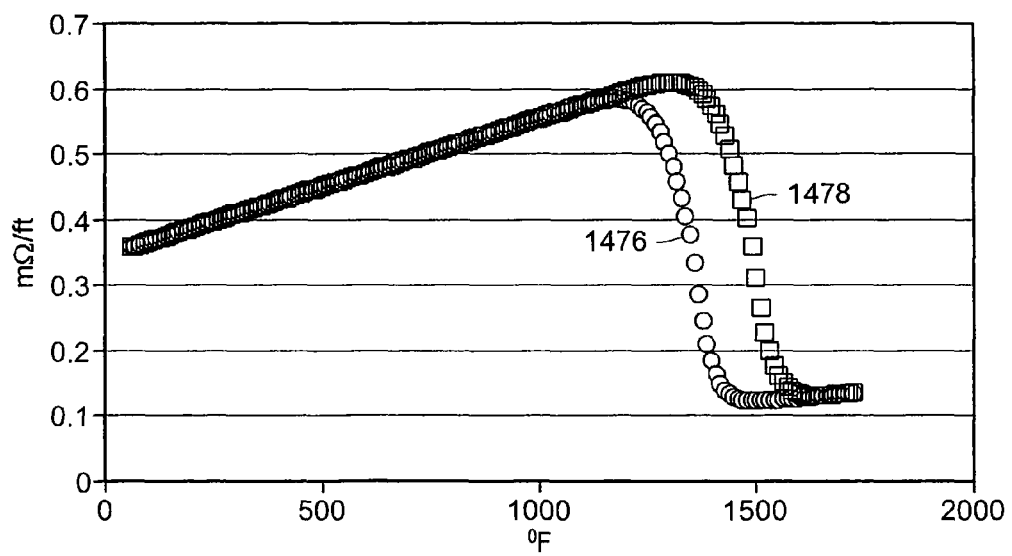

FIG. 225 depicts resistance per foot (mΩ/ft) versus temperature (° F.) for the second heater example.

Figure 226:
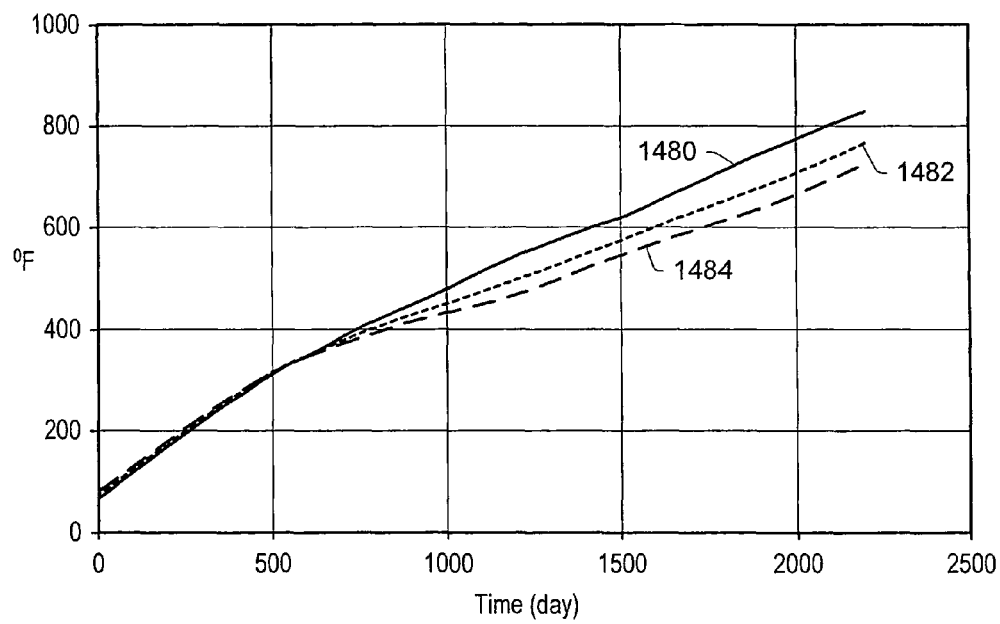

FIG. 226 depicts average temperature in the formation (° F.) versus time (days) as determined by the simulation for the second example.

Figure 227:
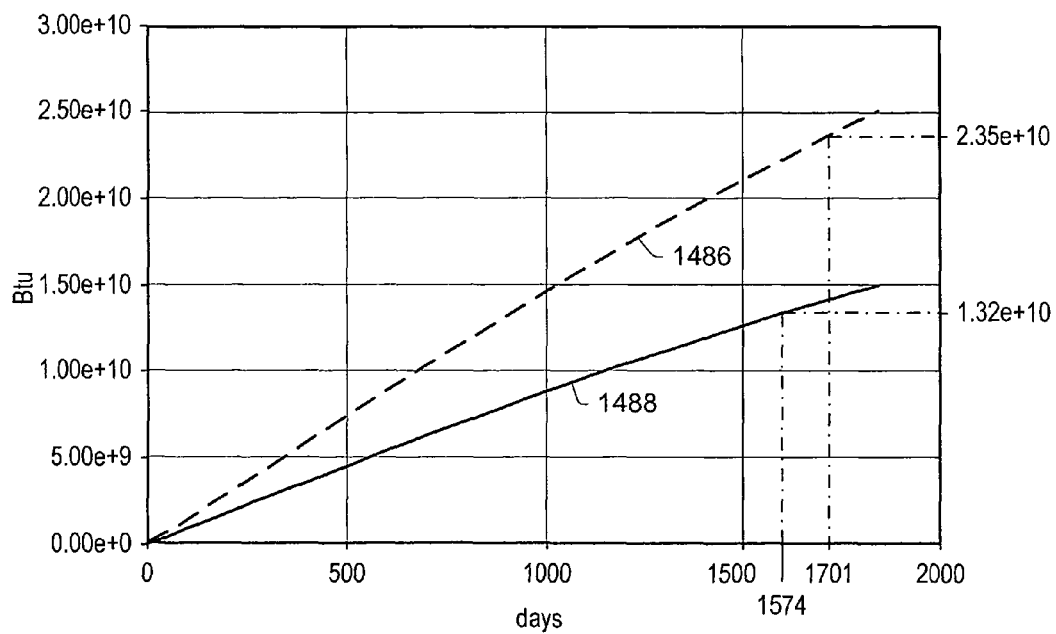

FIG. 227 depicts net heater energy input (Btu) versus time (days) for the second example.

Figure 228:
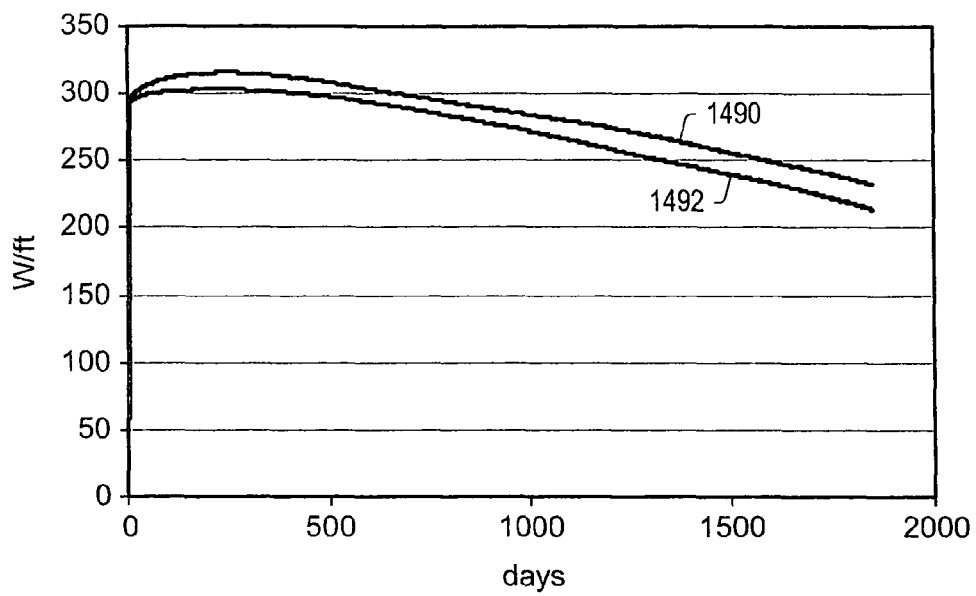

FIG. 228 depicts power injection per foot (W/ft) versus time (days) for the second example.

Figure 229:
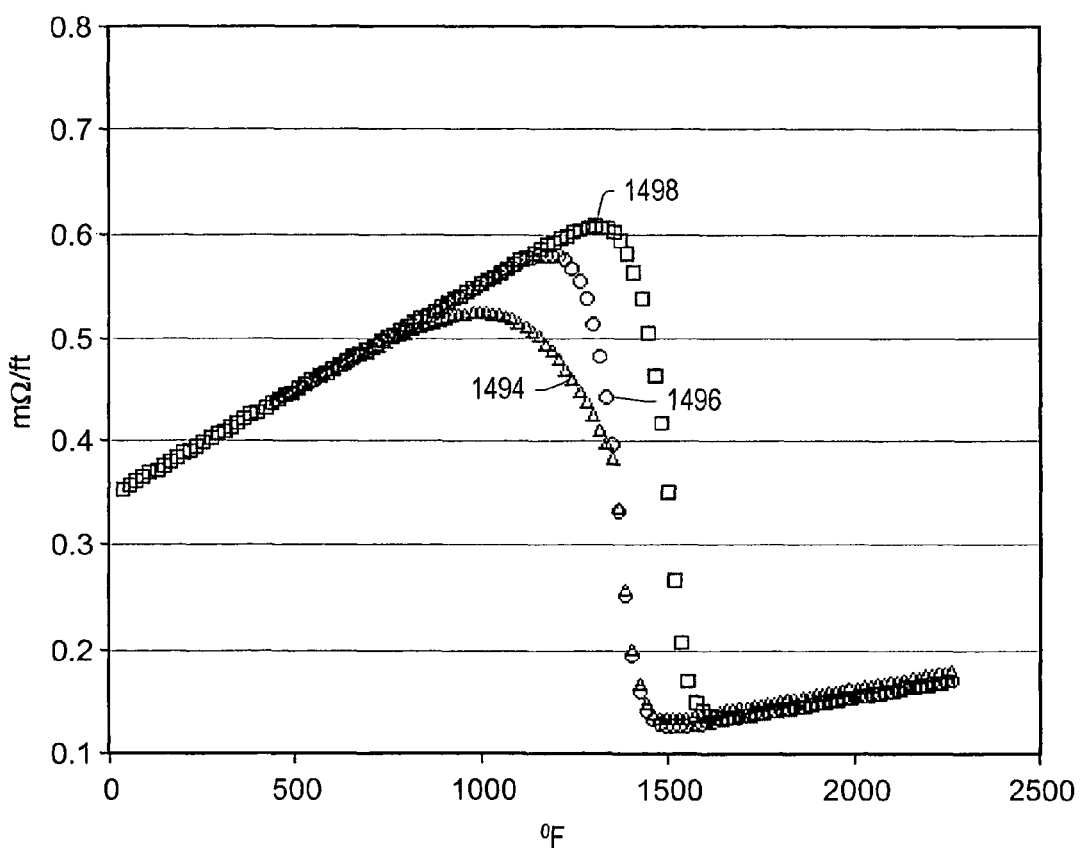

FIG. 229 depicts resistance per foot (mΩ/ft) versus temperature (° F.) for the third heater example.

Figure 230:
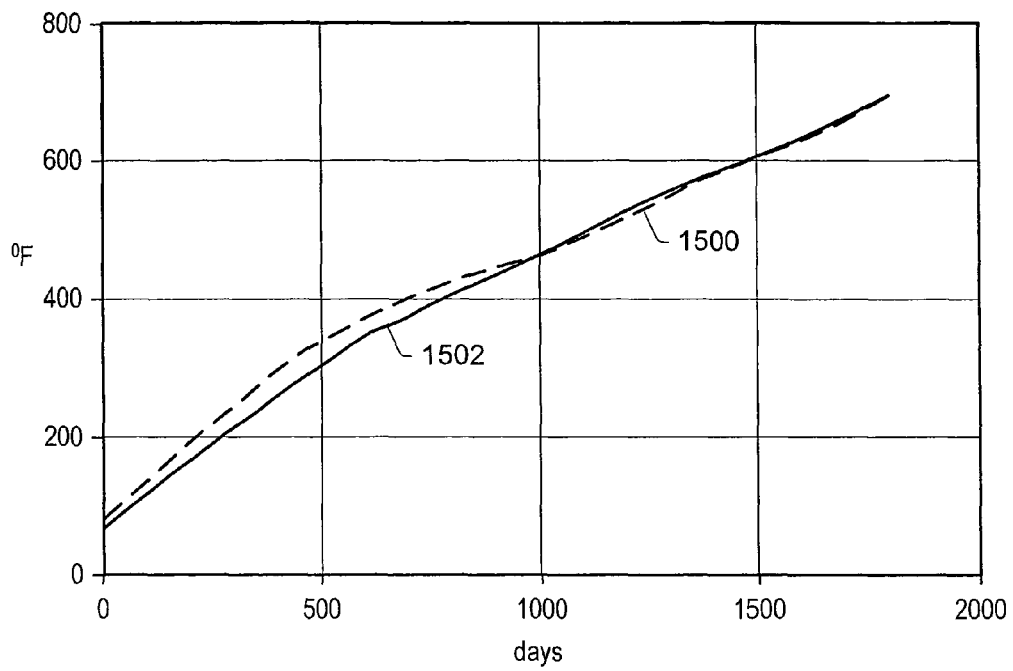

FIG. 230 depicts average temperature in the formation (° F.) versus time (days) as determined by the simulation for the third example.

Figure 231:
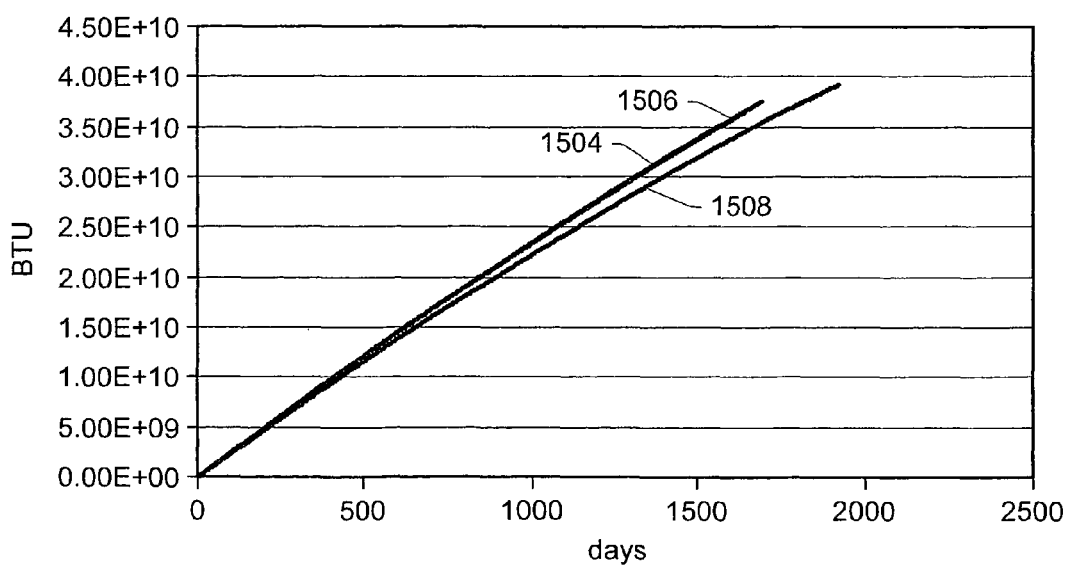

FIG. 231 depicts cumulative energy injection (Btu) versus time (days) for each of the three heater examples.

Figure 232:
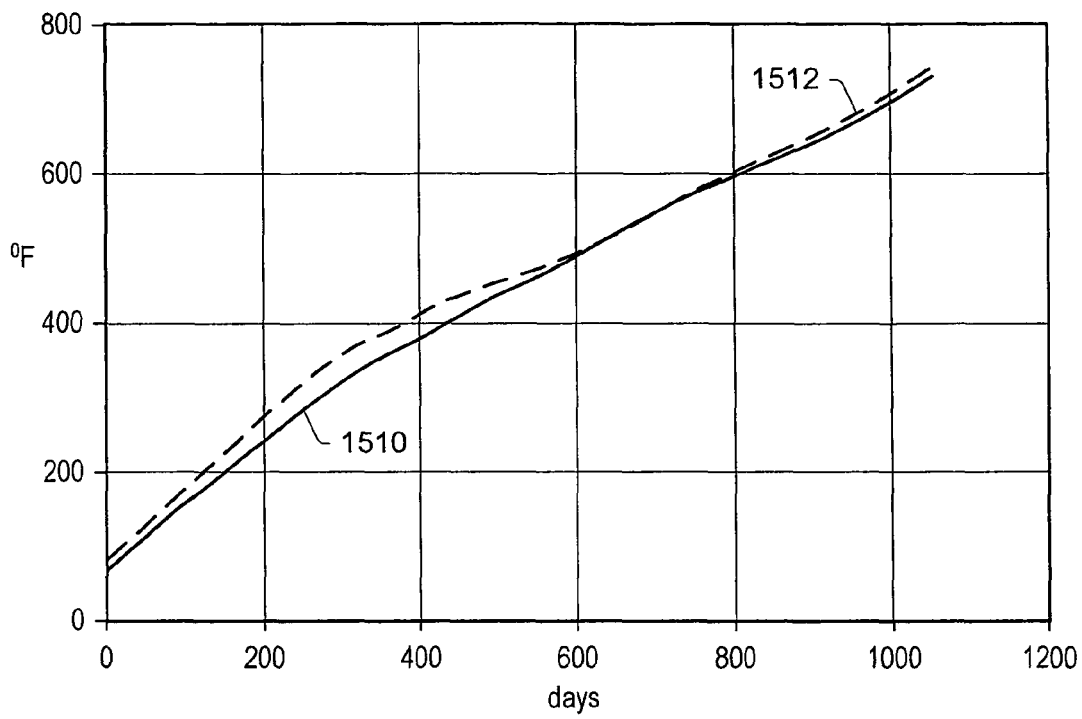

FIG. 232 depicts average temperature (° F.) versus time (days) for the third heater example with a 30 foot spacing between heaters in the formation as determined by the simulation.

Figure 124:
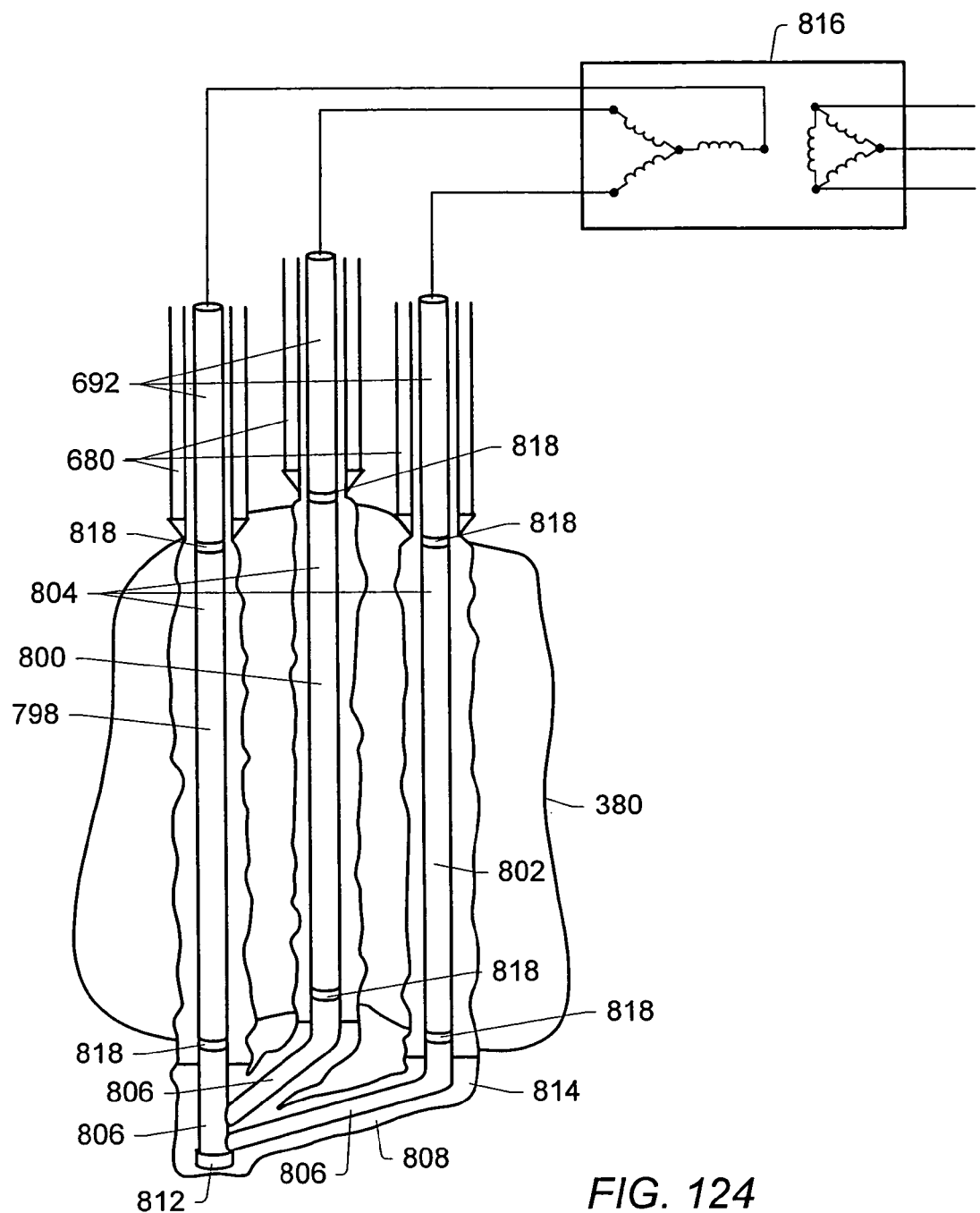
FIG. 124 depicts an embodiment of three heaters coupled in a three-phase configuration.
Figure 126:
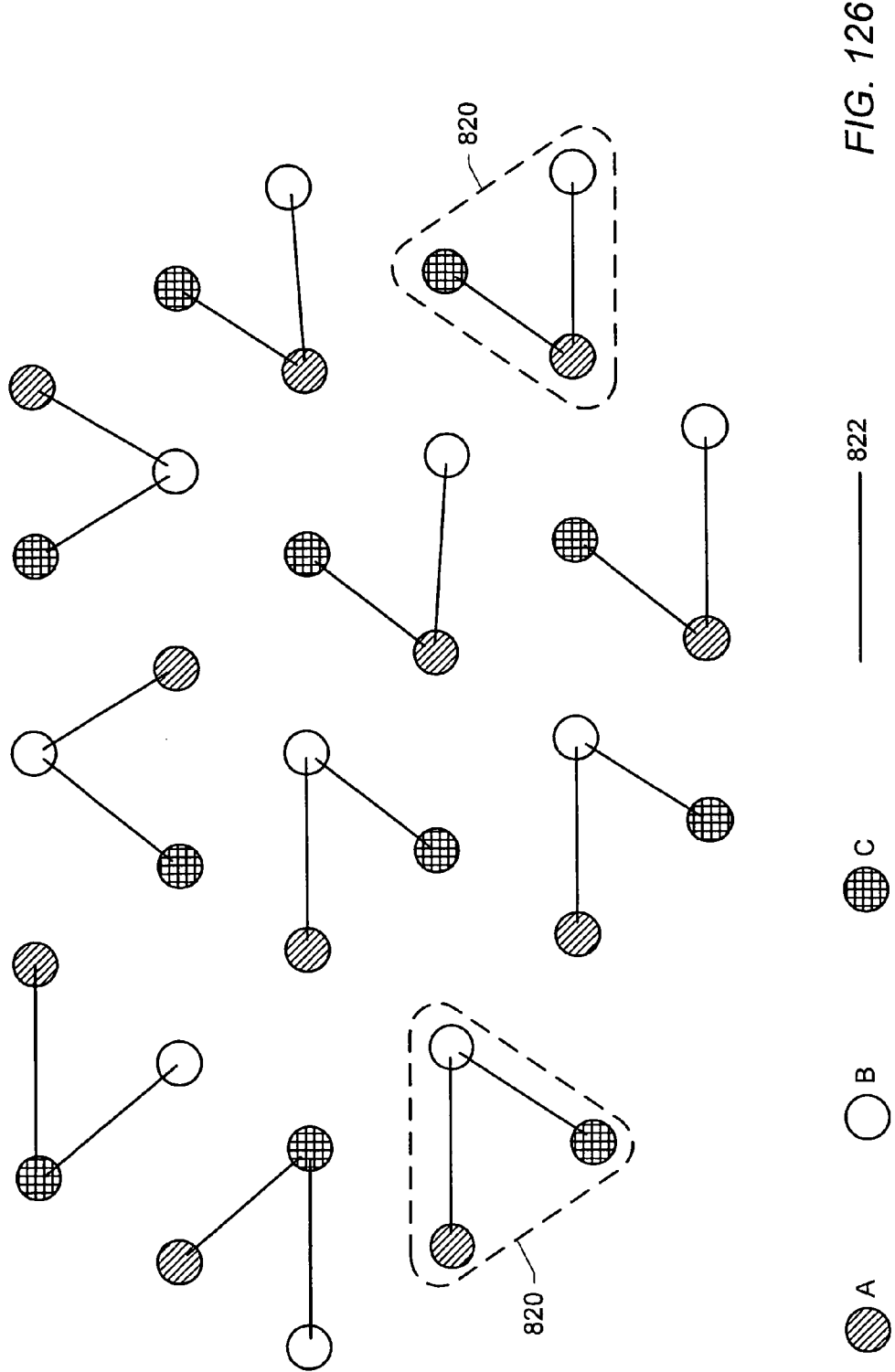
FIG. 126 depicts a top view representation of an embodiment of a plurality of triads of three-phase heaters in a formation.
Figure 233:
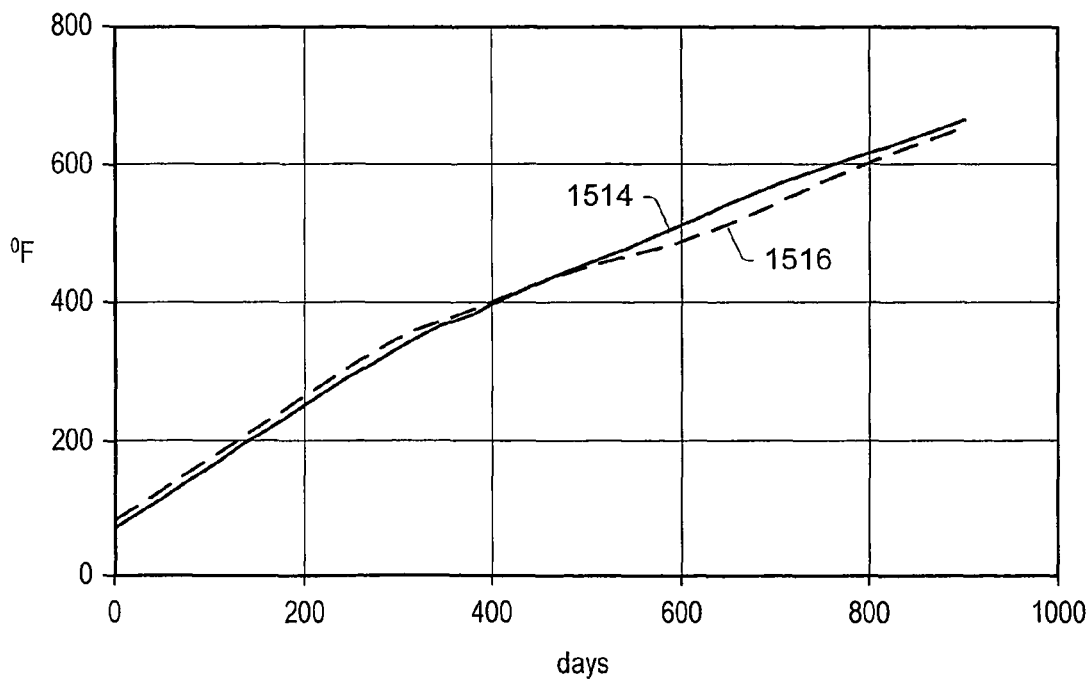

FIG. 233 depicts average temperature (° F.) versus time (days) for the fourth heater example using the heater configuration and pattern depicted in FIGS. 124 and 126 as determined by the simulation.

Figure 234:
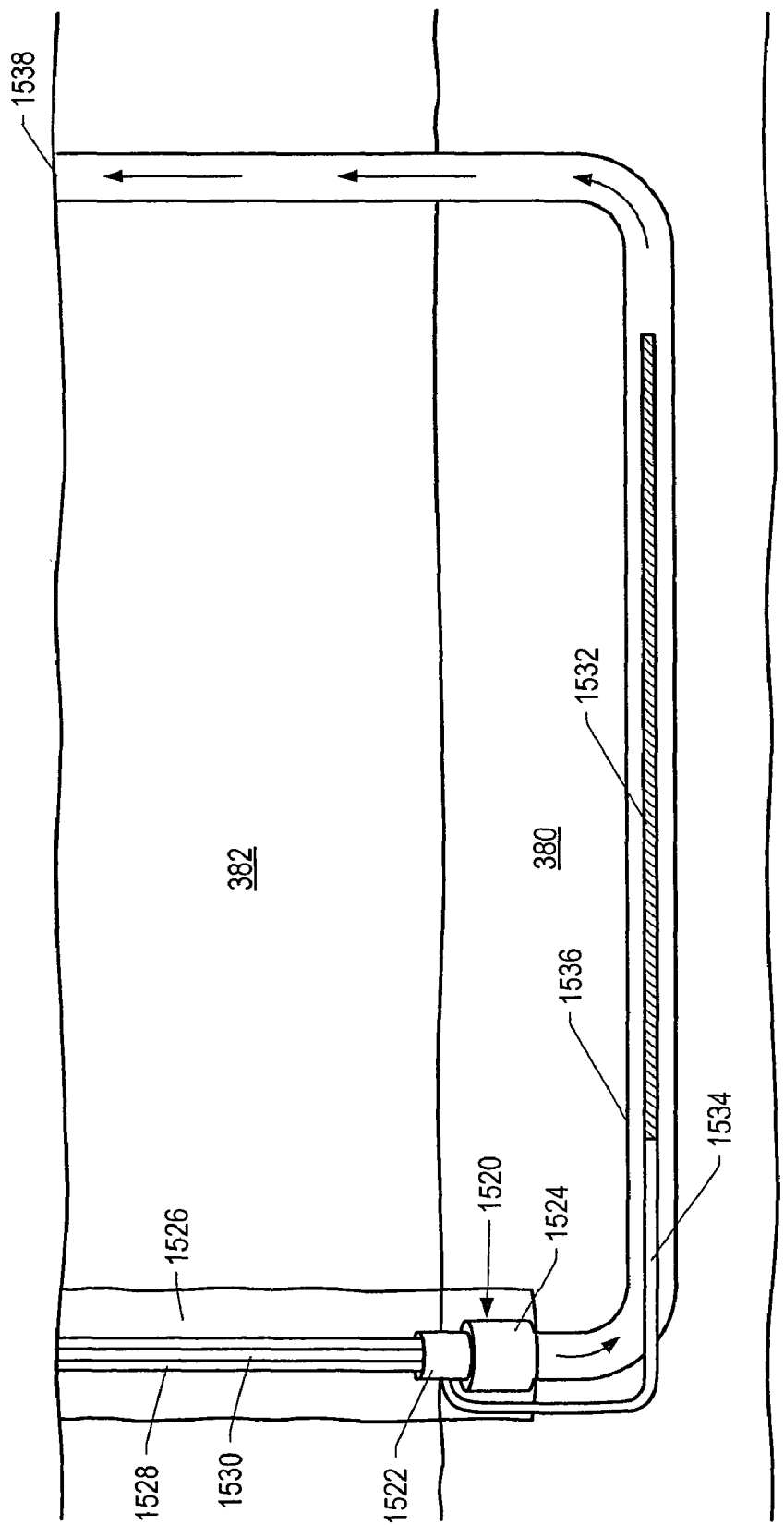

FIG. 234 depicts a schematic representation of an embodiment of a heating system with a downhole gas turbine.

Figure 235:
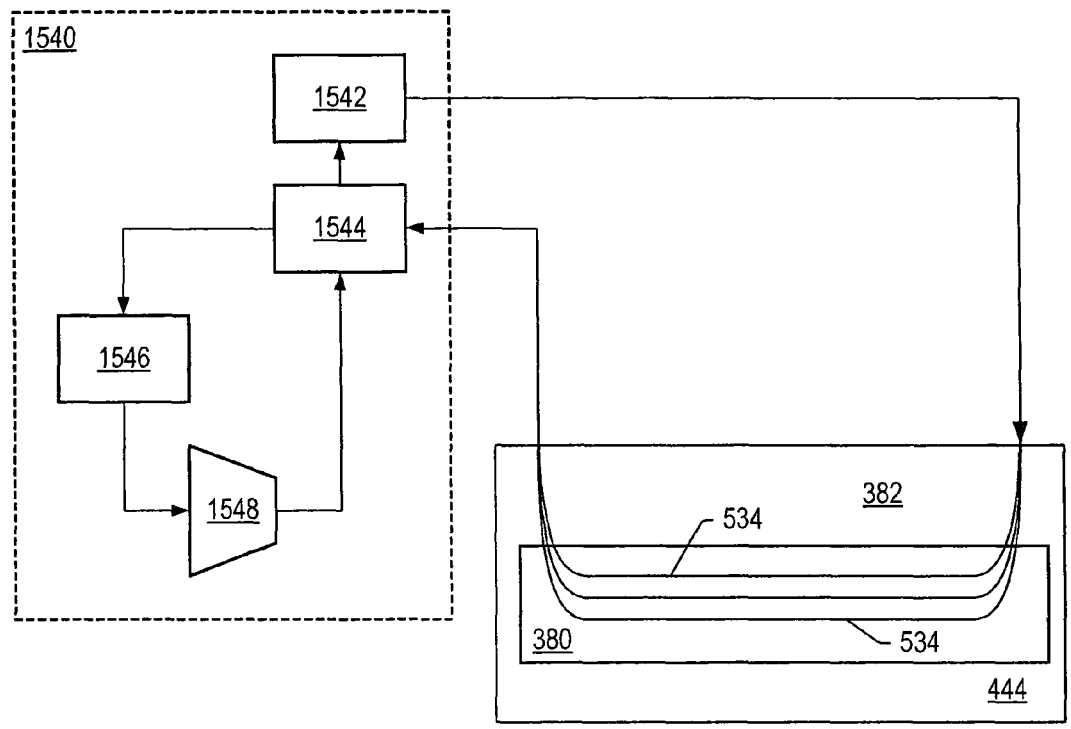

FIG. 235 depicts a schematic representation of a closed loop circulation system for heating a portion of a formation.

Figure 236:
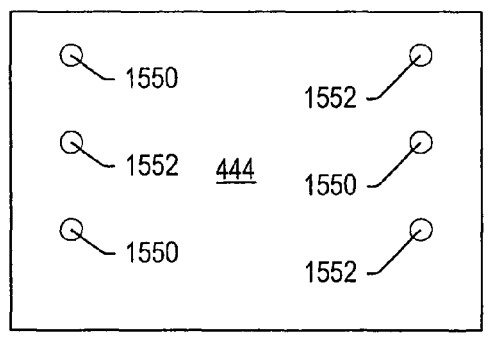

FIG. 236 depicts a plan view of wellbore entries and exits from a portion of a formation to be heated using a closed loop circulation system.

Figure 237:
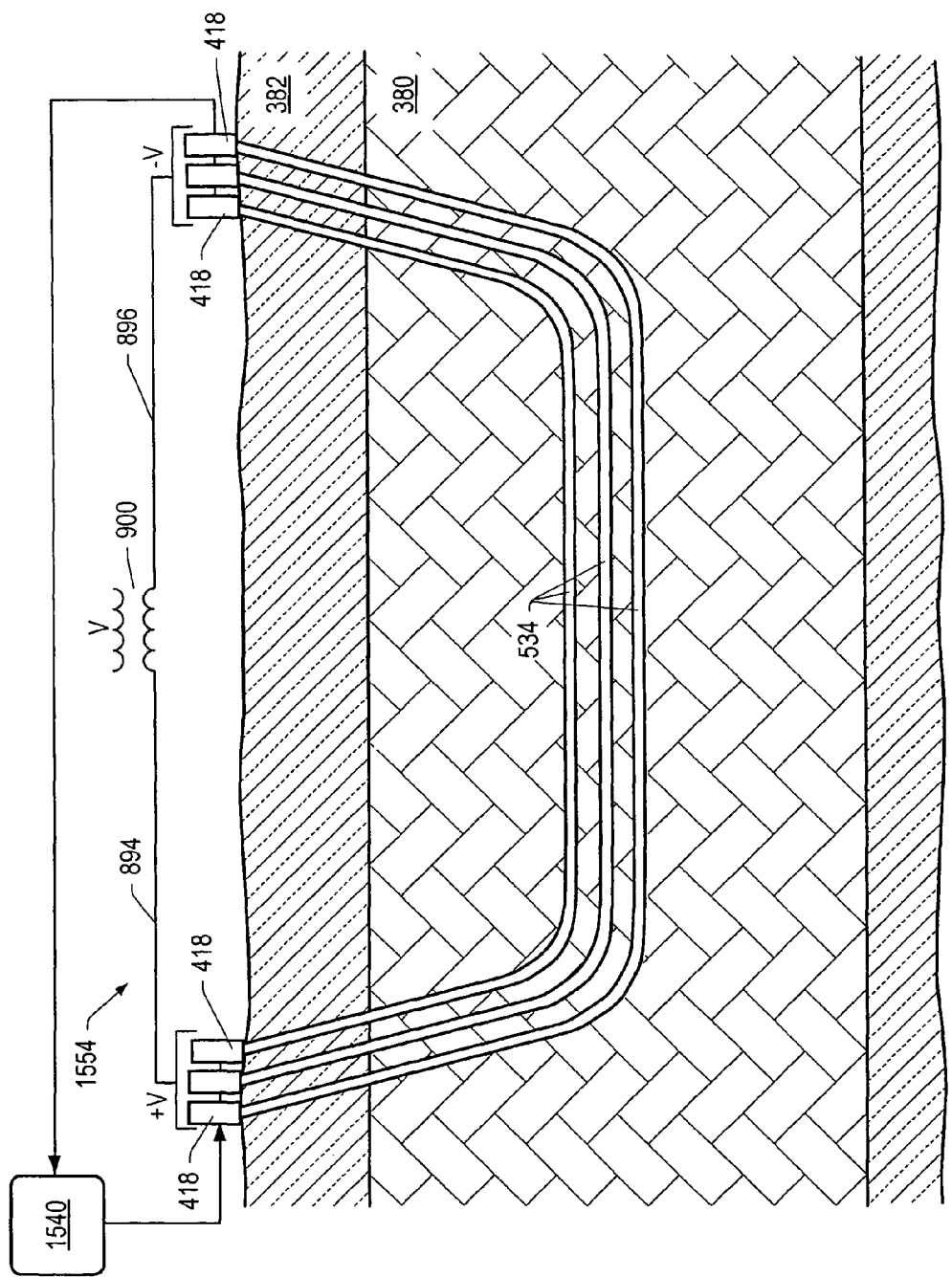

FIG. 237 depicts a side view representation of an embodiment of a system for heating the formation that can use a closed loop circulation system and/or electrical heating.

Figure 238:
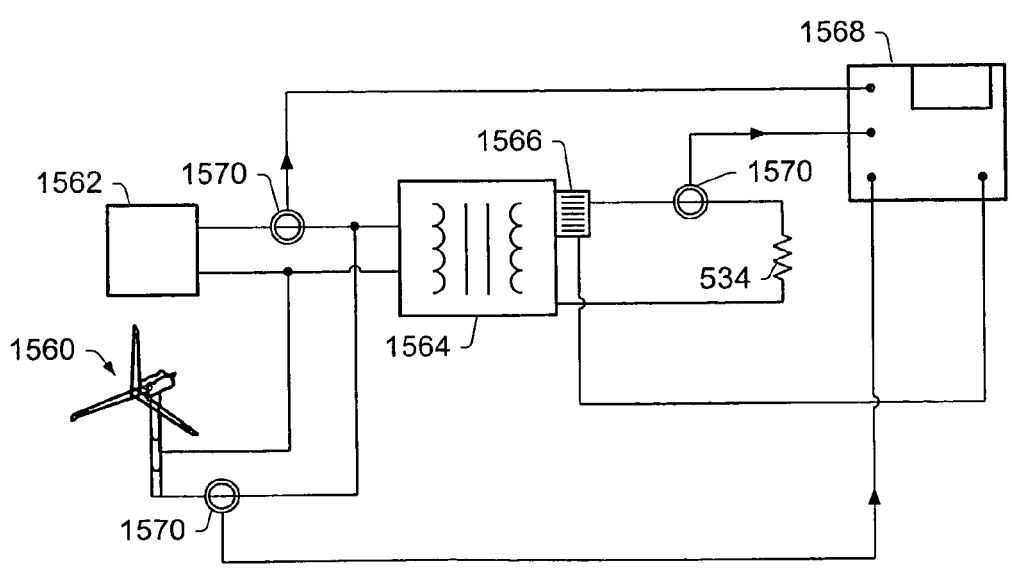

FIG. 238 depicts an embodiment of a windmill for generating electricity for subsurface heaters.

Figure 239:
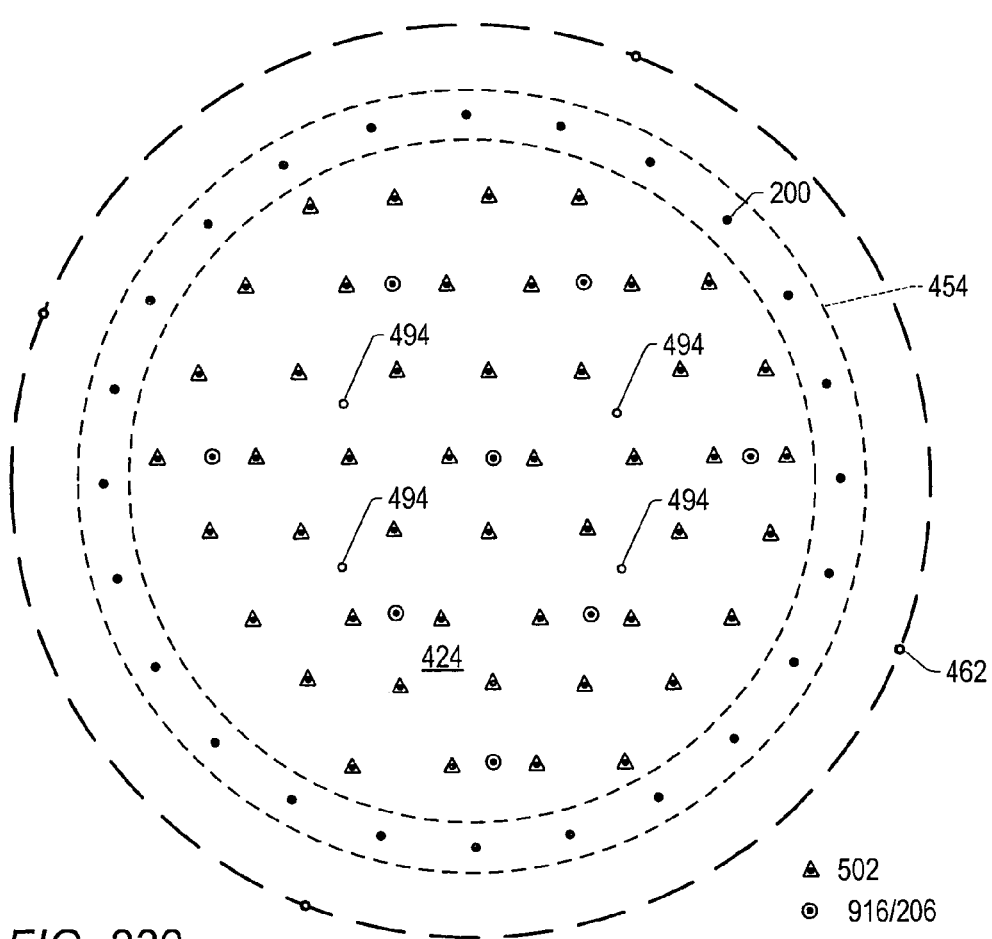

FIG. 239 depicts an embodiment for solution mining a formation.

Figure 240:
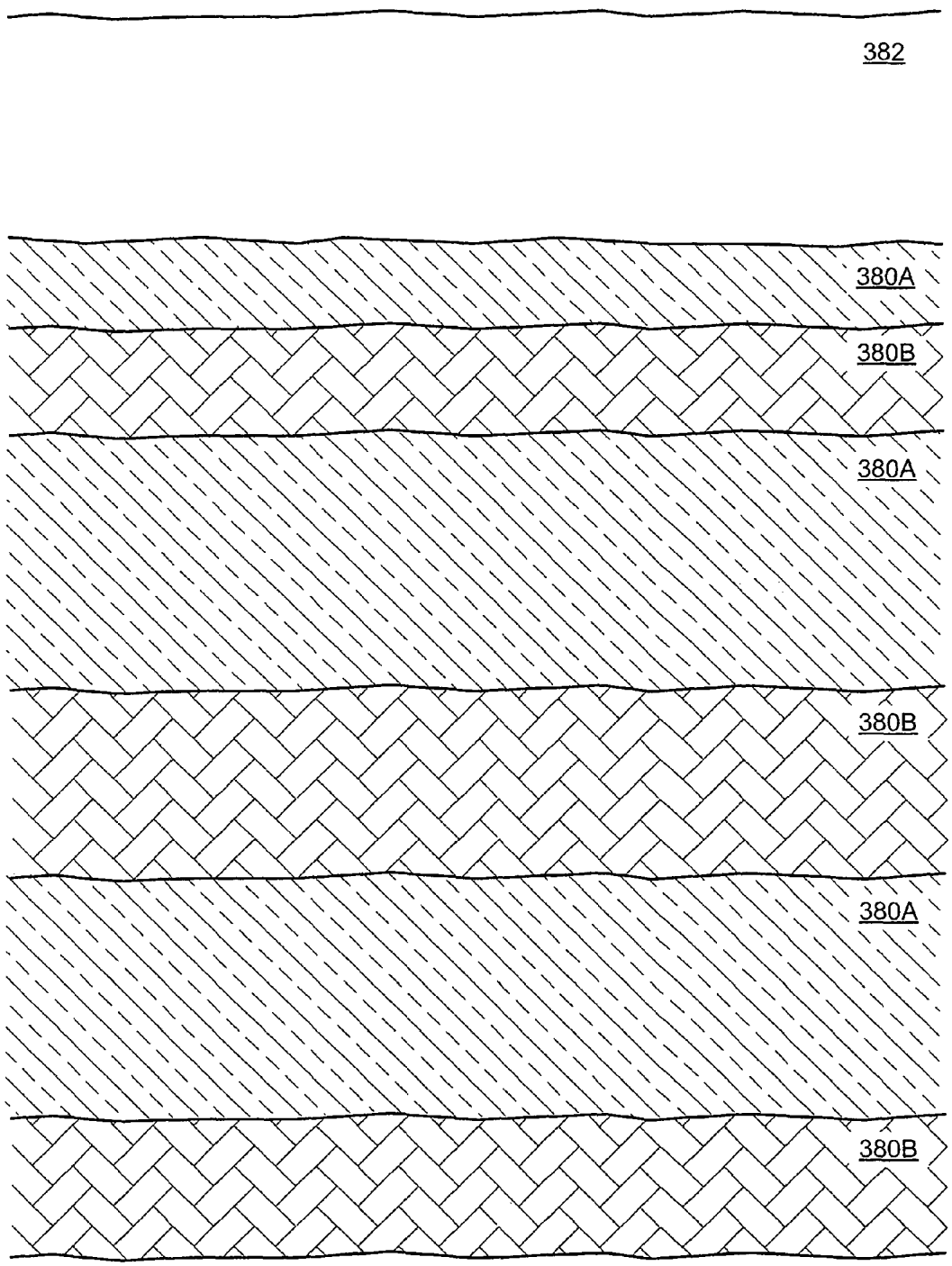

FIG. 240 depicts an embodiment of a formation with nahcolite layers in the formation before solution mining nahcolite from the formation.

Figure 241:
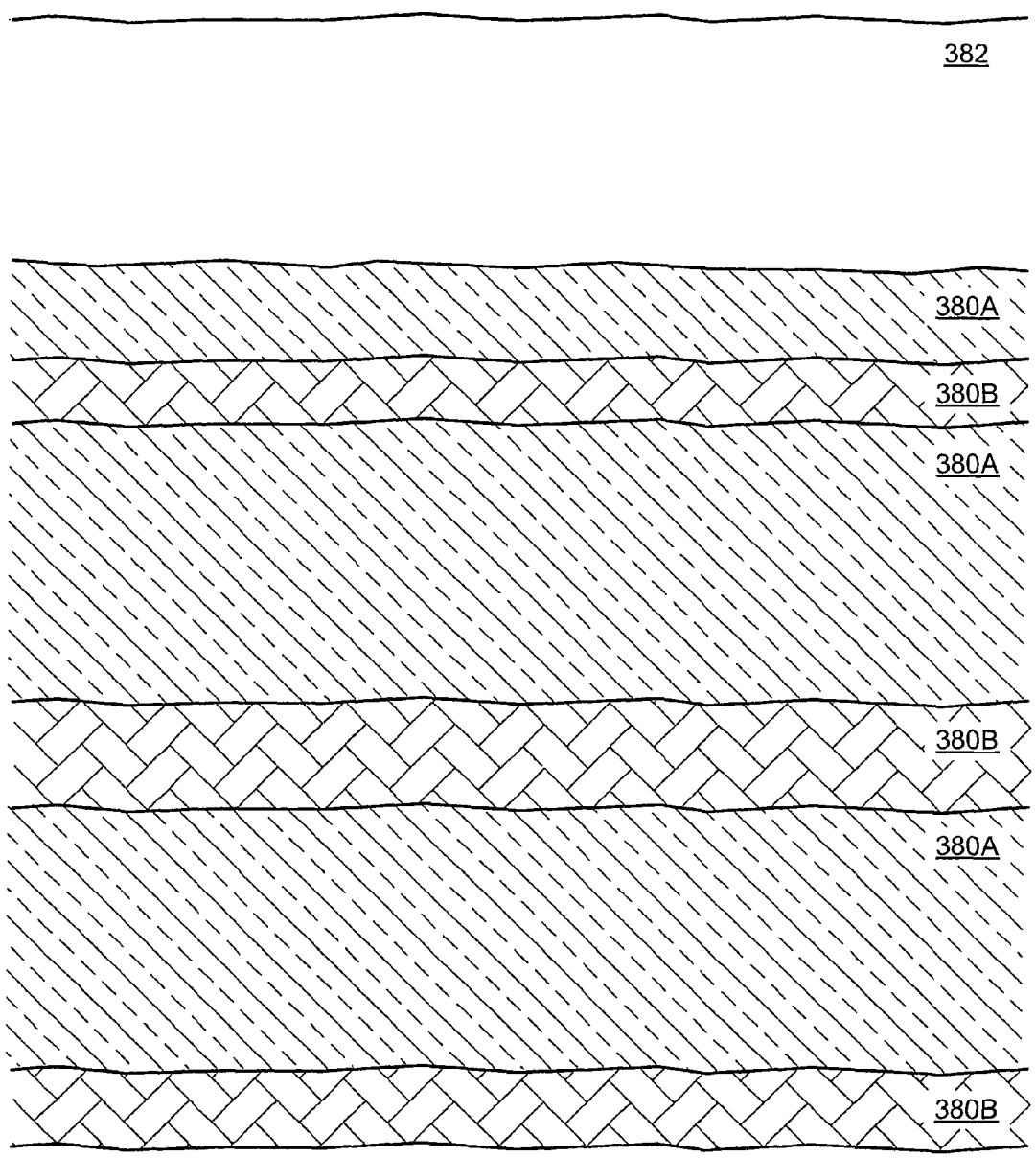

FIG. 241 depicts the formation of FIG. 240 after the nahcolite has been solution mined.

Figure 242:
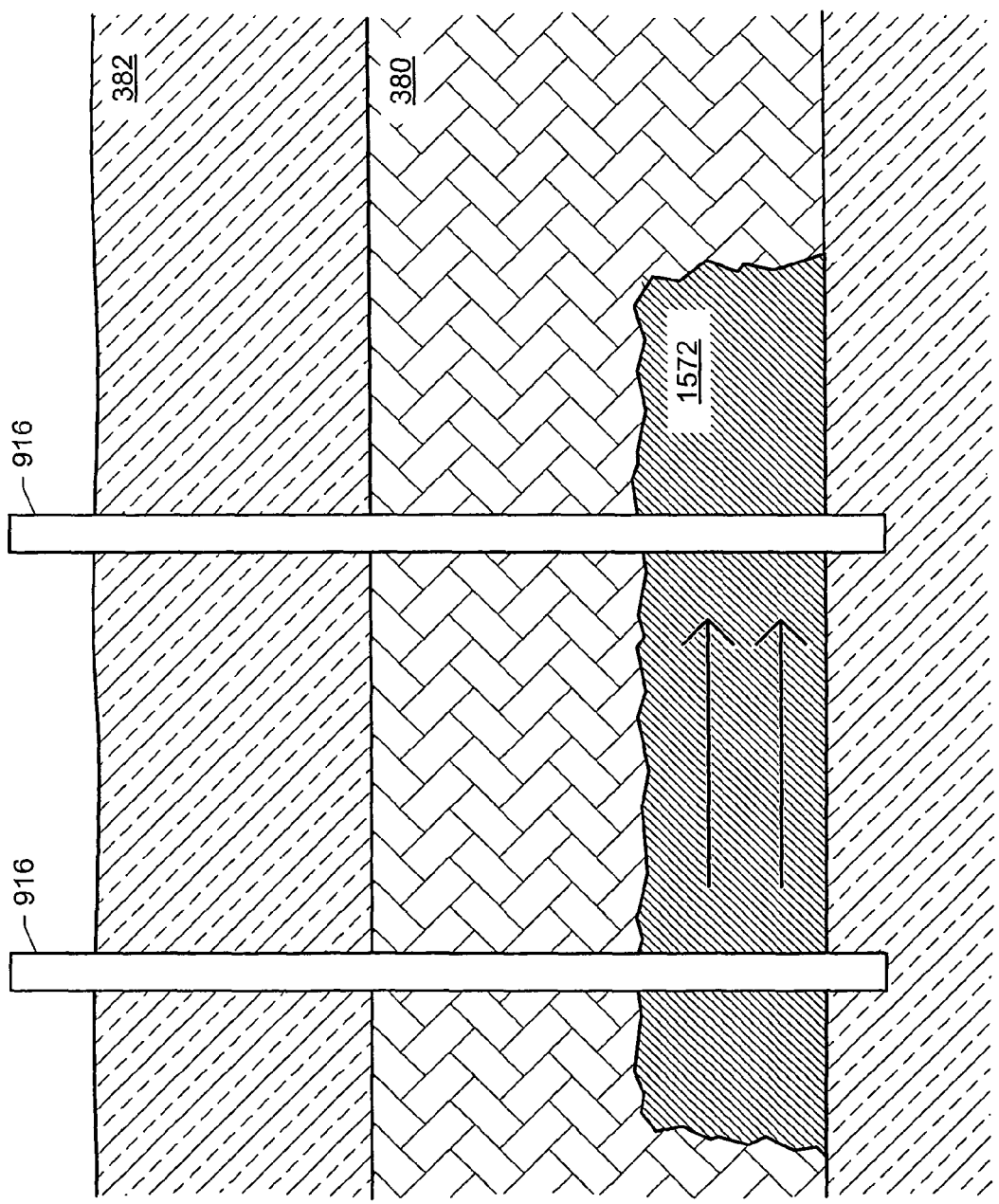

FIG. 242 depicts an embodiment of two injection wells interconnected by a zone that has been solution mined to remove nahcolite from the zone.

Figure 243:
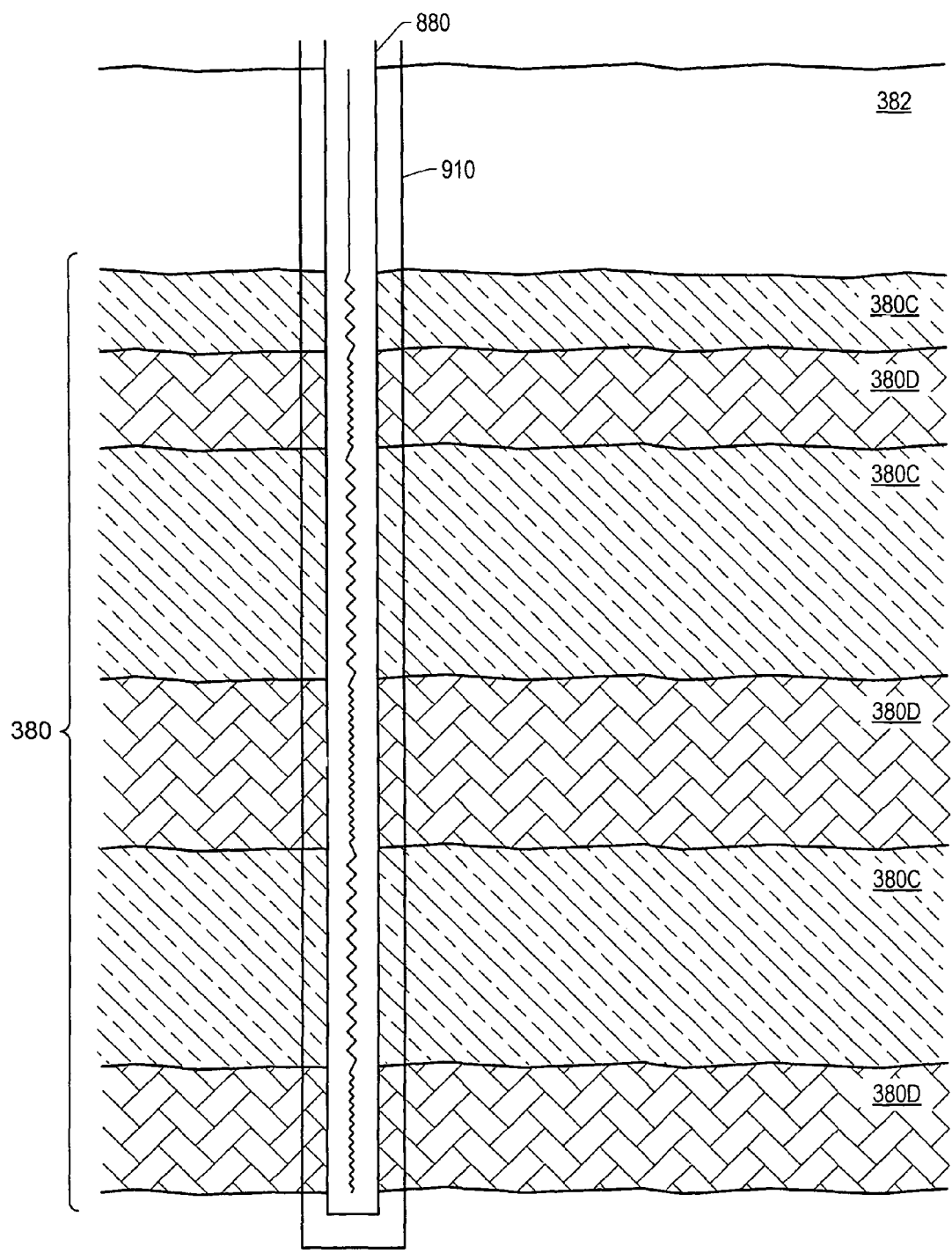

FIG. 243 depicts an embodiment for heating a formation with dawsonite in the formation.

Figure 244:
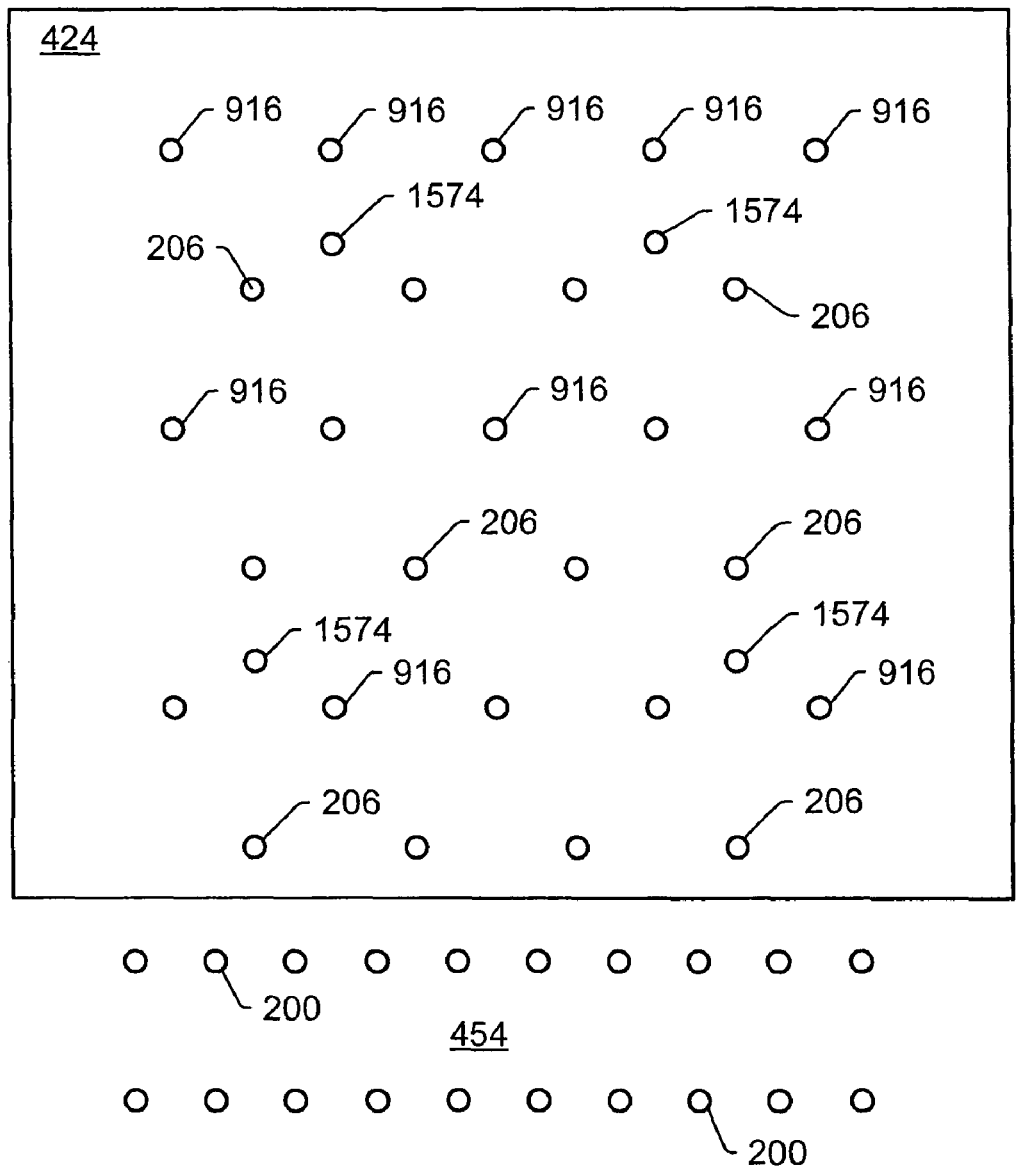

FIG. 244 depicts an embodiment of treating a hydrocarbon containing formation with a combustion front.

Figure 245:
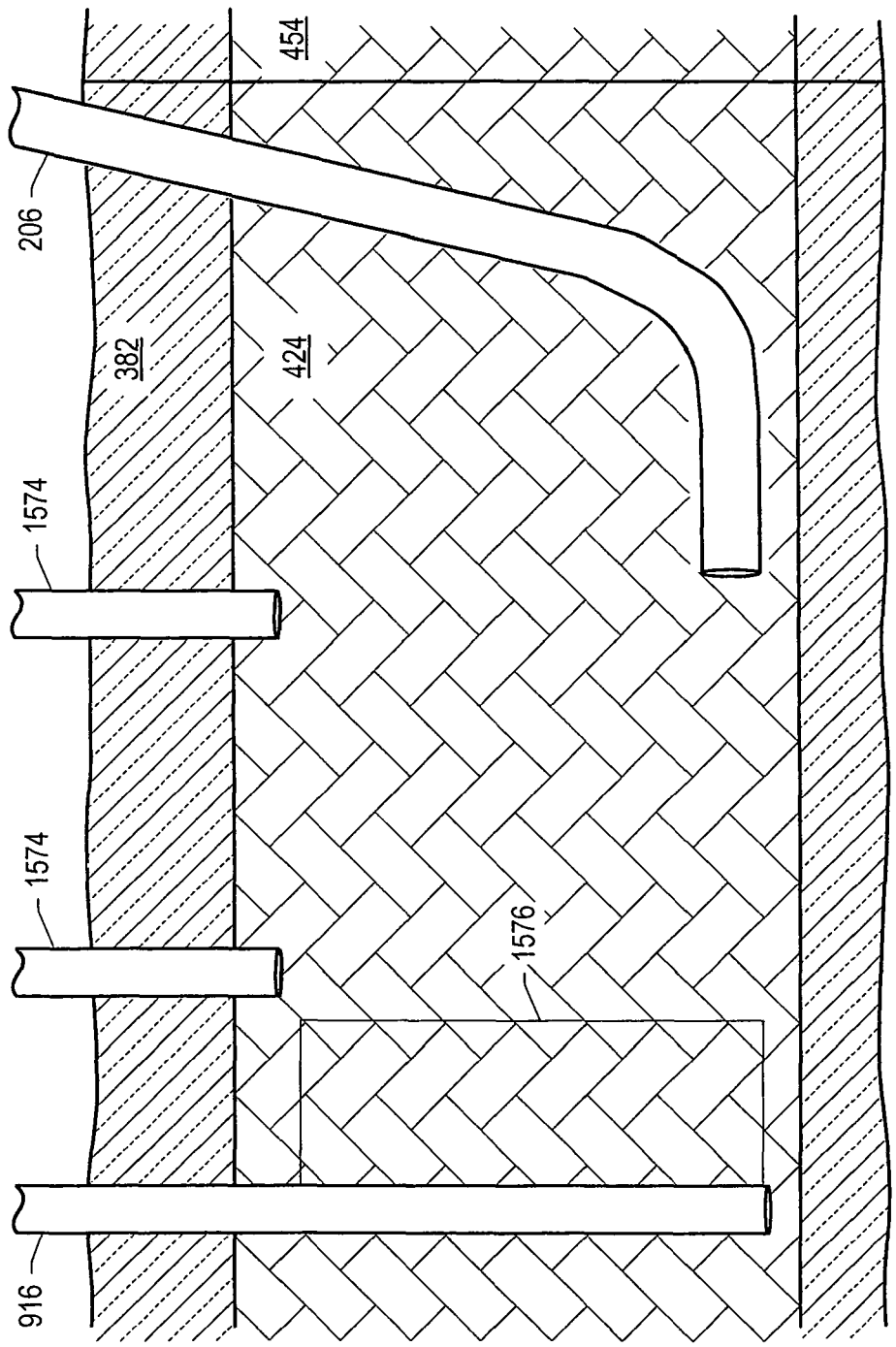

FIG. 245 depicts an embodiment of cross-sectional view of treating a hydrocarbon containing formation with a combustion front.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

The following description generally relates to systems and methods for treating hydrocarbons in the formations. Such formations may be treated to yield hydrocarbon products, hydrogen, and other products.

"Hydrocarbons" are generally defined as molecules formed primarily by carbon and hydrogen atoms. Hydrocarbons may also include other elements such as, but not limited to, halogens, metallic elements, nitrogen, oxygen, and/or sulfur. Hydrocarbons may be, but are not limited to, kerogen, bitumen, pyrobitumen, oils, natural mineral waxes, and asphaltites. Hydrocarbons may be located in or adjacent to mineral matrices in the earth. Matrices may include, but are not limited to, sedimentary rock, sands, silicilytes, carbonates, diatomites, and other porous media. "Hydrocarbon fluids" are fluids that include hydrocarbons. Hydrocarbon fluids may include, entrain, or be entrained in non-hydrocarbon fluids such as hydrogen, nitrogen, carbon monoxide, carbon dioxide, hydrogen sulfide, water, and ammonia.

A "formation" includes one or more hydrocarbon containing layers, one or more non-hydrocarbon layers, an overburden, and/or an underburden. The "overburden" and/or the "underburden" include one or more different types of impermeable materials. For example, overburden and/or underburden may include rock, shale, mudstone, or wet/tight carbonate. In some embodiments of in situ conversion processes, the overburden and/or the underburden may include a hydrocarbon containing layer or hydrocarbon containing layers that are relatively impermeable and are not subjected to temperatures during in situ conversion processing that result in significant characteristic changes of the hydrocarbon containing layers of the overburden and/or the underburden. For example, the underburden may contain shale or mudstone, but the underburden is not allowed to heat to pyrolysis temperatures during the in situ conversion process. In some cases, the overburden and/or the underburden may be somewhat permeable.

"Kerogen" is a solid, insoluble hydrocarbon that has been converted by natural degradation and that principally contains carbon, hydrogen, nitrogen, oxygen, and sulfur. Coal and oil shale are typical examples of materials that contain kerogen. "Bitumen" is a non-crystalline solid or viscous hydrocarbon material that is substantially soluble in carbon disulfide. "Oil" is a fluid containing a mixture of condensable hydrocarbons.

"Formation fluids" refer to fluids present in a formation and may include pyrolyzation fluid, synthesis gas, mobilized hydrocarbon, and water (steam). Formation fluids may include hydrocarbon fluids as well as non-hydrocarbon fluids. The term "mobilized fluid" refers to fluids in a hydrocarbon containing formation that are able to flow as a result of thermal treatment of the formation. "Produced fluids" refer to fluids removed from the formation.

"Thermally conductive fluid" includes fluid that has a higher thermal conductivity than air at standard temperature and pressure (STP) (0° C. and 101.325 kPa).

"Carbon number" refers to the number of carbon atoms in a molecule. A hydrocarbon fluid may include various hydrocarbons with different carbon numbers. The hydrocarbon fluid may be described by a carbon number distribution. Carbon numbers and/or carbon number distributions may be determined by true boiling point distribution and/or gas-liquid chromatography.

A "heat source" is any system for providing heat to at least a portion of a formation substantially by conductive and/or radiative heat transfer. For example, a heat source may include electric heaters such as an insulated conductor, an elongated member, and/or a conductor disposed in a conduit. A heat source may also include systems that generate heat by burning a fuel external to or in a formation. The systems may be surface burners, downhole gas burners, flameless distributed combustors, and natural distributed combustors. In some embodiments, heat provided to or generated in one or more heat sources may be supplied by other sources of energy. The other sources of energy may directly heat a formation, or the energy may be applied to a transfer medium that directly or indirectly heats the formation. It is to be understood that one or more heat sources that are applying heat to a formation may use different sources of energy. Thus, for example, for a given formation some heat sources may supply heat from electric resistance heaters, some heat sources may provide heat from combustion, and some heat sources may provide heat from one or more other energy sources (for example, chemical reactions, solar energy, wind energy, biomass, or other sources of renewable energy). A chemical reaction may include an exothermic reaction (for example, an oxidation reaction). A heat source may also include a heater that provides heat to a zone proximate and/or surrounding a heating location such as a heater well.

A "heater" is any system or heat source for generating heat in a well or a near wellbore region. Heaters may be, but are not limited to, electric heaters, burners, combustors that react with material in or produced from a formation, and/or combinations thereof.

An "in situ conversion process" refers to a process of heating a hydrocarbon containing formation from heat sources to raise the temperature of at least a portion of the formation above a pyrolysis temperature so that pyrolyzation fluid is produced in the formation.

"Insulated conductor" refers to any elongated material that is able to conduct electricity and that is covered, in whole or in part, by an electrically insulating material.

An elongated member may be a bare metal heater or an exposed metal heater. "Bare metal" and "exposed metal" refer to metals that do not include a layer of electrical insulation, such as mineral insulation, that is designed to provide electrical insulation for the metal throughout an operating temperature range of the elongated member. Bare metal and exposed metal may encompass a metal that includes a corrosion inhibiter such as a naturally occurring oxidation layer, an applied oxidation layer, and/or a film. Bare metal and exposed metal include metals with polymeric or other types of electrical insulation that cannot retain electrical insulating properties at typical operating temperature of the elongated member. Such material may be placed on the metal and may be thermally degraded during use of the heater.

"Temperature limited heater" generally refers to a heater that regulates heat output (for example, reduces heat output) above a specified temperature without the use of external controls such as temperature controllers, power regulators, rectifiers, or other devices. Temperature limited heaters may be AC (alternating current) or modulated (for example, "chopped") DC (direct current) powered electrical resistance heaters.

"Curie temperature" is the temperature above which a ferromagnetic material loses all of its ferromagnetic properties. In addition to losing all of its ferromagnetic properties above the Curie temperature, the ferromagnetic material begins to lose its ferromagnetic properties when an increasing electrical current is passed through the ferromagnetic material.

"Time-varying current" refers to electrical current that produces skin effect electricity flow in a ferromagnetic conductor and has a magnitude that varies with time. Time-varying current includes both alternating current (AC) and modulated direct current (DC).

"Alternating current (AC)" refers to a time-varying current that reverses direction substantially sinusoidally. AC produces skin effect electricity flow in a ferromagnetic conductor.

"Modulated direct current (DC)" refers to any substantially non-sinusoidal time-varying current that produces skin effect electricity flow in a ferromagnetic conductor.

"Turndown ratio" for the temperature limited heater is the ratio of the highest AC or modulated DC resistance below the Curie temperature to the lowest resistance above the Curie temperature for a given current.

In the context of reduced heat output heating systems, apparatus, and methods, the term "automatically" means such systems, apparatus, and methods function in a certain way without the use of external control (for example, external controllers such as a controller with a temperature sensor and a feedback loop, PID controller, or predictive controller).

"Nitride" refers to a compound of nitrogen and one or more other elements of the Periodic Table. Nitrides include, but are not limited to, silicon nitride, boron nitride, or alumina nitride.

The term "wellbore" refers to a hole in a formation made by drilling or insertion of a conduit into the formation. A wellbore may have a substantially circular cross section, or another cross-sectional shape. As used herein, the terms "well" and "opening," when referring to an opening in the formation may be used interchangeably with the term "wellbore."

A "u-shaped wellbore" refers to a wellbore that extends from a first opening in the formation, through at least a portion of the formation, and out through a second opening in the formation. In this context, the wellbore may be only roughly in the shape of a "v" or "u", with the understanding that the "legs" of the "u" do not need to be parallel to each other, or perpendicular to the "bottom" of the "u" for the wellbore to be considered "u-shaped".

"Triad" refers to a group of three items (for example, heaters, wellbores, or other objects) coupled together.

"Orifices" refer to openings, such as openings in conduits, having a wide variety of sizes and cross-sectional shapes including, but not limited to, circles, ovals, squares, rectangles, triangles, slits, or other regular or irregular shapes.

"Pyrolysis" is the breaking of chemical bonds due to the application of heat. For example, pyrolysis may include transforming a compound into one or more other substances by heat alone. Heat may be transferred to a section of the formation to cause pyrolysis.

"Pyrolyzation fluids" or "pyrolysis products" refers to fluid produced substantially during pyrolysis of hydrocarbons. Fluid produced by pyrolysis reactions may mix with other fluids in a formation. The mixture would be considered pyrolyzation fluid or pyrolyzation product. As used herein, "pyrolysis zone" refers to a volume of a formation (for example, a relatively permeable formation such as a tar sands formation) that is reacted or reacting to form a pyrolyzation fluid.

"Cracking" refers to a process involving decomposition and molecular recombination of organic compounds to produce a greater number of molecules than were initially present. In cracking, a series of reactions take place accompanied by a transfer of hydrogen atoms between molecules. For example, naphtha may undergo a thermal cracking reaction to form ethene and $H_2$.

"Clogging" refers to impeding and/or inhibiting flow of one or more compositions through a process vessel or a conduit.

"Superposition of heat" refers to providing heat from two or more heat sources to a selected section of a formation such that the temperature of the formation at least at one location between the heat sources is influenced by the heat sources.

"Thermal conductivity" is a property of a material that describes the rate at which heat flows, in steady state, between two surfaces of the material for a given temperature difference between the two surfaces.

"Fluid pressure" is a pressure generated by a fluid in a formation. "Lithostatic pressure" (sometimes referred to as "lithostatic stress") is a pressure in a formation equal to a weight per unit area of an overlying rock mass. "Hydrostatic pressure" is a pressure in a formation exerted by a column of water.

"Condensable hydrocarbons" are hydrocarbons that condense at 25° C. and one atmosphere absolute pressure. Condensable hydrocarbons may include a mixture of hydrocarbons having carbon numbers greater than 4. "Non-condensable hydrocarbons" are hydrocarbons that do not condense at 25° C. and one atmosphere absolute pressure. Non-condensable hydrocarbons may include hydrocarbons having carbon numbers less than 5.

"Olefins" are molecules that include unsaturated hydrocarbons having one or more non-aromatic carbon-carbon double bonds.

"Naphtha" refers to hydrocarbon components with a boiling range distribution between 38° C. and 200° C. at 0.101 MPa. Naphtha content is determined by American Standard Testing and Materials (ASTM) Method D5307.

"Kerosene" refers to hydrocarbons with a boiling range distribution between 204° C. and 260° C. at 0.101 MPa. Kerosene content is determined by ASTM Method D2887.

"Diesel" refers to hydrocarbons with a boiling range distribution between 260° C. and 343° C. (500-650° F.) at 0.101 MPa. Diesel content is determined by ASTM Method D2887.

"VGO" or "vacuum gas oil" refers to hydrocarbons with a boiling range distribution between 343° C. and 538° C. at 0.101 MPa. VGO content is determined by ASTM Method D5307.

"API gravity" refers to API gravity at 15.5° C. (60° F.). API gravity is as determined by ASTM Method D6822.

"Synthesis gas" is a mixture including hydrogen and carbon monoxide. Additional components of synthesis gas may include water, carbon dioxide, nitrogen, methane, and other gases. Synthesis gas may be generated by a variety of processes and feedstocks. Synthesis gas may be used for synthesizing a wide range of compounds.

"Subsidence" is a downward movement of a portion of a formation relative to an initial elevation of the surface.

"Thickness" of a layer refers to the thickness of a cross section of the layer, wherein the cross section is normal to a face of the layer.

"Coring" is a process that generally includes drilling a hole into a formation and removing a substantially solid mass of the formation from the hole.

"Enriched air" refers to air having a larger mole fraction of oxygen than air in the atmosphere. Air is typically enriched to increase combustion-supporting ability of the air.

"Rich layers" in a hydrocarbon containing formation are relatively thin layers (typically about 0.2 m to about 0.5 m thick). Rich layers generally have a richness of about 0.150 L/kg or greater. Some rich layers have a richness of about 0.170 L/kg or greater, of about 0.190 L/kg or greater, or of about 0.210 L/kg or greater. Lean layers of the formation have a richness of about 0.100 L/kg or less and are generally thicker than rich layers. The richness and locations of layers are determined, for example, by coring and subsequent Fischer assay of the core, density or neutron logging, or other logging methods. Rich layers have a lower initial thermal conductivity than other layers of the formation. Typically, rich layers have a thermal conductivity 1.5 times to 3 times lower than the thermal conductivity of lean layers. In addition, rich layers have a higher thermal expansion coefficient than lean layers of the formation.

"Heavy hydrocarbons" are viscous hydrocarbon fluids. Heavy hydrocarbons may include highly viscous hydrocarbon fluids such as heavy oil, tar, and/or asphalt. Heavy hydrocarbons may include carbon and hydrogen, as well as smaller concentrations of sulfur, oxygen, and nitrogen. Additional elements may also be present in heavy hydrocarbons in trace amounts. Heavy hydrocarbons may be classified by API gravity. Heavy hydrocarbons generally have an API gravity below about 20°. Heavy oil, for example, generally has an API gravity of about 10-20°, whereas tar generally has an API gravity below about 10°. The viscosity of heavy hydrocarbons is generally greater than about 100 centipoise at 15° C. Heavy hydrocarbons may include aromatics or other complex ring hydrocarbons.

Heavy hydrocarbons may be found in a relatively permeable formation. The relatively permeable formation may include heavy hydrocarbons entrained in, for example, sand or carbonate. "Relatively permeable" is defined, with respect to formations or portions thereof, as an average permeability of 10 millidarcy or more (for example, 10 or 100 millidarcy). "Relatively low permeability" is defined, with respect to formations or portions thereof, as an average permeability of less than about 10 millidarcy. One darcy is equal to about 0.99 square micrometers. An impermeable layer generally has a permeability of less than about 0.1 millidarcy.

"Tar" is a viscous hydrocarbon that generally has a viscosity greater than about 10,000 centipoise at 15° C. The specific gravity of tar generally is greater than 1.000. Tar may have an API gravity less than 10°.

A "tar sands formation" is a formation in which hydrocarbons are predominantly present in the form of heavy hydrocarbons and/or tar entrained in a mineral grain framework or other host lithology (for example, sand or carbonate).

In some cases, a portion or all of a hydrocarbon portion of a relatively permeable formation may be predominantly heavy hydrocarbons and/or tar with no supporting mineral grain framework and only floating (or no) mineral matter (for example, asphalt lakes).

Certain types of formations that include heavy hydrocarbons may also be, but are not limited to, natural mineral waxes, or natural asphaltites. "Natural mineral waxes" typically occur in substantially tubular veins that may be several meters wide, several kilometers long, and hundreds of meters deep. "Natural asphaltites" include solid hydrocarbons of an aromatic composition and typically occur in large veins. In situ recovery of hydrocarbons from formations such as natural mineral waxes and natural asphaltites may include melting to form liquid hydrocarbons and/or solution mining of hydrocarbons from the formations.

"Upgrade" refers to increasing the quality of hydrocarbons. For example, upgrading heavy hydrocarbons may result in an increase in the API gravity of the heavy hydrocarbons.

"Thermal fracture" refers to fractures created in a formation caused by expansion or contraction of a formation and/or fluids in the formation, which is in turn caused by increasing/decreasing the temperature of the formation and/or fluids in the formation, and/or by increasing/decreasing a pressure of fluids in the formation due to heating.

"Periodic Table" refers to the Periodic Table as specified by the International Union of Pure and Applied Chemistry (IUPAC), November 2003.

"Column X metal" or "Column X metals" refer to one or more metals of Column X of the Periodic Table and/or one or more compounds of one or more metals of Column X of the Periodic Table, in which X corresponds to a column number (for example, 1-12) of the Periodic Table. For example, "Column 6 metals" refer to metals from Column 6 of the Periodic Table and/or compounds of one or more metals from Column 6 of the Periodic Table.

"Column X element" or "Column X elements" refer to one or more elements of Column X of the Periodic Table, and/or one or more compounds of one or more elements of Column X of the Periodic Table, in which X corresponds to a column number (for example, 13-18) of the Periodic Table. For example, "Column 15 elements" refer to elements from Column 15 of the Periodic Table and/or compounds of one or more elements from Column 15 of the Periodic Table.

In the scope of this application, weight of a metal from the Periodic Table, weight of a compound of a metal from the Periodic Table, weight of an element from the Periodic Table, or weight of a compound of an element from the Periodic Table is calculated as the weight of metal or the weight of element. For example, if 0.1 grams of $MoO_3$ is used per gram of catalyst, the calculated weight of the molybdenum metal in the catalyst is 0.067 grams per gram of catalyst.

Figure 1:
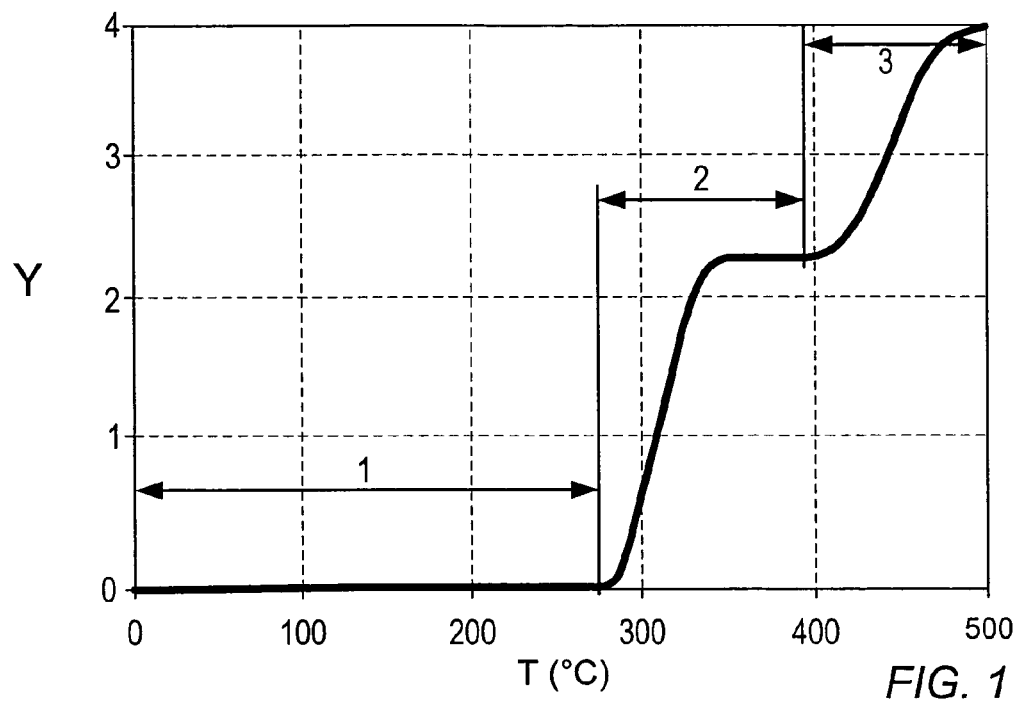
FIG. 1 depicts an illustration of stages of heating a hydrocarbon containing formation.

Hydrocarbons in formations may be treated in various ways to produce many different products. In certain embodiments, hydrocarbons in formations are treated in stages. FIG. 1 depicts an illustration of stages of heating the hydrocarbon containing formation. FIG. 1 also depicts an example of yield ("Y") in barrels of oil equivalent per ton (y axis) of formation fluids from the formation versus temperature ("T") of the heated formation in degrees Celsius (x axis).

Desorption of methane and vaporization of water occurs during stage 1 heating. Heating of the formation through stage 1 may be performed as quickly as possible. For example, when the hydrocarbon containing formation is initially heated, hydrocarbons in the formation desorb adsorbed methane. The desorbed methane may be produced from the formation. If the hydrocarbon containing formation is heated further, water in the hydrocarbon containing formation is vaporized. Water may occupy, in some hydrocarbon containing formations, between 10% and 50% of the pore volume in the formation. In other formations, water occupies larger or smaller portions of the pore volume. Water typically is vaporized in a formation between 160° C. and 285° C. at pressures of 600 kPa absolute to 7000 kPa absolute. In some embodiments, the vaporized water produces wettability changes in the formation and/or increased formation pressure. The wettability changes and/or increased pressure may affect pyrolysis reactions or other reactions in the formation. In certain embodiments, the vaporized water is produced from the formation. In other embodiments, the vaporized water is used for steam extraction and/or distillation in the formation or outside the formation. Removing the water from and increasing the pore volume in the formation increases the storage space for hydrocarbons in the pore volume.

In certain embodiments, after stage 1 heating, the formation is heated further, such that a temperature in the formation reaches (at least) an initial pyrolyzation temperature (such as a temperature at the lower end of the temperature range shown as stage 2). Hydrocarbons in the formation may be pyrolyzed throughout stage 2. A pyrolysis temperature range varies depending on the types of hydrocarbons in the formation. The pyrolysis temperature range may include temperatures between 250° C. and 900° C. The pyrolysis temperature range for producing desired products may extend through only a portion of the total pyrolysis temperature range. In some embodiments, the pyrolysis temperature range for producing desired products may include temperatures between 250° C. and 400° C. or temperatures between 270° C. and 350° C. If a temperature of hydrocarbons in the formation is slowly raised through the temperature range from 250° C. to 400° C., production of pyrolysis products may be substantially complete when the temperature approaches 400° C. Average temperature of the hydrocarbons may be raised at a rate of less than 5° C. per day, less than 2° C. per day, less than 1° C. per day, or less than 0.5° C. per day through the pyrolysis temperature range for producing desired products. Heating the hydrocarbon containing formation with a plurality of heat sources may establish thermal gradients around the heat sources that slowly raise the temperature of hydrocarbons in the formation through the pyrolysis temperature range.

The rate of temperature increase through the pyrolysis temperature range for desired products may affect the quality and quantity of the formation fluids produced from the hydrocarbon containing formation. Raising the temperature slowly through the pyrolysis temperature range for desired products may inhibit mobilization of large chain molecules in the formation. Raising the temperature slowly through the pyrolysis temperature range for desired products may limit reactions between mobilized hydrocarbons that produce undesired products. Slowly raising the temperature of the formation through the pyrolysis temperature range for desired products may allow for the production of high quality, high API gravity hydrocarbons from the formation. Slowly raising the temperature of the formation through the pyrolysis temperature range for desired products may allow for the removal of a large amount of the hydrocarbons present in the formation as hydrocarbon product.

In some in situ conversion embodiments, a portion of the formation is heated to a desired temperature instead of slowly heating the temperature through a temperature range. In some embodiments, the desired temperature is 300° C., 325° C., or 350° C. Other temperatures may be selected as the desired temperature. Superposition of heat from heat sources allows the desired temperature to be relatively quickly and efficiently established in the formation. Energy input into the formation from the heat sources may be adjusted to maintain the temperature in the formation substantially at the desired temperature. The heated portion of the formation is maintained substantially at the desired temperature until pyrolysis declines such that production of desired formation fluids from the formation becomes uneconomical. Parts of the formation that are subjected to pyrolysis may include regions brought into a pyrolysis temperature range by heat transfer from only one heat source.

In certain embodiments, formation fluids including pyrolyzation fluids are produced from the formation. As the temperature of the formation increases, the amount of condensable hydrocarbons in the produced formation fluid may decrease. At high temperatures, the formation may produce mostly methane and/or hydrogen. If the hydrocarbon containing formation is heated throughout an entire pyrolysis range, the formation may produce only small amounts of hydrogen towards an upper limit of the pyrolysis range. After all of the available hydrogen is depleted, a minimal amount of fluid production from the formation will typically occur.

After pyrolysis of hydrocarbons, a large amount of carbon and some hydrogen may still be present in the formation. A significant portion of carbon remaining in the formation can be produced from the formation in the form of synthesis gas. Synthesis gas generation may take place during stage 3 heating depicted in FIG. 1. Stage 3 may include heating a hydrocarbon containing formation to a temperature sufficient to allow synthesis gas generation. For example, synthesis gas may be produced in a temperature range from about 400° C. to about 1200° C., about 500° C. to about 1100° C., or about 550° C. to about 1000° C. The temperature of the heated portion of the formation when the synthesis gas generating fluid is introduced to the formation determines the composition of synthesis gas produced in the formation. The generated synthesis gas may be removed from the formation through a production well or production wells.

Total energy content of fluids produced from the hydrocarbon containing formation may stay relatively constant throughout pyrolysis and synthesis gas generation. During pyrolysis at relatively low formation temperatures, a significant portion of the produced fluid may be condensable hydrocarbons that have a high energy content. At higher pyrolysis temperatures, however, less of the formation fluid may include condensable hydrocarbons. More non-condensable formation fluids may be produced from the formation. Energy content per unit volume of the produced fluid may decline slightly during generation of predominantly non-condensable formation fluids. During synthesis gas generation, energy content per unit volume of produced synthesis gas declines significantly compared to energy content of pyrolyzation fluid. The volume of the produced synthesis gas, however, will in many instances increase substantially, thereby compensating for the decreased energy content.

Figure 2:
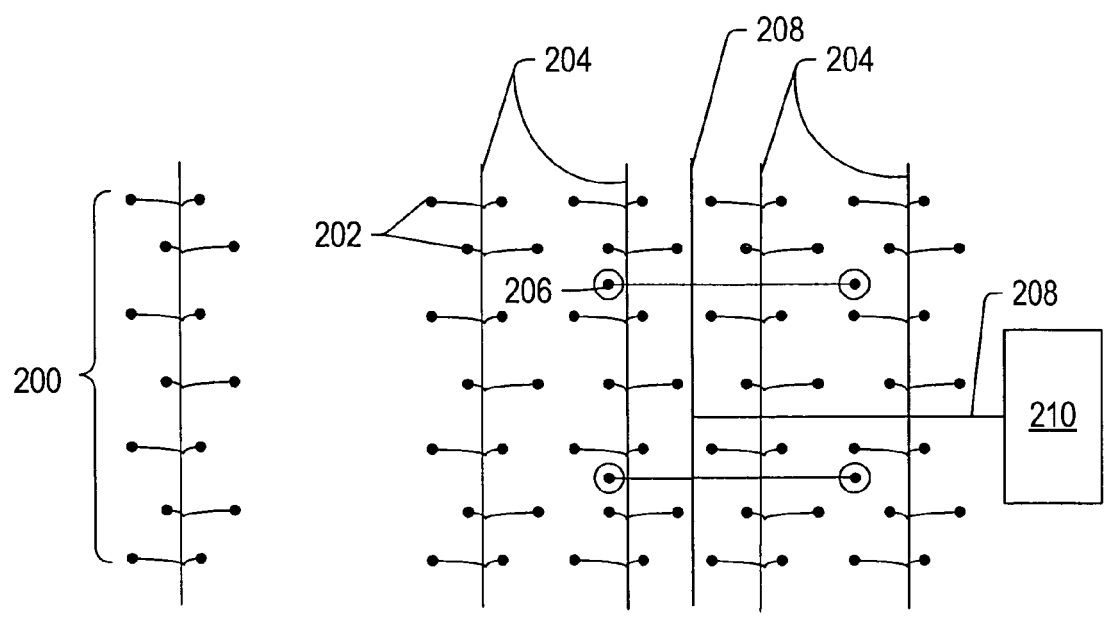
FIG. 2 shows a schematic view of an embodiment of a portion of an in situ conversion system for treating a hydrocarbon containing formation.

FIG. 2 depicts a schematic view of an embodiment of a portion of the in situ conversion system for treating the hydrocarbon containing formation. The in situ conversion system may include barrier wells 200. Barrier wells are used to form a barrier around a treatment area. The barrier inhibits fluid flow into and/or out of the treatment area. Barrier wells include, but are not limited to, dewatering wells, vacuum wells, capture wells, injection wells, grout wells, freeze wells, or combinations thereof. In some embodiments, barrier wells 200 are dewatering wells. Dewatering wells may remove liquid water and/or inhibit liquid water from entering a portion of the formation to be heated, or to the formation being heated. In the embodiment depicted in FIG. 2, the barrier wells 200 are shown extending only along one side of heat sources 202, but the barrier wells typically encircle all heat sources 202 used, or to be used, to heat a treatment area of the formation.

Heat sources 202 are placed in at least a portion of the formation. Heat sources 202 may include heaters such as insulated conductors, conductor-in-conduit heaters, surface burners, flameless distributed combustors, and/or natural distributed combustors. Heat sources 202 may also include other types of heaters. Heat sources 202 provide heat to at least a portion of the formation to heat hydrocarbons in the formation. Energy may be supplied to heat sources 202 through supply lines 204. Supply lines 204 may be structurally different depending on the type of heat source or heat sources used to heat the formation. Supply lines 204 for heat sources may transmit electricity for electric heaters, may transport fuel for combustors, or may transport heat exchange fluid that is circulated in the formation.

When the formation is heated, the heat input into the formation may cause expansion of the formation and geomechanical motion. Computer simulations may model formation response to heating. The computer simulations may be used to develop a pattern and time sequence for activating heat sources in the formation so that geomechanical motion of the formation does not adversely affect the functionality of heat sources, production wells, and other equipment in the formation.

Heating the formation may cause an increase in permeability and/or porosity of the formation. Increases in permeability and/or porosity may result from a reduction of mass in the formation due to vaporization and removal of water, removal of hydrocarbons, and/or creation of fractures. Fluid may flow more easily in the heated portion of the formation because of the increased permeability and/or porosity of the formation. Fluid in the heated portion of the formation may move a considerable distance through the formation because of the increased permeability and/or porosity. The considerable distance may be over 1000 m depending on various factors, such as permeability of the formation, properties of the fluid, temperature of the formation, and pressure gradient allowing movement of the fluid. The ability of fluid to travel considerable distance in the formation allows production wells 206 to be spaced relatively far apart in the formation.

Production wells 206 are used to remove formation fluid from the formation. In some embodiments, production well 206 includes a heat source. The heat source in the production well may heat one or more portions of the formation at or near the production well. In some in situ conversion process embodiments, the amount of heat supplied to the formation from the production well per meter of the production well is less than the amount of heat applied to the formation from a heat source that heats the formation per meter of the heat source. Heat applied to the formation from the production well may increase formation permeability adjacent to the production well by vaporizing and removing liquid phase fluid adjacent to the production well and/or by increasing the permeability of the formation adjacent to the production well by formation of macro and/or micro fractures.

More than one heat source may be positioned in the production well. A heat source in a lower portion of the production well may be turned off when superposition of heat from adjacent heat sources heats the formation sufficiently to counteract benefits provided by heating the formation with the production well. In some embodiments, the heat source in an upper portion of the production well may remain on after the heat source in the lower portion of the production well is deactivated. The heat source in the upper portion of the well may inhibit condensation and reflux of formation fluid.

In some embodiments, the heat source in production well 206 allows for vapor phase removal of formation fluids from the formation. Providing heating at or through the production well may: (1) inhibit condensation and/or refluxing of production fluid when such production fluid is moving in the production well proximate the overburden, (2) increase heat input into the formation, (3) increase production rate from the production well as compared to a production well without a heat source, (4) inhibit condensation of high carbon number compounds ($C_6$ and above) in the production well, and/or (5) increase formation permeability at or proximate the production well.

Subsurface pressure in the formation may correspond to the fluid pressure generated in the formation. As temperatures in the heated portion of the formation increase, the pressure in the heated portion may increase as a result of increased fluid generation and vaporization of water. Controlling rate of fluid removal from the formation may allow for control of pressure in the formation. Pressure in the formation may be determined at a number of different locations, such as near or at production wells, near or at heat sources, or at monitor wells.

In some hydrocarbon containing formations, production of hydrocarbons from the formation is inhibited until at least some hydrocarbons in the formation have been pyrolyzed. Formation fluid may be produced from the formation when the formation fluid is of a selected quality. In some embodiments, the selected quality includes an API gravity of at least about 20°, 30°, or 40°. Inhibiting production until at least some hydrocarbons are pyrolyzed may increase conversion of heavy hydrocarbons to light hydrocarbons. Inhibiting initial production may minimize the production of heavy hydrocarbons from the formation. Production of substantial amounts of heavy hydrocarbons may require expensive equipment and/or reduce the life of production equipment.

In some hydrocarbon containing formations, hydrocarbons in the formation may be heated to pyrolysis temperatures before substantial permeability has been generated in the heated portion of the formation. An initial lack of permeability may inhibit the transport of generated fluids to production wells 206. During initial heating, fluid pressure in the formation may increase proximate the heat sources 202. The increased fluid pressure may be released, monitored, altered, and/or controlled through one or more heat sources 202. For example, selected heat sources 202 or separate pressure relief wells may include pressure relief valves that allow for removal of some fluid from the formation.

In some embodiments, pressure generated by expansion of pyrolysis fluids or other fluids generated in the formation may be allowed to increase although an open path to production wells 206 or any other pressure sink may not yet exist in the formation. The fluid pressure may be allowed to increase towards a lithostatic pressure. Fractures in the hydrocarbon containing formation may form when the fluid approaches the lithostatic pressure. For example, fractures may form from heat sources 202 to production wells 206 in the heated portion of the formation. The generation of fractures in the heated portion may relieve some of the pressure in the portion. Pressure in the formation may have to be maintained below a selected pressure to inhibit unwanted production, fracturing of the overburden or underburden, and/or coking of hydrocarbons in the formation.

After pyrolysis temperatures are reached and production from the formation is allowed, pressure in the formation may be varied to alter and/or control a composition of formation fluid produced, to control a percentage of condensable fluid as compared to non-condensable fluid in the formation fluid, and/or to control an API gravity of formation fluid being produced. For example, decreasing pressure may result in production of a larger condensable fluid component. The condensable fluid component may contain a larger percentage of olefins.

In some in situ conversion process embodiments, pressure in the formation may be maintained high enough to promote production of formation fluid with an API gravity of greater than 20°. Maintaining increased pressure in the formation may inhibit formation subsidence during in situ conversion. Maintaining increased pressure may facilitate vapor phase production of fluids from the formation. Vapor phase production may allow for a reduction in size of collection conduits used to transport fluids produced from the formation. Maintaining increased pressure may reduce or eliminate the need to compress formation fluids at the surface to transport the fluids in collection conduits to treatment facilities.

Maintaining increased pressure in a heated portion of the formation may surprisingly allow for production of large quantities of hydrocarbons of increased quality and of relatively low molecular weight. Pressure may be maintained so that formation fluid produced has a minimal amount of compounds above a selected carbon number. The selected carbon number may be at most 25, at most 20, at most 12, or at most 8. Some high carbon number compounds may be entrained in vapor in the formation and may be removed from the formation with the vapor. Maintaining increased pressure in the formation may inhibit entrainment of high carbon number compounds and/or multi-ring hydrocarbon compounds in the vapor. High carbon number compounds and/or multi-ring hydrocarbon compounds may remain in a liquid phase in the formation for significant time periods. The significant time periods may provide sufficient time for the compounds to pyrolyze to form lower carbon number compounds.

Generation of relatively low molecular weight hydrocarbons is believed to be due, in part, to autogenous generation and reaction of hydrogen in a portion of the hydrocarbon containing formation. For example, maintaining an increased pressure may force hydrogen generated during pyrolysis into the liquid phase within the formation. Heating the portion to a temperature in a pyrolysis temperature range may pyrolyze hydrocarbons in the formation to generate liquid phase pyrolyzation fluids. The generated liquid phase pyrolyzation fluids components may include double bonds and/or radicals. Hydrogen ($H_2$) in the liquid phase may reduce double bonds of the generated pyrolyzation fluids, thereby reducing a potential for polymerization or formation of long chain compounds from the generated pyrolyzation fluids. In addition, $H_2$ may also neutralize radicals in the generated pyrolyzation fluids. Therefore, $H_2$ in the liquid phase may inhibit the generated pyrolyzation fluids from reacting with each other and/or with other compounds in the formation.

Formation fluid produced from production wells 206 may be transported through collection piping 208 to treatment facilities 210. Formation fluids may also be produced from heat sources 202. For example, fluid may be produced from heat sources 202 to control pressure in the formation adjacent to the heat sources. Fluid produced from heat sources 202 may be transported through tubing or piping to collection piping 208 or the produced fluid may be transported through tubing or piping directly to treatment facilities 210. Treatment facilities 210 may include separation units, reaction units, upgrading units, fuel cells, turbines, storage vessels, and/or other systems and units for processing produced formation fluids. The treatment facilities may form transportation fuel from at least a portion of the hydrocarbons produced from the formation. In some embodiments, the transportation fuel may be jet fuel, such as JP-8.

Formation fluid may be hot when produced from the formation through the production wells. Hot formation fluid may be produced during solution mining processes and/or during in situ conversion processes. In some embodiments, electricity may be generated using the heat of the fluid produced from the formation. Also, heat recovered from the formation after the in situ process may be used to generate electricity. The generated electricity may be used to supply power to the in situ conversion process. For example, the electricity may be used to power heaters, or to power a refrigeration system for forming or maintaining a low temperature barrier. Electricity may be generated using a Kalina cycle or a modified Kalina cycle.

Figure 3:
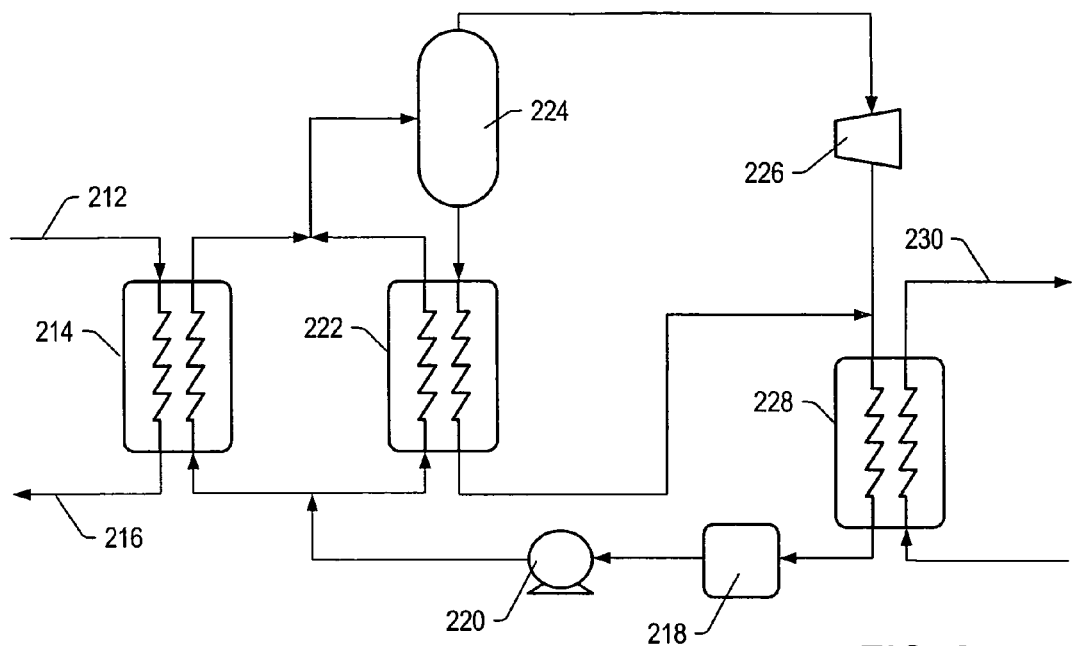
FIG. 3 depicts a schematic of an embodiment of a Kalina cycle for producing electricity.

FIG. 3 depicts a schematic representation of a Kalina cycle that uses relatively high pressure aqua ammonia as the working fluid. Hot produced fluid from the formation may pass through line 212 to heat exchanger 214. The produced fluid may have a temperature greater than about 100° C. Line 216 from heat exchanger 214 may direct the produced fluid to a separator or other treatment unit. In some embodiments, the produced fluid is a mineral containing fluid produced during solution mining. In some embodiments, the produced fluid includes hydrocarbons produced using an in situ conversion process or using an in situ mobilization process. Heat from the produced fluid is used to evaporate aqua ammonia in heat exchanger 214.

Aqua ammonia from tank 218 is directed by pump 220 to heat exchanger 214 and heat exchanger 222. Aqua ammonia from heat exchangers 214, 222 passes to separator 224. Separator 224 forms a rich ammonia gas stream and a lean ammonia gas stream. The rich ammonia gas stream is sent to turbine 226 to generate electricity.

The lean ammonia gas stream from separator 224 passes through heat exchanger 222. The lean gas stream leaving heat exchanger 222 is combined with the rich ammonia gas stream leaving turbine 226. The combination stream is passed through heat exchanger 228 and returned to tank 218. Heat exchanger 228 may be water cooled. Heater water from heat exchanger 228 may be sent to a surface water reservoir through line 230.

Figure 4:
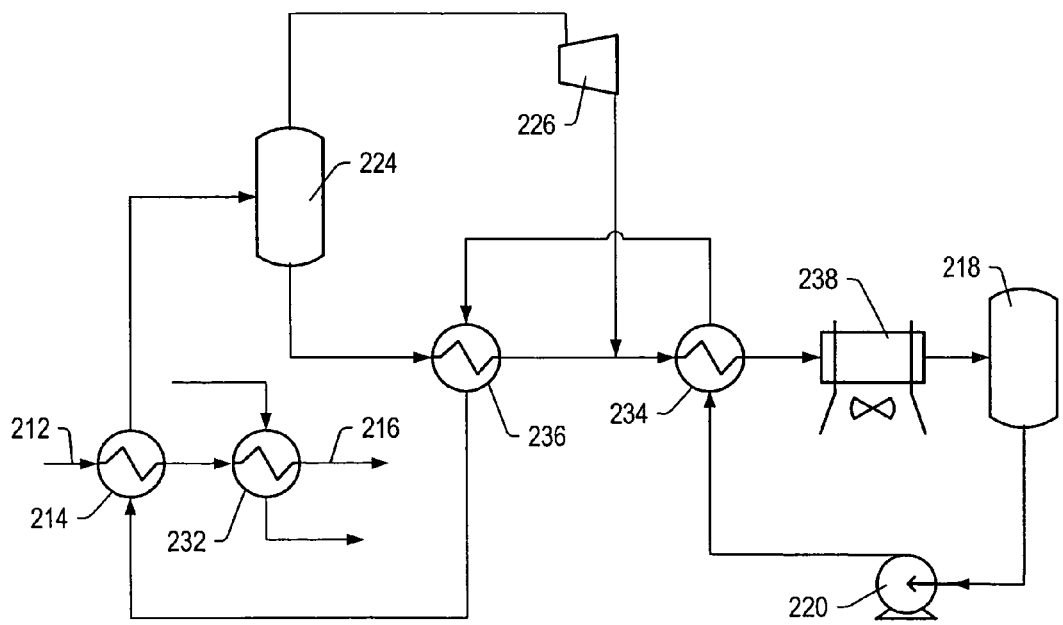
FIG. 4 depicts a schematic of an embodiment of a Kalina cycle for producing electricity.

FIG. 4 depicts a schematic representation of a modified Kalina cycle that uses lower pressure aqua ammonia as the working fluid. Hot produced fluid from the formation may pass through line 212 to heat exchanger 214. The produced fluid may have a temperature greater than about 100° C. Second heat exchanger 232 may further reduce the temperature of the produced fluid from the formation before the fluid is sent through line 216 to a separator or other treatment unit. Second heat exchanger may be water cooled.

Aqua ammonia from tank 218 is directed by pump 220 to heat exchanger 234. The temperature of the aqua ammonia from tank 218 is heated in heat exchanger 234 by transfer with a combined aqua ammonia stream from turbine 226 and separator 224. The aqua ammonia stream from heat exchanger 234 passes to heat exchanger 236. The temperature of the stream is raised again by transfer of heat with a lean ammonia stream that exits separator 224. The stream then passes to heat exchanger 214. Heat from the produced fluid is used to evaporate aqua ammonia in heat exchanger 214. The aqua ammonia passes to separator 224

Separator 224 forms a rich ammonia gas stream and a lean ammonia gas stream. The rich ammonia gas stream is sent to turbine 226 to generate electricity. The lean ammonia gas stream passes through heat exchanger 236. After heat exchanger 236, the lean ammonia gas stream is combined with the rich ammonia gas stream leaving turbine 226. The combined gas stream is passed through heat exchanger 234 to cooler 238. After cooler 238, the stream returns to tank 218.

In some embodiments, formation fluid produced from the in situ conversion process is sent to a separator to split the stream into one or more in situ conversion process liquid streams and/or one or more in situ conversion process gas streams. The liquid streams and the gas streams may be further treated to yield desired products.

In some embodiments, in situ process conversion gas is treated at the site of the formation to produce hydrogen. Treatment processes to produce hydrogen from the in situ process conversion gas may include steam methane reforming, autothermal reforming, and/or partial oxidation reforming.

All or at least a portion of a gas stream may be treated to yield a gas that meets natural gas pipeline specifications. FIGS. 5, 6, 7, 8, and 9 depict schematic representations of embodiments of systems for producing pipeline gas from the in situ conversion process gas stream.

Figure 5:
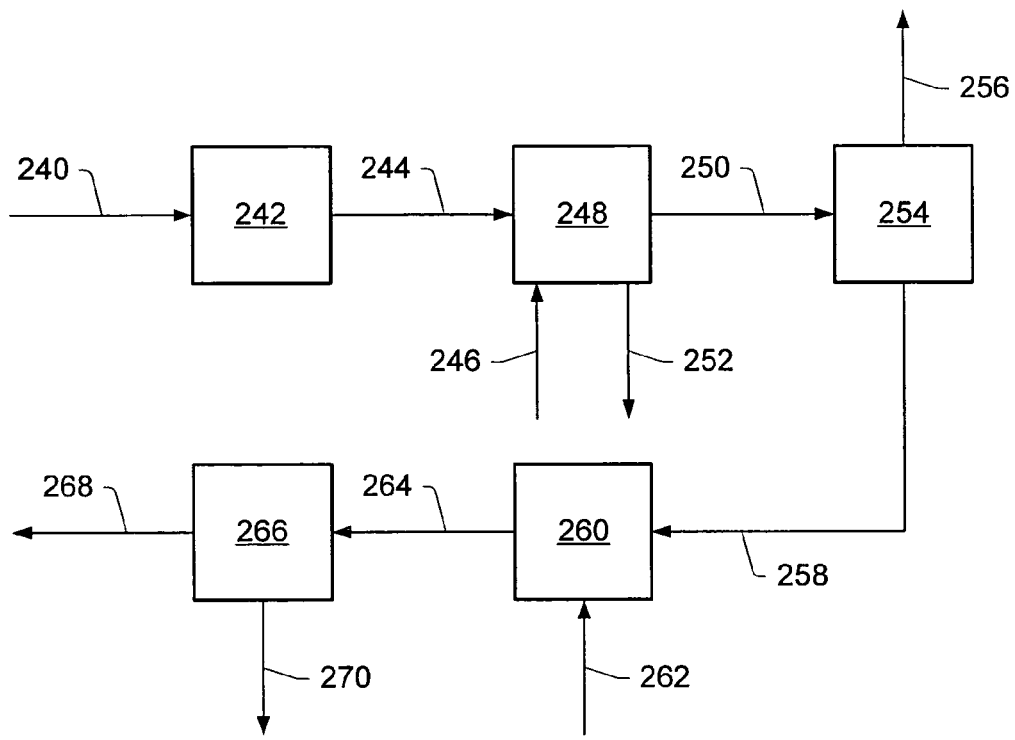
FIG. 5 depicts a schematic representation of an embodiment of a system for producing pipeline gas.

As depicted in FIG. 5, in situ conversion process gas 240 enters unit 242. In unit 242, treatment of in situ conversion process gas 240 removes sulfur compounds, carbon dioxide, and/or hydrogen to produce gas stream 244. Unit 242 may include a physical treatment system and/or a chemical treatment system. The physical treatment system includes, but is not limited to, a membrane unit, a pressure swing adsorption unit, a liquid absorption unit, and/or a cryogenic unit. The chemical treatment system may include units that use amines (for example, diethanolamine or di-isopropanolamine), zinc oxide, sulfolane, water, or mixtures thereof in the treatment process. In some embodiments, unit 242 uses a Sulfinol gas treatment process for removal of sulfur compounds. Carbon dioxide may be removed using Catacarb® (Catacarb, Overland Park, Kans., U.S.A.) and/or Benfield (UOP, Des Plaines, Ill., U.S.A.) gas treatment processes.

Gas stream 244 may include, but is not limited to, hydrogen, carbon monoxide, methane, and hydrocarbons having a carbon number of at least 2 or mixtures thereof. In some embodiments, gas stream 244 includes nitrogen and/or rare gases such as argon or helium. In some embodiments, gas stream 244 includes from about 0.0001 grams (g) to about 0.1 g, from about 0.001 g to about 0.05 g, or from about 0.01 g to about 0.03 g of hydrogen, per gram of gas stream. In certain embodiments, gas stream 244 includes from about 0.01 g to about 0.6 g, from about 0.1 g to about 0.5 g, or from about 0.2 g to 0.4 g of methane, per gram of gas stream.

In some embodiments, gas stream 244 includes from about 0.00001 g to about 0.01 g, from about 0.0005 g to about 0.005 g, or from about 0.0001 g to about 0.001 g of carbon monoxide, per gram of gas stream. In certain embodiments, gas stream 244 includes trace amounts of carbon dioxide.

In certain embodiments, gas stream 244 may include from about 0.0001 g to about 0.5 g, from about 0.001 g to about 0.2 g, or from about 0.01 g to about 0.1 g of hydrocarbons having a carbon number of at least 2, per gram of gas stream. Hydrocarbons having a carbon number of at least 2 include paraffins and olefins. Paraffins and olefins include, but are not limited to, ethane, ethylene, acetylene, propane, propylene, butanes, butylenes, or mixtures thereof. In some embodiments, hydrocarbons having a carbon number of at least 2 include from about 0.0001 g to about 0.5 g, from about 0.001 g to about 0.2 g, or from about 0.01 g to about 0.1 g of a mixture of ethylene, ethane, and propylene. In some embodiments, hydrocarbons having a carbon number of at least 2 includes trace amounts of hydrocarbons having a carbon number of at least 4.

Pipeline gas (for example, natural gas) after treatment to remove the hydrogen sulfide, includes methane, ethane, propane, butane, carbon dioxide, oxygen, nitrogen, and small amounts of rare gases. Typically, treated natural gas includes, per gram of natural gas, about 0.7 g to about 0.98 g of methane; about 0.0001 g to about 0.2 g or from about 0.001 g to about 0.05 g of a mixture of ethane, propane, and butane; about 0.0001 g to about 0.8 g or from about 0.001 g to about 0.02 g of carbon dioxide; about 0.00001 g to about 0.02 g or from about 0.0001 to about 0.002 of oxygen; trace amounts of rare gases; and the balance being nitrogen. Such treated natural gas has a heat content of about 40 MJ/Nm$^3$ to about 50 MJ/Nm$^3$.

Since gas stream 244 differs in composition from treated natural gas, gas stream 244 may not meet pipeline gas requirements. Emissions generated during burning of gas stream 244 may be unacceptable and/or not meet regulatory standards if the gas stream is to be used as a fuel. Gas stream 244 may include components or amounts of components that make the gas stream undesirable for use as a feed stream for making additional products.

In some embodiments, hydrocarbons having a carbon number greater than 2 are separated from gas stream 244. These hydrocarbons may be separated using cryogenic processes, adsorption processes, and/or membrane processes. Removal of hydrocarbons having a carbon number greater than 2 from gas stream 244 may facilitate and/or enhance further processing of the gas stream.

Process units as described herein may be operated at the following temperatures, pressures, hydrogen source flows, and gas stream flows, or operated otherwise as known in the art. Temperatures may range from about 50° C. to about 600° C., from about 100° C. to about 500° C., or from about 200° C. to about 400° C. Pressures may range from about 0.1 MPa to about 20 MPa, from about 1 MPa to about 12 MPa, from about 4 MPa to about 10 MPa, or from about 6 MPa to about 8 MPa. Flows of gas streams through units described herein may range from about 5 metric tons of gas stream per day ("MT/D") to about 15,000 MT/D. In some embodiments, flows of gas streams through units described herein range from about 10 MT/D to 10,000 MT/D or from about 15 MT/D to about 5,000 MT/D. In some embodiments, the hourly volume of gas processed is 5,000 to 25,000 times the volume of catalyst in one or more processing units.

As depicted in FIG. 5, gas stream 244 and hydrogen source 246 enter hydrogenation unit 248. Hydrogen source 246 includes, but is not limited to, hydrogen gas, hydrocarbons, and/or any compound capable of donating a hydrogen atom. In some embodiments, hydrogen source 246 is mixed with gas stream 244 prior to entering hydrogenation unit 248. In some embodiments, the hydrogen source is hydrogen and/or hydrocarbons present in gas stream 244. In hydrogenation unit 248, contact of gas stream 244 with hydrogen source 246 in the presence of one or more catalysts hydrogenates unsaturated hydrocarbons in gas stream 244 and produces gas stream 250. Gas stream 250 may include hydrogen and saturated hydrocarbons such as methane, ethane, and propane. Hydrogenation unit 248 may include a knock-out pot. The knock-out pot removes any heavy by-products 252 from the product gas stream.

Gas stream 250 exits hydrogenation unit 248 and enters hydrogen separation unit 254. Hydrogen separation unit 254 is any suitable unit capable of separating hydrogen from the incoming gas stream. Hydrogen separation unit 254 may be a membrane unit, a pressure swing adsorption unit, a liquid absorption unit, or a cryogenic unit. In certain embodiments, hydrogen separation unit 254 is a membrane unit. Hydrogen separation unit 254 may include PRISM® membranes available from Air Products and Chemicals, Inc. (Allentown, Pa., U.S.A.). The membrane separation unit may be operated at a temperature ranging from about 50° C. to about 80° C. (for examples, at a temperature of about 66° C.). In hydrogen separation unit 254, separation of hydrogen from gas stream 250 produces hydrogen rich stream 256 and gas stream 258. Hydrogen rich stream 256 may be used in other processes, or, in some embodiments, as hydrogen source 246 for hydrogenation unit 248.

In some embodiments, hydrogen separation unit 254 is a cryogenic unit. When hydrogen separation unit 254 is a cryogenic unit, gas stream 250 may be separated into a hydrogen rich stream, a methane rich stream, and/or a gas stream that contains components having a boiling point greater than or equal to ethane.

In some embodiments, hydrogen content in gas stream 258 is acceptable and further separation of hydrogen from gas stream 258 is not needed. When the hydrogen content in gas stream 258 is acceptable, the gas stream may be suitable for use as pipeline gas.

Further removal of hydrogen from gas stream 258 may be desired. In some embodiments, hydrogen is separated from gas stream 258 using a membrane. An example of a hydrogen separation membrane is described in U.S. Pat. No. 6,821,501 to Matzakos et al, which is incorporated by reference as if fully set forth herein.

In some embodiments, a method of removing hydrogen from gas stream 258 includes converting hydrogen to water. Gas stream 258 exits hydrogen separation unit 254 and enters oxidation unit 260, as shown in FIG. 5. Oxidation source 262 also enters oxidation unit 260. In oxidation unit 260, contact of gas stream 258 with oxidation source 262 produces gas stream 264. Gas stream 264 may include water produced as a result of the oxidation. The oxidation source may include, but is not limited to, pure oxygen, air, or oxygen enriched air. Since air or oxygen enriched air includes nitrogen, monitoring the quantity of air or oxygen enriched air provided to oxidation unit 260 may be desired to ensure the product gas meets the desired pipeline specification for nitrogen. Oxidation unit 260 includes, in some embodiments, a catalyst. Oxidation unit 260 is, in some embodiments, operated at a temperature in a range from about 50° C. to 500° C., from about 100° C. to about 400° C., or from about 200° C. to about 300° C.

Gas stream 264 exits oxidation unit 260 and enters dehydration unit 266. In dehydration unit 266, separation of water from gas stream 264 produces pipeline gas 268 and water 270. Dehydration unit 266 may be, for example, a standard gas plant glycol dehydration unit and/or molecular sieves.

In some embodiments, a change in the amount of methane in pipeline gas produced from an in situ conversion process gas is desired. The amount of methane in pipeline gas may be enhanced through removal of components and/or through chemical modification of components in the in situ conversion process gas.

Figure 6:
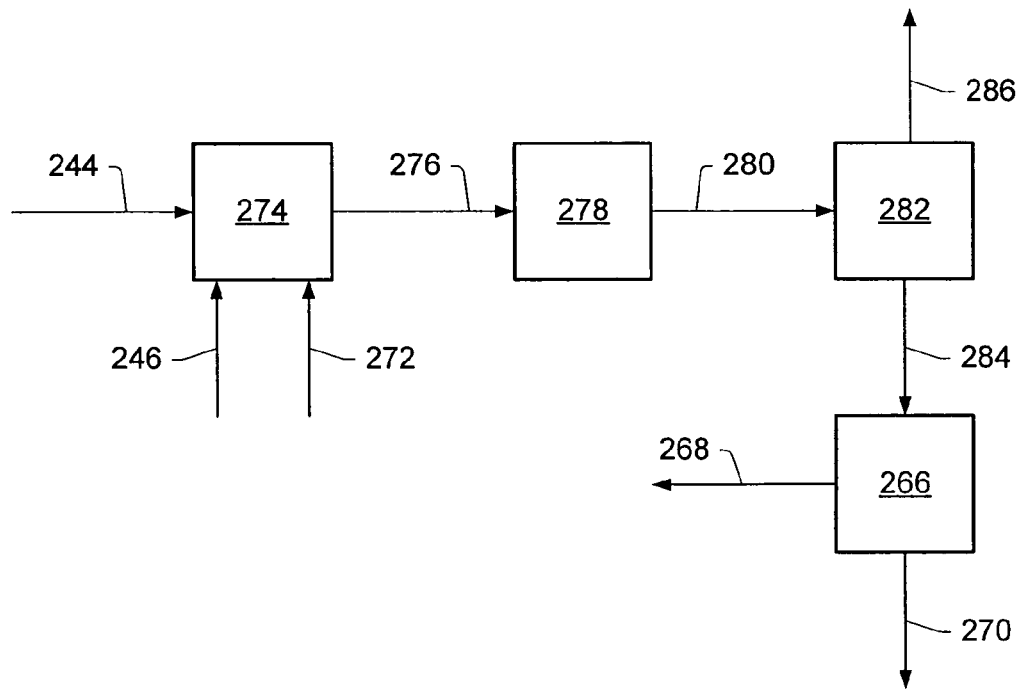
FIG. 6 depicts a schematic representation of an embodiment of a system for producing pipeline gas.

FIG. 6 depicts a schematic representation of an embodiment to enhance the amount of methane in pipeline gas through reformation and methanation of the in situ conversion process gas.

Treatment of in situ conversion process gas as described herein produces gas stream 244. Gas stream 244, hydrogen source 246, and steam source 272 enter reforming unit 274. In some embodiments, gas stream 244, hydrogen source 246, and/or steam source 272 are mixed together prior to entering reforming unit 274. In some embodiments, gas stream 244 includes an acceptable amount of a hydrogen source, and thus external addition of hydrogen source 246 is not needed. In reforming unit 274, contact of gas stream 244 with hydrogen source 246 in the presence of one or more catalysts and steam source 272 produces gas stream 276. The catalysts and operating parameters may be selected such that reforming of methane in gas stream 244 is minimized. Gas stream 276 includes methane, carbon monoxide, carbon dioxide, and/or hydrogen. The carbon dioxide in gas stream 276, at least a portion of the carbon monoxide in gas stream 276, and at least a portion of the hydrogen in gas stream 276 is from conversion of hydrocarbons with a carbon number greater than 2 (for example, ethylene, ethane, or propylene) to carbon monoxide and hydrogen. Methane in gas stream 276, at least a portion of the carbon monoxide in gas stream 276, and at least a portion of the hydrogen in gas stream 276 is from gas stream 244 and hydrogen source 246.

Reforming unit 274 may be operated at temperatures and pressures described herein, or operated otherwise as known in the art. In some embodiments, reforming unit 274 is operated at temperatures ranging from about 250° C. to about 500° C. In some embodiments, pressures in reforming unit 274 range from about 1 MPa to about 5 MPa.

Removal of excess carbon monoxide in gas stream 276 to meet, for example, pipeline specifications may be desired. Carbon monoxide may be removed from gas stream 276 using a methanation process. Methanation of carbon monoxide produces methane and water. Gas stream 276 exits reforming unit 274 and enters methanation unit 278. In methanation unit 278, contact of gas stream 276 with a hydrogen source in the presence of one or more catalysts produces gas stream 280. The hydrogen source may be provided by hydrogen and/or hydrocarbons present in gas stream 276. In some embodiments, an additional hydrogen source is added to the methanation unit and/or the gas stream. Gas stream 280 may include water, carbon dioxide, and methane.

Methanation unit 278 may be operated at temperatures and pressures described herein or operated otherwise as known in the art. In some embodiments, methanation unit 278 is operated at temperatures ranging from about 260° C. to about 320° C. In some embodiments, pressures in methanation unit 278 range from about 1 MPa to about 5 MPa.

Carbon dioxide may be separated from gas stream 280 in carbon dioxide separation unit 282. In some embodiments, gas stream 280 exits methanation unit 278 and passes through a heat exchanger prior to entering carbon dioxide separation unit 282. In carbon dioxide separation unit 282, separation of carbon dioxide from gas stream 280 produces gas stream 284 and carbon dioxide stream 286. In some embodiments, the separation process uses amines to facilitate the removal of carbon dioxide from gas stream 280. Gas stream 284 includes, in some embodiments, at most 0.1 g, at most 0.08 g, at most 0.06, or at most 0.04 g of carbon dioxide per gram of gas stream. In some embodiments, gas stream 284 is substantially free of carbon dioxide.

Gas stream 284 exits carbon dioxide separation unit 282 and enters dehydration unit 266. In dehydration unit 266, separation of water from gas stream 284 produces pipeline gas 268 and water 270.

Figure 7:
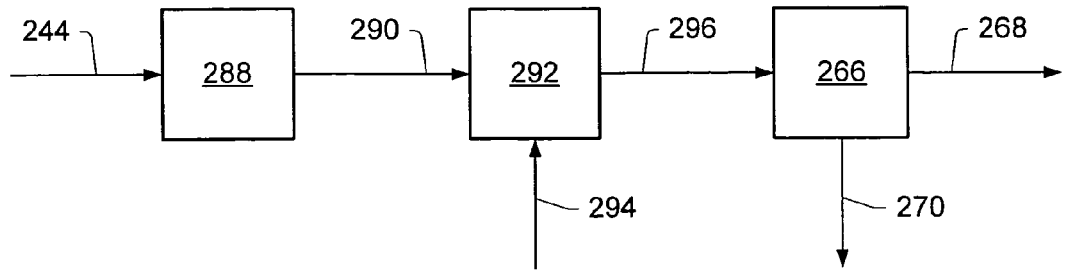
FIG. 7 depicts a schematic representation of an embodiment of a system for producing pipeline gas.

FIG. 7 depicts a schematic representation of an embodiment to enhance the amount of methane in pipeline gas through concurrent hydrogenation and methanation of in situ conversion process gas. Hydrogenation and methanation of carbon monoxide and hydrocarbons having a carbon number greater than 2 in the in situ conversion process gas produces methane. Concurrent hydrogenation and methanation in one processing unit may inhibit formation of impurities. Inhibiting the formation of impurities enhances production of methane from the in situ conversion process gas. In some embodiments, the hydrogen source content of the in situ conversion process gas is acceptable and an external source of hydrogen is not needed.

Treatment of in situ conversion process gas as described herein produces gas stream 244. Gas stream 244 enters hydrogenation and methanation unit 288. In hydrogenation and methanation unit 288, contact of gas stream 244 with a hydrogen source in the presence of a catalyst or multiple catalysts produces gas stream 290. The hydrogen source may be provided by hydrogen and/or hydrocarbons in gas stream 244. In some embodiments, an additional hydrogen source is added to hydrogenation and methanation unit 288 and/or gas stream 244. Gas stream 290 may include methane, hydrogen, and, in some embodiments, at least a portion of gas stream 244. In some embodiments, gas stream 290 includes from about 0.05 g to about 1 g, from about 0.8 g to about 0.99 g, or from about 0.9 g to 0.95 g of methane, per gram of gas stream. Gas stream 290 may include, per gram of gas stream, at most 0.1 g of hydrocarbons having a carbon number of at least 2 and at most 0.01 g of carbon monoxide. In some embodiments, gas stream 290 includes trace amounts of carbon monoxide and/or hydrocarbons having a carbon number of at least 2.

Hydrogenation and methanation unit 288 may be operated at temperatures, and pressures, described herein, or operated otherwise as known in the art. In some embodiments, hydrogenation and methanation unit 288 is operated at a temperature ranging from about 200° C. to about 350° C. In some embodiments, pressure in hydrogenation and methanation unit 288 is about 2 MPa to about 12 MPa, about 4 MPa to about 10 MPa, or about 6 MPa to about 8 MPa. In certain embodiments, pressure in hydrogenation and methanation unit 288 is about 4 MPa.

The removal of hydrogen from gas stream 290 may be desired. Removal of hydrogen from gas stream 290 may allow the gas stream to meet pipeline specification and/or handling requirements.

In FIG. 7, gas stream 290 exits methanation unit 288 and enters polishing unit 292. Carbon dioxide stream 294 also enters polishing unit 292, or it mixes with gas stream 290 upstream of the polishing unit. In polishing unit 292, contact of the gas stream 290 with carbon dioxide stream 294 in the presence of one or more catalysts produces gas stream 296. The reaction of hydrogen with carbon dioxide produces water and methane. Gas stream 296 may include methane, water, and, in some embodiments, at least a portion of gas stream 290. In some embodiments, polishing unit 292 is a portion of hydrogenation and methanation unit 288 with a carbon dioxide feed line.

Polishing unit 292 may be operated at temperatures and pressures described herein, or operated as otherwise known in the art. In some embodiments, polishing unit 292 is operated at a temperature ranging from about 200° C. to about 400° C. In some embodiments, pressure in polishing unit 292 is about 2 MPa to about 12 MPa, about 4 MPa to about 10 MPa, or about 6 MPa to about 8 MPa. In certain embodiments, pressure in polishing unit 292 is about 4 MPa.

Gas stream 296 enters dehydration unit 266. In dehydration unit 266, separation of water from gas stream 296 produces pipeline gas 268 and water 270.

Figure 8:
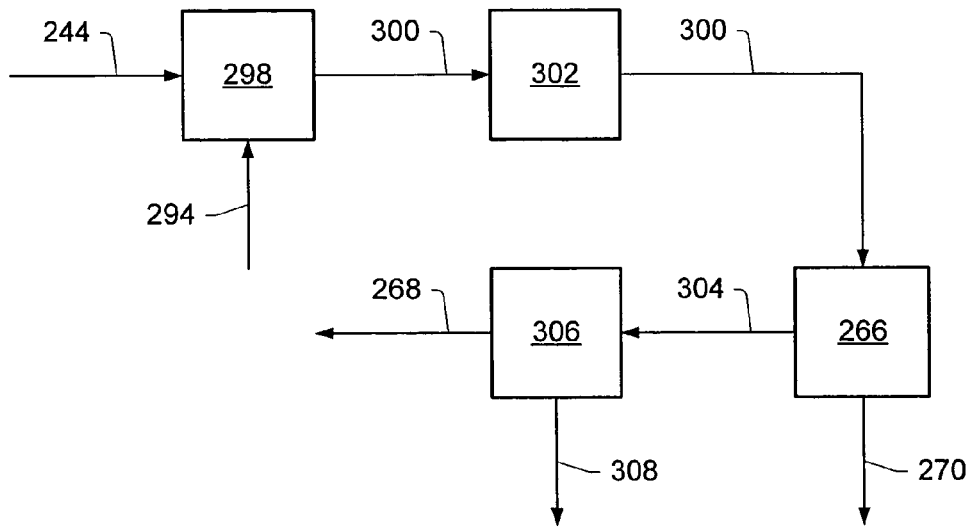
FIG. 8 depicts a schematic representation of an embodiment of a system for producing pipeline gas.

FIG. 8 depicts a schematic representation of an embodiment to enhance the amount of methane in pipeline gas through concurrent hydrogenation and methanation of in situ conversion process gas in the presence of excess carbon dioxide and the separation of ethane and heavier hydrocarbons. Hydrogen not used in the hydrogenation methanation process may react with carbon dioxide to form water and methane. Water may then be separated from the process stream. Concurrent hydrogenation and methanation in the presence of carbon dioxide in one processing unit may inhibit formation of impurities.

Treatment of in situ conversion process gas as described herein produces gas stream 244. Gas stream 244 and carbon dioxide stream 294 enter hydrogenation and methanation unit 298. In hydrogenation and methanation unit 298, contact of gas stream 244 with a hydrogen source in the presence of one or more catalysts and carbon dioxide produces gas stream 300. The hydrogen source may be provided by hydrogen and/or hydrocarbons in gas stream 244. In some embodiments, the hydrogen source is added to hydrogenation and methanation unit 298 or to gas stream 244. The quantity of hydrogen in hydrogenation and methanation unit 298 may be controlled and/or the flow of carbon dioxide may be controlled to provide a minimum quantity of hydrogen in gas stream 300.

Gas stream 300 may include water, hydrogen, methane, ethane, and, in some embodiments, at least a portion of the hydrocarbons having a carbon number greater than 2 from gas stream 244. In some embodiments, gas stream 300 includes from about 0.05 g to about 0.7 g, from about 0.1 g to about 0.6 g, or from about 0.2 g to 0.5 g of methane, per gram of gas stream. Gas stream 300 includes from about 0.0001 g to about 0.4 g, from about 0.001 g to about 0.2 g, or from about 0.01 g to 0.1 g of ethane, per gram of gas stream. In some embodiments, gas stream 300 includes a trace amount of carbon monoxide and olefins.

Hydrogenation and methanation unit 298 may be operated at temperatures and pressures, described herein, or operated otherwise as known in the art. In some embodiments, hydrogenation and methanation unit 298 is operated at a temperature ranging from about 60° C. to about 350° C. and a pressure ranging from about 1 MPa to about 12 MPa, about 2 MPa to about 10 MPa, or about 4 MPa to about 8 MPa.

In some embodiments, separation of ethane from methane is desirable. Separation may be performed using membrane and/or cryogenic techniques. Cryogenic processes may require that water levels in a gas stream be at most 1-10 part per million by weight.

Water in gas stream 300 may be removed using generally known water removal techniques. Gas stream 300 exits hydrogenation and methanation unit 298, passes through heat exchanger 302 and then enters dehydration unit 266. In dehydration unit 266, separation of water from gas stream 300 as previously described, as well as by contact with absorption units and/or molecular sieves, produces gas stream 304 and water 270. Gas stream 304 may have a water content of at most 10 ppm, at most 5 ppm, or at most 1 ppm. In some embodiments, water content in gas stream 304 ranges from about 0.01 ppm to about 10 ppm, from about 0.05 ppm to about 5 ppm, or from about 0.1 ppm to about 1 ppm.

Cryogenic separator 306 separates gas stream 304 into pipeline gas 268 and hydrocarbon stream 308. Pipeline gas stream 268 includes methane and/or carbon dioxide. Hydrocarbon stream 308 includes ethane and, in some embodiments, residual hydrocarbons having a carbon number of at least 2. In some embodiments, hydrocarbons having a carbon number of at least 2 may be separated into ethane and additional hydrocarbons and/or sent to other operating units.

Figure 9:
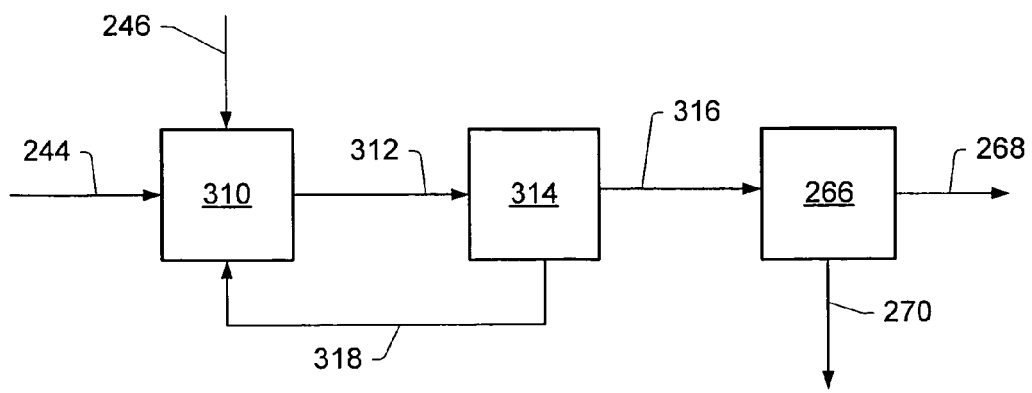
FIG. 9 depicts a schematic representation of an embodiment of a system for producing pipeline gas.

FIG. 9 depicts a schematic representation of an embodiment to enhance the amount of methane in pipeline gas through concurrent hydrogenation and methanation of in situ conversion process gas in the presence of excess hydrogen. The use of excess hydrogen during the hydrogenation and methanation process may prolong catalyst life, control reaction rates, and/or inhibit formation of impurities.

Treatment of in situ conversion process gas as described herein produces gas stream 244. Gas stream 244 and hydrogen source 246 enter hydrogenation and methanation unit 310. In some embodiments, hydrogen source 246 is added to gas stream 244. In hydrogenation and methanation unit 310, contact of gas stream 244 with hydrogen source 246 in the presence of one or more catalysts produces gas stream 312. In some embodiments, carbon dioxide may be added to hydrogen and methanation unit 310. The quantity of hydrogen in hydrogenation and methanation unit 310 may be controlled to provide an excess quantity of hydrogen to the hydrogenation and methanation unit.

Gas stream 312 may include water, hydrogen, methane, ethane, and, in some embodiments, at least a portion of the hydrocarbons having a carbon number greater than 2 from gas stream 244. In some embodiments, gas stream 312 includes from about 0.05 g to about 0.9 g, from about 0.1 g to about 0.6 g, or from about 0.2 g to 0.5 g of methane, per gram of gas stream. Gas stream 312 includes from about 0.0001 g to about 0.4 g, from about 0.001 g to about 0.2 g, or from about 0.01 g to 0.1 g of ethane, per gram of gas stream. In some embodiments, gas stream 312 includes carbon monoxide and trace amounts of olefins.

Hydrogenation and methanation unit 310 may be operated at temperatures and pressures, described herein, or operated otherwise as known in the art. In some embodiments, hydrogenation and methanation unit 310 is operated at a temperature ranging from about 60° C. to about 400° C. and a hydrogen partial pressure ranging from about 1 MPa to about 12 MPa, about 2 MPa to about 8 MPa, or about 3 MPa to about 5 MPa. In some embodiments, the hydrogen partial pressure in hydrogenation and methanation unit 310 is about 3 MPa.

Gas stream 312 enters gas separation unit 314. Gas separation unit 314 is any suitable unit or combination of units that is capable of separating hydrogen and/or carbon dioxide from gas stream 312. Gas separation unit may be a pressure swing adsorption unit, a membrane unit, a liquid absorption unit, and/or a cryogenic unit. In some embodiments, gas stream 312 exits hydrogenation and methanation unit 310 and passes through a heat exchanger prior to entering gas separation unit 314. In gas separation unit 314, separation of hydrogen from gas stream 312 produces gas stream 316 and hydrogen stream 318. Hydrogen stream 318 may be recycled to hydrogenation and methanation unit 310, mixed with gas stream 244 and/or mixed with hydrogen source 246 upstream of the hydrogenation methanation unit. In embodiments in which carbon dioxide is added to hydrogenation and methanation unit 310, carbon dioxide is separated from gas stream 316 in separation unit 314. The separated carbon dioxide may be recycled to the hydrogenation and methanation unit, mixed with gas stream 244 upstream of the hydrogenation and methanation unit, and/or mixed with the carbon dioxide stream entering the hydrogenation and methanation unit.

Gas stream 316 enters dehydration unit 266. In dehydration unit 266, separation of water from gas stream 316 produces pipeline gas 268 and water 270.

It should be understood that gas stream 244 may be treated by combinations of one or more of the processes described in FIGS. 5, 6, 7, 8, and 9. For example, all or at least a portion of gas streams from reforming unit 274 (FIG. 6) may be treated in hydrogenation and methanation units 288 (FIG. 7), 298 (FIG. 8), or 308 (FIG. 9). All or at least a portion of the gas stream produced from hydrogenation unit 248 may enter, or be combined with gas streams entering, reforming unit 274, hydrogenation and methanation unit 288, and/or hydrogenation and methanation unit 298. In some embodiments, gas stream 244 may be hydrotreated and/or used in other processing units.

Catalysts used to produce natural gas that meets pipeline specifications may be bulk metal catalysts or supported catalysts. Bulk metal catalysts include Columns 6-10 metals. Supported catalysts include Columns 6-10 metals on a support. Columns 6-10 metals include, but are not limited to, vanadium, chromium, molybdenum, tungsten, manganese, technetium, rhenium, iron, cobalt, nickel, ruthenium, palladium, rhodium, osmium, iridium, platinum, or mixtures thereof. The catalyst may have, per gram of catalyst, a total Columns 6-10 metals content of at least 0.0001 g, at least 0.001 g, at least 0.01 g, or in a range from about 0.0001-0.6 g, about 0.005-0.3 g, about 0.001-0.1 g, or about 0.01-0.08 g. In some embodiments, the catalyst includes a Column 15 element in addition to the Columns 6-10 metals. An example of a Column 15 element is phosphorus. The catalyst may have a total Column 15 elements content, per gram of catalyst, in a range from about 0.000001-0.1 g, about 0.00001-0.06 g, about 0.00005-0.03 g, or about 0.0001-0.001 g. In some embodiments, the catalyst includes a combination of Column 6 metals with one or more Columns 7-10 metals. A molar ratio of Column 6 metals to Columns 7-10 metals may be in a range from 0.1-20, 1-10, or 2-5. In some embodiments, the catalyst includes Column 15 elements in addition to the combination of Column 6 metals with one or more Columns 7-10 metals.

In some embodiments, Columns 6-10 metals are incorporated in, or deposited on, a support to form the catalyst. In certain embodiments, Columns 6-10 metals in combination with Column 15 elements are incorporated in, or deposited on, the support to form the catalyst. In embodiments in which the metals and/or elements are supported, the weight of the catalyst includes all support, all metals, and all elements. The support may be porous and may include refractory oxides; oxides of tantalum, niobium, vanadium, scandium, or lanthanide metals; porous carbon based materials; zeolites; or combinations thereof. Refractory oxides may include, but are not limited to, alumina, silica, silica-alumina, titanium oxide, zirconium oxide, magnesium oxide, or mixtures thereof. Supports may be obtained from a commercial manufacturer such as CRI/Criterion Inc. (Houston, Tex., U.S.A.). Porous carbon based materials include, but are not limited to, activated carbon and/or porous graphite. Examples of zeolites include Y-zeolites, beta zeolites, mordenite zeolites, ZSM-5 zeolites, and ferrierite zeolites. Zeolites may be obtained from a commercial manufacturer such as Zeolyst (Valley Forge, Pa., U.S.A.).

Supported catalysts may be prepared using generally known catalyst preparation techniques. Examples of catalyst preparations are described in U.S. Pat. No. 6,218,333 to Gabrielov et al.; U.S. Pat. No. 6,290,841 to Gabrielov et al.; U.S. Pat. No. 5,744,025 to Boon et al., and U.S. Pat. No. 6,759,364 to Bhan, all of which are incorporated by reference herein.

In some embodiments, the support is impregnated with metal to form the catalyst. In certain embodiments, the support is heat treated at temperatures in a range from about 400° C. to about 1200° C., from about 450° C. to about 1000° C., or from about 600° C. to about 900° C. prior to impregnation with a metal. In some embodiments, impregnation aids are used during preparation of the catalyst. Examples of impregnation aids include a citric acid component, ethylenediaminetetraacetic acid (EDTA), ammonia, or mixtures thereof.

The Columns 6-10 metals and support may be mixed with suitable mixing equipment to form a Columns 6-10 metals/support mixture. The Columns 6-10 metals/support mixture may be mixed using suitable mixing equipment. Examples of suitable mixing equipment include tumblers, stationary shells or troughs, Muller mixers (batch type or continuous type), impact mixers, and any other generally known mixer, or other device, that will suitably provide the Columns 6-10 metals support mixture. In certain embodiments, the materials are mixed until the Columns 6-10 metals are substantially homogeneously dispersed in the support.

In some embodiments, the catalyst is heat treated at temperatures from 150-750° C., from 200-740° C., or from 400-730° C. after combining the support with the metal. In some embodiments, the catalyst is heat treated in the presence of hot air and/or oxygen rich air at a temperature in a range between 400° C. and 1000° C. to remove volatile matter and to convert at least a portion of the Columns 6-10 metals to the corresponding metal oxide.

In other embodiments, a catalyst precursor is heat treated in the presence of air at temperatures in a range from 35-500° C. for a period of time in a range from 1-3 hours to remove a majority of the volatile components without converting the Columns 6-10 metals to the corresponding metal oxide. Catalysts prepared by such a method are generally referred to as "uncalcined" catalysts. When catalysts are prepared in this manner, in combination with a sulfiding method, the active metals may be substantially dispersed in the support. Preparations of such catalysts are described in U.S. Pat. No. 6,218, 333 to Gabrielov et al., and U.S. Pat. No. 6,290,841 to Gabrielov et al.

In some embodiments, the catalyst and/or a catalyst precursor is sulfided to form metal sulfides (prior to use) using techniques known in the art (for example, ACTICAT™ process, CRI International, Inc. (Houston, Tex., U.S.A.)). In some embodiments, the catalyst is dried then sulfided. Alternatively, the catalyst may be sulfided in situ by contact of the catalyst with a gas stream that includes sulfur-containing compounds. In situ sulfurization may utilize either gaseous hydrogen sulfide in the presence of hydrogen or liquid-phase sulfurizing agents such as organosulfur compounds (including alkylsulfides, polysulfides, thiols, and sulfoxides). Ex-situ sulfurization processes are described in U.S. Pat. No. 5,468,372 to Seamans et al., and U.S. Pat. No. 5,688,736 to Seamans et al., all of which are incorporated by reference herein.

In some embodiments, a first type of catalyst ("first catalyst") includes Columns 6-10 metals and the support. The first catalyst is, in some embodiments, an uncalcined catalyst. In some embodiments, the first catalyst includes molybdenum and nickel. In certain embodiments, the first catalyst includes phosphorus. In some embodiments, the first catalyst includes Columns 9-10 metals on a support. The Column 9 metal may be cobalt and the Column 10 metal may be nickel. In some embodiments, the first catalyst includes Columns 10-11 metals. The Column 10 metal may be nickel and the Column 11 metal may be copper.

The first catalyst may assist in the hydrogenation of olefins to alkanes. In some embodiments, the first catalyst is used in the hydrogenation unit. The first catalyst may include at least 0.1 g, at least 0.2 g, or at least 0.3 g of Column 10 metals per gram of support. In some embodiments, the Column 10 metal is nickel. In certain embodiments, the Column 10 metal is palladium and/or a mixed alloy of platinum and palladium. Use of a mixed alloy catalyst may enhance processing of gas streams with sulfur containing compounds. In some embodiments, the first catalyst is a commercial catalyst. Examples of commercial first catalysts include, but are not limited to, Criterion 424, DN-140, DN-200, and DN-3100, KL6566, KL6560, KL6562, KL6564, KL7756; KL7762, KL7763, KL7731, C-624, C654, all of which are available from CRI/Criterion Inc.

In some embodiments, a second type of catalyst ("second catalyst") includes Column 10 metal on a support. The Column 10 metal may be platinum and/or palladium. In some embodiments, the catalyst includes about 0.001 g to about 0.05 g, or about 0.01 g to about 0.02 g of platinum and/or palladium per gram of catalyst. The second catalyst may assist in the oxidation of hydrogen to form water. In some embodiments, the second catalyst is used in the oxidation unit. In some embodiments, the second catalyst is a commercial catalyst. An example of commercial second catalyst includes KL87748, available from CRI/Criterion Inc.

In some embodiments, a third type of catalyst ("third catalyst") includes Columns 6-10 metals on a support. In some embodiments, the third catalyst includes Columns 9-10 metals on a support. The Column 9 metal may be cobalt and the Column 10 metal may be nickel. In some embodiments, the content of nickel metal is from about 0.1 g to about 0.3 g, per gram of catalyst. The support for a third catalyst may include zirconia. The third catalyst may assist in the reforming of hydrocarbons having a carbon number greater than 2 to carbon monoxide and hydrogen. The third catalyst may be used in the reforming unit. In some embodiments, the third catalyst is a commercial catalyst. Examples of commercial third catalysts include, but are not limited to, CRG-FR and/or CRG-LH available from Johnson Matthey (London, England).

In some embodiments, a fourth type of catalyst ("fourth catalyst") includes Columns 6-10 metals on a support. In some embodiments, the fourth catalyst includes Column 8 metals in combination with Column 10 metals on a support. The Column 8 metal may be ruthenium and the Column 10 metal may be nickel, palladium, platinum, or mixtures thereof. In some embodiments, the fourth catalyst support includes oxides of tantalum, niobium, vanadium, the lanthanides, scandium, or mixtures thereof. The fourth catalyst may be used to convert carbon monoxide and hydrogen to methane and water. In some embodiments, the fourth catalyst is used in the methanation unit. In some embodiments, the fourth catalyst is a commercial catalyst. Examples of commercial fourth catalysts, include, but are not limited to, KATALCO® 11-4 and/or KATALCO® 11-4R available from Johnson Matthey.

In some embodiments, a fifth type of catalyst ("fifth catalyst") includes Columns 6-10 metals on a support. In some embodiments, the fifth catalyst includes a Column 10 metal. The fifth catalyst may include from about 0.1 g to about 0.99 g, from about 0.3 g to about 0.9 g, from about 0.5 g to about 0.8 g, or from 0.6 g to about 0.7 g of Column 10 metal per gram of fifth catalyst. In some embodiments, the Column 10 metal is nickel. In some embodiments, a catalyst that has at least 0.5 g of nickel per gram of fifth catalyst has enhanced stability in a hydrogenation and methanation process. The fifth catalyst may assist in the conversion of hydrocarbons and carbon dioxide to methane. The fifth catalyst may be used in hydrogenation and methanation units and/or polishing units. In some embodiments, the fifth catalyst is a commercial catalyst. An example of a commercial fifth catalyst is KL6524-T, available from CRI/Criterion Inc.

Formation fluid produced from the in situ conversion process may be sent to the separator to split the stream into the in situ conversion process liquid stream and the in situ conversion process gas stream. The liquid stream and the gas stream may be further treated to yield desired products. When the liquid stream is treated using generally known conditions to produce commercial products, processing equipment may be adversely affected. For example, the processing equipment may clog. Examples of processes to produce commercial products include, but are not limited to, alkylation, distillation, hydrocracking, hydrotreating, hydrogenation, hydrodesulfurization, catalytic cracking, or combinations thereof. Processes to produce commercial products are described in "Refining Processes 2000," Hydrocarbon Processing, Gulf Publishing Co., pp. 87-142, which is incorporated by reference herein. Examples of commercial products include, but are not limited to, diesel, gasoline, hydrocarbon gases, jet fuel, kerosene, naphtha, vacuum gas oil ("VGO"), or mixtures thereof.

Process equipment may become clogged by compositions in the in situ conversion process liquid. Compositions may include, but are not limited to, hydrocarbons and/or solids produced from the in situ conversion process. Compositions that cause clogging may be formed during heating of the in situ conversion process liquid. The compositions may adhere to parts of the equipment and inhibit the flow of the liquid stream through processing units.

Solids may include, but are not limited to, organometallic compounds, inorganic compounds, minerals, mineral compounds, and/or mixtures thereof. The solids may have a particle size such that filtration may not remove the solids from the liquid stream. Hydrocarbons may include, but are not limited to, hydrocarbons that contain heteroatoms, aromatic hydrocarbon, cyclic hydrocarbons, cyclic olefins, and/or acyclic olefins. In some embodiments, solids and/or hydrocarbons present in the in situ conversion process liquid that cause clogging are partially soluble or insoluble in the situ conversion process liquid. In some embodiments, filtration of the liquid stream prior to or during heating is insufficient and/or ineffective for removal of all or some of the compositions that clog process equipment.

In some embodiments, clogging of process equipment is inhibited by hydrotreating at least a portion of the liquid stream. The hydrotreated liquid stream may be further processed to produce commercial products.

FIG. 10 depicts a schematic representation of an embodiment of a system for producing crude products and/or commercial products from the in situ conversion process liquid stream and/or the in situ conversion process gas stream Formation fluid 320 enters gas/liquid separation unit 322 and is separated into in situ conversion process liquid stream 324, in situ conversion process gas 240, and aqueous stream 326.

In situ conversion process gas 240 may enter gas separation unit 328 to separate gas hydrocarbon stream 330 from the in situ conversion process gas. The gas separation unit is, in some embodiments, a rectified adsorption unit. Gas hydrocarbon stream 330 includes hydrocarbons having a carbon number of at least 3.

In situ conversion process liquid stream 324 enters liquid separation unit 332. In liquid separation unit 332, separation of in situ conversion liquid stream 324 produces gas hydrocarbon stream 336 and liquid stream 334. Gas hydrocarbon stream 336 may include hydrocarbons having a carbon number of at most 5.

Liquid stream 334 includes, but is not limited to, hydrocarbons having a carbon number of at least 5 and/or hydrocarbon containing heteroatoms (for example, hydrocarbons containing nitrogen, oxygen, sulfur, and phosphorus). Liquid stream 334 may include at least 0.001 g, at least 0.005 g, or at least 0.01 g of hydrocarbons with a boiling range distribution between 95° C. and 200° C. at 0.101 MPa; at least 0.01 g, at least 0.005 g, or at least 0.001 g of hydrocarbons with a boiling range distribution between 200° C. and 300° C. at 0.101 MPa; at least 0.001 g, at least 0.005 g, or at least 0.01 g of hydrocarbons with a boiling range distribution between 300° C. and 400° C. at 0.101 MPa; and at least 0.001 g, at least 0.005 g, or at least 0.01 g of hydrocarbons with a boiling range distribution between 400° C. and 650° C. at 0.101 MPa.

Process units as described herein for the production of crude products and/or commercial products may be operated at the following temperatures, pressures, hydrogen source flows, liquid stream flows, or combinations thereof, or operated otherwise as known in the art. Temperatures range from about 200° C. to about 800° C., from about 300° C. to about 700° C., or from about 400° C. to about 600° C. Pressures range from about 0.1 MPa to about 20 MPa, from about 1 MPa to about 12 MPa, from about 4 MPa to about 10 MPa, or from about 6 MPa to about 8 MPa. Liquid hourly space velocities ("LHSV") of the liquid stream range from about 0.1 $h^{-1}$ to about 30 $h^{-1}$, from about 0.5 $h^{-1}$ to about 25 $h^{-1}$, from about 1 $h^{-1}$ to about 20 $h^{-1}$, from about 1.5 $h^{-1}$ to about 15 $h^{-1}$, or from about 2 $h^{-1}$ to about 10 $h^{-1}$.

Liquid stream 334 and hydrogen source 246 enter hydrotreating unit 338. Hydrogen source 246 may be added to liquid stream 334 before entering hydrotreating unit 338. In some embodiments, sufficient hydrogen is present in liquid stream 334 and hydrogen source 246 is not needed. In hydrotreating unit 338, contact of liquid stream 334 with hydrogen source 246 in the presence of one or more catalysts produces liquid stream 340. Hydrotreating unit 338 may be operated such that all or at least a portion of liquid stream 340 is changed sufficiently to remove compositions and/or inhibit formation of compositions that may clog equipment positioned downstream of the hydrotreating unit 338. The catalyst used in hydrotreating unit 338 may be a commercially available catalyst.

Liquid stream 340 exits hydrotreating unit 338 and enters one or more processing units positioned downstream of hydrotreating unit 338. The units positioned downstream of hydrotreating unit 338 may include distillation units, hydrocracking units, hydrotreating units, hydrogenation units, hydrodesulfurization units, catalytic cracking units, or combinations thereof.

Liquid stream 340 may exit hydrotreating unit 338 and enter fractionation unit 342. Fractionation unit 342 produces one or more crude products. Fractionation may include, but is not limited to, an atmospheric distillation process and/or a vacuum distillation process. Crude products include, but are not limited to, $C_3$-$C_5$ hydrocarbon stream 344, naphtha stream 346, kerosene stream 348, diesel stream 350, VGO stream 352, and bottoms stream 354. Bottoms stream 354 generally includes hydrocarbons having a boiling point range greater than 538° C. at 0.101 MPa. One or more of the crude products may be sold and/or further processed to gasoline or other commercial products.

To enhance the use of the streams produced from formation fluid, hydrocarbons produced during fractionation of the liquid stream and hydrocarbon gases produced during separating the process gas may be combined to form hydrocarbons having a higher carbon number. The produced hydrocarbon gas stream may include a level of olefins acceptable for alkylation reactions.

$C_3$-$C_5$ hydrocarbon stream 344 produced from fractionation unit 342 and hydrocarbon gas stream 330 enter alkylation unit 356. In alkylation unit 356, reaction of the olefins in hydrocarbon gas stream 330 (for example, ethylene and propylene) with the alkanes in $C_3$-$C_5$ hydrocarbon stream 344 produces hydrocarbon stream 358. In some embodiments, the olefin content in hydrocarbon gas stream 330 is acceptable and an additional source of olefins is not needed. Hydrocarbon stream 358 includes hydrocarbons having a carbon number of at least 4. Hydrocarbons having a carbon number of at least 4 include, but are not limited to, butanes, pentanes, hexanes, and heptanes.

In some embodiments, bottoms stream 354 may be hydrocracked to produce naphtha and/or other products. The resulting naphtha may, however, need fortification to alter the octane level so that the product may be sold commercially as gasoline. Alternatively, bottoms stream 354 may be treated in a catalytic cracker to produce high octane naphtha and/or feed for an alkylation unit.

In FIG. 10, bottoms stream 354 from fractionation unit 342 enters catalytic cracking unit 360. In catalytic cracking unit 360, contact of bottoms stream 354 with a catalyst under controlled temperatures produces additional $C_3$-$C_5$ hydrocarbon stream 344', gasoline stream 362, and additional kerosene stream 348'. Additional $C_3$-$C_5$ hydrocarbon stream 344' may be sent to alkylation unit 356, combined with $C_3$-$C_5$ hydrocarbon stream 344, and/or combined with hydrocarbon gas stream 330. In some embodiments, the olefin content in hydrocarbon gas stream 330 is acceptable and an additional source of olefins is not needed.

Heating a portion of the subsurface formation may cause the mineral structure of the formation to change and form particles. The particles may be dispersed and/or become partially dissolved in the formation fluid. The particles may include metals and/or compounds of metals from Columns 1-2 and Columns 4-13 of the Periodic Table (for example, aluminum, silicon, magnesium, calcium, potassium sodium, beryllium, lithium, chromium, magnesium, copper, zirconium, and so forth). In some embodiments, the particles are coated, for example, with hydrocarbons of the formation fluid. In certain embodiments, the particles include zeolites.

A concentration of particles in formation fluid may range from about 1 ppm to about 3000 ppm, from about 50 ppm to about 2000 ppm, or from about 100 ppm to about 1000 ppm. The size of particles may range from 0.5 micron to about 200 microns, from 5 micron to about 150 microns, from about 10 microns to about 100 microns, or about 20 microns to about 50 microns.

In certain embodiments, formation fluid may include a distribution of particles. The distribution of particles may be, but is not limited to, a trimodal or a bimodal distribution. For example, a trimodal distribution of particles may include from about 1 ppm to about 50 ppm of particles with a size of about 5 microns to about 10 microns, from about 2 ppm to about 2000 ppm of particles with a size of about 50 microns to about 80 microns, and from about 1 ppm to about 100 ppm with a size of about 100 micron to about 200 microns. A bimodal distribution of particles may include from about 1 ppm to 60 ppm of particles with a size of between about 50 and 60 microns and from about 2 ppm to about 2000 ppm of particles with a size between about 100 and 200 microns.

In some embodiments, the particles may contact the formation fluid and catalyze formation of compounds having a carbon number of at most 25, at most 20, at most 12, or at most 8. In certain embodiments, the zeolitic particles may assist in the oxidation and/or reduction of formation fluids to produce compounds not generally found in fluids produced using conventional production methods. Contact of formation fluid with hydrogen in the presence of zeolitic particles may catalyze reduction of double bond compounds in the formation fluid.

In some embodiments, all or a portion of the particles in the produced fluid may be removed from the produced fluid. The particles may be removed by using a centrifuge, by washing, by acid washing, by filtration, by electrostatic precipitation, by froth flotation, and/or by another type of separation process.

Many wells are needed for treating a hydrocarbon formation using an in situ conversion process. In some embodiments, vertical or substantially vertical wells are formed in the formation. In some embodiments, horizontal or U-shaped wells are formed in the formation. In some embodiments, combinations of horizontal and vertical wells are formed in the formation. Wells may be formed using drilling rigs.

In an embodiment, a rig for drilling wells includes equipment on the rig for drilling multiple wellbores simultaneously. The rig may include one or more systems for constructing the wells, including drilling, fluid handling, and cementing of the wells through the overburden, drilling to total depth, and placing completion equipment such as heaters and casing. The rig may be particularly useful for forming closely spaced wells, such as freeze wells.

In some embodiments, wells are drilled in sequential stages with different drilling machines. The wells may be barrier wells, heater wells, production wells, production/heater wells, monitor wells, injection wells, or other types of wells. A conductor drilling machine may set the conductor of the well. A main hole drilling machine may drill the wellbore to depth. A completion drilling machine may place casing, cement, tubing, cables, heaters, and perform other well completion tasks. The drilling machines may be on the same location moving 3 to 10 meters between wells for 2 to 3 years. The size and the shape of the drilling machines may not have to meet existing road transportation regulations since once in the field, the drilling machines may remain there for the duration of the project. The major components of the drilling machines may be transported to location and assembled there. The drilling machines may not have to be disassembled for a multi-mile move for several years.

One or more central plants may support the drilling machines. The use of a central plant may allow for smaller drilling machines. The central plant may include prime movers, mud tanks, solids handling equipment, pipe handling, power, and other equipment common to the drilling machines. The equipment of the central plant may be coupled to the drilling machines by flexible umbilicals, by easily modifiable piping, and/or by quick release electrical connections. Several wells may be drilled before the need to move the central plant arises. In some embodiments, the central plant may be moved while connected to one or more operating drilling machines. The drilling machines and central plant may be designed with integrated drip pans to capture leaks and spills.

In some embodiments, the drilling machines are powered directly off the electric grid. In other embodiments, the drilling machines are diesel powered. Using diesel power may avoid complications associated with interfering with the installation of electrical and other systems needed for the wells of the in situ conversion process.

The drilling machines may be automated so that little or no human interaction is required. The tubulars used by the drilling machines may be stacked and stored on or by the drilling machines so that the drilling machines can access and manipulate the tubulars with minimal or no human intervention. For example, a carousel or other device may be used to store a tubular and move the tubular from storage to the drilling mast. The carousel or other device may also be used to move the tubular from the drilling mast to storage.

The drilling machines may include propulsion units so that the drilling machines do not need to be skidded. The central plant may also include propulsion units. Skidding involves extra equipment not used for drilling the wells and may be complicated by the dense concentration of surface facilities and equipment. In some embodiments, the drilling machines and/or central plant may include tracks or a walking mechanism to eliminate railroad-type tracks. Eliminating railroad-type tracks may reduce the amount of pre-work road and rail formation that needs to be completed before drilling operations can begin. In some embodiments, the propulsion units may include a fixed-movement mechanism. The fixed-movement mechanism may advance the drilling machine a set distance when activated so that the drilling machine is located at the next well location. Fine adjustment may allow for exact positioning of the drilling machine after initial position location by the fixed-movement mechanism.

In some embodiments, drilling machines and/or the central plant are positioned on a central track or access lane. The drilling equipment may be extended from one side to the other of the central track to form the wells. The drilling machine is able to stay in one place while an arm or cantilever mechanism allows multiples of wells to be drilled around the drilling machine. The wells may be drilled in very close proximity if required.

The drilling machines and the central plant may be self-leveling and able to function on up to a 10% grade or higher. In some embodiments, the drilling machines include hydraulic and/or mechanical leveling systems. The drilling machines and central plant may have ground clearances of at least 1 meter so that the units may be moved unobstructed over wellheads. Each drilling machine may include a mechanism for precisely placing the working components of the drilling machine over the hole center of the well being formed. In some embodiments, the mechanism adjusts the position of a derrick of the drilling machine.

The drilling machines may be moved from one well to another with derricks of the drilling machines in upright or inclined positions. The term "derrick" is used to represent whatever top drive support device is employed on the rig, whether the top drive support device is a derrick, stiff mast, or hydraulic arm. Because some drilling machines may use three 10 m pipe sections, the derrick may have to be lowered for rig moves. If the derrick must be lowered, lowering and raising the derrick needs to be a quick and safe operation. In some embodiments, the derrick is lowered with the bottom hole assembly racked in the derrick to save time handling the bottom hole assembly. In other embodiments, the bottom hole assembly is separated from the derrick for servicing during a move of the drilling machine.

In some embodiments, one of the drilling machines is able to do more than one stage of well formation. In some embodiments, a freeze wall or other barrier is formed around all or a portion of a treatment area. There may be about a year or more of time from when the last freeze well is drilled to the time that main holes for heater and producer wells can be drilled. In the intervening time, the drilling machine used to drill the main hole of a well may be used to preset conductors for heater wells and/or production wells in the treatment area.

In some embodiments, two or more drilling machines are placed on the same carrier. For example, the carrier may include equipment that presets the conductor for a well. The carrier may also carry equipment for forming the main hole. One portion of the machine could be presetting a conductor while another portion of the machine could be simultaneously forming the main hole of a second well.

Running drill pipe to replace bits, running in down hole equipment and pulling the equipment out after use may be time consuming and expensive. To save time and expense, all drilling and completion tools may go into the hole and not come out. For example, drill pipe may become casing. Once data is obtained from logging runs, the logging tools are left in the hole and drilling proceeds through them or past them if necessary. Downhole equipment is integrated into the drill pipe. In some embodiments, the drill pipe becomes a conduit of a conduit-in-conduit heater.

In some embodiments, a retractable drilling assembly is used. Using a retractable drilling assembly may be beneficial when using continuous coiled tubing. When total depth of the well is reached, the drill bit and bottom hole assembly may be retracted to a smaller diameter. The drill bit and bottom hole assembly may be brought to the surface through the coiled tubing. The coiled tubing may be left in the hole as casing.

In some embodiments, the main hole drilling machine and the completion drilling machine include a quick-connect device for attaching the fluid diverter spool (drilling wellhead) to the conductor casing. The use of a quick-connect device may be faster than threading or welding the diverter to the conductor casing. The quick-connect device may be a snap-on or clamp-on type diverter. Wellheads are typically designed to fit a multitude of casing configurations, everything from 48 inch conductor to 2⅜ inch tubing. For an in situ conversion process, the wellheads may not need to span such a large casing diameter set or have multiple string requirements. The wellheads may only handle a very limited pipe diameter range and only one or two casing strings. Having a fit for purpose wellhead may significantly reduce the cost of fabricating and installing the wellheads for the wells of the in situ conversion process.

In some embodiments, the main hole drilling machine includes a slickline/boom system. The slickline/boom system may allow running ranging equipment in a close offset well while drilling the well the drilling machine is positioned over. The use of the slickline/boom system on the drilling machine may eliminate the need for additional equipment for employing the ranging equipment.

In some embodiments, the conductor drilling machine is a blast-hole rig. The blast-hole rig may be mounted on a crawler or carrier with metal tracks. Air or gas compression is on board the blast-hole rig. Tubulars may be racked horizontally on the blast-hole rig. The derrick of the blast-hole rig may be adjusted to hole center. The bottom hole drilling assembly of the blast-hole rig may be left in the derrick when the blast-hole rig is moved. In some embodiments, the blast-hole rig includes an integral drilling fluid tank, solids control equipment, and a mist collector. In some embodiments, the drilling fluid tank, the solids control equipment, and/or the mist collector is part of the central plant.

During well formation with jointed pipe, one time consuming task is making connections. To reduce the number of connections needed during formation of wells, long lengths of pipe may be used. In some embodiments, the drilling machines are able to use pipe with a length of about 25 m to 30 m. The 25 m to 30 m piping may be made up of two or more shorter joints, but is preferably a single joint of the appropriate length. Using a single joint may decrease the complexity of pipe handling and result in fewer potential leak paths in the drill string. In some embodiments, the drilling machines use jointed pipe having other lengths, such as 20 m lengths, or 10 m lengths.

The drilling machine may use a top drive system. In some embodiments, the top drive system functions using a rack and pinion. In some embodiments, the top drive system functions using a hydraulic system.

The drilling machines may include automated pipe handling systems. The automated pipe handling system may be able to lift pipe, make connections, and have another joint in the raised position ready for the next connection. The automated pipe handling systems may include an iron roughneck to make and break connections. In some embodiments, the pipe skid for the drilling machine is an integral component of the drilling machine.

String floats (check valves) may be needed in the drill string because air and/or liquid will be used during drilling. An integral float valve may be positioned in each joint used by the drilling machine. Including a string float in each joint may minimize circulating times at connections and speed up the connection process.

Drilling the wells may be done at low operating pressures. In some embodiments, a quick-connect coupler is used to connect drill pipe together because of the low operating pressures. Using quick-connect couplers to join drill pipe may reduce drilling time and simplify pipe handling automation.

In certain embodiments, the main hole drilling machine is designed to drill 6¼ inch or 6½ inch holes. The pumping capabilities needed to support the main hole drilling machine may include 3×900 scfm air compressors, a 2000 psi booster, and a liquid pump with an operational maximum of 325 gpm. A 35 gpm pump may also be included if mist drilling is required.

In some embodiments, the main hole drilling machine and/or the completion drilling machine uses coiled tubing. Coiled tubing may allow for minimal or no pipe connections above the bottom hole assembly. However, the drilling machine still needs the ability to deploy and retrieve the individual components of the bottom hole assembly. In some embodiments, components are automatically retrieved by a carousel, deployed, and made up over the hole when running in the hole. The process may be reversed when tripping out of the hole. Alternatively, components may be racked horizontally on the drilling machine. The components may be maneuvered with automatic pipe arms.

The drilling machine may employ a split injector system. When coiled tubing operations are halted, the two sides of the injector may be remotely unlatched and retracted to allow for over hole access.

In some embodiments that use coiled tubing, a bottom hole assembly handling rig is used to make up and deploy the bottom hole assembly in the well conductor of a well to be drilled to total depth. The drilling machine may leave the current bottom hole assembly in the well after reaching total depth and prior to moving to the next well. After latching on to the bottom hole assembly in the follow up well, the bottom hole assembly handling rig may pull the bottom hole assembly from the previous well and prepare it for the next well in sequence. The mast for the bottom hole assembly handling rig may be a very simple arrangement supporting a sandline for bottom hole assembly handling.

A reel used by the drilling machine may have 500-1000 m of pipe. To increase the number of cycles the coiled tubing may be used, the reel may have a large diameter and be relatively narrow. In some embodiments, the coiled tubing reel is the wellhead. Having the wellhead and the reel as one unit eliminates the additional handling of a separate wellhead and an empty reel.

Wellbores may be formed in the ground using any desired method. Wellbores may be drilled, impacted, and/or vibrated in the ground. In some embodiments, wellbores are formed using reverse circulation drilling. Reverse circulation drilling may minimize formation damage due to contact with drilling muds and cuttings. Reverse circulation drilling may inhibit contamination of cuttings so that recovered cuttings can be used as a substitute for coring. Reverse circulation drilling may significantly reduce the volume of drilling fluid used to form a wellbore. Reverse circulation drilling enables fast penetration rates and the use of low density drilling fluid. The drilling fluid may be, for example, air, mist, water, brine, or drilling mud. The reduction in volume of drilling fluid may significantly reduce drilling costs. Formation water production is reduced when using reverse circulation drilling. Reverse circulation drilling permits use of air drilling without resulting in excessive air pockets being left in the formation. Prevention of air pockets in the formation during formation of wellbores is desirable, especially if the wellbores are to be used as freeze wells for forming a barrier around a treatment area.

Reverse circulation drilling systems may include components to enable directional drilling. For example, steerable motors, bent subs for altering the direction of the borehole, or autonomous drilling packages could be included.

Reverse circulation drilling enables fast penetration rates and the use of low density drilling fluid such as air or mist. When tri-cone rock bits are used, a skirted rock bit assembly replaces the conventional tri-cone bit. The skirt directs the drilling fluid from the pipe-in-pipe drill rod annulus to the outside portion of the hole being drilled. As the cuttings are generated by the action of the rotating drill bit, the cuttings mix with the drilling fluid, pass through a hole in the center of the bit and are carried out of the hole through the center of the drill rods. When a non-skirted drill bit is used, a reverse-circulation crossover is installed between the standard bit and the drill rods. The crossover redirects the drilling fluid from the pipe-in-pipe drill rod annulus to the inside of the drill string about a meter above the bit. The drilling fluid passes through the bit jets, mixes with the cuttings, and returns up the drill string. At the crossover, the fluid/cuttings mixture enters the drill string and continues to the surface inside the inner tube of the drill rod.

FIG. 11 depicts a schematic drawing of a reverse-circulating polycrystalline diamond compact drill bit design. The reverse-circulating polycrystalline diamond compact (RC-PDC) drill bit design eliminates the crossover. RC-PDC bit 364 may include skirt 366 that directs the drilling fluid from pipe-in-pipe drill rod annulus 368 to bottom portion 370 of the wellbore being formed. In bottom portion 370, the drilling fluid mixes with the cuttings generated by cutters 372 of the RC-PDC bit. The drilling fluid and cuttings pass through opening 374 in the center of RC-PDC bit 364 and are carried out of the wellbore through drill rod center 376.

In some embodiments, the cuttings generated during drilling are milled and used as a filler material in a slurry used for forming a grout wall. Cuttings that contain hydrocarbon material may be retorted to extract the hydrocarbons. Retorting the cuttings may be environmentally beneficial because the reinjected cuttings are free of organic material. Recovering the hydrocarbons may offset a portion of the milling cost.

When drilling a wellbore, a magnet or magnets may be inserted into a first opening to provide a magnetic field used to guide a drilling mechanism that forms an adjacent opening or adjacent openings. The magnetic field may be detected by a 3-axis fluxgate magnetometer in the opening being drilled. A control system may use information detected by the magnetometer to determine and implement operation parameters needed to form an opening that is a selected distance away from the first opening (within desired tolerances).

Various types of wellbores may be formed using magnetic tracking. For example, wellbores formed by magnetic tracking may be used for in situ conversion processes, for steam assisted gravity drainage processes, for the formation of perimeter barriers or frozen barriers, and/or for soil remediation processes. Magnetic tracking may be used to form wellbores for processes that require relatively small tolerances or variations in distances between adjacent wellbores. For example, vertical and/or horizontally positioned heater wells and/or production wells may need to be positioned parallel to each other with relatively little or no variance in parallel alignment to allow for substantially uniform heating and/or production from the treatment area in the formation. Also, freeze wells need to be positioned parallel to each other with relatively little or no variance in parallel alignment to allow formation of overlapping cold zones that will result in a solid frozen barrier around the treatment area.

In certain embodiments, a magnetic string is placed in a vertical well. The magnetic string in the vertical well is used to guide the drilling of a horizontal well such that the horizontal well connects to the vertical well at a desired location, passes the vertical well at a selected distance relative to the vertical well at a selected depth in the formation, or stops a selected distance away from the vertical well. In some embodiments, the magnetic string is placed in a horizontal well. The magnetic string in the horizontal well is used to guide the drilling of a vertical well such that the vertical well connects to the horizontal well at a desired location, passes the horizontal well at a selected distance relative to the horizontal well, or stops at a selected distance away from the horizontal well.

Analytical equations may be used to determine the spacing between adjacent wellbores using measurements of magnetic field strengths. The magnetic field from a first wellbore may be measured by a magnetometer in a second wellbore. Analysis of the magnetic field strengths using derivations of analytical equations may determine the coordinates of the second wellbore relative to the first wellbore.

Figure 12:
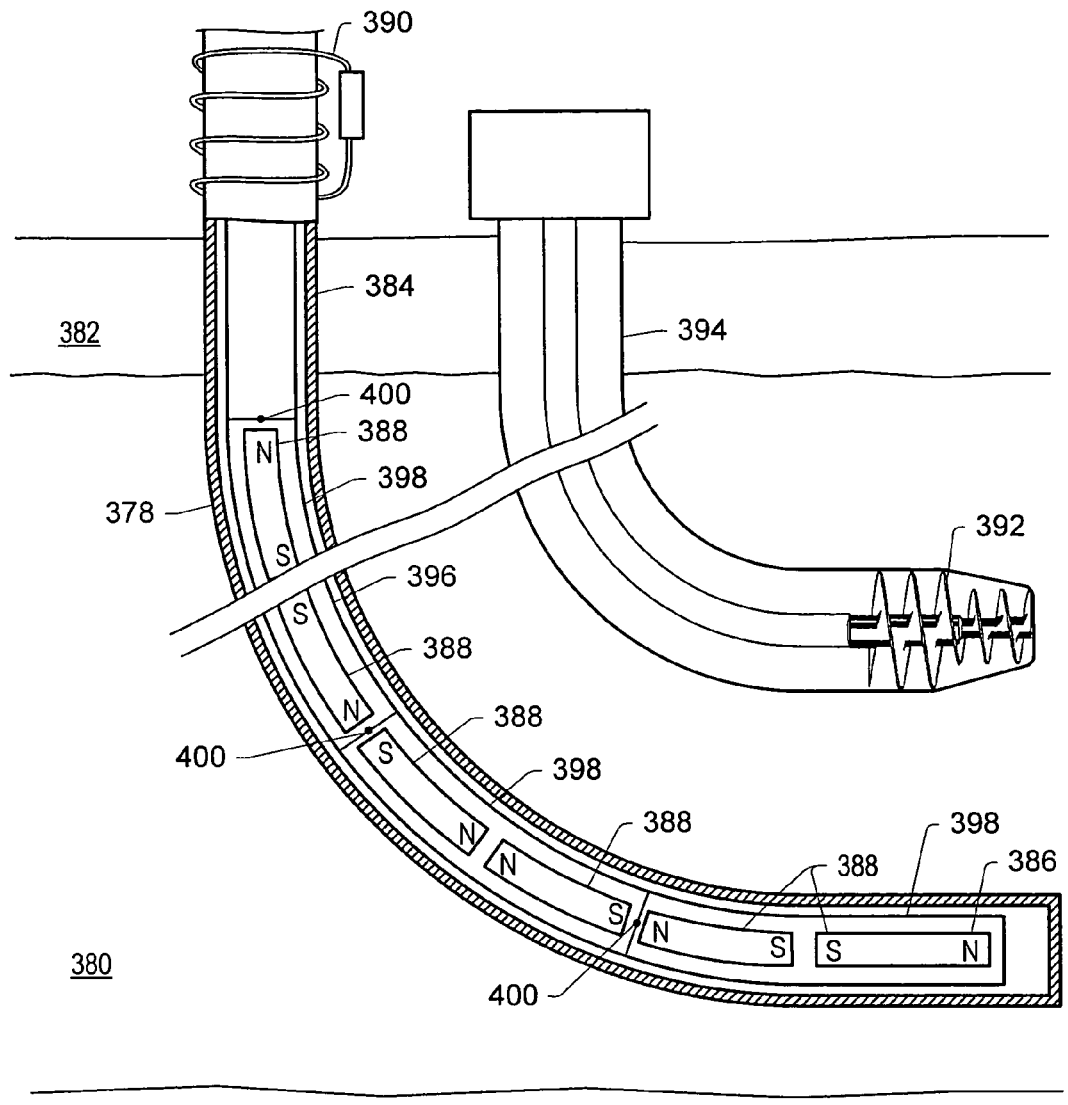
FIG. 12 depicts a schematic representation of an embodiment of a magnetostatic drilling operation to form an opening that is an approximate desired distance away from a drilled opening.

FIG. 12 depicts a schematic representation of an embodiment of a magnetostatic drilling operation to form an opening that is a desired distance (for example, a desired substantially parallel distance) away from a drilled opening. In some embodiments, the magnetostatic drilling operation forms the opening parallel to the drilled opening. Opening 378 may be formed in hydrocarbon layer 380. Opening 378 may be used for any type of application, including but not limited to, barrier formation, soil remediation, solution mining, steam-assisted gravity drainage (SAGD), and/or in situ conversion. A portion of opening 378 may be oriented substantially horizontally in hydrocarbon layer 380. For example, opening 378 may be formed substantially parallel to a boundary (for example, the surface or a boundary between hydrocarbon layer 380 and overburden 382) of the formation. Opening 378 may be formed in other orientations in hydrocarbon layer 380 depending on, for example, a desired use of the opening, formation depth, formation type, or other factors. Opening 378 may include casing 384. In certain embodiments, opening 378 is an open (or uncased) wellbore. In some embodiments, magnetic string 386 is inserted into opening 378. Magnetic string 386 may be unwound from a reel into opening 378. In an embodiment, magnetic string 386 includes one or more magnet segments 388.

Magnet segments 388 may include one or more movable magnets that are magnetizable and demagnetizable using a magnetic coil. Magnetic coil 390 is located at or near the surface of the formation. Magnetic coil 390 is used to magnetize and demagnetize magnetic string 386. In certain embodiments, magnetic string 386 is magnetized by magnetic coil 390 as the string is placed into opening 378. In an embodiment, as magnetic string 386 is removed from opening 378, magnetic coil 390 demagnetizes the magnetic string. Demagnetizing magnetic string 386 as the magnetic string is removed makes the magnetic string safer and more efficient to transport (for example, shipping to another location or moving to another location or opening in the formation).

In other embodiments, magnetic string 386 includes one or more movable permanent longitudinal magnets. A movable permanent longitudinal magnet may have a north pole and a south pole. Magnetic string 386 may have a longitudinal axis that is substantially parallel (for example, within about 5%, within about 10%, or within about 15% of parallel) or coaxial with a longitudinal axis of opening 378.

Magnetic strings may be moved (for example, pushed and/or pulled) through an opening using a variety of methods. In an embodiment, a magnetic string may be coupled to a drill string and moved through the opening as the drill string moves through the opening. Alternatively, magnetic strings may be installed using coiled tubing rigs. Some embodiments may include coupling a magnetic string to a tractor system that moves through the opening. Commercially available tractor systems from Welltec Well Technologies (Denmark) or Schlumberger Technology Co. (Houston, Tex., U.S.A.) may be used. In certain embodiments, magnetic strings are pulled by cable or wireline from either end portion of the opening. In an embodiment, magnetic strings are pumped through the opening using air and/or water. For example, a pig may be moved through the opening by pumping air and/or water through the opening and the magnetic string may be coupled to the pig.

In some embodiments, casing 384 is a conduit. Casing 384 may be made of a material that is not significantly influenced by a magnetic field (for example, non-magnetic alloy such as non-magnetic stainless steel (for example, 304, 310, or 316 stainless steel), reinforced polymer pipe, or brass tubing). The casing may be a conduit of a conductor-in-conduit heater, a perforated liner, or a perforated casing. If the casing is not significantly influenced by a magnetic field, then the magnetic flux will not be shielded.

In some embodiments, the casing is made of a ferromagnetic material (for example, carbon steel). Ferromagnetic material may have a magnetic permeability greater than about 1. The use of ferromagnetic material may weaken the strength of the magnetic field to be detected by drilling apparatus 392 in adjacent opening 394. For example, carbon steel may weaken the magnetic field strength outside of the casing (for example, by a factor of 3 depending on the diameter, wall thickness, and/or magnetic permeability of the casing). Measurements may be made with the magnetic string inside the carbon steel casing (or other magnetically shielding casing) at the surface to determine the effective pole strengths of the magnetic string when shielded by the ferromagnetic material. Measurements of the magnetic field produced by magnetic string 386 in adjacent opening 394 may be used to determine the relative coordinates of adjacent opening 394 to opening 378.

In some embodiments, drilling apparatus 392 includes a magnetic guidance sensor probe. The magnetic guidance sensor probe may contain a 3-axis fluxgate magnetometer and a 3-axis inclinometer. The inclinometer is typically used to determine the rotation of the sensor probe relative to Earth's gravitational field (the "toolface angle"). A general magnetic guidance sensor probe may be obtained from Tensor Energy Products (Round Rock, Tex., U.S.A.). The magnetic guidance sensor may be placed inside the drilling string coupled to a drill bit. In certain embodiments, the magnetic guidance sensor probe is located inside the drilling string of a river crossing rig.

Magnet segments 388 may be placed in conduit 396. Conduit 396 may be a threaded tubular or seamless tubular. Conduit 396 may be formed by coupling one or more sections 398. Sections 398 may include non-magnetic materials such as, but not limited to, stainless steel. In certain embodiments, conduit 396 is formed by coupling several threaded tubular sections. Sections 398 may have any length desired (for example, the sections may have a standard length for threaded tubulars). Sections 398 may have a length chosen to produce magnetic fields with selected distances between junctions of opposing poles in magnetic string 386. The distance between junctions of opposing poles may determine the sensitivity of a magnetic steering method, which corresponds to the accuracy in determining the distance between adjacent wellbores. Typically, the distance between junctions of opposing poles is chosen to be on the same scale as the distance between adjacent wellbores (for example, the distance between junctions may be in a range of about 0.5 m to about 750 m, of about 1 m to about 500 m or, of about 2 m to about 200 m).

Conduit 396 may be a threaded stainless steel tubular. In an embodiment, conduit 396 is 2½ inch Schedule 40, 304 stainless steel tubular formed from 20 ft long sections 398. With 20 ft long sections 398, the distance between opposing poles will be about 20 ft. In some embodiments, sections 398 may be coupled as the conduit is formed and/or inserted into opening 378. Conduit 396 may have a length between about 375 ft and about 525 ft. Shorter or longer lengths of conduit 396 may be used depending on a desired application of the magnetic string.

In an embodiment, sections 398 of conduit 396 includes two magnet segments 388. In an embodiment, sections 398 of conduit 396 include only one magnet segment. In some embodiments, sections 398 of conduit 396 include more than two magnet segments. Magnet segments 388 may be arranged in sections 398 such that adjacent magnet segments have opposing polarities at the junction of the segments, as shown in FIG. 12. In an embodiment, one section 398 includes two magnet segments 388 of opposing polarities. The polarity between adjacent sections 398 may be arranged such that the sections have attracting polarities, as shown in FIG. 12. Arranging the opposing poles approximate the center of each section may make assembly of the magnet segments in each section relatively easy. In an embodiment, the approximate centers of adjacent sections 398 have opposite poles. For example, the approximate center of one section may have north poles and the adjacent section (or sections on each end of the one section) may have south poles as shown in FIG. 12.

Fasteners 400 may be placed at the ends of sections 398 to hold magnet segments 388 in the sections. Fasteners 400 may include, but are not limited to, pins, bolts, or screws. Fasteners 400 may be made of non-magnetic materials. In some embodiments, ends of sections 398 are closed off (for example, end caps are placed on the ends) to enclose magnet segments 388 in the sections. In certain embodiments, fasteners 400 are also placed at junctions of opposing poles of adjacent magnet segments 388 to inhibit the adjacent segments from moving apart.

Figure 13:
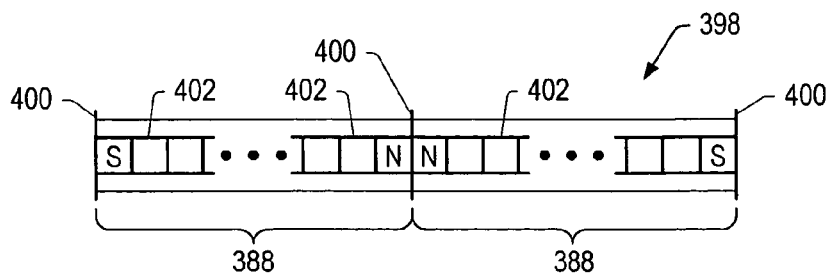
FIG. 13 depicts an embodiment of a section of a conduit with two magnet segments.

FIG. 13 depicts an embodiment of section 398 with two magnet segments 388 with opposing poles. Magnet segments 388 may include one or more magnets 402 coupled to form a single magnet segment. Magnet segments 388 and/or magnets 402 may be positioned in a linear array. Magnets 402 may be Alnico magnets or other types of magnets (such as neodymium iron or samarium cobalt) with sufficient magnetic strength to produce a magnetic field that can be detected in a nearby wellbore. Alnico magnets are made primarily from alloys of aluminum, nickel, and cobalt and may be obtained, for example, from Adams Magnetic Products Co. (Elmhurst, Ill., U.S.A.). In certain embodiment, using permanent magnets in magnet segments 388 may reduce the infrastructure associated with magnetic tracking compared to using inductive coils or magnetic field producing wires since there is no need to provide electrical current. In an embodiment, magnets 402 are Alnico magnets about 6 cm in diameter and about 15 cm in length. Assembling a magnet segment from several individual magnets increases the strength of the magnetic field produced by the magnet segment. Increasing the strength of the magnetic fields produced by magnet segments may advantageously increase the maximum distance for detecting the magnetic fields. The pole strength of a magnet segment may be between about 100 Gauss and about 2000 Gauss, or between about 1000 Gauss and about 2000 Gauss. In an embodiment, the pole strength of the magnet segment is 1500 Gauss. Magnets 402 may be coupled with attracting poles coupled such that magnet segment 388 is formed with a south pole at one end and a north pole at a second end. In one embodiment, 40 magnets 402 of about 15 cm in length are coupled to form magnet segment 388 of about 6 m in length. Opposing poles of magnet segments 388 may be aligned proximate the center of section 398 as shown in FIGS. 12 and 13. Magnet segments 388 may be placed in section 398 and the magnet segments may be held in the section with fasteners 400. One or more sections 398 may be coupled as shown in FIG. 12 to form a magnetic string. In certain embodiments, un-magnetized magnet segments 388 may be coupled together inside sections 398. Sections 398 may be magnetized with a magnetizing coil after magnet segments 388 have been assembled together into the sections.

Figure 14:
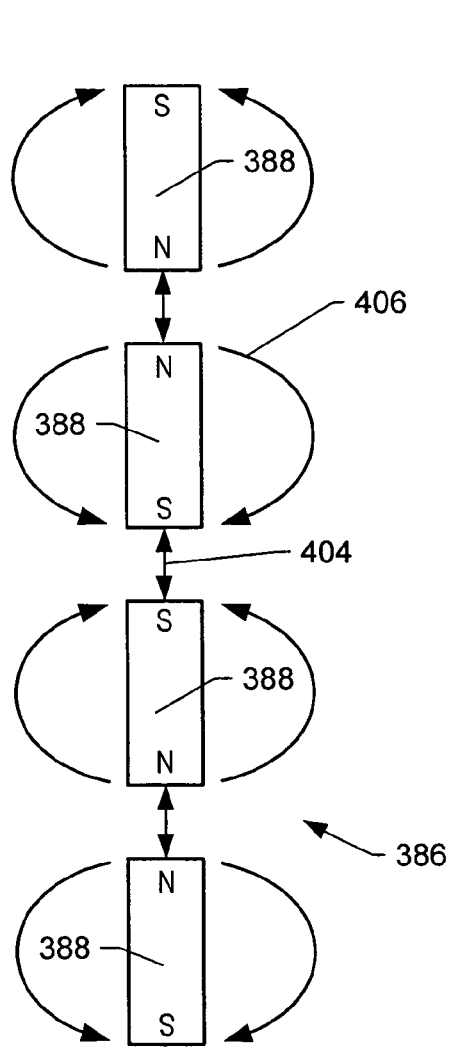
FIG. 14 depicts a schematic of a portion of a magnetic string.

FIG. 14 depicts a schematic of an embodiment of a portion of magnetic string 386. Magnet segments 388 may be positioned such that adjacent segments have opposing poles. In some embodiments, force is applied to minimize distance 404 between magnet segments 388. Additional segments may be added to increase the length of magnetic string 386. Magnet segments 388 may be located in sections 398, as shown in FIG. 12. Magnetic strings may be coiled after assembling. Installation of the magnetic string may include uncoiling the magnetic string. Coiling and uncoiling of the magnetic string may also be used to change position of the magnetic string relative to a sensor in a nearby wellbore, for example, drilling apparatus 392 in opening 394, as shown in FIG. 12.

Magnetic strings may include multiple south-south and north-north opposing pole junctions. As shown in FIG. 14, the multiple opposing pole junctions may induce a series of magnetic fields 406. Alternating the polarity of portions in the magnetic string may provide a sinusoidal variation of the magnetic field along the length of the magnetic string. The magnetic field variations may allow for control of the desired spacing between drilled wellbores. A series of magnetic fields 406 may be detected at greater distances than individual magnetic fields. Increasing the distance between opposing pole junctions in the magnetic string may increase the radial distance at which a magnetometer can detect the magnetic field. In some embodiments, the distance between opposing pole junctions in the magnetic string is varied. For example, more magnets may be used in portions proximate Earth's surface than in portions positioned deeper in the formation.

Some wellbores formed in the formation may be used to facilitate formation of a perimeter barrier around a treatment area. Heat sources in the treatment area may heat hydrocarbons in the formation within the treatment area. The perimeter barrier may be, but is not limited to, a low temperature or frozen barrier formed by freeze wells, dewatering wells, a grout wall formed in the formation, a sulfur cement barrier, a barrier formed by a gel produced in the formation, a barrier formed by precipitation of salts in the formation, a barrier formed by a polymerization reaction in the formation, and/or sheets driven into the formation. Heat sources, production wells, injection wells, dewatering wells, and/or monitoring wells may be installed in the treatment area defined by the barrier prior to, simultaneously with, or after installation of the barrier.

A low temperature zone around at least a portion of a treatment area may be formed by freeze wells. In an embodiment, refrigerant is circulated through freeze wells to form low temperature zones around each freeze well. The freeze wells are placed in the formation so that the low temperature zones overlap and form a low temperature zone around the treatment area. The low temperature zone established by freeze wells is maintained below the freezing temperature of aqueous fluid in the formation. Aqueous fluid entering the low temperature zone freezes and forms the frozen barrier. In other embodiments, the freeze barrier is formed by batch operated freeze wells. A cold fluid, such as liquid nitrogen, is introduced into the freeze wells to form low temperature zones around the freeze wells. The fluid is replenished as needed.

In some embodiments, two or more rows of freeze wells are located about all or a portion of the perimeter of the treatment area to form a thick interconnected low temperature zone. Thick low temperature zones may be formed adjacent to areas in the formation where there is a high flow rate of aqueous fluid in the formation. The thick barrier may ensure that breakthrough of the frozen barrier established by the freeze wells does not occur.

Vertically positioned freeze wells and/or horizontally positioned freeze wells may be positioned around sides of the treatment area. If the upper layer (the overburden) or the lower layer (the underburden) of the formation is likely to allow fluid flow into the treatment area or out of the treatment area, horizontally positioned freeze wells may be used to form an upper and/or a lower barrier for the treatment area. In some embodiments, an upper barrier and/or a lower barrier may not be necessary if the upper layer and/or the lower layer are at least substantially impermeable. If the upper freeze barrier is formed, portions of heat sources, production wells, injection wells, and/or dewatering wells that pass through the low temperature zone created by the freeze wells forming the upper freeze barrier wells may be insulated and/or heat traced so that the low temperature zone does not adversely affect the functioning of the heat sources, production wells, injection wells and/or dewatering wells passing through the low temperature zone.

Spacing between adjacent freeze wells may be a function of a number of different factors. The factors may include, but are not limited to, physical properties of formation material, type of refrigeration system, coldness and thermal properties of the refrigerant, flow rate of material into or out of the treatment area, time for forming the low temperature zone, and economic considerations. Consolidated or partially consolidated formation material may allow for a large separation distance between freeze wells. A separation distance between freeze wells in consolidated or partially consolidated formation material may be from about 3 m to about 20 m, about 4 m to about 15 m, or about 5 m to about 10 m. In an embodiment, the spacing between adjacent freeze wells is about 5 m. Spacing between freeze wells in unconsolidated or substantially unconsolidated formation material, such as in tar sand, may need to be smaller than spacing in consolidated formation material. A separation distance between freeze wells in unconsolidated material may be from about 1 m to about 5 m.

Freeze wells may be placed in the formation so that there is minimal deviation in orientation of one freeze well relative to an adjacent freeze well. Excessive deviation may create a large separation distance between adjacent freeze wells that may not permit formation of an interconnected low temperature zone between the adjacent freeze wells. Factors that influence the manner in which freeze wells are inserted into the ground include, but are not limited to, freeze well insertion time, depth that the freeze wells are to be inserted, formation properties, desired well orientation, and economics.

Relatively low depth wellbores for freeze wells may be impacted and/or vibrationally inserted into some formations. Wellbores for freeze wells may be impacted and/or vibrationally inserted into formations to depths from about 1 m to about 100 m without excessive deviation in orientation of freeze wells relative to adjacent freeze wells in some types of formations.

Wellbores for freeze wells placed deep in the formation, or wellbores for freeze wells placed in formations with layers that are difficult to impact or vibrate a well through, may be placed in the formation by directional drilling and/or geosteering. Acoustic signals, electrical signals, magnetic signals, and/or other signals produced in a first wellbore may be used to guide directionally drilling of adjacent wellbores so that desired spacing between adjacent wells is maintained. Tight control of the spacing between wellbores for freeze wells is an important factor in minimizing the time for completion of barrier formation.

After formation of the wellbore for the freeze well, the wellbore may be backflushed with water adjacent to the part of the formation that is to be reduced in temperature to form a portion of the freeze barrier. The water may displace drilling fluid remaining in the wellbore. The water may displace indigenous gas in cavities adjacent to the formation. In some embodiments, the wellbore is filled with water from a conduit up to the level of the overburden. In some embodiments, the wellbore is backflushed with water in sections. The wellbore maybe treated in sections having lengths of about 6 m, 10 m, 14 m, 17 m, or greater. Pressure of the water in the wellbore is maintained below the fracture pressure of the formation. In some embodiments, the water, or a portion of the water is removed from the wellbore, and a freeze well is placed in the formation.

Figure 15:
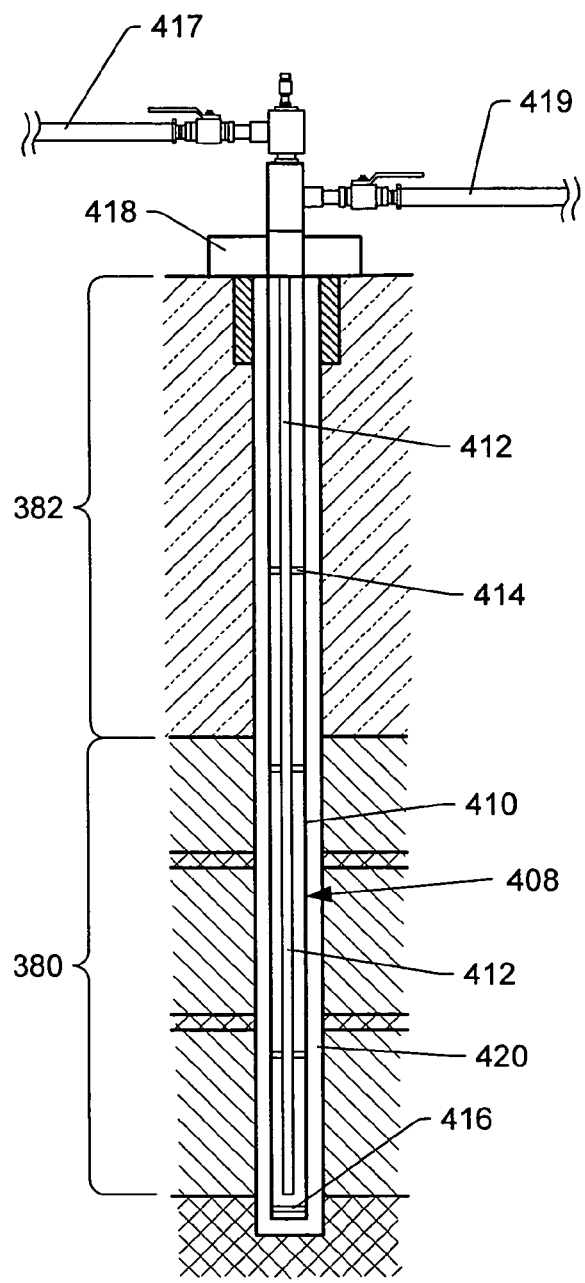
FIG. 15 depicts an embodiment of a freeze well for a circulated liquid refrigeration system, wherein a cutaway view of the freeze well is represented below ground surface.

FIG. 15 depicts an embodiment of freeze well 408. Freeze well 408 may include canister 410, inlet conduit 412, spacers 414, and wellcap 416. Spacers 414 may position inlet conduit 412 in canister 410 so that an annular space is formed between the canister and the conduit. Spacers 414 may promote turbulent flow of refrigerant in the annular space between inlet conduit 412 and canister 410, but the spacers may also cause a significant fluid pressure drop. Turbulent fluid flow in the annular space may be promoted by roughening the inner surface of canister 410, by roughening the outer surface of inlet conduit 412, and/or by having a small cross-sectional area annular space that allows for high refrigerant velocity in the annular space. In some embodiments, spacers are not used. Wellhead 418 may suspend canister 410 in wellbore 420.

Formation refrigerant may flow through cold side conduit 417 from a refrigeration unit to inlet conduit 412 of freeze well 408. The formation refrigerant may flow through an annular space between inlet conduit 412 and canister 410 to warm side conduit 419. Heat may transfer from the formation to canister 410 and from the canister to the formation refrigerant in the annular space. Inlet conduit 412 may be insulated to inhibit heat transfer to the formation refrigerant during passage of the formation refrigerant into freeze well 408. In an embodiment, inlet conduit 412 is a high density polyethylene tube. At cold temperatures, some polymers may exhibit a large amount of thermal contraction. For example, a 260 m initial length of polyethylene conduit subjected to a temperature of about −25° C. may contract by 6 m or more. If a high density polyethylene conduit, or other polymer conduit, is used, the large thermal contraction of the material must be taken into account in determining the final depth of the freeze well. For example, the freeze well may be drilled deeper than needed, and the conduit may be allowed to shrink back during use. In some embodiments, inlet conduit 412 is an insulated metal tube. In some embodiments, the insulation may be a polymer coating, such as, but not limited to, polyvinylchloride, high density polyethylene, and/or polystyrene.

Freeze well 408 may be introduced into the formation using a coiled tubing rig. In an embodiment, canister 410 and inlet conduit 412 are wound on a single reel. The coiled tubing rig introduces the canister and inlet conduit 412 into the formation. In an embodiment, canister 410 is wound on a first reel and inlet conduit 412 is wound on a second reel. The coiled tubing rig introduces canister 410 into the formation. Then, the coiled tubing rig is used to introduce inlet conduit 412 into the canister. In other embodiments, freeze well is assembled in sections at the wellbore site and introduced into the formation.

An insulated section of freeze well 408 may be placed adjacent to overburden 382. An uninsulated section of freeze well 408 may be placed adjacent to layer or layers 380 where a low temperature zone is to be formed. In some embodiments, uninsulated sections of the freeze wells may be positioned adjacent only to aquifers or other permeable portions of the formation that would allow fluid to flow into or out of the treatment area. Portions of the formation where uninsulated sections of the freeze wells are to be placed may be determined using analysis of cores and/or logging techniques.

Various types of refrigeration systems may be used to form a low temperature zone. Determination of an appropriate refrigeration system may be based on many factors, including, but not limited to: a type of freeze well; a distance between adjacent freeze wells; a refrigerant; a time frame in which to form a low temperature zone; a depth of the low temperature zone; a temperature differential to which the refrigerant will be subjected; one or more chemical and/or physical properties of the refrigerant; one or more environmental concerns related to potential refrigerant releases, leaks or spills; one or more economic factors; water flow in the formation; composition and/or properties of formation water including the salinity of the formation water; and one or more properties of the formation such as thermal conductivity, thermal diffusivity, and heat capacity.

A circulated fluid refrigeration system may utilize a liquid refrigerant (formation refrigerant) that is circulated through freeze wells. Some of the desired properties for the formation refrigerant are: low working temperature, low viscosity at and near the working temperature, high density, high specific heat capacity, high thermal conductivity, low cost, low corrosiveness, and low toxicity. A low working temperature of the formation refrigerant allows a large low temperature zone to be established around a freeze well. The low working temperature of formation refrigerant should be about −20° C. or lower. Formation refrigerants having low working temperatures of at least −60° C. may include aqua ammonia, potassium formate solutions such as Dynalene® HC-50 (Dynalene® Heat Transfer Fluids (Whitehall, Pa., U.S.A.)) or FREEZIUM® (Kemira Chemicals (Helsinki, Finland)); silicone heat transfer fluids such as Syltherm XLT® (Dow Corning Corporation (Midland, Mich., U.S.A.); hydrocarbon refrigerants such as propylene; and chlorofluorocarbons such as R-22. Aqua ammonia is a solution of ammonia and water with a weight percent of ammonia between about 20% and about 40%. Aqua ammonia has several properties and characteristics that make use of aqua ammonia as the formation refrigerant desirable. Such properties and characteristics include, but are not limited to, a very low freezing point, a low viscosity, ready availability, and low cost.

Formation refrigerant that is capable of being chilled below a freezing temperature of aqueous formation fluid may be used to form the low temperature zone around the treatment area. The following equation (the Sanger equation) may be used to model the time $t_1$ needed to form a frozen barrier of radius R around a freeze well having a surface temperature of $T_s$:

$$t_1 = \frac{R^2 L_1}{4 k_f v_s} \left( 2\ln\frac{R}{r_o} - 1 + \frac{c_{vf} v_s}{L_1} \right) \quad (1)$$

in which:

$$L_1 = L \frac{a_r^2 - 1}{2 \ln a_r} c_{vu} v_o$$

$$a_r = \frac{R_A}{R}.$$

In these equations, $k_f$ is the thermal conductivity of the frozen material; $c_{vf}$ and $c_{vu}$ are the volumetric heat capacity of the frozen and unfrozen material, respectively; $r_o$ is the radius of the freeze well; $v_s$ is the temperature difference between the freeze well surface temperature $T_s$ and the freezing point of water $T_o$; $v_o$ is the temperature difference between the ambient ground temperature $T_g$ and the freezing point of water $T_o$; L is the volumetric latent heat of freezing of the formation; R is the radius at the frozen-unfrozen interface; and $R_A$ is a radius at which there is no influence from the refrigeration pipe. The Sanger equation may provide a conservative estimate of the time needed to form a frozen barrier of radius R because the equation does not take into consideration superposition of cooling from other freeze wells. The temperature of the formation refrigerant is an adjustable variable that may significantly affect the spacing between freeze wells.

EQN. 1 implies that a large low temperature zone may be formed by using a refrigerant having an initial temperature that is very low. The use of formation refrigerant having an initial cold temperature of about −30° C. or lower is desirable. Formation refrigerants having initial temperatures warmer than about −30° C. may also be used, but such formation refrigerants require longer times for the low temperature zones produced by individual freeze wells to connect. In addition, such formation refrigerants may require the use of closer freeze well spacings and/or more freeze wells.

The physical properties of the material used to construct the freeze wells may be a factor in the determination of the coldest temperature of the formation refrigerant used to form the low temperature zone around the treatment area. Carbon steel may be used as a construction material of freeze wells. ASTM A333 grade 6 steel alloys and ASTM A333 grade 3 steel alloys may be used for low temperature applications. ASTM A333 grade 6 steel alloys typically contain little or no nickel and have a low working temperature limit of about −50° C. ASTM A333 grade 3 steel alloys typically contain nickel and have a much colder low working temperature limit. The nickel in the ASTM A333 grade 3 alloy adds ductility at cold temperatures, but also significantly raises the cost of the metal. In some embodiments, the coldest temperature of the refrigerant is from about −35° C. to about −55° C., from about −38° C. to about −47° C., or from about −40° C. to about −45° C. to allow for the use of ASTM A333 grade 6 steel alloys for construction of canisters for freeze wells. Stainless steels, such as 304 stainless steel, may be used to form freeze wells, but the cost of stainless steel is typically much more than the cost of ASTM A333 grade 6 steel alloy.

In some embodiments, the metal used to form the canisters of the freeze wells may be provided as pipe. In some embodiments, the metal used to form the canisters of the freeze wells may be provided in sheet form. The sheet metal may be longitudinally welded to form pipe and/or coiled tubing. Forming the canisters from sheet metal may improve the economics of the system by allowing for coiled tubing insulation and by reducing the equipment and manpower needed to form and install the canisters using pipe.

A refrigeration unit may be used to reduce the temperature of formation refrigerant to the low working temperature. In some embodiments, the refrigeration unit may utilize an ammonia vaporization cycle. Refrigeration units are available from Cool Man Inc. (Milwaukee, Wis., U.S.A.), Gartner Refrigeration & Manufacturing (Minneapolis, Minn., U.S.A.), and other suppliers. In some embodiments, a cascading refrigeration system may be utilized with a first stage of ammonia and a second stage of carbon dioxide. The circulating refrigerant through the freeze wells may be 30% by weight ammonia in water (aqua ammonia). Alternatively, a single stage carbon dioxide refrigeration system may be used.

Figure 16:
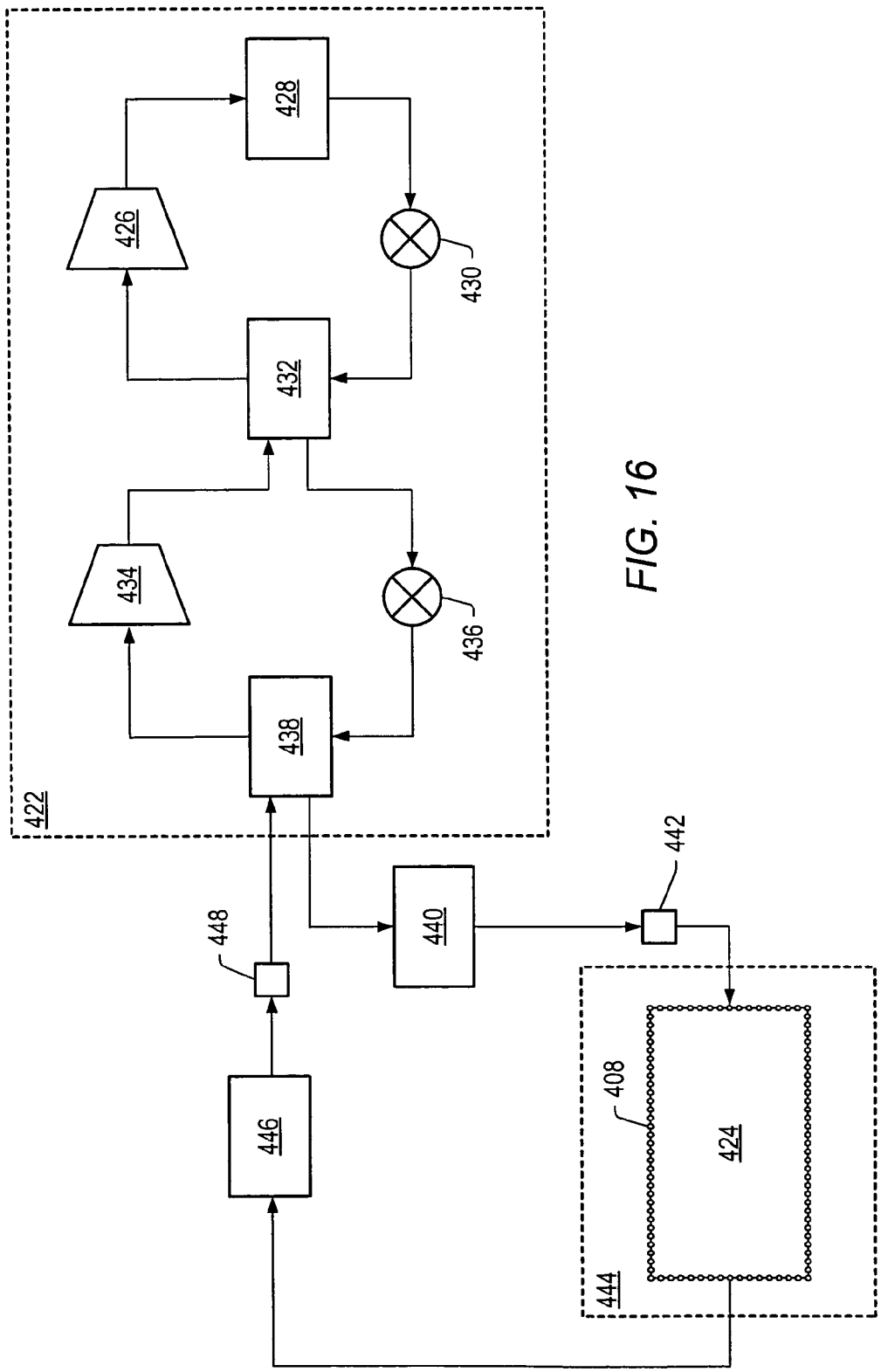
FIG. 16 depicts a schematic representation of an embodiment of a refrigeration system for forming a low temperature zone around a treatment area.

FIG. 16 depicts an embodiment of refrigeration system 422 used to cool formation refrigerant that forms a low temperature zone around treatment area 424. Refrigeration system 422 may include a high stage refrigeration system and a low stage refrigeration system arranged in a cascade relationship. The high stage refrigeration system and the low stage refrigeration system may utilize conventional vapor compression refrigeration cycles.

The high stage refrigeration system includes compressor 426, condenser 428, expansion valve 430, and heat exchanger 432. In some embodiments, the high stage refrigeration system uses ammonia as the refrigerant. The low stage refrigeration system includes compressor 434, heat exchanger 432, expansion valve 436, and heat exchanger 438. In some embodiments, the low stage refrigeration system uses carbon dioxide as the refrigerant. High stage refrigerant from high stage expansion valve 430 cools low stage refrigerant exiting low stage compressor 434 in heat exchanger 432.

Low stage refrigerant exiting low stage expansion valve 436 is used to cool formation refrigerant in heat exchanger 438. The formation refrigerant passes from heat exchanger 438 to storage vessel 440. Pump 442 transports formation refrigerant from storage vessel 440 to freeze wells 408 in formation 444. Refrigeration system 422 is operated so that the formation refrigerant from pump 442 is at the desired temperature. The desired temperature may be in the range from about −35° C. to about −55° C.

Formation refrigerant passes from the freeze wells 408 to storage vessel 446. Pump 448 is used to transport the formation refrigerant from storage vessel 446 to heat exchanger 438. In some embodiments, storage vessel 440 and storage vessel 446 are a single tank with a warm side for formation refrigerant returning from the freeze wells, and a cold side for formation refrigerant from heat exchanger 438.

In some embodiments, a double barrier system is used to isolate a treatment area. The double barrier system may be formed with a first barrier and a second barrier. The first barrier may be formed around at least a portion of the treatment area to inhibit fluid from entering or exiting the treatment area. The second barrier may be formed around at least a portion of the first barrier to isolate an inter-barrier zone between the first barrier and the second barrier. The double barrier system may allow greater project depths than a single barrier system. Greater depths are possible with the double barrier system because the stepped differential pressures across the first barrier and the second barrier is less than the differential pressure across a single barrier. The smaller differential pressures across the first barrier and the second barrier make a breach of the double barrier system less likely to occur at depth for the double barrier system as compared to the single barrier system.

The double barrier system reduces the probability that a barrier breach will affect the treatment area or the formation on the outside of the double barrier. That is, the probability that the location and/or time of occurrence of the breach in the first barrier will coincide with the location and/or time of occurrence of the breach in the second barrier is low, especially if the distance between the first barrier and the second barrier is relatively large (for example, greater than about 15 m). Having a double barrier may reduce or eliminate influx of fluid into the treatment area following a breach of the first barrier or the second barrier. The treatment area may not be affected if the second barrier breaches. If the first barrier breaches, only a portion of the fluid in the inter-barrier zone is able to enter the contained zone. Also, fluid from the contained zone will not pass the second barrier. Recovery from a breach of a barrier of the double barrier system may require less time and fewer resources than recovery from a breach of a single barrier system. For example, reheating a treatment area zone following a breach of a double barrier system may require less energy than reheating a similarly sized treatment area zone following a breach of a single barrier system.

The first barrier and the second barrier may be the same type of barrier or different types of barriers. In some embodiments, the first barrier and the second barrier are formed by freeze wells. In some embodiments, the first barrier is formed by freeze wells, and the second barrier is a grout wall. The grout wall may be formed of cement, sulfur, sulfur cement, or combinations thereof. In some embodiments, a portion of the first barrier and/or a portion of the second barrier is a natural barrier, such as an impermeable rock formation.

Figure 17:
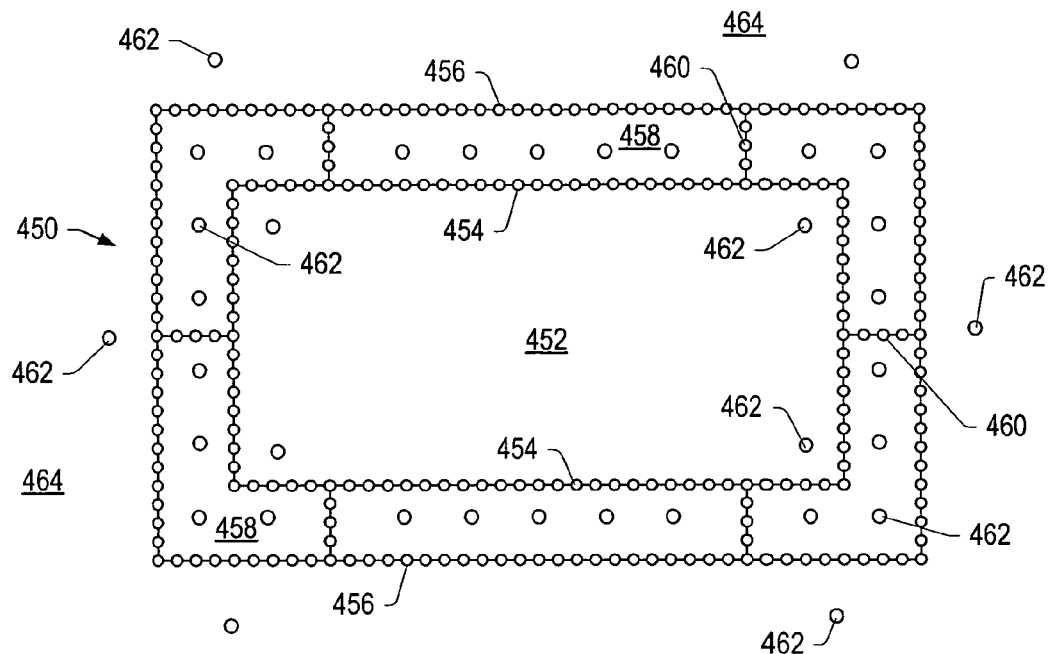
FIG. 17 depicts a schematic representation of a double barrier containment system.

FIG. 17 depicts an embodiment of double barrier system 450. The perimeter of treatment area 452 may be surrounded by first barrier 454. First barrier 454 may be surrounded by second barrier 456. Inter-barrier zones 458 may be isolated between first barrier 454, second barrier 456 and partitions 460. Creating sections with partitions 460 between first barrier 454 and second barrier 456 limits the amount of fluid held in individual inter-barrier zones 458. Partitions 460 may strengthen double barrier system 450. In some embodiments, the double barrier system may not include partitions.

The inter-barrier zone may have a thickness from about 1 m to about 300 m. In some embodiments, the thickness of the inter-barrier zone is from about 10 m to about 100 m, or from about 20 m to about 50 m.

Pumping/monitor wells 462 may be positioned in contained zone 452, inter-barrier zones 458, and/or outer zone 464 outside of second barrier 456. Pumping/monitor wells 462 allow for removal of fluid from treatment area 452, inter-barrier zones 458, or outer zone 464. Pumping/monitor wells 462 also allow for monitoring of fluid levels in treatment area 452, inter-barrier zones 458, and outer zone 464.

In some embodiments, a portion of treatment area 452 is heated by heat sources. The closest heat sources to first barrier 454 may be installed a desired distance away from the first barrier. In some embodiments, the desired distance between the closest heat sources and first barrier 454 is in a range between about 5 m and about 300 m, between about 10 m and about 200 m, or between about 15 m and about 50 m. For example, the desired distance between the closest heat sources and first barrier 454 may be about 40 m.

Figure 18:
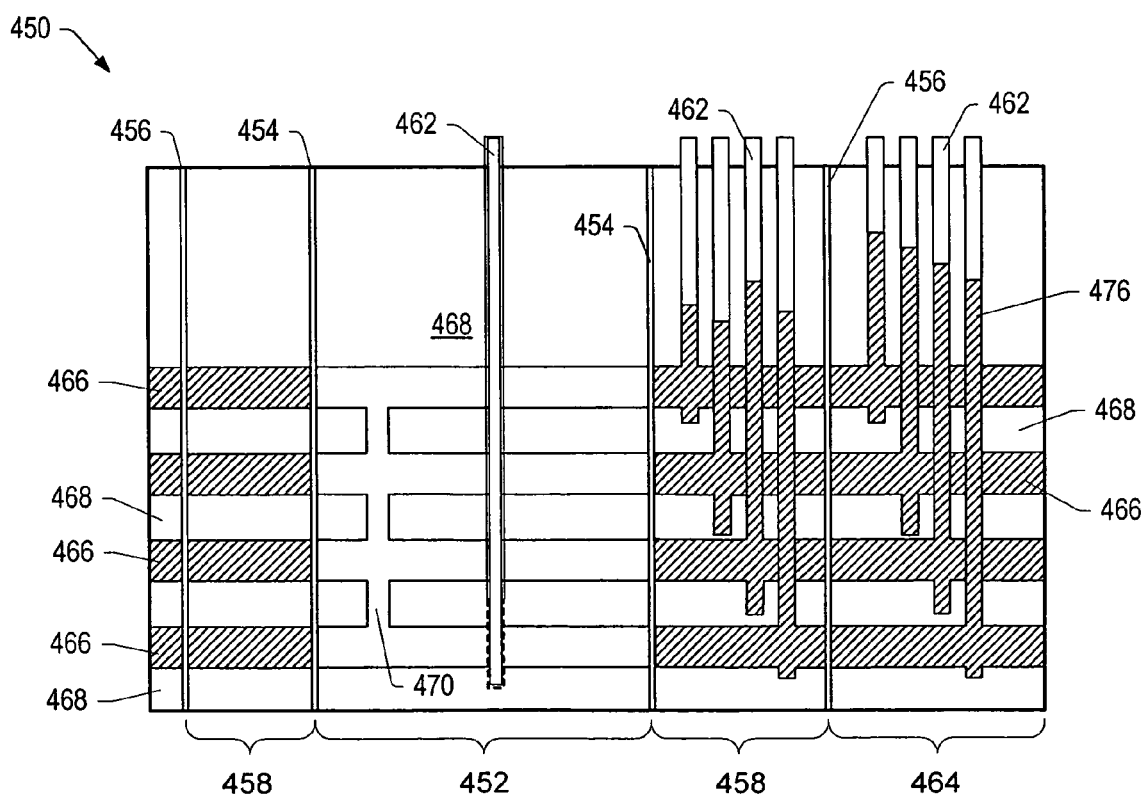
FIG. 18 depicts a cross-sectional view of a double barrier containment system.

FIG. 18 depicts a cross-sectional view of double barrier system 450 used to isolate treatment area 452 in the formation. The formation may include one or more fluid bearing zones 466 and one or more impermeable zones 468. First barrier 454 may at least partially surround treatment area 452. Second barrier 456 may at least partially surround first barrier 454. In some embodiments, impermeable zones 468 are located above and/or below treatment area 452. Thus, treatment area 452 is sealed around the sides and from the top and bottom. In some embodiments, one or more paths 470 are formed to allow communication between two or more fluid bearing zones 466 in treatment area 452. Fluid in treatment area 452 may be pumped from the zone. Fluid in inter-barrier zone 458 and fluid in outer zone 464 is inhibited from reaching the treatment area. During in situ conversion of hydrocarbons in treatment area 452, formation fluid generated in the treatment area is inhibited from passing into inter-barrier zone 458 and outer zone 464.

After sealing treatment area 452, fluid levels in a given fluid bearing zone 466 may be changed so that the fluid head in inter-barrier zone 458 and the fluid head in outer zone 464 are different. The amount of fluid and/or the pressure of the fluid in individual fluid bearing zones 466 may be adjusted after first barrier 454 and second barrier 456 are formed. The ability to maintain different amounts of fluid and/or pressure in fluid bearing zones 466 may indicate the formation and completeness of first barrier 454 and second barrier 456. Having different fluid head levels in treatment area 452, fluid bearing zones 466 in inter-barrier zone 458, and in the fluid bearing zones in outer zone 464 allows for determination of the occurrence of a breach in first barrier 454 and/or second barrier 456. In some embodiments, the differential pressure across first barrier 454 and second barrier 456 is adjusted to reduce stresses applied to first barrier 454 and/or second barrier 456, or stresses on certain strata of the formation.

Some fluid bearing zones 466 may contain native fluid that is difficult to freeze because of a high salt content or compounds that reduce the freezing point of the fluid. If first barrier 454 and/or second barrier 456 are low temperature zones established by freeze wells, the native fluid that is difficult to freeze may be removed from fluid bearing zones 466 in inter-barrier zone 458 through pumping/monitor wells 462. The native fluid is replaced with a fluid that the freeze wells are able to more easily freeze.

In some embodiments, pumping/monitor wells 462 may be positioned in treatment area 452, inter-barrier zone 458, and/or outer zone 464. Pumping/monitor wells 462 may be used to test for freeze completion of frozen barriers and/or for pressure testing frozen barriers and/or strata. Pumping/monitor wells 462 may be used to remove fluid and/or to monitor fluid levels in treatment area 452, inter-barrier zone 458, and/or outer zone 464. Using pumping/monitor wells 462 to monitor fluid levels in contained zone 452, inter-barrier zone 458, and/or outer zone 464 may allow detection of a breach in first barrier 454 and/or second barrier 456. Pumping/monitor wells 462 allow pressure in treatment area 452, each fluid bearing zone 466 in inter-barrier zone 458, and each fluid bearing zone in outer zone 464 to be independently monitored so that the occurrence and/or the location of a breach in first barrier 454 and/or second barrier 456 can be determined.

In some embodiments, fluid pressure in inter-barrier zone 458 is maintained greater than the fluid pressure in treatment area 452, and less than the fluid pressure in outer zone 464. If a breach of first barrier 454 occurs, fluid from inter-barrier zone 458 flows into treatment area 452, resulting in a detectable fluid level drop in the inter-barrier zone. If a breach of second barrier 456 occurs, fluid from the outer zone flows into inter-barrier zone 458, resulting in a detectable fluid level rise in the inter-barrier zone.

Figure 19:
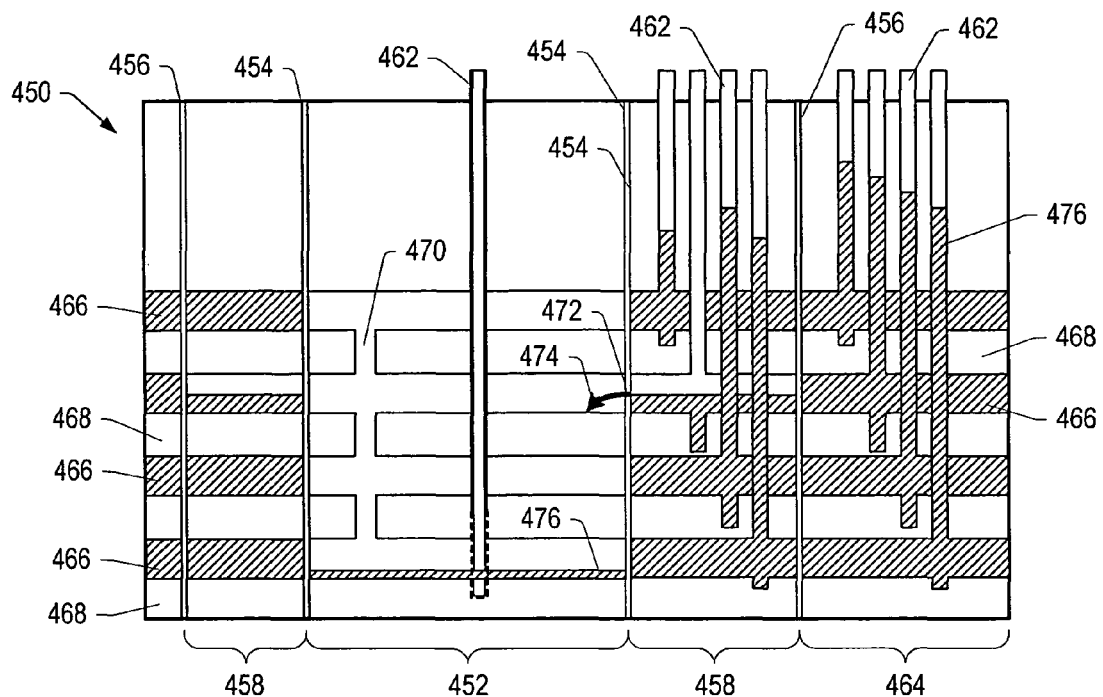
FIG. 19 depicts a schematic representation of a breach in the first barrier of a double barrier containment system.

A breach of first barrier 454 may allow fluid from inter-barrier zone 458 to enter treatment area 452. FIG. 19 depicts breach 472 in first barrier 454 of double barrier containment system 450. Arrow 474 indicates flow direction of fluid 476 from inter-barrier zone 458 to treatment area 452 through breach 472. The fluid level in fluid bearing zone 466 proximate breach 472 of inter-barrier zone 458 falls to the height of the breach.

Path 470 allows fluid 476 to flow from breach 472 to the bottom of treatment area 452, increasing the fluid level in the bottom of the contained zone. The volume of fluid that flows into treatment area 452 from inter-barrier zone 458 is typically small compared to the volume of the treatment area. The volume of fluid able to flow into treatment area 452 from inter-barrier zone 458 is limited because second barrier 456 inhibits recharge of fluid 476 into the affected fluid bearing zone. In some embodiments, the fluid that enters treatment area 452 may be pumped from the treatment area using pumping/monitor wells 462 in the treatment area. In some embodiments, the fluid that enters treatment area 452 may be evaporated by heaters in the treatment area that are part of the in situ conversion process system. The recovery time for the heated portion of treatment area 452 from cooling caused by the introduction of fluid from inter-barrier zone 458 is brief. The recovery time may be less than a month, less than a week, or less than a day.

Pumping/monitor wells 462 in inter-barrier zone 458 may allow assessment of the location of breach 472. When breach 472 initially forms, fluid flowing into treatment area 452 from fluid bearing zone 466 proximate the breach creates a cone of depression in the fluid level of the affected fluid bearing zone in inter-barrier zone 458. Time analysis of fluid level data from pumping/monitor wells 462 in the same fluid bearing zone as breach 472 can be used to determine the general location of the breach.

When breach 472 of first barrier 454 is detected, pumping/monitor wells 462 located in the fluid bearing zone that allows fluid to flow into treatment area 452 may be activated to pump fluid out of the inter-barrier zone. Pumping the fluid out of the inter-barrier zone reduces the amount of fluid 476 that can pass through breach 472 into treatment area 452.

Breach 472 may be caused by ground shift. If first barrier 454 is a low temperature zone formed by freeze wells, the temperature of the formation at breach 472 in the first barrier is below the freezing point of fluid 476 in inter-barrier zone 458. Passage of fluid 476 from inter-barrier zone 458 through breach 472 may result in freezing of the fluid in the breach and self-repair of first barrier 454.

Figure 20:
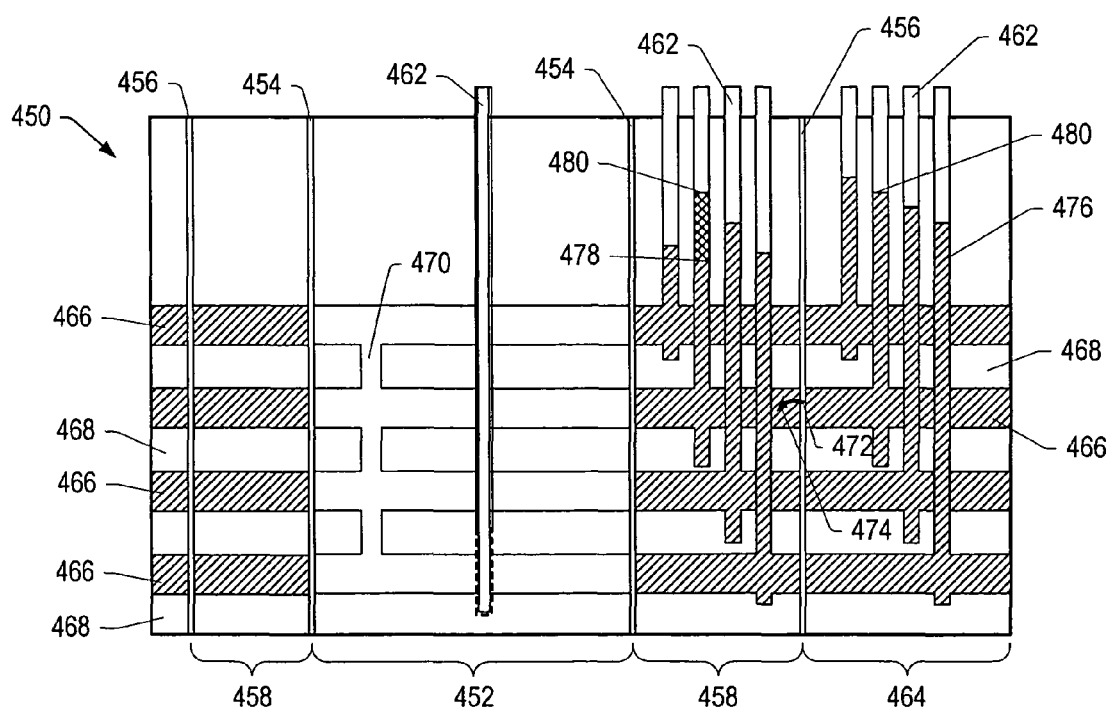
FIG. 20 depicts a schematic representation of a breach in the second barrier of a double barrier containment system.

A breach of the second barrier may allow fluid in the outer zone to enter the inter-barrier zone. The first barrier may inhibit fluid entering the inter-barrier zone from reaching the treatment area. FIG. 20 depicts breach 472 in second barrier 456 of double barrier system 450. Arrow 474 indicates flow direction of fluid 476 from outside of second barrier 456 to inter-barrier zone 458 through breach 472. As fluid 476 flows through breach 472 in second barrier 456, the fluid level in the portion of inter-barrier zone 458 proximate the breach rises from initial level 478 to a level that is equal to level 480 of fluid in the same fluid bearing zone in outer zone 464. An increase of fluid 476 in fluid bearing zone 466 may be detected by pumping/monitor well 462 positioned in the fluid bearing zone proximate breach 472.

Breach 472 may be caused by ground shift. If second barrier 456 is a low temperature zone formed by freeze wells, the temperature of the formation at breach 472 in the second barrier is below the freezing point of fluid 476 entering from outer zone 464. Fluid from outer zone 464 in breach 472 may freeze and self-repair second barrier 456.

First barrier and second barrier of the double barrier containment system may be formed by freeze wells. In an embodiment, first barrier is formed first. The cooling load needed to maintain the first barrier is significantly less than the cooling load needed to form the first barrier. After formation of the first barrier, the excess cooling capacity that the refrigeration system used to form the first barrier may be used to form a portion of the second barrier. In some embodiments, the second barrier is formed first and the excess cooling capacity that the refrigeration system used to form the second barrier is used to form a portion of the first barrier. After the first and second barriers are formed, excess cooling capacity supplied by the refrigeration system or refrigeration systems used to form the first barrier and the second barrier may be used to form a barrier or barriers around the next contained zone that is to be processed by the in situ conversion process.

Grout may be used in combination with freeze wells to provide a barrier for the in situ conversion process. The grout fills cavities (vugs) in the formation and reduces the permeability of the formation. Grout may have better thermal conductivity than gas and/or formation fluid that fills cavities in the formation. Placing grout in the cavities may allow for faster low temperature zone formation. The grout forms a perpetual barrier in the formation that may strengthen the formation. The use of grout in unconsolidated or substantially unconsolidated formation material may allow for larger well spacing than is possible without the use of grout. The combination of grout and the low temperature zone formed by freeze wells may constitute a double barrier for environmental regulation purposes.

Grout may be introduced into the formation through freeze well wellbores. The grout may be allowed to set. The integrity of the grout wall may be checked. The integrity of the grout wall may be checked by logging techniques and/or by hydrostatic testing. If the permeability of a grouted section is too high, additional grout may be introduced into the formation through freeze well wellbores. After the permeability of the grouted section is sufficiently reduced, freeze wells may be installed in the freeze well wellbores.

Grout may be injected into the formation at a pressure that is high, but below the fracture pressure of the formation. In some embodiments, grouting is performed in 16 m increments in the freeze wellbore. Larger or smaller increments may be used if desired. In some embodiments, grout is only applied to certain portions of the formation. For example, grout may be applied to the formation through the freeze wellbore only adjacent to aquifer zones and/or to relatively high permeability zones (for example, zones with a permeability greater than about 0.1 darcy). Applying grout to aquifers may inhibit migration of water from one aquifer to a different aquifer when an established low temperature zone thaws.

Grout used in the formation may be any type of grout including, but not limited to, fine cement, micro fine cement, sulfur, sulfur cement, viscous thermoplastics, or combinations thereof. Fine cement may be ASTM type 3 Portland cement. Fine cement may be less expensive than micro fine cement. In an embodiment, a freeze wellbore is formed in the formation. Selected portions of the freeze wellbore are grouted using fine cement. Then, micro fine cement is injected into the formation through the freeze wellbore. The fine cement may reduce the permeability down to about 10 millidarcy. The micro fine cement may further reduce the permeability to about 0.1 millidarcy. After the grout is introduced into the formation, a freeze wellbore canister may be inserted into the formation. The process may be repeated for each freeze well that will be used to form the barrier.

In some embodiments, fine cement is introduced into every other freeze wellbore. Micro fine cement is introduced into the remaining wellbores. For example, grout may be used in a formation with freeze wellbores set at about 5 m spacing. A first wellbore is drilled and fine cement is introduced into the formation through the wellbore. A freeze well canister is positioned in the first wellbore. A second wellbore is drilled 10 m away from the first wellbore. Fine cement is introduced into the formation through the second wellbore. A freeze well canister is positioned in the second wellbore. A third wellbore is drilled between the first wellbore and the second wellbore. In some embodiments, grout from the first and/or second wellbores may be detected in the cuttings of the third wellbore. Micro fine cement is introduced into the formation through the third wellbore. A freeze wellbore canister is positioned in the third wellbore. The same procedure is used to form the remaining freeze wells that will form the barrier around the treatment area.

In some embodiments, in situ vitrification is used to form the barrier of the treatment area. During in situ vitrification, formation is melted. The melted formation is allowed to slowly solidify to form the barrier. In situ vitrification is described in U.S. Pat. No. 5,114,277 to Murphy et al., which is incorporated by reference as if fully set forth herein. In some embodiments, in situ vitrification is used to form the barrier before the in situ conversion process produces hydrocarbons from the treatment area. In some embodiments, in situ vitrification is used after in situ conversion to isolate the treated area. In some embodiments, in situ vitrification is used to strengthen or seal one or more portions of a perimeter barrier during the in situ conversion process. In situ vitrification may be used to seal off selected portions of the treatment area such as aquifer zones that would allow water entry into the treatment area.

In some embodiments, in situ vitrification is used in combination with freeze wells to form a double barrier containment system for treating the formation. Wellbores for the freeze wells may be formed in the formation. An electrically conductive fluid may be injected into the wellbores and used with the in situ vitrification process to form a barrier in the formation. The relatively close spacing of the freeze wells may facilitate formation of an interconnected perimeter barrier by the in situ vitrification process. After in situ vitrification, freeze wells may be installed in the wellbores. The freeze wells may be activated to form the low temperature zone. Formation fluid entering the low temperature zone freezes to form the frozen barrier. The frozen barrier and the solidified wall formed by the in situ vitrification process form the double barrier containment system.

In an embodiment, freeze wells are installed and activated to form the frozen barrier that isolates the treatment area. Heater wells and production wells are formed in the treatment area. The heater wells are activated and the production wells are used to remove hydrocarbons from the treatment area using the in situ conversion process. After the hydrocarbons are produced from the formation, a desired row or rows of heater wells may be utilized for the in situ vitrification process to form a permanent barrier. The heaters in the desired row or rows of heater wells may be removed from the formation. The desired row or rows of wells may be the outermost row or rows of heaters wells. Monitor wells and/or production wells may also be used in the in situ vitrification process if needed or desired. The in situ process prepares the formation for in situ vitrification by removing water, heating the formation to a high temperature, and increasing the permeability adjacent to the outermost row or rows of wells. The increased permeability allows an electrically conductive fluid injected into the formation to permeate throughout the portions of the formation to be subjected to in situ vitrification.

If selected portions adjacent to the wells are to be subjected to in situ vitrification, packers or isolators may be inserted into the wells to define the portions to be treated so that the whole depth of the perimeter does not need to be treated. Formation adjacent to the desired row or rows of wells may be flushed with carbon dioxide, nitrogen, or other fluid to remove residual contaminants and oxygen from the formation. Graphite or molybdenum electrodes may be inserted into one or more of the wells to be used for in situ vitrification. An electrically conductive material, such as a graphite solution or slurry, may be injected into the wells to flow to adjacent wells to electrically couple electrodes in the wells to electrodes in the adjacent wells. Electrical current is applied to the electrodes and the electrically conductive material to raise the temperature of the formation adjacent to the electrodes and electrically conductive material to a temperature in a range from about 1250° C. to about 1600° C. Raising the temperature of the formation into this temperature range forms molten formation. The molten formation may be drawn into the pores and vugs of the formation. The molten formation slowly solidifies to form an impermeable barrier when the electrical current is terminated or the molten formation flows sufficiently far away from the electrodes, electrically conductive material, and the molten formation cools. Vapors produced during the in situ vitrification process may be removed from the formation through production wells in the treatment area. After formation of the impermeable barrier by the in situ vitrification process, maintenance of the freeze wall may be ended.

In certain embodiments, a barrier may be formed in the formation after an in situ conversion process or a solution mining process by introducing a fluid into the formation. The in situ conversion process may heat the treatment area and greatly increase the permeability of the treatment area. The solution mining process may remove material from the treatment area and greatly increase the permeability of the treatment area. In certain embodiments, the treatment area has an increased permeability of at least 0.1 darcy. In some embodiments, the treatment area has an increased permeability of at least 1 darcy, of at least 10 darcy, or of at least 100 darcy. The increased permeability allows the fluid to spread in the formation into fractures, microfractures, and/or pore spaces in the formation. The fluid may include bitumen, heavy oil, sulfur, polymer, saturated saline solution, and/or a reactant or reactants that react to form a precipitate, solid or a high viscosity fluid in the formation. In some embodiments, bitumen, heavy oil, and/or sulfur used to form the barrier are obtained from treatment facilities of the in situ conversion process.

The fluid may be introduced into the formation as a liquid, vapor, or mixed phase fluid. The fluid may be introduced into a portion of the formation that is at an elevated temperature. In some embodiments, the fluid is introduced into the formation through wells located near a perimeter of the treatment area. The fluid may be directed away from the treatment area. The elevated temperature of the formation maintains or allows the fluid to have a low viscosity so that the fluid moves away from the wells. A portion of the fluid may spread outwards in the formation towards a cooler portion of the formation. In the cooler portion of the formation, the viscosity of the fluid increases, a portion of the fluid precipitates, and/or the fluid solidifies so that the fluid forms the barrier to flow of formation fluid into or out of the treatment area.

In some embodiments, a low temperature barrier formed by freeze wells surrounds all or a portion of the treatment area. As the fluid introduced into the formation approaches the low temperature barrier, the temperature of the formation becomes colder. The colder temperature increases the viscosity of the fluid, enhances precipitation, and/or solidifies the fluid to form the barrier to the flow of formation fluid into or out of the formation. The fluid may remain in the formation as a highly viscous fluid or a solid after the low temperature barrier has dissipated.

In certain embodiments, saturated saline solution is introduced into the formation. Particles in the saturated saline solution may precipitate out of solution when the solution reaches a colder temperature. The solidified particles may form the barrier to the flow of formation fluid into or out of the formation. The solidified particles may be substantially insoluble in formation fluid.

In certain embodiments, brine with a selected crystallogy is introduced into the formation as a reactant. A second reactant, such a carbon dioxide may be introduced into the formation to react with the brine and form a mineral complex in the formation that is substantially insoluble to formation fluid. In an embodiment, the brine solution includes a sodium and aluminum solution. The second reactant introduced in the formation is carbon dioxide. The carbon dioxide reacts with the brine solution to produce dawsonite. The minerals may solidify and form the barrier to the flow of formation fluid into or out of the formation.

In some embodiments, the barrier may be formed using sulfur. Sulfur may be introduced into the formation through wells located near the perimeter of the treatment area. At least a portion of the sulfur spreads outwards from the treatment area towards a cooler portion of the formation. The introduced sulfur spreads outward and solidifies in the formation to form a sulfur barrier. The solidified sulfur in the formation forms a barrier to formation fluid flow into or out of the treatment area.

A temperature monitoring system may be installed in wellbores of freeze wells and/or in monitor wells adjacent to the freeze wells to monitor the temperature profile of the freeze wells and/or the low temperature zone established by the freeze wells. The monitoring system may be used to monitor progress of low temperature zone formation. The monitoring system may be used to determine the location of high temperature areas, potential breakthrough locations, or breakthrough locations after the low temperature zone has formed. Periodic monitoring of the temperature profile of the freeze wells and/or low temperature zone established by the freeze wells may allow additional cooling to be provided to potential trouble areas before breakthrough occurs. Additional cooling may be provided at or adjacent to breakthroughs and high temperature areas to ensure the integrity of the low temperature zone around the treatment area. Additional cooling may be provided by increasing refrigerant flow through selected freeze wells, installing an additional freeze well or freeze wells, and/or by providing a cryogenic fluid, such as liquid nitrogen, to the high temperature areas. Providing additional cooling to potential problem areas before breakthrough occurs may be more time efficient and cost efficient than sealing a breach, reheating a portion of the treatment area that has been cooled by influx of fluid, and/or remediating an area outside of the breached frozen barrier.

In some embodiments, a traveling thermocouple may be used to monitor the temperature profile of selected freeze wells or monitor wells. In some embodiments, the temperature monitoring system includes thermocouples placed at discrete locations in the wellbores of the freeze wells, in the freeze wells, and/or in the monitoring wells. In some embodiments, the temperature monitoring system comprises a fiber optic temperature monitoring system.

Fiber optic temperature monitoring systems are available from Sensornet (London, United Kingdom), Sensa (Houston, Tex., U.S.A.), Luna Energy (Blacksburg, Va., U.S.A.), Lios Technology GMBH (Cologne, Germany), Oxford Electronics Ltd. (Hampshire, United Kingdom), and Sabeus Sensor Systems (Calabasas, Calif., U.S.A.). The fiber optic temperature monitoring system includes a data system and one or more fiber optic cables. The data system includes one or more lasers for sending light to the fiber optic cable; and one or more computers, software and peripherals for receiving, analyzing, and outputting data. The data system may be coupled to one or more fiber optic cables.

A single fiber optic cable may be several kilometers long. The fiber optic cable may be installed in many freeze wells and/or monitor wells. In some embodiments, two fiber optic cables may be installed in each freeze well and/or monitor well. The two fiber optic cables may be coupled. Using two fiber optic cables per well allows for compensation due to optical losses that occur in the wells and allows for better accuracy of measured temperature profiles.

A fiber of a fiber optic cable may be placed in a polymer tube. The polymer tube may be filled with a heat transfer fluid. The heat transfer fluid may be a gel or liquid that does not freeze at or above the temperature of formation refrigerant used to cool the formation. In some embodiments the heat transfer fluid in the polymer tube is the same as the formation refrigerant, for example, a fluid available from Dynalene® Heat Transfer Fluids or aqua ammonia. In some embodiments, the fiber is blown into the tube using the heat transfer fluid. Using the heat transfer fluid to insert the fiber into the polymer tube removes moisture from the polymer tube.

Figure 21:
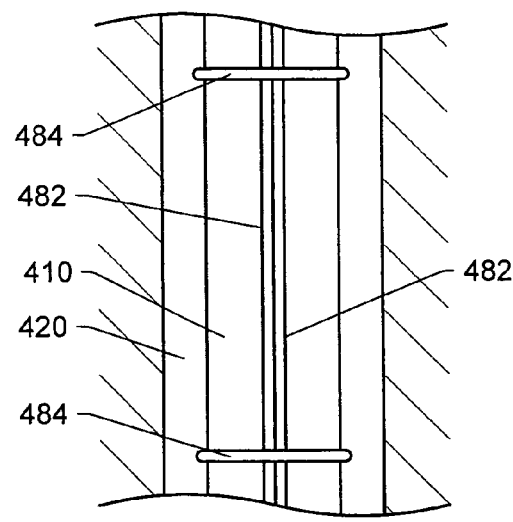
FIG. 21 depicts a representation of a protective sleeve strapped to a canister of a freeze well.

In some embodiments, a protective sleeve is strapped to the canister of the freeze well as the canister is introduced into the formation. The protective sleeve may be in a u-shape. A turn-around sub near the end of the canister may accommodate the u-turn in the protective sleeve. A fiber may be inserted in the protective sleeve. FIG. 21 depicts a portion of canister 410 with protective sleeve 482 coupled to the canister by straps 484. Protective sleeve 482 may be stainless steel tubing or other tubing.

The polymer tube and fiber may be placed in the protective sleeve, such as 14 inch 304 stainless steel tubing, to form the fiber optic cable. The protective sleeve may be prestressed to accommodate thermal contraction at low temperatures. The protective sleeve may be filled with the heat transfer fluid. In some embodiments, the polymer tube is blown into the protective sleeve with the heat transfer fluid. Using the heat transfer fluid to insert the polymer tube and fiber into the protective sleeve removes moisture from the protective sleeve. In some embodiments, two fibers are positioned in the same stainless steel tube. In some embodiments, the fiber is placed directly in the protective sleeve without being placed in a polymer tube.

In some embodiments, the fiber optic cable is strapped to the canister of the freeze well as the canister is inserted into the formation. The fiber optic cable may be coiled around the canister adjacent to the portions of the formation that are to be reduced to low temperature to form the low temperature zone. Coiling the fiber optic cable around the canister allows a large length of the fiber optic cable to be adjacent to areas that are to be reduced to low temperature. The large length allows for better resolution of the temperature profile for the areas to be reduced to low temperatures. In some embodiments, the fiber optic cable is placed in the canister of the freeze well.

Figure 22:
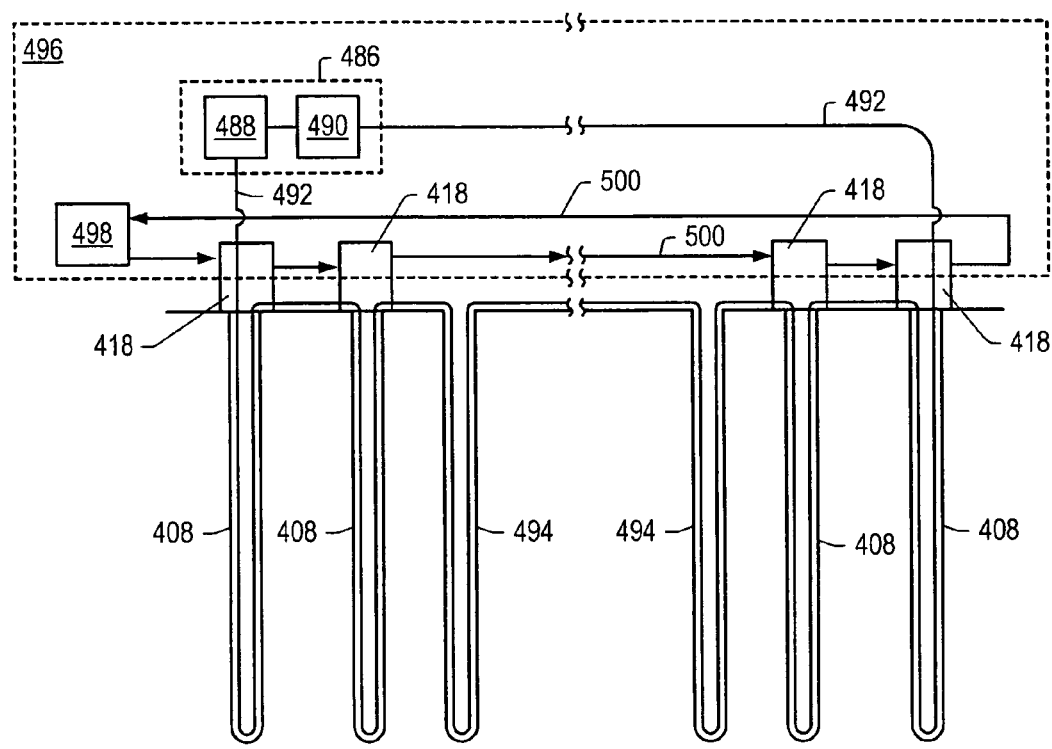
FIG. 22 depicts a schematic representation of a fiber optic cable system used to monitor temperature in and near freeze wells.

FIG. 22 depicts a schematic representation of a fiber optic temperature monitoring system. Data system 486 includes laser 488 and analyzer 490. Laser 488 injects short, intense light pulses into fiber optic cable 492. Fiber optic cable 492 is positioned in a plurality of freeze wells 408 and monitor wells 494. Fiber optic cable 492 may be strapped to the canisters of the freeze wells as the canisters are installed in the formation. In some embodiments, the fiber optic cable is strapped to supports and inserted into the monitor wells. In some embodiments, the protective sleeve of the fiber optic cable may be suspended in the monitor wells without an additional support. Backscattering and reflection of light in fiber optic cable 492 may be measured as a function of time by analyzer 490 of the data system 486. Analysis of the backscattering and reflection of light data yields a temperature profile along the length of fiber optic cable 492.

In some embodiments, the data system is a double ended system. The data system may include one or more lasers that send light pulses into each end of the fiber optic cable. In some embodiments, the laser is one laser. The laser sends pulses to each end of the fiber optic cable in an alternating manner. The return signals received by the data system allows for compensation of signal attenuation in the optical fiber.

In some embodiments, computer control system 496 is in communication with the fiber optic temperature monitoring system and the formation refrigeration circulation system. The formation refrigeration circulation system may include refrigeration system 498. Refrigeration system 498 sends chilled formation refrigerant to wellheads 418 of freeze wells 408 through piping 500. In some embodiments, the formation refrigerant passes down the inlet conduit of the freeze well and up through the annular space between the inlet conduit and the freeze well canister. The formation refrigerant then passes through piping 500 to the next freeze well.

Computer control system 496 may allow for automatic monitoring of the low temperature zone established by freeze wells 408. Computer control system 496 may periodically shut down the flow of formation refrigerant to a set of freeze wells for a given time. For example, computer control system 496 may shut down the flow of formation refrigerant to a specific set of freeze wells every 60 days for a period of two days and activate data system 486 to monitor the temperature profile near the shut down freeze wells. The temperature profile of the freeze wells with no formation refrigerant flow will begin to rise.

Computer control system 496 may monitor the rate of increase of temperature. If there is a problem area, the temperature profile near the problem area will show a greater rate of change than the temperature profile of adjacent areas. If a larger than expected temperature increase occurs at approximately the same depth location at or near two adjacent wells, the computer control system may signal that there is a problem to an operator of the system. The location of the problem area may be estimated/modeled/assessed by comparing the temperature increases between adjacent wells. For example, if the temperature increase in a first well is twice as large as the temperature increase in a second well, then the location of the problem area is likely closer to the first well. Extra cooling and/or extra monitoring can be provided to problem areas. Extra cooling may be provided by increasing the flow of formation refrigerant to the problem area and/or by installing one or more additional freeze wells. If no problems are detected during the given time, the computer system restarts the flow of formation fluid to the specific set of freeze wells and begins a test of another set of freeze wells. Using computer control system 496 to monitor the low temperature zone established by freeze wells allows for problems to be detected and fixed before a breach of the barrier formed by the freeze wells occurs.

In some embodiments, the fiber optic temperature monitoring system utilizes Brillouin or Raman scattering systems. Such systems provide spatial resolution of 1 m and temperature resolution of 0.1° C. With sufficient averaging and temperature calibration, the systems may be accurate to 0.5° C.

In some embodiments, the fiber optic temperature monitoring system may be a Bragg system that uses a fiber optic cable etched with closely spaced Bragg gratings. The Bragg gratings may be formed in 1 foot increments along selected lengths of the fiber. Fibers with Bragg gratings are available from Luna Energy. The Bragg system only requires a single fiber optic cable to be placed in each well that is to be monitored. The Bragg system is able to measure the fiber temperature in a few seconds.

The fiber optic temperature monitoring system may be used to detect the location of a breach or a potential breach in a frozen barrier. The search for potential breaches may be performed at scheduled intervals, for example, every two or three months. To determine the location of the breach or potential breach, flow of formation refrigerant to the freeze wells of interest is stopped. In some embodiments, the flow of formation refrigerant to all of the freeze wells is stopped. The rise in the temperature profiles, as well as the rate of change of the temperature profiles, provided by the fiber optic temperature monitoring system for each freeze well can be used to determine the location of any breaches or hot spots in the low temperature zone maintained by the freeze wells. The temperature profile monitored by the fiber optic temperature monitoring system for the two freeze wells closest to the hot spot or fluid flow will show the quickest and greatest rise in temperature. A temperature change of a few degrees Centigrade in the temperature profiles of the freeze wells closest to a troubled area may be sufficient to isolate the location of the trouble area. The shut down time of flow of circulation fluid in the freeze wells of interest needed to detect breaches, potential breaches, and hot spots may be on the order of a few hours or days, depending on the well spacing and the amount of fluid flow affecting the low temperature zone.

Fiber optic temperature monitoring systems may also be used to monitor temperatures in heated portions of the formation during in situ conversion processes. The fiber of a fiber optic cable used in the heated portion of the formation may be clad with a reflective material to facilitate retention of a signal or signals transmitted down the fiber. In some embodiments, the fiber is clad with gold, copper, nickel, aluminum and/or alloys thereof. The cladding may be formed of a material that is able to withstand chemical and temperature conditions in the heated portion of the formation. For example, gold cladding may allow an optical sensor to be used up to temperatures of 700° C. In some embodiments, the fiber is clad with aluminum. The fiber may be dipped in or run through a bath of liquid aluminum. The clad fiber may then be allowed to cool to secure the aluminum to the fiber. The gold or aluminum cladding may reduce hydrogen darkening of the optical fiber.

Figure 23:
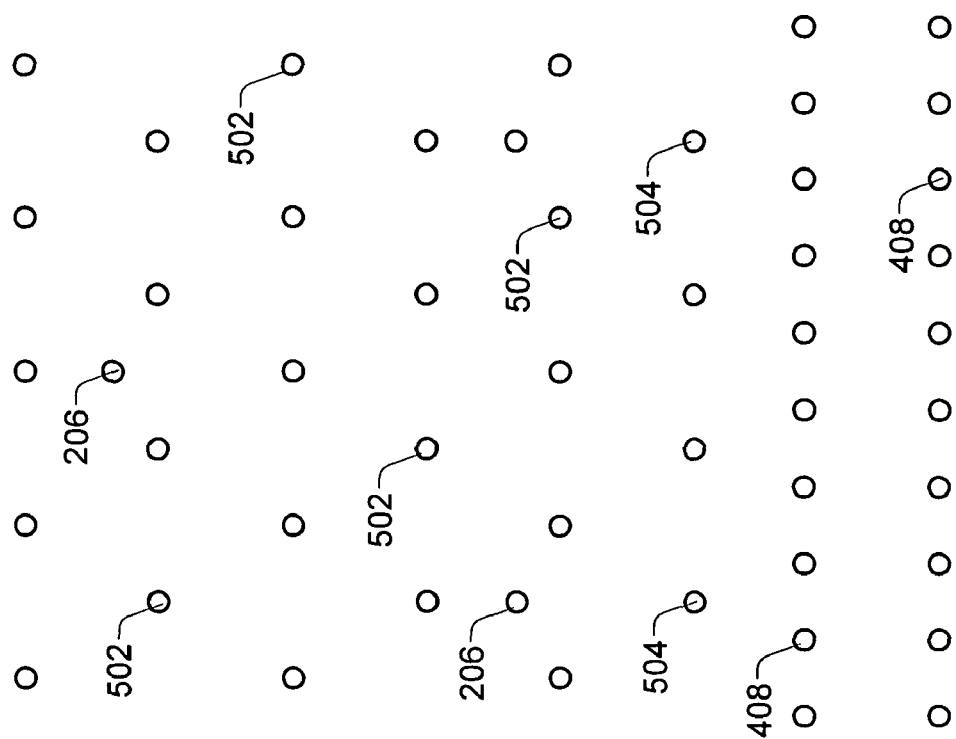
FIG. 23 depicts a schematic view of a well layout including heat interceptor wells.

In some embodiments, heaters that heat hydrocarbons in the formation may be close to the low temperature zone established by freeze wells. In some embodiments, heaters may be may be 20 m, 10 m, 5 m or less from an edge of the low temperature zone established by freeze wells. In some embodiments, heat interceptor wells may be positioned between the low temperature zone and the heaters to reduce the heat load applied to the low temperature zone from the heated part of the formation. FIG. 23 depicts a schematic view of the well layout plan for heater wells 502, production wells 206, heat interceptor wells 504, and freeze wells 408 for a portion of an in situ conversion system embodiment. Heat interceptor wells 504 are positioned between heater wells 502 and freeze wells 408.

Some heat interceptor wells may be formed in the formation specifically for the purpose of reducing the heat load applied to the low temperature zone established by freeze wells. Some heat interceptor wells may be heater wellbores, monitor wellbores, production wellbores, dewatering wellbores, or other type of wellbores that are converted for use as heat interceptor wells.

In some embodiments, heat interceptor wells may function as heat pipes to reduce the heat load applied to the low temperature zone. A liquid heat transfer fluid may be placed in the heat interceptor wellbores. The liquid may include, but is not limited to, water, alcohol, and/or alkanes. Heat supplied to the formation from the heaters may advance to the heat interceptor wellbores and vaporize the liquid heat transfer fluid in the heat interceptor wellbores. The resulting vapor may rise in the wellbores. Above the heated portion of the formation adjacent to the overburden, the vapor may condense and flow by gravity back to the area adjacent to the heated part of the formation. The heat absorbed by changing the phase of the liquid heat transfer fluid reduces the heat load applied to the low temperature zone. Using heat interceptor wells that function as heat pipes may be advantageous for formations with thick overburdens that are able to absorb the heat applied as the heat transfer fluid changes phase from vapor to liquid. The wellbore may include wicking material, packing to increase surface area adjacent to a portion of the overburden, or other material to promote heat transfer to or from the formation and the heat transfer fluid.

In some embodiments, a heat transfer fluid is circulated through the heat interceptor wellbores in a closed loop system. A heat exchanger reduces the temperature of the heat transfer fluid after the heat transfer fluid leaves the heat interceptor wellbores. Cooled heat transfer fluid is pumped through the heat interceptor wellbores. In some embodiments, the heat transfer fluid does not undergo a phase change during use. In some embodiments, the heat transfer fluid may change phases during use. The heat transfer fluid may be, but is not limited to, water, alcohol, and/or glycol.

A potential source of heat loss from the heated formation is due to reflux in wells. Refluxing occurs when vapors condense in a well and flow into a portion of the well adjacent to the heated portion of the formation. Vapors may condense in the well adjacent to the overburden of the formation to form condensed fluid. Condensed fluid flowing into the well adjacent to the heated formation absorbs heat from the formation. Heat absorbed by condensed fluids cools the formation and necessitates additional energy input into the formation to maintain the formation at a desired temperature. Some fluids that condense in the overburden and flow into the portion of the well adjacent to the heated formation may react to produce undesired compounds and/or coke. Inhibiting fluids from refluxing may significantly improve the thermal efficiency of the in situ conversion system and/or the quality of the product produced from the in situ conversion system.

For some well embodiments, the portion of the well adjacent to the overburden section of the formation is cemented to the formation. In some well embodiments, the well includes packing material placed near the transition from the heated section of the formation to the overburden. The packing material inhibits formation fluid from passing from the heated section of the formation into the section of the wellbore adjacent to the overburden. Cables, conduits, devices, and/or instruments may pass through the packing material, but the packing material inhibits formation fluid from passing up the wellbore adjacent to the overburden section of the formation.

In some embodiments, a gas may be introduced into the formation through wellbores to inhibit reflux in the wellbores. In some embodiments, gas may be introduced into wellbores that include baffle systems to inhibit reflux of fluid in the wellbores. The gas may be carbon dioxide, methane, nitrogen or other desired gas.

Figure 24:
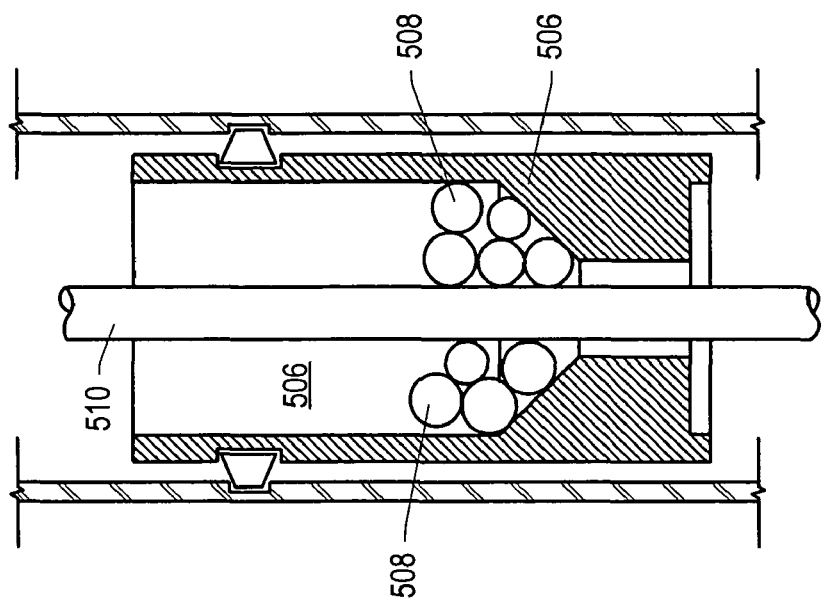
FIG. 24 depicts an embodiment of a ball type reflux baffle system positioned in a heater well.

In some well embodiments, a ball type reflux baffle system may be used in heater wells to inhibit reflux. FIG. 24 depicts an embodiment of ball type reflux baffle system positioned in a cased portion of a heater well. Ball type reflux baffle may include insert 506, and balls 508. A portion of heater element 510 passes through insert 506. The portion of heater element 510 that passes through insert 506 is a portion of the heater element that does not heat to a high temperature. Insert 506 may be made of metal, plastic and/or steel able to withstand temperatures of over 160° C. In an embodiment, insert 506 is made of phenolic resin.

Insert 506 may be guided down the casing of the wellbore using a coil tubing guide string. Insert 506 may be set in position using slips that fit in one or more indentions in the insert, using protrusions of the insert that fit in one or more recesses in the casing, or the insert may rest on a shoulder of the casing. After removal of the coil tubing guide string, balls 508 may be dropped down the casing onto insert 506. Balls may be made of any desired material able to withstand temperatures of over 160° C. In some embodiments, balls 510 are made of silicon nitride. Balls of varying diameters may be used. Balls inhibit fluid convection.

During the in situ conversion process, heater element 510 may need to be pulled from the well. When heater element 510 is removed from the well, balls 508 may pass through insert 506 to the bottom of the well. Another heater element may be installed in the well, and additional balls may be dropped down the well to land on insert 506.

In some embodiments, one or more circular baffles may be coupled to a portion of a heating element to inhibit convection of fluid. The baffles may substantially fill the annular space between the heating element and the casing. The baffles may be made of an electrically insulative material such as a ceramic, or plastic. In some embodiments, the baffles may be made of fiberglass or silicon nitride. The baffles may position the heating element in the center of the casing.

The ball type baffle system and/or the circular baffle system may work better if a gas purge is introduced into the wellbore. The gas purge may maintain sufficient pressure in the wellbore to inhibit fluid flow from the heated portion of the formation into the wellbore. The gas purge may enhance heat exchange at the baffle system to help maintain a top portion of the baffle system colder than the lower portion of the baffle system.

The flow of production fluid up the well to the surface is desired for some types of wells, especially for production wells. Flow of production fluid up the well is also desirable for some heater wells that are used to control pressure in the formation. The overburden, or a conduit in the well used to transport formation fluid from the heated portion of the formation to the surface, may be heated to inhibit condensation on or in the conduit. Providing heat in the overburden, however, may be costly and/or may lead to increased cracking or coking of formation fluid as the formation fluid is being produced from the formation.

To avoid the need to heat the overburden or to heat the conduit passing through the overburden, one or more diverters may be placed in the wellbore to inhibit fluid from refluxing into the wellbore adjacent to the heated portion of the formation. In some embodiments, the diverter retains fluid above the heated portion of the formation. Fluids retained in the diverter may be removed from the diverter using a pump, gas lifting, and/or other fluid removal technique. In some embodiments, the diverter directs fluid to a pump, gas lift assembly, or other fluid removal device located below the heated portion of the formation.

Figure 25:
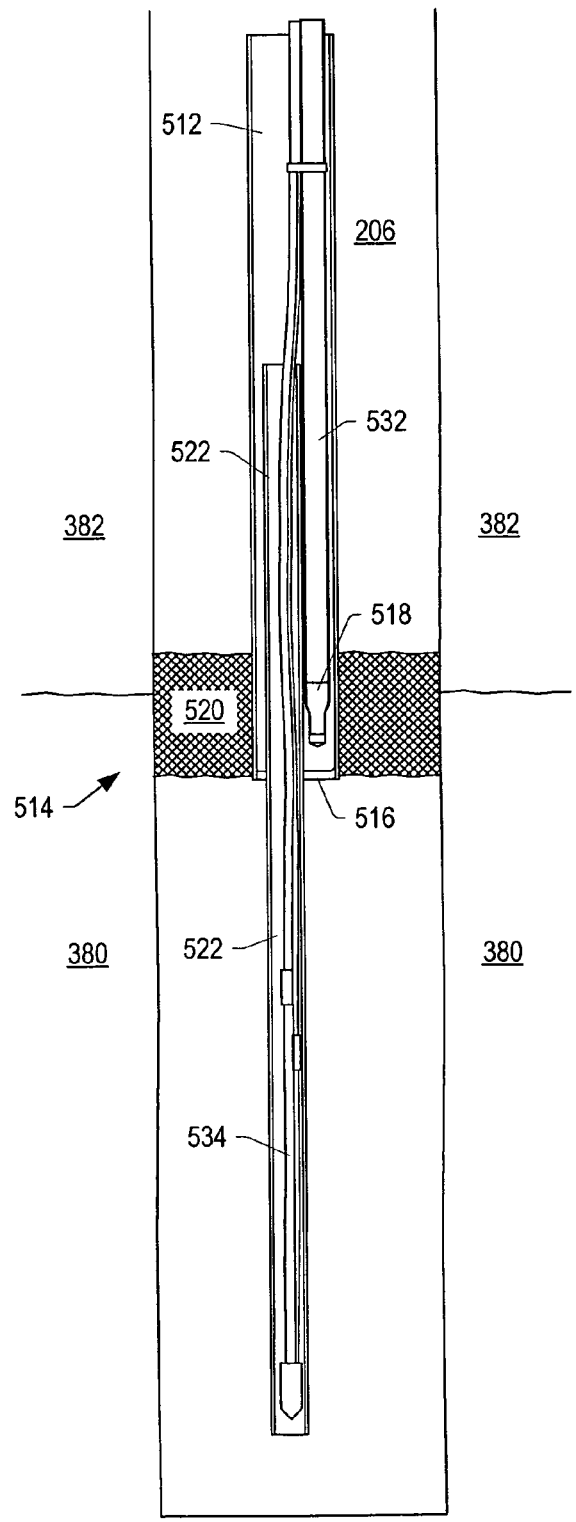
FIG. 25 depicts a schematic representation of an embodiment of a diverter device in the production well.

FIG. 25 depicts an embodiment of a diverter in a production well. Production well 206 includes conduit 512. In some embodiments, diverter 514 is coupled to or located proximate production conduit 512 in overburden 382. In some embodiments, the diverter is placed in the heated portion of the formation. Diverter 514 may be located at or near an interface of overburden 382 and hydrocarbon layer 380. Hydrocarbon layer 380 is heated by heat sources located in the formation. Diverter 514 may include packing 520, riser 522, and seal 516 in production conduit 512. Formation fluid in the vapor phase from the heated formation moves from hydrocarbon layer 380 into riser 522. In some embodiments, riser 522 is perforated below packing 520 to facilitate movement of fluid into the riser. Packing 520 inhibits passage of the vapor phase formation fluid into an upper portion of production well 206. Formation fluid in the vapor phase moves through riser 522 into production conduit 512. A non-condensable portion of the formation fluid rises through production conduit 512 to the surface. The vapor phase formation fluid in production conduit 512 may cool as it rises towards the surface in the production conduit. If a portion of the vapor phase formation fluid condenses to liquid in production conduit 512, the liquid flows by gravity towards seal 516. Seal 516 inhibits liquid from entering the heated portion of the formation. Liquid collected above seal 516 is removed by pump 518 through conduit 532. Pump 518 may be, but is not limited to being, a sucker rod pump, an electrical pump, or a progressive cavity pump (Moyno style). In some embodiments, liquid above seal 516 is gas lifted through conduit 532. Producing condensed fluid may reduce costs associated with removing heat from fluids at the wellhead of the production well.

In some embodiments, production well 206 includes heater 534. Heater 534 provides heat to vaporize liquids in a portion of production well 206 proximate hydrocarbon layer 380. Heater 534 may be located in production conduit 512 or may be coupled to the outside of the production conduit. In embodiments where the heater is located outside of the production conduit, a portion of the heater passes through the packing material.

In some embodiments, a diluent may be introduced into production conduit 512 and/or conduit 532. The diluent is used to inhibit clogging in production conduit 512, pump 518, and/or conduit 532. The diluent may be, but is not limited to being, water, an alcohol, a solvent, and/or a surfactant.

In some embodiments, riser 522 extends to the surface of production well 206. Perforations and a baffle in riser 522 located above seal 516 direct condensed liquid from the riser into production conduit 512.

In certain embodiments, two or more diverters may be located in the production well. Two or more diverters provide a simple way of separating initial fractions of condensed fluid produced from the in situ conversion system. A pump may be placed in each of the diverters to remove condensed fluid from the diverters.

Figure 26:
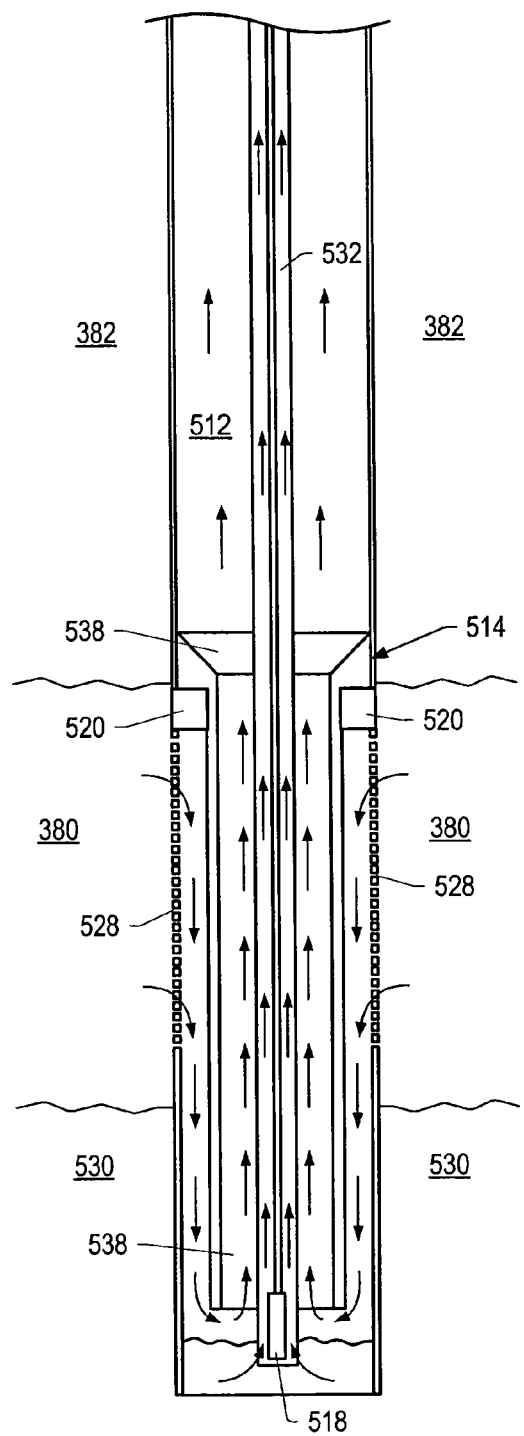
FIG. 26 depicts a schematic representation of an embodiment of the baffle in the production well.

In some embodiments, fluids (gases and liquids) may be directed towards the bottom of the production well using the diverter. The fluids may be produced from the bottom of the production well. FIG. 26 depicts an embodiment of the diverter that directs fluid towards the bottom of the production well. Diverter 514 may include packing material 520 and baffle 538 positioned in production conduit 512. Baffle may be a pipe positioned around conduit 532. Production conduit 512 may have openings 528 that allow fluids to enter the production conduit from hydrocarbon layer 380. In some embodiments, all or a portion of the openings are adjacent to a non-hydrocarbon layer of the formation through which heated formation fluid flows. Openings 528 include, but are not limited to, screens, perforations, slits, and/or slots. Hydrocarbon layer 380 may be heated using heaters located in other portions of the formation and/or a heater located in production conduit 512.

Baffle 538 and packing material 520 direct formation fluid entering production conduit 512 to unheated zone 530. Unheated zone 530 is in the underburden of the formation. A portion of the formation fluid may condense on the outer surface of baffle 538 or on walls of production conduit 512 adjacent to unheated zone 530. Liquid fluid from the formation and/or condensed fluid may flow by gravity to a sump or bottom portion of production conduit 512. Liquid and condensate in the bottom portion of production conduit 512 may be pumped to the surface through conduit 532 using pump 518. Pump 518 may be placed 1 m, 5 m, 10 m, 20 m or more into the underburden. In some embodiments, the pump may be placed in a non-cased (open) portion of the wellbore. Non-condensed fluid initially travels through the annular space between baffle 538 and conduit 532, and then through the annular space between production conduit 512 and conduit 532 to the surface, as indicated by arrows in FIG. 26. If a portion of the non-condensed fluid condenses adjacent to overburden 382 while traveling to the surface, the condensed fluid will flow by gravity toward the bottom portion of production conduit 512 to the intake for pump 518. Heat absorbed by the condensed fluid as the fluid passes through the heated portion of the formation is from contact with baffle 538, not from direct contact with the formation. Baffle 538 is heated by formation fluid and radiative heat transfer from the formation. Significantly less heat from the formation is transferred to the condensed fluid as the fluid flows through baffle 538 adjacent to the heated portion than if the condensed fluid was able to contact the formation. The condensed fluid flowing down the baffle may absorb enough heat from the vapor in the wellbore to condense a portion of the vapor on the outer surface of baffle 538. The condensed portion of the vapor may flow down the baffle to the bottom portion of the wellbore.

In some embodiments, diluent may be introduced into production conduit 512 and/or conduit 532. The diluent is used to inhibit clogging in production conduit 512, pump 518, and conduit 532. The diluent may include, but is not limited to, water, an alcohol, a solvent, a surfactant, or combinations thereof. Different diluents may be introduced at different times. For example, a solvent may be introduced when production first begins to put into solution high molecular weight hydrocarbons that are initially produced from the formation. At a later time, water may be substituted for the solvent.

Figure 27:
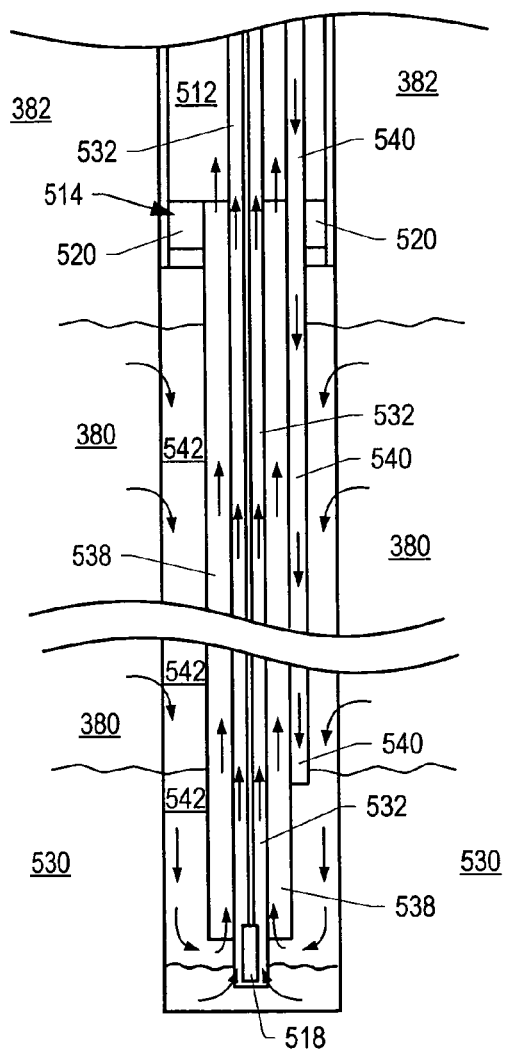
FIG. 27 depicts a schematic representation of an embodiment of the baffle in the production well.

In some embodiments, a separate conduit may introduce the diluent to the wellbore near the underburden, as depicted in FIG. 27. Production conduit 512 directs vapor produced from the formation to the surface through overburden 382. If a portion of the vapor condenses in production conduit 512, the condensate can flow down baffle 538 to the intake for pump 518. Diverter 514, comprising packing material 520 and baffle 538, directs formation fluid flow from heated hydrocarbon layer 380 to unheated zone 530. Liquid formation fluid is transported by pump 518 through conduit 532 to the surface. Vapor formation fluid is transported through baffle 538 to production conduit 512. Conduit 540 may be strapped to baffle 538. Conduit 540 may introduce the diluent to wellbore 542 adjacent to unheated zone 530. The diluent may promote condensation of formation fluid and/or inhibit clogging of pump 518. Diluent in conduit 540 may be at a high pressure. If the diluent changes phase from liquid to vapor while passing through the heated portion of the formation, the change in pressure as the diluent leaves conduit 540 allows the diluent to condense.

In some embodiments, the intake of the pump system is located in casing in the sump. In some embodiments, the intake of the pump system is located in an open wellbore. The sump is below the heated portion of the formation. The intake of the pump may be located 1 m, 5 m, 10 m, 20 m or more below the deepest heater used to heat the heated portion of the formation. The sump may be at a cooler temperature than the heated portion of the formation. The sump may be more than 10° C., more than 50° C., more than 75° C., or more than 100° C. below the temperature of the heated portion of the formation. A portion of the fluid entering the sump may be liquid. A portion of the fluid entering the sump may condense within the sump.

Production well lift systems may be used to efficiently transport formation fluid from the bottom of the production wells to the surface. Production well lift systems may provide and maintain the maximum required well drawdown (minimum reservoir producing pressure) and producing rates. The production well lift systems may operate efficiently over a wide range of high temperature/multiphase fluids (gas/vapor/steam/water/hydrocarbon liquids) and production rates expected during the life of a typical project.

Figure 28:
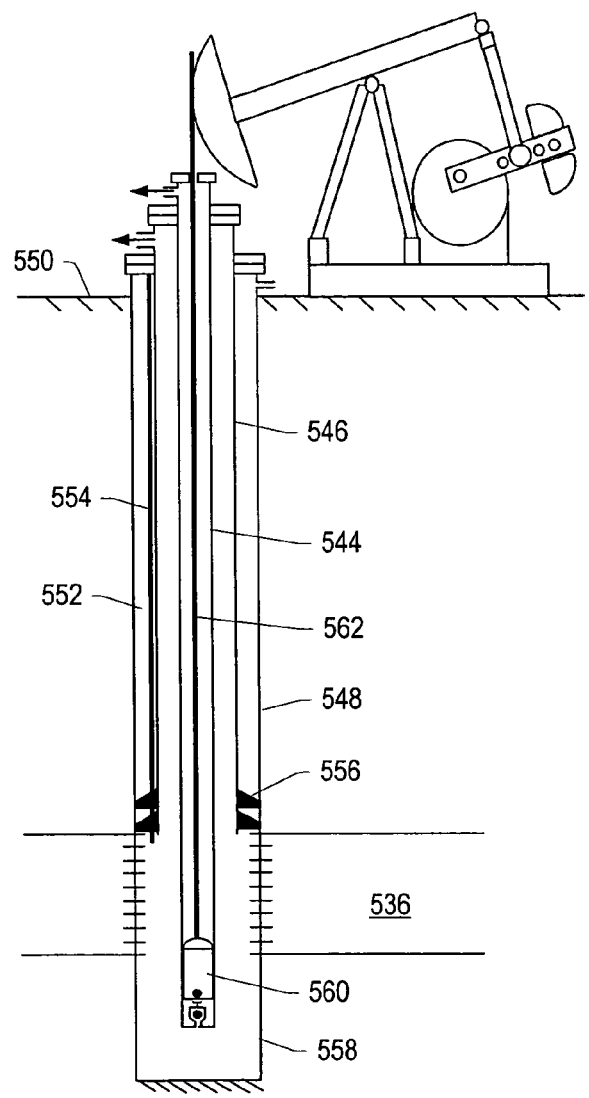
FIG. 28 depicts an embodiment of a dual concentric rod pump system.

FIG. 28 illustrates an embodiment of a dual concentric rod pump lift system for use in production wells. The formation fluid enters the wellbore from heated portion 536. Formation fluid may be transported to the surface through inner conduit 544 and outer conduit 546. Inner conduit 544 and outer conduit 546 may be concentric. Concentric conduits may be advantageous over dual (side by side) conduits in conventional oilfield production wells. Inner conduit 544 may be used for production of liquids. Outer conduit 546 may allow vapor and/or gaseous phase formation fluids to flow to the surface along with some entrained liquids.

The diameter of outer conduit 546 may be chosen to allow a desired range of flow rates and/or to minimize the pressure drop and flowing reservoir pressure. Reflux seal 556 at the base of outer conduit 546 may inhibit hot produced gases and/or vapors from contacting the relatively cold wall of well casing 548 above heated portion 536. This minimizes potentially damaging and wasteful energy losses from heated portion 536 via condensation and recycling of fluids. Reflux seal 556 may be a dynamic seal, allowing outer conduit 546 to thermally expand and contract while being fixed at surface 550. Reflux seal 556 may be a one-way seal designed to allow fluids to be pumped down annulus 552 for treatment or for well kill operations. For example, down-facing elastomeric-type cups may be used in reflux seal 556 to inhibit fluids from flowing upward through annulus 552. In some embodiments, reflux seal 556 is a "fixed" design, with a dynamic wellhead seal that allows outer conduit 546 to move at surface 550, thereby reducing thermal stresses and cycling.

Conditions in any particular well or project could allow both ends of outer conduit 546 to be fixed. Outer conduit 546 may require no or infrequent retrieval for maintenance over the expected useful life of the production well. In some embodiments, utility bundle 554 is coupled to the outside of outer conduit 546. Utility bundle 554 may include, but is not limited to, conduits for monitoring, control, and/or treatment equipment such as temperature/pressure monitoring devices, chemical treatment lines, diluent injection lines, and cold fluid injection lines for cooling of the liquid pumping system. Coupling utility bundle 554 to outer conduit 546 may allow the utility bundle (and thus the potentially complex and sensitive equipment included in this bundle) to remain in place during retrieval and/or maintenance of inner conduit 544. In certain embodiments, outer conduit 546 is removed one or more times over the expected useful life of the production well.

Annulus 552 between well casing 548 and outer conduit 546 may provide a space to run utility bundle 554 and instrumentation, as well as thermal insulation to optimize and/or control temperature and/or behavior of the produced fluid. In some embodiments, annulus 552 is filled with one or more fluids or gases (pressurized or not) to allow regulation of the overall thermal conductivity and resulting heat transfer between the overburden and the formation fluid being produced. Using annulus 552 as a thermal barrier may allow: 1) optimization of temperature and/or phase behavior of the fluid stream for subsequent processing of the fluid stream at the surface, and/or 2) optimization of multiphase behavior to enable maximum natural flow of fluids and liquid stream pumping. The concentric configuration of outer conduit 546 and inner conduit 544 is advantageous in that the heat transfer/thermal effects on the fluid streams are more uniform than a conventional dual (parallel tubing) configuration.

Inner conduit 544 may be used for production of liquids. Liquids produced from inner conduit 544 may include fluids in liquid form that are not entrained with gas/vapor produced from outer conduit 546, as well as liquids that condense in the outer conduit. In some embodiments, the base of inner conduit 544 is positioned below the base of heated portion 536 (in sump 558) to assist in natural gravity separation of the liquid phase. Sump 558 may be a separation sump. Sump 558 may also provide thermal benefits (for example, cooler pump operation and reduced liquid flashing in the pump) depending upon the length/depth of the sump and overall fluid rates and/or temperatures.

Inner conduit 544 may include a pump system. In some embodiments, pump system 560 is an oilfield-type reciprocating rod pump. Such pumps are available in a wide variety of designs and configurations. Reciprocating rod pumps have the advantages of being widely available and cost effective. In addition, surveillance/evaluation analysis methods are well-developed and understood for this system. In certain embodiments, the prime mover is advantageously located on the surface for accessibility and maintenance. Location of the prime mover on the surface also protects the prime mover from the extreme temperature/fluid environment of the wellbore. FIG. 28 depicts a conventional oilfield-type beam-pumping unit on surface 550 for reciprocation of rod string 562. Other types of pumping units may be used including, but not limited to, hydraulic units, long-stroke units, air-balance units, surface-driven rotary units, and MII units. A variety of surface unit/pump combinations may be employed depending on well conditions and desired pumping rates. In certain embodiments, inner conduit 544 is anchored to limit movement and wear of the inner conduit.

Concentric placement of outer conduit 546 and inner conduit 544 may facilitate maintenance of the inner conduit and the associated pump system, including intervention and/or replacement of downhole components. The concentric design allows for maintenance/removal/replacement of inner conduit 544 without disturbing outer conduit 546 and related components, thus lowering overall expenses, reducing well downtime, and/or improving overall project performance compared to a conventional parallel double conduit configuration. The concentric configuration may also be modified to account for unexpected changes in well conditions over time. The pump system can be quickly removed and both conduits may be utilized for flowing production in the event of lower liquid rates or much higher vapor/gas rates than anticipated. Conversely, a larger or different system can easily be installed in the inner conduit without affecting the balance of the system components.

Various methods may be used to control the pump system to enhance efficiency and well production. These methods may include, for example, the use of on/off timers, pump-off detection systems to measure surface loads and model the downhole conditions, direct fluid level sensing devices, and sensors suitable for high-temperature applications (capillary tubing, etc.) to allow direct downhole pressure monitoring. In some embodiments, the pumping capacity is matched with available fluid to be pumped from the well.

Various design options and/or configurations for the conduits and/or rod string (including materials, physical dimensions, and connections) may be chosen to enhance overall reliability, cost, ease of initial installation, and subsequent intervention and/or maintenance for a given production well. For example, connections may be threaded, welded, or designed for a specific application. In some embodiments, sections of one or more of the conduits are connected as the conduit is lowered into the well. In certain embodiments, sections of one or more of the conduits are connected prior to insertion in the well, and the conduit is spooled (for example, at a different location) and later unspooled into the well. The specific conditions within each production well determine equipment parameters such as equipment sizing, conduit diameters, and sump dimensions for optimal operation and performance.

FIG. 29 illustrates an embodiment of the dual concentric rod pump system including 2-phase separator 564 at the bottom of inner conduit 544 to aid in additional separation and exclusion of gas/vapor phase fluids from rod pump 560. Use of 2-phase separator 564 may be advantageous at higher vapor and gas/liquid ratios. Use of 2-phase separator 564 may help prevent gas locking and low pump efficiencies in inner conduit 544.

FIG. 30 depicts an embodiment of the dual concentric rod pump system that includes gas/vapor shroud 566 extending down into sump 558. Gas/vapor shroud 566 may force the majority of the produced fluid stream down through the area surrounding sump 558, increasing the natural liquid separation. Gas/vapor shroud 566 may include sized gas/vapor vent 568 at the top of the heated zone to inhibit gas/vapor pressure from building up and being trapped behind the shroud. Thus, gas/vapor shroud 566 may increase overall well drawdown efficiency, and becomes more important as the thickness of heated portion 536 increases. The size of gas/vapor vent 568 may vary and can be determined based on the expected fluid volumes and desired operating pressures for any particular production well.

Figure 31:
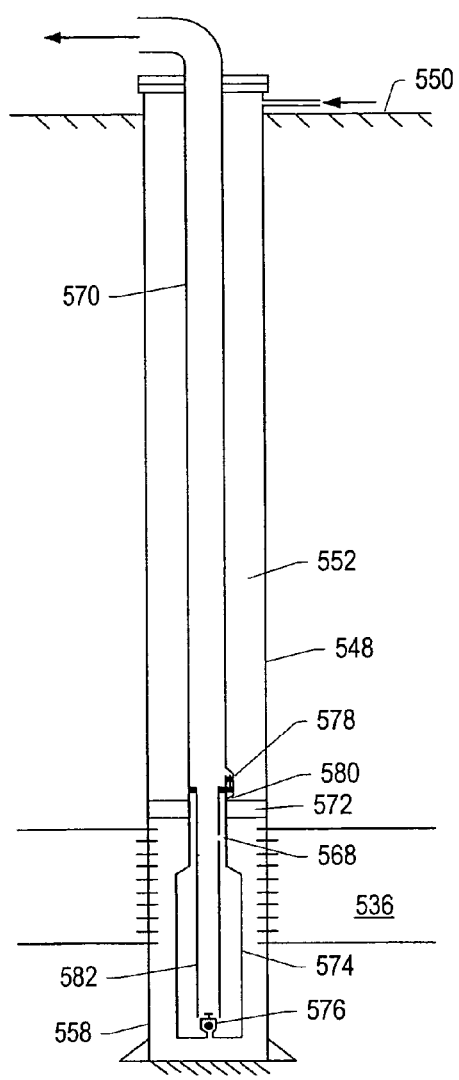
FIG. 31 depicts an embodiment of a gas lift system.

FIG. 31 depicts an embodiment of a chamber lift system for use in production wells. Conduit 570 provides a path for fluids of all phases to be transported from heated portion 536 to surface 550. Packer/reflux seal assembly 572 is located above heated portion 536 to inhibit produced fluids from entering annulus 552 between conduit 570 and well casing 548 above the heated portion. Packer/reflux seal assembly 572 may reduce the refluxing of the fluid, thereby advantageously reducing energy losses. In this configuration, packer/reflux seal assembly 572 may substantially isolate the pressurized lift gas in annulus 552 above the packer/reflux seal assembly from heated portion 536. Thus, heated portion 536 may be exposed to the desired minimum drawdown pressure, maximizing fluid inflow to the well. As an additional aid in maintaining a minimum drawdown pressure, sump 558 may be located in the wellbore below heated portion 536. Produced fluids/liquids may therefore collect in the wellbore below heated portion 536 and not cause excessive backpressure on the heated portion. This becomes more advantageous as the thickness of heated portion 536 increases.

Fluids of all phases may enter the well from heated portion 536. These fluids are directed downward to sump 558. The fluids enter lift chamber 574 through check valve 576 at the base of the lift chamber. After sufficient fluid has entered lift chamber 574, lift gas injection valve 578 opens and allows pressurized lift gas to enter the top of the lift chamber. Crossover port 580 allows the lift gas to pass through packer/reflux seal assembly 572 into the top of lift chamber 574. The resulting pressure increase in lift chamber 574 closes check valve 576 at the base and forces the fluids into the bottom of diptube 582, up into conduit 570, and out of the lift chamber. Lift gas injection valve 578 remains open until sufficient lift gas has been injected to evacuate the fluid in lift chamber 574 to a collection device. Lift gas injection valve 578 then closes and allows lift chamber 574 to fill with fluid again. This "lift cycle" repeats (intermittent operation) as often as necessary to maintain the desired drawdown pressure within heated portion 536. Sizing of equipment, such as conduits, valves, and chamber lengths and/or diameters, is dependent upon the expected fluid rates produced from heated portion 536 and the desired minimum drawdown pressure to be maintained in the production well.

In some embodiments, the entire chamber lift system may be retrievable from the well for repair, maintenance, and periodic design revisions due to changing well conditions. However, the need for retrieving conduit 570, packer/reflux seal assembly 572, and lift chamber 574 may be relatively infrequent. In some embodiments, lift gas injection valve 578 is configured to be retrieved from the well along with conduit 570. In certain embodiments, lift gas injection valve 578 is configured to be separately retrievable via wireline or similar means without removing conduit 570 or other system components from the well. Check valve 576 and/or diptube 582 may be individually installed and/or retrieved in a similar manner. The option to retrieve diptube 582 separately may allow re-sizing of gas/vapor vent 568. The option to retrieve these individual components (items that would likely require the most frequent well intervention, repair, and maintenance) greatly improves the attractiveness of the system from a well intervention and maintenance cost perspective.

Gas/vapor vent 568 may be located at the top of diptube 582 to allow gas and/or vapor entering the lift chamber from heated portion 536 to continuously vent into conduit 570 and inhibit an excess buildup of chamber pressure. Inhibiting an excess buildup of chamber pressure may increase overall system efficiency. Gas/vapor vent 568 may be sized to avoid excessive bypassing of injected lift gas into conduit 570 during the lift cycle, thereby promoting flow of the injected lift gas around the base of diptube 582.

The embodiment depicted in FIG. 31 includes a single lift gas injection valve 578 (rather than multiple intermediate "unloading" valves typically used in gas lift applications). Having a single lift gas injection valve greatly simplifies the downhole system design and/or mechanics, thereby reducing the complexity and cost, and increasing the reliability of the overall system. Having a single lift gas injection valve, however, does require that the available gas lift system pressure be sufficient to overcome and displace the heaviest fluid that might fill the entire wellbore, or some other means to initially "unload" the well in that event. Unloading valves may be used in some embodiments where the production wells are deep in the formation, for example, greater than 900 m deep, greater than 1000 m deep, or greater than 1500 m deep in the formation.

In some embodiments, the chamber/well casing internal diameter ratio is kept as high as possible to maximize volumetric efficiency of the system. Keeping the chamber/well casing internal diameter ratio as high as possible may allow overall drawdown pressure and fluid production into the well to be maximized while pressure imposed on the heated portion is minimized.

Lift gas injection valve 578 and the gas delivery and control system may be designed to allow large volumes of gas to be injected into lift chamber 574 in a relatively short period of time to maximize the efficiency and minimize the time period for fluid evacuation. This may allow liquid fallback in conduit 570 to be decreased (or minimized) while overall well fluid production potential is increased (or maximized).

Various methods may be used to allow control of lift gas injection valve 578 and the amount of gas injected during each lift cycle. Lift gas injection valve 578 may be designed to be self-controlled, sensitive to either lift chamber pressure or casing pressure. That is, lift gas injection valve 578 may be similar to tubing pressure-operated or casing pressure-operated valves routinely used in conventional oilfield gas lift applications. Alternatively, lift gas injection valve 578 may be controlled from the surface via either electric or hydraulic signal. These methods may be supplemented by additional controls that regulate the rate and/or pressure at which lift gas is injected into annulus 552 at surface 550. Other design and/or installation options for chamber lift systems (for example, types of conduit connections and/or method of installation) may be chosen from a range of approaches known in the art.

Figure 32:
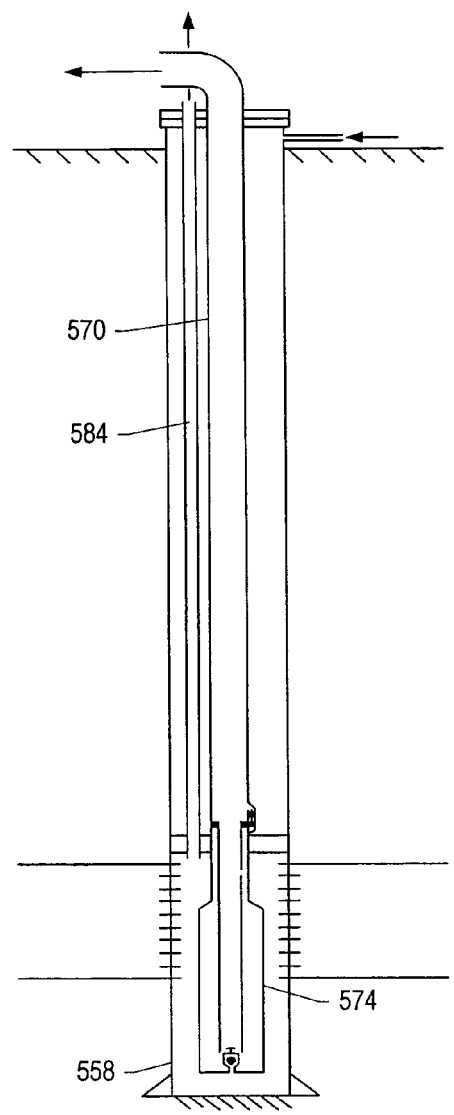
FIG. 32 depicts an embodiment of a gas lift system with an additional production conduit.

FIG. 32 illustrates an embodiment of a chamber lift system that includes an additional parallel production conduit. Conduit 584 may allow continual flow of produced gas and/or vapor, bypassing lift chamber 574. Bypassing lift chamber 574 may avoid passing large volumes of gas and/or vapor through the lift chamber, which may reduce the efficiency of the system when the volumes of gas and/or vapor are large. In this embodiment, the lift chamber evacuates any liquids from the well accumulating in sump 558 that do not flow from the well along with the gas/vapor phases. Sump 558 would aid the natural separation of liquids for more efficient operation.

Figure 33:
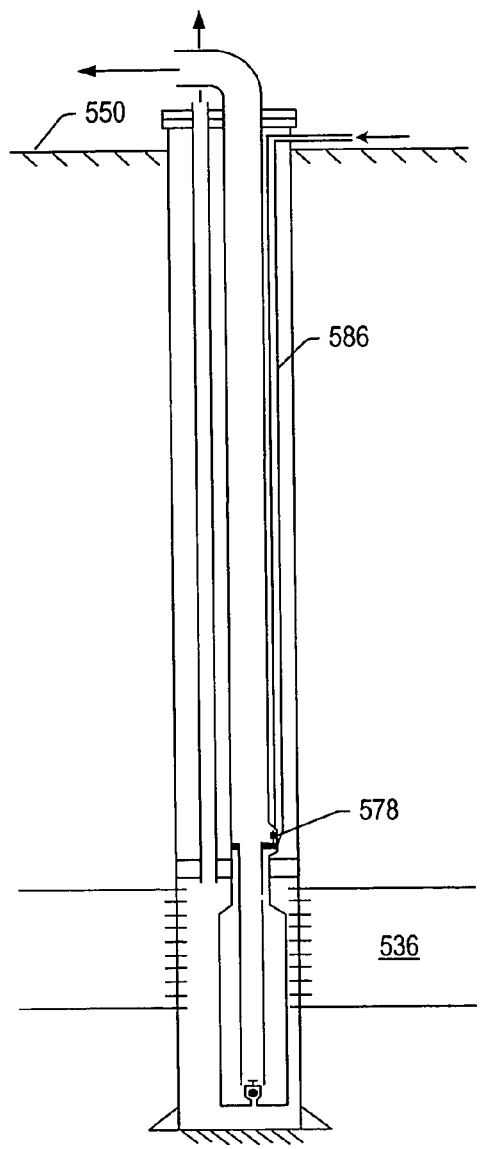
FIG. 33 depicts an embodiment of a gas lift system with an injection gas supply conduit.

FIG. 33 depicts an embodiment of a chamber lift system including injection gas supply conduit 586 from surface 550 down to lift gas injection valve 578. There may be some advantages to this arrangement (for example, relating to wellbore integrity and/or barrier issues) compared to use of the casing annulus to transport the injection gas. While lift gas injection valve 578 is positioned downhole for control, this configuration may also facilitate the alternative option to control the lift gas injection entirely from surface 550. Controlling the lift gas injection entirely from surface 550 may eliminate the need for downhole injection valve 578 and reduce the need for and/or costs associated with wellbore intervention. Providing a separate lift gas conduit also permits the annulus around the production tubulars to be kept at a low pressure, or even under a vacuum, thus decreasing heat transfer from the production tubulars. This reduces condensation in conduit 584 and thus reflux back into heated portion 536.

Figure 34:
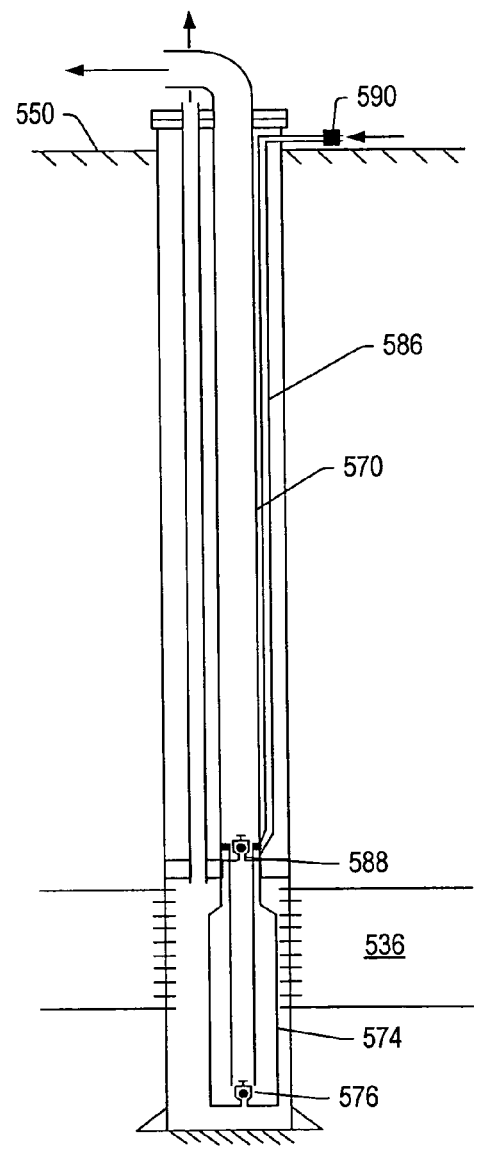
FIG. 34 depicts an embodiment of a gas lift system with an additional check valve.

FIG. 34 depicts an embodiment of a chamber lift system with an additional check valve located at the top of the lift chamber/diptube. Check valve 588 may be retrieved separately via wireline or other means to reduce maintenance and reduce the complexity and/or cost associated with well intervention. Check valve 588 may inhibit liquid fallback from conduit 570 from returning to lift chamber 574 between lift cycles. In addition, check valve 588 may allow lift chamber 574 to be evacuated by displacing the chamber fluids and/or liquids only into the base of conduit 570 (the conduit remains full of fluid between cycles), potentially optimizing injection gas usage and energy. In some embodiments, the injection gas tubing pressure is bled down between injection cycles in this displacement mode to allow maximum drawdown pressure to be achieved with the surface injection gas control depicted in FIG. 34.

As depicted in FIG. 34, the downhole lift gas injection valve has been eliminated, and injection gas control valve 590 is located above surface 550. In some embodiments, the downhole valve is used in addition to or in lieu of injection gas control valve 590. Using the downhole control valve along with injection gas control valve 590 may allow the injection gas tubing pressure to be retained in the displacement cycle mode.

Figure 35:
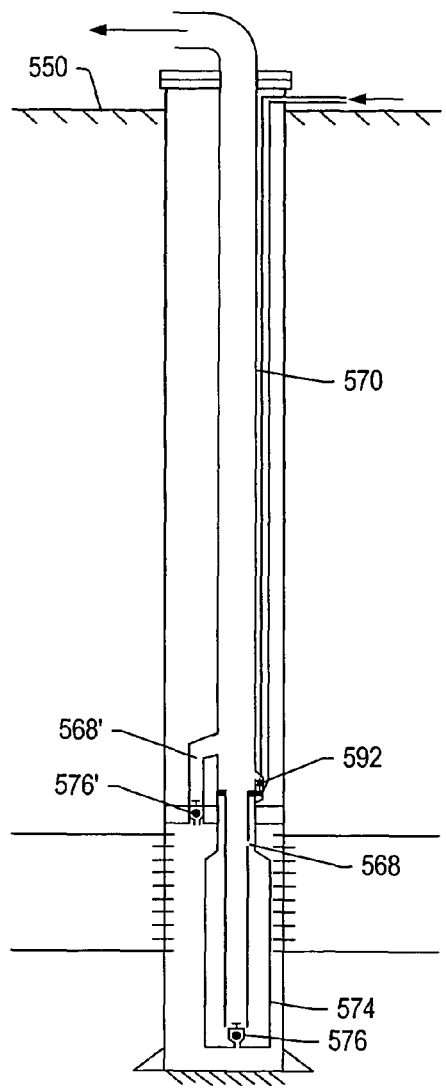
FIG. 35 depicts an embodiment of a gas lift system that allows mixing of the gas/vapor stream into the production conduit without a separate gas/vapor conduit for gas.

FIG. 35 depicts an embodiment of a chamber lift system that allows mixing of the gas/vapor stream into conduit 570 (without a separate conduit for gas and/or vapor), while bypassing lift chamber 574. Additional gas/vapor vent 568' equipped with additional check valve 576' may allow continuous production of the gas/vapor phase fluids into conduit 570 above lift chamber 574 between lift cycles. Check valve 576' may be separately retrievable as previously described for the other operating components. The embodiment depicted in FIG. 35 may allow simplification of the downhole equipment arrangement through elimination of a separate conduit for gas/vapor production. In some embodiments, lift gas injection is controlled via downhole gas injection valve 592. In certain embodiments, lift gas injection is controlled at surface 550.

Figure 36:
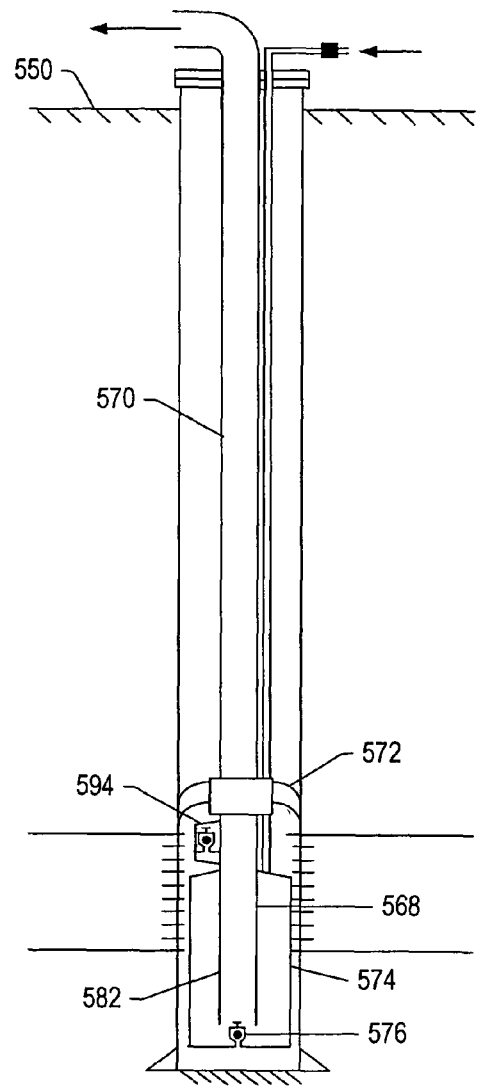
FIG. 36 depicts an embodiment of a gas lift system with a check valve/vent assembly below a packer/reflux seal assembly.

FIG. 36 depicts an embodiment of a chamber lift system with check valve/vent assembly 594 below packer/reflux seal assembly 572, eliminating the flow through the packer/reflux seal assembly. With check valve/vent assembly 594 below packer/reflux seal assembly 572, the gas/vapor stream bypasses lift chamber 574 while retaining the single, commingled production stream to surface 550. Check valve 594 may be independently retrievable, as previously described.

As depicted in FIG. 36, diptube 582 may be an integral part of conduit 570 and lift chamber 574. With diptube 582 an integral part of conduit 570 and lift chamber 574, check valve 576 at the bottom of the lift chamber may be more easily accessed (for example, via non-rig intervention methods including, but not limited to, wireline and coil tubing), and a larger diptube diameter may be used for higher liquid/fluid volumes. The retrievable diptube arrangement, as previously described, may be applied here as well, depending upon specific well requirements.

Figure 37:
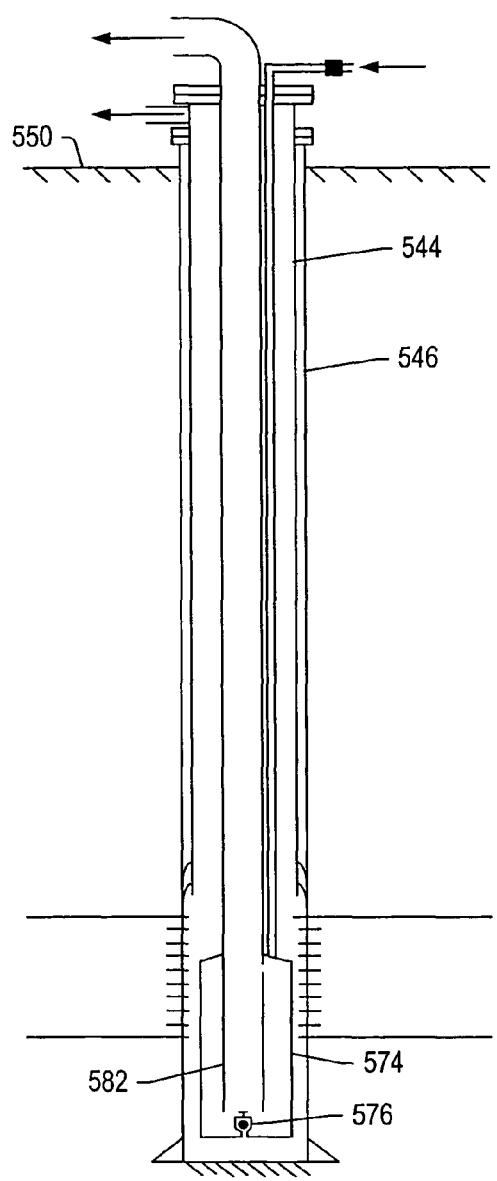
FIG. 37 depicts an embodiment of a gas lift system with concentric conduits.

FIG. 37 depicts an embodiment of a chamber lift system with a separate flowpath to surface 550 for the gas/vapor phase of the production stream via a concentric conduit approach similar to that described previously for the rod pumping system concepts. This embodiment eliminates the need for a check valve/vent system to commingle the gas/vapor stream into the production tubing with the liquid stream from the chamber as depicted in FIGS. 35 and 36 while including advantages of the concentric inner conduit 544 and outer conduit 546 depicted in FIGS. 28-30.

Figure 38:
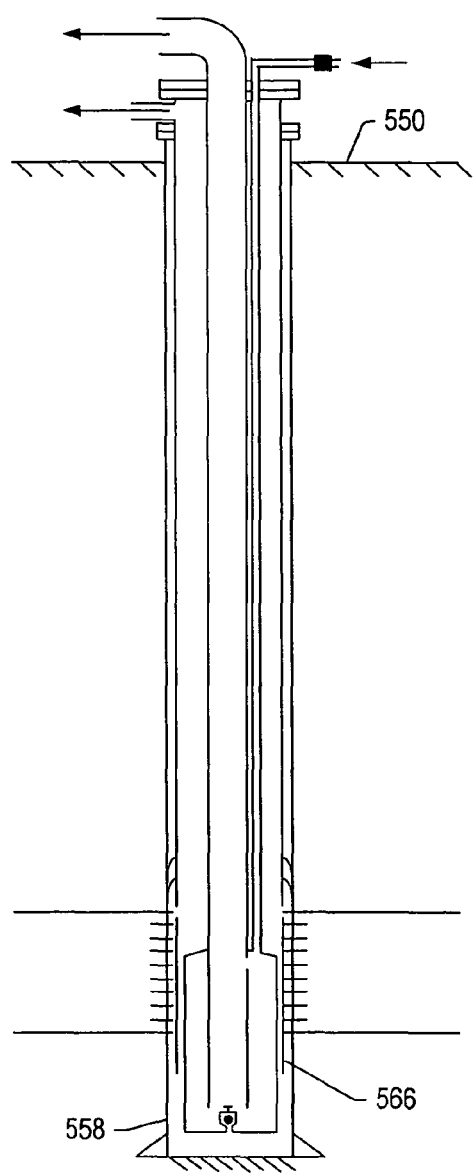
FIG. 38 depicts an embodiment of a gas lift system with a gas/vapor shroud and sump.

FIG. 38 depicts an embodiment of a chamber lift system with gas/vapor shroud 566 extending down into the sump 558. Gas/vapor shroud 566 and sump 558 provide the same advantages as described with respect to FIG. 30.

Temperature limited heaters may be in configurations and/or may include materials that provide automatic temperature limiting properties for the heater at certain temperatures. In certain embodiments, ferromagnetic materials are used in temperature limited heaters. Ferromagnetic material may self-limit temperature at or near the Curie temperature of the material to provide a reduced amount of heat at or near the Curie temperature when a time-varying current is applied to the material. In certain embodiments, the ferromagnetic material self-limits temperature of the temperature limited heater at a selected temperature that is approximately the Curie temperature. In certain embodiments, the selected temperature is within about 35° C., within about 25° C., within about 20° C., or within about 10° C. of the Curie temperature. In certain embodiments, ferromagnetic materials are coupled with other materials (for example, highly conductive materials, high strength materials, corrosion resistant materials, or combinations thereof) to provide various electrical and/or mechanical properties. Some parts of the temperature limited heater may have a lower resistance (caused by different geometries and/or by using different ferromagnetic and/or non-ferromagnetic materials) than other parts of the temperature limited heater. Having parts of the temperature limited heater with various materials and/or dimensions allows for tailoring the desired heat output from each part of the heater.

Temperature limited heaters may be more reliable than other heaters. Temperature limited heaters may be less apt to break down or fail due to hot spots in the formation. In some embodiments, temperature limited heaters allow for substantially uniform heating of the formation. In some embodiments, temperature limited heaters are able to heat the formation more efficiently by operating at a higher average heat output along the entire length of the heater. The temperature limited heater operates at the higher average heat output along the entire length of the heater because power to the heater does not have to be reduced to the entire heater, as is the case with typical constant wattage heaters, if a temperature along any point of the heater exceeds, or is about to exceed, a maximum operating temperature of the heater. Heat output from portions of a temperature limited heater approaching a Curie temperature of the heater automatically reduces without controlled adjustment of the time-varying current applied to the heater. The heat output automatically reduces due to changes in electrical properties (for example, electrical resistance) of portions of the temperature limited heater. Thus, more power is supplied by the temperature limited heater during a greater portion of a heating process.

In certain embodiments, the system including temperature limited heaters initially provides a first heat output and then provides a reduced (second heat output) heat output, near, at, or above the Curie temperature of an electrically resistive portion of the heater when the temperature limited heater is energized by a time-varying current. The first heat output is the heat output at temperatures below which the temperature limited heater begins to self-limit. In some embodiments, the first heat output is the heat output at a temperature 50° C., 75° C., 100° C., or 125° C. below the Curie temperature of the ferromagnetic material in the temperature limited heater.

The temperature limited heater may be energized by time-varying current (alternating current or modulated direct current) supplied at the wellhead. The wellhead may include a power source and other components (for example, modulation components, transformers, and/or capacitors) used in supplying power to the temperature limited heater. The temperature limited heater may be one of many heaters used to heat a portion of the formation.

In certain embodiments, the temperature limited heater includes a conductor that operates as a skin effect or proximity effect heater when time-varying current is applied to the conductor. The skin effect limits the depth of current penetration into the interior of the conductor. For ferromagnetic materials, the skin effect is dominated by the magnetic permeability of the conductor. The relative magnetic permeability of ferromagnetic materials is typically between 10 and 1000 (for example, the relative magnetic permeability of ferromagnetic materials is typically at least 10 and may be at least 50, 100, 500, 1000 or greater). As the temperature of the ferromagnetic material is raised above the Curie temperature and/or as the applied electrical current is increased, the magnetic permeability of the ferromagnetic material decreases substantially and the skin depth expands rapidly (for example, the skin depth expands as the inverse square root of the magnetic permeability). The reduction in magnetic permeability results in a decrease in the AC or modulated DC resistance of the conductor near, at, or above the Curie temperature and/or as the applied electrical current is increased. When the temperature limited heater is powered by a substantially constant current source, portions of the heater that approach, reach, or are above the Curie temperature may have reduced heat dissipation. Sections of the temperature limited heater that are not at or near the Curie temperature may be dominated by skin effect heating that allows the heater to have high heat dissipation due to a higher resistive load.

Curie temperature heaters have been used in soldering equipment, heaters for medical applications, and heating elements for ovens (for example, pizza ovens). Some of these uses are disclosed in U.S. Pat. No. 5,579,575 to Lamome et al.; U.S. Pat. No. 5,065,501 to Henschen et al.; and U.S. Pat. No. 5,512,732 to Yagnik et al., all of which are incorporated by reference as if fully set forth herein. U.S. Pat. No. 4,849,611 to Whitney et al., which is incorporated by reference as if fully set forth herein, describes a plurality of discrete, spaced-apart heating units including a reactive component, a resistive heating component, and a temperature responsive component.

An advantage of using the temperature limited heater to heat hydrocarbons in the formation is that the conductor is chosen to have a Curie temperature in a desired range of temperature operation. Operation within the desired operating temperature range allows substantial heat injection into the formation while maintaining the temperature of the temperature limited heater, and other equipment, below design limit temperatures. Design limit temperatures are temperatures at which properties such as corrosion, creep, and/or deformation are adversely affected. The temperature limiting properties of the temperature limited heater inhibits overheating or burnout of the heater adjacent to low thermal conductivity "hot spots" in the formation. In some embodiments, the temperature limited heater is able to lower or control heat output and/or withstand heat at temperatures above 25° C., 37° C., 100° C., 250° C., 500° C., 700° C., 800° C., 900° C., or higher up to 1131° C., depending on the materials used in the heater.

The temperature limited heater allows for more heat injection into the formation than constant wattage heaters because the energy input into the temperature limited heater does not have to be limited to accommodate low thermal conductivity regions adjacent to the heater. For example, in Green River oil shale there is a difference of at least a factor of 3 in the thermal conductivity of the lowest richness oil shale layers and the highest richness oil shale layers. When heating such a formation, substantially more heat is transferred to the formation with the temperature limited heater than with the conventional heater that is limited by the temperature at low thermal conductivity layers. The heat output along the entire length of the conventional heater needs to accommodate the low thermal conductivity layers so that the heater does not overheat at the low thermal conductivity layers and burn out. The heat output adjacent to the low thermal conductivity layers that are at high temperature will reduce for the temperature limited heater, but the remaining portions of the temperature limited heater that are not at high temperature will still provide high heat output. Because heaters for heating hydrocarbon formations typically have long lengths (for example, at least 10 m, 100 m, 300 m, 500 m, 1 km or more up to about 10 km), the majority of the length of the temperature limited heater may be operating below the Curie temperature while only a few portions are at or near the Curie temperature of the temperature limited heater.

The use of temperature limited heaters allows for efficient transfer of heat to the formation. Efficient transfer of heat allows for reduction in time needed to heat the formation to a desired temperature. For example, in Green River oil shale, pyrolysis typically requires 9.5 years to 10 years of heating when using a 12 m heater well spacing with conventional constant wattage heaters. For the same heater spacing, temperature limited heaters may allow a larger average heat output while maintaining heater equipment temperatures below equipment design limit temperatures. Pyrolysis in the formation may occur at an earlier time with the larger average heat output provided by temperature limited heaters than the lower average heat output provided by constant wattage heaters. For example, in Green River oil shale, pyrolysis may occur in 5 years using temperature limited heaters with a 12 m heater well spacing. Temperature limited heaters counteract hot spots due to inaccurate well spacing or drilling where heater wells come too close together. In certain embodiments, temperature limited heaters allow for increased power output over time for heater wells that have been spaced too far apart, or limit power output for heater wells that are spaced too close together. Temperature limited heaters also supply more power in regions adjacent the overburden and underburden to compensate for temperature losses in these regions.

Temperature limited heaters may be advantageously used in many types of formations. For example, in tar sands formations or relatively permeable formations containing heavy hydrocarbons, temperature limited heaters may be used to provide a controllable low temperature output for reducing the viscosity of fluids, mobilizing fluids, and/or enhancing the radial flow of fluids at or near the wellbore or in the formation. Temperature limited heaters may be used to inhibit excess coke formation due to overheating of the near wellbore region of the formation.

The use of temperature limited heaters, in some embodiments, eliminates or reduces the need for expensive temperature control circuitry. For example, the use of temperature limited heaters eliminates or reduces the need to perform temperature logging and/or the need to use fixed thermocouples on the heaters to monitor potential overheating at hot spots.

In certain embodiments, phase transformation (for example, crystalline phase transformation or a change in the crystal structure) of materials used in a temperature limited heater change the selected temperature at which the heater self-limits. Ferromagnetic material used in the temperature limited heater may have a phase transformation (for example, a transformation from ferrite to austenite) that decreases the magnetic permeability of the ferromagnetic material. This reduction in magnetic permeability is similar to reduction in magnetic permeability due to the magnetic transition of the ferromagnetic material at the Curie temperature. The Curie temperature is the magnetic transition temperature of the ferrite phase of the ferromagnetic material. The reduction in magnetic permeability results in a decrease in the AC or modulated DC resistance of the temperature limited heater near, at, or above the temperature of the phase transformation and/or the Curie temperature of the ferromagnetic material.

The phase transformation of the ferromagnetic material may occur over a temperature range. The temperature range of the phase transformation depends on the ferromagnetic material and may vary, for example, over a range of about 20° C. to a range of about 200° C. Because the phase transformation takes place over a temperature range, the reduction in the magnetic permeability due to the phase transformation takes place over the temperature range. The reduction in magnetic permeability may also occur irregularly over the temperature range of the phase transformation. In some embodiments, the phase transformation back to the lower temperature phase of the ferromagnetic material is slower than the phase transformation to the higher temperature phase (for example, the transition from austenite back to ferrite is slower than the transition from ferrite to austenite). The slower phase transformation back to the lower temperature phase may cause irregular operation of the heater at or near the phase transformation temperature range.

In some embodiments, the phase transformation temperature range overlaps with the reduction in the magnetic permeability when the temperature approaches the Curie temperature of the ferromagnetic material. The overlap may produce a slower drop in electrical resistance versus temperature than if the reduction in magnetic permeability is solely due to the temperature approaching the Curie temperature. The overlap may also produce irregular behavior of the temperature limited heater near the Curie temperature and/or in the phase transformation temperature range.

In certain embodiments, alloy additions are made to the ferromagnetic material to adjust the temperature range of the phase transformation. For example, adding carbon to the ferromagnetic material may increase the phase transformation temperature range and lower the onset temperature of the phase transformation. Adding titanium to the ferromagnetic material may increase the onset temperature of the phase transformation and decrease the phase transformation temperature range. Alloy compositions may be adjusted to provide desired Curie temperature and phase transformation properties for the ferromagnetic material. The alloy composition of the ferromagnetic material may be chosen based on desired properties for the ferromagnetic material (such as, but not limited to, magnetic permeability transition temperature or temperature range, resistance versus temperature profile, or power output). Addition of titanium may allow higher Curie temperatures to be obtained when adding cobalt to 410 stainless steel by raising the ferrite to austenite phase transformation temperature range to a temperature range that is above, or well above, the Curie temperature of the ferromagnetic material.

In certain embodiments, the temperature limited heater is deformation tolerant. Localized movement of material in the wellbore may result in lateral stresses on the heater that could deform its shape. Locations along a length of the heater at which the wellbore approaches or closes on the heater may be hot spots where a standard heater overheats and has the potential to burn out. These hot spots may lower the yield strength and creep strength of the metal, allowing crushing or deformation of the heater. The temperature limited heater may be formed with S curves (or other non-linear shapes) that accommodate deformation of the temperature limited heater without causing failure of the heater.

In some embodiments, temperature limited heaters are more economical to manufacture or make than standard heaters. Typical ferromagnetic materials include iron, carbon steel, or ferritic stainless steel. Such materials are inexpensive as compared to nickel-based heating alloys (such as nichrome, Kanthal™ (Bulten-Kanthal AB, Sweden), and/or LOHM™ (Driver-Harris Company, Harrison, N.J., U.S.A.)) typically used in insulated conductor (mineral insulated cable) heaters. In one embodiment of the temperature limited heater, the temperature limited heater is manufactured in continuous lengths as an insulated conductor heater to lower costs and improve reliability.

In some embodiments, the temperature limited heater is placed in the heater well using a coiled tubing rig. A heater that can be coiled on a spool may be manufactured by using metal such as ferritic stainless steel (for example, 409 stainless steel) that is welded using electrical resistance welding (ERW). To form a heater section, a metal strip from a roll is passed through a first former where it is shaped into a tubular and then longitudinally welded using ERW. The tubular is passed through a second former where a conductive strip (for example, a copper strip) is applied, drawn down tightly on the tubular through a die, and longitudinally welded using ERW. A sheath may be formed by longitudinally welding a support material (for example, steel such as 347H or 347HH) over the conductive strip material. The support material may be a strip rolled over the conductive strip material. An overburden section of the heater may be formed in a similar manner.

FIG. 39 depicts an embodiment of a device for longitudinal welding of a tubular using ERW. Metal strip 596 is shaped into tubular form as it passes through ERW coil 598. Metal strip 596 is then welded into a tubular inside shield 600. As metal strip 596 is joined inside shield 600, inert gas (for example, argon or another suitable welding gas) is provided inside the forming tubular by gas inlets 602. Flushing the tubular with inert gas inhibits oxidation of the tubular as it is formed. Shield 600 may have window 604. Window 604 allows an operator to visually inspect the welding process. Tubular 606 is formed by the welding process.

In certain embodiments, the overburden section uses a non-ferromagnetic material such as 304 stainless steel or 316 stainless steel instead of a ferromagnetic material. The heater section and overburden section may be coupled using standard techniques such as butt welding using an orbital welder. In some embodiments, the overburden section material (the non-ferromagnetic material) may be pre-welded to the ferromagnetic material before rolling. The pre-welding may eliminate the need for a separate coupling step (for example, butt welding). In an embodiment, a flexible cable (for example, a furnace cable such as a MGT 1000 furnace cable) may be pulled through the center after forming the tubular heater. An end bushing on the flexible cable may be welded to the tubular heater to provide an electrical current return path. The tubular heater, including the flexible cable, may be coiled onto a spool before installation into a heater well. In an embodiment, the temperature limited heater is installed using the coiled tubing rig. The coiled tubing rig may place the temperature limited heater in a deformation resistant container in the formation. The deformation resistant container may be placed in the heater well using conventional methods.

In an embodiment, a Curie heater includes a furnace cable inside a ferromagnetic conduit (for example, a ¾" Schedule 80 446 stainless steel pipe). The ferromagnetic conduit may be clad with copper or another suitable conductive material. The ferromagnetic conduit may be placed in a deformation-tolerant conduit or deformation resistant container. The deformation-tolerant conduit may tolerate longitudinal deformation, radial deformation, and creep. The deformation-tolerant conduit may also support the ferromagnetic conduit and furnace cable. The deformation-tolerant conduit may be selected based on creep and/or corrosion resistance near or at the Curie temperature. In one embodiment, the deformation-tolerant conduit is 1½" Schedule 80 347H stainless steel pipe (outside diameter of about 4.826 cm) or 1½" Schedule 160 347H stainless steel pipe (outside diameter of about 4.826 cm).

The diameter and/or materials of the deformation-tolerant conduit may vary depending on, for example, characteristics of the formation to be heated or desired heat output characteristics of the heater. In certain embodiments, air is removed from the annulus between the deformation-tolerant conduit and the clad ferromagnetic conduit. The space between the deformation-tolerant conduit and the clad ferromagnetic conduit may be flushed with a pressurized inert gas (for example, helium, nitrogen, argon, or mixtures thereof). In some embodiments, the inert gas may include a small amount of hydrogen to act as a "getter" for residual oxygen. The inert gas may pass down the annulus from the surface, enter the inner diameter of the ferromagnetic conduit through a small hole near the bottom of the heater, and flow up inside the ferromagnetic conduit. Removal of the air in the annulus may reduce oxidation of materials in the heater (for example, the nickel-coated copper wires of the furnace cable) to provide a longer life heater, especially at elevated temperatures. Thermal conduction between the furnace cable and the ferromagnetic conduit, and between the ferromagnetic conduit and the deformation-tolerant conduit, may be improved when the inert gas is helium. The pressurized inert gas in the annular space may also provide additional support for the deformation-tolerant conduit against high formation pressures. Pressurized inert gas also inhibits arcing between metal conductors in the annular space compared to inert gas at atmospheric pressure.

In certain embodiments, a thermally conductive fluid such as helium may be placed inside void volumes of the temperature limited heater where heat is transferred. Placing thermally conductive fluid inside void volumes of the temperature limited heater may improve thermal conduction inside the void volumes. Thermally conductive fluids include, but are not limited to, gases that are thermally conductive, electrically insulating, and radiantly transparent. In certain embodiments, thermally conductive fluid in the void volumes has a higher thermal conductivity than air at standard temperature and pressure (STP) (0° C. and 101.325 kPa). Radiantly transparent gases include gases with diatomic or single atoms that do not absorb a significant amount of infrared energy. In certain embodiments, thermally conductive fluids include helium and/or hydrogen. Thermally conductive fluids may also be thermally stable at operating temperatures in the temperature limited heater so that the thermally conductive fluids do not thermally crack at operating temperature in the temperature limited heater.

Thermally conductive fluid may be placed inside a conductor, inside a conduit, and/or inside a jacket of a temperature limited heater. The thermally conductive fluid may be placed in the space (the annulus) between one or more components (for example, conductor, conduit, or jacket) of the temperature limited heater. In some embodiments, thermally conductive fluid is placed in the space (the annulus) between the temperature limited heater and a conduit.

In certain embodiments, air and/or other fluid in the space (the annulus) is displaced by a flow of thermally conductive fluid during introduction of the thermally conductive fluid into the space. In some embodiments, air and/or other fluid is removed (for example, vacuumed, flushed, or pumped out) from the space before introducing thermally conductive fluid in the space. Reducing the partial pressure of oxygen in the space reduces the rate of oxidation of heater components in the space. The thermally conductive fluid is introduced in a specific volume and/or to a selected pressure in the space. Thermally conductive fluid may be introduced such that the space has at least a minimum volume percentage of thermally conductive fluid above a selected value. In certain embodiments, the space has at least 50%, 75%, or 90% by volume of thermally conductive fluid.

Placing thermally conductive fluid inside the space of the temperature limited heater increases thermal heat transfer in the space. The increased thermal heat transfer is caused by reducing resistance to heat transfer in the space with the thermally conductive fluid. Reducing resistance to heat transfer in the space allows for increased power output from the temperature limited heater to the subsurface formation. Reducing the resistance to heat transfer inside the space with the thermally conductive fluid allows for smaller diameter electrical conductors (for example, a smaller diameter inner conductor, a smaller diameter outer conductor, and/or a smaller diameter conduit), a larger outer radius (for example, a larger radius of a conduit or a jacket), and/or an increased space width. Reducing the diameter of electrical conductors reduces material costs. Increasing the outer radius of the conduit or the jacket and/or increasing the annulus space width provides additional annular space. Additional annular space may accommodate deformation of the conduit and/or the jacket without causing heater failure. Increasing the outer radius of the conduit or the jacket and/or increasing the annulus width may provide additional annular space to protect components (for example, spacers, connectors, and/or conduits) in the annulus.

As the annular width of the temperature limited heater is increased, however, greater heat transfer is needed across the annular space to maintain good heat output properties for the heater. In some embodiments, especially for low temperature heaters, radiative heat transfer is minimally effective in transferring heat across the annular space of the heater. Conductive heat transfer in the annular space is important in such embodiments to maintain good heat output properties for the heater. A thermally conductive fluid provides increased heat transfer across the annular space.

In certain embodiments, the thermally conductive fluid located in the space is also electrically insulating to inhibit arcing between conductors in the temperature limited heater. Arcing across the space or gap is a problem with longer heaters that require higher operating voltages. Arcing may be a problem with shorter heaters and/or at lower voltages depending on the operating conditions of the heater. Increasing the pressure of the fluid in the space increases the spark gap breakdown voltage in the space and inhibits arcing across the space. Certain gases, such as $SF_6$ or $N_2$, have greater resistance to electrical breakdown but have lower thermal conductivities than helium or hydrogen because of their higher molecular weights. Thus, gases such as $SF_6$ or $N_2$ may be less desirable in some embodiments.

Pressure of thermally conductive fluid in the space may be increased to a pressure between 200 kPa and 60,000 kPa, between 500 kPa and 50,000 kPa, between 700 kPa and 45,000 kPa, or between 1000 kPa and 40,000 kPa. In an embodiment, the pressure of the thermally conductive fluid is increased to at least 700 kPa or at least 1000 kPa. In certain embodiments, the pressure of the thermally conductive fluid needed to inhibit arcing across the space depends on the temperature in the space. Electrons may track along surfaces (for example, insulators, connectors, or shields) in the space and cause arcing or electrical degradation of the surfaces. High pressure fluid in the space may inhibit electron tracking along surfaces in the space. Helium has about one-seventh the breakdown voltage of air at atmospheric pressure. Thus, higher pressures of helium (for example, 7 atm (707 kPa) or greater of helium) may be used to compensate for the lower breakdown voltage of helium as compared to air.

Temperature limited heaters may be used for heating hydrocarbon formations including, but not limited to, oil shale formations, coal formations, tar sands formations, and formations with heavy viscous oils. Temperature limited heaters may also be used in the field of environmental remediation to vaporize or destroy soil contaminants. Embodiments of temperature limited heaters may be used to heat fluids in a wellbore or sub-sea pipeline to inhibit deposition of paraffin or various hydrates. In some embodiments, a temperature limited heater is used for solution mining a subsurface formation (for example, an oil shale or a coal formation). In certain embodiments, a fluid (for example, molten salt) is placed in a wellbore and heated with a temperature limited heater to inhibit deformation and/or collapse of the wellbore. In some embodiments, the temperature limited heater is attached to a sucker rod in the wellbore or is part of the sucker rod itself. In some embodiments, temperature limited heaters are used to heat a near wellbore region to reduce near wellbore oil viscosity during production of high viscosity crude oils and during transport of high viscosity oils to the surface. In some embodiments, a temperature limited heater enables gas lifting of a viscous oil by lowering the viscosity of the oil without coking the oil. Temperature limited heaters may be used in sulfur transfer lines to maintain temperatures between about 110° C. and about 130° C.

Certain embodiments of temperature limited heaters may be used in chemical or refinery processes at elevated temperatures that require control in a narrow temperature range to inhibit unwanted chemical reactions or damage from locally elevated temperatures. Some applications may include, but are not limited to, reactor tubes, cokers, and distillation towers. Temperature limited heaters may also be used in pollution control devices (for example, catalytic converters, and oxidizers) to allow rapid heating to a control temperature without complex temperature control circuitry. Additionally, temperature limited heaters may be used in food processing to avoid damaging food with excessive temperatures. Temperature limited heaters may also be used in the heat treatment of metals (for example, annealing of weld joints). Temperature limited heaters may also be used in floor heaters, cauterizers, and/or various other appliances. Temperature limited heaters may be used with biopsy needles to destroy tumors by raising temperatures in vivo.

Some embodiments of temperature limited heaters may be useful in certain types of medical and/or veterinary devices. For example, a temperature limited heater may be used to therapeutically treat tissue in a human or an animal. A temperature limited heater for a medical or veterinary device may have ferromagnetic material including a palladium-copper alloy with a Curie temperature of about 50° C. A high frequency (for example, a frequency greater than about 1 MHz) may be used to power a relatively small temperature limited heater for medical and/or veterinary use.

The ferromagnetic alloy or ferromagnetic alloys used in the temperature limited heater determine the Curie temperature of the heater. Curie temperature data for various metals is listed in "American Institute of Physics Handbook," Second Edition, McGraw-Hill, pages 5-170 through 5-176. Ferromagnetic conductors may include one or more of the ferromagnetic elements (iron, cobalt, and nickel) and/or alloys of these elements. In some embodiments, ferromagnetic conductors include iron-chromium (Fe—Cr) alloys that contain tungsten (W) (for example, HCM12A and SAVE12 (Sumitomo Metals Co., Japan) and/or iron alloys that contain chromium (for example, Fe—Cr alloys, Fe—Cr—W alloys, Fe—Cr—V (vanadium) alloys, and Fe—Cr—Nb (Niobium) alloys). Of the three main ferromagnetic elements, iron has a Curie temperature of approximately 770° C.; cobalt (Co) has a Curie temperature of approximately 1131° C.; and nickel has a Curie temperature of approximately 358° C. An iron-cobalt alloy has a Curie temperature higher than the Curie temperature of iron. For example, iron-cobalt alloy with 2% by weight cobalt has a Curie temperature of approximately 800° C.; iron-cobalt alloy with 12% by weight cobalt has a Curie temperature of approximately 900° C.; and iron-cobalt alloy with 20% by weight cobalt has a Curie temperature of approximately 950° C. Iron-nickel alloy has a Curie temperature lower than the Curie temperature of iron. For example, iron-nickel alloy with 20% by weight nickel has a Curie temperature of approximately 720° C., and iron-nickel alloy with 60% by weight nickel has a Curie temperature of approximately 560° C.

Some non-ferromagnetic elements used as alloys raise the Curie temperature of iron. For example, an iron-vanadium alloy with 5.9% by weight vanadium has a Curie temperature of approximately 815° C. Other non-ferromagnetic elements (for example, carbon, aluminum, copper, silicon, and/or chromium) may be alloyed with iron or other ferromagnetic materials to lower the Curie temperature. Non-ferromagnetic materials that raise the Curie temperature may be combined with non-ferromagnetic materials that lower the Curie temperature and alloyed with iron or other ferromagnetic materials to produce a material with a desired Curie temperature and other desired physical and/or chemical properties. In some embodiments, the Curie temperature material is a ferrite such as $NiFe_2O_4$. In other embodiments, the Curie temperature material is a binary compound such as $FeNi_3$ or $Fe_3Al$.

Certain embodiments of temperature limited heaters may include more than one ferromagnetic material. Such embodiments are within the scope of embodiments described herein if any conditions described herein apply to at least one of the ferromagnetic materials in the temperature limited heater.

Ferromagnetic properties generally decay as the Curie temperature is approached. The "Handbook of Electrical Heating for Industry" by C. James Erickson (IEEE Press, 1995) shows a typical curve for 1% carbon steel (steel with 1% carbon by weight). The loss of magnetic permeability starts at temperatures above 650° C. and tends to be complete when temperatures exceed 730° C. Thus, the self-limiting temperature may be somewhat below the actual Curie temperature of the ferromagnetic conductor. The skin depth for current flow in 1% carbon steel is 0.132 cm at room temperature and increases to 0.445 cm at 720° C. From 720° C. to 730° C., the skin depth sharply increases to over 2.5 cm. Thus, a temperature limited heater embodiment using 1% carbon steel begins to self-limit between 650° C. and 730° C.

Skin depth generally defines an effective penetration depth of time-varying current into the conductive material. In general, current density decreases exponentially with distance from an outer surface to the center along the radius of the conductor. The depth at which the current density is approximately 1/e of the surface current density is called the skin depth. For a solid cylindrical rod with a diameter much greater than the penetration depth, or for hollow cylinders with a wall thickness exceeding the penetration depth, the skin depth, δ, is:

$$\delta = 1981.5 * (\rho/(\mu * f))^{1/2}; \quad (2)$$

in which:
 δ=skin depth in inches;
 ρ=resistivity at operating temperature (ohm-cm);
 μ=relative magnetic permeability; and
 f=frequency (Hz).

EQN. 2 is obtained from "Handbook of Electrical Heating for Industry" by C. James Erickson (IEEE Press, 1995). For most metals, resistivity (ρ) increases with temperature. The relative magnetic permeability generally varies with temperature and with current. Additional equations may be used to assess the variance of magnetic permeability and/or skin depth on both temperature and/or current. The dependence of μ on current arises from the dependence of μ on the magnetic field.

Materials used in the temperature limited heater may be selected to provide a desired turndown ratio. Turndown ratios of at least 1.1:1, 2:1, 3:1, 4:1, 5:1, 10:1, 30:1, or 50:1 may be selected for temperature limited heaters. Larger turndown ratios may also be used. A selected turndown ratio may depend on a number of factors including, but not limited to, the type of formation in which the temperature limited heater is located (for example, a higher turndown ratio may be used for an oil shale formation with large variations in thermal conductivity between rich and lean oil shale layers) and/or a temperature limit of materials used in the wellbore (for example, temperature limits of heater materials). In some embodiments, the turndown ratio is increased by coupling additional copper or another good electrical conductor to the ferromagnetic material (for example, adding copper to lower the resistance above the Curie temperature).

The temperature limited heater may provide a maximum heat output (power output) below the Curie temperature of the heater. In certain embodiments, the maximum heat output is at least 400 W/m (Watts per meter), 600 W/m, 700 W/m, 800 W/m, or higher up to 2000 W/m. The temperature limited heater reduces the amount of heat output by a section of the heater when the temperature of the section of the heater approaches or is above the Curie temperature. The reduced amount of heat may be substantially less than the heat output below the Curie temperature. In some embodiments, the reduced amount of heat is at most 400 W/m, 200 W/m, 100 W/m or may approach 0 W/m.

In certain embodiments, the temperature limited heater operates substantially independently of the thermal load on the heater in a certain operating temperature range. "Thermal load" is the rate that heat is transferred from a heating system to its surroundings. It is to be understood that the thermal load may vary with temperature of the surroundings and/or the thermal conductivity of the surroundings. In an embodiment, the temperature limited heater operates at or above the Curie temperature of the temperature limited heater such that the operating temperature of the heater increases at most by 3° C., 2° C., 1.5° C., 1° C., or 0.5° C. for a decrease in thermal load of 1 W/m proximate to a portion of the heater. In certain embodiments, the temperature limited heater operates in such a manner at a relatively constant current.

The AC or modulated DC resistance and/or the heat output of the temperature limited heater may decrease as the temperature approaches the Curie temperature and decrease sharply near or above the Curie temperature due to the Curie effect. In certain embodiments, the value of the electrical resistance or heat output above or near the Curie temperature is at most one-half of the value of electrical resistance or heat output at a certain point below the Curie temperature. In some embodiments, the heat output above or near the Curie temperature is at most 90%, 70%, 50%, 30%, 20%, 10%, or less (down to 1%) of the heat output at a certain point below the Curie temperature (for example, 30° C. below the Curie temperature, 40° C. below the Curie temperature, 50° C. below the Curie temperature, or 100° C. below the Curie temperature). In certain embodiments, the electrical resistance above or near the Curie temperature decreases to 80%, 70%, 60%, 50%, or less (down to 1%) of the electrical resistance at a certain point below the Curie temperature (for example, 30° C. below the Curie temperature, 40° C. below the Curie temperature, 50° C. below the Curie temperature, or 100° C. below the Curie temperature).

In some embodiments, AC frequency is adjusted to change the skin depth of the ferromagnetic material. For example, the skin depth of 1% carbon steel at room temperature is 0.132 cm at 60 Hz, 0.0762 cm at 180 Hz, and 0.046 cm at 440 Hz. Since heater diameter is typically larger than twice the skin depth, using a higher frequency (and thus a heater with a smaller diameter) reduces heater costs. For a fixed geometry, the higher frequency results in a higher turndown ratio. The turndown ratio at a higher frequency is calculated by multiplying the turndown ratio at a lower frequency by the square root of the higher frequency divided by the lower frequency. In some embodiments, a frequency between 100 Hz and 1000 Hz, between 140 Hz and 200 Hz, or between 400 Hz and 600 Hz is used (for example, 180 Hz, 540 Hz, or 720 Hz). In some embodiments, high frequencies may be used. The frequencies may be greater than 1000 Hz.

To maintain a substantially constant skin depth until the Curie temperature of the temperature limited heater is reached, the heater may be operated at a lower frequency when the heater is cold and operated at a higher frequency when the heater is hot. Line frequency heating is generally favorable, however, because there is less need for expensive components such as power supplies, transformers, or current modulators that alter frequency. Line frequency is the frequency of a general supply of current. Line frequency is typically 60 Hz, but may be 50 Hz or another frequency depending on the source for the supply of the current. Higher frequencies may be produced using commercially available equipment such as solid state variable frequency power supplies. Transformers that convert three-phase power to single-phase power with three times the frequency are commercially available. For example, high voltage three-phase power at 60 Hz may be transformed to single-phase power at 180 Hz and at a lower voltage. Such transformers are less expensive and more energy efficient than solid state variable frequency power supplies. In certain embodiments, transformers that convert three-phase power to single-phase power are used to increase the frequency of power supplied to the temperature limited heater.

In certain embodiments, modulated DC (for example, chopped DC, waveform modulated DC, or cycled DC) may be used for providing electrical power to the temperature limited heater. A DC modulator or DC chopper may be coupled to a DC power supply to provide an output of modulated direct current. In some embodiments, the DC power supply may include means for modulating DC. One example of a DC modulator is a DC-to-DC converter system. DC-to-DC converter systems are generally known in the art. DC is typically modulated or chopped into a desired waveform. Waveforms for DC modulation include, but are not limited to, square-wave, sinusoidal, deformed sinusoidal, deformed square-wave, triangular, and other regular or irregular waveforms.

The modulated DC waveform generally defines the frequency of the modulated DC. Thus, the modulated DC waveform may be selected to provide a desired modulated DC frequency. The shape and/or the rate of modulation (such as the rate of chopping) of the modulated DC waveform may be varied to vary the modulated DC frequency. DC may be modulated at frequencies that are higher than generally available AC frequencies. For example, modulated DC may be provided at frequencies of at least 1000 Hz. Increasing the frequency of supplied current to higher values advantageously increases the turndown ratio of the temperature limited heater.

In certain embodiments, the modulated DC waveform is adjusted or altered to vary the modulated DC frequency. The DC modulator may be able to adjust or alter the modulated DC waveform at any time during use of the temperature limited heater and at high currents or voltages. Thus, modulated DC provided to the temperature limited heater is not limited to a single frequency or even a small set of frequency values. Waveform selection using the DC modulator typically allows for a wide range of modulated DC frequencies and for discrete control of the modulated DC frequency. Thus, the modulated DC frequency is more easily set at a distinct value whereas AC frequency is generally limited to multiples of the line frequency. Discrete control of the modulated DC frequency allows for more selective control over the turndown ratio of the temperature limited heater. Being able to selectively control the turndown ratio of the temperature limited heater allows for a broader range of materials to be used in designing and constructing the temperature limited heater.

In certain embodiments, electrical power for the temperature limited heater is initially supplied using non-modulated DC or very low frequency modulated DC. Using DC, or low frequency DC, at earlier times of heating reduces inefficiencies associated with higher frequencies. DC and/or low frequency modulated DC may also be cheaper to use during initial heating times. After a selected temperature is reached in a temperature limited heater; modulated DC, higher frequency modulated DC, or AC is used for providing electrical power to the temperature limited heater so that the heat output will decrease near, at, or above the Curie temperature.

In some embodiments, the modulated DC frequency or the AC frequency is adjusted to compensate for changes in properties (for example, subsurface conditions such as temperature or pressure) of the temperature limited heater during use. The modulated DC frequency or the AC frequency provided to the temperature limited heater is varied based on assessed downhole conditions. For example, as the temperature of the temperature limited heater in the wellbore increases, it may be advantageous to increase the frequency of the current provided to the heater, thus increasing the turndown ratio of the heater. In an embodiment, the downhole temperature of the temperature limited heater in the wellbore is assessed.

In certain embodiments, the modulated DC frequency, or the AC frequency, is varied to adjust the turndown ratio of the temperature limited heater. The turndown ratio may be adjusted to compensate for hot spots occurring along a length of the temperature limited heater. For example, the turndown ratio is increased because the temperature limited heater is getting too hot in certain locations. In some embodiments, the modulated DC frequency, or the AC frequency, are varied to adjust a turndown ratio without assessing a subsurface condition.

At or near the Curie temperature of the ferromagnetic material, a relatively small change in voltage may cause a relatively large change in current to the load. The relatively small change in voltage may produce problems in the power supplied to the temperature limited heater, especially at or near the Curie temperature. The problems include, but are not limited to, reducing the power factor, tripping a circuit breaker, and/or blowing a fuse. In some cases, voltage changes may be caused by a change in the load of the temperature limited heater. In certain embodiments, an electrical current supply (for example, a supply of modulated DC or AC) provides a relatively constant amount of current that does not substantially vary with changes in load of the temperature limited heater. In an embodiment, the electrical current supply provides an amount of electrical current that remains within 15%, within 10%, within 5%, or within 2% of a selected constant current value when a load of the temperature limited heater changes.

Temperature limited heaters may generate an inductive load. The inductive load is due to some applied electrical current being used by the ferromagnetic material to generate a magnetic field in addition to generating a resistive heat output. As downhole temperature changes in the temperature limited heater, the inductive load of the heater changes due to changes in the ferromagnetic properties of ferromagnetic materials in the heater with temperature. The inductive load of the temperature limited heater may cause a phase shift between the current and the voltage applied to the heater.

A reduction in actual power applied to the temperature limited heater may be caused by a time lag in the current waveform (for example, the current has a phase shift relative to the voltage due to an inductive load) and/or by distortions in the current waveform (for example, distortions in the current waveform caused by introduced harmonics due to a non-linear load). Thus, it may take more current to apply a selected amount of power due to phase shifting or waveform distortion. The ratio of actual power applied and the apparent power that would have been transmitted if the same current were in phase and undistorted is the power factor. The power factor is always less than or equal to 1. The power factor is 1 when there is no phase shift or distortion in the waveform.

Actual power applied to a heater due to a phase shift may be described by EQN. 3:

$$P = I \times V \times \cos(\theta); \quad (3)$$

in which P is the actual power applied to a heater; I is the applied current; V is the applied voltage; and θ is the phase angle difference between voltage and current. Other phenomena such as waveform distortion may contribute to further lowering of the power factor. If there is no distortion in the waveform, then $\cos(\theta)$ is equal to the power factor.

At higher frequencies (for example, modulated DC frequencies of at least 1000 Hz, 1500 Hz, or 2000 Hz), the problem with phase shifting and/or distortion is more pronounced. In certain embodiments, a capacitor is used to compensate for phase shifting caused by the inductive load. Capacitive load may be used to balance the inductive load because current for capacitance is 180 degrees out of phase from current for inductance. In some embodiments, a variable capacitor (for example, a solid state switching capacitor) is used to compensate for phase shifting caused by a varying inductive load. In an embodiment, the variable capacitor is placed at the wellhead for the temperature limited heater. Placing the variable capacitor at the wellhead allows the capacitance to be varied more easily in response to changes in the inductive load of the temperature limited heater. In certain embodiments, the variable capacitor is placed subsurface with the temperature limited heater, subsurface within the heater, or as close to the heating conductor as possible to minimize line losses due to the capacitor. In some embodiments, the variable capacitor is placed at a central location for a field of heater wells (in some embodiments, one variable capacitor may be used for several temperature limited heaters). In one embodiment, the variable capacitor is placed at the electrical junction between the field of heaters and the utility supply of electricity.

In certain embodiments, the variable capacitor is used to maintain the power factor of the temperature limited heater or the power factor of the electrical conductors in the temperature limited heater above a selected value. In some embodiments, the variable capacitor is used to maintain the power factor of the temperature limited heater above the selected value of 0.85, 0.9, or 0.95. In certain embodiments, the capacitance in the variable capacitor is varied to maintain the power factor of the temperature limited heater above the selected value.

In some embodiments, the modulated DC waveform is pre-shaped to compensate for phase shifting and/or harmonic distortion. The waveform may be pre-shaped by modulating the waveform into a specific shape. For example, the DC modulator is programmed or designed to output a waveform of a particular shape. In certain embodiments, the pre-shaped waveform is varied to compensate for changes in the inductive load of the temperature limited heater caused by changes in the phase shift and/or the harmonic distortion. Electrical measurements may be used to assess the phase shift and/or the harmonic distortion. In certain embodiments, heater conditions (for example, downhole temperature or pressure) are assessed and used to determine the pre-shaped waveform. In some embodiments, the pre-shaped waveform is determined through the use of a simulation or calculations based on the heater design. Simulations and/or heater conditions may also be used to determine the capacitance needed for the variable capacitor.

In some embodiments, the modulated DC waveform modulates DC between 100% (full current load) and 0% (no current load). For example, a square-wave may modulate 100 A DC between 100% (100 A) and 0% (0 A) (full wave modulation), between 100% (100 A) and 50% (50 A), or between 75% (75 A) and 25% (25 A). The lower current load (for example, the 0%, 25%, or 50% current load) may be defined as the base current load.

Generally, a temperature limited heater designed for higher voltage and lower current will have a smaller skin depth. Decreasing the current may decrease the skin depth of the ferromagnetic material. The smaller skin depth allows the temperature limited heater to have a smaller diameter, thereby reducing equipment costs. In certain embodiments, the applied current is at least 1 amp, 10 amps, 70 amps, 100 amps, 200 amps, 500 amps, or greater up to 2000 amps. In some embodiments, current is supplied at voltages above 200 volts, above 480 volts, above 650 volts, above 1000 volts, above 1500 volts, or higher up to 10000 volts.

In certain embodiments, the temperature limited heater includes an inner conductor inside an outer conductor. The inner conductor and the outer conductor are radially disposed about a central axis. The inner and outer conductors may be separated by an insulation layer. In certain embodiments, the inner and outer conductors are coupled at the bottom of the temperature limited heater. Electrical current may flow into the temperature limited heater through the inner conductor and return through the outer conductor. One or both conductors may include ferromagnetic material.

The insulation layer may comprise an electrically insulating ceramic with high thermal conductivity, such as magnesium oxide, aluminum oxide, silicon dioxide, beryllium oxide, boron nitride, silicon nitride, or combinations thereof. The insulating layer may be a compacted powder (for example, compacted ceramic powder). Compaction may improve thermal conductivity and provide better insulation resistance. For lower temperature applications, polymer insulation made from, for example, fluoropolymers, polyimides, polyamides, and/or polyethylenes, may be used. In some embodiments, the polymer insulation is made of perfluoroalkoxy (PFA) or polyetheretherketone (PEEK™ (Victrex Ltd, England)). The insulating layer may be chosen to be substantially infrared transparent to aid heat transfer from the inner conductor to the outer conductor. In an embodiment, the insulating layer is transparent quartz sand. The insulation layer may be air or a non-reactive gas such as helium, nitrogen, or sulfur hexafluoride. If the insulation layer is air or a non-reactive gas, there may be insulating spacers designed to inhibit electrical contact between the inner conductor and the outer conductor. The insulating spacers may be made of, for example, high purity aluminum oxide or another thermally conducting, electrically insulating material such as silicon nitride. The insulating spacers may be a fibrous ceramic material such as Nextel™ 312 (3M Corporation, St. Paul, Minn., U.S.A.), mica tape, or glass fiber. Ceramic material may be made of alumina, alumina-silicate, alumina-borosilicate, silicon nitride, boron nitride, or other materials.

The insulation layer may be flexible and/or substantially deformation tolerant. For example, if the insulation layer is a solid or compacted material that substantially fills the space between the inner and outer conductors, the temperature limited heater may be flexible and/or substantially deformation tolerant. Forces on the outer conductor can be transmitted through the insulation layer to the solid inner conductor, which may resist crushing. Such a temperature limited heater may be bent, dog-legged, and spiraled without causing the outer conductor and the inner conductor to electrically short to each other. Deformation tolerance may be important if the wellbore is likely to undergo substantial deformation during heating of the formation.

In certain embodiments, an outermost layer of the temperature limited heater (for example, the outer conductor) is chosen for corrosion resistance, yield strength, and/or creep resistance. In one embodiment, austenitic (non-ferromagnetic) stainless steels such as 201, 304H, 347H, 347HH, 316H, 310H, 347HP, NF709 (Nippon Steel Corp., Japan) stainless steels, or combinations thereof may be used in the outer conductor. The outermost layer may also include a clad conductor. For example, a corrosion resistant alloy such as 800H or 347H stainless steel may be clad for corrosion protection over a ferromagnetic carbon steel tubular. If high temperature strength is not required, the outermost layer may be constructed from ferromagnetic metal with good corrosion resistance such as one of the ferritic stainless steels. In one embodiment, a ferritic alloy of 82.3% by weight iron with 17.7% by weight chromium (Curie temperature of 678° C.) provides desired corrosion resistance.

The Metals Handbook, vol. 8, page 291 (American Society of Materials (ASM)) includes a graph of Curie temperature of iron-chromium alloys versus the amount of chromium in the alloys. In some temperature limited heater embodiments, a separate support rod or tubular (made from 347H stainless steel) is coupled to the temperature limited heater made from an iron-chromium alloy to provide yield strength and/or creep resistance. In certain embodiments, the support material and/or the ferromagnetic material is selected to provide a 100,000 hour creep-rupture strength of at least 20.7 MPa at 650° C. In some embodiments, the 100,000 hour creep-rupture strength is at least 13.8 MPa at 650° C. or at least 6.9 MPa at 650° C. For example, 347H steel has a favorable creep-rupture strength at or above 650° C. In some embodiments, the 100,000 hour creep-rupture strength ranges from 6.9 MPa to 41.3 MPa or more for longer heaters and/or higher earth or fluid stresses.

In temperature limited heater embodiments with both an inner ferromagnetic conductor and an outer ferromagnetic conductor, the skin effect current path occurs on the outside of the inner conductor and on the inside of the outer conductor. Thus, the outside of the outer conductor may be clad with the corrosion resistant alloy, such as stainless steel, without affecting the skin effect current path on the inside of the outer conductor.

A ferromagnetic conductor with a thickness of at least the skin depth at the Curie temperature allows a substantial decrease in resistance of the ferromagnetic material as the skin depth increases sharply near the Curie temperature. In certain embodiments when the ferromagnetic conductor is not clad with a highly conducting material such as copper, the thickness of the conductor may be 1.5 times the skin depth near the Curie temperature, 3 times the skin depth near the Curie temperature, or even 10 or more times the skin depth near the Curie temperature. If the ferromagnetic conductor is clad with copper, thickness of the ferromagnetic conductor may be substantially the same as the skin depth near the Curie temperature. In some embodiments, the ferromagnetic conductor clad with copper has a thickness of at least three-fourths of the skin depth near the Curie temperature.

In certain embodiments, the temperature limited heater includes a composite conductor with a ferromagnetic tubular and a non-ferromagnetic, high electrical conductivity core. The non-ferromagnetic, high electrical conductivity core reduces a required diameter of the conductor. For example, the conductor may be composite 1.19 cm diameter conductor with a core of 0.575 cm diameter copper clad with a 0.298 cm thickness of ferritic stainless steel or carbon steel surrounding the core. The core or non-ferromagnetic conductor may be copper or copper alloy. The core or non-ferromagnetic conductor may also be made of other metals that exhibit low electrical resistivity and relative magnetic permeabilities near 1 (for example, substantially non-ferromagnetic materials such as aluminum and aluminum alloys, phosphor bronze, beryllium copper, and/or brass). A composite conductor allows the electrical resistance of the temperature limited heater to decrease more steeply near the Curie temperature. As the skin depth increases near the Curie temperature to include the copper core, the electrical resistance decreases very sharply.

The composite conductor may increase the conductivity of the temperature limited heater and/or allow the heater to operate at lower voltages. In an embodiment, the composite conductor exhibits a relatively flat resistance versus temperature profile at temperatures below a region near the Curie temperature of the ferromagnetic conductor of the composite conductor. In some embodiments, the temperature limited heater exhibits a relatively flat resistance versus temperature profile between 100° C. and 750° C. or between 300° C. and 600° C. The relatively flat resistance versus temperature profile may also be exhibited in other temperature ranges by adjusting, for example, materials and/or the configuration of materials in the temperature limited heater. In certain embodiments, the relative thickness of each material in the composite conductor is selected to produce a desired resistivity versus temperature profile for the temperature limited heater.

In certain embodiments, the relative thickness of each material in a composite conductor is selected to produce a desired resistivity versus temperature profile for a temperature limited heater. In an embodiment, the composite conductor is an inner conductor surrounded by 0.127 cm thick magnesium oxide powder as an insulator. The outer conductor may be 304H stainless steel with a wall thickness of 0.127 cm. The outside diameter of the heater may be about 1.65 cm.

A composite conductor (for example, a composite inner conductor or a composite outer conductor) may be manufactured by methods including, but not limited to, coextrusion, roll forming, tight fit tubing (for example, cooling the inner member and heating the outer member, then inserting the inner member in the outer member, followed by a drawing operation and/or allowing the system to cool), explosive or electromagnetic cladding, arc overlay welding, longitudinal strip welding, plasma powder welding, billet coextrusion, electroplating, drawing, sputtering, plasma deposition, coextrusion casting, magnetic forming, molten cylinder casting (of inner core material inside the outer or vice versa), insertion followed by welding or high temperature braising, shielded active gas welding (SAG), and/or insertion of an inner pipe in an outer pipe followed by mechanical expansion of the inner pipe by hydroforming or use of a pig to expand and swage the inner pipe against the outer pipe. In some embodiments, a ferromagnetic conductor is braided over a non-ferromagnetic conductor. In certain embodiments, composite conductors are formed using methods similar to those used for cladding (for example, cladding copper to steel). A metallurgical bond between copper cladding and base ferromagnetic material may be advantageous. Composite conductors produced by a coextrusion process that forms a good metallurgical bond (for example, a good bond between copper and 446 stainless steel) may be provided by Anomet Products, Inc. (Shrewsbury, Mass., U.S.A.).

Several methods may also be used to form a composite conductor of more than two conductors (for example, a three part composite conductor or a four part composite conductor). One method is to form two parts of the composite conductor by coextrusion and then swaging down the third and/or fourth parts of the composite conductor onto the coextruded parts. A second method involves forming two or more parts of the composite conductor by coextrusion or another method, bending a strip of the outer conductor around the formed parts, and then welding the outer conductor together. The welding of the outer conductor may penetrate deep enough to create good electrical contact to the inner parts of the composite conductor. Another method is to swage all parts of the composite conductor onto one another either simultaneously or in two or more steps. In another method, all parts of the composite conductor are coextruded simultaneously. In another method, explosive cladding may be used to form a composite conductor. Explosive cladding may involve placing a first material in a second material and submerging the composite material in a substantially non-compressible fluid. An explosive charge may be set off in the fluid to bind the first material to the second material.

In an embodiment, two or more conductors are joined to form a composite conductor by various methods (for example, longitudinal strip welding) to provide tight contact between the conducting layers. In certain embodiments, two or more conducting layers and/or insulating layers are combined to form a composite heater with layers selected such that the coefficient of thermal expansion decreases with each successive layer from the inner layer toward the outer layer. As the temperature of the heater increases, the innermost layer expands to the greatest degree. Each successive outwardly lying layer expands to a slightly lesser degree, with the outermost layer expanding the least. This sequential expansion may provide relatively intimate contact between layers for good electrical contact between layers.

In an embodiment, two or more conductors are drawn together to form a composite conductor. In certain embodiments, a relatively malleable ferromagnetic conductor (for example, iron such as 1018 steel) may be used to form a composite conductor. A relatively soft ferromagnetic conductor typically has a low carbon content. A relatively malleable ferromagnetic conductor may be useful in drawing processes for forming composite conductors and/or other processes that require stretching or bending of the ferromagnetic conductor. In a drawing process, the ferromagnetic conductor may be annealed after one or more steps of the drawing process. The ferromagnetic conductor may be annealed in an inert gas atmosphere to inhibit oxidation of the conductor. In some embodiments, oil is placed on the ferromagnetic conductor to inhibit oxidation of the conductor during processing.

The diameter of a temperature limited heater may be small enough to inhibit deformation of the heater by a collapsing formation. In certain embodiments, the outside diameter of a temperature limited heater is less than about 5 cm. In some embodiments, the outside diameter of a temperature limited heater is less than about 4 cm, less than about 3 cm, or between about 2 cm and about 5 cm.

In heater embodiments described herein (including, but not limited to, temperature limited heaters, insulated conductor heaters, conductor-in-conduit heaters, and elongated member heaters), a largest transverse cross-sectional dimension of a heater may be selected to provide a desired ratio of the largest transverse cross-sectional dimension to wellbore diameter (for example, initial wellbore diameter). The largest transverse cross-sectional dimension is the largest dimension of the heater on the same axis as the wellbore diameter (for example, the diameter of a cylindrical heater or the width of a vertical heater). In certain embodiments, the ratio of the largest transverse cross-sectional dimension to wellbore diameter is selected to be less than about 1:2, less than about 1:3, or less than about 1:4. The ratio of heater diameter to wellbore diameter may be chosen to inhibit contact and/or deformation of the heater by the formation during heating. For example, the ratio of heater diameter to wellbore diameter may be chosen to inhibit closing in of the wellbore on the heater during heating. In certain embodiments, the wellbore diameter is determined by a diameter of a drill bit used to form the wellbore.

A wellbore diameter may shrink from an initial value of about 16.5 cm to about 6.4 cm during heating of a formation (for example, for a wellbore in oil shale with a richness greater than about 0.12 L/kg). At some point, expansion of formation material into the wellbore during heating results in a balancing between the hoop stress of the wellbore and the compressive strength due to thermal expansion of hydrocarbon, or kerogen, rich layers. The hoop stress of the wellbore itself may reduce the stress applied to a conduit (for example, a liner) located in the wellbore. At this point, the formation may no longer have the strength to deform or collapse a heater or a liner. For example, the radial stress provided by formation material may be about 12,000 psi (82.7 MPa) at a diameter of about 16.5 cm, while the stress at a diameter of about 6.4 cm after expansion may be about 3000 psi (20.7 MPa). A heater diameter may be selected to be less than about 3.8 cm to inhibit contact of the formation and the heater. A temperature limited heater may advantageously provide a higher heat output over a significant portion of the wellbore (for example, the heat output needed to provide sufficient heat to pyrolyze hydrocarbons in a hydrocarbon containing formation) than a constant wattage heater for smaller heater diameters (for example, less than about 5.1 cm).

FIG. 40 depicts an embodiment of an apparatus used to form a composite conductor. Ingot 608 may be a ferromagnetic conductor (for example, iron or carbon steel). Ingot 608 may be placed in chamber 610. Chamber 610 may be made of materials that are electrically insulating and able to withstand temperatures of about 800° C. or higher. In one embodiment, chamber 610 is a quartz chamber. In some embodiments, an inert, or non-reactive, gas (for example, argon or nitrogen with a small percentage of hydrogen) may be placed in chamber 610. In certain embodiments, a flow of inert gas is provided to chamber 610 to maintain a pressure in the chamber. Induction coil 612 may be placed around chamber 610. An alternating current may be supplied to induction coil 612 to inductively heat ingot 608. Inert gas inside chamber 610 may inhibit oxidation or corrosion of ingot 608.

Inner conductor 614 may be placed inside ingot 608. Inner conductor 614 may be a non-ferromagnetic conductor (for example, copper or aluminum) that melts at a lower temperature than ingot 608. In an embodiment, ingot 608 may be heated to a temperature above the melting point of inner conductor 614 and below the melting point of the ingot. Inner conductor 614 may melt and substantially fill the space inside ingot 608 (for example, the inner annulus of the ingot). A cap may be placed at the bottom of ingot 608 to inhibit inner conductor 614 from flowing and/or leaking out of the inner annulus of the ingot. After inner conductor 614 has sufficiently melted to substantially fill the inner annulus of ingot 608, the inner conductor and the ingot may be allowed to cool to room temperature. Ingot 608 and inner conductor 614 may be cooled at a relatively slow rate to allow inner conductor 614 to form a good soldering bond with ingot 608. The rate of cooling may depend on, for example, the types of materials used for the ingot and the inner conductor.

In some embodiments, a composite conductor may be formed by tube-in-tube milling of dual metal strips, such as the process performed by Precision Tube Technology (Houston, Tex., U.S.A.). A tube-in-tube milling process may also be used to form cladding on a conductor (for example, copper cladding inside carbon steel) or to form two materials into a tight fit tube-within-a-tube configuration.

FIG. 41 depicts a cross-section representation of an embodiment of an inner conductor and an outer conductor formed by a tube-in-tube milling process. Outer conductor 616 may be coupled to inner conductor 618. Outer conductor 616 may be weldable material such as steel. Inner conductor 618 may have a higher electrical conductivity than outer conductor 616. In an embodiment, inner conductor 618 is copper or aluminum. Weld bead 620 may be formed on outer conductor 616.

In a tube-in-tube milling process, flat strips of material for the outer conductor may have a thickness substantially equal to the desired wall thickness of the outer conductor. The width of the strips may allow formation of a tube of a desired inner diameter. The flat strips may be welded end-to-end to form an outer conductor of a desired length. Flat strips of material for the inner conductor may be cut such that the inner conductor formed from the strips fit inside the outer conductor. The flat strips of inner conductor material may be welded together end-to-end to achieve a length substantially the same as the desired length of the outer conductor. The flat strips for the outer conductor and the flat strips for the inner conductor may be fed into separate accumulators. Both accumulators may be coupled to a tube mill. The two flat strips may be sandwiched together at the beginning of the tube mill.

The tube mill may form the flat strips into a tube-in-tube shape. After the tube-in-tube shape has been formed, a non-contact high frequency induction welder may heat the ends of the strips of the outer conductor to a forging temperature of the outer conductor. The ends of the strips then may be brought together to forge weld the ends of the outer conductor into a weld bead. Excess weld bead material may be cut off. In some embodiments, the tube-in-tube produced by the tube mill is further processed (for example, annealed and/or pressed) to achieve a desired size and/or shape. The result of the tube-in-tube process may be an inner conductor in an outer conductor, as shown in FIG. 41.

FIGS. 42-87 depict various embodiments of temperature limited heaters. One or more features of an embodiment of the temperature limited heater depicted in any of these figures may be combined with one or more features of other embodiments of temperature limited heaters depicted in these figures. In certain embodiments described herein, temperature limited heaters are dimensioned to operate at a frequency of 60 Hz AC. It is to be understood that dimensions of the temperature limited heater may be adjusted from those described herein in order for the temperature limited heater to operate in a similar manner at other AC frequencies or with modulated DC current.

FIG. 42 depicts a cross-sectional representation of an embodiment of the temperature limited heater with an outer conductor having a ferromagnetic section and a non-ferromagnetic section. FIGS. 43 and 44 depict transverse cross-sectional views of the embodiment shown in FIG. 42. In one embodiment, ferromagnetic section 622 is used to provide heat to hydrocarbon layers in the formation. Non-ferromagnetic section 624 is used in the overburden of the formation. Non-ferromagnetic section 624 provides little or no heat to the overburden, thus inhibiting heat losses in the overburden and improving heater efficiency. Ferromagnetic section 622 includes a ferromagnetic material such as 409 stainless steel or 410 stainless steel. Ferromagnetic section 622 has a thickness of 0.3 cm. Non-ferromagnetic section 624 is copper with a thickness of 0.3 cm. Inner conductor 626 is copper. Inner conductor 626 has a diameter of 0.9 cm. Electrical insulator 628 is silicon nitride, boron nitride, magnesium oxide powder, or another suitable insulator material. Electrical insulator 628 has a thickness of 0.1 cm to 0.3 cm.

FIG. 45 depicts a cross-sectional representation of an embodiment of a temperature limited heater with an outer conductor having a ferromagnetic section and a non-ferromagnetic section placed inside a sheath. FIGS. 46, 47, and 48 depict transverse cross-sectional views of the embodiment shown in FIG. 45. Ferromagnetic section 622 is 410 stainless steel with a thickness of 0.6 cm. Non-ferromagnetic section 624 is copper with a thickness of 0.6 cm. Inner conductor 626 is copper with a diameter of 0.9 cm. Outer conductor 630 includes ferromagnetic material. Outer conductor 630 provides some heat in the overburden section of the heater. Providing some heat in the overburden inhibits condensation or refluxing of fluids in the overburden. Outer conductor 630 is 409, 410, or 446 stainless steel with an outer diameter of 3.0 cm and a thickness of 0.6 cm. Electrical insulator 628 includes compacted magnesium oxide powder with a thickness of 0.3 cm. In some embodiments, electrical insulator 628 includes silicon nitride, boron nitride, or hexagonal type boron nitride. Conductive section 632 may couple inner conductor 626 with ferromagnetic section 622 and/or outer conductor 630.

FIG. 49 depicts a cross-sectional representation of an embodiment of a temperature limited heater with a ferromagnetic outer conductor. The heater is placed in a corrosion resistant jacket. A conductive layer is placed between the outer conductor and the jacket. FIGS. 50 and 51 depict transverse cross-sectional views of the embodiment shown in FIG. 49. Outer conductor 630 is a ¾" Schedule 80 446 stainless steel pipe. In an embodiment, conductive layer 634 is placed between outer conductor 630 and jacket 636. Conductive layer 634 is a copper layer. Outer conductor 630 is clad with conductive layer 634. In certain embodiments, conductive layer 634 includes one or more segments (for example, conductive layer 634 includes one or more copper tube segments). Jacket 636 is a 1¼" Schedule 80 347H stainless steel pipe or a 1½" Schedule 160 347H stainless steel pipe. In an embodiment, inner conductor 626 is 4/0 MGT-1000 furnace cable with stranded nickel-coated copper wire with layers of mica tape and glass fiber insulation. 4/0 MGT-1000 furnace cable is UL type 5107 (available from Allied Wire and Cable (Phoenixville, Pa., U.S.A.)). Conductive section 632 couples inner conductor 626 and jacket 636. In an embodiment, conductive section 632 is copper.

FIG. 52 depicts a cross-sectional representation of an embodiment of a temperature limited heater with an outer conductor. The outer conductor includes a ferromagnetic section and a non-ferromagnetic section. The heater is placed in a corrosion resistant jacket. A conductive layer is placed between the outer conductor and the jacket. FIGS. 53 and 54 depict transverse cross-sectional views of the embodiment shown in FIG. 52. Ferromagnetic section 622 is 409, 410, or 446 stainless steel with a thickness of 0.9 cm. Non-ferromagnetic section 624 is copper with a thickness of 0.9 cm. Ferromagnetic section 622 and non-ferromagnetic section 624 are placed in jacket 636. Jacket 636 is 304 or 347H stainless steel with a thickness of 0.1 cm. Conductive layer 634 is a copper layer. Electrical insulator 628 includes compacted silicon nitride, boron nitride, or magnesium oxide powder with a thickness of 0.1 to 0.3 cm. Inner conductor 626 is copper with a diameter of 1.0 cm.

In an embodiment, ferromagnetic section 622 is 446 stainless steel with a thickness of 0.9 cm. Jacket 636 is 410 stainless steel with a thickness of 0.6 cm. 410 stainless steel has a higher Curie temperature than 446 stainless steel. Such a temperature limited heater may "contain" current such that the current does not easily flow from the heater to the surrounding formation and/or to any surrounding water (for example, brine, groundwater, or formation water). In this embodiment, a majority of the current flows through ferromagnetic section 622 until the Curie temperature of the ferromagnetic section is reached. After the Curie temperature of ferromagnetic section 622 is reached, a majority of the current flows through conductive layer 634. The ferromagnetic properties of jacket 636 (410 stainless steel) inhibit the current from flowing outside the jacket and "contain" the current. Jacket 636 may also have a thickness that provides strength to the temperature limited heater.

FIG. 55 depicts a cross-sectional representation of an embodiment of a temperature limited heater. The heating section of the temperature limited heater includes non-ferromagnetic inner conductors and a ferromagnetic outer conductor. The overburden section of the temperature limited heater includes a non-ferromagnetic outer conductor. FIGS. 56, 57, and 58 depict transverse cross-sectional views of the embodiment shown in FIG. 55. Inner conductor 626 is copper with a diameter of 1.0 cm. Electrical insulator 628 is placed between inner conductor 626 and conductive layer 634. Electrical insulator 628 includes compacted silicon nitride, boron nitride, or magnesium oxide powder with a thickness of 0.1 cm to 0.3 cm. Conductive layer 634 is copper with a thickness of 0.1 cm. Insulation layer 638 is in the annulus outside of conductive layer 634. The thickness of the annulus may be 0.3 cm. Insulation layer 638 is quartz sand.

Heating section 640 may provide heat to one or more hydrocarbon layers in the formation. Heating section 640 includes ferromagnetic material such as 409 stainless steel or 410 stainless steel. Heating section 640 has a thickness of 0.9 cm. Endcap 642 is coupled to an end of heating section 640. Endcap 642 electrically couples heating section 640 to inner conductor 626 and/or conductive layer 634. Endcap 642 is 304 stainless steel. Heating section 640 is coupled to overburden section 644. Overburden section 644 includes carbon steel and/or other suitable support materials. Overburden section 644 has a thickness of 0.6 cm. Overburden section 644 is lined with conductive layer 646. Conductive layer 646 is copper with a thickness of 0.3 cm.

FIG. 59 depicts a cross-sectional representation of an embodiment of a temperature limited heater with an overburden section and a heating section. FIGS. 60 and 61 depict transverse cross-sectional views of the embodiment shown in FIG. 59. The overburden section includes portion 626A of inner conductor 626. Portion 626A is copper with a diameter of 1.3 cm. The heating section includes portion 626B of inner conductor 626. Portion 626B is copper with a diameter of 0.5 cm. Portion 626B is placed in ferromagnetic conductor 654. Ferromagnetic conductor 654 is 446 stainless steel with a thickness of 0.4 cm. Electrical insulator 628 includes compacted silicon nitride, boron nitride, or magnesium oxide powder with a thickness of 0.2 cm. Outer conductor 630 is copper with a thickness of 0.1 cm. Outer conductor 630 is placed in jacket 636. Jacket 636 is 316H or 347H stainless steel with a thickness of 0.2 cm.

FIG. 62A and FIG. 62B depict cross-sectional representations of an embodiment of a temperature limited heater with a ferromagnetic inner conductor. Inner conductor 626 is a 1" Schedule XXS 446 stainless steel pipe. In some embodiments, inner conductor 626 includes 409 stainless steel, 410 stainless steel, Invar 36, alloy 42-6, alloy 52, or other ferromagnetic materials. Inner conductor 626 has a diameter of 2.5 cm. Electrical insulator 628 includes compacted silicon nitride, boron nitride, or magnesium oxide powders; or polymers, Nextel ceramic fiber, mica, or glass fibers. Outer conductor 630 is copper or any other non-ferromagnetic material such as aluminum. Outer conductor 630 is coupled to jacket 636. Jacket 636 is 304H, 316H, or 347H stainless steel. In this embodiment, a majority of the heat is produced in inner conductor 626.

FIG. 63A and FIG. 63B depict cross-sectional representations of an embodiment of a temperature limited heater with a ferromagnetic inner conductor and a non-ferromagnetic core. Inner conductor 626 may be made of 446 stainless steel, 409 stainless steel, 410 stainless steel, carbon steel, Armco ingot iron, iron-cobalt alloys, or other ferromagnetic materials. Core 656 may be tightly bonded inside inner conductor 626. Core 656 is copper or other non-ferromagnetic material. In certain embodiments, core 656 is inserted as a tight fit inside inner conductor 626 before a drawing operation. In some embodiments, core 656 and inner conductor 626 are coextrusion bonded. Outer conductor 630 is 347H stainless steel. A drawing or rolling operation to compact electrical insulator 628 (for example, compacted silicon nitride, boron nitride, or magnesium oxide powder) may ensure good electrical contact between inner conductor 626 and core 656. In this embodiment, heat is produced primarily in inner conductor 626 until the Curie temperature is approached. Resistance then decreases sharply as current penetrates core 656.

FIG. 64A and FIG. 64B depict cross-sectional representations of an embodiment of a temperature limited heater with a ferromagnetic outer conductor. Inner conductor 626 is nickel-clad copper. Electrical insulator 628 is silicon nitride, boron nitride, or magnesium oxide. Outer conductor 630 is a 1" Schedule XXS carbon steel pipe. In this embodiment, heat is produced primarily in outer conductor 630, resulting in a small temperature differential across electrical insulator 628.

Figure 65B:
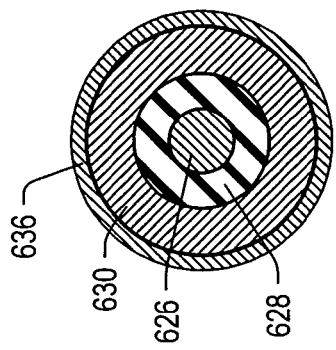
FIGS. 65A and 65B depict cross-sectional representations of an embodiment of a temperature limited heater.
Figure 65A:
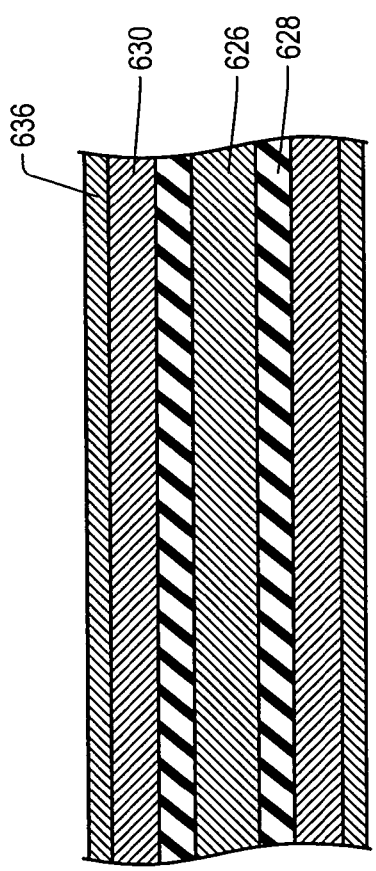

FIG. 65A and FIG. 65B depict cross-sectional representations of an embodiment of a temperature limited heater with a ferromagnetic outer conductor that is clad with a corrosion resistant alloy. Inner conductor 626 is copper. Outer conductor 630 is a 1" Schedule XXS carbon steel pipe. Outer conductor 630 is coupled to jacket 636. Jacket 636 is made of corrosion resistant material (for example, 347H stainless steel). Jacket 636 provides protection from corrosive fluids in the wellbore (for example, sulfidizing and carburizing gases). Heat is produced primarily in outer conductor 630, resulting in a small temperature differential across electrical insulator 628.

Figure 66B:
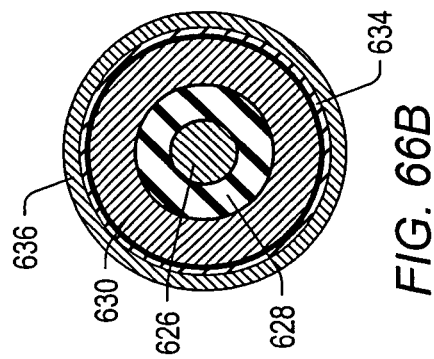
FIGS. 66A and 66B depict cross-sectional representations of an embodiment of a temperature limited heater.
Figure 66A:
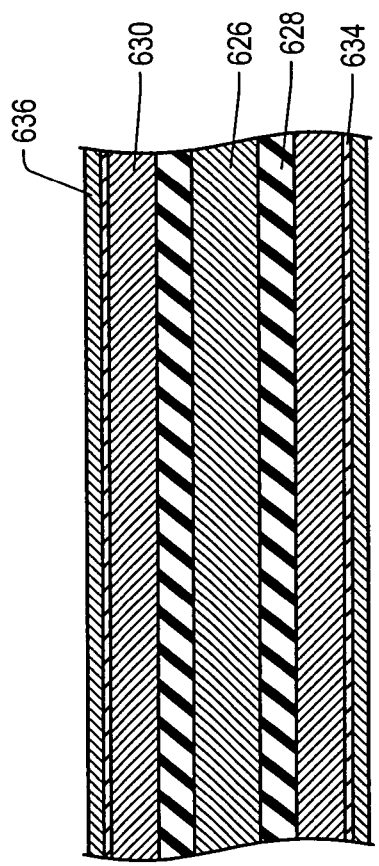

FIG. 66A and FIG. 66B depict cross-sectional representations of an embodiment of a temperature limited heater with a ferromagnetic outer conductor. The outer conductor is clad with a conductive layer and a corrosion resistant alloy. Inner conductor 626 is copper. Electrical insulator 628 is silicon nitride, boron nitride, or magnesium oxide. Outer conductor 630 is a 1" Schedule 80 446 stainless steel pipe. Outer conductor 630 is coupled to jacket 636. Jacket 636 is made from corrosion resistant material such as 347H stainless steel. In an embodiment, conductive layer 634 is placed between outer conductor 630 and jacket 636. Conductive layer 634 is a copper layer. Heat is produced primarily in outer conductor 630, resulting in a small temperature differential across electrical insulator 628. Conductive layer 634 allows a sharp decrease in the resistance of outer conductor 630 as the outer conductor approaches the Curie temperature. Jacket 636 provides protection from corrosive fluids in the wellbore.

In an embodiment, a temperature limited heater includes triaxial conductors. FIG. 67A and FIG. 67B depict cross-sectional representations of an embodiment of a temperature limited heater with triaxial conductors. Inner conductor 626 may be copper or another highly conductive material. Electrical insulator 628 may be silicon nitride, boron nitride, or magnesium oxide (in certain embodiments, as compacted powders). Middle conductor 658 may include ferromagnetic material (for example, 446 stainless steel). In the embodiment of FIGS. 67A and 67B, outer conductor 630 is separated from middle conductor 658 by electrical insulator 628. Outer conductor 630 may include corrosion resistant, electrically conductive material (for example, stainless steel). In some embodiments, electrical insulator 628 is a space between conductors (for example, an air gap or other gas gap) that electrically insulates the conductors (for example, conductors 626, 630, and 658 may be in a conductor-in-conduit-in-conduit arrangement).

In a temperature limited heater with triaxial conductors, such as depicted in FIGS. 67A and 67B, electrical current may propagate through two conductors in one direction and through the third conductor in an opposite direction. In FIGS. 67A and 67B, electrical current may propagate in through middle conductor 658 in one direction and return through inner conductor 626 and outer conductor 630 in an opposite direction, as shown by the arrows in FIG. 67A and the +/− signs in FIG. 67B. In an embodiment, electrical current is split approximately in half between inner conductor 626 and outer conductor 630. Splitting the electrical current between inner conductor 626 and outer conductor 630 causes current propagating through middle conductor 658 to flow through both inside and outside skin depths of the middle conductor.

Current flows through both the inside and outside skin depths due to reduced magnetic field intensity from the current being split between the outer conductor and the inner conductor. Reducing the magnetic field intensity allows the skin depth of middle conductor 658 to remain relatively small with the same magnetic permeability. Thus, the thinner inside and outside skin depths may produce an increased Curie effect compared to the same thickness of ferromagnetic material with only one skin depth. The thinner inside and outside skin depths may produce a sharper turndown than one single skin depth in the same ferromagnetic material. Splitting the current between outer conductor 630 and inner conductor 626 may allow a thinner middle conductor 658 to produce the same Curie effect as a thicker middle conductor. In certain embodiments, the materials and thicknesses used for outer conductor 630, inner conductor 626 and middle conductor 658 have to be balanced to produce desired results in the Curie effect and turndown ratio of a triaxial temperature limited heater.

In some embodiments, the conductor (for example, an inner conductor, an outer conductor, or a ferromagnetic conductor) is the composite conductor that includes two or more different materials. In certain embodiments, the composite conductor includes two or more ferromagnetic materials. In some embodiments, the composite ferromagnetic conductor includes two or more radially disposed materials. In certain embodiments, the composite conductor includes a ferromagnetic conductor and a non-ferromagnetic conductor. In some embodiments, the composite conductor includes the ferromagnetic conductor placed over a non-ferromagnetic core. Two or more materials may be used to obtain a relatively flat electrical resistivity versus temperature profile in a temperature region below the Curie temperature and/or a sharp decrease (a high turndown ratio) in the electrical resistivity at or near the Curie temperature. In some cases, two or more materials are used to provide more than one Curie temperature for the temperature limited heater.

In certain embodiments, a composite electrical conductor is formed using a billet coextrusion process. A billet coextrusion process may include coupling together two or more electrical conductors at relatively high temperatures (for example, at temperatures that are near or above 75% of the melting temperature of a conductor). The electrical conductors may be drawn together at the relatively high temperatures (for example, under vacuum). Coextrusion at high temperatures under vacuum exposes fresh metal surfaces during drawing while inhibiting oxidation of the metal surfaces. This type of coextrusion improves the metallurgical bond between coextruded metals. The drawn together conductors may then be cooled to form a composite electrical conductor made from the two or more electrical conductors. In some embodiments, the composite electrical conductor is a solid composite electrical conductor. In certain embodiments, the composite electrical conductor may be a tubular composite electrical conductor.

In one embodiment, a copper core is billet coextruded with a stainless steel conductor (for example, 446 stainless steel). The copper core and the stainless steel conductor may be heated to a softening temperature in vacuum. At the softening temperature, the stainless steel conductor may be drawn over the copper core to form a tight fit. The stainless steel conductor and copper core may then be cooled to form a composite electrical conductor with the stainless steel surrounding the copper core.

In some embodiments, a long, composite electrical conductor is formed from several sections of composite electrical conductor. The sections of composite electrical conductor may be formed by a billet coextrusion process. The sections of composite electrical conductor may be coupled using a welding process. FIGS. 68, 69, and 70 depict embodiments of coupled sections of composite electrical conductors. In FIG. 68, core 656 extends beyond the ends of inner conductor 626 in each section of a composite electrical conductor. In an embodiment, core 656 is copper and inner conductor 626 is 446 stainless steel. Cores 656 from each section of the composite electrical conductor may be coupled by, for example, brazing the core ends together. Core coupling material 650 may couple the core ends, as shown in FIG. 68. Core coupling material 650 may be, for example Everdur, a copper-silicon alloy material (for example, an alloy with about 3% by weight silicon in copper). Alternatively, the copper core may be autogenously welded or filled with copper.

Inner conductor coupling material 652 may couple inner conductors 626 from each section of the composite electrical conductor. Inner conductor coupling material 652 may be material used for welding sections of inner conductor 626 together. In certain embodiments, inner conductor coupling material 652 may be used for welding stainless steel inner conductor sections together. In some embodiments, inner conductor coupling material 652 is 304 stainless steel or 310 stainless steel. A third material (for example, 309 stainless steel) may be used to couple inner conductor coupling material 652 to ends of inner conductor 626. The third material may be needed or desired to produce a better bond (for example, a better weld) between inner conductor 626 and inner conductor coupling material 652. The third material may be non-magnetic to reduce the potential for a hot spot to occur at the coupling.

In certain embodiments, inner conductor coupling material 652 surrounds the ends of cores 656 that protrude beyond the ends of inner conductors 626, as shown in FIG. 68. Inner conductor coupling material 652 may include one or more coupled portions. Inner conductor coupling material 652 may be placed in a clam shell configuration around the ends of cores 656 that protrude beyond the ends of inner conductors 626, as shown in the end view depicted in FIG. 69. Coupling material 660 may be used to couple together portions (for example, halves) of inner conductor coupling material 652. Coupling material 660 may be the same material as inner conductor coupling material 652 or another material suitable for coupling together portions of the inner conductor coupling material.

In some embodiments, a composite electrical conductor includes inner conductor coupling material 652 with 304 stainless steel or 310 stainless steel and inner conductor 626 with 446 stainless steel or another ferromagnetic material. In such an embodiment, inner conductor coupling material 652 produces significantly less heat than inner conductor 626. The portions of the composite electrical conductor that include the inner conductor coupling material (for example, the welded portions or "joints" of the composite electrical conductor) may remain at lower temperatures than adjacent material during application of applied electrical current to the composite electrical conductor. The reliability and durability of the composite electrical conductor may be increased by keeping the joints of the composite electrical conductor at lower temperatures.

FIG. 70 depicts an embodiment for coupling together sections of a composite electrical conductor. Ends of cores 656 and ends of inner conductors 626 are beveled to facilitate coupling the sections of the composite electrical conductor. Core coupling material 650 may couple (for example, braze) the ends of each core 656. The ends of each inner conductor 626 may be coupled (for example, welded) together with inner conductor coupling material 652. Inner conductor coupling material 652 may be 309 stainless steel or another suitable welding material. In some embodiments, inner conductor coupling material 652 is 309 stainless steel. 309 stainless steel may reliably weld to both an inner conductor having 446 stainless steel and a core having copper. Using beveled ends when coupling together sections of a composite electrical conductor may produce a reliable and durable coupling between the sections of composite electrical conductor. FIG. 70 depicts a weld formed between ends of sections that have beveled surfaces.

The composite electrical conductor may be used as the conductor in any electrical heater embodiment described herein. For example, the composite conductor may be used as the conductor in a conductor-in-conduit heater or an insulated conductor heater. In certain embodiments, the composite conductor may be coupled to a support member such as a support conductor. The support member may be used to provide support to the composite conductor so that the composite conductor is not relied upon for strength at or near the Curie temperature. The support member may be useful for heaters of lengths of at least 100 m. The support member may be a non-ferromagnetic member that has good high temperature creep strength. Examples of materials that are used for a support member include, but are not limited to, Haynes® 625 alloy and Haynes® HR120® alloy (Haynes International, Kokomo, Ind., U.S.A.), NF709, Incoloy® 800H alloy and 347HP alloy (Allegheny Ludlum Corp., Pittsburgh, Pa., U.S.A.). In some embodiments, materials in a composite conductor are directly coupled (for example, brazed, metallurgically bonded, or swaged) to each other and/or the support member. Using a support member may reduce the need for the ferromagnetic member to provide support for the temperature limited heater, especially at or near the Curie temperature. Thus, the temperature limited heater may be designed with more flexibility in the selection of ferromagnetic materials.

Figure 71:
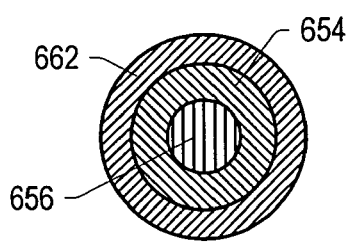
FIG. 71 depicts a cross-sectional representation of an embodiment of a composite conductor with a support member.

FIG. 71 depicts a cross-sectional representation of an embodiment of the composite conductor with the support member. Core 656 is surrounded by ferromagnetic conductor 654 and support member 662. In some embodiments, core 656, ferromagnetic conductor 654, and support member 662 are directly coupled (for example, brazed together or metallurgically bonded together). In one embodiment, core 656 is copper, ferromagnetic conductor 654 is 446 stainless steel, and support member 662 is 347H alloy. In certain embodiments, support member 662 is a Schedule 80 pipe. Support member 662 surrounds the composite conductor having ferromagnetic conductor 654 and core 656. Ferromagnetic conductor 654 and core 656 may be joined to form the composite conductor by, for example, a coextrusion process. For example, the composite conductor is a 1.9 cm outside diameter 446 stainless steel ferromagnetic conductor surrounding a 0.95 cm diameter copper core.

In certain embodiments, the diameter of core 656 is adjusted relative to a constant outside diameter of ferromagnetic conductor 654 to adjust the turndown ratio of the temperature limited heater. For example, the diameter of core 656 may be increased to 1.14 cm while maintaining the outside diameter of ferromagnetic conductor 654 at 1.9 cm to increase the turndown ratio of the heater.

Figure 72:
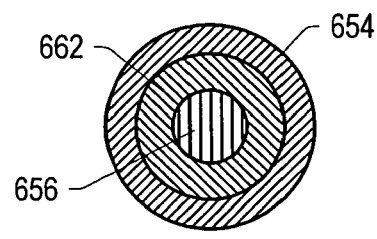
FIG. 72 depicts a cross-sectional representation of an embodiment of a composite conductor with a support member separating the conductors.

In some embodiments, conductors (for example, core 656 and ferromagnetic conductor 654) in the composite conductor are separated by support member 662. FIG. 72 depicts a cross-sectional representation of an embodiment of the composite conductor with support member 662 separating the conductors. In one embodiment, core 656 is copper with a diameter of 0.95 cm, support member 662 is 347H alloy with an outside diameter of 1.9 cm, and ferromagnetic conductor 654 is 446 stainless steel with an outside diameter of 2.7 cm. The support member depicted in FIG. 72 has a lower creep strength relative to the support members depicted in FIG. 71.

Figure 73:
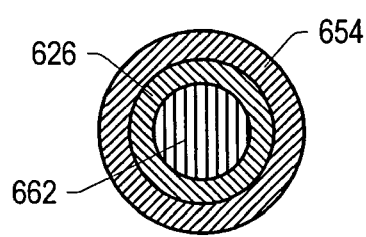
FIG. 73 depicts a cross-sectional representation of an embodiment of a composite conductor surrounding a support member.

In certain embodiments, support member 662 is located inside the composite conductor. FIG. 73 depicts a cross-sectional representation of an embodiment of the composite conductor surrounding support member 662. Support member 662 is made of 347H alloy. Inner conductor 626 is copper. Ferromagnetic conductor 654 is 446 stainless steel. In one embodiment, support member 662 is 1.25 cm diameter 347H alloy, inner conductor 626 is 1.9 cm outside diameter copper, and ferromagnetic conductor 654 is 2.7 cm outside diameter 446 stainless steel. The turndown ratio is higher than the turndown ratio for the embodiments depicted in FIGS. 71, 72, and 74 for the same outside diameter, but it has a lower creep strength.

In some embodiments, the thickness of inner conductor 626, which is copper, is reduced and the thickness of support member 662 is increased to increase the creep strength at the expense of reduced turndown ratio. For example, the diameter of support member 662 is increased to 1.6 cm while maintaining the outside diameter of inner conductor 626 at 1.9 cm to reduce the thickness of the conduit. This reduction in thickness of inner conductor 626 results in a decreased turndown ratio relative to the thicker inner conductor embodiment but an increased creep strength.

Figure 74:
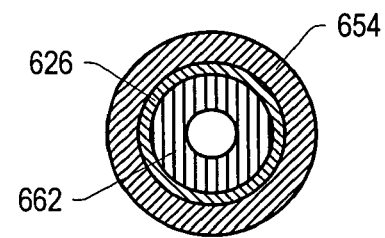
FIG. 74 depicts a cross-sectional representation of an embodiment of a composite conductor surrounding a conduit support member.

In one embodiment, support member 662 is a conduit (or pipe) inside inner conductor 626 and ferromagnetic conductor 654. FIG. 74 depicts a cross-sectional representation of an embodiment of the composite conductor surrounding support member 662. In one embodiment, support member 662 is 347H alloy with a 0.63 cm diameter center hole. In some embodiments, support member 662 is a preformed conduit. In certain embodiments, support member 662 is formed by having a dissolvable material (for example, copper dissolvable by nitric acid) located inside the support member during formation of the composite conductor. The dissolvable material is dissolved to form the hole after the conductor is assembled. In an embodiment, support member 662 is 347H alloy with an inside diameter of 0.63 cm and an outside diameter of 1.6 cm, inner conductor 626 is copper with an outside diameter of 1.8 cm, and ferromagnetic conductor 654 is 446 stainless steel with an outside diameter of 2.7 cm.

In certain embodiments, the composite electrical conductor is used as the conductor in the conductor-in-conduit heater. For example, the composite electrical conductor may be used as conductor 666 in FIG. 75

Figure 75:
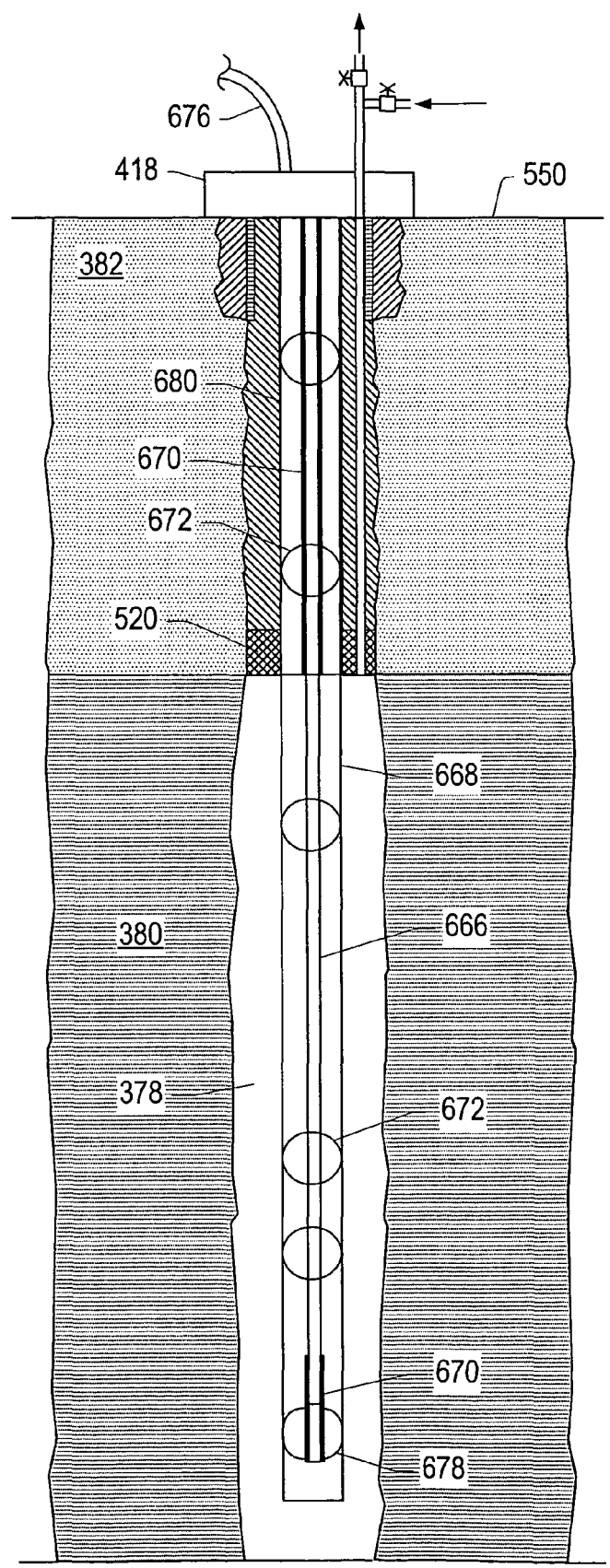
FIG. 75 depicts a cross-sectional representation of an embodiment of a conductor-in-conduit heat source.

FIG. 75 depicts a cross-sectional representation of an embodiment of the conductor-in-conduit heater. Conductor 666 is disposed in conduit 668. Conductor 666 is a rod or conduit of electrically conductive material. Low resistance sections 670 are present at both ends of conductor 666 to generate less heating in these sections. Low resistance section 670 is formed by having a greater cross-sectional area of conductor 666 in that section, or the sections are made of material having less resistance. In certain embodiments, low resistance section 670 includes a low resistance conductor coupled to conductor 666.

Conduit 668 is made of an electrically conductive material. Conduit 668 is disposed in opening 378 in hydrocarbon layer 380. Opening 378 has a diameter that accommodates conduit 668.

Conductor 666 may be centered in conduit 668 by centralizers 672. Centralizers 672 electrically isolate conductor 666 from conduit 668. Centralizers 672 inhibit movement and properly locate conductor 666 in conduit 668. Centralizers 672 are made of ceramic material or a combination of ceramic and metallic materials. Centralizers 672 inhibit deformation of conductor 666 in conduit 668. Centralizers 672 are touching or spaced at intervals between approximately 0.1 m (meters) and approximately 3 m or more along conductor 666.

A second low resistance section 670 of conductor 666 may couple conductor 666 to wellhead 418, as depicted in FIG. 75. Electrical current may be applied to conductor 666 from power cable 676 through low resistance section 670 of conductor 666. Electrical current passes from conductor 666 through sliding connector 678 to conduit 668. Conduit 668 may be electrically insulated from overburden casing 680 and from wellhead 418 to return electrical current to power cable 676. Heat may be generated in conductor 666 and conduit 668. The generated heat may radiate in conduit 668 and opening 378 to heat at least a portion of hydrocarbon layer 380.

Overburden casing 680 may be disposed in overburden 382. Overburden casing 680 is, in some embodiments, surrounded by materials (for example, reinforcing material and/or cement) that inhibit heating of overburden 382. Low resistance section 670 of conductor 666 may be placed in overburden casing 680. Low resistance section 670 of conductor 666 is made of, for example, carbon steel. Low resistance section 670 of conductor 666 may be centralized in overburden casing 680 using centralizers 672. Centralizers 672 are spaced at intervals of approximately 6 m to approximately 12 m or, for example, approximately 9 m along low resistance section 670 of conductor 666. In a heater embodiment, low resistance section 670 of conductor 666 is coupled to conductor 666 by one or more welds. In other heater embodiments, low resistance sections are threaded, threaded and welded, or otherwise coupled to the conductor. Low resistance section 670 generates little or no heat in overburden casing 680. Packing 520 may be placed between overburden casing 680 and opening 378. Packing 520 may be used as a cap at the junction of overburden 382 and hydrocarbon layer 380 to allow filling of materials in the annulus between overburden casing 680 and opening 378. In some embodiments, packing 520 inhibits fluid from flowing from opening 378 to surface 550.

Figure 76:
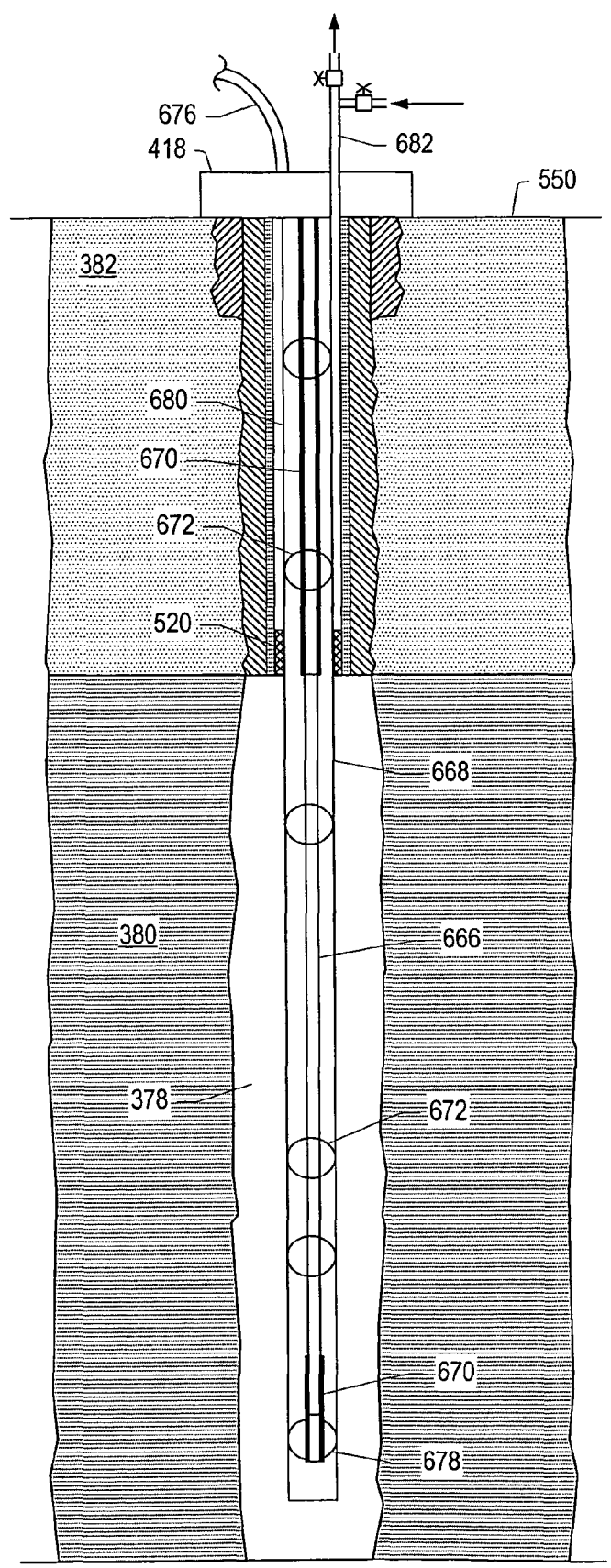
FIG. 76 depicts a cross-sectional representation of an embodiment of a removable conductor-in-conduit heat source.

FIG. 76 depicts a cross-sectional representation of an embodiment of a removable conductor-in-conduit heat source. Conduit 668 may be placed in opening 378 through overburden 382 such that a gap remains between the conduit and overburden casing 680. Fluids may be removed from opening 378 through the gap between conduit 668 and overburden casing 680. Fluids may be removed from the gap through conduit 682. Conduit 668 and components of the heat source included in the conduit that are coupled to wellhead 418 may be removed from opening 378 as a single unit. The heat source may be removed as a single unit to be repaired, replaced, and/or used in another portion of the formation.

Water or other fluids inside conduit 668 can adversely affect heating using the conductor-in-conduit heater. In certain embodiments, fluid inside conduit 668 is removed to reduce the pressure inside the conduit. The fluid may be removed by vacuum pumping or other means for reducing the pressure inside conduit 668. In some embodiments, the pressure is reduced outside conduit 668 and inside opening 378. In certain embodiments, the space inside conduit 668 or the space outside the conduit is vacuum pumped to a pressure below the vapor pressure of water at the downhole temperature of the conduit. For example, at a downhole temperature of 25° C., the space inside or outside conduit 668 would be vacuum pumped to a pressure below about 101 kPa.

In certain embodiments, the space inside or outside conduit 668 is vacuum pumped to a pressure below the vapor pressure of water at ice temperatures. The vapor pressure of ice at 0° C. is 610 Pa. As conduit 668 is vacuum pumped, water in the conduit gets colder until the water freezes. Thus, vacuum pumping to a pressure below the vapor pressure of water at ice temperatures indicates that most or all of the water has been removed from the space inside or outside conduit 668. In certain embodiments, high pumping capacity vacuum pumps (for example, a Kinney® CB245 vacuum pump available from Tuthill Co. (Burr Ridge, Ill., U.S.A.)) are used to vacuum pump below pressures of about 1 Pa. In some embodiments, a vacuum gauge is coupled between the vacuum pump and the wellhead for the heater. In some embodiments, a cold trap (for example, a dry ice trap or liquid nitrogen trap) is placed between conduit 668 and the vacuum pump to condense water from the conduit and inhibit water from contaminating pump oil.

As pressure in conduit 668 is decreased, ice in the conduit gets colder, and the vapor pressure of the ice further decreases. For example, the vapor pressure of ice at (−10)° C. is 260 Pa. Thus, in certain embodiments, the space inside or outside conduit 668 is vacuum pumped to a pressure below 1 kPa, below 750 Pa, below 600 Pa, below 500 Pa, below 100 Pa, 15 Pa, below 10 Pa, below 5 Pa, or less. Vacuum pumping to such pressures improves the removal of water from conduit 668.

In some embodiments, conduit 668 is vacuum pumped to a selected pressure and then the conduit is closed off (pressure sealed), for example, by closing a valve on the wellhead. The pressure in conduit 668 is monitored for any pressure rise. If the pressure rises to a value near the vapor pressure of water or ice and at least temporarily stabilizes, there is most likely more water in the conduit and the conduit is then vacuum pumped again. If the pressure does not rise up to the vapor pressure of ice or water, then conduit 668 is considered dry. If the pressure continuously rises to pressures above the vapor pressure of ice or water, then there may be a leak in conduit 668 causing the pressure rise.

In certain embodiments, heat is provided by conductor 666 and/or conduit 668 during vacuum pumping of the conduit. The provided heat may increase the vapor pressure of water or ice in conduit 668. The provided heat may inhibit ice from forming in conduit 668. Providing heat in conduit 668 may decrease the time needed to remove (vacuum pump) water from the conduit. Providing heat in conduit 668 may increase the likelihood of removing substantially all the water from the conduit.

In some embodiments, a non-condensable gas (for example, dry nitrogen, argon, or helium) is backfilled inside or outside conduit 668 after vacuum pumping. In some embodiments, the space inside or outside conduit 668 is backfilled with the non-condensable gas to a pressure between 101 kPa and 10 MPa, between 202 kPa and 5 MPa, or between 500 kPa and 1 MPa. In some embodiments, the inside or outside of conduit 668 is vacuum pumped for a time, then backfilled with non-condensable gas, and then vacuum pumped again. This process may be repeated for several cycles to more completely remove water and other fluids from inside or outside conduit 668. In some embodiments, conduit 668 is operated with the backfilled non-condensable gas remaining inside or outside the conduit.

In some embodiments, a small amount of an oxidizing fluid, such as oxygen, is added to the non-condensable gas backfilled in conduit 668. The oxidizing fluid may oxidize metals of conduit 668 and/or conductor 666. The oxidation may increase the emissivity of the conduit and/or conductor metals. The small amount of oxidizing fluid may be between about 100 ppm and 25 ppm, between about 75 ppm and 40 ppm, or between about 60 ppm and 50 ppm in the non-condensable gas. In one embodiment, at most 50 ppm of oxidizing fluid is in the non-condensable gas in conduit 668.

Figure 77:
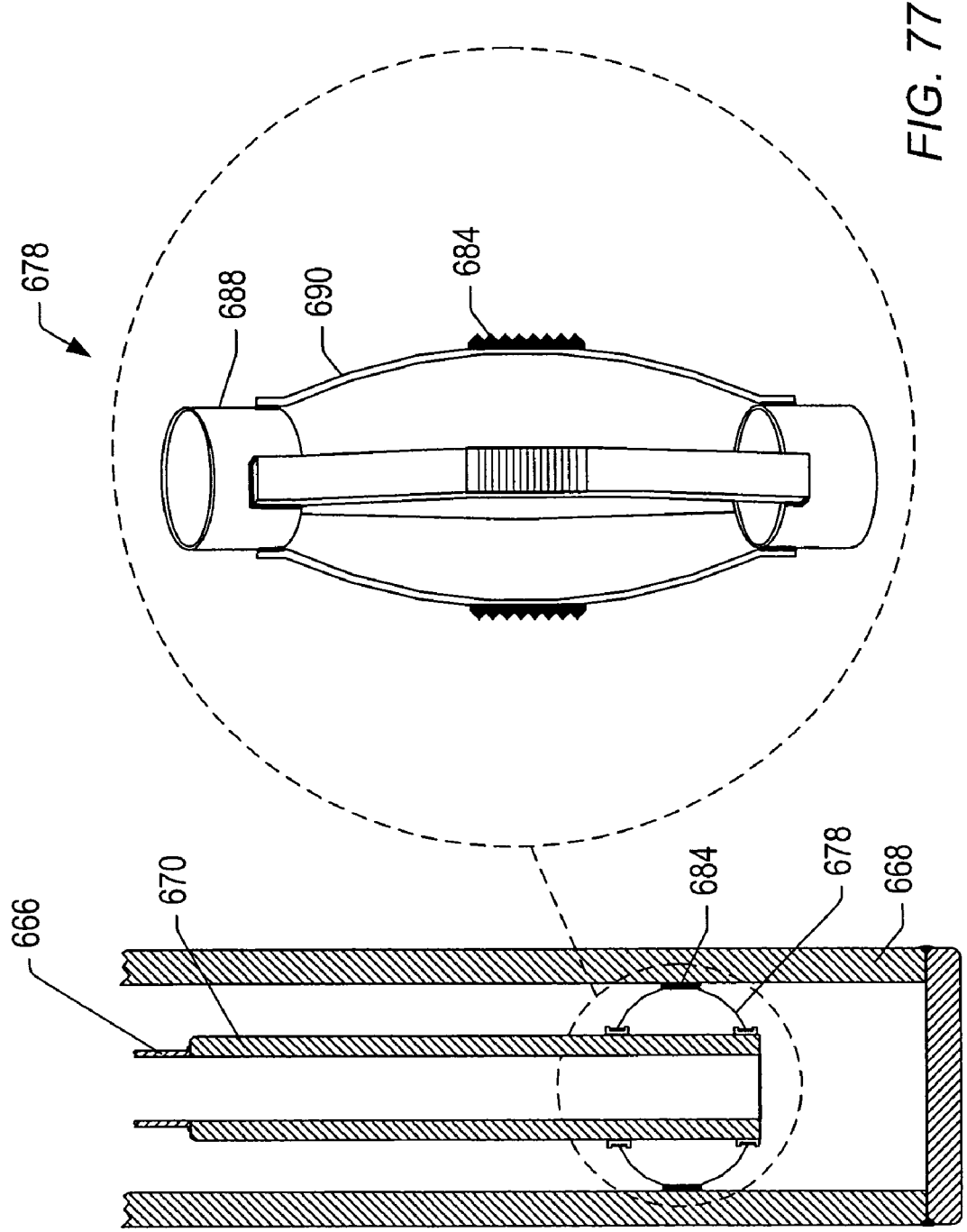
FIG. 77 depicts an embodiment of a sliding connector.

FIG. 77 depicts an embodiment of a sliding connector. Sliding connector 678 may be coupled near an end of conductor 666. Sliding connector 678 may be positioned near a bottom end of conduit 668. Sliding connector 678 may electrically couple conductor 666 to conduit 668. Sliding connector 678 may move during use to accommodate thermal expansion and/or contraction of conductor 666 and conduit 668 relative to each other. In some embodiments, sliding connector 678 may be attached to low resistance section 670 of conductor 666. The lower resistance of low resistance section 670 may allow the sliding connector to be at a temperature that does not exceed about 90° C. Maintaining sliding connector 678 at a relatively low temperature may inhibit corrosion of the sliding connector and promote good contact between the sliding connector and conduit 668.

Sliding connector 678 may include scraper 684. Scraper 684 may abut an inner surface of conduit 668 at point 686. Scraper 684 may include any metal or electrically conducting material (for example, steel or stainless steel). Centralizer 688 may couple to conductor 666. In some embodiments, sliding connector 678 is positioned on low resistance section 670 of conductor 666. Centralizer 688 may include any electrically conducting material (for example, a metal or metal alloy). Spring bow 690 may couple scraper 684 to centralizer 688. Spring bow 690 may include any metal or electrically conducting material (for example, copper-beryllium alloy). In some embodiments, centralizer 688, spring bow 690, and/or scraper 684 are welded together.

More than one sliding connector 678 may be used for redundancy and to reduce the current through each scraper 684. In addition, a thickness of conduit 668 may be increased for a length adjacent to sliding connector 678 to reduce heat generated in that portion of conduit. The length of conduit 668 with increased thickness may be, for example, approximately 6 m. In certain embodiments, electrical contact may be made between centralizer 688 and scraper 684 (shown in FIG. 77) on sliding connector 678 using an electrical conductor (for example, a copper wire) that has a lower electrical resistance than spring bow 690. Electrical current may flow through the electrical conductor rather than spring bow 690 so that the spring bow has a longer lifetime.

Figures 78A, 78B:
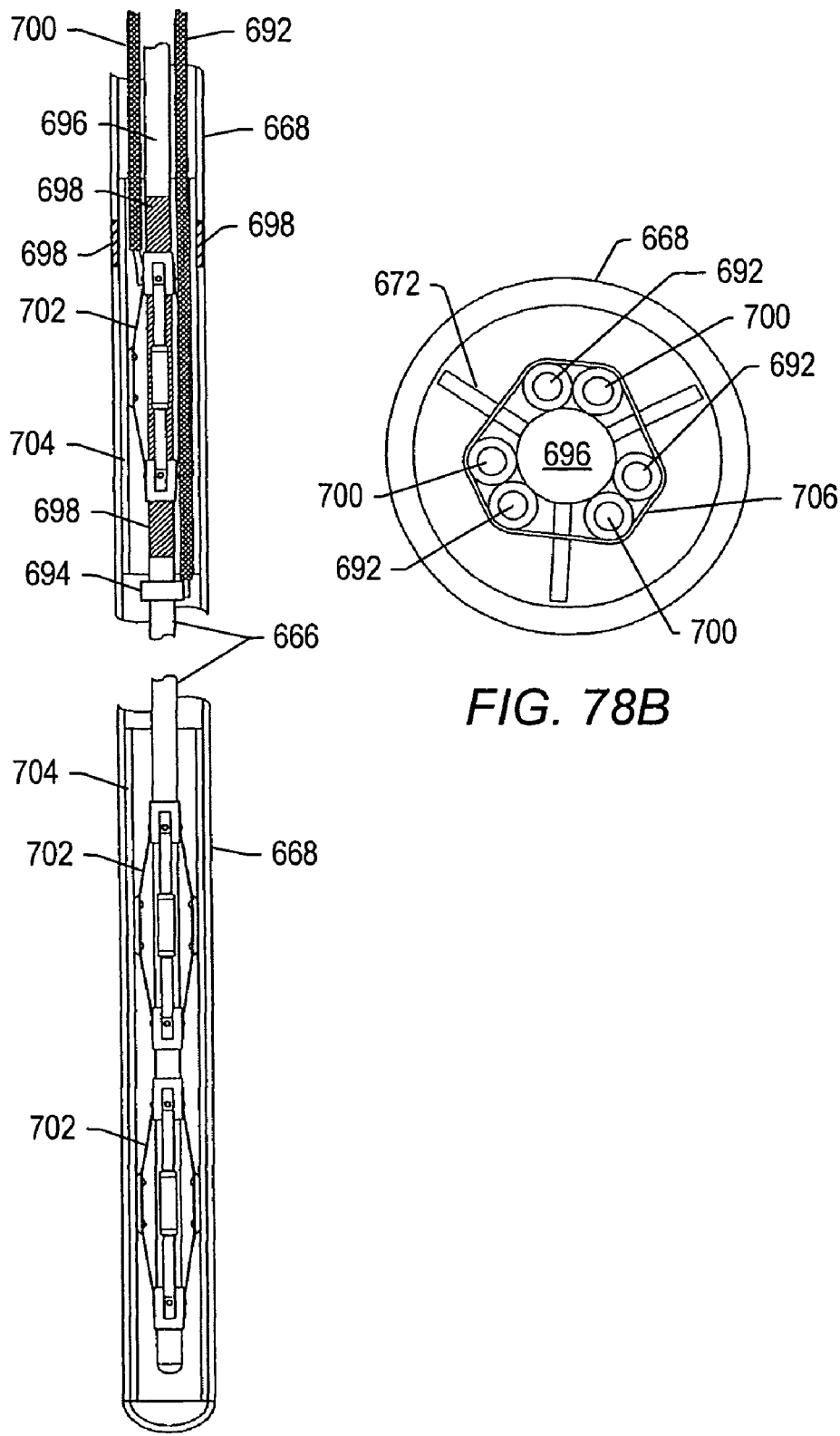
FIG. 78A depicts an embodiment of contacting sections for a conductor-in-conduit heater.
FIG. 78B depicts an aerial view of the upper contact section of the conductor-in-conduit heater in FIG. 78A.

FIG. 78A depicts an embodiment of contacting sections for a conductor-in-conduit heater. Conductor 666 and conduit 668 form the conductor-in-conduit heater. In the upper contact section, lead-in cable 692 provides power to conductor 666 and conduit 668. Connector 694 couples lead-in cable 692 to conductor 666. Conductor 666 is supported by rod 696. In certain embodiments, rod 696 is a sucker rod such as a fiberglass, stainless steel, or carbon steel sucker rod. A fiberglass sucker rod may have lower proximity effect losses than a sucker rod made of stainless steel or carbon steel. Rod 696 and conductor 666 are electrically isolated by isolation sub 698.

Return electrical current enters the upper contacting section through conduit 668. Conduit 668 is electrically coupled to return cable 700 through contactor 702. In certain embodiments, liner 704 is located on the inside of conduit 668 to promote electrical contact between the conduit and contactor 702. In certain embodiments, liner 704 is copper. In some embodiments, conduit 668 includes one or more isolation subs 698. Isolation subs 698 in conduit 668 inhibit any current flow to sections above the contacting section of the conduit. Isolation subs 698 may be, for example fiberglass sections of conduit 668 or electrically insulating epoxy threaded sections in the conduit.

Lead-in cable 692 and return cable 700 may be 4-0 copper cable with TEFLON® insulation. Using copper cables to make electrical contact in the upper contacting section may be less expensive than other contacting methods such as cladding. In certain embodiments, more than one cable is used for lead-in cable 692 and/or return cable 700. FIG. 78B depicts an aerial view of the upper contact section of the conductor-in-conduit heater in FIG. 78A with three lead-in cables 692 and three return cables 700. The cables are coupled to rod 696 with strap 706. Centralizers 672 maintain a position of rod 696 in conduit 668. The lead-in cables and return cables may be paired off in three pairs. Each pair may have one lead-in cable 692 and one return cable 700. Thus, in each cable pair, one cable carries current downwards (lead-in cables) and one cable carries current upwards (return cables). This opposite current flow in each pair reduces skin effect losses in the upper contacting section. In addition, splitting the lead-in and return current between several cables reduces electrical loss and heat loss in the upper contacting section.

In the lower contacting section shown in FIG. 78A, conductor 666 is electrically coupled to conduit 668 through contactors 702. In certain embodiments, liner 704 is located on the inside of conduit 668 to promote electrical contact between the conduit and contactors 702.

In some embodiments, a fiber optic system including an optical sensor is used to continuously monitor parameters (for example, temperature, pressure, and/or strain) along a portion and/or the entire length of a heater assembly. In certain embodiments, an optical sensor is used to monitor composition of gas at one or more locations along the optical sensor. The optical sensor may include, but is not limited to, a high temperature rated optical fiber (for example, a single mode fiber or a multimode fiber) or fiber optic cable. A Sensornet DTS system (Sensornet; London, U.K.) includes an optical fiber that is used to monitor temperature along a length of a heater assembly. A Sensornet DTS system includes an optical fiber that is used to monitor temperature and strain (and/or pressure) at the same time along a length of a heater assembly.

In some embodiments, an optical sensor used to monitor temperature, strain, and/or pressure is protected by positioning, at least partially, the optical sensor in a protective sleeve (such as an enclosed tube) resistant to conditions in a downhole environment. In certain embodiments, the protective sleeve is a small stainless steel tube. In some embodiments, an open-ended sleeve is used to allow determination of gas composition at the surface and/or at the terminal end of an oxidizer assembly. The optical sensor may be pre-installed in a protective sleeve and coiled on a reel. The sleeve may be uncoiled from the reel and coupled to a heater assembly. In some embodiments, an optical sensor in a protective sleeve is lowered into a section of the formation with a heater assembly.

In certain embodiments, the sleeve is placed down a hollow conductor of a conductor-in-conduit heater. In some embodiments, the fiber optic cable is a high temperature rated fiber optic cable. FIG. 79 depicts an embodiment of sleeve 708 in a conductor-in-conduit heater. Conductor 666 may be a hollow conductor. Sleeve 708 may be placed inside conductor 666. Sleeve 708 may be moved to a position inside conductor 666 by providing a pressurized fluid (for example, a pressurized inert gas) into the conductor to move the sleeve along a length of the conductor. Sleeve 708 may have a plug 710 located at an end of the sleeve so that the sleeve is moved by the pressurized fluid. Plug 710 may be of a diameter slightly smaller than an inside diameter of conductor 666 so that the plug is allowed to move along the inside of the conductor. In some embodiments, plug 710 has small openings to allow some fluid to flow past the plug. Conductor 666 may have an open end or a closed end with openings at the end to allow pressure release from the end of the conductor so that sleeve 708 and plug 710 can move along the inside of the conductor. Sleeve 708 may be placed inside any hollow conduit or conductor in any type of heater.

Using a pressurized fluid to position sleeve 708 inside conductor 666 allows for selected positioning of the sleeve. The pressure of the fluid used to move sleeve 708 inside conductor 666 may be set to move the sleeve a selected distance in the conductor so that the sleeve is positioned as desired. In certain embodiments, sleeve 708 may be removable from conductor 666 so that the sleeve can be repaired and/or replaced.

Temperatures monitored by the fiber optic cable may depend upon positioning of sleeve 708. In certain embodiments, sleeve 708 is positioned in an annulus between the conduit and the conductor or between the conduit and an opening in the formation. In certain embodiments, sleeve 708 with enclosed fiber optic cable is wrapped spirally to enhance resolution.

In certain embodiments, centralizers (such as centralizers 672 depicted in FIGS. 75 and 76) are made of silicon nitride. In some embodiments, silicon nitride is gas pressure sintered reaction bonded silicon nitride. Gas pressure sintered reaction bonded silicon nitride can be made by sintering the silicon nitride at 1800° C. in a 10.3 MPa nitrogen atmosphere to inhibit degradation of the silicon nitride during sintering. One example of a gas pressure sintered reaction bonded silicon nitride is obtained from Ceradyne, Inc. (Costa Mesa, Calif., U.S.A.) as Ceralloy® 147-31N.

Gas pressure sintered reaction bonded silicon nitride may be ground to a fine finish. The fine finish (which gives a very low surface porosity of the silicon nitride) allows the silicon nitride to slide easily along metal surfaces without picking up metal particles from the surfaces. Gas pressure sintered reaction bonded silicon nitride is a very dense material with high tensile strength, high flexural mechanical strength, and high thermal impact stress characteristics. Gas pressure sintered reaction bonded silicon nitride is an excellent high temperature electrical insulator. Gas pressure sintered reaction bonded silicon nitride has about the same leakage current at 900° C. as alumina ($Al_2O_3$) at 760° C. Gas pressure sintered reaction bonded silicon nitride has a thermal conductivity of 25 watts per meter·K. The relatively high thermal conductivity promotes heat transfer away from the center conductor of a conductor-in-conduit heater.

Other types of silicon nitride such as, but not limited to, reaction-bonded silicon nitride or hot isostatically pressed silicon nitride may be used. Hot isostatic pressing includes sintering granular silicon nitride and additives at 100-200 MPa in nitrogen gas. Some silicon nitrides are made by sintering silicon nitride with yttrium oxide or cerium oxide to lower the sintering temperature so that the silicon nitride does not degrade (for example, by releasing nitrogen) during sintering. However, adding other material to the silicon nitride may increase the leakage current of the silicon nitride at elevated temperatures compared to purer forms of silicon nitride.

FIG. 80 depicts an embodiment of a conductor-in-conduit temperature limited heater. Conductor 666 is coupled to ferromagnetic conductor 654 (for example, clad, coextruded, press fit, drawn inside). In some embodiments, ferromagnetic conductor 654 is coextruded over conductor 666. Ferromagnetic conductor 654 is coupled to the outside of conductor 666 so that current propagates only through the skin depth of the ferromagnetic conductor at room temperature. Ferromagnetic conductor 654 provides mechanical support for conductor 666 at elevated temperatures. Ferromagnetic conductor 654 is, for example, iron, iron alloy, or any other ferromagnetic material. In an embodiment, conductor 666 is copper and ferromagnetic conductor 654 is 446 stainless steel.

Conductor 666 and ferromagnetic conductor 654 are electrically coupled to conduit 668 with sliding connector 678. Conduit 668 is a non-ferromagnetic material such as, but not limited to, 347H stainless steel. In one embodiment, conduit 668 is a 1½" Schedule 80 347H stainless steel pipe. In another embodiment, conduit 668 is a Schedule XXH 347H stainless steel pipe. One or more centralizers 672 maintain the gap between conduit 668 and ferromagnetic conductor 654. In an embodiment, centralizer 672 is made of gas pressure sintered reaction bonded silicon nitride. Centralizer 672 may be held in position on ferromagnetic conductor 654 by one or more weld tabs located on the ferromagnetic conductor.

In certain embodiments, the composite electrical conductor may be used as a conductor in an insulated conductor heater. FIG. 81A and FIG. 81B depict an embodiment of the insulated conductor heater. Insulated conductor 712 includes core 656 and inner conductor 626. Core 656 and inner conductor 626 are a composite electrical conductor. Core 656 and inner conductor 626 are located within insulator 628. Core 656, inner conductor 626, and insulator 628 are located inside outer conductor 630. Insulator 628 is silicon nitride, boron nitride, magnesium oxide, or another suitable electrical insulator. Outer conductor 630 is copper, steel, or any other electrical conductor.

In certain embodiments, insulator 628 is a powdered insulator. In some embodiments, insulator 628 is an insulator with a preformed shape (for example, preformed half-shells). Insulated conductor 712 may be formed using several techniques known in the art. Examples of techniques for forming insulated conductors include a "weld-fill-draw" method or a "fill-draw" method. Insulated conductors made using these techniques may be made by, for example, Tyco International, Inc. (Princeton, N.J., U.S.A.) or Watlow Electric Manufacturing Co. (St. Louis, Mo., U.S.A.).

In some embodiments, jacket 636 is located outside outer conductor 630, as shown in FIG. 82A and FIG. 82B. In some embodiments, jacket 636 is 304 stainless steel and outer conductor 630 is copper. Jacket 636 provides corrosion resistance for the insulated conductor heater. In some embodiments, jacket 636 and outer conductor 630 are preformed strips that are drawn over insulator 628 to form insulated conductor 712.

In certain embodiments, insulated conductor 712 is located in a conduit that provides protection (for example, corrosion protection, degradation protection, and mechanical deformation protection) for the insulated conductor. In FIG. 83, insulated conductor 712 is located inside conduit 668 with gap 714 separating the insulated conductor from the conduit.

For a temperature limited heater in which the ferromagnetic conductor provides a majority of the resistive heat output below the Curie temperature, a majority of the current flows through material with highly non-linear functions of magnetic field (H) versus magnetic induction (B). These non-linear functions may cause strong inductive effects and distortion that lead to decreased power factor in the temperature limited heater at temperatures below the Curie temperature. These effects may render the electrical power supply to the temperature limited heater difficult to control and may result in additional current flow through surface and/or overburden power supply conductors. Expensive and/or difficult to implement control systems such as variable capacitors or modulated power supplies may be used to attempt to compensate for these effects and to control temperature limited heaters where the majority of the resistive heat output is provided by current flow through the ferromagnetic material.

In certain temperature limited heater embodiments, the ferromagnetic conductor confines a majority of the flow of electrical current to an electrical conductor coupled to the ferromagnetic conductor when the temperature limited heater is below or near the Curie temperature of the ferromagnetic conductor. The electrical conductor may be a sheath, jacket, support member, corrosion resistant member, or other electrically resistive member. In some embodiments, the ferromagnetic conductor confines a majority of the flow of electrical current to the electrical conductor positioned between an outermost layer and the ferromagnetic conductor. The ferromagnetic conductor is located in the cross section of the temperature limited heater such that the magnetic properties of the ferromagnetic conductor at or below the Curie temperature of the ferromagnetic conductor confine the majority of the flow of electrical current to the electrical conductor. The majority of the flow of electrical current is confined to the electrical conductor due to the skin effect of the ferromagnetic conductor. Thus, the majority of the current is flowing through material with substantially linear resistive properties throughout most of the operating range of the heater.

In certain embodiments, the ferromagnetic conductor and the electrical conductor are located in the cross section of the temperature limited heater so that the skin effect of the ferromagnetic material limits the penetration depth of electrical current in the electrical conductor and the ferromagnetic conductor at temperatures below the Curie temperature of the ferromagnetic conductor. Thus, the electrical conductor provides a majority of the electrically resistive heat output of the temperature limited heater at temperatures up to a temperature at or near the Curie temperature of the ferromagnetic conductor. In certain embodiments, the dimensions of the electrical conductor may be chosen to provide desired heat output characteristics.

Because the majority of the current flows through the electrical conductor below the Curie temperature, the temperature limited heater has a resistance versus temperature profile that at least partially reflects the resistance versus temperature profile of the material in the electrical conductor. Thus, the resistance versus temperature profile of the temperature limited heater is substantially linear below the Curie temperature of the ferromagnetic conductor if the material in the electrical conductor has a substantially linear resistance versus temperature profile. For example, the temperature limited heater in which the majority of the current flows in the electrical conductor below the Curie temperature may have a resistance versus temperature profile similar to the profile shown in FIG. 182. The resistance of the temperature limited heater has little or no dependence on the current flowing through the heater until the temperature nears the Curie temperature. The majority of the current flows in the electrical conductor rather than the ferromagnetic conductor below the Curie temperature.

Resistance versus temperature profiles for temperature limited heaters in which the majority of the current flows in the electrical conductor also tend to exhibit sharper reductions in resistance near or at the Curie temperature of the ferromagnetic conductor. For example, the reduction in resistance shown in FIG. 182 is sharper than the reduction in resistance shown in FIG. 166. The sharper reductions in resistance near or at the Curie temperature are easier to control than more gradual resistance reductions near the Curie temperature.

In certain embodiments, the material and/or the dimensions of the material in the electrical conductor are selected so that the temperature limited heater has a desired resistance versus temperature profile below the Curie temperature of the ferromagnetic conductor.

Temperature limited heaters in which the majority of the current flows in the electrical conductor rather than the ferromagnetic conductor below the Curie temperature are easier to predict and/or control. Behavior of temperature limited heaters in which the majority of the current flows in the electrical conductor rather than the ferromagnetic conductor below the Curie temperature may be predicted by, for example, its resistance versus temperature profile and/or its power factor versus temperature profile. Resistance versus temperature profiles and/or power factor versus temperature profiles may be assessed or predicted by, for example, experimental measurements that assess the behavior of the temperature limited heater, analytical equations that assess or predict the behavior of the temperature limited heater, and/or simulations that assess or predict the behavior of the temperature limited heater.

In certain embodiments, assessed or predicted behavior of the temperature limited heater is used to control the temperature limited heater. The temperature limited heater may be controlled based on measurements (assessments) of the resistance and/or the power factor during operation of the heater. In some embodiments, the power, or current, supplied to the temperature limited heater is controlled based on assessment of the resistance and/or the power factor of the heater during operation of the heater and the comparison of this assessment versus the predicted behavior of the heater. In certain embodiments, the temperature limited heater is controlled without measurement of the temperature of the heater or a temperature near the heater. Controlling the temperature limited heater without temperature measurement eliminates operating costs associated with downhole temperature measurement. Controlling the temperature limited heater based on assessment of the resistance and/or the power factor of the heater also reduces the time for making adjustments in the power or current supplied to the heater compared to controlling the heater based on measured temperature.

As the temperature of the temperature limited heater approaches or exceeds the Curie temperature of the ferromagnetic conductor, reduction in the ferromagnetic properties of the ferromagnetic conductor allows electrical current to flow through a greater portion of the electrically conducting cross section of the temperature limited heater. Thus, the electrical resistance of the temperature limited heater is reduced and the temperature limited heater automatically provides reduced heat output at or near the Curie temperature of the ferromagnetic conductor. In certain embodiments, a highly electrically conductive member is coupled to the ferromagnetic conductor and the electrical conductor to reduce the electrical resistance of the temperature limited heater at or above the Curie temperature of the ferromagnetic conductor. The highly electrically conductive member may be an inner conductor, a core, or another conductive member of copper, aluminum, nickel, or alloys thereof.

The ferromagnetic conductor that confines the majority of the flow of electrical current to the electrical conductor at temperatures below the Curie temperature may have a relatively small cross section compared to the ferromagnetic conductor in temperature limited heaters that use the ferromagnetic conductor to provide the majority of resistive heat output up to or near the Curie temperature. A temperature limited heater that uses the electrical conductor to provide a majority of the resistive heat output below the Curie temperature has low magnetic inductance at temperatures below the Curie temperature because less current is flowing through the ferromagnetic conductor as compared to the temperature limited heater where the majority of the resistive heat output below the Curie temperature is provided by the ferromagnetic material. Magnetic field (H) at radius (r) of the ferromagnetic conductor is proportional to the current (I) flowing through the ferromagnetic conductor and the core divided by the radius, or:

$$H \propto I/r. \tag{4}$$

Since only a portion of the current flows through the ferromagnetic conductor for a temperature limited heater that uses the outer conductor to provide a majority of the resistive heat output below the Curie temperature, the magnetic field of the temperature limited heater may be significantly smaller than the magnetic field of the temperature limited heater where the majority of the current flows through the ferromagnetic material. The relative magnetic permeability ($\mu$) may be large for small magnetic fields.

The skin depth ($\delta$) of the ferromagnetic conductor is inversely proportional to the square root of the relative magnetic permeability ($\mu$):

$$\delta \propto (1/\mu)^{1/2}. \tag{5}$$

Increasing the relative magnetic permeability decreases the skin depth of the ferromagnetic conductor. However, because only a portion of the current flows through the ferromagnetic conductor for temperatures below the Curie temperature, the radius (or thickness) of the ferromagnetic conductor may be decreased for ferromagnetic materials with large relative magnetic permeabilities to compensate for the decreased skin depth while still allowing the skin effect to limit the penetration depth of the electrical current to the electrical conductor at temperatures below the Curie temperature of the ferromagnetic conductor. The radius (thickness) of the ferromagnetic conductor may be between 0.3 mm and 8 mm, between 0.3 mm and 2 mm, or between 2 mm and 4 mm depending on the relative magnetic permeability of the ferromagnetic conductor. Decreasing the thickness of the ferromagnetic conductor decreases costs of manufacturing the temperature limited heater, as the cost of ferromagnetic material tends to be a significant portion of the cost of the temperature limited heater. Increasing the relative magnetic permeability of the ferromagnetic conductor provides a higher turndown ratio and a sharper decrease in electrical resistance for the temperature limited heater at or near the Curie temperature of the ferromagnetic conductor.

Ferromagnetic materials (such as purified iron or iron-cobalt alloys) with high relative magnetic permeabilities (for example, at least 200, at least 1000, at least $1 \times 10^4$, or at least $1 \times 10^5$) and/or high Curie temperatures (for example, at least 600° C., at least 700° C., or at least 800° C.) tend to have less corrosion resistance and/or less mechanical strength at high temperatures. The electrical conductor may provide corrosion resistance and/or high mechanical strength at high temperatures for the temperature limited heater. Thus, the ferromagnetic conductor may be chosen primarily for its ferromagnetic properties.

Confining the majority of the flow of electrical current to the electrical conductor below the Curie temperature of the ferromagnetic conductor reduces variations in the power factor. Because only a portion of the electrical current flows through the ferromagnetic conductor below the Curie temperature, the non-linear ferromagnetic properties of the ferromagnetic conductor have little or no effect on the power factor of the temperature limited heater, except at or near the Curie temperature. Even at or near the Curie temperature, the effect on the power factor is reduced compared to temperature limited heaters in which the ferromagnetic conductor provides a majority of the resistive heat output below the Curie temperature. Thus, there is less or no need for external compensation (for example, variable capacitors or waveform modification) to adjust for changes in the inductive load of the temperature limited heater to maintain a relatively high power factor.

In certain embodiments, the temperature limited heater, which confines the majority of the flow of electrical current to the electrical conductor below the Curie temperature of the ferromagnetic conductor, maintains the power factor above 0.85, above 0.9, or above 0.95 during use of the heater. Any reduction in the power factor occurs only in sections of the temperature limited heater at temperatures near the Curie temperature. Most sections of the temperature limited heater are typically not at or near the Curie temperature during use. These sections have a high power factor that approaches 1.0. The power factor for the entire temperature limited heater is maintained above 0.85, above 0.9, or above 0.95 during use of the heater even if some sections of the heater have power factors below 0.85.

Maintaining high power factors also allows for less expensive power supplies and/or control devices such as solid state power supplies or SCRs (silicon controlled rectifiers). These devices may fail to operate properly if the power factor varies by too large an amount because of inductive loads. With the power factors maintained at the higher values; however, these devices may be used to provide power to the temperature limited heater. Solid state power supplies also have the advantage of allowing fine tuning and controlled adjustment of the power supplied to the temperature limited heater.

In some embodiments, transformers are used to provide power to the temperature limited heater. Multiple voltage taps may be made into the transformer to provide power to the temperature limited heater. Multiple voltage taps allows the current supplied to switch back and forth between the multiple voltages. This maintains the current within a range bound by the multiple voltage taps.

The highly electrically conductive member, or inner conductor, increases the turndown ratio of the temperature limited heater. In certain embodiments, thickness of the highly electrically conductive member is increased to increase the turndown ratio of the temperature limited heater. In some embodiments, the thickness of the electrical conductor is reduced to increase the turndown ratio of the temperature limited heater. In certain embodiments, the turndown ratio of the temperature limited heater is between 1.1 and 10, between 2 and 8, or between 3 and 6 (for example, the turndown ratio is at least 1.1, at least 2, or at least 3).

Figure 84:
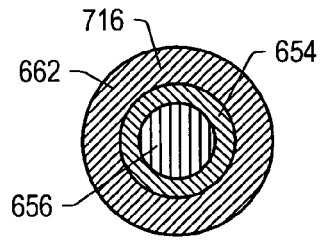
FIG. 84 depicts an embodiment of a temperature limited heater in which the support member provides a majority of the heat output below the Curie temperature of the ferromagnetic conductor.

FIG. 84 depicts an embodiment of a temperature limited heater in which the support member provides a majority of the heat output below the Curie temperature of the ferromagnetic conductor. Core 656 is an inner conductor of the temperature limited heater. In certain embodiments, core 656 is a highly electrically conductive material such as copper or aluminum. In some embodiments, core 656 is a copper alloy that provides mechanical strength and good electrically conductivity such as a dispersion strengthened copper. In one embodiment, core 656 is Glidcop® (SCM Metal Products, Inc., Research Triangle Park, N.C., U.S.A.). Ferromagnetic conductor 654 is a thin layer of ferromagnetic material between electrical conductor 716 and core 656. In certain embodiments, electrical conductor 716 is also support member 662. In certain embodiments, ferromagnetic conductor 654 is iron or an iron alloy. In some embodiments, ferromagnetic conductor 654 includes ferromagnetic material with a high relative magnetic permeability. For example, ferromagnetic conductor 654 may be purified iron such as Armco ingot iron (AK Steel Ltd., United Kingdom). Iron with some impurities typically has a relative magnetic permeability on the order of 400. Purifying the iron by annealing the iron in hydrogen gas ($H_2$) at 1450° C. increases the relative magnetic permeability of the iron. Increasing the relative magnetic permeability of ferromagnetic conductor 654 allows the thickness of the ferromagnetic conductor to be reduced. For example, the thickness of unpurified iron may be approximately 4.5 mm while the thickness of the purified iron is approximately 0.76 mm.

In certain embodiments, electrical conductor 716 provides support for ferromagnetic conductor 654 and the temperature limited heater. Electrical conductor 716 may be made of a material that provides good mechanical strength at temperatures near or above the Curie temperature of ferromagnetic conductor 654. In certain embodiments, electrical conductor 716 is a corrosion resistant member. Electrical conductor 716 (support member 662) may provide support for ferromagnetic conductor 654 and corrosion resistance. Electrical conductor 716 is made from a material that provides desired electrically resistive heat output at temperatures up to and/or above the Curie temperature of ferromagnetic conductor 654.

In an embodiment, electrical conductor 716 is 347H stainless steel. In some embodiments, electrical conductor 716 is another electrically conductive, good mechanical strength, corrosion resistant material. For example, electrical conductor 716 may be 304H, 316H, 347HH, NF709, Incoloy® 800H alloy (Inco Alloys International, Huntington, West Va., U.S.A.), Haynes® HR120® alloy, or Inconel® 617 alloy.

In some embodiments, electrical conductor 716 (support member 662) includes different alloys in different portions of the temperature limited heater. For example, a lower portion of electrical conductor 716 (support member 662) is 347H stainless steel and an upper portion of the electrical conductor (support member) is NF709. In certain embodiments, different alloys are used in different portions of the electrical conductor (support member) to increase the mechanical strength of the electrical conductor (support member) while maintaining desired heating properties for the temperature limited heater.

In some embodiments, ferromagnetic conductor 654 includes different ferromagnetic conductors in different portions of the temperature limited heater. Different ferromagnetic conductors may be used in different portions of the temperature limited heater to vary the Curie temperature and, thus, the maximum operating temperature in the different portions. In some embodiments, the Curie temperature in an upper portion of the temperature limited heater is lower than the Curie temperature in a lower portion of the heater. The lower Curie temperature in the upper portion increases the creep-rupture strength lifetime in the upper portion of the heater.

In the embodiment depicted in FIG. 84, ferromagnetic conductor 654, electrical conductor 716, and core 656 are dimensioned so that the skin depth of the ferromagnetic conductor limits the penetration depth of the majority of the flow of electrical current to the support member when the temperature is below the Curie temperature of the ferromagnetic conductor. Thus, electrical conductor 716 provides a majority of the electrically resistive heat output of the temperature limited heater at temperatures up to a temperature at or near the Curie temperature of ferromagnetic conductor 654. In certain embodiments, the temperature limited heater depicted in FIG. 84 is smaller (for example, an outside diameter of 3 cm, 2.9 cm, 2.5 cm, or less) than other temperature limited heaters that do not use electrical conductor 716 to provide the majority of electrically resistive heat output. The temperature limited heater depicted in FIG. 84 may be smaller because ferromagnetic conductor 654 is thin as compared to the size of the ferromagnetic conductor needed for a temperature limited heater in which the majority of the resistive heat output is provided by the ferromagnetic conductor.

Figure 85:
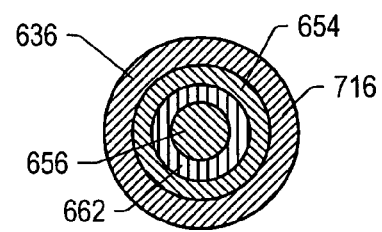
FIGS. 85 and 86 depict embodiments of temperature limited heaters in which the jacket provides a majority of the heat output below the Curie temperature of the ferromagnetic conductor.
Figure 86:
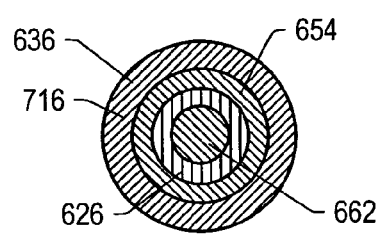

In some embodiments, the support member and the corrosion resistant member are different members in the temperature limited heater. FIGS. 85 and 86 depict embodiments of temperature limited heaters in which the jacket provides a majority of the heat output below the Curie temperature of the ferromagnetic conductor. In these embodiments, electrical conductor 716 is jacket 636. Electrical conductor 716, ferromagnetic conductor 654, support member 662, and core 656 (in FIG. 85) or inner conductor 626 (in FIG. 86) are dimensioned so that the skin depth of the ferromagnetic conductor limits the penetration depth of the majority of the flow of electrical current to the thickness of the jacket. In certain embodiments, electrical conductor 716 is a material that is corrosion resistant and provides electrically resistive heat output below the Curie temperature of ferromagnetic conductor 654. For example, electrical conductor 716 is 825 stainless steel or 347H stainless steel. In some embodiments, electrical conductor 716 has a small thickness (for example, on the order of 0.5 mm).

In FIG. 85, core 656 is highly electrically conductive material such as copper or aluminum. Support member 662 is 347H stainless steel or another material with good mechanical strength at or near the Curie temperature of ferromagnetic conductor 654.

In FIG. 86, support member 662 is the core of the temperature limited heater and is 347H stainless steel or another material with good mechanical strength at or near the Curie temperature of ferromagnetic conductor 654. Inner conductor 626 is highly electrically conductive material such as copper or aluminum.

In certain embodiments, middle conductor 658 in the temperature limited heater with triaxial conductors, depicted in FIG. 67A and FIG. 67B, includes an electrical conductor in addition to the ferromagnetic material. The electrical conductor may be on the outside of middle conductor 658. The electrical conductor and the ferromagnetic material are dimensioned so that the skin depth of the ferromagnetic material limits the penetration depth of the majority of the flow of electrical current to the electrical conductor when the temperature is below the Curie temperature of the ferromagnetic material. The electrical conductor provides a majority of the electrically resistive heat output of middle conductor 658 (and the triaxial temperature limited heater) at temperatures up to a temperature at or near the Curie temperature of ferromagnetic conductor. The electrical conductor is made from a material that provides desired electrically resistive heat output at temperatures up to and/or above the Curie temperature of ferromagnetic member. For example, the electrical conductor is 347H stainless steel, 304H, 316H, 347HH, NF709, Incoloy® 800H alloy, Haynes® HR120® alloy, or Inconel® 617 alloy.

Figure 87:
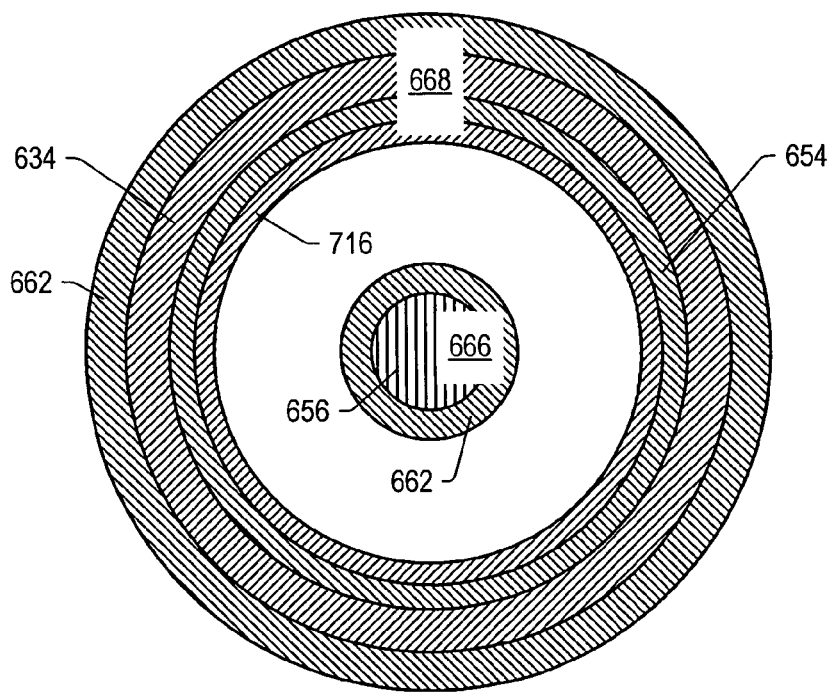
FIG. 87 depicts a high temperature embodiment of a temperature limited heater.

In certain embodiments, the materials and design of the temperature limited heater are chosen to allow use of the heater at high temperatures (for example, above 850° C.). FIG. 87 depicts a high temperature embodiment of the temperature limited heater. The heater depicted in FIG. 87 operates as a conductor-in-conduit heater with the majority of heat being generated in conduit 668. The conductor-in-conduit heater may provide a higher heat output because the majority of heat is generated in conduit 668 rather than conductor 666. Having the heat generated in conduit 668 reduces heat losses associated with transferring heat between the conduit and conductor 666.

Core 656 and conductive layer 634 are copper. In some embodiments, core 656 and conductive layer 634 are nickel if the operating temperatures is to be near or above the melting point of copper. Support members 662 are electrically conductive materials with good mechanical strength at high temperatures. Materials for support members 662 that withstand at least a maximum temperature of about 870° C. may be, but are not limited to, MO-RE® alloys (Duraloy Technologies, Inc. (Scottdale, Pa., U.S.A.)), CF8C+ (Metaltek Intl. (Waukesha, Wis., U.S.A.)), or Inconel® 617 alloy. Materials for support members 662 that withstand at least a maximum temperature of about 980° C. include, but are not limited to, Incoloy® Alloy MA 956. Support member 662 in conduit 668 provides mechanical support for the conduit. Support member 662 in conductor 666 provides mechanical support for core 656.

Electrical conductor 716 is a thin corrosion resistant material. In certain embodiments, electrical conductor 716 is 347H, 617, 625, or 800H stainless steel. Ferromagnetic conductor 654 is a high Curie temperature ferromagnetic material such as iron-cobalt alloy (for example, a 15% by weight cobalt, iron-cobalt alloy).

In certain embodiments, electrical conductor 716 provides the majority of heat output of the temperature limited heater at temperatures up to a temperature at or near the Curie temperature of ferromagnetic conductor 654. Conductive layer 634 increases the turndown ratio of the temperature limited heater.

Figure 88:
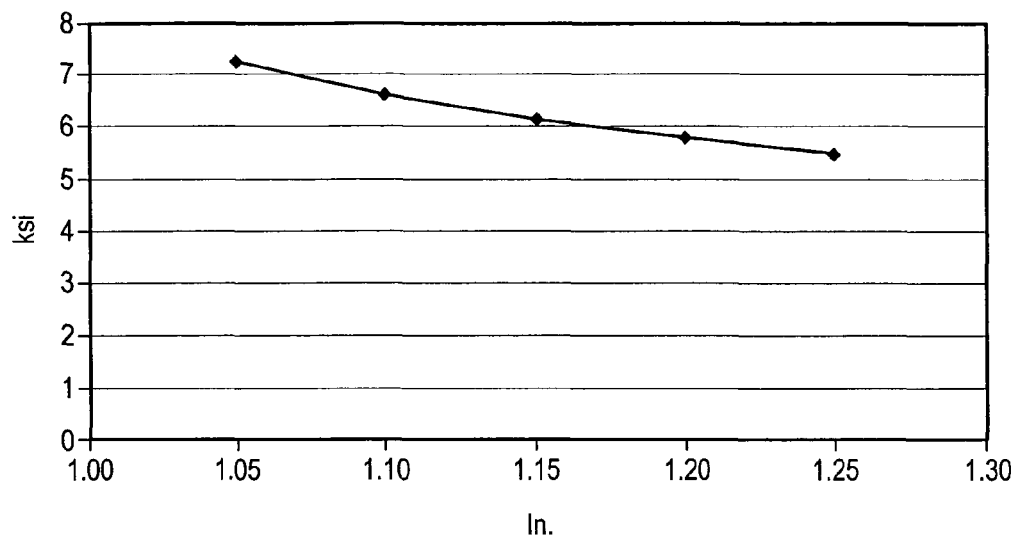
FIG. 88 depicts hanging stress versus outside diameter for the temperature limited heater shown in FIG. 84 with 347H as the support member.

For long vertical temperature limited heaters (for example, heaters at least 300 m, at least 500 m, or at least 1 km in length), the hanging stress becomes important in the selection of materials for the temperature limited heater. Without the proper selection of material, the support member may not have sufficient mechanical strength (for example, creep-rupture strength) to support the weight of the temperature limited heater at the operating temperatures of the heater. FIG. 88 depicts hanging stress (ksi (kilopounds per square inch)) versus outside diameter (in.) for the temperature limited heater shown in FIG. 84 with 347H as the support member. The hanging stress was assessed with the support member outside a 0.5" copper core and a 0.75" outside diameter carbon steel ferromagnetic conductor. This assessment assumes the support member bears the entire load of the heater and that the heater length is 1000 ft. (about 305 m). As shown in FIG. 88, increasing the thickness of the support member decreases the hanging stress on the support member. Decreasing the hanging stress on the support member allows the temperature limited heater to operate at higher temperatures.

In certain embodiments, materials for the support member are varied to increase the maximum allowable hanging stress at operating temperatures of the temperature limited heater and, thus, increase the maximum operating temperature of the temperature limited heater. Altering the materials of the support member affects the heat output of the temperature limited heater below the Curie temperature because changing the materials changes the resistance versus temperature profile of the support member. In certain embodiments, the support member is made of more than one material along the length of the heater so that the temperature limited heater maintains desired operating properties (for example, resistance versus temperature profile below the Curie temperature) as much as possible while providing sufficient mechanical properties to support the heater.

Figure 89:
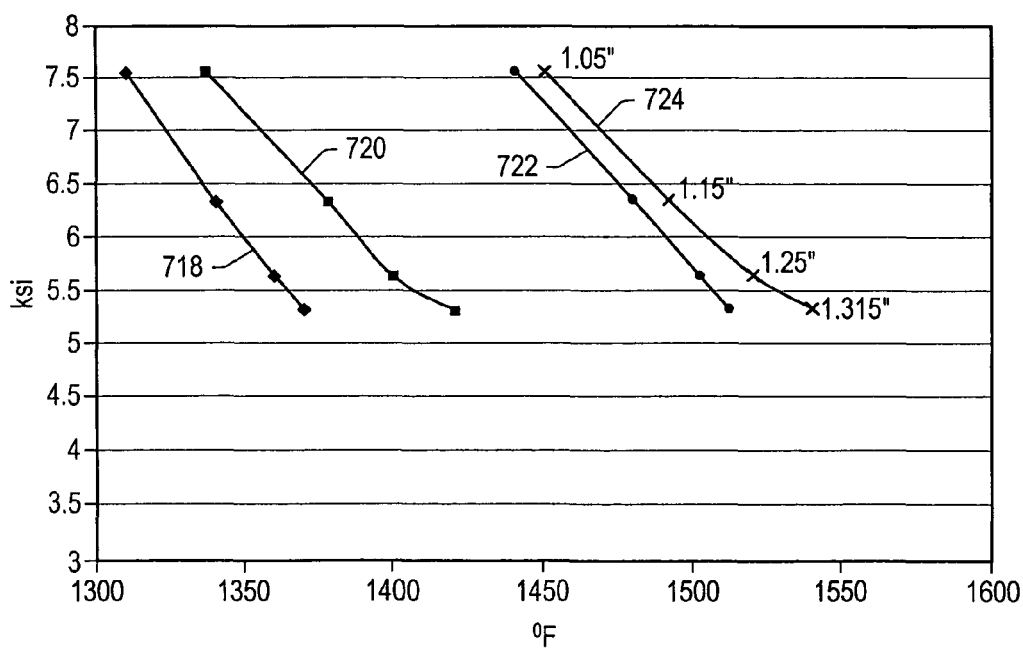
FIG. 89 depicts hanging stress versus temperature for several materials and varying outside diameters of the temperature limited heater.

FIG. 89 depicts hanging stress (ksi) versus temperature (° F.) for several materials and varying outside diameters for the temperature limited heaters. Curve 718 is for 347H stainless steel. Curve 720 is for Incoloy® alloy 800H. Curve 722 is for Haynes® HR120® alloy. Curve 724 is for NF709. Each of the curves includes four points that represent various outside diameters of the support member. The point with the highest stress for each curve corresponds to outside diameter of 1.05". The point with the second highest stress for each curve corresponds to outside diameter of 1.15". The point with the second lowest stress for each curve corresponds to outside diameter of 1.25". The point with the lowest stress for each curve corresponds to outside diameter of 1.315". As shown in FIG. 89, increasing the strength and/or outside diameter of the material and the support member increases the maximum operating temperature of the temperature limited heater.

Figure 90:
FIGS. 90, 91, 92, and 93 depict examples of embodiments for temperature limited heaters that vary the materials and/or dimensions along the length of the heaters to provide desired operating properties.
Figure 91:
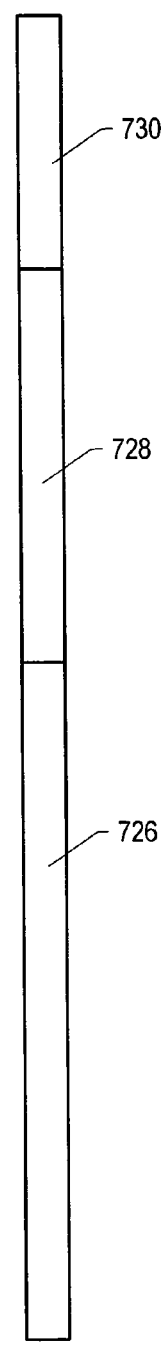
Figure 92:
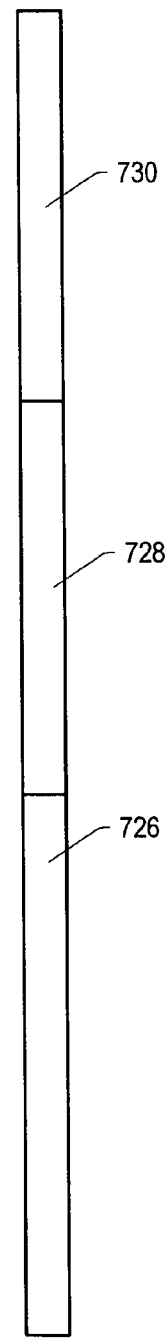

FIGS. 90, 91, 92, and 93 depict examples of embodiments for temperature limited heaters able to provide desired heat output and mechanical strength for operating temperatures up to about 770° C. for 30,000 hrs. creep-rupture lifetime. The depicted temperature limited heaters have lengths of 1000 ft, copper cores of 0.5" diameter, and iron ferromagnetic conductors with outside diameters of 0.765". In FIG. 90, the support member in heater portion 726 is 347H stainless steel. The support member in heater portion 728 is Incoloy® alloy 800H. Portion 726 has a length of 750 ft. and portion 728 has a length of 250 ft. The outside diameter of the support member is 1.315". In FIG. 91, the support member in heater portion 726 is 347H stainless steel. The support member in heater portion 728 is Incoloy® alloy 800H. The support member in heater portion 730 is Haynes® HR120® alloy. Portion 726 has a length of 650 ft., portion 728 has a length of 300 ft., and portion 730 has a length of 50 ft. The outside diameter of the support member is 1.15". In FIG. 92, the support member in heater portion 726 is 347H stainless steel. The support member in heater portion 728 is Incoloy® alloy 800H. The support member in heater portion 730 is Haynes® HR120® alloy. Portion 726 has a length of 550 ft., portion 728 has a length of 250 ft., and portion 730 has a length of 200 ft. The outside diameter of the support member is 1.05".

Figure 93:
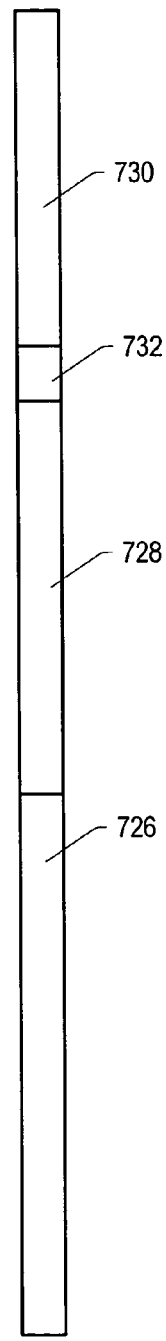

In some embodiments, a transition section is used between sections of the heater. For example, if one or more portions of the heater have varying Curie temperatures, a transition section may be used between portions to provide strength that compensates for the differences in temperatures in the portions. FIG. 93 depicts another example of an embodiment of a temperature limited heater able to provide desired heat output and mechanical strength. The support member in heater portion 726 is 347H stainless steel. The support member in heater portion 728 is NF709. The support member in heater portion 730 is 347H. Portion 726 has a length of 550 ft. and a Curie temperature of 843° C., portion 728 has a length of 250 ft. and a Curie temperature of 843° C., and portion 730 has a length of 180 ft. and a Curie temperature of 770° C. Transition section 732 has a length of 20 ft., a Curie temperature of 770° C., and the support member is NF709.

The materials of the support member along the length of the temperature limited heater may be varied to achieve a variety of desired operating properties. The choice of the materials of the temperature limited heater is adjusted depending on a desired use of the temperature limited heater. TABLE 1 lists examples of materials that may be used for the support member. The table provides the hanging stresses (a) of the support members and the maximum operating temperatures of the temperature limited heaters for several different outside diameters (OD) of the support member. The core diameter and the outside diameter of the iron ferromagnetic conductor in each case are 0.5" and 0.765", respectively.

TABLE 1

| Material | OD = 1.05" | | OD = 1.15" | | OD = 1.25" | | OD = 1.315" | |
|---|---|---|---|---|---|---|---|---|
| | σ (ksi) | T (° F.) | σ (ksi) | T (° F.) | σ (ksi) | T (° F.) | σ (ksi) | T (° F.) |
| 347H stainless steel | 7.55 | 1310 | 6.33 | 1340 | 5.63 | 1360 | 5.31 | 1370 |
| Incoloy ® alloy 800H | 7.55 | 1337 | 6.33 | 1378 | 5.63 | 1400 | 5.31 | 1420 |
| Haynes ® HR120 ® alloy | 7.57 | 1450 | 6.36 | 1492 | 5.65 | 1520 | 5.34 | 1540 |
| HA230 | 7.91 | 1475 | 6.69 | 1510 | 5.99 | 1530 | 5.67 | 1540 |
| Haynes ® alloy 556 | 7.65 | 1458 | 6.43 | 1492 | 5.72 | 1512 | 5.41 | 1520 |
| NF709 | 7.57 | 1440 | 6.36 | 1480 | 5.65 | 1502 | 5.34 | 1512 |

Figure 95:
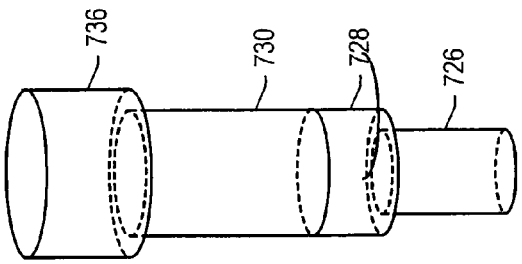
FIGS. 94 and 95 depict examples of embodiments for temperature limited heaters that vary the diameter and/or materials of the support member along the length of the heaters to provide desired operating properties and sufficient mechanical properties.
Figure 94:
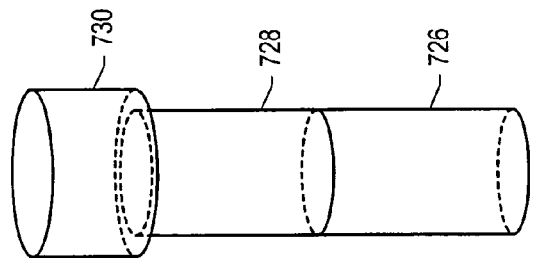

In certain embodiments, one or more portions of the temperature limited heater have varying outside diameters and/or materials to provide desired properties for the heater. FIGS. 94 and 95 depict examples of embodiments for temperature limited heaters that vary the diameter and/or materials of the support member along the length of the heaters to provide desired operating properties and sufficient mechanical properties (for example, creep-rupture strength properties) for operating temperatures up to about 834° C. for 30,000 hrs., heater lengths of 850 ft, a copper core diameter of 0.5", and an iron-cobalt (6% by weight cobalt) ferromagnetic conductor outside diameter of 0.75". In FIG. 94, portion 726 is 347H stainless steel with a length of 300 ft and an outside diameter of 1.15". Portion 728 is NF709 with a length of 400 ft and an outside diameter of 1.15". Portion 730 is NF709 with a length of 150 ft and an outside diameter of 1.25". In FIG. 95, portion 726 is 347H stainless steel with a length of 300 ft and an outside diameter of 1.15". Portion 728 is 347H stainless steel with a length of 100 ft and an outside diameter of 1.20". Portion 730 is NF709 with a length of 350 ft and an outside diameter of 1.20". Portion 736 is NF709 with a length of 100 ft and an outside diameter of 1.25".

In certain embodiments, one or more portions of the temperature limited heater have varying dimensions and/or varying materials to provide different power outputs along the length of the heater. More or less power output may be provided by varying the selected temperature (for example, the Curie temperature) of the temperature limited heater by using different ferromagnetic materials along its length and/or by varying the electrical resistance of the heater by using different dimensions in the heat generating member along the length of the heater. Different power outputs along the length of the temperature limited heater may be needed to compensate for different thermal properties in the formation adjacent to the heater. For example, an oil shale formation may have different water-filled porosities, dawsonite compositions, and/or nahcolite compositions at different depths in the formation. Portions of the formation with higher water-filled porosities, higher dawsonite compositions, and/or higher nahcolite compositions may need more power input than portions with lower water-filled porosities, lower dawsonite compositions, and/or lower nahcolite compositions to achieve a similar heating rate. Power output may be varied along the length of the heater so that the portions of the formation with different properties (such as water-filled porosities, dawsonite compositions, and/or nahcolite compositions) are heated at approximately the same heating rate.

In certain embodiments, portions of the temperature limited heater have different selected self-limiting temperatures (for example, Curie temperatures), materials, and/or dimensions to compensate for varying thermal properties of the formation along the length of the heater. For example, Curie temperatures, support member materials, and/or dimensions of the portions of the heaters depicted in FIGS. 90-95 may be varied to provide varying power outputs and/or operating temperatures along the length of the heater.

As one example, in an embodiment of the temperature limited heater depicted in FIG. 90, portion 728 may be used to heat portions of the formation that, on average, have higher water-filled porosities, dawsonite compositions, and/or nahcolite compositions than portions of the formation heated by portion 726. Portion 728 may provide less power output than portion 726 to compensate for the differing thermal properties of the different portions of the formation so that the entire formation is heated at an approximately constant heating rate. Portion 728 may require less power output because, for example, portion 728 is used to heat portions of the formation with low water-filled porosities and/or little or no dawsonite. In one embodiment, portion 728 has a Curie temperature of 770° C. (pure iron) and portion 726 has a Curie temperature of 843° C. (iron with added cobalt). Such an embodiment may provide more power output from portion 726 so that the temperature lag between the two portions is reduced. Adjusting the Curie temperature of portions of the heater adjusts the selected temperature at which the heater self-limits. In some embodiments, the dimensions of portion 728 are adjusted to further reduce the temperature lag so that the formation is heated at an approximately constant heating rate throughout the formation. Dimensions of the heater may be adjusted to adjust the heating rate of one or more portions of the heater. For example, the thickness of an outer conductor in portion 728 may be increased relative to the ferromagnetic member and/or the core of the heater so that the portion has a higher electrical resistance and the portion provides a higher power output below the Curie temperature of the portion.

Reducing the temperature lag between different portions of the formation may reduce the overall time needed to bring the formation to a desired temperature. Reducing the time needed to bring the formation to the desired temperature reduces heating costs and produces desirable production fluids more quickly.

Temperature limited heaters with varying Curie temperatures may also have varying support member materials to provide mechanical strength for the heater (for example, to compensate for hanging stress of the heater and/or provide sufficient creep-rupture strength properties). For example, in the embodiment of the temperature limited heater depicted in FIG. 93, portions 726 and 728 have a Curie temperature of 843° C. Portion 726 has a support member made of 347H stainless steel. Portion 728 has a support member made of NF709. Portion 730 has a Curie temperature of 770° C. and a support member made of 347H stainless steel. Transition section 732 has a Curie temperature of 770° C. and a support member made of NF709. Transition section 732 may be short in length compared to portions 726, 728, and 730. Transition section 732 may be placed between portions 728 and 730 to compensate for the temperature and material differences between the portions. For example, transition section 732 may be used to compensate for differences in creep properties between portions 728 and 730.

Such a substantially vertical temperature limited heater may have less expensive, lower strength materials in portion 730 because of the lower Curie temperature in this portion of the heater. For example, 347H stainless steel may be used for the support member because of the lower maximum operating temperature of portion 730 as compared to portion 728. Portion 728 may require the more expensive, higher strength material because of the higher operating temperature of portion 728 due to the higher Curie temperature in this portion.

In some embodiments, a relatively thin conductive layer is used to provide the majority of the electrically resistive heat output of the temperature limited heater at temperatures up to a temperature at or near the Curie temperature of the ferromagnetic conductor. Such a temperature limited heater may be used as the heating member in an insulated conductor heater. The heating member of the insulated conductor heater may be located inside a sheath with an insulation layer between the sheath and the heating member.

Figure 96B:
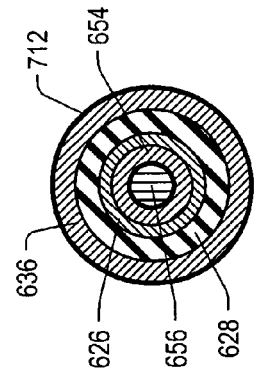
FIGS. 96A and 96B depict cross-sectional representations of an embodiment of a temperature limited heater component used in an insulated conductor heater.
Figure 96A:
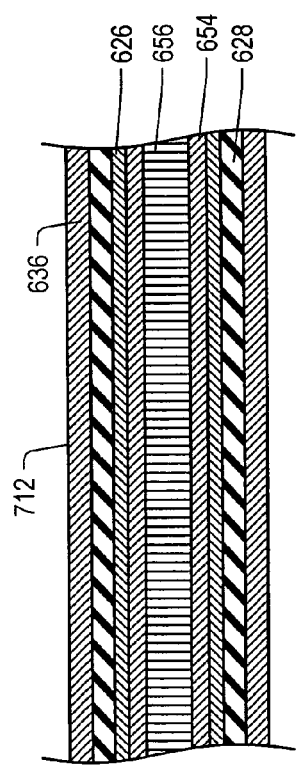

FIGS. 96A and 96B depict cross-sectional representations of an embodiment of the insulated conductor heater with the temperature limited heater as the heating member. Insulated conductor 712 includes core 656, ferromagnetic conductor 654, inner conductor 626, electrical insulator 628, and jacket 636. Core 656 is a copper core. Ferromagnetic conductor 654 is, for example, iron or an iron alloy.

Inner conductor 626 is a relatively thin conductive layer of non-ferromagnetic material with a higher electrical conductivity than ferromagnetic conductor 654. In certain embodiments, inner conductor 626 is copper. Inner conductor 626 may also be a copper alloy. Copper alloys typically have a flatter resistance versus temperature profile than pure copper. A flatter resistance versus temperature profile may provide less variation in the heat output as a function of temperature up to the Curie temperature. In some embodiments, inner conductor 626 is copper with 6% by weight nickel (for example, CuNi6 or LOHM™). In some embodiments, inner conductor 626 is CuNi10Fe1Mn alloy. Below the Curie temperature of ferromagnetic conductor 654, the magnetic properties of the ferromagnetic conductor confine the majority of the flow of electrical current to inner conductor 626. Thus, inner conductor 626 provides the majority of the resistive heat output of insulated conductor 712 below the Curie temperature.

In certain embodiments, inner conductor 626 is dimensioned, along with core 656 and ferromagnetic conductor 654, so that the inner conductor provides a desired amount of heat output and a desired turndown ratio. For example, inner conductor 626 may have a cross-sectional area that is around 2 or 3 times less than the cross-sectional area of core 656. Typically, inner conductor 626 has to have a relatively small cross-sectional area to provide a desired heat output if the inner conductor is copper or copper alloy. In an embodiment with copper inner conductor 626, core 656 has a diameter of 0.66 cm, ferromagnetic conductor 654 has an outside diameter of 0.91 cm, inner conductor 626 has an outside diameter of 1.03 cm, electrical insulator 628 has an outside diameter of 1.53 cm, and jacket 636 has an outside diameter of 1.79 cm. In an embodiment with a CuNi6 inner conductor 626, core 656 has a diameter of 0.66 cm, ferromagnetic conductor 654 has an outside diameter of 0.91 cm, inner conductor 626 has an outside diameter of 1.12 cm, electrical insulator 628 has an outside diameter of 1.63 cm, and jacket 636 has an outside diameter of 1.88 cm. Such insulated conductors are typically smaller and cheaper to manufacture than insulated conductors that do not use the thin inner conductor to provide the majority of heat output below the Curie temperature.

Electrical insulator 628 may be magnesium oxide, aluminum oxide, silicon dioxide, beryllium oxide, boron nitride, silicon nitride, or combinations thereof. In certain embodiments, electrical insulator 628 is a compacted powder of magnesium oxide. In some embodiments, electrical insulator 628 includes beads of silicon nitride.

In certain embodiments, a small layer of material is placed between electrical insulator 628 and inner conductor 626 to inhibit copper from migrating into the electrical insulator at higher temperatures. For example, the small layer of nickel (for example, about 0.5 mm of nickel) may be placed between electrical insulator 628 and inner conductor 626.

Jacket 636 is made of a corrosion resistant material such as, but not limited to, 347 stainless steel, 347H stainless steel, 446 stainless steel, or 825 stainless steel. In some embodiments, jacket 636 provides some mechanical strength for insulated conductor 712 at or above the Curie temperature of ferromagnetic conductor 654. In certain embodiments, jacket 636 is not used to conduct electrical current.

In certain embodiments of temperature limited heaters, three temperature limited heaters are coupled together in a three-phase wye configuration. Coupling three temperature limited heaters together in the three-phase wye configuration lowers the current in each of the individual temperature limited heaters because the current is split between the three individual heaters. Lowering the current in each individual temperature limited heater allows each heater to have a small diameter. The lower currents allow for higher relative magnetic permeabilities in each of the individual temperature limited heaters and, thus, higher turndown ratios. In addition, there may be no return current needed for each of the individual temperature limited heaters. Thus, the turndown ratio remains higher for each of the individual temperature limited heaters than if each temperature limited heater had its own return current path.

In the three-phase wye configuration, individual temperature limited heaters may be coupled together by shorting the sheaths, jackets, or canisters of each of the individual temperature limited heaters to the electrically conductive sections (the conductors providing heat) at their terminating ends (for example, the ends of the heaters at the bottom of a heater wellbore). In some embodiments, the sheaths, jackets, canisters, and/or electrically conductive sections are coupled to a support member that supports the temperature limited heaters in the wellbore.

FIG. 97A depicts an embodiment for installing and coupling heaters in a wellbore. The embodiment in FIG. 97A depicts insulated conductor heaters being installed into the wellbore. Other types of heaters, such as conductor-in-conduit heaters, may also be installed in the wellbore using the embodiment depicted. Also, in FIG. 97A, two insulated conductors 712 are shown while a third insulated conductor is not seen from the view depicted. Typically, three insulated conductors 712 would be coupled to support member 738, as shown in FIG. 97B. In an embodiment, support member 738 is a thick walled 347H pipe. In some embodiments, thermocouples or other temperature sensors are placed inside support member 738. The three insulated conductors may be coupled in a three-phase wye configuration.

In FIG. 97A, insulated conductors 712 are coiled on coiled tubing rigs 740. As insulated conductors 712 are uncoiled from rigs 740, the insulated conductors are coupled to support member 738. In certain embodiments, insulated conductors 712 are simultaneously uncoiled and/or simultaneously coupled to support member 738. Insulated conductors 712 may be coupled to support member 738 using metal (for example, 304 stainless steel or Inconel® alloys) straps 742. In some embodiments, insulated conductors 712 are coupled to support member 738 using other types of fasteners such as buckles, wire holders, or snaps. Support member 738 along with insulated conductors 712 are installed into opening 378. In some embodiments, insulated conductors 712 are coupled together without the use of a support member. For example, one or more straps 742 may be used to couple insulated conductors 712 together.

Insulated conductors 712 may be electrically coupled to each other at a lower end of the insulated conductors. In a three-phase wye configuration, insulated conductors 712 operate without a current return path. In certain embodiments, insulated conductors 712 are electrically coupled to each other in contactor section 744. In section 744, sheaths, jackets, canisters, and/or electrically conductive sections are electrically coupled to each other and/or to support member 738 so that insulated conductors 712 are electrically coupled in the section.

In certain embodiments, the sheaths of insulated conductors 712 are shorted to the conductors of the insulated conductors. FIG. 97C depicts an embodiment of insulated conductor 712 with the sheath shorted to the conductors. Sheath 636 is electrically coupled to core 656, ferromagnetic conductor 654, and inner conductor 626 using termination 746. Termination 746 may be a metal strip or a metal plate at the lower end of insulated conductor 712. For example, termination 746 may be a copper plate coupled to sheath 636, core 656, ferromagnetic conductor 654, and inner conductor 626 so that they are shorted together. In some embodiments, termination 746 is welded or brazed to sheath 636, core 656, ferromagnetic conductor 654, and inner conductor 626.

The sheaths of individual insulated conductors 712 may be shorted together to electrically couple the conductors of the insulated conductors, depicted in FIGS. 97A and 97B. In some embodiments, the sheaths may be shorted together because the sheaths are in physical contact with each other. For example, the sheaths may in physical contact if the sheaths are strapped together by straps 742. In some embodiments, the lower ends of the sheaths are physically coupled (for example, welded) at the surface of opening 378 before insulated conductors 712 are installed into the opening.

Figure 98A:
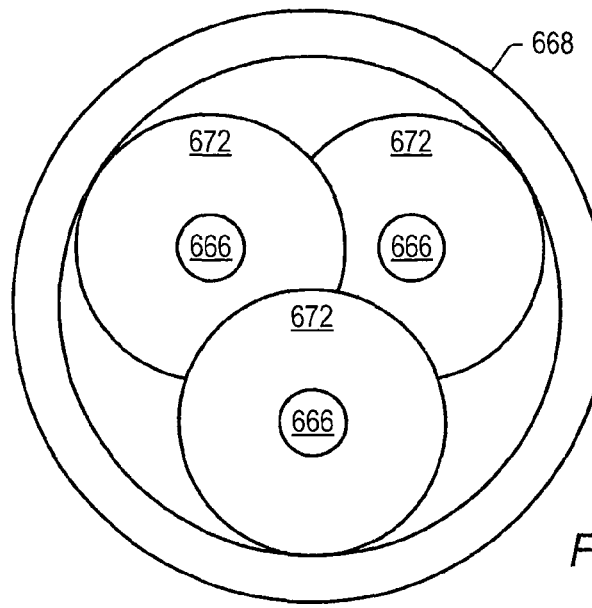
FIGS. 98A and 98B depict an embodiment of a three conductor-in-conduit heater.
Figure 98B:
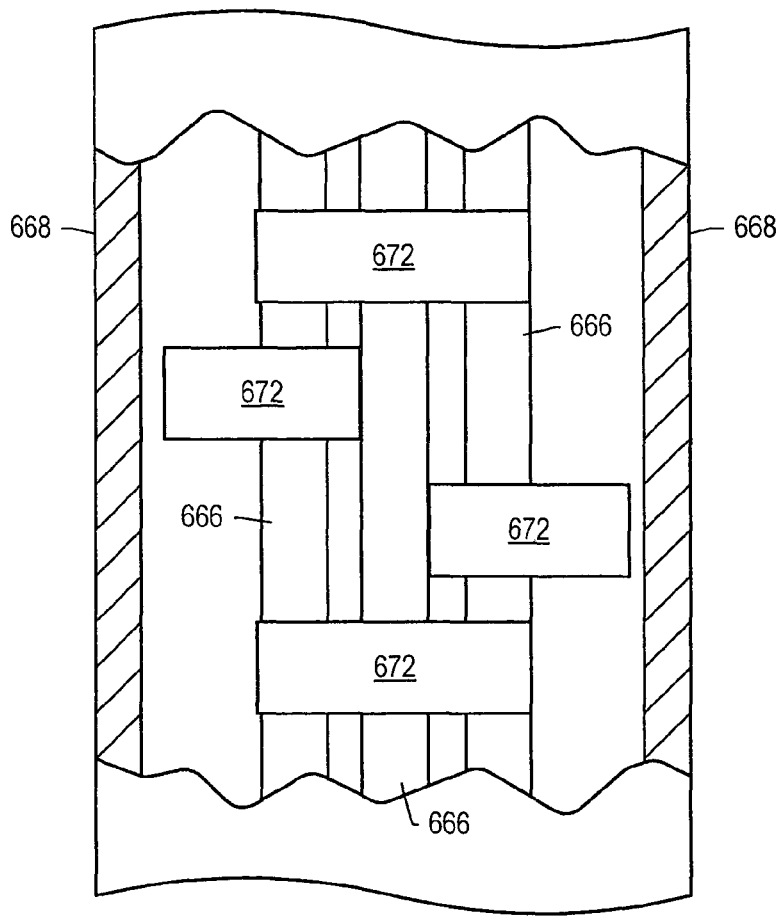

In certain embodiments, three conductors are located inside a single conduit to form a three conductor-in-conduit heater. FIGS. 98A and 98B depict an embodiment of a three conductor-in-conduit heater. FIG. 98A depicts a top down view of the three conductor-in-conduit heater. FIG. 98B depicts a side view representation with a cutout to show the internals of the three conductor-in-conduit heater. Three conductors 666 are located inside conduit 668. The three conductors 666 are substantially evenly spaced within conduit 668. In some embodiments, the three conductors 666 are coupled in a spiral configuration.

One or more centralizers 672 are placed around each conductor 666. Centralizers 672 are made from electrically insulating material such as silicon nitride or boron nitride. Centralizers 672 maintain a position of conductors 666 in conduit 668. Centralizers 672 also inhibit electrical contact between conductors 666 and conduit 668. In certain embodiments, centralizers 672 are spaced along the length of conductors 666 so that the centralizers surrounding one conductor overlap (as seen from the top down view) centralizers from another conductor. This reduces the number of centralizers needed for each conductor and allows for tight spacing of the conductors.

In certain embodiments, the three conductors 666 are coupled in a three-phase wye configuration. The three conductors 666 may be coupled at or near the bottom of the heaters in the three-phase wye configuration. In the three-phase wye configuration, conduit 668 is not electrically coupled to the three conductors 666. Thus, conduit 668 may only be used to provide strength for and/or inhibit corrosion of the three conductors 666.

Figure 99:
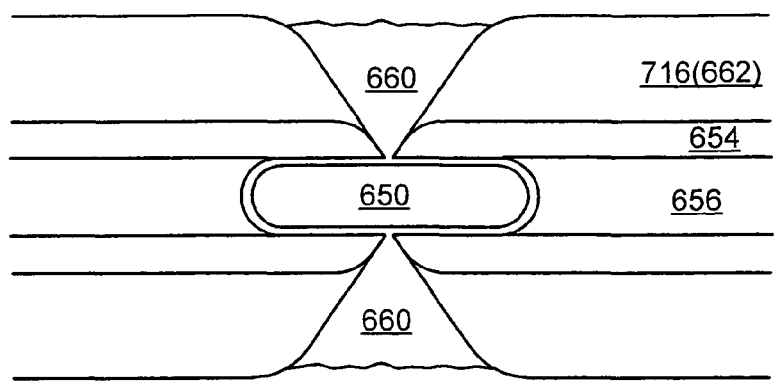
FIG. 99 depicts an embodiment for coupling together sections of a long temperature limited heater.

In some embodiments, a long temperature limited heater (for example, a temperature limited heater in which the support member provides a majority of the heat output below the Curie temperature of the ferromagnetic conductor) is formed from several sections of heater. The sections of heater may be coupled using a welding process. FIG. 99 depicts an embodiment for coupling together sections of a long temperature limited heater. Ends of ferromagnetic conductors 654 and ends of electrical conductors 716 (support members 662) are beveled to facilitate coupling the sections of the heater. Core 656 has recesses to allow core coupling material 650 to be placed inside the abutted ends of the heater. Core coupling material 650 may be a pin or dowel that fits tightly in the recesses of cores 656. Core coupling material 650 may be made out of the same material as cores 656 or a material suitable for coupling the cores together. Core coupling material 650 allows the heaters to be coupled together without welding cores 656 together. Cores 656 are coupled together as a "pin" or "box" joint.

Beveled ends of ferromagnetic conductors 654 and electrical conductors 716 may be coupled together with coupling material 660. In certain embodiments, ends of ferromagnetic conductors 654 and electrical conductors 716 are welded (for example, orbital welded) together. Coupling material 660 may be 625 stainless steel or any other suitable non-ferromagnetic material for welding together ferromagnetic conductors 654 and/or electrical conductors 716. Using beveled ends when coupling together sections of the heater may produce a reliable and durable coupling between the sections of the heater.

During heating with the temperature limited heater, core coupling material 650 may expand more radially than ferromagnetic conductors 654, electrical conductors 716, and/or coupling material 660. The greater expansion of core coupling material 650 maintains good electrical contact with the core coupling material. At the coupling junction of the heater, electricity flows through core coupling material 650 rather than coupling material 660. This flow of electricity inhibits heat generation at the coupling junction so that the junction remains at lower temperatures than other portions of the heater during application of electrical current to the heater. The corrosion resistance and strength of the coupling junction is increased by maintaining the junction at lower temperatures.

In certain embodiments, the junction may be enclosed in a shield during orbital welding to ensure reliability of the weld. If the junction is not enclosed, disturbance of the inert gas caused by wind, humidity or other conditions may cause oxidation and/or porosity of the weld. Without a shield, a first portion of the weld was formed and allowed to cool. A grinder would be used to remove the oxide layer. The process would be repeated until the weld was complete. Enclosing the junction in the shield with an inert gas allows the weld to be formed with no oxidation, thus allowing the weld to be formed in one pass with no need for grinding. Enclosing the junction increases the safety of forming the weld because the arc of the orbital welder is enclosed in the shield during welding. Enclosing the junction in the shield may reduce the time needed to form the weld. Without a shield, producing each weld may take 30 minutes or more. With the shield, each weld may take 10 minutes or less.

Figure 100:
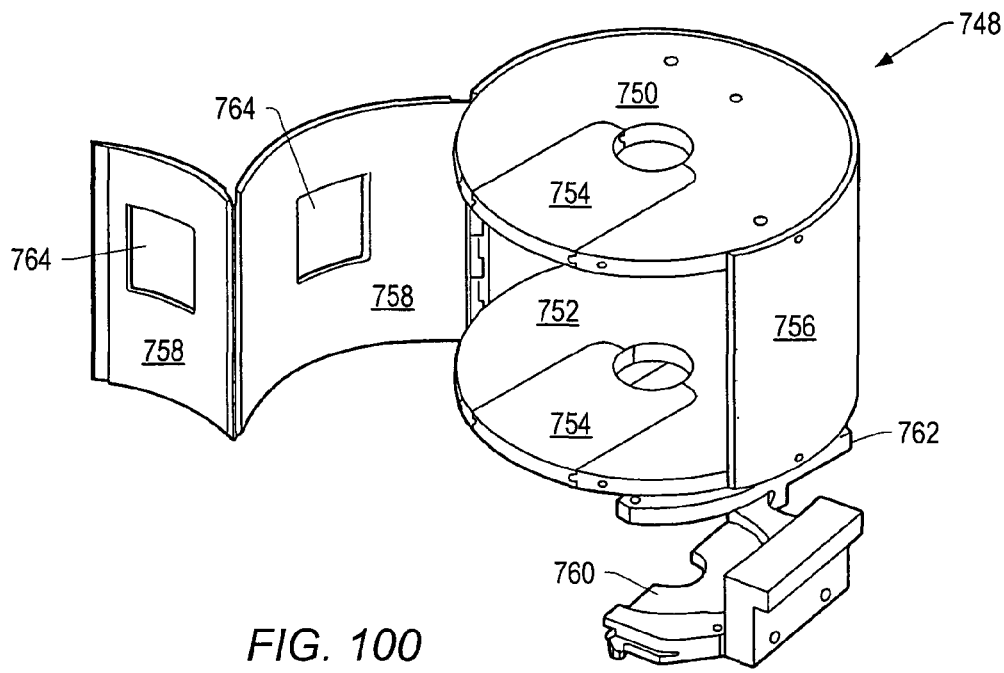
FIG. 100 depicts an embodiment of a shield for orbital welding together sections of a long temperature limited heater.

FIG. 100 depicts an embodiment of a shield for orbital welding sections of a long temperature limited heater. Orbital welding may also be used to form canisters for freeze wells from sections of pipe. Shield 748 may include upper plate 750, lower plate 752, inserts 754, wall 756, hinged door 758, first clamp member 760, and second clamp member 762. Wall 756 may include one or more inert gas inlets. Wall 756, upper plate 750, and/or lower plate 752 may include one or more openings for monitoring equipment or gas purging. Shield 748 is configured to work with an orbital welder, such as AMI Power Supply (Model 227) and AMI Orbital Weld Head (Model 97-2375) available from Arc Machines, Inc. (Pacoima, Calif., U.S.A.). Inserts 754 may be withdrawn from upper plate 750 and lower plate 752. The orbital weld head may be positioned in shield 748. Shield 748 may be placed around a lower conductor of the conductors that are to be welded together. When shield is positioned so that the end of the lower conductor is at a desired position in the middle of the shield, first clamp member may be fastened to second clamp member to secure shield 748 to the lower conductor. The upper conductor may be positioned in shield 748. Inserts 754 may be placed in upper plate 750 and lower plate 752.

Hinged door 758 may be closed. The orbital welder may be used to weld the lower conductor to the upper conductor. Progress of the welding operation may be monitored through viewing windows 764. When the weld is complete, shield 748 may be supported and first clamp member 760 may be unfastened from second clamp member 762. One or both inserts 754 may be removed or partially removed from lower plate 752 and upper plate 750 to facilitate lowering of the conductor. The conductor may be lowered in the wellbore until the end of the conductor is located at a desired position in shield 748. Shield 748 may be secured to the conductor with first clamp member 760 and second clamp member 762. Another conductor may be positioned in the shield. Inserts 754 may be positioned in upper and lower plates 750, 752, hinged door is closed 758, and the orbital welder is used to weld the conductors together. The process may be repeated until a desired length of conductor is formed.

Figure 101:
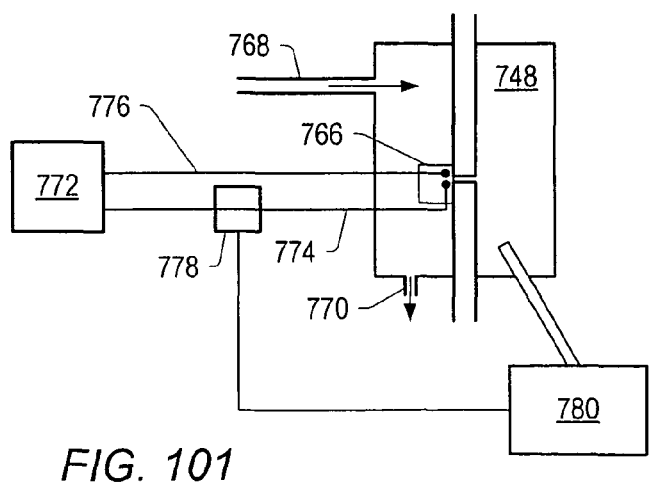
FIG. 101 depicts a schematic representation of a shut off circuit for an orbital welding machine.

The shield may be used to weld joints of pipe over an opening in the hydrocarbon containing formation. Hydrocarbon vapors from the formation may create an explosive atmosphere in the shield even though the inert gas supplied to the shield inhibits the formation of dangerous concentrations of hydrocarbons in the shield. A control circuit may be coupled to a power supply for the orbital welder to stop power to the orbital welder to shut off the arc forming the weld if the hydrocarbon level in the shield rises above a selected concentration. FIG. 101 depicts a schematic representation of a shut off circuit for orbital welding machine 766. An inert gas, such as argon, may enter shield 748 through inlet 768. Gas may exit shield 748 through purge 770. Power supply 772 supplies electricity to orbital welding machine 766 through lines 774, 776. Switch 778 may be located in line 774 to orbital welding machine 766. Switch 778 may be electrically coupled to hydrocarbon monitor 780. Hydrocarbon monitor 780 may detect the hydrocarbon concentration in shield 748. If the hydrocarbon concentration in shield becomes too high, for example, over 25% of a lower explosion limit concentration, hydrocarbon monitor 780 may open switch 778. When switch 778 is open, power to orbital welder 766 is interrupted and the arc formed by the orbital welder ends.

In some embodiments, the temperature limited heater is used to achieve lower temperature heating (for example, for heating fluids in a production well, heating a surface pipeline, or reducing the viscosity of fluids in a wellbore or near wellbore region). Varying the ferromagnetic materials of the temperature limited heater allows for lower temperature heating. In some embodiments, the ferromagnetic conductor is made of material with a lower Curie temperature than that of 446 stainless steel. For example, the ferromagnetic conductor may be an alloy of iron and nickel. The alloy may have between 30% by weight and 42% by weight nickel with the rest being iron. In one embodiment, the alloy is Invar 36. Invar 36 is 36% by weight nickel in iron and has a Curie temperature of 277° C. In some embodiments, an alloy is a three component alloy with, for example, chromium, nickel, and iron. For example, an alloy may have 6% by weight chromium, 42% by weight nickel, and 52% by weight iron. A 2.5 cm diameter rod of Invar 36 has a turndown ratio of approximately 2 to 1 at the Curie temperature. Placing the Invar 36 alloy over a copper core may allow for a smaller rod diameter. A copper core may result in a high turndown ratio. The insulator in lower temperature heater embodiments may be made of a high performance polymer insulator (such as PFA or PEEK™) when used with alloys with a Curie temperature that is below the melting point or softening point of the polymer insulator.

In certain embodiments, a conductor-in-conduit temperature limited heater is used in lower temperature applications by using lower Curie temperature ferromagnetic materials. For example, a lower Curie temperature ferromagnetic material may be used for heating inside sucker pump rods. Heating sucker pump rods may be useful to lower the viscosity of fluids in the sucker pump or rod and/or to maintain a lower viscosity of fluids in the sucker pump rod. Lowering the viscosity of the oil may inhibit sticking of a pump used to pump the fluids. Fluids in the sucker pump rod may be heated up to temperatures less than about 250° C. or less than about 300° C. Temperatures need to be maintained below these values to inhibit coking of hydrocarbon fluids in the sucker pump system.

For lower temperature applications, ferromagnetic conductor 654 in FIG. 80 may be Alloy 42-6 coupled to conductor 666. Conductor 666 may be copper. In one embodiment, ferromagnetic conductor 654 is 1.9 cm outside diameter Alloy 42-6 over copper conductor 666 with a 2:1 outside diameter to copper diameter ratio. In some embodiments, ferromagnetic conductor 654 includes other lower temperature ferromagnetic materials such as Alloy 32, Alloy 52, Invar 36, iron-nickel-chromium alloys, iron-nickel alloys, nickel-chromium alloys, or other nickel alloys. Conduit 668 may be a hollow sucker rod made from carbon steel. The carbon steel or other material used in conduit 668 confines current to the inside of the conduit to inhibit stray voltages at the surface of the formation. Centralizer 672 may be made from gas pressure sintered reaction bonded silicon nitride. In some embodiments, centralizer 672 is made from polymers such as PFA or PEEK™. In certain embodiments, polymer insulation is clad along an entire length of the heater. Conductor 666 and ferromagnetic conductor 654 are electrically coupled to conduit 668 with sliding connector 678.

Figure 102:
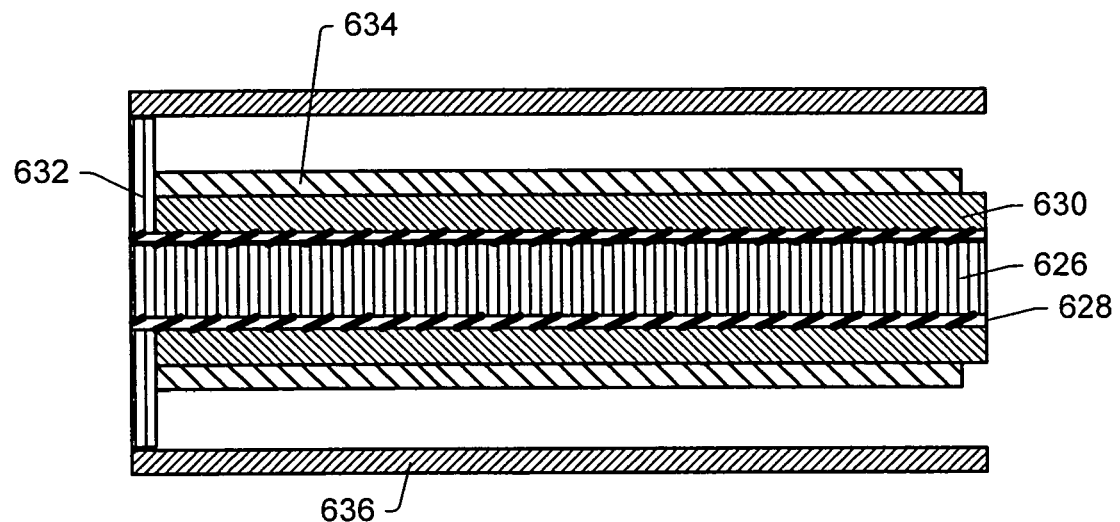
FIG. 102 depicts an embodiment of a temperature limited heater with a low temperature ferromagnetic outer conductor.

FIG. 102 depicts an embodiment of a temperature limited heater with a low temperature ferromagnetic outer conductor. Outer conductor 630 is glass sealing Alloy 42-6. Alloy 42-6 may be obtained from Carpenter Metals (Reading, Pa., U.S.A.) or Anomet Products, Inc. In some embodiments, outer conductor 630 includes other compositions and/or materials to get various Curie temperatures (for example, Carpenter Temperature Compensator "32" (Curie temperature of 199° C.; available from Carpenter Metals) or Invar 36). In an embodiment, conductive layer 634 is coupled (for example, clad, welded, or brazed) to outer conductor 630. Conductive layer 634 is a copper layer. Conductive layer 634 improves a turndown ratio of outer conductor 630. Jacket 636 is a ferromagnetic metal such as carbon steel. Jacket 636 protects outer conductor 630 from a corrosive environment. Inner conductor 626 may have electrical insulator 628. Electrical insulator 628 may be a mica tape winding with overlaid fiberglass braid. In an embodiment, inner conductor 626 and electrical insulator 628 are a 4/0 MGT-1000 furnace cable or 3/0 MGT-1000 furnace cable. 4/0 MGT-1000 furnace cable or 3/0 MGT-1000 furnace cable is available from Allied Wire and Cable. In some embodiments, a protective braid such as a stainless steel braid may be placed over electrical insulator 628.

Conductive section 632 electrically couples inner conductor 626 to outer conductor 630 and/or jacket 636. In some embodiments, jacket 636 touches or electrically contacts conductive layer 634 (for example, if the heater is placed in a horizontal configuration). If jacket 636 is a ferromagnetic metal such as carbon steel (with a Curie temperature above the Curie temperature of outer conductor 630), current will propagate only on the inside of the jacket. Thus, the outside of the jacket remains electrically uncharged during operation. In some embodiments, jacket 636 is drawn down (for example, swaged down in a die) onto conductive layer 634 so that a tight fit is made between the jacket and the conductive layer. The heater may be spooled as coiled tubing for insertion into a wellbore. In other embodiments, an annular space is present between conductive layer 634 and jacket 636, as depicted in FIG. 102.

Figure 103:
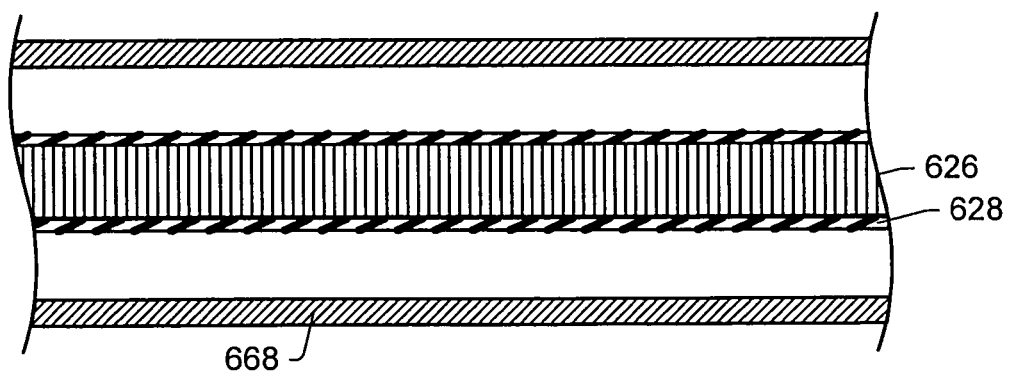
FIG. 103 depicts an embodiment of a temperature limited conductor-in-conduit heater.

FIG. 103 depicts an embodiment of a temperature limited conductor-in-conduit heater. Conduit 668 is a hollow sucker rod made of a ferromagnetic metal such as Alloy 42-6, Alloy 32, Alloy 52, Invar 36, iron-nickel-chromium alloys, iron-nickel alloys, nickel alloys, or nickel-chromium alloys. Inner conductor 626 has electrical insulator 628. Electrical insulator 628 is a mica tape winding with overlaid fiberglass braid. In an embodiment, inner conductor 626 and electrical insulator 628 are a 4/0 MGT-1000 furnace cable or 3/0 MGT-1000 furnace cable. In some embodiments, polymer insulations are used for lower temperature Curie heaters. In certain embodiments, a protective braid is placed over electrical insulator 628. Conduit 668 has a wall thickness that is greater than the skin depth at the Curie temperature (for example, 2 to 3 times the skin depth at the Curie temperature). In some embodiments, a more conductive conductor is coupled to conduit 668 to increase the turndown ratio of the heater.

Figure 104:
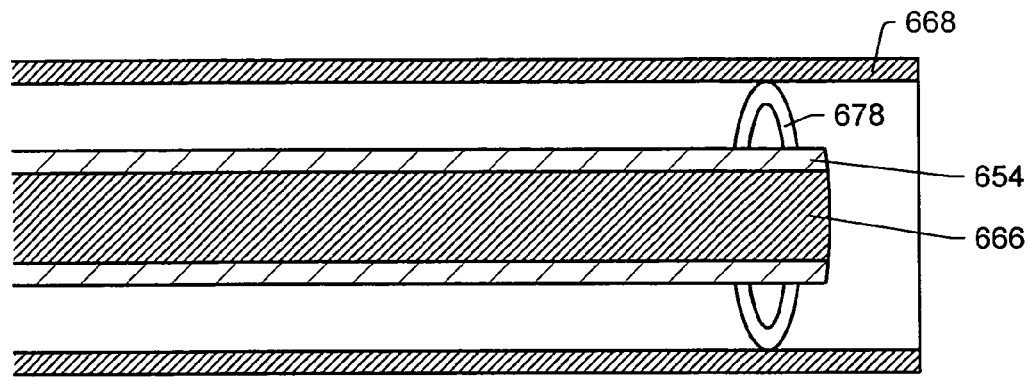
FIG. 104 depicts a cross-sectional representation of an embodiment of a conductor-in-conduit temperature limited heater.

FIG. 104 depicts a cross-sectional representation of an embodiment of a conductor-in-conduit temperature limited heater. Conductor 666 is coupled (for example, clad, coextruded, press fit, drawn inside) to ferromagnetic conductor 654. A metallurgical bond between conductor 666 and ferromagnetic conductor 654 is favorable. Ferromagnetic conductor 654 is coupled to the outside of conductor 666 so that current propagates through the skin depth of the ferromagnetic conductor at room temperature. Conductor 666 provides mechanical support for ferromagnetic conductor 654 at elevated temperatures. Ferromagnetic conductor 654 is iron, an iron alloy (for example, iron with 10% to 27% by weight chromium for corrosion resistance), or any other ferromagnetic material. In one embodiment, conductor 666 is 304 stainless steel and ferromagnetic conductor 654 is 446 stainless steel. Conductor 666 and ferromagnetic conductor 654 are electrically coupled to conduit 668 with sliding connector 678. Conduit 668 may be a non-ferromagnetic material such as austenitic stainless steel.

Figure 105:
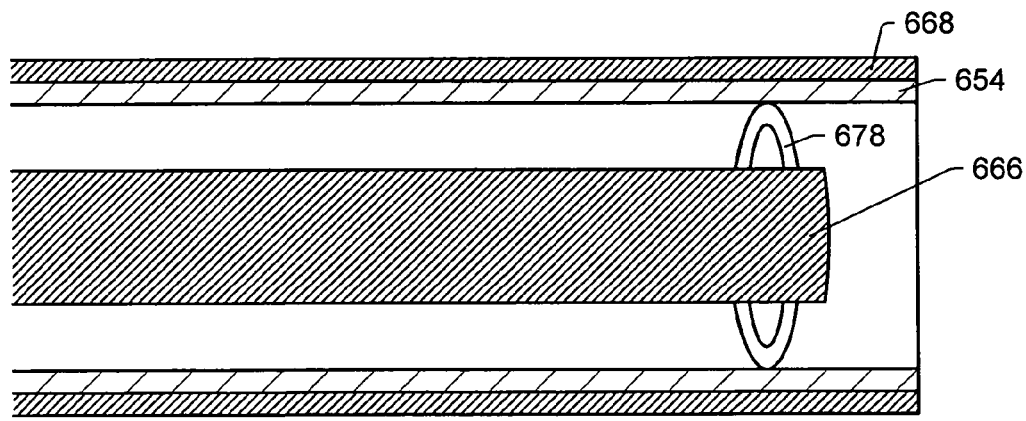
FIG. 105 depicts a cross-sectional representation of an embodiment of a conductor-in-conduit temperature limited heater.

FIG. 105 depicts a cross-sectional representation of an embodiment of a conductor-in-conduit temperature limited heater. Conduit 668 is coupled to ferromagnetic conductor 654 (for example, clad, press fit, or drawn inside of the ferromagnetic conductor). Ferromagnetic conductor 654 is coupled to the inside of conduit 668 to allow current to propagate through the skin depth of the ferromagnetic conductor at room temperature. Conduit 668 provides mechanical support for ferromagnetic conductor 654 at elevated temperatures. Conduit 668 and ferromagnetic conductor 654 are electrically coupled to conductor 666 with sliding connector 678.

Figure 106:
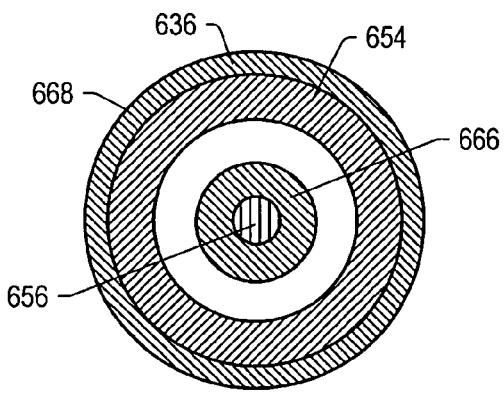
FIG. 106 depicts a cross-sectional view of an embodiment of a conductor-in-conduit temperature limited heater.

FIG. 106 depicts a cross-sectional view of an embodiment of a conductor-in-conduit temperature limited heater. Conductor 666 may surround core 656. In an embodiment, conductor 666 is 347H stainless steel and core 656 is copper. Conductor 666 and core 656 may be formed together as a composite conductor. Conduit 668 may include ferromagnetic conductor 654. In an embodiment, ferromagnetic conductor 654 is Sumitomo HCM12A or 446 stainless steel. Ferromagnetic conductor 654 may have a Schedule XXH thickness so that the conductor is inhibited from deforming. In certain embodiments, conduit 668 also includes jacket 636. Jacket 636 may include corrosion resistant material that inhibits electrons from flowing away from the heater and into a subsurface formation at higher temperatures (for example, temperatures near the Curie temperature of ferromagnetic conductor 654). For example, jacket 636 may be about a 0.4 cm thick sheath of 410 stainless steel. Inhibiting electrons from flowing to the formation may increase the safety of using the heater in the subsurface formation.

Figure 107:
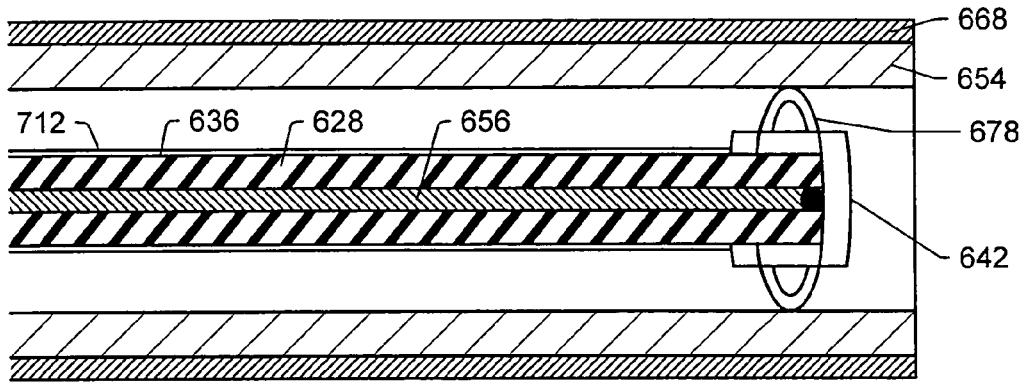
FIG. 107 depicts a cross-sectional representation of an embodiment of a conductor-in-conduit temperature limited heater with an insulated conductor.

FIG. 107 depicts a cross-sectional representation of an embodiment of a conductor-in-conduit temperature limited heater with an insulated conductor. Insulated conductor 712 may include core 656, electrical insulator 628, and jacket 636. Jacket 636 may be made of a corrosion resistant material (for example, stainless steel). Endcap 642 may be placed at an end of insulated conductor 712 to couple core 656 to sliding connector 678. Endcap 642 may be made of non-corrosive, electrically conducting materials such as nickel or stainless steel. Endcap 642 may be coupled to the end of insulated conductor 712 by any suitable method (for example, welding, soldering, braising). Sliding connector 678 may electrically couple core 656 and endcap 642 to ferromagnetic conductor 654. Conduit 668 may provide support for ferromagnetic conductor 654 at elevated temperatures.

Figure 108:
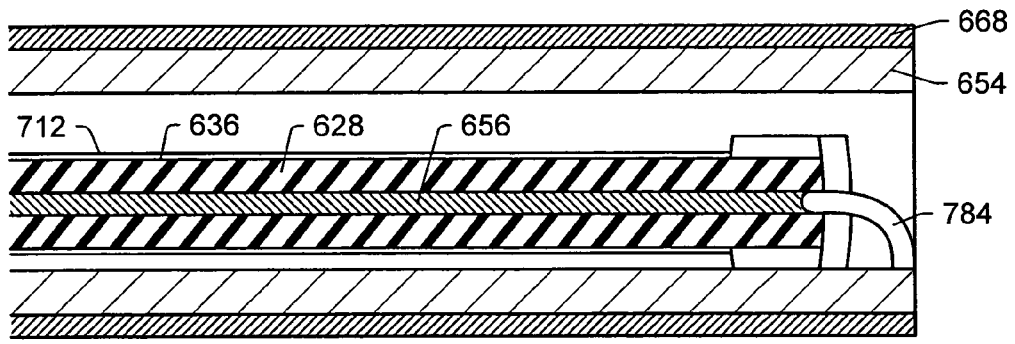
FIG. 108 depicts a cross-sectional representation of an embodiment of an insulated conductor-in-conduit temperature limited heater.

FIG. 108 depicts a cross-sectional representation of an embodiment of an insulated conductor-in-conduit temperature limited heater. Insulated conductor 712 may include core 656, electrical insulator 628, and jacket 636. Insulated conductor 712 may be coupled to ferromagnetic conductor 654 with connector 784. Connector 784 may be made of non-corrosive, electrically conducting materials such as nickel or stainless steel. Connector 784 may be coupled to insulated conductor 712 and coupled to ferromagnetic conductor 654 using suitable methods for electrically coupling (for example, welding, soldering, braising). Insulated conductor 712 may be placed along a wall of ferromagnetic conductor 654. Insulated conductor 712 may provide mechanical support for ferromagnetic conductor 654 at elevated temperatures. In some embodiments, other structures (for example, a conduit) are used to provide mechanical support for ferromagnetic conductor 654.

Figure 109:
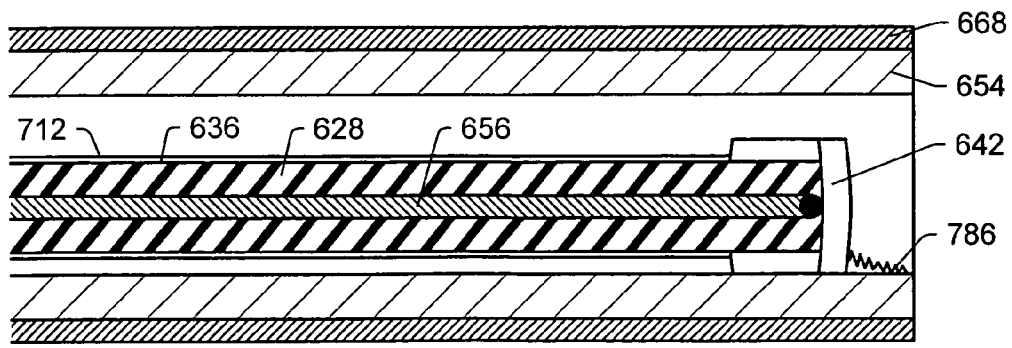
FIG. 109 depicts a cross-sectional representation of an embodiment of an insulated conductor-in-conduit temperature limited heater.

FIG. 109 depicts a cross-sectional representation of an embodiment of an insulated conductor-in-conduit temperature limited heater. Insulated conductor 712 may be coupled to endcap 642. Endcap 642 may be coupled to coupling 786. Coupling 786 may electrically couple insulated conductor 712 to ferromagnetic conductor 654. Coupling 786 may be a flexible coupling. For example, coupling 786 may include flexible materials (for example, braided wire). Coupling 786 may be made of corrosion resistant material such as nickel, stainless steel, and/or copper.

Figure 110:
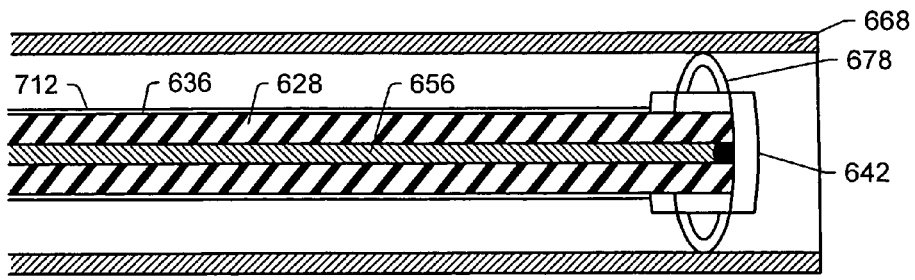
FIG. 110 depicts a cross-sectional representation of an embodiment of a conductor-in-conduit temperature limited heater with an insulated conductor.

FIG. 110 depicts a cross-sectional representation of an embodiment of a conductor-in-conduit temperature limited heater with an insulated conductor. Insulated conductor 712 includes core 656, electrical insulator 628, and jacket 636. Jacket 636 is made of a highly electrically conductive material such as copper. Core 656 is made of a lower temperature ferromagnetic material such as such as Alloy 42-6, Alloy 32, Invar 36, iron-nickel-chromium alloys, iron-nickel alloys, nickel alloys, or nickel-chromium alloys. In certain embodiments, the materials of jacket 636 and core 656 are reversed so that the jacket is the ferromagnetic conductor and the core is the highly conductive portion of the heater. Ferromagnetic material used in jacket 636 or core 656 may have a thickness greater than the skin depth at the Curie temperature (for example, 2 to 3 times the skin depth at the Curie temperature). Endcap 642 is placed at an end of insulated conductor 712 to couple core 656 to sliding connector 678. Endcap 642 is made of corrosion resistant, electrically conducting materials such as nickel or stainless steel. In certain embodiments, conduit 668 is a hollow sucker rod made from, for example, carbon steel.

Figure 111:
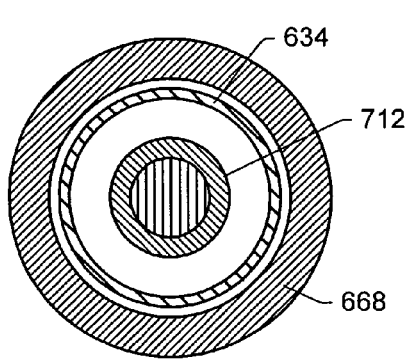
FIGS. 111 and 112 depict cross-sectional views of an embodiment of a temperature limited heater that includes an insulated conductor.
Figure 112:
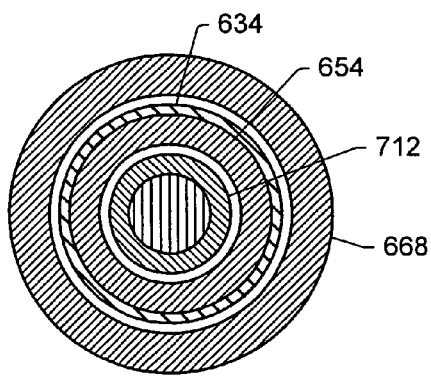

FIGS. 111 and 112 depict cross-sectional views of an embodiment of a temperature limited heater that includes an insulated conductor. FIG. 111 depicts a cross-sectional view of an embodiment of the overburden section of the temperature limited heater. The overburden section may include insulated conductor 712 placed in conduit 668. Conduit 668 may be 1¼" Schedule 80 carbon steel pipe internally clad with copper in the overburden section. Insulated conductor 712 may be a mineral insulated cable or polymer insulated cable. Conductive layer 634 may be placed in the annulus between insulated conductor 712 and conduit 668. Conductive layer 634 may be approximately 2.5 cm diameter copper tubing. The overburden section may be coupled to the heating section of the heater. FIG. 112 depicts a cross-sectional view of an embodiment of a heating section of the temperature limited heater. Insulated conductor 712 in the heating section may be a continuous portion of insulated conductor 712 in the overburden section. Ferromagnetic conductor 654 may be coupled to conductive layer 634. In certain embodiments, conductive layer 634 in the heating section is copper drawn over ferromagnetic conductor 654 and coupled to conductive layer 634 in the overburden section. Conduit 668 may include a heating section and an overburden section. These two sections may be coupled to form conduit 668. The heating section may be 1¼" Schedule 80 347H stainless steel pipe. An end cap, or other suitable electrical connector, may couple ferromagnetic conductor 654 to insulated conductor 712 at a lower end of the heater. The lower end of the heater is the end farthest from the point the heater enters the hydrocarbon layer from the overburden section.

Figure 113:
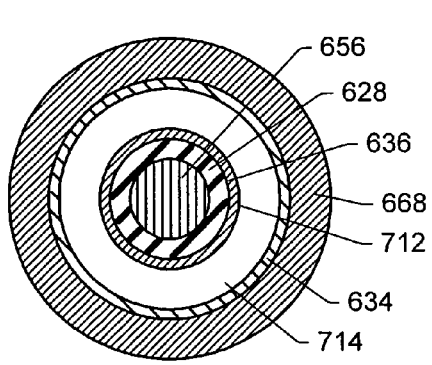
FIGS. 113 and 114 depict cross-sectional views of an embodiment of a temperature limited heater that includes an insulated conductor.
Figure 114:
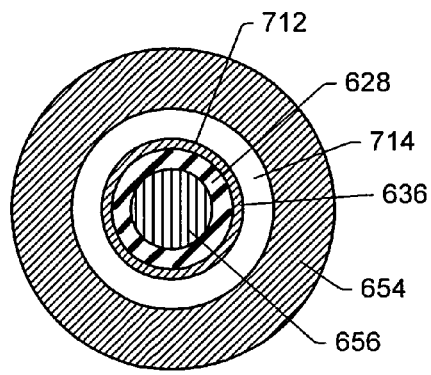

FIGS. 113 and 114 depict cross-sectional views of an embodiment of a temperature limited heater that includes an insulated conductor. FIG. 113 depicts a cross-sectional view of an embodiment of the overburden section of the temperature limited heater. Insulated conductor 712 may include core 656, electrical insulator 628, and jacket 636. Insulated conductor 712 may have a diameter of about 1.5 cm. Core 656 may be copper. Electrical insulator 628 may be silicon nitride, boron nitride, or magnesium oxide. Jacket 636 may be copper in the overburden section to reduce heat losses. Conduit 668 may be 1" Schedule 40 carbon steel in the overburden section. Conductive layer 634 may be coupled to conduit 668. Conductive layer 634 may be copper with a thickness of about 0.2 cm to reduce heat losses in the overburden section. Gap 714 may be an annular space between insulated conductor 712 and conduit 668. FIG. 114 depicts a cross-sectional view of an embodiment of a heating section of the temperature limited heater. Insulated conductor 712 in the heating section may be coupled to insulated conductor 712 in the overburden section. Jacket 636 in the heating section may be made of a corrosion resistant material (for example, 825 stainless steel). Ferromagnetic conductor 654 may be coupled to conduit 668 in the overburden section. Ferromagnetic conductor 654 may be Schedule 160 409, 410, or 446 stainless steel pipe. Gap 714 may be between ferromagnetic conductor 654 and insulated conductor 712. An end cap, or other suitable electrical connector, may couple ferromagnetic conductor 654 to insulated conductor 712 at a distal end of the heater. The distal end of the heater is the end farthest from the overburden section.

In certain embodiments, a temperature limited heater includes a flexible cable (for example, a furnace cable) as the inner conductor. For example, the inner conductor may be a 27% nickel-clad or stainless steel-clad stranded copper wire with four layers of mica tape surrounded by a layer of ceramic and/or mineral fiber (for example, alumina fiber, aluminosilicate fiber, borosilicate fiber, or aluminoborosilicate fiber). A stainless steel-clad stranded copper wire furnace cable may be available from Anomet Products, Inc. The inner conductor may be rated for applications at temperatures of 1000° C. or higher. The inner conductor may be pulled inside a conduit. The conduit may be a ferromagnetic conduit (for example, a ¾" Schedule 80 446 stainless steel pipe). The conduit may be covered with a layer of copper, or other electrical conductor, with a thickness of about 0.3 cm or any other suitable thickness. The assembly may be placed inside a support conduit (for example, a 1¼" Schedule 80 347H or 347HH stainless steel tubular). The support conduit may provide additional creep-rupture strength and protection for the copper and the inner conductor. For uses at temperatures greater than about 1000° C., the inner copper conductor may be plated with a more corrosion resistant alloy (for example, Incoloy® 825) to inhibit oxidation. In some embodiments, the top of the temperature limited heater is sealed to inhibit air from contacting the inner conductor.

In some embodiments, a ferromagnetic conductor of a temperature limited heater includes a copper core (for example, a 1.27 cm diameter copper core) placed inside a first steel conduit (for example, a ½" Schedule 80 347H or 347HH stainless steel pipe). A second steel conduit (for example, a 1" Schedule 80 446 stainless steel pipe) may be drawn down over the first steel conduit assembly. The first steel conduit may provide strength and creep resistance while the copper core may provide a high turndown ratio.

In some embodiments, a ferromagnetic conductor of a temperature limited heater (for example, a center or inner conductor of a conductor-in-conduit temperature limited heater) includes a heavy walled conduit (for example, an extra heavy wall 410 stainless steel pipe). The heavy walled conduit may have a diameter of about 2.5 cm. The heavy walled conduit may be drawn down over a copper rod. The copper rod may have a diameter of about 1.3 cm. The resulting heater may include a thick ferromagnetic sheath containing the copper rod. The thick ferromagnetic sheath may be the heavy walled conduit with, for example, about a 2.6 cm outside diameter after drawing. The heater may have a turndown ratio of about 8:1. The thickness of the heavy walled conduit may be selected to inhibit deformation of the heater. A thick ferromagnetic conduit may provide deformation resistance while adding minimal expense to the cost of the heater.

In another embodiment, a temperature limited heater includes a substantially U-shaped heater with a ferromagnetic cladding over a non-ferromagnetic core (in this context, the "U" may have a curved or, alternatively, orthogonal shape). A U-shaped, or hairpin, heater may have insulating support mechanisms (for example, polymer or ceramic spacers) that inhibit the two legs of the hairpin from electrically shorting to each other. In some embodiments, a hairpin heater is installed in a casing (for example, an environmental protection casing). The insulators may inhibit electrical shorting to the casing and may facilitate installation of the heater in the casing. The cross section of the hairpin heater may be, but is not limited to, circular, elliptical, square, or rectangular.

Figures 115, 116:
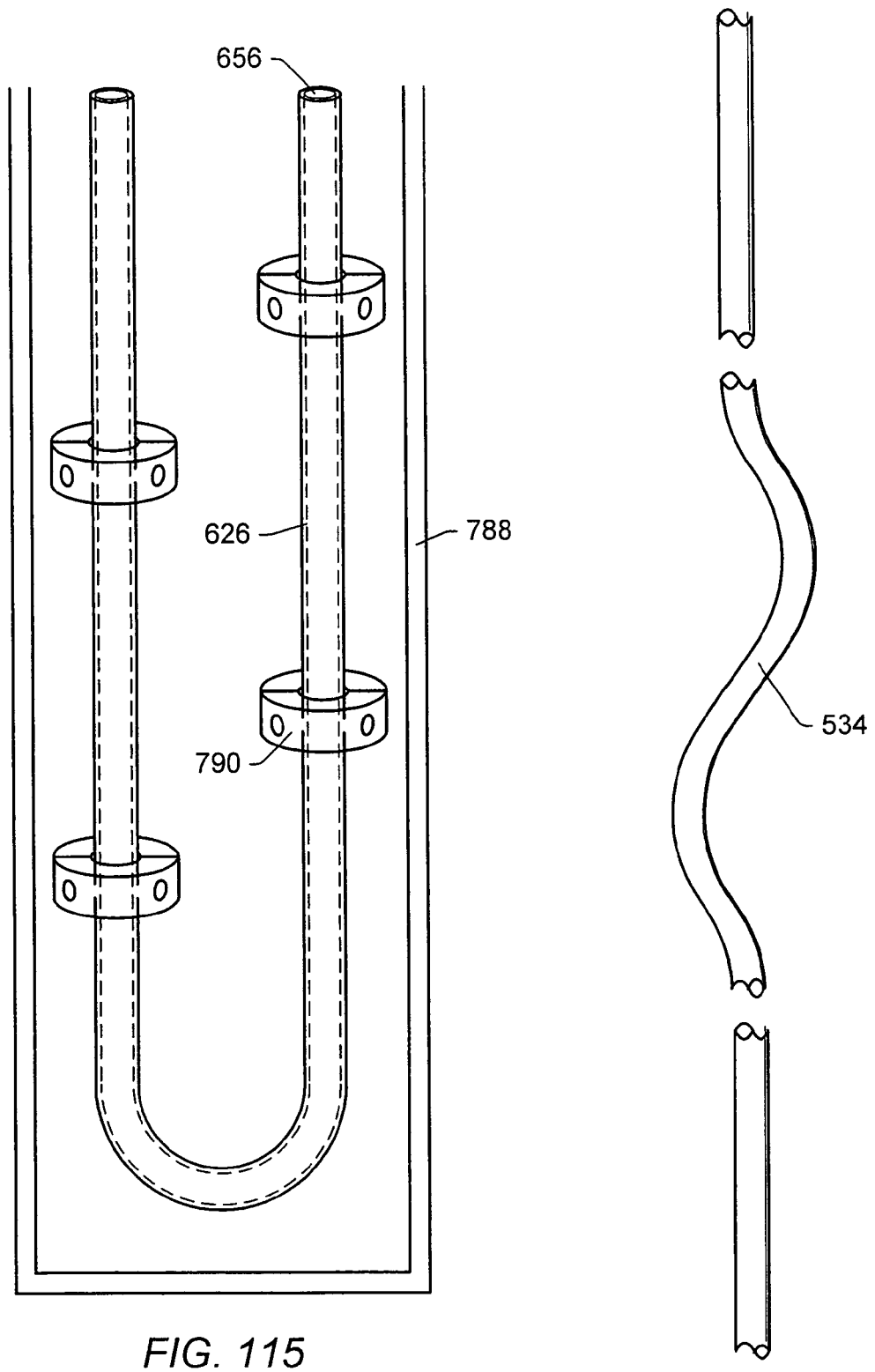
FIG. 115 depicts a schematic of an embodiment of a temperature limited heater.
FIG. 116 depicts an embodiment of an "S" bend in a heater.

FIG. 115 depicts an embodiment of a temperature limited heater with a hairpin inner conductor. Inner conductor 626 may be placed in a hairpin configuration with two legs coupled by a substantially U-shaped section at or near the bottom of the heater. Current may enter inner conductor 626 through one leg and exit through the other leg. Inner conductor 626 may be, but is not limited to, ferritic stainless steel, carbon steel, or iron. Core 656 may be placed inside inner conductor 626. In certain embodiments, inner conductor 626 may be clad to core 656. Core 656 may be a copper rod. The legs of the heater may be insulated from each other and from casing 788 by spacers 790. Spacers 790 may be alumina spacers (for example, about 90% to about 99.8% alumina) or silicon nitride spacers. Weld beads or other protrusions may be placed on inner conductor 626 to maintain a location of spacers 790 on the inner conductor. In some embodiments, spacers 790 include two sections that are fastened together around inner conductor 626. Casing 788 may be an environmentally protective casing made of, for example, stainless steel.

In certain embodiments, a temperature limited heater incorporates curves, helixes, bends, or waves in a relatively straight heater to allow thermal expansion and contraction of the heater without overstressing materials in the heater. When a cool heater is heated or a hot heater is cooled, the heater expands or contracts in proportion to the change in temperature and the coefficient of thermal expansion of materials in the heater. For long straight heaters that undergo wide variations in temperature during use and are fixed at more than one point in the wellbore (for example, due to mechanical deformation of the wellbore), the expansion or contraction may cause the heater to bend, kink, and/or pull apart. Use of an "S" bend or other curves, helixes, bends, or waves in the heater at intervals in the heated length may provide a spring effect and allow the heater to expand or contract more gently so that the heater does not bend, kink, or pull apart.

A 310 stainless steel heater subjected to about 500° C. temperature change may shrink/grow approximately 0.85% of the length of the heater with this temperature change. Thus, a length of about 3 m of a heater would contract about 2.6 cm when it cools through 500° C. If a long heater were affixed at about 3 m intervals, such a change in length could stretch and, possibly, break the heater. FIG. 116 depicts an embodiment of an "S" bend in a heater. The additional material in the "S" bend may allow for thermal contraction or expansion of heater 534 without damage to the heater.

In some embodiments, a temperature limited heater includes a sandwich construction with both current supply and current return paths separated by an insulator. The sandwich heater may include two outer layers of conductor, two inner layers of ferromagnetic material, and a layer of insulator between the ferromagnetic layers. The cross-sectional dimensions of the heater may be optimized for mechanical flexibility and spoolability. The sandwich heater may be formed as a bimetallic strip that is bent back upon itself. The sandwich heater may be inserted in a casing, such as an environmental protection casing. The sandwich heater may be separated from the casing with an electrical insulator.

A heater may include a section that passes through an overburden. In some embodiments, the portion of the heater in the overburden does not need to supply as much heat as a portion of the heater adjacent to hydrocarbon layers that are to be subjected to in situ conversion. In certain embodiments, a substantially non-heating section of a heater has limited or no heat output. A substantially non-heating section of a heater may be located adjacent to layers of the formation (for example, rock layers, non-hydrocarbon layers, or lean layers) that remain advantageously unheated. A substantially non-heating section of a heater may include a copper or aluminum conductor instead of a ferromagnetic conductor. In some embodiments, a substantially non-heating section of a heater includes a copper or copper alloy inner conductor. A substantially non-heating section may also include a copper outer conductor clad with a corrosion resistant alloy. In some embodiments, an overburden section includes a relatively thick ferromagnetic portion to inhibit crushing.

In certain embodiments, a temperature limited heater provides some heat to the overburden portion of a heater well and/or production well. Heat supplied to the overburden portion may inhibit formation fluids (for example, water and hydrocarbons) from refluxing or condensing in the wellbore. Refluxing fluids may use a large portion of heat energy supplied to a target section of the wellbore, thus limiting heat transfer from the wellbore to the target section.

A temperature limited heater may be constructed in sections that are coupled (welded). The sections may be 10 m long or longer. Construction materials for each section are chosen to provide a selected heat output for different parts of the formation. For example, an oil shale formation may contain layers with highly variable richnesses. Providing selected amounts of heat to individual layers, or multiple layers with similar richnesses, improves heating efficiency of the formation and/or inhibits collapse of the wellbore. A splice section may be formed between the sections, for example, by welding the inner conductors, filling the splice section with an insulator, and then welding the outer conductor. Alternatively, the heater is formed from larger diameter tubulars and drawn down to a desired length and diameter. A boron nitride, silicon nitride, magnesium oxide, or other type of insulation layer may be added by a weld-fill-draw method (starting from metal strip) or a fill-draw method (starting from tubulars) well known in the industry in the manufacture of mineral insulated heater cables. The assembly and filling can be done in a vertical or a horizontal orientation. The final heater assembly may be spooled onto a large diameter spool (for example, 1 m, 2 m, 3 m, or more in diameter) and transported to a site of the formation for subsurface deployment. Alternatively, the heater may be assembled on site in sections as the heater is lowered vertically into a wellbore.

The temperature limited heater may be a single-phase heater or a three-phase heater. In a three-phase heater embodiment, the temperature limited heater has a delta or a wye configuration. Each of the three ferromagnetic conductors in the three-phase heater may be inside a separate sheath. A connection between conductors may be made at the bottom of the heater inside a splice section. The three conductors may remain insulated from the sheath inside the splice section.

Figure 117:
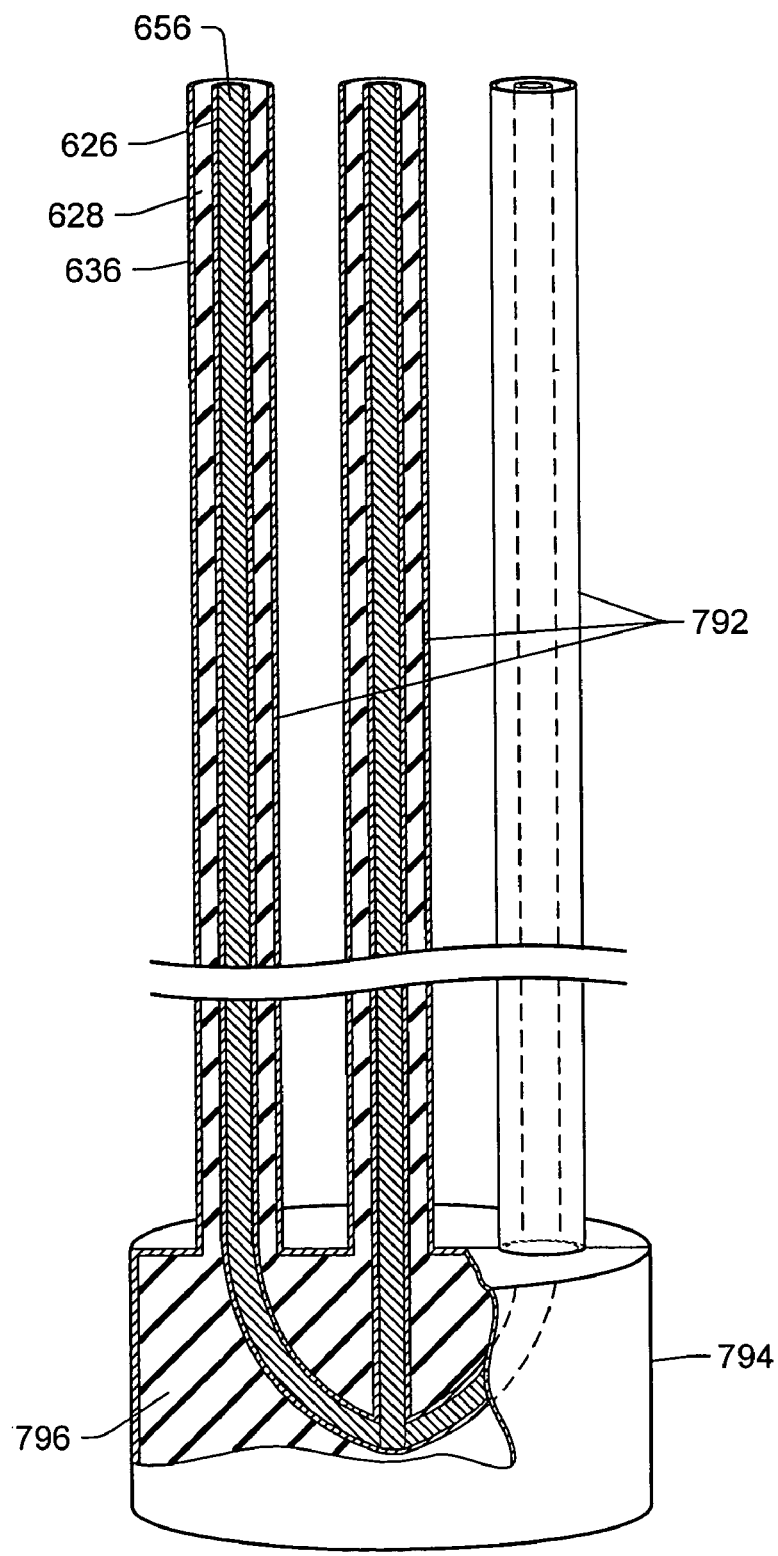
FIG. 117 depicts an embodiment of a three-phase temperature limited heater, with a portion shown in cross section.

FIG. 117 depicts an embodiment of a three-phase temperature limited heater with ferromagnetic inner conductors. Each leg 792 has inner conductor 626, core 656, and jacket 636. Inner conductors 626 are ferritic stainless steel or 1% carbon steel. Inner conductors 626 have core 656. Core 656 may be copper. Each inner conductor 626 is coupled to its own jacket 636. Jacket 636 is a sheath made of a corrosion resistant material (such as 304H stainless steel). Electrical insulator 628 is placed between inner conductor 626 and jacket 636. Inner conductor 626 is ferritic stainless steel or carbon steel with an outside diameter of 1.14 cm and a thickness of 0.445 cm. Core 656 is a copper core with a 0.25 cm diameter. Each leg 792 of the heater is coupled to terminal block 794. Terminal block 794 is filled with insulation material 796 and has an outer surface of stainless steel. Insulation material 796 is, in some embodiments, silicon nitride, boron nitride, magnesium oxide or other suitable electrically insulating material. Inner conductors 626 of legs 792 are coupled (welded) in terminal block 794. Jackets 636 of legs 792 are coupled (welded) to an outer surface of terminal block 794. Terminal block 794 may include two halves coupled around the coupled portions of legs 792.

In an embodiment, the heated section of a three-phase heater is about 245 m long. The three-phase heater may be wye connected and operated at a current of about 150 A. The resistance of one leg of the heater may increase from about 1.1 ohms at room temperature to about 3.1 ohms at about 650° C. The resistance of one leg may decrease rapidly above about 720° C. to about 1.5 ohms. The voltage may increase from about 165 V at room temperature to about 465 V at 650° C. The voltage may decrease rapidly above about 720° C. to about 225 V. The heat output per leg may increase from about 102 watts/meter at room temperature to about 285 watts/meter at 650° C. The heat output per leg may decrease rapidly above about 720° C. to about 1.4 watts/meter. Other embodiments of inner conductor 626, core 656, jacket 636, and/or electrical insulator 628 may be used in the three-phase temperature limited heater shown in FIG. 117. Any embodiment of a single-phase temperature limited heater may be used as a leg of a three-phase temperature limited heater.

In some three-phase heater embodiments, three ferromagnetic conductors are separated by insulation inside a common outer metal sheath. The three conductors may be insulated from the sheath or the three conductors may be connected to the sheath at the bottom of the heater assembly. In another embodiment, a single outer sheath or three outer sheaths are ferromagnetic conductors and the inner conductors may be non-ferromagnetic (for example, aluminum, copper, or a highly conductive alloy). Alternatively, each of the three non-ferromagnetic conductors are inside a separate ferromagnetic sheath, and a connection between the conductors is made at the bottom of the heater inside a splice section. The three conductors may remain insulated from the sheath inside the splice section.

Figure 118:
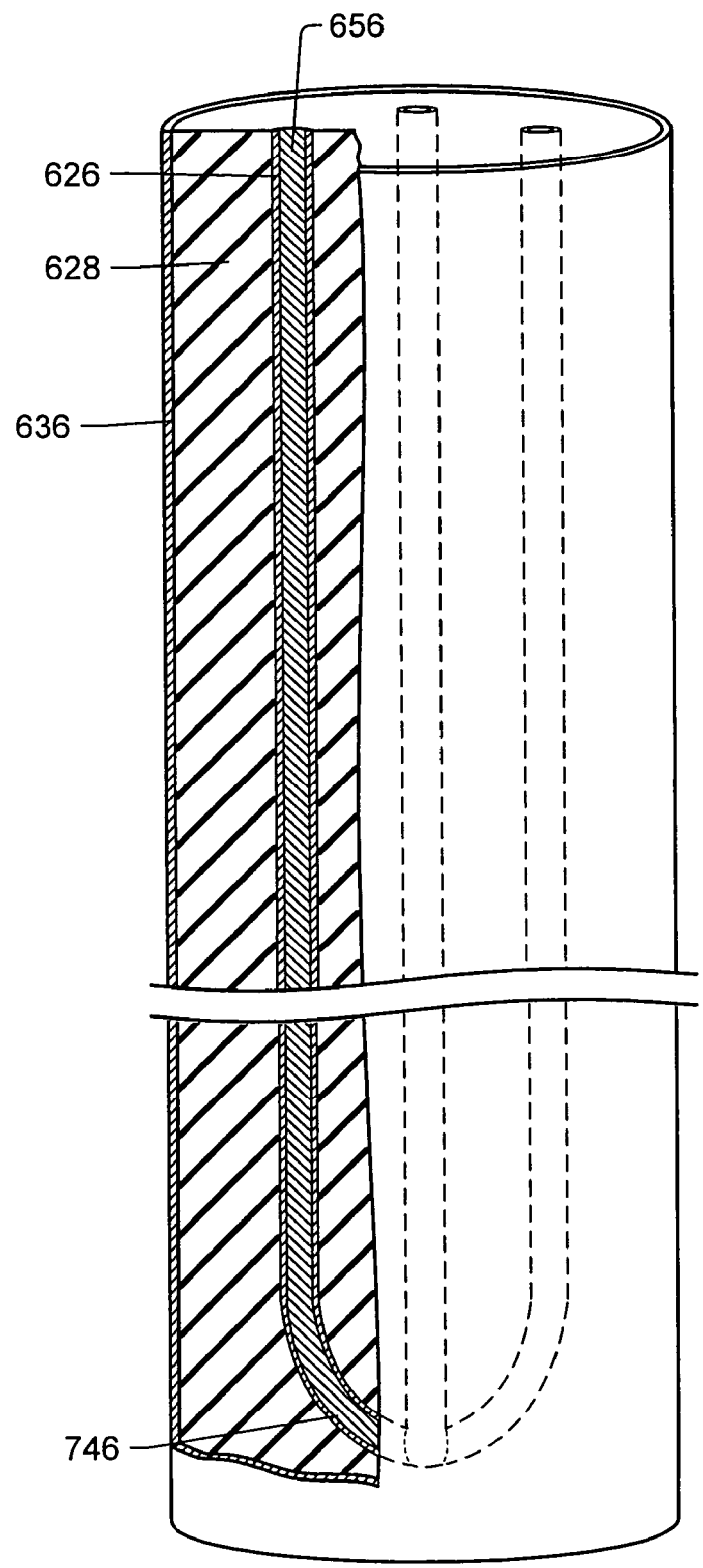
FIG. 118 depicts an embodiment of a three-phase temperature limited heater, with a portion shown in cross section.

FIG. 118 depicts an embodiment of a three-phase temperature limited heater with ferromagnetic inner conductors in a common jacket. Inner conductors 626 surround cores 656. Inner conductors 626 are placed in electrical insulator 628. Inner conductors 626 and electrical insulator 628 are placed in a single jacket 636. Jacket 636 is a sheath made of corrosion resistant material such as stainless steel. Jacket 636 has an outside diameter of between 2.5 cm and 5 cm (for example, 3.1 cm, 3.5 cm, or 3.8 cm). Inner conductors 626 are coupled at or near the bottom of the heater at termination 746. Termination 746 is a welded termination of inner conductors 626. Inner conductors 626 may be coupled in a wye configuration.

Figure 119:
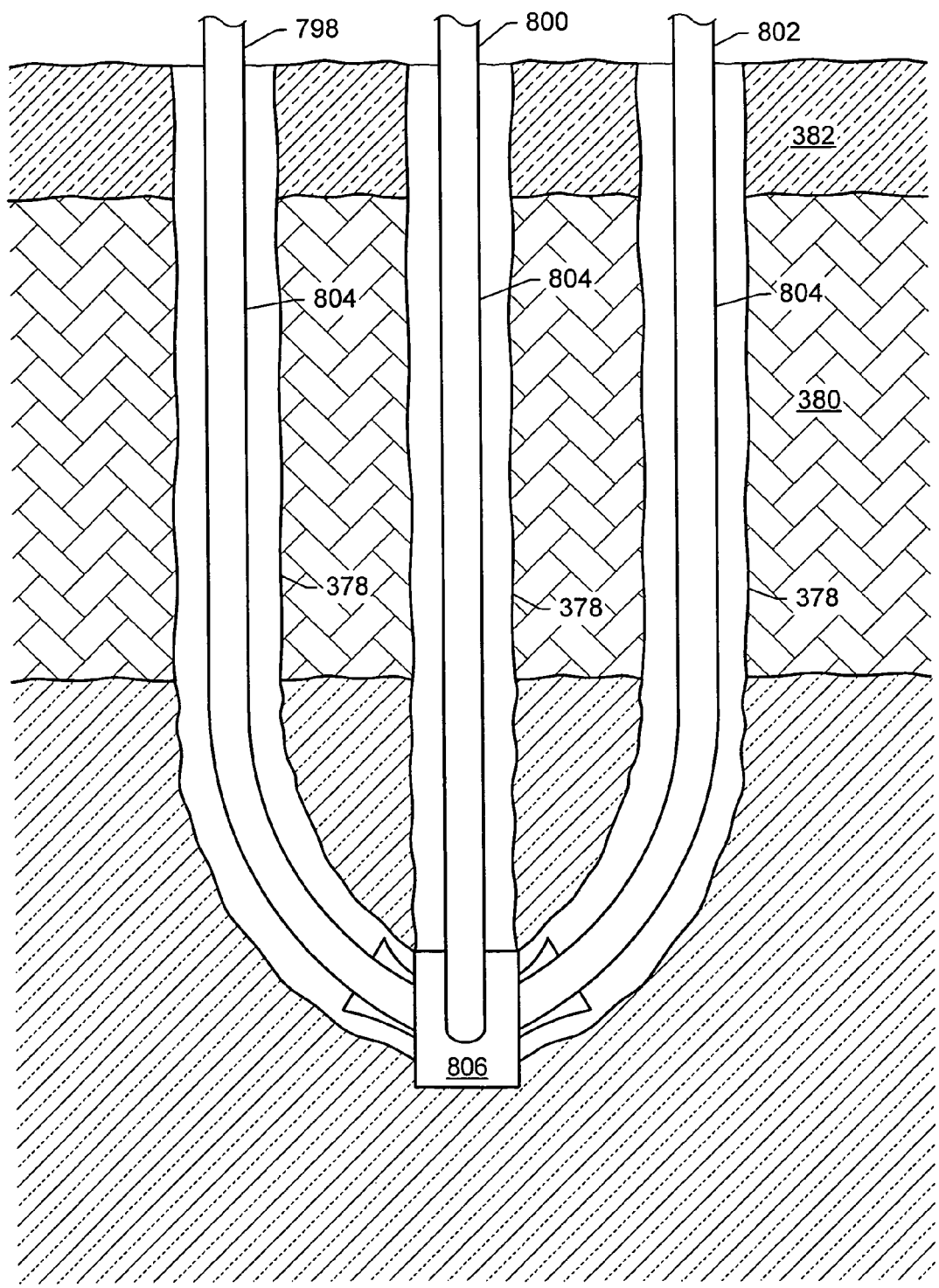
FIG. 119 depicts an embodiment of temperature limited heaters coupled together in a three-phase configuration.

In some embodiments, the three-phase heater includes three legs that are located in separate wellbores. The legs may be coupled in a common contacting section (for example, a central wellbore, a connecting wellbore, or a solution filled contacting section). FIG. 119 depicts an embodiment of temperature limited heaters coupled in a three-phase configuration. Each leg 798, 800, 802 may be located in separate openings 378 in hydrocarbon layer 380. Each leg 798, 800, 802 may include heating element 804. Each leg 798, 800, 802 may be coupled to single contacting element 806 in one opening 378. Contacting element 806 may electrically couple legs 798, 800, 802 together in a three-phase configuration. Contacting element 806 may be located in, for example, a central opening in the formation. Contacting element 806 may be located in a portion of opening 378 below hydrocarbon layer 380 (for example, in the underburden). In certain embodiments, magnetic tracking of a magnetic element located in a central opening (for example, opening 378 with leg 800) is used to guide the formation of the outer openings (for example, openings 378 with legs 798 and 802) so that the outer openings intersect the central opening. The central opening may be formed first using standard wellbore drilling methods. Contacting element 806 may include funnels, guides, or catchers for allowing each leg to be inserted into the contacting element.

Figure 120:
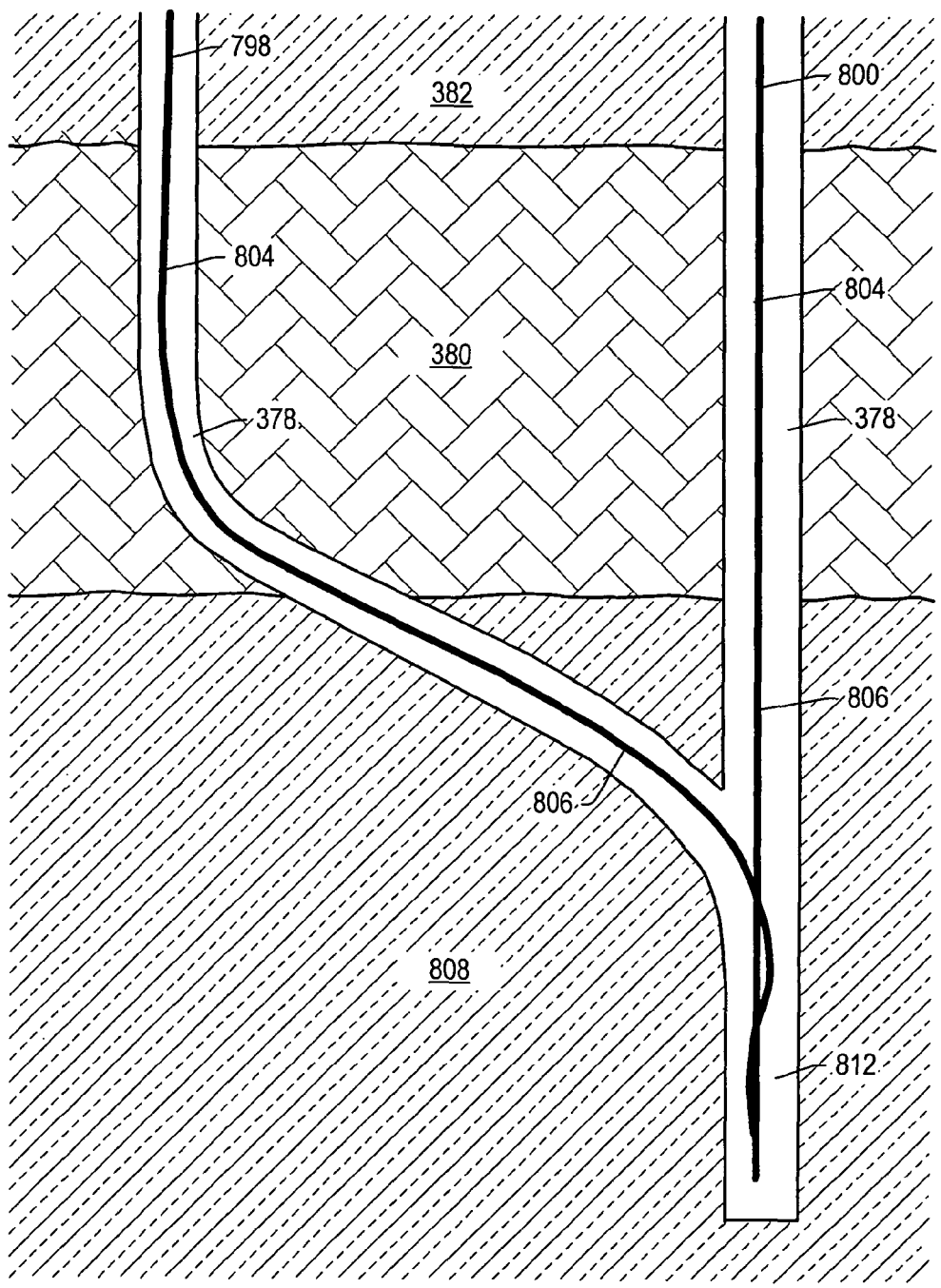
FIG. 120 depicts an embodiment of two temperature limited heaters coupled together in a single contacting section.

In certain embodiments, two legs in separate wellbores intercept in a single contacting section. FIG. 120 depicts an embodiment of two temperature limited heaters coupled in a single contacting section. Legs 798 and 800 include one or more heating elements 804. Heating elements 804 may include one or more electrical conductors. In certain embodiments, legs 798 and 800 are electrically coupled in a single-phase configuration with one leg positively biased versus the other leg so that current flows downhole through one leg and returns through the other leg.

Heating elements 804 in legs 798 and 800 may be temperature limited heaters. In certain embodiments, heating elements 804 are solid rod heaters. For example, heating elements 804 may be rods made of a single ferromagnetic conductor element or composite conductors that include ferromagnetic material. During initial heating when water is present in the formation being heated, heating elements 804 may leak current into hydrocarbon layer 380. The current leaked into hydrocarbon layer 380 may resistively heat the hydrocarbon layer.

In some embodiments (for example, in oil shale formations), heating elements 804 do not need support members. Heating elements 804 may be partially or slightly bent, curved, made into an S-shape, or made into a helical shape to allow for expansion and/or contraction of the heating elements. In certain embodiments, solid rod heating elements 804 are placed in small diameter wellbores (for example, about 3¾" (about 9.5 cm) diameter wellbores). Small diameter wellbores may be less expensive to drill or form than larger diameter wellbores, and there will be less cuttings to dispose of.

In certain embodiments, portions of legs 798 and 800 in overburden 382 have insulation (for example, polymer insulation) to inhibit heating the overburden. Heating elements 804 may be substantially vertical and substantially parallel to each other in hydrocarbon layer 380. At or near the bottom of hydrocarbon layer 380, leg 798 may be directionally drilled towards leg 800 to intercept leg 800 in contacting section 808. Directional drilling may be done by, for example, Vector Magnetics LLC (Ithaca, N.Y., U.S.A.). The depth of contacting section 808 depends on the length of bend in leg 798 needed to intercept leg 800. For example, for a 40 ft (about 12 m) spacing between vertical portions of legs 798 and 800, about 200 ft (about 61 m) is needed to allow the bend of leg 798 to intercept leg 800.

Figure 121:
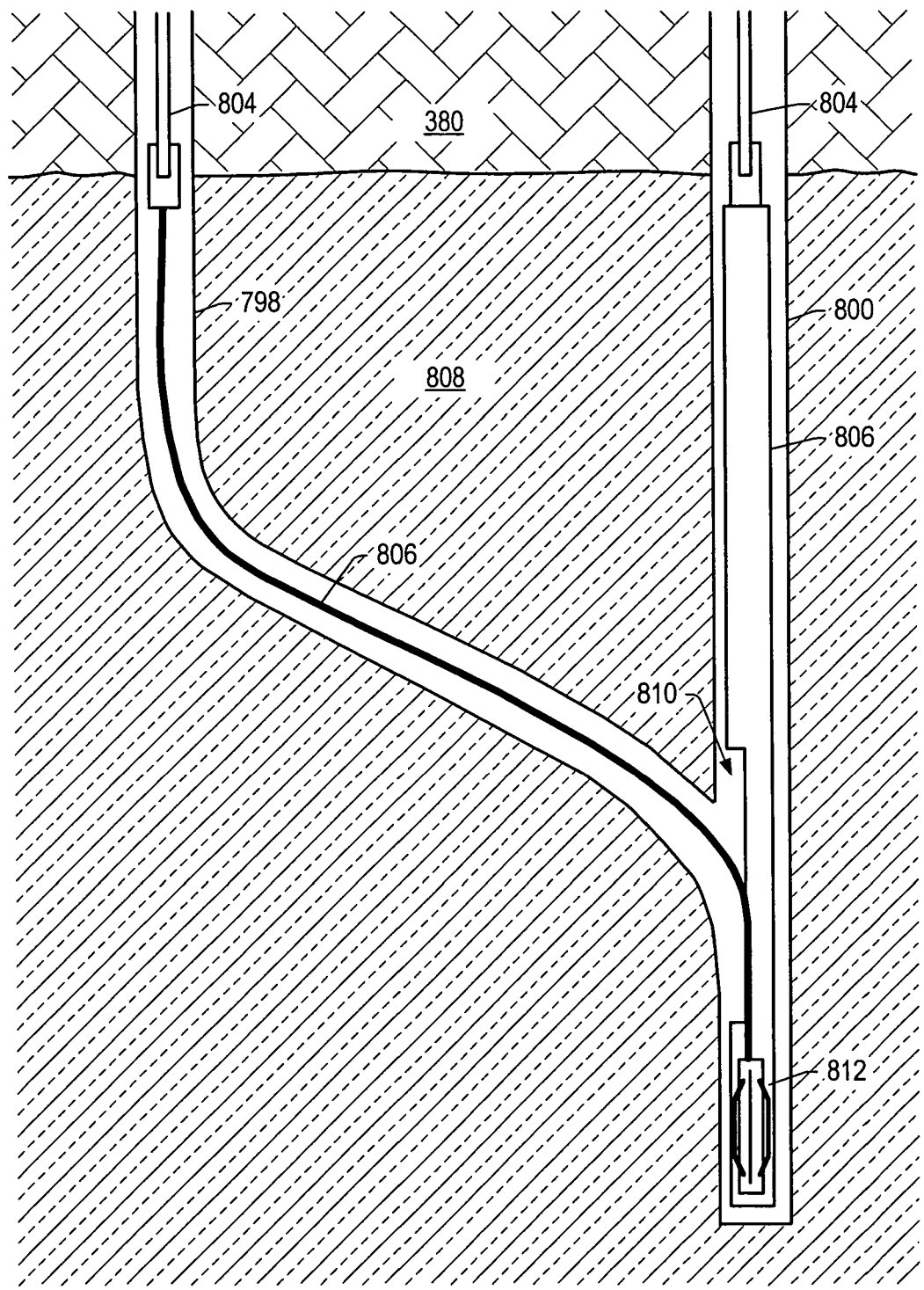
FIG. 121 depicts an embodiment of two temperature limited heaters with legs coupled in a contacting section.

FIG. 121 depicts an embodiment for coupling legs 798 and 800 in contacting section 808. Heating elements 804 are coupled to contacting elements 806 at or near junction of contacting section 808 and hydrocarbon layer 380. Contacting elements 806 may be copper or another suitable electrical conductor. In certain embodiments, contacting element 806 in leg 800 is a liner with opening 810. Contacting element 806 from leg 798 passes through opening 810. Contactor 812 is coupled to the end of contacting element 806 from leg 798. Contactor 812 provides electrical coupling between contacting elements in legs 798 and 800.

Figure 122:
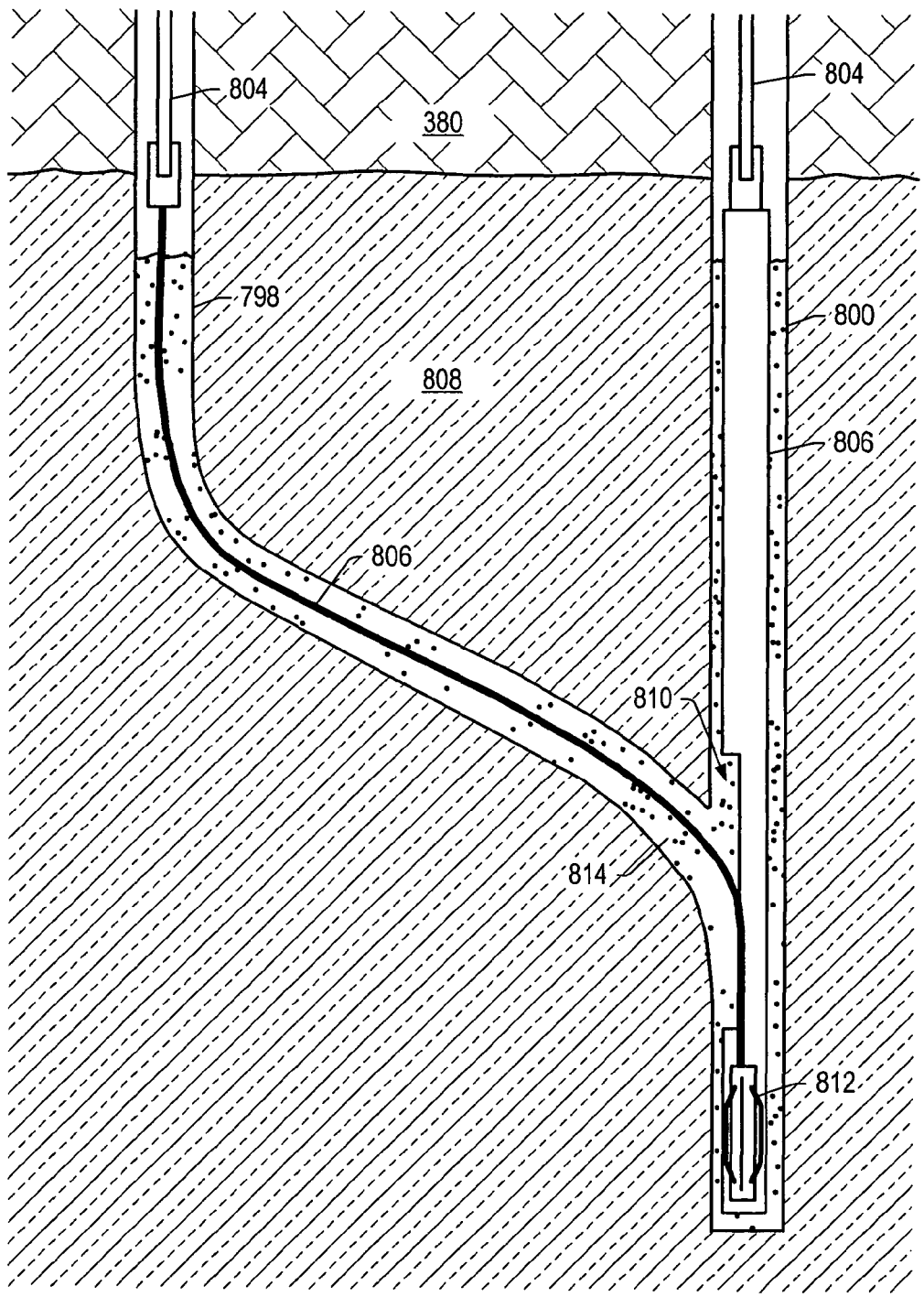
FIG. 122 depicts an embodiment of two temperature limited heaters with legs coupled in a contacting section with contact solution.

FIG. 122 depicts an embodiment for coupling legs 798 and 800 in contacting section 808 with contact solution 814 in the contacting section. Contact solution 814 is placed in portions of leg 798 and/or portions of leg 800 with contacting elements 806. Contact solution 814 promotes electrical contact between contacting elements 806. Contact solution 814 may be graphite based cement or another high electrical conductivity cement or solution (for example, brine or other ionic solutions).

Figure 123:
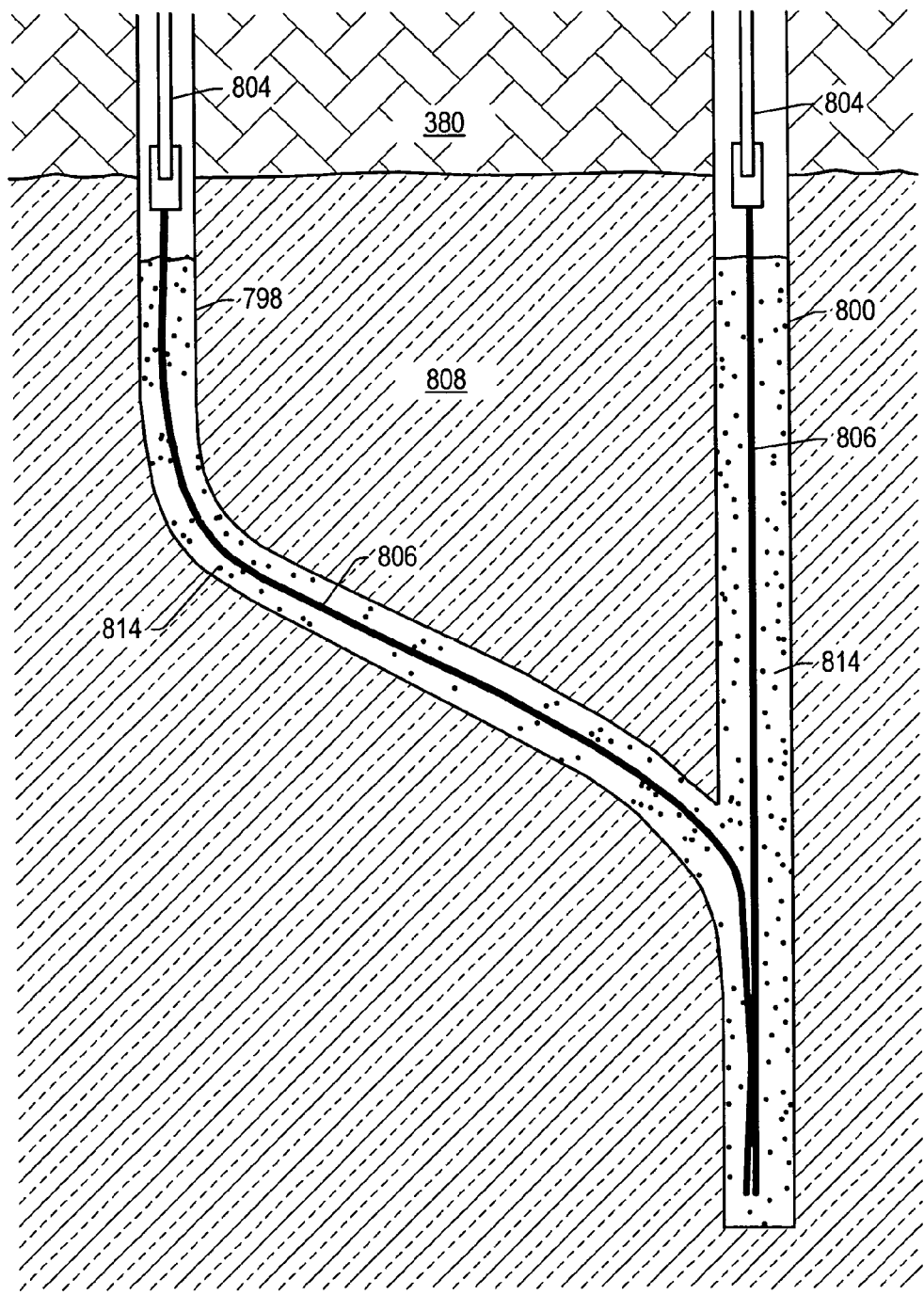
FIG. 123 depicts an embodiment of two temperature limited heaters with legs coupled without a contactor in a contacting section.

In some embodiments, electrical contact is made between contacting elements 806 using only contact solution 814. FIG. 123 depicts an embodiment for coupling legs 798 and 800 in contacting section 808 without contactor 812. Contacting elements 806 may or may not touch in contacting section 808. Electrical contact between contacting elements 806 in contacting section 808 is made using contact solution 814.

In certain embodiments, contacting elements 806 include one or more fins or projections. The fins or projections may increase an electrical contact area of contacting elements 806. In some embodiments, legs 798 and 800 (for example, electrical conductors in heating elements 804) are electrically coupled but do not physically contact each other. This type of electrical coupling may be accomplished with, for example, contact solution 814.

FIG. 124 depicts an embodiment of three heaters coupled in a three-phase configuration. Conductor "legs" 798, 800, 802 are coupled to three-phase transformer 816. Transformer 816 may be an isolated three-phase transformer. In certain embodiments, transformer 816 provides three-phase output in a wye configuration, as shown in FIG. 124. Input to transformer 816 may be made in any input configuration (such as the delta configuration shown in FIG. 124). Legs 798, 800, 802 each include lead-in conductors 692 in the overburden of the formation coupled to heating elements 804 in hydrocarbon layer 380. Lead-in conductors 692 include copper with an insulation layer. For example, lead-in conductors 692 may be a 4-0 copper cables with TEFLON® insulation, a copper rod with polyurethane insulation, or other metal conductors such as bare copper or aluminum. In certain embodiments, lead-in conductors 692 are located in an overburden portion of the formation. The overburden portion may include overburden casings 680. Heating elements 804 may be temperature limited heater heating elements. In an embodiment, heating elements 804 are 410 stainless steel rods (for example, 3.1 cm diameter 410 stainless steel rods). In some embodiments, heating elements 804 are composite temperature limited heater heating elements (for example, 347 stainless steel, 410 stainless steel, copper composite heating elements; 347 stainless steel, iron, copper composite heating elements; or 410 stainless steel and copper composite heating elements). In certain embodiments, heating elements 804 have a length of at least about 10 m to about 2000 m, about 20 m to about 400 m, or about 30 m to about 300 m.

In certain embodiments, heating elements 804 are exposed to hydrocarbon layer 380 and fluids from the hydrocarbon layer. Thus, heating elements 804 are "bare metal" or "exposed metal" heating elements. Heating elements 804 may be made from a material that has an acceptable sulfidation rate at high temperatures used for pyrolyzing hydrocarbons. In certain embodiments, heating elements 804 are made from material that has a sulfidation rate that decreases with increasing temperature over at least a certain temperature range (for example, 530° C. to 650° C.), such as 410 stainless steel. Using such materials reduces corrosion problems due to sulfur-containing gases (such as $H_2S$) from the formation. Heating elements 804 may also be substantially inert to galvanic corrosion.

In some embodiments, heating elements 804 have a thin electrically insulating layer such as aluminum oxide or thermal spray coated aluminum oxide. In some embodiments, the thin electrically insulating layer is a ceramic composition such as an enamel coating. Enamel coatings include, but are not limited to, high temperature porcelain enamels. High temperature porcelain enamels may include silicon dioxide, boron oxide, alumina, and alkaline earth oxides (CaO or MgO), and minor amounts of alkali oxides ($Na_2O$, $IC_2O$, LiO). The enamel coating may be applied as a finely ground slurry by dipping the heating element into the slurry or spray coating the heating element with the slurry. The coated heating element is then heated in a furnace until the glass transition temperature is reached so that the slurry spreads over the surface of the heating element and makes the porcelain enamel coating. The porcelain enamel coating contracts when cooled below the glass transition temperature so that the coating is in compression. Thus, when the coating is heated during operation of the heater, the coating is able to expand with the heater without cracking.

The thin electrically insulating layer has low thermal impedance allowing heat transfer from the heating element to the formation while inhibiting current leakage between heating elements in adjacent openings and/or current leakage into the formation. In certain embodiments, the thin electrically insulating layer is stable at temperatures above at least 350° C., above 500° C., or above 800° C. In certain embodiments, the thin electrically insulating layer has an emissivity of at least 0.7, at least 0.8, or at least 0.9. Using the thin electrically insulating layer may allow for long heater lengths in the formation with low current leakage.

Heating elements 804 may be coupled to contacting elements 806 at or near the underburden of the formation. Contacting elements 806 are copper or aluminum rods or other highly conductive materials. In certain embodiments, transition sections 818 are located between lead-in conductors 692 and heating elements 804, and/or between heating elements 804 and contacting elements 806. Transition sections 818 may be made of a conductive material that is corrosion resistant such as 347 stainless steel over a copper core. In certain embodiments, transition sections 818 are made of materials that electrically couple lead-in conductors 692 and heating elements 804 while providing little or no heat output. Thus, transition sections 818 help to inhibit overheating of conductors and insulation used in lead-in conductors 692 by spacing the lead-in conductors from heating elements 804. Transition section 818 may have a length of between about 3 m and about 9 m (for example, about 6 m).

Contacting elements 806 are coupled to contactor 812 in contacting section 808 to electrically couple legs 798, 800, 802 to each other. In some embodiments, contact solution 814 (for example, conductive cement) is placed in contacting section 808 to electrically couple contacting elements 806 in the contacting section. In certain embodiments, legs 798, 800, 802 are substantially parallel in hydrocarbon layer 380 and leg 798 continues substantially vertically into contacting section 808. The other two legs 800, 802 are directed (for example, by directionally drilling the wellbores for the legs) to intercept leg 798 in contacting section 808.

Each leg 798, 800, 802 may be one leg of a three-phase heater embodiment so that the legs are substantially electrically isolated from other heaters in the formation and are substantially electrically isolated from the formation. Legs 798, 800, 802 may be arranged in a triangular pattern so that the three legs form a triangular shaped three-phase heater. In an embodiment, legs 798, 800, 802 are arranged in a triangular pattern with 12 m spacing between the legs (each side of the triangle has a length of 12 m).

Figure 125:
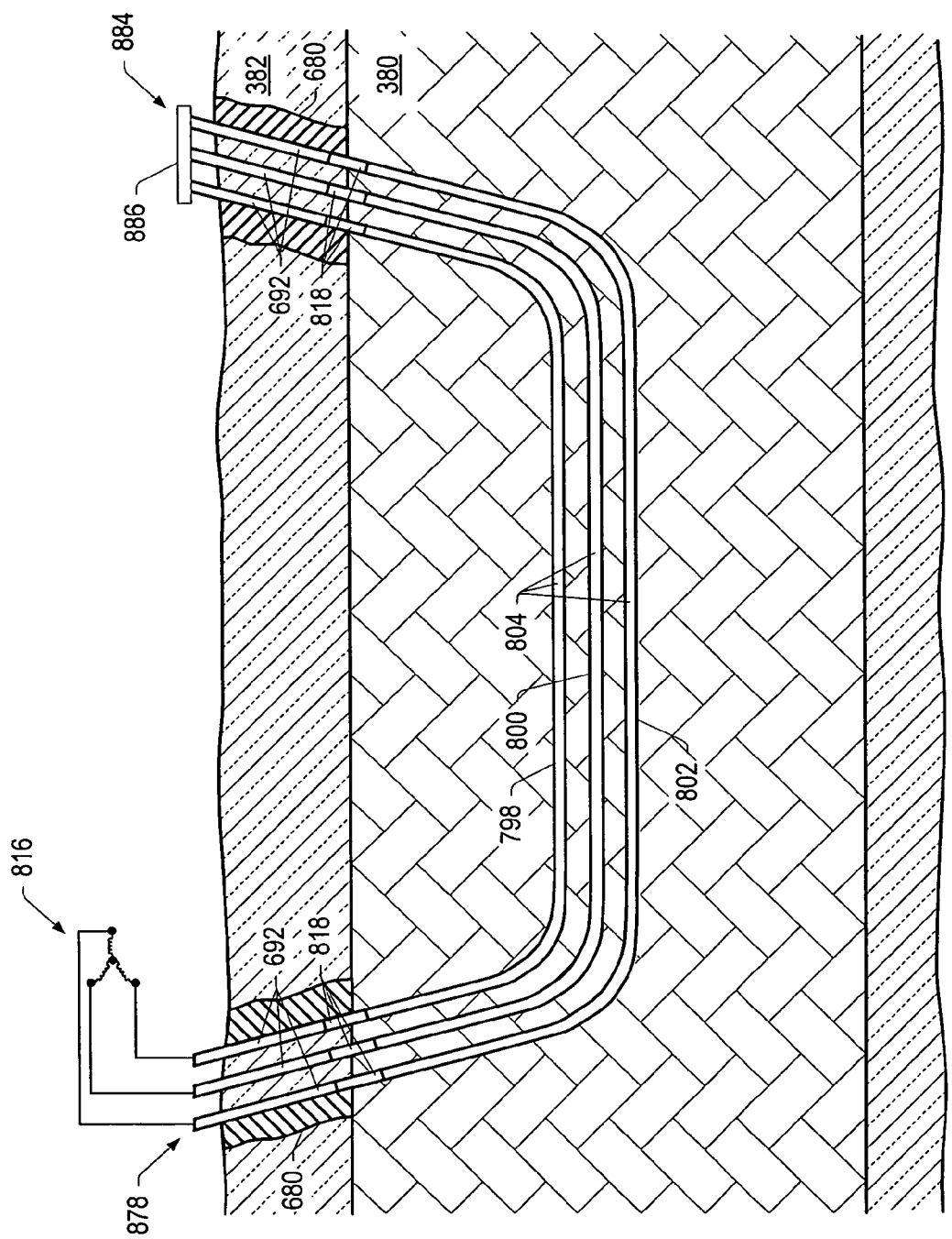
FIG. 125 depicts a side view representation of an embodiment of a substantially u-shaped three-phase heater.

In certain embodiments, the thin electrically insulating layer allows for relatively long, substantially horizontal heater leg lengths in the hydrocarbon layer with a substantially u-shaped heater. FIG. 125 depicts a side-view representation of an embodiment of a substantially u-shaped three-phase heater. First ends of legs 798, 800, 802 are coupled to transformer 816 at first location 878. In an embodiment, transformer 816 is a three-phase AC transformer. Ends of legs 798, 800, 802 are electrically coupled together with connector 886 at second location 884. Connector 886 electrically couples the ends of legs 798, 800, 802 so that the legs can be operated in a three-phase configuration. In certain embodiments, legs 798, 800, 802 are coupled to operate in a three-phase wye configuration. In certain embodiments, legs 798, 800, 802 are substantially parallel in hydrocarbon layer 380. In certain embodiments, legs 798, 800, 802 are arranged in a triangular pattern in hydrocarbon layer 380. In certain embodiments, heating elements 804 include a thin electrically insulating material (such as a porcelain enamel coating) to inhibit current leakage from the heating elements. In certain embodiments, legs 798, 800, 802 are electrically coupled so that the legs are substantially electrically isolated from other heaters in the formation and are substantially electrically isolated from the formation.

In certain embodiments, overburden casings (for example, overburden casings 680, depicted in FIGS. 124 and 125) in overburden 382 include materials that inhibit ferromagnetic effects in the casings. Inhibiting ferromagnetic effects in casings 680 reduces heat losses to the overburden. In some embodiments, casings 680 may include non-metallic materials such as fiberglass, polyvinylchloride (PVC), chlorinated polyvinylchloride (CPVC), or high-density polyethylene (HDPE). HDPEs with working temperatures in a range for use in overburden 382 include HDPEs available from Dow Chemical Co., Inc. (Midland, Mich., U.S.A.). A non-metallic casing may also eliminate the need for an insulated overburden conductor. In some embodiments, casings 680 include carbon steel coupled on the inside diameter of a non-ferromagnetic metal (for example, carbon steel clad with copper or aluminum) to inhibit ferromagnetic effects or inductive effects in the carbon steel. Other non-ferromagnetic metals include, but are not limited to, manganese steels with at least 10% by weight manganese, iron aluminum alloys with at least 18% by weight aluminum, and austentitic stainless steels such as 304 stainless steel or 316 stainless steel.

In certain embodiments, one or more non-ferromagnetic materials used in casings 680 are used in a wellhead coupled to the casings and legs 798, 800, 802. Using non-ferromagnetic materials in the wellhead inhibits undesirable heating of components in the wellhead. In some embodiments, a purge gas (for example, carbon dioxide, nitrogen or argon) is introduced into the wellhead and/or inside of casings 680 to inhibit reflux of heated gases into the wellhead and/or the casings.

In certain embodiments, one or more of legs 798, 800, 802 are installed in the formation using coiled tubing. In certain embodiments, coiled tubing is installed in the formation, the leg is installed inside the coiled tubing, and the coiled tubing is pulled out of the formation to leave the leg installed in the formation. The leg may be placed concentrically inside the coiled tubing. In some embodiments, coiled tubing with the leg inside the coiled tubing is installed in the formation and the coiled tubing is removed from the formation to leave the leg installed in the formation. The coiled tubing may extend only to a junction of hydrocarbon layer 380 and contacting section 808 or to a point at which the leg begins to bend in the contacting section.

FIG. 126 depicts a top view representation of an embodiment of a plurality of triads of three-phase heaters in the formation. Each triad 820 includes legs A, B, C (which may correspond to legs 798, 800, 802 depicted in FIGS. 124 and 125) that are electrically coupled by linkage 822. Each triad 820 is coupled to its own electrically isolated three-phase transformer so that the triads are substantially electrically isolated from each other. Electrically isolating the triads inhibits net current flow between triads.

The phases of each triad 820 may be arranged so that legs A, B, C correspond between triads as shown in FIG. 126. In FIG. 126, legs A, B, C are arranged such that a phase leg (for example, leg A) in a given triad is about two triad heights from a same phase leg (leg A) in an adjacent triad. The triad height is the distance from a vertex of the triad to a midpoint of the line intersecting the other two vertices of the triad. In certain embodiments, the phases of triads 820 are arranged to inhibit net current flow between individual triads. There may be some leakage of current within an individual triad but little net current flows between two triads due to the substantial electrical isolation of the triads and, in certain embodiments, the arrangement of the triad phases.

In the early stages of heating, an exposed heating element (for example, heating element 804 depicted in FIGS. 124 and 125) may leak some current to water or other fluids that are electrically conductive in the formation so that the formation itself is heated. After water or other electrically conductive fluids are removed from the wellbore (for example, vaporized or produced), the heating elements become electrically isolated from the formation. Later, when water is removed from the formation, the formation becomes even more electrically resistant and heating of the formation occurs even more predominantly via thermally conductive and/or radiative heating. Typically, the formation (the hydrocarbon layer) has an initial electrical resistance that averages at least 10 ohm·m. In some embodiments, the formation has an initial electrical resistance of at least 100 ohm·m or of at least 300 ohm·m.

Using the temperature limited heaters as the heating elements limits the effect of water saturation on heater efficiency. With water in the formation and in heater wellbores, there is a tendency for electrical current to flow between heater elements at the top of the hydrocarbon layer where the voltage is highest and cause uneven heating in the hydrocarbon layer. This effect is inhibited with temperature limited heaters because the temperature limited heaters reduce localized overheating in the heating elements and in the hydrocarbon layer.

Figure 127:
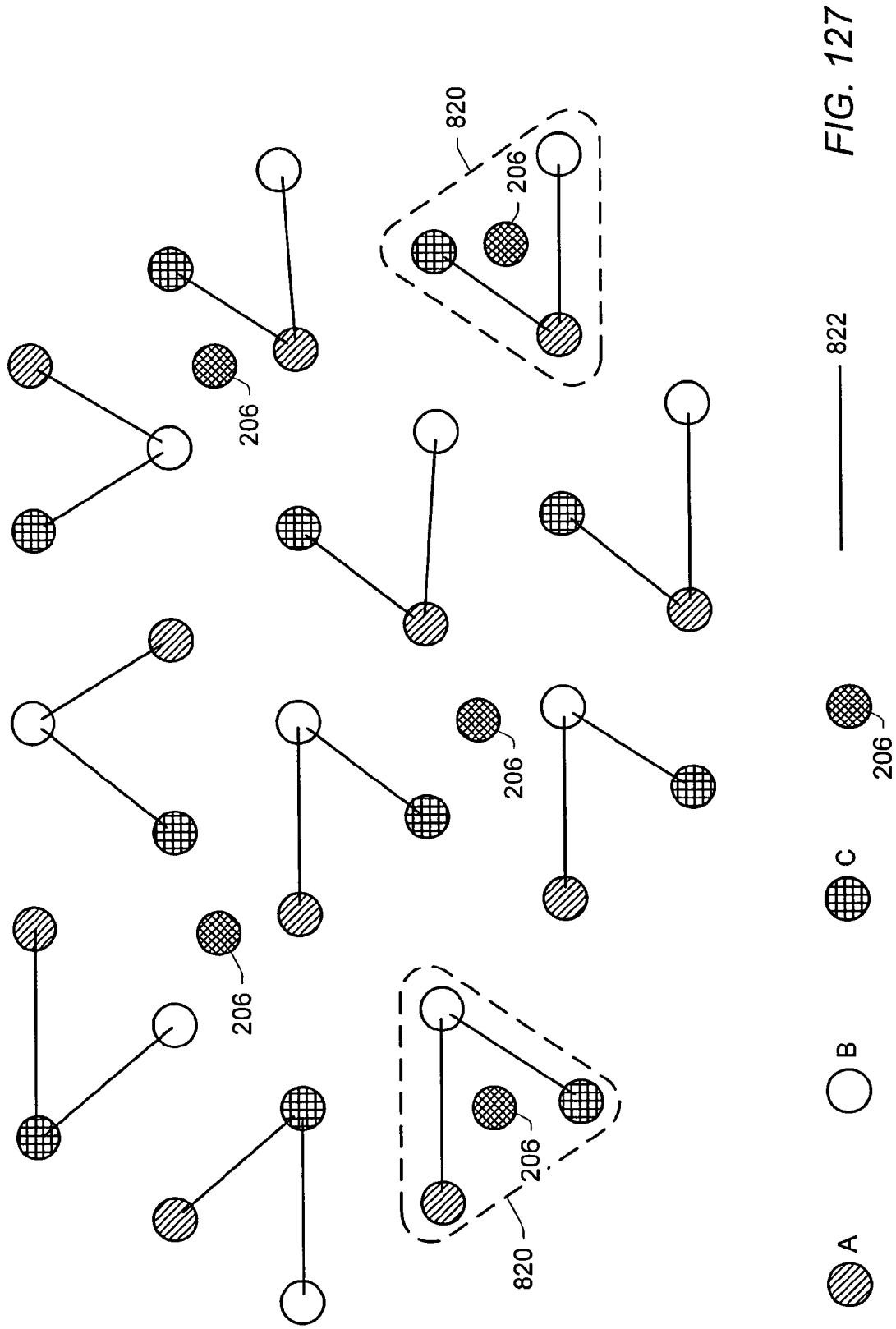
FIG. 127 depicts a top view representation of the embodiment depicted in FIG. 126 with production wells.

In certain embodiments, production wells are placed at a location at which there is relatively little or zero voltage potential. This location minimizes stray potentials at the production well. Placing production wells at such locations improves the safety of the system and reduces or inhibits undesired heating of the production wells caused by electrical current flow in the production wells. FIG. 127 depicts a top view representation of the embodiment depicted in FIG. 126 with production wells 206. In certain embodiments, production wells 206 are located at or near center of triad 820. In certain embodiments, production wells 206 are placed at a location between triads at which there is relatively little or zero voltage potential (at a location at which voltage potentials from vertices of three triads average out to relatively little or zero voltage potential). For example, production well 206 may be at a location equidistant from legs A of one triad, leg B of a second triad, and leg C of a third triad, as shown in FIG. 127.

FIG. 128 depicts a top view representation of an embodiment of a plurality of triads of three-phase heaters in a hexagonal pattern in the formation. FIG. 129 depicts a top view representation of an embodiment of a hexagon from FIG. 128. Hexagon 824 includes two triads of heaters. The first triad includes legs A1, B1, C1 electrically coupled together by linkages 822 in a three-phase configuration. The second triad includes legs A2, B2, C2 electrically coupled together by linkages 822 in a three-phase configuration. The triads are arranged so that corresponding legs of the triads (for example, A1 and A2, B1 and B2, C1 and C2) are at opposite vertices of hexagon 824. The triads are electrically coupled and arranged so that there is relatively little or zero voltage potential at or near the center of hexagon 824.

Production well 206 may be placed at or near the center of hexagon 824. Placing production well 206 at or near the center of hexagon 824 places the production well at a location that reduces or inhibits undesired heating due to electromagnetic effects caused by electrical current flow in the legs of the triads and increases the safety of the system. Having two triads in hexagon 824 provides for redundant heating around production well 206. Thus, if one triad fails or has to be turned off, production well 206 still remains at a center of one triad.

As shown in FIG. 128, hexagons 824 may be arranged in a pattern in the formation such that adjacent hexagons are offset. Using electrically isolated transformers on adjacent hexagons may inhibit electrical potentials in the formation so that little or no net current leaks between hexagons.

Triads of heaters and/or heater legs may be arranged in any shape or desired pattern. For example, as described above, triads may include three heaters and/or heater legs arranged in a equilateral triangular pattern. In some embodiments, triads include three heaters and/or heater legs arranged in other triangular shapes (for example, an isosceles triangle or a right angle triangle). In some embodiments, heater legs in the triad cross each other (for example, criss-cross) in the formation. In certain embodiments, triads includes three heaters and/or heater legs arranged sequentially along a straight line.

FIG. 130 depicts an embodiment with triads coupled to a horizontal connector well. Triad 820A includes legs 798A, 800A, 802A. Triad 820B includes legs 798B, 800B, 802B. Legs 798A, 800A, 802A and legs 798B, 800B, 802B may be arranged along a straight line on the surface of the formation. In some embodiments, legs 798A, 800A, 802A are arranged along a straight line and offset from legs 798B, 800B, 802B, which may be arranged along a straight line. Legs 798A, 800A, 802A and legs 798B, 800B, 802B include heating elements 804 located in hydrocarbon layer 380. Lead-in conductors 692 couple heating elements 804 to the surface of the formation. Heating elements 804 are coupled to contacting elements 806 at or near the underburden of the formation. In certain embodiments, transition sections (for example, transition sections 818 depicted in FIG. 124) are located between lead-in conductors 692 and heating elements 804, and/or between heating elements 804 and contacting elements 806.

Contacting elements 806 are coupled to contactor 812 in contacting section 808 to electrically couple legs 798A, 800A, 802A to each other to form triad 820A and electrically couple legs 798B, 800B, 802B to each other to form triad 820B. In certain embodiments, contactor 812 is a ground conductor so that triad 820A and/or triad 820B may be coupled in three-phase wye configurations. In certain embodiments, triad 820A and triad 820B are electrically isolated from each other. In some embodiments, triad 820A and triad 820B are electrically coupled to each other (for example, electrically coupled in series or parallel).

In certain embodiments, contactor 812 is a substantially horizontal contactor located in contacting section 808. Contactor 812 may be a casing or a solid rod placed in a wellbore drilled substantially horizontally in contacting section 808. Legs 798A, 800A, 802A and legs 798B, 800B, 802B may be electrically coupled to contactor 812 by any method described herein or any method known in the art. For example, containers with thermite powder are coupled to contactor 812 (for example, by welding or brazing the containers to the contactor), legs 798A, 800A, 802A and legs 798B, 800B, 802B are placed inside the containers, and the thermite powder is activated to electrically couple the legs to the contactor. The containers may be coupled to contactor 812 by, for example, placing the containers in holes or recesses in contactor 812 or coupled to the outside of the contactor and then brazing or welding the containers to the contactor.

Figure 131:
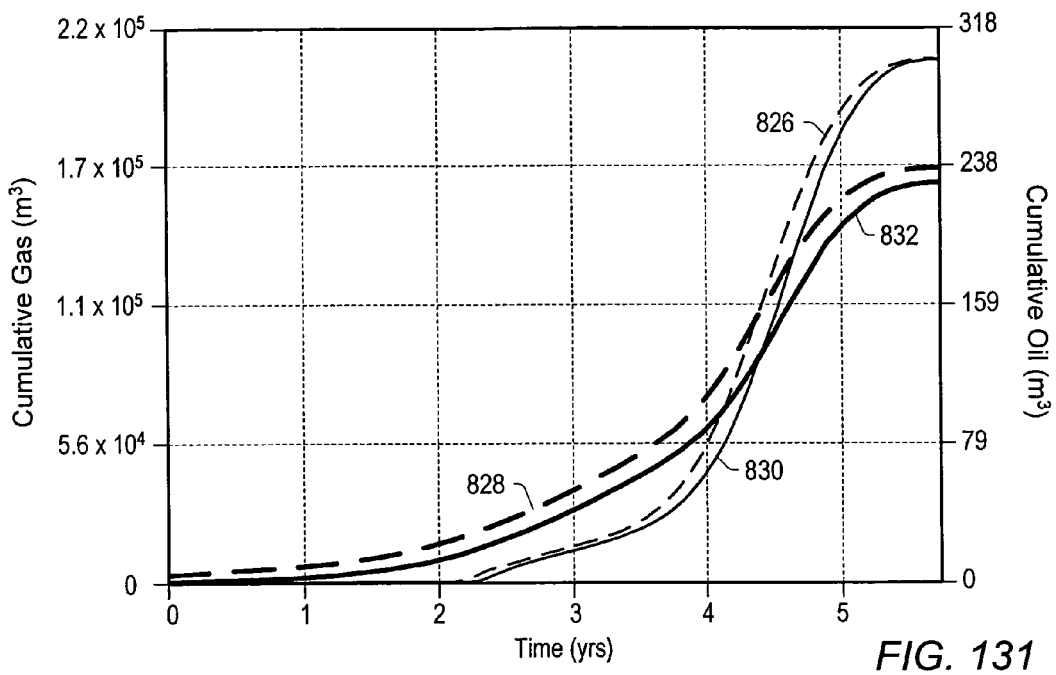
FIG. 131 depicts cumulative gas production and cumulative oil production versus time found from a STARS simulation using the heaters and heater pattern depicted in FIGS. 124 and 126.

FIG. 131 depicts cumulative gas production and cumulative oil production versus time (years) found from a STARS simulation (Computer Modelling Group, LTD., Calgary, Alberta, Canada) using the temperature limited heaters and heater pattern depicted in FIGS. 124 and 126. Curve 826 depicts cumulative oil production ($m^3$) for an initial water saturation of 15%. Curve 828 depicts cumulative gas production ($m^3$) for the initial water saturation of 15%. Curve 830 depicts cumulative oil production ($m^3$) for an initial water saturation of 85%. Curve 832 depicts cumulative gas production ($m^3$) for the initial water saturation of 85%. As shown by the small differences between curves 826 and 830 for cumulative oil production and curves 828 and 832 for cumulative gas production, the initial water saturation does not substantially alter heating of the formation. As a result, the overall production of hydrocarbons from the formation is also not substantially changed by the initial water saturation: Using the temperature limited heaters inhibits variances in heating of the formation that otherwise may be caused by the differences in the initial water saturation.

Figures 132, 133, 134:
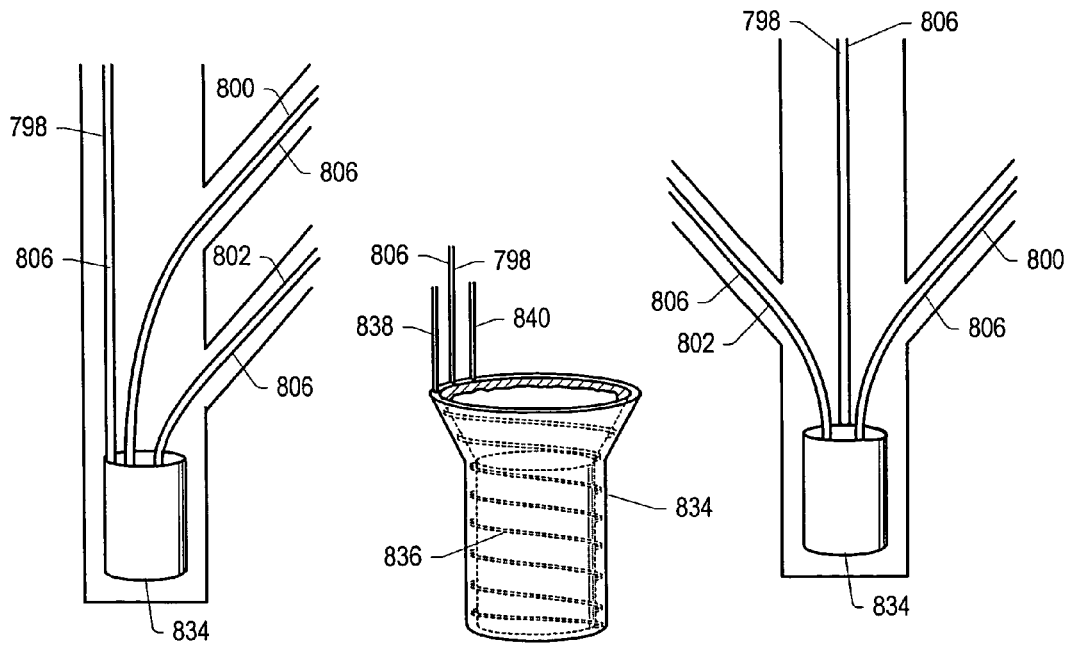
FIGS. 132 and 133 depict embodiments for coupling contacting elements of three legs of a heater.
FIG. 134 depicts an embodiment of a container with an initiator for melting the coupling material.

As shown in FIG. 124, contacting elements 806 of legs 798, 800, 802 may be coupled using contactor 812 and/or contact solution 814. In certain embodiments, contacting elements 806 of legs 798, 800, 802 are physically coupled, for example, through soldering, welding, or other techniques. FIGS. 132 and 133 depict embodiments for coupling contacting elements 806 of legs 798, 800, 802. Legs 800, 802 may enter the wellbore of leg 798 from any direction desired. In one embodiment, legs 800, 802 enter the wellbore of leg 798 from approximately the same side of the wellbore, as shown in FIG. 132. In an alternative embodiment, legs 800, 802 enter the wellbore of leg 798 from approximately opposite sides of the wellbore, as shown in FIG. 133.

Container 834 is coupled to contacting element 806 of leg 798. Container 834 may be soldered, welded, or otherwise electrically coupled to contacting element 806. Container 834 is a metal can or other container with at least one opening for receiving one or more contacting elements 806. In an embodiment, container 834 is a can that has an opening for receiving contacting elements 806 from legs 800, 802, as shown in FIG. 132. In certain embodiments, wellbores for legs 800, 802 are drilled parallel to the wellbore for leg 798 through the hydrocarbon layer that is to be heated and directionally drilled below the hydrocarbon layer to intercept wellbore for leg 798 at an angle between about 10° and about 20° from vertical. Wellbores may be directionally drilled using known techniques such as techniques used by Vector Magnetics, Inc.

In some embodiments, contacting elements 806 contact the bottom of container 834. Contacting elements 806 may contact the bottom of container 834 and/or each other to promote electrical connection between the contacting elements and/or the container. In certain embodiments, end portions of contacting elements 806 are annealed to a "dead soft" condition to facilitate entry into container 834. In some embodiments, rubber or other softening material is attached to end portions of contacting elements 806 to facilitate entry into container 834. In some embodiments, contacting elements 806 include reticulated sections, such as knuckle-joints or limited rotation knuckle-joints, to facilitate entry into container 834.

In certain embodiments, an electrical coupling material is placed in container 834. The electrical coupling material may line the walls of container 834 or fill up a portion of the container. In certain embodiments, the electrical coupling material lines an upper portion, such as the funnel-shaped portion shown in FIG. 134, of container 834. The electrical coupling material includes one or more materials that when activated (for example, heated, ignited, exploded, combined, mixed, and/or reacted) form a material that electrically couples one or more elements to each other. In an embodiment, the coupling material electrically couples contacting elements 806 in container 834. In some embodiments, the coupling material metallically bonds to contacting elements 806 so that the contacting elements are metallically bonded to each other. In some embodiments, container 834 is initially filled with a high viscosity water-based polymer fluid to inhibit drill cuttings or other materials from entering the container prior to using the coupling material to couple the contacting elements. The polymer fluid may be, but is not limited to, a cross-linked XC polymer (available from Baroid Industrial Drilling Products (Houston, Tex., U.S.A.), a frac gel, or a cross-linked polyacrylamide gel.

In certain embodiments, the electrical coupling material is a low-temperature solder that melts at relatively low temperature and when cooled forms an electrical connection to exposed metal surfaces. In certain embodiments, the electrical coupling material is a solder that melts at a temperature below the boiling point of water at the depth of container 834. In one embodiment, the electrical coupling material is a 58% by weight bismuth and 42% by weight tin eutectic alloy: Other examples of such solders include, but are not limited to, a 54% by weight bismuth, 16% by weight tin, 30% by weight indium alloy, and a 48% by weight tin, 52% by weight indium alloy. Such low-temperature solders will displace water upon melting so that the water moves to the top of container 834. Water at the top of container 834 may inhibit heat transfer into the container and thermally insulate the low-temperature solder so that the solder remains at cooler temperatures and does not melt during heating of the formation using the heating elements.

Container 834 may be heated to activate the electrical coupling material to facilitate the connection of contacting elements 806. In certain embodiments, container 834 is heated to melt the electrical coupling material in the container. The electrical coupling material flows when melted and surrounds contacting elements 806 in container 834. Any water within container 834 will float to the surface of the metal when the metal is melted. The electrical coupling material is allowed to cool and electrically connects contacting elements 806 to each other. In certain embodiments, contacting elements 806 of legs 800, 802, the inside walls of container 834, and/or the bottom of the container are initially pre-tinned with electrical coupling material.

End portions of contacting elements 806 of legs 798, 800, 802 may have shapes and/or features that enhance the electrical connection between the contacting elements and the coupling material. The shapes and/or features of contacting elements 806 may also enhance the physical strength of the connection between the contacting elements and the coupling material (for example, the shape and/or features of the contacting element may anchor the contacting element in the coupling material). Shapes and/or features for end portions of contacting elements 806 include, but are not limited to, grooves, notches, holes, threads, serrated edges, openings, and hollow end portions. In certain embodiments, the shapes and/or features of the end portions of contacting elements 806 are initially pre-tinned with electrical coupling material.

FIG. 134 depicts an embodiment of container 834 with an initiator for melting the coupling material. The initiator is an electrical resistance heating element or any other element for providing heat that activates or melts the coupling material in container 834. In certain embodiments, heating element 836 is a heating element located in the walls of container 834. In some embodiments, heating element 836 is located on the outside of container 834. Heating element 836 may be, for example, a nichrome wire, a mineral-insulated conductor, a polymer-insulated conductor, a cable, or a tape that is inside the walls of container 834 or on the outside of the container. In some embodiments, heating element 836 wraps around the inside walls of the container or around the outside of the container. Lead-in wire 838 may be coupled to a power source at the surface of the formation. Lead-out wire 840 may be coupled to the power source at the surface of the formation. Lead-in wire 838 and/or lead-out wire 840 may be coupled along the length of leg 798 for mechanical support. Lead-in wire 838 and/or lead-out wire 840 may be removed from the wellbore after melting the coupling material. Lead-in wire 838 and/or lead-out wire 840 may be reused in other wellbores.

In some embodiments, container 834 has a funnel-shape, as shown in FIG. 134, that facilitates the entry of contacting elements 806 into the container. In certain embodiments, container 834 is made of or includes copper for good electrical and thermal conductivity. A copper container 834 makes good electrical contact with contacting elements (such as contacting elements 806 shown in FIGS. 132 and 133) if the contacting elements touch the walls and/or bottom of the container.

FIG. 135 depicts an embodiment of container 834 with bulbs on contacting elements 806. Protrusions 842 may be coupled to a lower portion of contacting elements 806. Protrusions 844 may be coupled to the inner wall of container 834. Protrusions 842, 844 may be made of copper or another suitable electrically conductive material. Lower portion of contacting element 806 of leg 802 may have a bulbous shape, as shown in FIG. 135. In certain embodiments, contacting element 806 of leg 802 is inserted into container 834. Contacting element 806 of leg 800 is inserted after insertion of contacting element 806 of leg 802. Both legs may then be pulled upwards simultaneously. Protrusions 842 may lock contacting elements 806 into place against protrusions 844 in container 834. A friction fit is created between contacting elements 806 and protrusions 842, 844.

Lower portions of contacting elements 806 inside container 834 may include 410 stainless steel or any other heat generating electrical conductor. Portions of contacting elements 806 above the heat generating portions of the contacting elements include copper or another highly electrically conductive material. Centralizers 672 may be located on the portions of contacting elements 806 above the heat generating portions of the contacting elements. Centralizers 672 inhibit physical and electrical contact of portions of contacting elements 806 above the heat generating portions of the contacting elements against walls of container 834.

When contacting elements 806 are locked into place inside container 834 by protrusions 842, 844, at least some electrical current may be pass between the contacting elements through the protrusions. As electrical current is passed through the heat generating portions of contacting elements 806, heat is generated in container 834. The generated heat may melt coupling material 846 located inside container 834. Water in container 834 may boil. The boiling water may convect heat to upper portions of container 834 and aid in melting of coupling material 846. Walls of container 834 may be thermally insulated to reduce heat losses out of the container and allow the inside of the container to heat up faster. Coupling material 846 flows down into the lower portion of container 834 as the coupling material melts. Coupling material 846 fills the lower portion of container 834 until the heat generating portions of contacting elements 806 are below the fill line of the coupling material. Coupling material 846 then electrically couples the portions of contacting elements 806 above the heat generating portions of the contacting elements. The resistance of contacting elements 806 decreases at this point and heat is no longer generated in the contacting elements and the coupling materials is allowed to cool.

In certain embodiments, container 834 includes insulation layer 848 inside the housing of the container. Insulation layer 848 may include thermally insulating materials to inhibit heat losses from the canister. For example, insulation layer 848 may include magnesium oxide, silicon nitride, or other thermally insulating materials that withstand operating temperatures in container 834. In certain embodiments, container 834 includes liner 850 on an inside surface of the container. Liner 850 may increase electrical conductivity inside container 834. Liner 850 may include electrically conductive materials such as copper or aluminum.

FIG. 136 depicts an alternative embodiment for container 834. Coupling material in container 834 includes powder 852. Powder 852 is a chemical mixture that produces a molten metal product from a reaction of the chemical mixture. In an embodiment, powder 852 is thermite powder. Powder 852 lines the walls of container 834 and/or is placed in the container. Igniter 854 is placed in powder 852. Igniter 854 may be, for example, a magnesium ribbon that when activated ignites the reaction of powder 852. When powder 852 reacts, a molten metal produced by the reaction flows and surrounds contacting elements 806 placed in container 834. When the molten metal cools, the cooled metal electrically connects contacting elements 806. In some embodiments, powder 852 is used in combination with another coupling material, such as a low-temperature solder, to couple contacting elements 806. The heat of reaction of powder 852 may be used to melt the low temperature-solder.

In certain embodiments, an explosive element is placed in container 834, depicted in FIG. 132 or FIG. 136. The explosive element may be, for example, a shaped charge explosive or other controlled explosive element. The explosive element may be exploded to crimp contacting elements 806 and/or container 834 together so that the contacting elements and the container are electrically connected. In some embodiments, an explosive element is used in combination with an electrical coupling material such as low-temperature solder or thermite powder to electrically connect contacting elements 806.

FIG. 137 depicts an alternative embodiment for coupling contacting elements 806 of legs 798, 800, 802. Container 834A is coupled to contacting element 806 of leg 800. Container 834B is coupled to contacting element 806 of leg 802. Container 834B is sized and shaped to be placed inside container 834A. Container 834C is coupled to contacting element 806 of leg 798. Container 834C is sized and shaped to be placed inside container 834B. In some embodiments, contacting element 806 of leg 798 is placed in container 834B without a container attached to the contacting element. One or more of containers 834A, 834B, 834C may be filled with a coupling material that is activated to facilitate an electrical connection between contacting elements 806 as described above.

Figure 138:
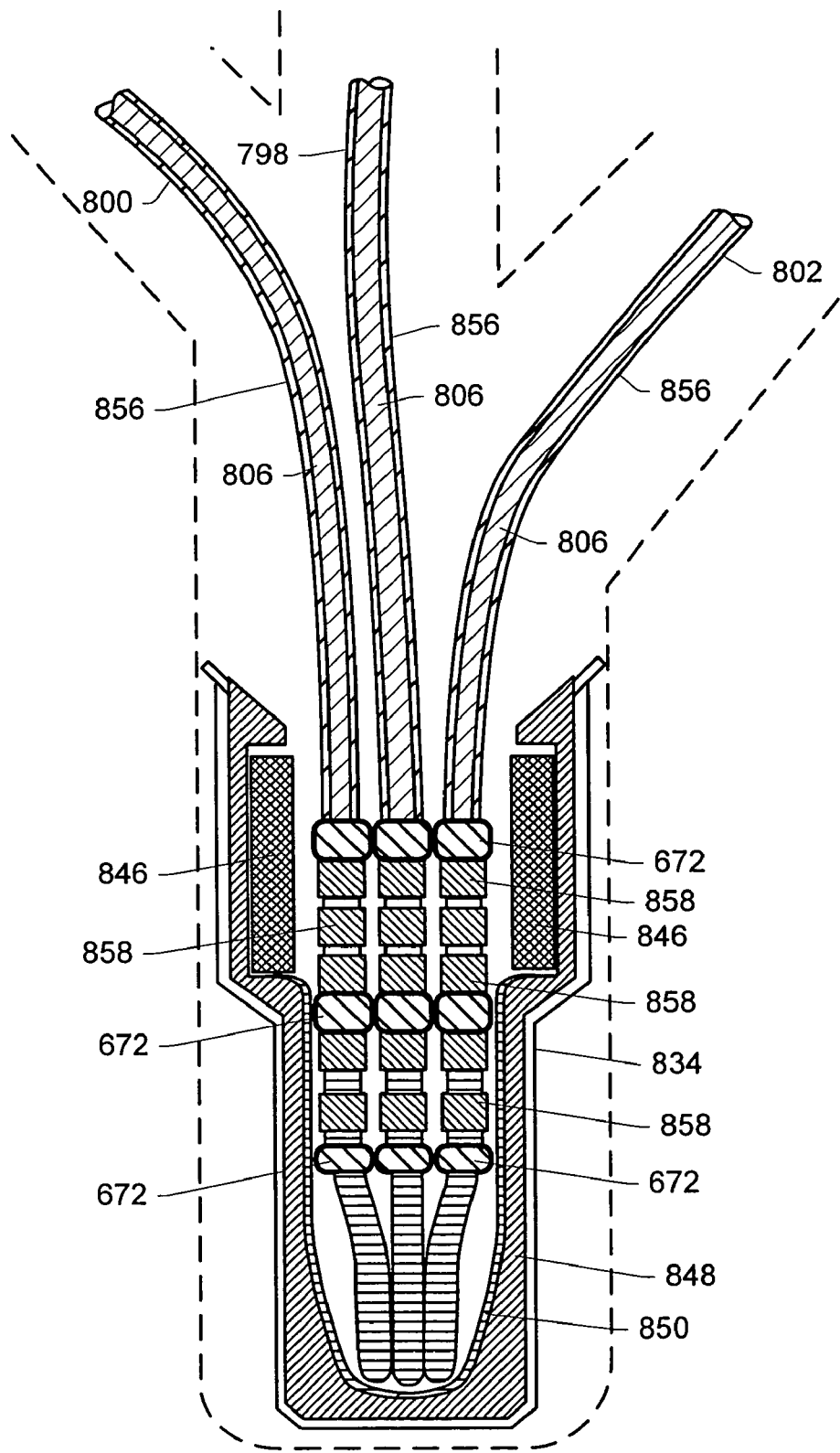

FIG. 138 depicts a side view representation of an embodiment for coupling contacting elements using temperature limited heating elements. Contacting elements 806 of legs 798, 800, 802 may have insulation 856 on portions of the contacting elements above container 834. Container 834 may be shaped and/or have guides at the top to guide the insertion of contacting elements 806 into the container. Coupling material 846 may be located inside container 834 at or near a top of the container. Coupling material 846 may be, for example, a solder material. In some embodiments, inside walls of container 834 are pre-coated with coupling material or another electrically conductive material such as copper or aluminum. Centralizers 672 may be coupled to contacting elements 806 to maintain a spacing of the contacting elements in container 834. Container 834 may be tapered at the bottom to push lower portions of contacting elements 806 together for at least some electrical contact between the lower portions of the contacting elements.

Heating elements 858 may be coupled to portions of contacting elements 806 inside container 834. Heating elements 858 may include ferromagnetic materials such as iron or stainless steel. In an embodiment, heating elements 858 are iron cylinders clad onto contacting elements 806. Heating elements 858 may be designed with dimensions and materials that will produce a desired amount of heat in container 834. In certain embodiments, walls of container 834 are thermally insulated with insulation layer 848, as shown in FIG. 138 to inhibit heat loss from the container. Heating elements 858 may be spaced so that contacting elements 806 have one or more portions of exposed material inside container 834. The exposed portions include exposed copper or another suitable highly electrically conductive material. The exposed portions allow for better electrical contact between contacting elements 806 and coupling material 846 after the coupling material has been melted, fills container 834, and is allowed to cool.

In certain embodiments, heating elements 858 operate as temperature limited heaters when a time-varying current is applied to the heating elements. For example, a 400 Hz, AC current may be applied to heating elements 858. Application of the time-varying current to contacting elements 806 causes heating elements 858 to generate heat and melt coupling material 846. Heating elements 858 may operate as temperature limited heating elements with a self-limiting temperature selected so that coupling material 846 is not overheated. As coupling material 846 fills container 834, the coupling material makes electrical contact between portions of exposed material on contacting elements 806 and electrical current begins to flow through the exposed material portions rather than heating elements 858. Thus, the electrical resistance between the contacting elements decreases. As this occurs, temperatures inside container 834 begin to decrease and coupling material 846 is allowed to cool to create an electrical contacting section between contacting elements 806. In certain embodiments, electrical power to contacting elements 806 and heating elements 858 is turned off when the electrical resistance in the system falls below a selected resistance. The selected resistance may indicate that the coupling material has sufficiently electrically connected the contacting elements. In some embodiments, electrical power is supplied to contacting elements 806 and heating elements 858 for a selected amount of time that is determined to provide enough heat to melt the mass of coupling material 846 provided in container 834.

Figure 139:
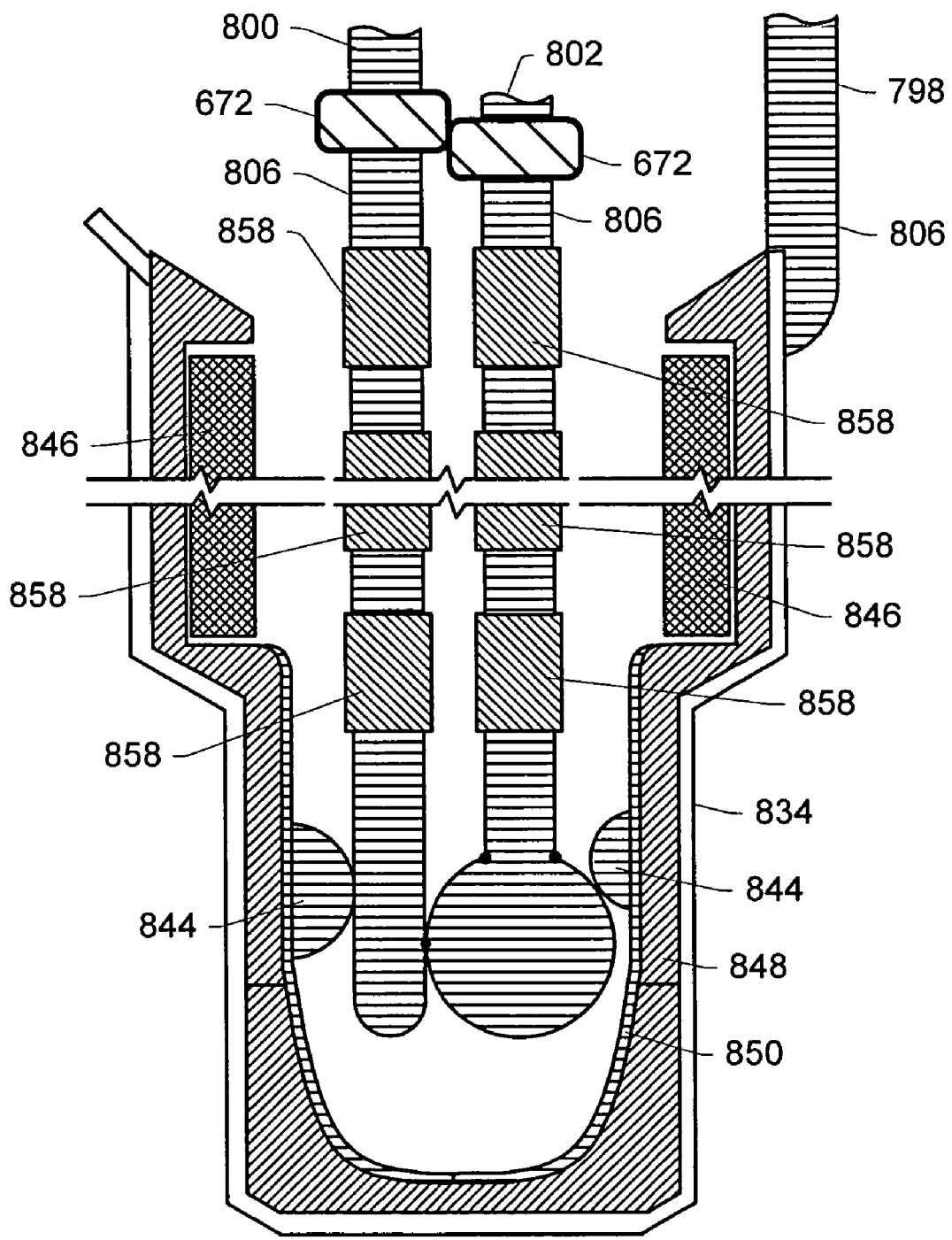
FIG. 139 depicts a side view representation of an alternative embodiment for coupling contacting elements using temperature limited heating elements.

FIG. 139 depicts a side view representation of an alternative embodiment for coupling contacting elements using temperature limited heating elements. Contacting element 806 of leg 798 may be coupled to container 834 by welding, brazing, or another suitable method. Lower portion of contacting element 806 of leg 802 may have a bulbous shape. Contacting element 806 of leg 802 is inserted into container 834. Contacting element 806 of leg 800 is inserted after insertion of contacting element 806 of leg 802. Both legs may then be pulled upwards simultaneously. Protrusions 844 may lock contacting elements 806 into place and a friction fit may be created between the contacting elements 806. Centralizers 672 may inhibit electrical contact between upper portions of contacting elements 806.

Time-varying electrical current may be applied to contacting elements 806 so that heating elements 858 generate heat. The generated heat may melt coupling material 846 located in container 834 and be allowed to cool, as described for the embodiment depicted in FIG. 138. After cooling of coupling material 846, contacting elements 806 of legs 800, 802, shown in FIG. 139, are electrically coupled in container 834 with the coupling material. In some embodiments, lower portions of contacting elements 806 have protrusions or openings that anchor the contacting elements in cooled coupling material. Exposed portions of the contacting elements provide a low electrical resistance path between the contacting elements and the coupling material.

Figure 140:
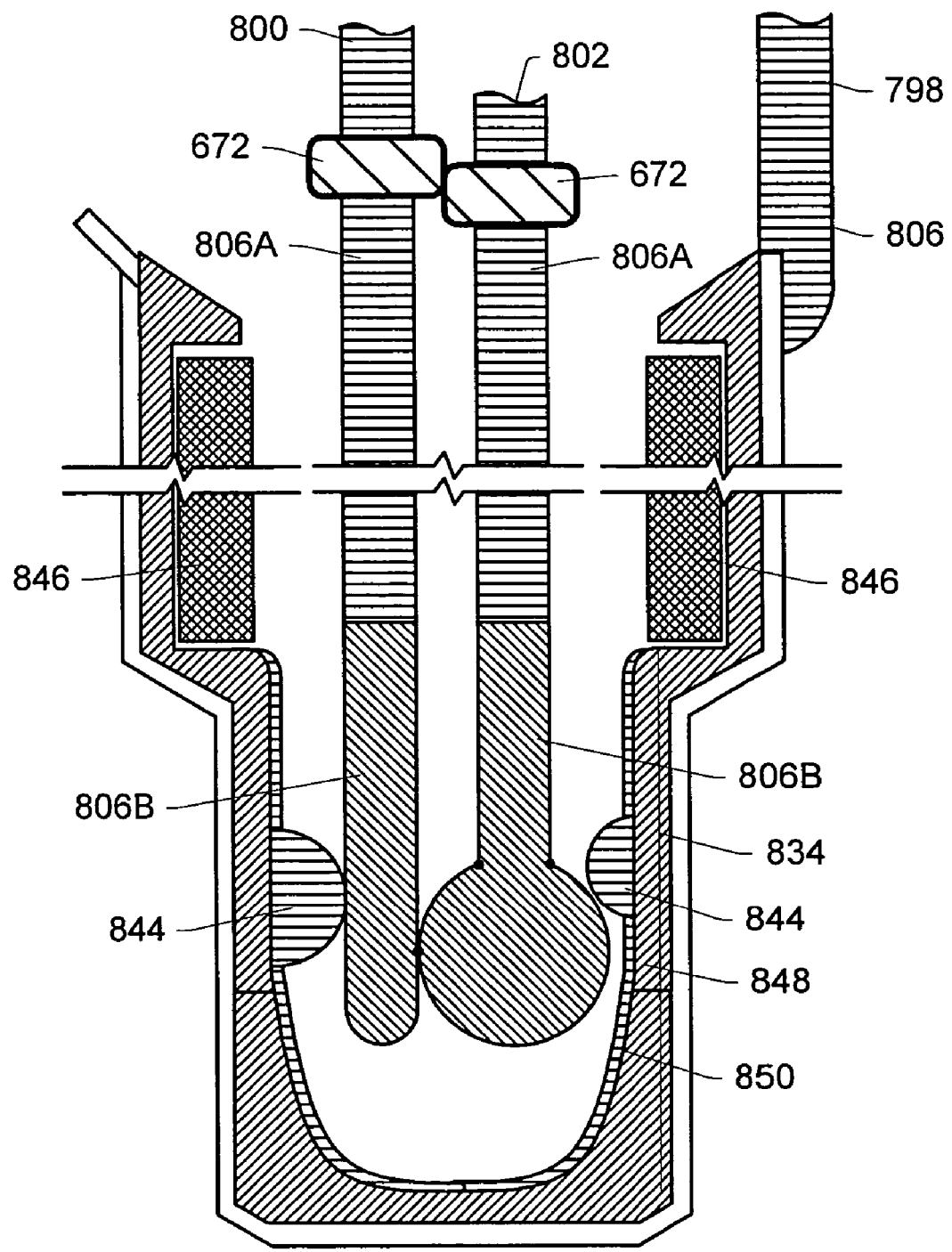

FIG. 140 depicts a side view representation of another embodiment for coupling contacting elements using temperature limited heating elements. Contacting element 806 of leg 798 may be coupled to container 834 by welding, brazing, or another suitable method. Lower portion of contacting element 806 of leg 802 may have a bulbous shape. Contacting element 806 of leg 802 is inserted into container 834. Contacting element 806 of leg 800 is inserted after insertion of contacting element 806 of leg 802. Both legs may then be pulled upwards simultaneously. Protrusions 844 may lock contacting elements 806 into place and a friction fit may be created between the contacting elements 806. Centralizers 672 may inhibit electrical contact between upper portions of contacting elements 806.

End portions 806B of contacting elements 806 may be made of a ferromagnetic material such as 410 stainless steel. Portions 806A may include non-ferromagnetic electrically conductive material such as copper or aluminum. Time-varying electrical current may be applied to contacting elements 806 so that end portions 806B generate heat due to the resistance of the end portions. The generated heat may melt coupling material 846 located in container 834 and be allowed to cool, as described for the embodiment depicted in FIG. 138. After cooling of coupling material 846, contacting elements 806 of legs 800, 802, shown in FIG. 139, are electrically coupled in container 834 with the coupling material. Portions 806A may be below the fill line of coupling material 846 so that these portions of the contacting elements provide a low electrical resistance path between the contacting elements and the coupling material.

Figure 141:
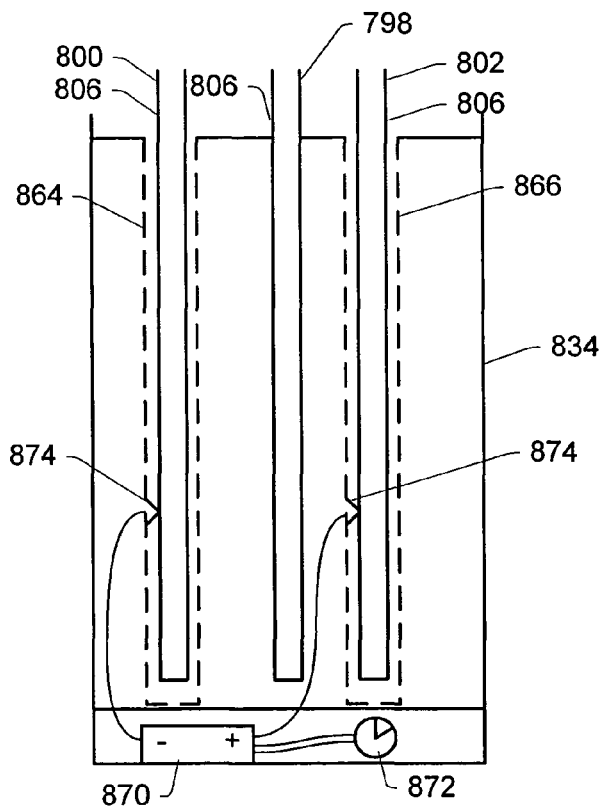
Figure 142:
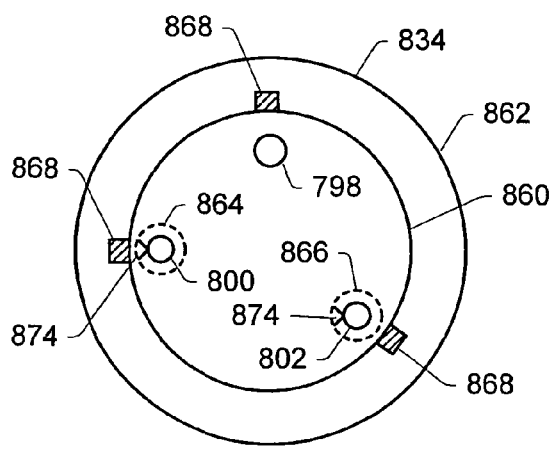

FIG. 141 depicts a side view representation of an alternative embodiment for coupling contacting elements of three legs of a heater. FIG. 142 depicts a top view representation of the alternative embodiment for coupling contacting elements of three legs of the heater depicted in FIG. 141. Container 834 may include inner container 860 and outer container 862. Inner container 860 may be made of copper or another malleable, electrically conductive metal such as aluminum. Outer container 862 may be made of a rigid material such as stainless steel. Outer container 862 protects inner container 860 and its contents from environmental conditions outside of container 834.

Inner container 860 may be substantially solid with two openings 864 and 866. Inner container 860 is coupled to contacting element 806 of leg 798. For example, inner container 860 may be welded or brazed to contacting element 806 of leg 798. Openings 864, 866 are shaped to allow contacting elements 806 of legs 800, 802 to enter the openings as shown in FIG. 141. Funnels or other guiding mechanisms may be coupled to the entrances to openings 864, 866 to guide contacting elements 806 of legs 800, 802 into the openings. Contacting elements 806 of legs 798, 800, 802 may be made of the same material as inner container 860.

Explosive elements 868 may be coupled to the outer wall of inner container 860. In certain embodiments, explosive elements 868 are elongated explosive strips that extend along the outer wall of inner container 860. Explosive elements 868 may be arranged along the outer wall of inner container 860 so that the explosive elements are aligned at or near the centers of contacting elements 806, as shown in FIG. 142. Explosive elements 868 are arranged in this configuration so that energy from the explosion of the explosive elements causes contacting elements 806 to be pushed towards the center of inner container 860.

Explosive elements 868 may be coupled to battery 870 and timer 872. Battery 870 may provide power to explosive elements 868 to initiate the explosion. Timer 872 may be used to control the time for igniting explosive elements 868. Battery 870 and timer 872 may be coupled to triggers 874. Triggers 874 may be located in openings 864, 866. Contacting elements 806 may set off triggers 874 as the contacting elements are placed into openings 864, 866. When both triggers 874 in openings 864, 866 are triggered, timer 872 may initiate a countdown before igniting explosive elements 868. Thus, explosive elements 868 are controlled to explode only after contacting elements 806 are placed sufficiently into openings 864, 866 so that electrical contact may be made between the contacting elements and inner container 860 after the explosions. Explosion of explosive elements 868 crimps contacting elements 806 and inner container 860 together to make electrical contact between the contacting elements and the inner container. In certain embodiments, explosive elements 868 fire from the bottom towards the top of inner container 860. Explosive elements 868 may be designed with a length and explosive power (band width) that gives an optimum electrical contact between contacting elements 806 and inner container 860.

In some embodiments, triggers 874, battery 870, and timer 872 may be used to ignite a powder (for example, copper thermite powder) inside a container (for example, container 834 or inner container 860). Battery 870 may charge a magnesium ribbon or other ignition device in the powder to initiate reaction of the powder to produce a molten metal product. The molten metal product may flow and then cool to electrically contact the contacting elements.

Figure 143:
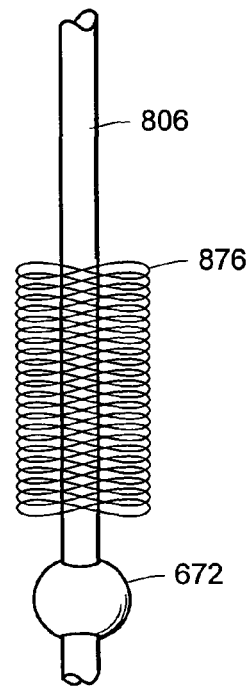

In certain embodiments, electrical connection is made between contacting elements 806 through mechanical means. FIG. 143 depicts an embodiment of contacting element 806 with a brush contactor. Brush contactor 876 is coupled to a lower portion of contacting element 806. Brush contactor 876 may be made of a malleable, electrically conductive material such as copper or aluminum. Brush contactor 876 may be a webbing of material that is compressible and/or flexible. Centralizer 672 may be located at or near the bottom of contacting element 806.

FIG. 144 depicts an embodiment for coupling contacting elements 806 with brush contactors 876. Brush contactors 876 are coupled to each contacting element 806 of legs 798, 800, 802. Brush contactors 876 compress against each other and interlace to electrically couple contacting elements 806 of legs 798, 800, 802. Centralizers 672 maintain spacing between contacting elements 806 of legs 798, 800, 802 so that interference and/or clearance issues between the contacting elements are inhibited.

In certain embodiments, contacting elements 806 (depicted in FIGS. 132-144) are coupled in a zone of the formation that is cooler than the layer of the formation to be heated (for example, in the underburden of the formation). Contacting elements 806 are coupled in a cooler zone to inhibit melting of the coupling material and/or degradation of the electrical connection between the elements during heating of the hydrocarbon layer above the cooler zone. In certain embodiments, contacting elements 806 are coupled in a zone that is at least about 3 m, at least about 6 m, or at least about 9 m below the layer of the formation to be heated. In some embodiments, the zone has a standing water level that is above a depth of containers 834.

In certain embodiments, exposed metal heating elements are used in substantially horizontal sections of u-shaped wellbores. Substantially u-shaped wellbores may be used in tar sands formations, oil shale formation, or other formations with relatively thin hydrocarbon layers. Tar sands or thin oil shale formations may have thin shallow layers that are more easily and uniformly heated using heaters placed in substantially u-shaped wellbores. Substantially u-shaped wellbores may also be used to process formations with thick hydrocarbon layers in formations. In some embodiments, substantially u-shaped wellbores are used to access rich layers in a thick hydrocarbon formation.

Heaters in substantially u-shaped wellbores may have long lengths compared to heaters in vertical wellbores because horizontal heating sections do not have problems with creep or hanging stress encountered with vertical heating elements. Substantially u-shaped wellbores may make use of natural seals in the formation and/or the limited thickness of the hydrocarbon layer. For example, the wellbores may be placed above or below natural seals in the formation without punching large numbers of holes in the natural seals, as would be needed with vertically oriented wellbores. Using substantially u-shaped wellbores instead of vertical wellbores may also reduce the number of wells needed to treat a surface footprint of the formation. Using less wells reduces capital costs for equipment and reduces the environmental impact of treating the formation by reducing the amount of wellbores on the surface and the amount of equipment on the surface. Substantially u-shaped wellbores may also utilize a lower ratio of overburden section to heated section than vertical wellbores.

Substantially u-shaped wellbores may allow for flexible placement of opening of the wellbores on the surface. Openings to the wellbores may be placed according to the surface topology of the formation. In certain embodiments, the openings of wellbores are placed at geographically accessible locations such as topological highs (for examples, hills). For example, the wellbore may have a first opening on a first topologic high and a second opening on a second topologic high and the wellbore crosses beneath a topologic low (for example, a valley with alluvial fill) between the first and second topologic highs. This placement of the openings may avoid placing openings or equipment in topologic lows or other inaccessible locations. In addition, the water level may not be artesian in topologically high areas. Wellbores may be drilled so that the openings are not located near environmentally sensitive areas such as, but not limited to, streams, nesting areas, or animal refuges.

FIG. 145 depicts a side-view representation of an embodiment of a heater with an exposed metal heating element placed in a substantially u-shaped wellbore. Heaters 880A, 880B, 880C have first end portions at first location 878 on surface 550 of the formation and second end portions at second location 884 on the surface. Heaters 880A, 880B, 880C have sections 888 in overburden 382. Sections 888 are configured to provide little or no heat output. In certain embodiments, sections 888 include an insulated electrical conductor such as insulated copper. Sections 888 are coupled to heating elements 804.

In certain embodiments, portions of heating elements 804 are substantially parallel in hydrocarbon layer 380. In certain embodiments, heating elements 804 are exposed metal heating elements. In certain embodiments, heating elements 804 are exposed metal temperature limited heating elements. Heating elements 804 may include ferromagnetic materials such as 9% by weight to 13% by weight chromium stainless steel like 410 stainless steel, chromium stainless steels such as T/P91 or T/P92, 409 stainless steel, VM12 (Vallourec and Mannesmann Tubes, France) or iron-cobalt alloys for use as temperature limited heaters. In some embodiments, heating elements 804 are composite temperature limited heating elements such as 410 stainless steel and copper composite heating elements or 347H, iron, copper composite heating elements. Heating elements 804 may have lengths of at least about 100 m, at least about 500 m, or at least about 1000 m, up to lengths of about 6000 m.

Heating elements 804 may be solid rods or tubulars. In certain embodiments, solid rod heating elements have diameters several times the skin depth at the Curie temperature of the ferromagnetic material. Typically, the solid rod heating elements may have diameters of 1.91 cm or larger (for example, 2.5 cm, 3.2 cm, 3.81 cm, or 5.1 cm). In certain embodiments, tubular heating elements have wall thicknesses of at least twice the skin depth at the Curie temperature of the ferromagnetic material. Typically, the tubular heating elements have outside diameters of between about 2.5 cm and about 15.2 cm and wall thickness in range between about 0.13 cm and about 1.01 cm.

In certain embodiments, tubular heating elements 804 allow fluids to be convected through the tubular heating elements. Fluid flowing through the tubular heating elements may be used to preheat the tubular heating elements, to initially heat the formation, and/or to recover heat from the formation after heating is completed for the in situ conversion process. Fluids that may be flow through the tubular heating elements include, but are not limited to, air, water, steam, helium, carbon dioxide or other fluids. In some embodiments, a hot fluid, such as carbon dioxide or helium, flows through the tubular heating elements to provide heat to the formation. The hot fluid may be used to provide heat to the formation before electrical heating is used to provide heat to the formation. In some embodiments, the hot fluid is used to provide heat in addition to electrical heating. Using the hot fluid to provide heat to the formation in addition to providing electrical heating may be less expensive than using electrical heating alone to provide heat to the formation. In some embodiments, water and/or steam flows through the tubular heating element to recover heat from the formation. The heated water and/or steam may be used for solution mining and/or other processes.

Transition sections 892 may couple heating elements 804 to sections 888. In certain embodiments, transition sections 892 include material that has a high electrical conductivity but is corrosion resistant, such as 347 stainless steel over copper. In an embodiment, transition sections include a composite of stainless steel clad over copper. Transition sections 892 inhibit overheating of copper and/or insulation in sections 888.

Figure 146:
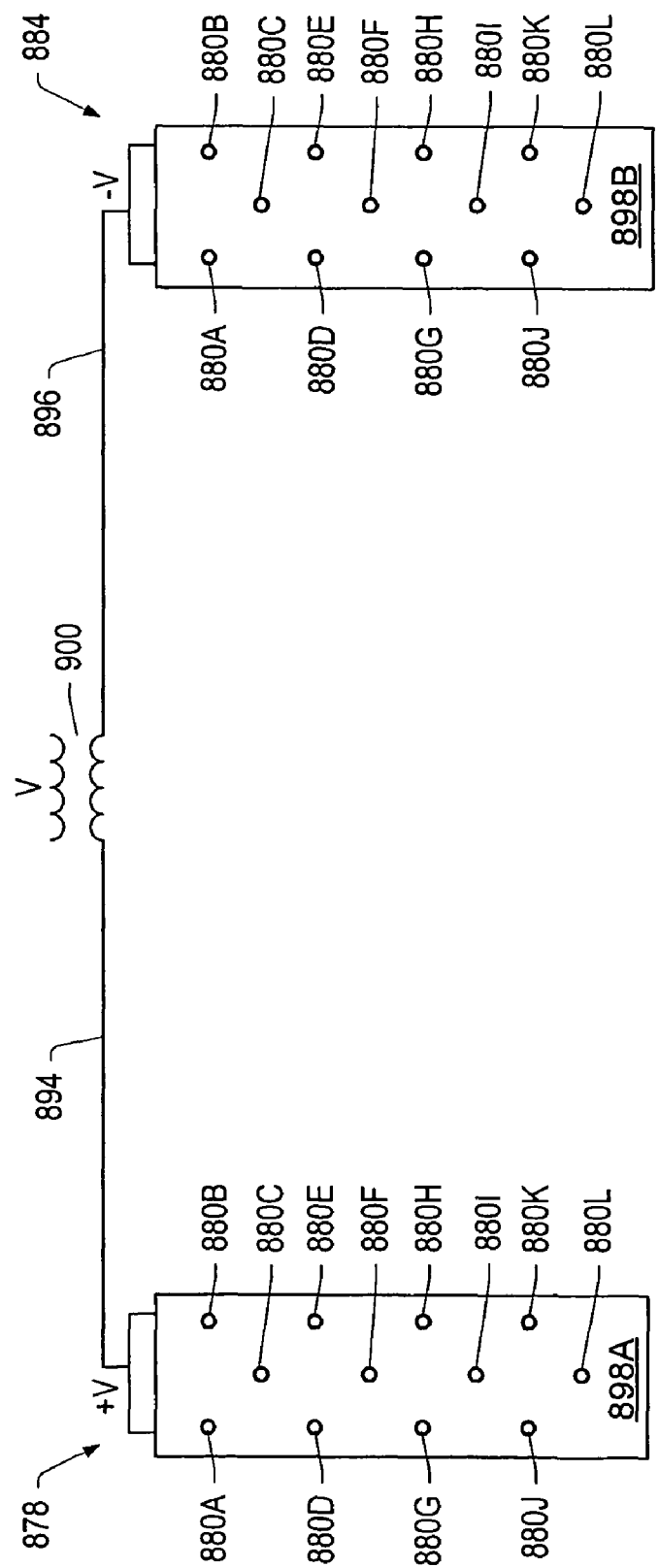

FIG. 146 depicts a representational top view of an embodiment of a surface pattern of heaters depicted in FIG. 145. Heaters 880A-L may be arranged in a repeating triangular pattern on the surface of the formation, as shown in FIG. 146. A triangle may be formed by heaters 880A, 880B, and 880C and a triangle formed by heaters 880C, 880D, and 880E. In some embodiments, heaters 880A-L are arranged in a straight line on the surface of the formation. Heaters 880A-L have first end portions at first location 878 on the surface and second end portions at second location 884 on the surface. Heaters 880A-L are arranged such that (a) the patterns at first location 878 and second location 884 correspond to each other, (b) the spacing between heaters is maintained at the two locations on the surface, and/or (c) the heaters all have substantially the same length (substantially the same horizontal distance between the end portions of the heaters on the surface as shown in the top view of FIG. 146).

As depicted in FIGS. 145 and 146, cables 894, 896 may be coupled to transformer 900 and one or more heater units, such as the heater unit including heaters 880A, 880B, 880C. Cables 894, 896 may carry a large amount of power. In certain embodiments, cables 894, 896 are capable of carrying high currents with low losses. For example, cables 894, 896 may be thick copper or aluminum conductors. The cables may also have thick insulation layers. In some embodiments, cable 894 and/or cable 896 may be superconducting cables. The superconducting cables may be cooled by liquid nitrogen. Superconducting cables are available from Superpower, Inc. (Schenectady, N.Y., U.S.A.). Superconducting cables may minimize power loss and reduce the size of the cables needed to couple transformer 900 to the heaters.

In certain embodiments, bus bar 898A is coupled to first end portions of heaters 880A-L and bus bar 898B is coupled to second end portions of heaters 880A-L. Bus bars 898A,B electrically couple heaters 880A-L to cables 894, 896 and transformer 900. Bus bars 898A,B distribute power to heaters 880A-L. In certain embodiments, bus bars 898A,B are capable of carrying high currents with low losses. In some embodiments, bus bars 898A,B are made of superconducting material such as the superconductor material used in cables 894, 896.

As shown in FIGS. 145 and 146, heaters 880A-L are coupled to a single transformer 900. In certain embodiments, transformer 900 is a source of time-varying current. In certain embodiments, transformer 900 is an electrically isolated, single-phase transformer. In certain embodiments, transformer 900 provides power to heaters 880A-L from an isolated secondary phase of the transformer. First end portions of heaters 880A-L may be coupled to one side of transformer 900 while second end portions of the heaters are coupled to the opposite side of the transformer. Transformer 900 provides a substantially common voltage to the first end portions of heaters 880A-L and a substantially common voltage to the second end portions of heaters 880A-L. In certain embodiments, transformer 900 applies a voltage potential to the first end portions of heaters 880A-L that is opposite in polarity and substantially equal in magnitude to a voltage potential applied to the second end portions of the heaters. For example, a +660 V potential may be applied to the first end portions of heaters 880A-L and a −660 V potential applied to the second end portions of the heaters at a selected point on the wave of time-varying current (such as AC or modulated DC). Thus, the voltages at the two end portion of the heaters may be equal in magnitude and opposite in polarity with an average voltage that is substantially at ground potential.

Figure 147:
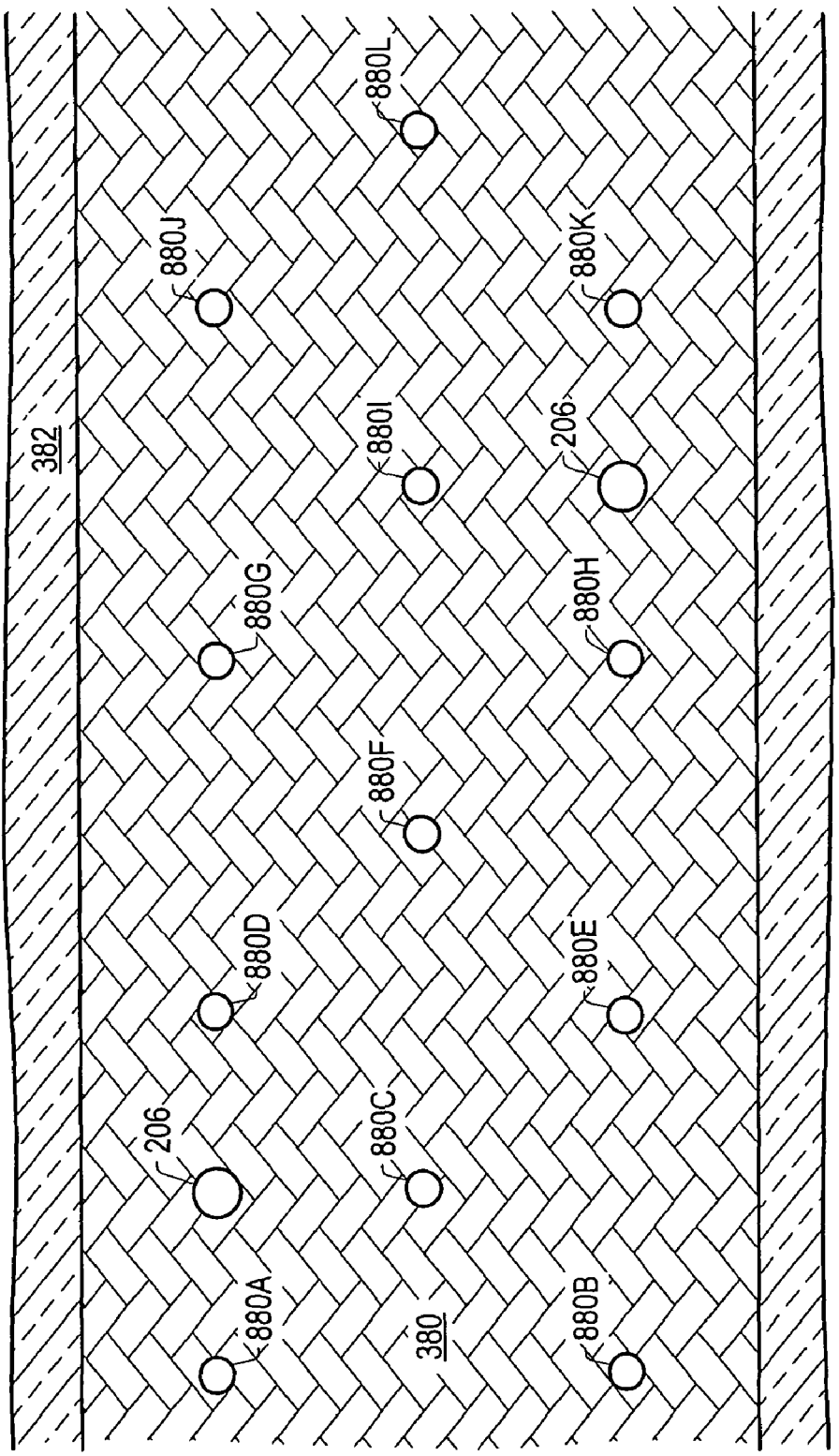

Applying the same voltage potentials to the end portions of all heaters 880A-L produces voltage potentials along the lengths of the heaters that are substantially the same along the lengths of the heaters. FIG. 147 depicts a cross-section representation, along a vertical plane, such as the plane A-A shown in FIG. 145, of substantially u-shaped heaters in a hydrocarbon layer. The voltage potential at the cross-sectional point shown in FIG. 147 along the length of heater 880A is substantially the same as the voltage potential at the corresponding cross-sectional points on heaters 880A-L shown in FIG. 147. At lines equidistant between heater wellheads, the voltage potential is approximately zero. Other wells, such as production wells or monitoring wells, may be located along these zero voltage potential lines, if desired. Production wells 206 located close to the overburden may be used to transport formation fluid that is initially in a vapor phase to the surface. Production wells located close to a bottom of the heated portion of the formation may be used to transport formation fluid that is initially in a liquid phase to the surface.

In certain embodiments, the voltage potential at the midpoint of heaters 880A-L is about zero. Having similar voltage potentials along the lengths of heaters 880A-L inhibits current leakage between the heaters. Thus, there is little or no current flow in the formation and the heaters may have long lengths as described above. Having the opposite polarity and substantially equal voltage potentials at the end portions of the heaters also halves the voltage applied at either end portion of the heater versus having one end portion of the heater grounded and one end portion at full potential. Reducing (halving) the voltage potential applied to an end portion of the heater generally reduces current leakage, reduces insulator requirements, and/or reduces arcing distances because of the lower voltage potential to ground applied at the end portions of the heaters.

Figure 148:
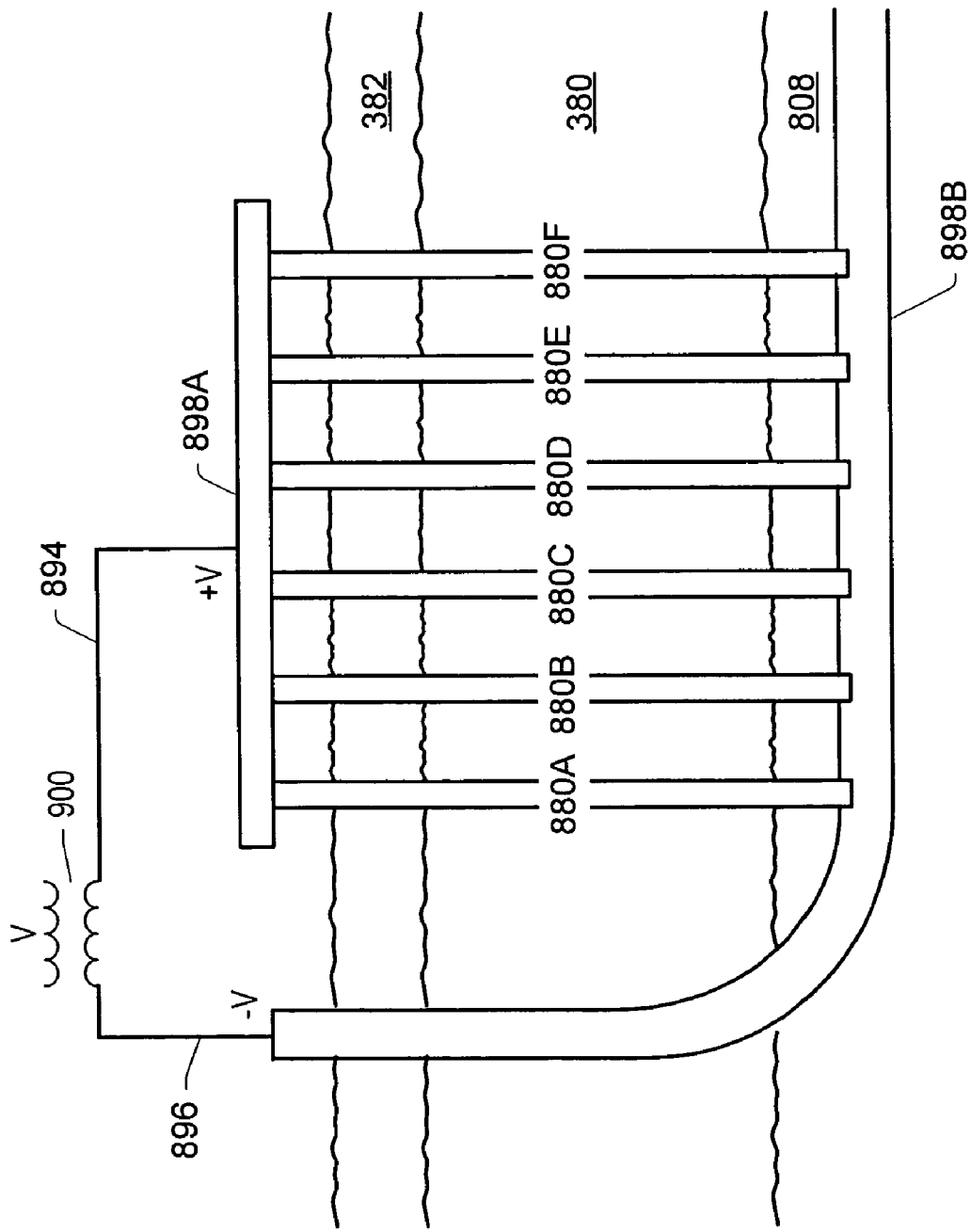

In certain embodiments, substantially vertical heaters are used to provide heat to the formation. Opposite polarity and substantially equal voltage potentials, as described above, may be applied to the end portions of the substantially vertical heaters. FIG. 148 depicts a side-view representation of substantially vertical heaters coupled to a substantially horizontal wellbore. Heaters 880A, 880B, 880C, 880D, 880E, 880F are located substantially vertical in hydrocarbon layer 380. First end portions of heaters 880A, 880B, 880C, 880D, 880E, 880F are coupled to bus bar 898A on a surface of the formation. Second end portions of heaters 880A, 880B, 880C, 880D, 880E, 880F are coupled to bus bar 898B in contacting section 808.

Bus bar 898B may be a bus bar located in a substantially horizontal wellbore in contacting section 808. Second end portions of heaters 880A, 880B, 880C, 880D, 880E, 880F may be coupled to bus bar 898B by any method described herein or any method known in the art. For example, containers with thermite powder are coupled to bus bar 898B (for example, by welding or brazing the containers to the bus bar), end portions of heaters 880A, 880B, 880C, 880D, 880E, 880F are placed inside the containers, and the thermite powder is activated to electrically couple the heaters to the bus bar. The containers may be coupled to bus bar 898B by, for example, placing the containers in holes or recesses in bus bar 898B or coupled to the outside of the bus bar and then brazing or welding the containers to the bus bar.

Bus bar 898A and bus bar 898B may be coupled to transformer 900 with cables 894, 896, as described above. Transformer 900 may provide voltages to bar 898A and bus bar 898B as described above for the embodiments depicted in FIGS. 145 and 146. For example, transformer 900 may apply a voltage potential to the first end portions of heaters 880A-F that is opposite in polarity and substantially equal in magnitude to a voltage potential applied to the second end portions of the heaters. Applying the same voltage potentials to the end portions of all heaters 880A-F may produce voltage potentials along the lengths of the heaters that are substantially the same along the lengths of the heaters. Applying the same voltage potentials to the end portions of all heaters 880A-F may inhibit current leakage between the heaters and/or into the formation.

In certain embodiments, it may be advantageous to allow some current leakage into the formation during early stages of heating to heat the formation at a faster rate. Current leakage from the heaters into the formation electrically heats the formation directly. The formation is heated by direct electrical heating in addition to conductive heat provided by the heaters. The formation (the hydrocarbon layer) may have an initial electrical resistance that averages at least 10 ohm·m. In some embodiments, the formation has an initial electrical resistance of at least 100 ohm·m or of at least 300 ohm·m. Direct electrical heating is achieved by having opposite potentials applied to adjacent heaters in the hydrocarbon layer. Current may be allowed to leak into the formation until a selected temperature is reached in the heaters or in the formation. The selected temperature may be below or near the temperature that water proximate one or more heaters boils off. After water boils off, the hydrocarbon layer is substantially electrically isolated from the heaters and direct heating of the formation is inefficient. After the selected temperature is reached, the voltage potential is applied in the opposite polarity and substantially equal magnitude manner described above for FIGS. 145 and 146 so that adjacent heaters will have the same voltage potential along their lengths.

Current is allowed to leak into the formation by reversing the polarity of one or more heaters shown in FIG. 146 so that a first group of heaters has a positive voltage potential at first location 878 and a second group of heaters has a negative voltage potential at the first location. The first end portions, at first location 878, of a first group of heaters (for example, heaters 880A, 880B, 880D, 880E, 880G, 880H, 880J, 880K, depicted in FIG. 146) are applied with a positive voltage potential that is substantially equal in magnitude to a negative voltage potential applied to the second end portions, at second location 884, of the first group of heaters. The first end portions, at first location 878, of the second group of heaters (for example, heaters 880C, 880F, 880I, 880L) are applied with a negative voltage potential that is substantially equal in magnitude to the positive voltage potential applied to the first end portions of the first group of heaters. Similarly, the second end portions, at second location 884, of the second group of heaters are applied with a positive voltage potential substantially equal in magnitude to the negative potential applied to the second end portions of the first group of heaters. After the selected temperature is reached, the first end portions of both groups of heaters are applied with voltage potential that is opposite in polarity and substantially similar in magnitude to the voltage potential applied to the second end portions of both groups of heaters.

In some embodiments, heating elements 804 have a thin electrically insulating layer, described above, to inhibit current leakage from the heating elements. In some embodiments, the thin electrically insulating layer is aluminum oxide or thermal spray coated aluminum oxide. In some embodiments, the thin electrically insulating layer is an enamel coating of a ceramic composition. The thin electrically insulating layer may inhibit heating elements of a three-phase heater from leaking current between the elements, from leaking current into the formation, and from leaking current to other heaters in the formation. Thus, the three-phase heater may have a longer heater length.

Figure 149:
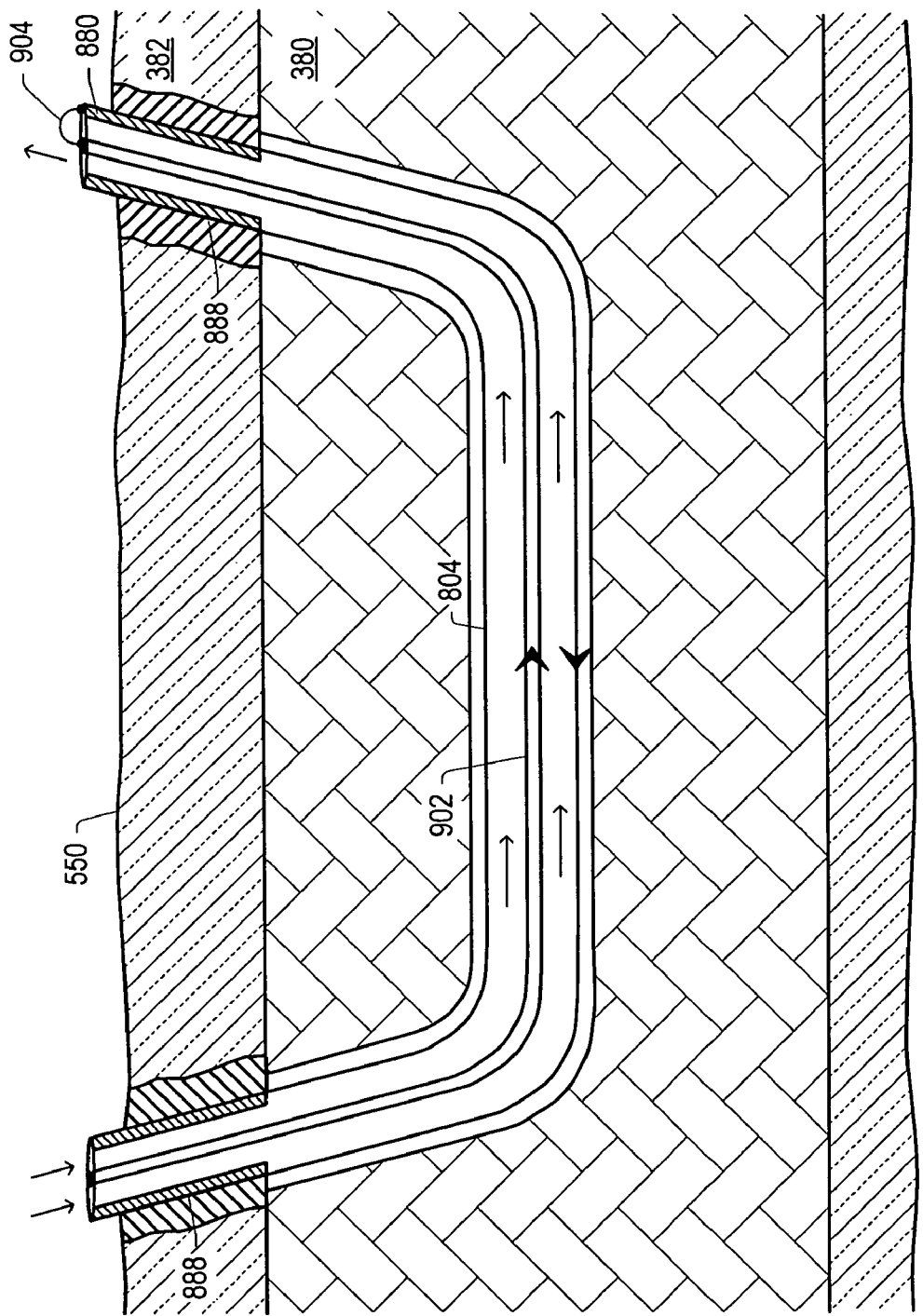

In certain embodiments, a heater becomes electrically isolated from the formation because the heater has little or no voltage potential on the outside of the heater. FIG. 149 depicts an embodiment of a substantially u-shaped heater that electrically isolates itself from the formation. Heater 880 has a first end portion at a first opening on surface 550 and a second end portion at a second opening on the surface. In some embodiments, heater 880 has only one end portion coupled to the surface.

Heater 880 includes heating element 804 located in hydrocarbon layer 380. Heating element 804 is a ferromagnetic conduit heating element or ferromagnetic tubular heating element. In certain embodiments, heating element 804 is a temperature limited heater tubular heating element. In certain embodiments, heating element 804 is a 9% by weight to 13% by weight chromium stainless steel tubular such as a 410 stainless steel tubular, a T/P91 stainless steel tubular, or a T/P92 stainless steel tubular. Heating element 804 is coupled to sections 888. Sections 888 are located in overburden 382. Sections 888 include higher electrical conductivity materials such as copper or aluminum. In certain embodiments, sections 888 are copper clad inside carbon steel.

Center conductor 902 is located at or near a center of heating element 804. In one embodiment, center conductor 902 is an insulated conductor (such as a mineral insulated conductor with a copper core, magnesium oxide insulation, and a stainless steel sheath). In an alternative embodiment, center conductor 902 is a conductor separated from heating element 804 by one or more electrically-insulating centralizers so that the heater is in a conductor-in-conduit configuration. The centralizers may include silicon nitride or another electrically insulating material.

Center conductor 902 is electrically coupled to heating element 804 at an end portion of the center conductor and the heating element at surface 550 (as shown by coupling 904 in FIG. 149). Center conductor 902 is used as a return conductor for heating element 804 so that current in the center conductor flows in an opposite direction from current in the heating element. The magnetic field generated by current flow in center conductor 902 substantially confines the flow of electrons and heat generation to the inside of heating element 804 below the Curie temperature of the ferromagnetic material in the heating element. Thus, the outside of heating element 804 is at substantially zero potential and the heating element is electrically isolated from the formation and any adjacent heater or heating element. In some embodiments, a fluid, such as carbon dioxide or another fluid with a high heat capacity, flows through heating element 804 to preheat the formation and/or to recover heat from the heating element.

Figure 150A:
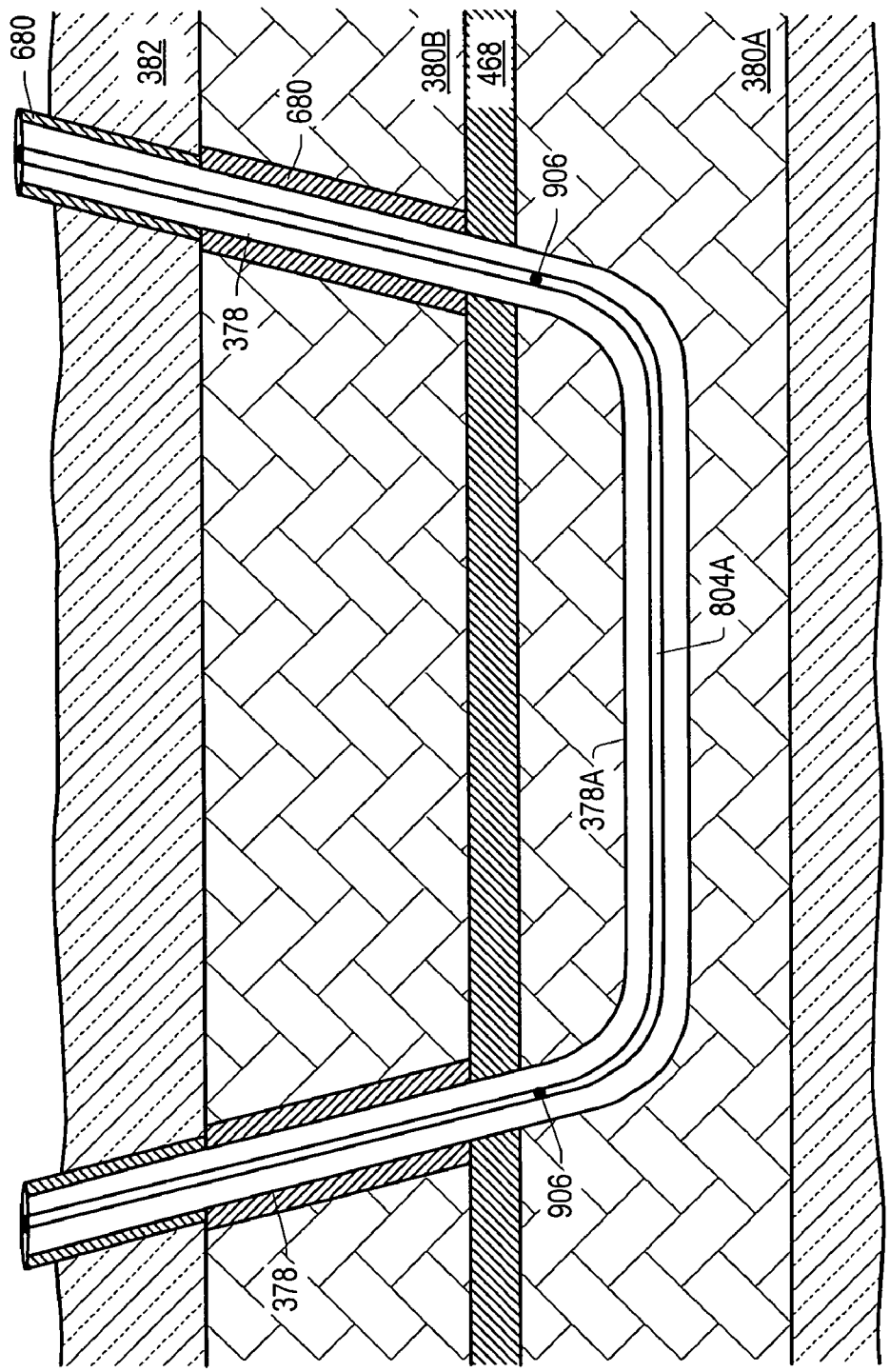
Figure 150B:
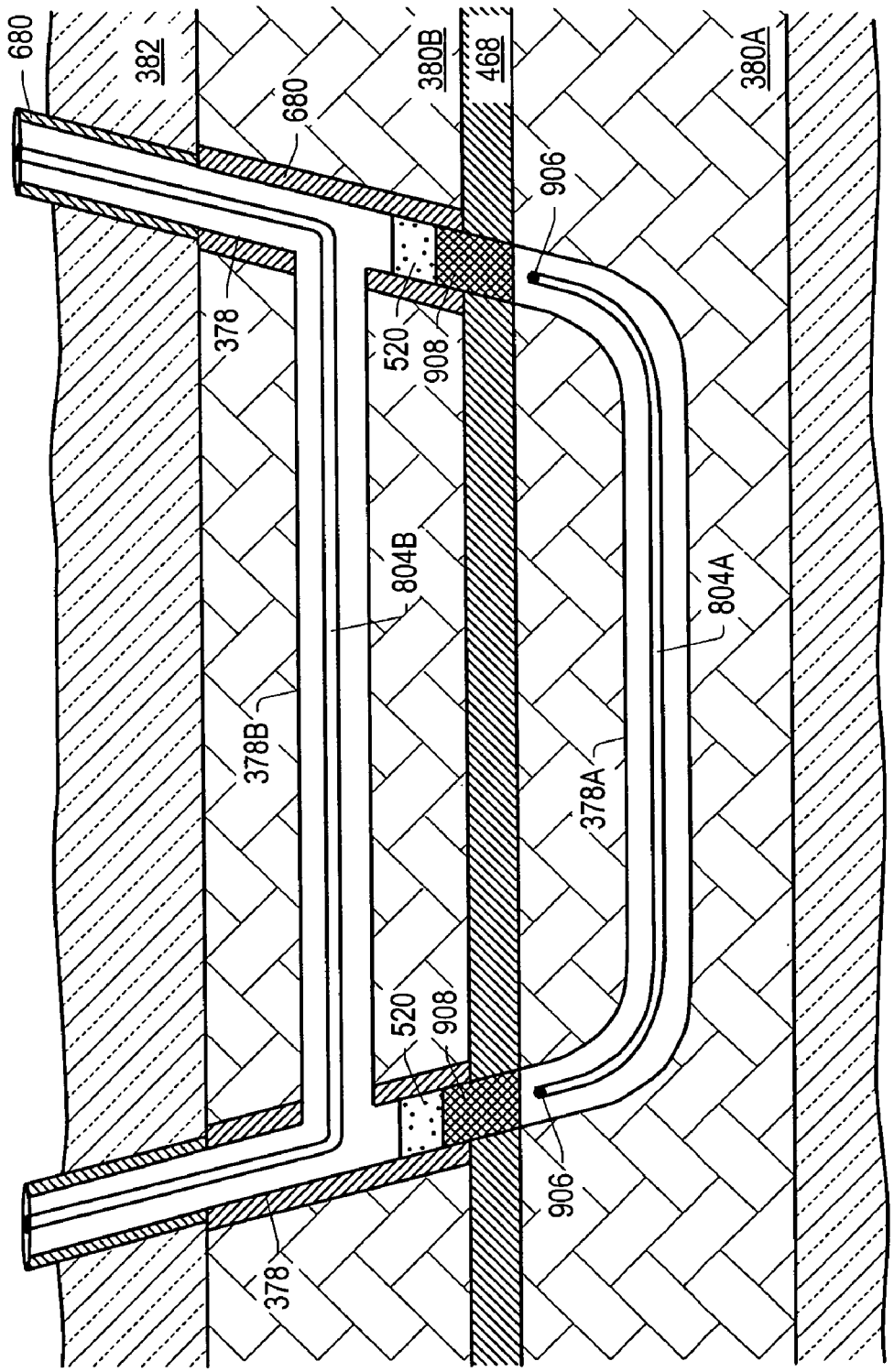

FIGS. 150A and 150B depict an embodiment for using substantially u-shaped wellbores to time sequence heat two layers in a hydrocarbon containing formation. In FIG. 150A, substantially horizontal opening 378A is formed in hydrocarbon layer 380A extending from relatively vertical openings 378. Hydrocarbon layer 380A is separated from hydrocarbon layer 380B by impermeable zone 468. Impermeable zone 468 provides a substantially impermeable seal for fluid flow between hydrocarbon layer 380A and hydrocarbon layer 380B. In certain embodiments (for example, in an oil shale formation), hydrocarbon layer 380A has a higher richness than hydrocarbon layer 380B.

Heating element 804A is placed in opening 378A in hydrocarbon layer 380A. Overburden casing 680 is placed along the relatively vertical walls of openings 378 in hydrocarbon layer 380B. Overburden casing 680 inhibits heat transfer to hydrocarbon layer 380B while heat is provided to hydrocarbon layer 380A by heating element 804A. Heating element 804A is used to provide heat to hydrocarbon layer 380A. Formation fluids, such as pyrolyzed hydrocarbons, may be produced from hydrocarbon layer 380A.

Heat may be provided to hydrocarbon layer 380A by heating element 804A for a selected length of time. The selected length of time may be based on a variety of factors including, but not limited to, formation characteristics, present or future economic factors, or capital costs. For example, for an oil shale formation, hydrocarbon layer 380A may have a richness of about 0.12 L/kg (30.5 gals/ton) so the layer is heated for about 25 years. Production of formation fluids from hydrocarbon layer 380A may continue from the layer until production slows down to an uneconomical rate.

After hydrocarbon layer 380A is heated for the selected time, heating element 804A is turned off. Heating element 804A may be pulled firmly (for example, yanked) upwards so that the heating element breaks off at links 906. Links 906 may be weak links designed to pull apart when a selected or sufficient amount of pulling force is applied to the links. The upper portions of heating element 804A are then pulled out of the formation and the substantially horizontal portion of heating element 804A is left in opening 378A, as shown in FIG. 150B. In some embodiments, only one link 906 may be broken so that the upper portion above the one link can be removed and the remaining portions of the heater can be removed by pulling on the opposite end of the heater. Thus, the entire length of heating element 804A may be removed from the formation.

After upper portions of heating element 804A are removed from openings 378, plugs 908 may be placed into openings 378 at a selected location in hydrocarbon layer 380B, as depicted in FIG. 150B. In certain embodiments, plugs 908 are placed into openings 378 at or near impermeable zone 468. Packing 520 may be placed into openings 378 above plugs 908. In some embodiments, packing 520 is filled into openings 378 without plugs in the openings.

After plugs 908 and/or packing 520 is set into place in openings 378, substantially horizontal opening 378B may be formed in hydrocarbon layer 380B through casing 680. Heating element 804B is placed into opening 378B. Heating element 804B is used to provide heat to hydrocarbon layer 380B. Formation fluids, such as pyrolyzed hydrocarbons, may be produced from hydrocarbon layer 380B.

Heating hydrocarbon layers 380A, 380B in the time-sequenced manner described above may be more economical than producing from only one layer or using vertical heaters to provide heat to the layers simultaneously: Using relatively vertical openings 378 to access both hydrocarbon layers at different times may save on capital costs associated with forming openings in the formation and providing surface facilities to power the heating elements. Heating hydrocarbon layer 380A first before heating hydrocarbon layer 380B may improve the economics of treating the formation (for example, the net present value of a project to treat the formation). In addition, impermeable zone 468 and packing 520 may provide a seal for hydrocarbon layer 380A after heating and production from the layer. This seal may be useful for abandonment of the hydrocarbon layer after treating the hydrocarbon layer.

In certain embodiments, portions of the wellbore that extend through the overburden include casings. The casings may include materials that inhibit inductive effects in the casings. Inhibiting inductive effects in the casings may inhibit induced currents in the casing and/or reduce heat losses to the overburden. In some embodiments, the overburden casings may include non-metallic materials such as fiberglass, polyvinylchloride (PVC), chlorinated PVC (CPVC), or high-density polyethylene (HDPE). HDPEs with working temperatures in a usable range include HDPEs available from Dow Chemical Co., Inc. (Midland, Mich., U.S.A.). In some embodiments, overburden casings may include non-magnetic metals such as aluminum or non-magnetic alloys such as manganese steels having at least 10% manganese, iron aluminum alloys with at least 18% aluminum, or austenitic stainless steels such as 304 stainless steel or 316 stainless steel. In some embodiments, overburden casings may include carbon steel or other ferromagnetic material coupled on the inside diameter to a highly conductive non-ferromagnetic metal (for example, copper or aluminum) to inhibit inductive effects or skin effects.

In certain embodiments, wellheads for the wellbores may be made of one or more non-ferromagnetic materials. The wellheads may include fiberglass, PVC, CPVC, HDPE, and/or non-magnetic alloys or metals. Using non-ferromagnetic materials in the wellhead may inhibit undesired heating of components in the wellhead. Ferromagnetic materials used in the wellhead may be electrically and/or thermally insulated from other components of the wellhead. In some embodiments, an inert gas (for example, nitrogen or argon) is purged inside the wellhead and/or inside of casings to inhibit reflux of heated gases into the wellhead and/or the casings.

In some embodiments, two or more substantially horizontal wellbores are branched off of a first substantially vertical wellbore drilled downwards from a first location on a surface of the formation. The substantially horizontal wellbores may be substantially parallel through a hydrocarbon layer. The substantially horizontal wellbores may reconnect at a second substantially vertical wellbore drilled downwards at a second location on the surface of the formation. Having multiple wellbores branching off of a single substantially vertical wellbore drilled downwards from the surface reduces the number of openings made at the surface of the formation.

In some embodiments, the temperature limited heater includes a single ferromagnetic conductor with current returning through the formation. The heating element may be a ferromagnetic tubular (in an embodiment, 446 stainless steel (with 25% by weight chromium and a Curie temperature above 620° C.) clad over 304H, 316H, or 347H stainless steel) that extends through the heated target section and makes electrical contact to the formation in an electrical contacting section. The electrical contacting section may be located below a heated target section in the underburden of the formation. In an embodiment, the electrical contacting section is a section 60 m deep with a larger diameter than the heater wellbore. The tubular in the electrical contacting section is a high electrical conductivity metal. The annulus in the electrical contacting section may be filled with a contact material/solution such as brine or other materials that enhance electrical contact with the formation (for example, metal beads, hematite, and/or graphite based cement). The electrical contacting section may be located in a low resistivity brine saturated zone (with higher porosity) to maintain electrical contact through the brine. In the electrical contacting section, the tubular diameter may also be increased to allow maximum current flow into the formation with lower heat dissipation in the fluid. Current may flow through the ferromagnetic tubular in the heated section and heat the tubular.

Figure 151:
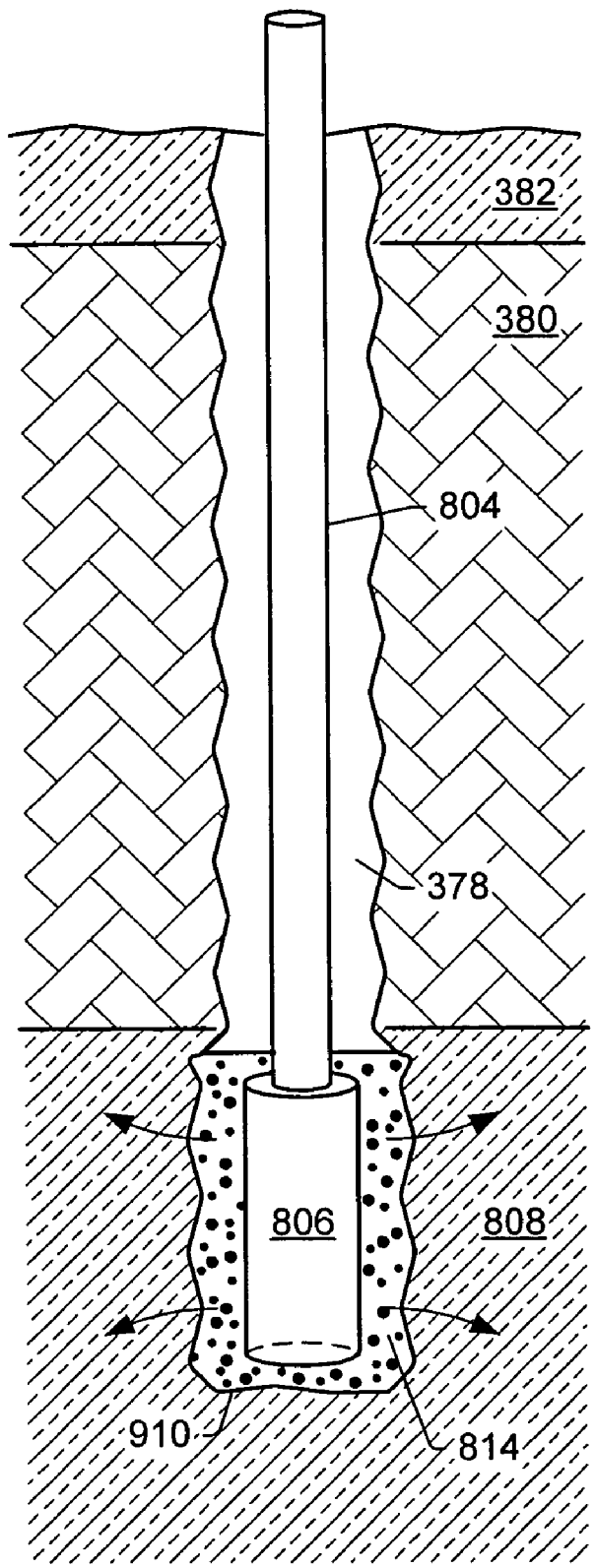

FIG. 151 depicts an embodiment of a temperature limited heater with current return through the formation. Heating element 804 may be placed in opening 378 in hydrocarbon layer 380. Heating element 804 may be 446 stainless steel clad over a 304H stainless steel tubular that extends through hydrocarbon layer 380. Heating element 804 may be coupled to contacting element 806. Contacting element 806 may have a higher electrical conductivity than heating element 804. Contacting element 806 may be placed in contacting section 808 below hydrocarbon layer 380. Contacting element 806 may make electrical contact with the earth in electrical contacting section 808. Contacting element 806 may be placed in contacting wellbore 910. Contacting element 806 may have a diameter between about 10 cm and about 20 cm (for example, about 15 cm). The diameter of contacting element 806 may be sized to increase contact area between contacting element 806 and contact solution 814. The contact area may be increased by increasing the diameter of contacting element 806. Increasing the diameter of contacting element 806 may increase the contact area without adding excessive cost to installation and use of the contacting element, contacting wellbore 910, and/or contact solution 814. Increasing the diameter of contacting element 806 may allow sufficient electrical contact to be maintained between the contacting element and contacting section 808. Increasing the contact area may also inhibit evaporation or reduction of contact solution 814.

Contacting wellbore 910 may be, for example, a section of about 60 m deep with a larger diameter wellbore than opening 378. The annulus of contacting wellbore 910 may be filled with contact solution 814. Contact solution 814 may be brine or other material (such as graphite based cement, electrically conducting particles such as hematite, or metal-coated sand or beads) that enhances electrical contact in contacting section 808. In some embodiments, contacting section 808 is a low resistivity brine saturated zone that maintains electrical contact through the brine. Contacting wellbore 910 may be under-reamed to a larger diameter (for example, a diameter between about 25 cm and about 50 cm) to allow maximum current flow into contacting section 808 with low heat output. Current may flow through heating element 804, boiling moisture from the wellbore, and heating until the heat output reduces near or at the Curie temperature.

In an embodiment, three-phase temperature limited heaters are made with current connection through the formation. Each heater includes a single Curie temperature heating element with an electrical contacting section in a brine saturated zone below a heated target section. In an embodiment, three such heaters are connected electrically at the surface in a three-phase wye configuration. The heaters may be deployed in a triangular pattern from the surface. In certain embodiments, the current returns through the earth to a neutral point between the three heaters. The three-phase Curie heaters may be replicated in a pattern that covers the entire formation.

FIG. 152 depicts an embodiment of a three-phase temperature limited heater with current connection through the formation. Legs 798, 800, 802 may be placed in the formation. Each leg 798, 800, 802 may have heating element 804 that is placed in opening 378 in hydrocarbon layer 380. Each leg may have contacting element 806 placed in contact solution 814 in contacting wellbore 910. Each contacting element 806 may be electrically coupled to electrical contacting section 808 through contact solution 814. Legs 798, 800, 802 may be connected in a wye configuration that results in a neutral point in electrical contacting section 808 between the three legs. FIG. 153 depicts an aerial view of the embodiment of FIG. 152 with neutral point 912 shown positioned centrally among legs 798, 800, 802.

FIG. 154 depicts an embodiment of three temperature limited heaters electrically coupled to a horizontal wellbore in the formation. Wellbore 420 may have a substantially horizontal portion in contacting section 808. Openings 378 may be directionally drilled to intersect wellbore 420 in contacting wellbores 910. In some embodiments, wellbore 420 is directionally drilled to intersect openings 378 in contacting wellbores 910. Contacting wellbores 910 may be underreamed. Underreaming may increase the likelihood of intersection between openings 378 and wellbore 420 during drilling and/or increase the contact volume in contacting wellbores 910.

In certain embodiments, legs 798, 800, 802 are coupled in a three-phase wye configuration. In some embodiments, legs 798, 800, 802, along with one or more other legs, are coupled through wellbore 420 in a single phase configuration in which the legs are alternately biased positively and negatively so that current alternately runs up and down the legs. In some embodiments, legs 798, 800, 802 are single phase heaters with current returning to the surface through wellbore 420.

In certain embodiments, legs 798, 800, 802 are electrically coupled in contacting wellbores 910 using contact solution 814. Contact solution 814 may be located in individual contacting wellbores 910 or may be located along the length of the horizontal portion of wellbore 420. In some embodiments, electrical contact is made between legs 798, 800, 802 and/or materials in wellbore 420 through other methods (for example, contactors or contacting elements such as funnels, guides, or catchers).

FIG. 155 depicts an embodiment of a three-phase temperature limited heater with a common current connection through the formation. In FIG. 155, each leg 798, 800, 802 couples to a single contacting element 806 in a single contacting wellbore 910. Legs 798 and 802 are directionally drilled to intercept leg 800 in wellbore 910. Contacting element 806 may include funnels, guides, or catchers for allowing each leg to be inserted into the contacting element. In some embodiments, graphite based cement is used for contact solution 814.

A section of heater through a high thermal conductivity zone may be tailored to deliver more heat dissipation in the high thermal conductivity zone. Tailoring of the heater may be achieved by changing cross-sectional areas of the heating elements (for example, by changing ratios of copper to iron), and/or using different metals in the heating elements. Thermal conductance of the insulation layer may also be modified in certain sections to control the thermal output to raise or lower the apparent Curie temperature zone.

In an embodiment, the temperature limited heater includes a hollow core or hollow inner conductor. Layers forming the heater may be perforated to allow fluids from the wellbore (for example, formation fluids or water) to enter the hollow core. Fluids in the hollow core may be transported (for example, pumped or gas lifted) to the surface through the hollow core. In some embodiments, the temperature limited heater with the hollow core or the hollow inner conductor is used as a heater/production well or a production well. Fluids such as steam may be injected into the formation through the hollow inner conductor.

In certain embodiments, a temperature limited heater is utilized for heavy oil applications (for example, treatment of relatively permeable formations or tar sands formations). A temperature limited heater may provide a relatively low Curie temperature so that a maximum average operating temperature of the heater is less than 350° C., 300° C., 250° C., 225° C., 200° C., or 150° C. In an embodiment (for example, for a tar sands formation), a maximum temperature of the heater is less than about 250° C. to inhibit olefin generation and production of other cracked products. In some embodiments, a maximum temperature of the heater above about 250° C. is used to produce lighter hydrocarbon products. For example, the maximum temperature of the heater may be at or less than about 500° C.

A heater may heat a volume of formation adjacent to a production wellbore (a near production wellbore region) so that the temperature of fluid in the production wellbore and in the volume adjacent to the production wellbore is less than the temperature that causes degradation of the fluid. The heat source may be located in the production wellbore or near the production wellbore. In some embodiments, the heat source is a temperature limited heater. In some embodiments, two or more heat sources may supply heat to the volume. Heat from the heat source may reduce the viscosity of crude oil in or near the production wellbore. In some embodiments, heat from the heat source mobilizes fluids in or near the production wellbore and/or enhances the radial flow of fluids to the production wellbore. In some embodiments, reducing the viscosity of crude oil allows or enhances gas lifting of heavy oil (approximately at most 10° API gravity oil) or intermediate gravity oil (approximately 12° to 20° API gravity oil) from the production wellbore. In certain embodiments, the initial API gravity of oil in the formation is at most 10°, at most 20°, at most 25°, or at most 30°. In certain embodiments, the viscosity of oil in the formation is at least 0.05 Pa·s (50 cp). In some embodiments, the viscosity of oil in the formation is at least 0.10 Pa·s (100 cp), at least 0.15 Pa·s (150 cp), or at least at least 0.20 Pa·s (200 cp). Large amounts of natural gas may have to be utilized to provide gas lift of oil with viscosities above 0.05 Pa·s. Reducing the viscosity of oil at or near the production wellbore in the formation to a viscosity of 0.05 Pa·s (50 cp), 0.03 Pa·s (30 cp), 0.02 Pa·s (20 cp), 0.01 Pa·s (10 cp), or less (down to 0.001 Pa·s (1 cp) or lower) lowers the amount of natural gas needed to lift oil from the formation. In some embodiments, reduced viscosity oil is produced by other methods such as pumping.

The rate of production of oil from the formation may be increased by raising the temperature at or near a production wellbore to reduce the viscosity of the oil in the formation in and adjacent to the production wellbore. In certain embodiments, the rate of production of oil from the formation is increased by 2 times, 3 times, 4 times, or greater up to 20 times over standard cold production, which has no external heating of formation during production. Certain formations may be more economically viable for enhanced oil production using the heating of the near production wellbore region. Formations that have a cold production rate approximately between 0.05 m³/(day per meter of wellbore length) and 0.20 m³/(day per meter of wellbore length) may have significant improvements in production rate using heating to reduce the viscosity in the near production wellbore region. In some formations, production wells up to 775 m, up to 1000 m, or up to 1500 m in length are used. For example, production wells between 450 m and 775 m in length are used, between 550 m and 800 m are used, or between 650 m and 900 m are used. Thus, a significant increase in production is achievable in some formations. Heating the near production wellbore region may be used in formations where the cold production rate is not between 0.05 m$^3$/(day per meter of wellbore length) and 0.20 m$^3$/(day per meter of wellbore length), but heating such formations may not be as economically favorable. Higher cold production rates may not be significantly increased by heating the near wellbore region, while lower production rates may not be increased to an economically useful value.

Using the temperature limited heater to reduce the viscosity of oil at or near the production well inhibits problems associated with non-temperature limited heaters and heating the oil in the formation due to hot spots. One possible problem is that non-temperature limited heaters can causing coking of oil at or near the production well if the heater overheats the oil because the heaters are at too high a temperature. Higher temperatures in the production well may also cause brine to boil in the well, which may lead to scale formation in the well. Non-temperature limited heaters that reach higher temperatures may also cause damage to other wellbore components (for example, screens used for sand control, pumps, or valves). Hot spots may be caused by portions of the formation expanding against or collapsing on the heater. In some embodiments, the heater (either the temperature limited heater or another type of non-temperature limited heater) has sections that are lower because of sagging over long heater distances. These lower sections may sit in heavy oil or bitumen that collects in lower portions of the wellbore. At these lower sections, the heater may develop hot spots due to coking of the heavy oil or bitumen. A standard non-temperature limited heater may overheat at these hot spots, thus producing a non-uniform amount of heat along the length of the heater. Using the temperature limited heater may inhibit overheating of the heater at hot spots or lower sections and provide more uniform heating along the length of the wellbore.

In some embodiments, oil or bitumen cokes in a perforated liner or screen in a heater/production wellbore (for example, coke may form between the heater and the liner or between the liner and the formation). Oil or bitumen may also coke in a toe section of a heel and toe heater/production wellbore, as shown in and described below for FIG. 165. A temperature limited heater may limit a temperature of a heater/production wellbore below a coking temperature to inhibit coking in the well so that the wellbore does not plug up.

In certain embodiments, fluids in the relatively permeable formation containing heavy hydrocarbons are produced with little or no pyrolyzation of hydrocarbons in the formation. In certain embodiments, the relatively permeable formation containing heavy hydrocarbons is a tar sands formation. The fluids produced from the formation are mobilized fluids. Producing mobilized fluids may be more economical than producing pyrolyzed fluids from the tar sands formation. Producing mobilized fluids may also increase the total amount of hydrocarbons produced from the tar sands formation.

FIG. 156 depicts a side view representation of an embodiment for producing mobilized fluids from the tar sands formation. In an embodiment, heaters 880 are placed in an alternating triangular pattern in hydrocarbon layer 380. Heaters 880 provide heat that mobilizes hydrocarbons (reduces the viscosity of the hydrocarbons) in hydrocarbon layer 380. Heat provided by heaters 880 is controlled so that little or no pyrolyzation occurs in hydrocarbon layer 380. Fluids mobilized in hydrocarbon layer 380 tend to flow towards the bottommost heaters in the hydrocarbon layer because of gravity and the heat gradient established by the heaters. The heat diffuses between the heaters to create a flow path between the heaters for mobilized fluids. This flow path, because of the triangular pattern that provides superposition of heat and because of gravity, directs mobilized fluids downwards towards production wells 206. Hydrocarbon layer 380 should have substantial vertical permeability to allow mobilized fluids to drain to production wells 206.

Production wells 206 are located below heaters 880 in the lower portion of hydrocarbon layer 380. Production wells 206 are located below and near heaters 880 at the bottom vertex of the triangular pattern of heaters. Production wells 206 are substantially vertically below the bottommost heaters in hydrocarbon layer 380. Locating production wells 206 substantially vertically below the bottommost heaters provides efficient collection of mobilized fluids in hydrocarbon layer 380. In certain embodiments, production wells 206 are located within about 2 m, within about 5 m, or within about 7 m of the bottommost heaters. In some embodiments, some heat is provided in production wells 206. Providing heat in production wells 206 maintains the mobility of the fluids in the production wells.

FIG. 157 depicts a representation of an embodiment for producing hydrocarbons from the tar sands formation. Hydrocarbon layer 380 includes one or more portions with heavy hydrocarbons. Hydrocarbons may be produced from hydrocarbon layer 380 using more than one process. In certain embodiments, hydrocarbons are produced from a first portion of hydrocarbon layer 380 using a steam injection process (for example, cyclic steam injection or steam-assisted gravity drainage) and a second portion of the hydrocarbon layer using an in situ conversion process. In the steam injection process, steam is injected into the first portion of hydrocarbon layer 380 through injection well 916. First hydrocarbons are produced from the first portion through production well 206A. The first hydrocarbons include hydrocarbons mobilized by the injection of steam. In certain embodiments, the first hydrocarbons have an API gravity of at most 10°, at most 8°, or at most 6°.

Heaters 880 are used to heat the second portion of hydrocarbon layer 380 to pyrolysis temperatures. Second hydrocarbons are produced from the first portion through production well 206B. In certain embodiments, the second hydrocarbons include at least some pyrolyzed hydrocarbons. In certain embodiments, the second hydrocarbons have an API gravity of at least 15°, at least 20°, or at least 25°.

Producing hydrocarbons through both processes increases the total recovery of hydrocarbons from hydrocarbon layer 380 and may be more economical than using either process alone. In some embodiments, the first portion is treated with the in situ conversion process after the steam injection process is completed. For example, after the steam injection process no longer produces viable amounts of hydrocarbon from the first portion, the in situ conversion process may be used on the first portion.

Steam is provided to injection well 916 from facility 918. Facility 918 is a steam and electricity cogeneration facility. Facility 918 may burn hydrocarbons in generators to make electricity. The electricity generated is used to provide electrical power for heaters 880. Waste heat from the generators is used to make steam. In some embodiments, some of the hydrocarbons produced from the formation are used to provide gas for heaters 880, if the heaters utilize gas to provide heat to the formation. The amount of electricity and steam generated by facility 918 may be controlled to vary the production rate and/or quality of hydrocarbons produced from the first portion and/or the second portion of hydrocarbon layer 380. The production rate and/or quality of hydrocarbons produced from the first portion and/or the second portion may be varied to produce a selected API gravity in a mixture made by blending the first hydrocarbons with the second hydrocarbons. The first hydrocarbon and the second hydrocarbons may be blended after production to produce the selected API gravity. The production from the first portion and/or the second portion may be varied in response to changes in the marketplace for either first hydrocarbons, second hydrocarbons, and/or a mixture of the first and second hydrocarbons.

First hydrocarbons produced from production well 206A and/or second hydrocarbons produced from production well 206B may be used as fuel for facility 918. In some embodiments, first hydrocarbons and/or second hydrocarbons are treated (for example, removing undesirable products) before being used as fuel for facility 918. The amount of first hydrocarbons and second hydrocarbons used as fuel for facility 918 may be determined, for example, by economics for the overall process, the marketplace for either first or second hydrocarbons, availability of treatment facilities for either first or second hydrocarbons, and/or transportation facilities available for either first or second hydrocarbons. In some embodiments, most or all the hydrocarbon gas produced from hydrocarbon layer 380 is used as fuel for facility 918. Burning all the hydrocarbon gas in facility 918 eliminates the need for treatment and/or transportation of gases produced from hydrocarbon layer 380.

The produced first hydrocarbons and the second hydrocarbons may be treated and/or blended in facility 920. In some embodiments, the first and second hydrocarbons are blended to make a mixture that is transportable through a pipeline. In some embodiments, the first and second hydrocarbons are blended to make a mixture that is useable as a feedstock for a refinery. The amount of first and second hydrocarbons produced may be varied based on changes in the requirements for treatment and/or blending of the hydrocarbons. In some embodiments, treated hydrocarbons are used in facility 918.

FIG. 158 depicts an embodiment for heating and producing from the formation with the temperature limited heater in a production wellbore. Production conduit 512 is located in wellbore 922. In certain embodiments, a portion of wellbore 922 is located substantially horizontally in formation 444. In some embodiments, the wellbore is located substantially vertically in the formation. In an embodiment, wellbore 922 is an open wellbore (an uncased wellbore). In some embodiments, the wellbore has a casing or liner with perforations or openings to allow fluid to flow into the wellbore.

Conduit 512 may be made from carbon steel or more corrosion resistant materials such as stainless steel. Conduit 512 may include apparatus and mechanisms for gas lifting or pumping produced oil to the surface. For example, conduit 512 includes gas lift valves used in a gas lift process. Examples of gas lift control systems and valves are disclosed in U.S. Pat. No. 6,715,550 to Vinegar et al. and U.S. Patent Application Publication Nos. 2002-0036085 to Bass et al. and 2003-0038734 to Hirsch et al., each of which is incorporated by reference as if fully set forth herein. Conduit 512 may include one or more openings (perforations) to allow fluid to flow into the production conduit. In certain embodiments, the openings in conduit 512 are in a portion of the conduit that remains below the liquid level in wellbore 922. For example, the openings are in a horizontal portion of conduit 512.

Heater 534 is located in conduit 512, as shown in FIG. 158. In some embodiments, heater 534 is located outside conduit 512, as shown in FIG. 159. The heater located outside the production conduit may be coupled (strapped) to the production conduit. In some embodiments, more than one heater (for example, two, three, or four heaters) are placed about conduit 512. The use of more than one heater may reduce bowing or flexing of the production conduit caused by heating on only one side of the production conduit. In an embodiment, heater 534 is a temperature limited heater. Heater 534 provides heat to reduce the viscosity of fluid (such as oil or hydrocarbons) in and near wellbore 922. In certain embodiments, heater 534 raises the temperature of the fluid in wellbore 922 up to a temperature of 250° C. or less (for example, 225° C., 200° C., or 150° C.). Heater 534 may be at higher temperatures (for example, 275° C., 300° C., or 325° C.) because the heater provides heat to conduit 512 and there is some temperature differential between the heater and the conduit. Thus, heat produced from the heater does not raise the temperature of fluids in the wellbore above 250° C.

In certain embodiments, heater 534 includes ferromagnetic materials such as Carpenter Temperature Compensator "32", Alloy 42-6, Alloy 52, Invar 36, or other iron-nickel or iron-nickel-chromium alloys. In certain embodiments, nickel or nickel-chromium alloys are used in heater 534. In some embodiments, heater 534 includes a composite conductor with a more highly conductive material such as copper on the inside of the heater to improve the turndown ratio of the heater. Heat from heater 534 heats fluids in or near wellbore 922 to reduce the viscosity of the fluids and increase a production rate through conduit 512.

In certain embodiments, portions of heater 534 above the liquid level in wellbore 922 (such as the vertical portion of the wellbore depicted in FIGS. 158 and 159) have a lower maximum temperature than portions of the heater located below the liquid level. For example, portions of heater 534 above the liquid level in wellbore 922 may have a maximum temperature of 100° C. while portions of the heater located below the liquid level have a maximum temperature of 250° C. In certain embodiments, such a heater includes two or more ferromagnetic sections with different Curie temperatures to achieve the desired heating pattern. Providing less heat to portions of wellbore 922 above the liquid level and closer to the surface may save energy.

In certain embodiments, heater 534 is electrically isolated on the heater's outside surface and allowed to move freely in conduit 512. In some embodiments, electrically insulating centralizers are placed on the outside of heater 534 to maintain a gap between conduit 512 and the heater.

In some embodiments, heater 534 is cycled (turned on and off) so that fluids produced through conduit 512 are not overheated. In an embodiment, heater 534 is turned on for a specified amount of time until a temperature of fluids in or near wellbore 922 reaches a desired temperature (for example, the maximum temperature of the heater). During the heating time (for example, 10 days, 20 days, or 30 days), production through conduit 512 may be stopped to allow fluids in the formation to "soak" and obtain a reduced viscosity. After heating is turned off or reduced, production through conduit 512 is started and fluids from the formation are produced without excess heat being provided to the fluids. During production, fluids in or near wellbore 922 will cool down without heat from heater 534 being provided. When the fluids reach a temperature at which production significantly slows down, production is stopped and heater 534 is turned back on to reheat the fluids. This process may be repeated until a desired amount of production is reached. In some embodiments, some heat at a lower temperature is provided to maintain a flow of the produced fluids. For example, low temperature heat (for example, 100° C., 125° C., or 150° C.) may be provided in the upper portions of wellbore 922 to keep fluids from cooling to a lower temperature.

FIG. 160 depicts an embodiment of a heating/production assembly that may be located in a wellbore for gas lifting. Heating/production assembly 924 may be located in a wellbore in the formation (for example, wellbore 922 depicted in FIG. 158 or 159). Conduit 512 is located inside casing 680. In an embodiment, conduit 512 is coiled tubing such as 6 cm diameter coiled tubing. Casing 680 has a diameter between 10 cm and 25 cm (for example, a diameter of 14 cm, 16 cm, or 18 cm). Heater 534 is coupled to an end of conduit 512. In some embodiments, heater 534 is located inside conduit 512. In some embodiments, heater 534 is a resistive portion of conduit 512. In some embodiments, heater 534 is coupled to a length of conduit 512.

Opening 926 is located at or near a junction of heater 534 and conduit 512. In some embodiments, opening 926 is a slot or a slit in conduit 512. In some embodiments, opening 926 includes more than one opening in conduit 512. Opening 926 allows production fluids to flow into conduit 512 from a wellbore. Perforated casing 928 allows fluids to flow into the heating/production assembly 924. In certain embodiments, perforated casing 928 is a wire wrapped screen. In one embodiment, perforated casing 928 is a 9 cm diameter wire wrapped screen.

Perforated casing 928 may be coupled to casing 680 with packing material 520. Packing material 520 inhibits fluids from flowing into casing 680 from outside perforated casing 928. Packing material 520 may also be placed inside casing 680 to inhibit fluids from flowing up the annulus between the casing and conduit 512. Seal assembly 920 is used to seal conduit 512 to packing material 520. Seal assembly 920 may fix a position of conduit 512 along a length of a wellbore. In some embodiments, seal assembly 920 allows for unsealing of conduit 512 so that the production conduit and heater 534 may be removed from the wellbore.

Feedthrough 932 is used to pass lead-in cable 692 to supply power to heater 534. Lead-in cable 692 may be secured to conduit 512 with clamp 934. In some embodiments, lead-in cable 692 passes through packing material 520 using a separate feedthrough.

A lifting gas (for example, natural gas, methane, carbon dioxide, propane, and/or nitrogen) may be provided to the annulus between conduit 512 and casing 680. Valves 936 are located along a length of conduit 512 to allow gas to enter the production conduit and provide for gas lifting of fluids in the production conduit. The lifting gas may mix with fluids in conduit 512 to lower the density of the fluids and allow for gas lifting of the fluids out of the formation. In certain embodiments, valves 936 are located in or near the overburden section of the formation so that gas lifting is provided in the overburden section. In some embodiments, fluids are produced through the annulus between conduit 512 and casing 680 and the lifting gas is supplied through valves 936.

In an embodiment, fluids are produced using a pump coupled to conduit 512. The pump may be a submersible pump (for example, an electric or gas powered submersible pump). In some embodiments, a heater is coupled to conduit 512 to maintain the reduced viscosity of fluids in the conduit and/or the pump.

In certain embodiments, an additional conduit such as an additional coiled tubing conduit is placed in the formation. Sensors may be placed in the additional conduit. For example, a production logging tool may be placed in the additional conduit to identify locations of producing zones and/or to assess flow rates. In some embodiments, a temperature sensor (for example, a distributed temperature sensor, a fiber optic sensor, and/or an array of thermocouples) is placed in the additional conduit to determine a subsurface temperature profile.

Some embodiments of the heating/production assembly are used in a well that preexists (for example, the heating/production assembly is retrofitted for a preexisting production well, heater well, or monitoring well). An example of the heating/production assembly that may be used in the preexisting well is depicted in FIG. 161. Some preexisting wells include a pump. The pump in the preexisting well may be left in the heating/production well retrofitted with the heating/production assembly.

FIG. 161 depicts an embodiment of the heating/production assembly that may be located in the wellbore for gas lifting. In FIG. 161, conduit 512 is located in outside production conduit 938. In an embodiment, outside production conduit 938 is 11.4 cm diameter production tubing. Casing 680 has a diameter of 24.4 cm. Perforated casing 928 has a diameter of 11.4 cm. Seal assembly 920 seals conduit 512 inside outside production conduit 938. In an embodiment, pump 518 is a jet pump such as a bottomhole assembly jet pump.

FIG. 162 depicts another embodiment of a heating/production assembly that may be located in a wellbore for gas lifting. Heater 534 is located inside perforated casing 928. Heater 534 is coupled to lead-in cable 692 through a feedthrough in packing material 520. Production conduit 512 extends through packing material 520. Pump 518 is located along conduit 512. In certain embodiments, pump 518 is a jet pump or a bean pump. Valves 936 are located along conduit 512 for supplying lift gas to the conduit.

In some embodiments, heat is inhibited from transferring into conduit 512. FIG. 163 depicts an embodiment of conduit 512 and heaters 534 that inhibit heat transfer into the conduit. Heaters 534 are coupled to conduit 512. Heaters 534 include ferromagnetic sections 622 and non-ferromagnetic sections 624. Ferromagnetic sections 622 provide heat at a temperature that reduces the viscosity of fluids in or near a wellbore. Non-ferromagnetic sections 624 provide little or no heat. In certain embodiments, ferromagnetic sections 622 and non-ferromagnetic sections 624 are 6 m in length. In some embodiments, ferromagnetic sections 622 and non-ferromagnetic sections 624 are between 3 m and 12 m in length, between 4 m and 11 m in length, or between 5 m and 10 m in length. In certain embodiments, non-ferromagnetic sections 624 include perforations 940 to allow fluids to flow to conduit 512. In some embodiments, heater 534 is positioned so that perforations are not needed to allow fluids to flow to conduit 512.

Conduit 512 may have perforations 940 to allow fluid to enter the conduit. Perforations 940 coincide with non-ferromagnetic sections 624 of heater 534. Sections of conduit 512 that coincide with ferromagnetic sections 622 include insulation conduit 942. Conduit 942 may be a vacuum insulated tubular. For example, conduit 942 may be a vacuum insulated production tubular available from Oil Tech Services, Inc. (Houston, Tex., U.S.A.). Conduit 942 inhibits heat transfer into conduit 512 from ferromagnetic sections 622. Limiting the heat transfer into conduit 512 reduces heat loss and/or inhibits overheating of fluids in the conduit. In an embodiment, heater 534 provides heat along an entire length of the heater and conduit 512 includes conduit 942 along an entire length of the production conduit.

In certain embodiments, more than one wellbore 922 is used to produce heavy oils from a formation using the temperature limited heater. FIG. 164 depicts an end view of an embodiment with wellbores 922 located in hydrocarbon layer 380. Portions of wellbores 922 are placed substantially horizontally in a triangular pattern in hydrocarbon layer 380. In certain embodiments, wellbores 922 have a spacing of 30 m to 60 m, 35 m to 55 m, or 40 m to 50 m. Wellbores 922 may include production conduits and heaters previously described. Fluids may be heated and produced through wellbores 922 at an increased production rate above a cold production rate for the formation. Production may continue for a selected time (for example, 5 years to 10 years, 6 years to 9 years, or 7 years to 8 years) until heat produced from each of wellbores 922 begins to overlap (superposition of heat begins). At such a time, heat from lower wellbores (such as wellbores 922 near the bottom of hydrocarbon layer 380) is continued, reduced, or turned off while production is continued. Production in upper wellbores (such as wellbores 922 near the top of hydrocarbon layer 380) may be stopped so that fluids in the hydrocarbon layer drain towards the lower wellbores. In some embodiments, power is increased to the upper wellbores and the temperature raised above the Curie temperature to increase the heat injection rate. Draining fluids in the formation in such a process increases total hydrocarbon recovery from the formation.

In an embodiment, a temperature limited heater is used in a horizontal heater/production well. The temperature limited heater may provide selected amounts of heat to the "toe" and the "heel" of the horizontal portion of the well. More heat may be provided to the formation through the toe than through the heel, creating a "hot portion" at the toe and a "warm portion" at the heel. Formation fluids may be formed in the hot portion and produced through the warm portion, as shown in FIG. 165.

FIG. 165 depicts an embodiment of a heater well for selectively heating a formation. Heat source 202 is placed in opening 378 in hydrocarbon layer 380. In certain embodiments, opening 378 is a substantially horizontal opening in hydrocarbon layer 380. Perforated casing 928 is placed in opening 378. Perforated casing 928 provides support that inhibits hydrocarbon and/or other material in hydrocarbon layer 380 from collapsing into opening 378. Perforations in perforated casing 928 allow for fluid flow from hydrocarbon layer 380 into opening 378. Heat source 202 may include hot portion 944. Hot portion 944 is a portion of heat source 202 that operates at higher heat output than adjacent portions of the heat source. For example, hot portion 944 may output between 650 W/m and 1650 W/m, 650 W/m and 1500 W/m, or 800 W/m and 1500 W/m. Hot portion 944 may extend from a "heel" of the heat source to the "toe" of the heat source. The heel of the heat source is the portion of the heat source closest to the point at which the heat source enters a hydrocarbon layer. The toe of the heat source is the end of the heat source furthest from the entry of the heat source into a hydrocarbon layer.

In an embodiment, heat source 202 includes warm portion 946. Warm portion 946 is a portion of heat source 202 that operates at lower heat outputs than hot portion 944. For example, warm portion 946 may output between 30 W/m and 1000 W/m, 30 W/m and 750 W/m, or 100 W/m and 750 W/m. Warm portion 946 may be located closer to the heel of heat source 202. In certain embodiments, warm portion 946 is a transition portion (for example, a transition conductor) between hot portion 944 and overburden portion 948. Overburden portion 948 is located in overburden 382. Overburden portion 948 provides a lower heat output than warm portion 946. For example, overburden portion 948 may output between 10 W/m and 90 W/m, 15 W/m and 80 W/m, or 25 W/m and 75 W/m. In some embodiments, overburden portion 948 provides as close to no heat (0 W/m) as possible to overburden 382. Some heat, however, may be used to maintain fluids produced through opening 378 in a vapor phase or at elevated temperature in overburden 382.

In certain embodiments, hot portion 944 of heat source 202 heats hydrocarbons to high enough temperatures to result in coke 950 forming in hydrocarbon layer 380. Coke 950 may occur in an area surrounding opening 378. Warm portion 946 may be operated at lower heat outputs so that coke does not form at or near the warm portion of heat source 202. Coke 950 may extend radially from opening 378 as heat from heat source 202 transfers outward from the opening. At a certain distance, however, coke 950 no longer forms because temperatures in hydrocarbon layer 380 at the certain distance will not reach coking temperatures. The distance at which no coke forms is a function of heat output (W/m from heat source 202), type of formation, hydrocarbon content in the formation, and/or other conditions in the formation.

The formation of coke 950 inhibits fluid flow into opening 378 through the coking. Fluids in the formation may, however, be produced through opening 378 at the heel of heat source 202 (for example, at warm portion 946 of the heat source) where there is little or no coke formation. The lower temperatures at the heel of heat source 202 reduce the possibility of increased cracking of formation fluids produced through the heel. Fluids may flow in a horizontal direction through the formation more easily than in a vertical direction. Typically, horizontal permeability in a relatively permeable formation is approximately 5 to 10 times greater than vertical permeability. Thus, fluids flow along the length of heat source 202 in a substantially horizontal direction. Producing formation fluids through opening 378 is possible at earlier times than producing fluids through production wells in hydrocarbon layer 380. The earlier production times through opening 378 is possible because temperatures near the opening increase faster than temperatures further away due to conduction of heat from heat source 202 through hydrocarbon layer 380. Early production of formation fluids may be used to maintain lower pressures in hydrocarbon layer 380 during start-up heating of the formation. Start-up heating of the formation is the time of heating before production begins at production wells in the formation. Lower pressures in the formation may increase liquid production from the formation. In addition, producing formation fluids through opening 378 may reduce the number of production wells needed in the formation.

In some embodiments, a temperature limited heater is used to heat a surface pipeline such as a sulfur transfer pipeline. For example, a surface sulfur pipeline may be heated to a temperature of about 100° C., about 110° C., or about 130° C. to inhibit solidification of fluids in the pipeline. Higher temperatures in the pipeline (for example, above about 130° C.) may induce undesirable degradation of fluids in the pipeline.

In some embodiments, a temperature limited heater positioned in a wellbore heats steam that is provided to the wellbore. The heated steam may be introduced into a portion of the formation. In certain embodiments, the heated steam may be used as a heat transfer fluid to heat a portion of the formation. In some embodiments, the steam is used to solution mine desired minerals from the formation. In some embodiments, the temperature limited heater positioned in the wellbore heats liquid water that is introduced into a portion of the formation.

In an embodiment, the temperature limited heater includes ferromagnetic material with a selected Curie temperature. The use of a temperature limited heater may inhibit a temperature of the heater from increasing beyond a maximum selected temperature (for example, at or about the Curie temperature). Limiting the temperature of the heater may inhibit potential burnout of the heater. The maximum selected temperature may be a temperature selected to heat the steam to above or near 100% saturation conditions, superheated conditions, or supercritical conditions. Using a temperature limited heater to heat the steam may inhibit overheating of the steam in the wellbore. Steam introduced into a formation may be used for synthesis gas production, to heat the hydrocarbon containing formation, to carry chemicals into the formation, to extract chemicals or minerals from the formation, and/or to control heating of the formation.

A portion of the formation where steam is introduced or that is heated with steam may be at significant depths below the surface (for example, greater than about 1000 m, about 2500, or about 5000 m below the surface). If steam is heated at the surface of the formation and introduced to the formation through a wellbore, a quality of the heated steam provided to the wellbore at the surface may have to be relatively high to accommodate heat losses to the wellbore casing and/or the overburden as the steam travels down the wellbore. Heating the steam in the wellbore may allow the quality of the steam to be significantly improved before the steam is provided to the formation. A temperature limited heater positioned in a lower section of the overburden and/or adjacent to a target zone of the formation may be used to controllably heat steam to improve the quality of the steam injected into the formation and/or inhibit condensation along the length of the heater. In certain embodiments, the temperature limited heater improves the quality of the steam injected and/or inhibits condensation in the wellbore for long steam injection wellbores (especially for long horizontal steam injection wellbores).

A temperature limited heater positioned in a wellbore may be used to heat the steam to above or near 100% saturation conditions or superheated conditions. In some embodiments, a temperature limited heater may heat the steam so that the steam is above or near supercritical conditions. The static head of fluid above the temperature limited heater may facilitate producing 100% saturation, superheated, and/or supercritical conditions in the steam. Supercritical or near supercritical steam may be used to strip hydrocarbon material and/or other materials from the formation. In certain embodiments, steam introduced into the formation may have a high density (for example, a specific gravity of about 0.8 or above). Increasing the density of the steam may improve the ability of the steam to strip hydrocarbon material and/or other materials from the formation.

Improved alloys containing manganese, copper and tungsten, in combination with niobium, carbon and nitrogen, may maintain a finer grain size despite high temperature solution annealing or processing. Such behavior may be beneficial in reducing a heat-affected-zone in welded material. Higher solution-annealing temperatures are particularly important for achieving the best NbC nano-carbide strengthening during high-temperature creep service, and such effects are amplified (finer nano-carbide structures that are stable) by compositions of the improved alloys. Tubing and canister applications that include the composition of the improved alloys and are wrought processed result in stainless steels that may be able to age-harden during service at about 700° C. to about 800° C. Improved alloys may be able to age-harden even more if the alloys are cold-strained prior to high-temperature service. Cold-prestraining may degrade rather than enhance high-temperature strength and long-term durability, and therefore may be limited or not permitted by, for example, construction codes.

An improved alloy may include, by weight: about 18% to about 22% chromium, about 12% to about 13% nickel, above 0% to about 4.5% copper, about 1% to about 5% manganese, about 0.3% to about 1% silicon, above 0% to about 1% niobium, about 0.3% to about 1% molybdenum, about 0.08% to about 0.2% carbon, about 0.2% to about 0.5% nitrogen, above 0% to about 2% tungsten, and with the balance being iron (for example, about 47.8% to about 68.12% iron). Such an improved alloy may be useful when processed by hot deformation, cold deformation, and/or welding into, for example, casings, canisters, or strength members for heaters. In some embodiments, the improved alloy includes, by weight: about 20% chromium, about 3% copper, about 4% manganese, about 0.3% molybdenum, about 0.77% niobium, about 13% nickel, about 0.5% silicon, about 1% tungsten, about 0.09% carbon, and about 0.26% nitrogen, with the balance being iron. In certain embodiments, the improved alloy includes, by weight: about 19% chromium, about 4.2% manganese, about 0.3% molybdenum, about 0.8% niobium, about 12.5% nickel, about 0.5% silicon, about 0.09% carbon, about 0.24% nitrogen by weight with the balance being iron. In some embodiments, improved alloys may vary an amount of manganese, amount of nickel, and/or a Mn/Ni ratio to enhance resistance to high temperature sulfidation, increase high temperature strength, and/or reduce cost.

In some embodiments, the improved alloys are processed to produce a wrought material. A 6" inside diameter, centrifugal cast pipe having a wall thickness of 1.5" may be cast from the improved alloy. A section may be removed from the casting and heat treated at at least about 1250° C. for, for example, about three hours. The heat treated section may be hot rolled at at least about 1200° C. to a 0.75" thickness, annealed at at least about 1200° C. for fifteen minutes, and then sandblasted. The sandblasted section may be cold rolled to a thickness of about 0.55". The cold rolled section may be annealed at at least about 1250° C. for about an hour in, for example, air with an argon cover, and then given a final additional heat treatment for about one hour at at least about 1250° C. in air with an argon cover. An alternative process may include any of the following: initially homogenizing the cast plate at least about 1200° C. for about 1½ hours; hot rolling at least about 1200° C. to a 1" thickness; and annealing the cold-rolled plate for about one hour at least about 1200° C.

The improved alloys may be extruded at, for example, about 1200° C., with, for example, a mandrel diameter of 0.9" and a die diameter of 1.35" to produce good quality tubes. The wrought material may be welded by, for example, laser welding. Thus, tubes may be produced by rolling plates and welding seams.

Improved alloys may have high temperature creep strengths and tensile strengths that are superior to conventional alloys. For example, niobium stabilized stainless steel alloys that include manganese, nitrogen, copper and tungsten may have high temperature creep strengths and tensile strengths that are improved, or substantially improved relative to conventional alloys such as 347H.

Improved alloys may have increased strength relative to standard stainless steel alloys such as Super 304H at high temperatures (for example, about 700° C., about 800° C., or above 1000° C.). Superior high temperature creep-rupture strength (for example, creep-rupture strength at about 800° C., about 900° C. or about 1250° C.) may be improved as a result of (a) composition, (b) stable, fine-grain microstructures induced by high temperature processing, and (c) age-induced precipitation structures in the improved alloys. Precipitation structures include, for example, micro-carbides that strengthen grain boundaries and stable nano-carbides that strengthen inside the grains. Presence of phases other than sigma and laves phases contribute to high temperature properties. Stable microstructures may be achieved by proper selection of components. High temperature aging induced or creep-induced microstructures have minimal or no intermetallic sigma and laves phases. Intermetallic sigma and lava phases may weaken the strength properties of alloys.

At about 800° C., the improved alloys may include at least 3% by weight of micro-carbides, other phases, and/or stable, fine grain microstructure that produce strength. At about 900° C., the improved alloys may include at least 1.5% by weight, at least 2% by weight, at least 3% by weight, at least 3.5% by weight, or at least 5% by weight micro-carbides, other phases, and/or stable, fine grain microstructure that produce strength. These values may be higher than the corresponding values in 347H or Super 304H stainless steel alloys at about 900° C. At about 1250° C. improved alloys may include at least 0.5% by weight micro-carbides, other phases, and/or stable, fine grain microstructure that produce strength. The resulting higher weight percent of micro-carbides, other phases, and/or stable, fine grain microstructure, and the exclusion of sigma and laves phases, may account for superior high temperature performance of the improved alloys.

Alloys having similar or superior high temperature performance to the improved alloys may be derived by modelling phase behaviour at elevated temperatures and selecting compositions that retain at least 1.5%, 2%, or 2.5% by weight of phases other than sigma or laves phases at, for example, about 900° C. For example, a stable microstructure may include an amount of niobium that is nearly ten times the amount of carbon, along with 1% to 5% of manganese, and nitrogen. Copper and tungsten may be included in the composition to increase the amount of stable microstructures. The choice of elements for the improved alloys allows processing by various methods and results in a stable, fine grain size, even after heat treatments of at least about 1250° C. Many prior art alloys tend to grain coarsen significantly when annealed at such high temperatures. In some embodiments, grain size is controlled to achieve desirable high temperature tensile and creep properties. Stable grain structure in the improved alloys reduces grain boundary sliding, and may be a contributing factor for the better strength relative to commercially available alloys at temperatures above, for example, about 650° C.

Non-Restrictive Examples are Set Forth Below.

FIGS. 166-183 depict experimental data for temperature limited heaters. FIG. 166 depicts electrical resistance (Ω) versus temperature (° C.) at various applied electrical currents for a 446 stainless steel rod with a diameter of 2.5 cm and a 410 stainless steel rod with a diameter of 2.5 cm. Both rods had a length of 1.8 m. Curves 952-958 depict resistance profiles as a function of temperature for the 446 stainless steel rod at 440 amps AC (curve 952), 450 amps AC (curve 954), 500 amps AC (curve 956), and 10 amps DC (curve 958). Curves 960-966 depict resistance profiles as a function of temperature for the 410 stainless steel rod at 400 amps AC (curve 960), 450 amps AC (curve 962), 500 amps AC (curve 964), 10 amps DC (curve 966). For both rods, the resistance gradually increased with temperature until the Curie temperature was reached. At the Curie temperature, the resistance fell sharply. Above the Curie temperature, the resistance decreased slightly with increasing temperature. Both rods show a trend of decreasing resistance with increasing AC current. Accordingly, the turndown ratio decreased with increasing current. Thus, the rods provide a reduced amount of heat near and above the Curie temperature of the rods. In contrast, the resistance gradually increased with temperature through the Curie temperature with the applied DC current.

FIG. 167 shows electrical resistance (Ω) profiles as a function of temperature (° C.) at various applied electrical currents for a copper rod contained in a conduit of Sumitomo HCM12A (a high strength 410 stainless steel). The Sumitomo conduit had a diameter of 5.1 cm, a length of 1.8 m, and a wall thickness of about 0.1 cm. Curves 968-978 show that at all applied currents (968: 300 amps AC; 970: 350 amps AC; 972: 400 amps AC; 974: 450 amps AC; 976: 500 amps AC; 978: 550 amps AC), resistance increased gradually with temperature until the Curie temperature was reached. At the Curie temperature, the resistance fell sharply. As the current increased, the resistance decreased, resulting in a smaller turndown ratio.

FIG. 168 depicts electrical resistance (Ω) versus temperature (° C.) at various applied electrical currents for a temperature limited heater. The temperature limited heater included a 4/0 MGT-1000 furnace cable inside an outer conductor of 3⁄4" Schedule 80 Sandvik (Sweden) 4C54 (446 stainless steel) with a 0.30 cm thick copper sheath welded onto the outside of the Sandvik 4C54 and a length of 1.8 m. Curves 980 through 998 show resistance profiles as a function of temperature for AC applied currents ranging from 40 amps to 500 amps (980: 40 amps; 982: 80 amps; 984: 120 amps; 986: 160 amps; 988: 250 amps; 990: 300 amps; 992: 350 amps; 994: 400 amps; 996: 450 amps; 998: 500 amps). FIG. 169 depicts the raw data for curve 994. FIG. 170 depicts the data for selected curves 990, 992, 994, 996, 998, and 1000. At lower currents (below 250 amps), the resistance increased with increasing temperature up to the Curie temperature. At the Curie temperature, the resistance fell sharply. At higher currents (above 250 amps), the resistance decreased slightly with increasing temperature up to the Curie temperature. At the Curie temperature, the resistance fell sharply. Curve 1000 shows resistance for an applied DC electrical current of 10 amps. Curve 1000 shows a steady increase in resistance with increasing temperature, with little or no deviation at the Curie temperature.

FIG. 171 depicts power (watts per meter (W/m)) versus temperature (° C.) at various applied electrical currents for a temperature limited heater. The temperature limited heater included a 4/0 MGT-1000 furnace cable inside an outer conductor of 3⁄4" Schedule 80 Sandvik (Sweden) 4C54 (446 stainless steel) with a 0.30 cm thick copper sheath welded onto the outside of the Sandvik 4C54 and a length of 1.8 m. Curves 1002-1010 depict power versus temperature for AC applied currents of 300 amps to 500 amps (1002: 300 amps; 1004: 350 amps; 1006: 400 amps; 1008: 450 amps; 1010: 500 amps). Increasing the temperature gradually decreased the power until the Curie temperature was reached. At the Curie temperature, the power decreased rapidly.

FIG. 172 depicts electrical resistance (mΩ) versus temperature (° C.) at various applied electrical currents for a temperature limited heater. The temperature limited heater included a copper rod with a diameter of 1.3 cm inside an outer conductor of 2.5 cm Schedule 80 410 stainless steel pipe with a 0.15 cm thick copper Everdur™ (DuPont Engineering, Wilmington, Del., U.S.A.) welded sheath over the 410 stainless steel pipe and a length of 1.8 m. Curves 1012-1022 show resistance profiles as a function of temperature for AC applied currents ranging from 300 amps to 550 amps (1012: 300 amps; 1014: 350 amps; 1016: 400 amps; 1018: 450 amps; 1020: 500 amps; 1022: 550 amps). For these AC applied currents, the resistance gradually increases with increasing temperature up to the Curie temperature. At the Curie temperature, the resistance falls sharply. In contrast, curve 1024 shows resistance for an applied DC electrical current of 10 amps. This resistance shows a steady increase with increasing temperature, and little or no deviation at the Curie temperature.

FIG. 173 depicts data of electrical resistance (mΩ) versus temperature (° C.) for a solid 2.54 cm diameter, 1.8 m long 410 stainless steel rod at various applied electrical currents. Curves 1026, 1028, 1030, 1032, and 1034 depict resistance profiles as a function of temperature for the 410 stainless steel rod at 40 amps AC (curve 1032), 70 amps AC (curve 1034), 140 amps AC (curve 1026), 230 amps AC (curve 1028), and 10 amps DC (curve 1030). For the applied AC currents of 140 amps and 230 amps, the resistance increased gradually with increasing temperature until the Curie temperature was reached. At the Curie temperature, the resistance fell sharply. In contrast, the resistance showed a gradual increase with temperature through the Curie temperature for the applied DC current.

FIG. 174 depicts data of electrical resistance (mΩ) versus temperature (° C.) for a composite 1.75 inch (1.9) diameter, 6 foot (1.8 m) long Alloy 42-6 rod with a 0.375 inch diameter copper core (the rod has an outside diameter to copper diameter ratio of 2:1) at various applied electrical currents. Curves 1036, 1038, 1040, 1042, 1044, 1046, 1048, and 1050 depict resistance profiles as a function of temperature for the copper cored alloy 42-6 rod at 300 A AC (curve 1036), 350 A AC (curve 1038), 400 A AC (curve 1040), 450 A AC (curve 1042), 500 A AC (curve 1044), 550 A AC (curve 1046), 600 A AC (curve 1048), and 10 A DC (curve 1050). For the applied AC currents, the resistance decreased gradually with increasing temperature until the Curie temperature was reached. As the temperature approaches the Curie temperature, the resistance decreased more sharply. In contrast, the resistance showed a gradual increase with temperature for the applied DC current.

FIG. 175 depicts data of power output (watts per foot (W/ft)) versus temperature (° C.) for a composite 1.75 inch (1.9 cm) diameter, 6 foot (1.8 m) long Alloy 42-6 rod with a 0.375 inch diameter copper core (the rod has an outside diameter to copper diameter ratio of 2:1) at various applied electrical currents. Curves 1052, 1054, 1056, 1058, 1060, 1062, 1064, and 1066 depict power as a function of temperature for the copper cored alloy 42-6 rod at 300 A AC (curve 1052), 350 A AC (curve 1054), 400 A AC (curve 1056), 450 A AC (curve 1058), 500 A AC (curve 1060), 550 A AC (curve 1062), 600 A AC (curve 1064), and 10 A DC (curve 1066). For the applied AC currents, the power output decreased gradually with increasing temperature until the Curie temperature was reached. As the temperature approaches the Curie temperature, the power output decreased more sharply. In contrast, the power output showed a relatively flat profile with temperature for the applied DC current.

FIG. 176 depicts data of electrical resistance (mΩ) versus temperature (° C.) for a composite 0.75" diameter, 6 foot long Alloy 52 rod with a 0.375" diameter copper core at various applied electrical currents. Curves 1068, 1070, 1072, 1074, and 1076 depict resistance profiles as a function of temperature for the copper cored Alloy 52 rod at 300 A AC (curve 1068), 400 A AC (curve 1070), 500 A AC (curve 1072), 600 A AC (curve 1074), and 10 A DC (curve 1076). For the applied AC currents, the resistance increased gradually with increasing temperature until around 320° C. After 320° C., the resistance began to decrease gradually, decreasing more sharply as the temperature approached the Curie temperature. At the Curie temperature, the AC resistance decreased very sharply. In contrast, the resistance showed a gradual increase with temperature for the applied DC current. The turndown ratio for the 400 A applied AC current (curve 1070) was 2.8.

FIG. 177 depicts data of power output (watts per foot (W/ft)) versus temperature (° C.) for a composite 1.75" diameter, 6 foot long Alloy 52 rod with a 0.375" diameter copper core at various applied electrical currents. Curves 1078, 1080, 1082, and 1084 depict power as a function of temperature for the copper cored Alloy 52 rod at 300 A AC (curve 1078), 400 A AC (curve 1080), 500 A AC (curve 1082), and 600 A AC (curve 1084). For the applied AC currents, the power output increased gradually with increasing temperature until around 320° C. After 320° C., the power output began to decrease gradually, decreasing more sharply as the temperature approached the Curie temperature. At the Curie temperature, the power output decreased very sharply.

FIG. 178 depicts data for values of skin depth (cm) versus temperature (° C.) for a solid 2.54 cm diameter, 1.8 m long 410 stainless steel rod at various applied AC electrical currents. The skin depth was calculated using EQN. 6:

$$\delta = R_1 - R_1 \times (1 - (1/R_{AC}/R_{DC}))^{1/2}; \qquad (6)$$

where δ is the skin depth, $R_1$ is the radius of the cylinder, $R_{AC}$ is the AC resistance, and $R_{DC}$ is the DC resistance. In FIG. 178, curves 1086-1104 show skin depth profiles as a function of temperature for applied AC electrical currents over a range of 50 amps to 500 amps (1086: 50 amps; 1088: 100 amps; 1090: 150 amps; 1092: 200 amps; 1094: 250 amps; 1096: 300 amps; 1098: 350 amps; 1100: 400 amps; 1102: 450 amps; 1104: 500 amps). For each applied AC electrical current, the skin depth gradually increased with increasing temperature up to the Curie temperature. At the Curie temperature, the skin depth increased sharply.

FIG. 179 depicts temperature (° C.) versus time (hrs) for a temperature limited heater. The temperature limited heater was a 1.83 m long heater that included a copper rod with a diameter of 1.3 cm inside a 2.5 cm Schedule XXR 410 stainless steel pipe and a 0.325 cm copper sheath. The heater was placed in an oven for heating. Alternating current was applied to the heater when the heater was in the oven. The current was increased over two hours and reached a relatively constant value of 400 amps for the remainder of the time. Temperature of the stainless steel pipe was measured at three points at 0.46 m intervals along the length of the heater. Curve 1106 depicts the temperature of the pipe at a point 0.46 m inside the oven and closest to the lead-in portion of the heater. Curve 1108 depicts the temperature of the pipe at a point 0.46 m from the end of the pipe and furthest from the lead-in portion of the heater. Curve 1110 depicts the temperature of the pipe at about a center point of the heater. The point at the center of the heater was further enclosed in a 0.3 m section of 2.5 cm thick Fiberfrax® (Unifrax Corp., Niagara Falls, N.Y., U.S.A.) insulation. The insulation was used to create a low thermal conductivity section on the heater (a section where heat transfer to the surroundings is slowed or inhibited (a "hot spot")). The temperature of the heater increased with time as shown by curves 1110, 1108, and 1106. Curves 1110, 1108, and 1106 show that the temperature of the heater increased to about the same value for all three points along the length of the heater. The resulting temperatures were substantially independent of the added Fiberfrax® insulation. Thus, the operating temperatures of the temperature limited heater were substantially the same despite the differences in thermal load (due to the insulation) at each of the three points along the length of the heater. Thus, the temperature limited heater did not exceed the selected temperature limit in the presence of a low thermal conductivity section.

FIG. 180 depicts temperature (° C.) versus log time (hrs) data for a 2.5 cm solid 410 stainless steel rod and a 2.5 cm solid 304 stainless steel rod. At a constant applied AC electrical current, the temperature of each rod increased with time. Curve 1112 shows data for a thermocouple placed on an outer surface of the 304 stainless steel rod and under a layer of insulation. Curve 1114 shows data for a thermocouple placed on an outer surface of the 304 stainless steel rod without a layer of insulation. Curve 1116 shows data for a thermocouple placed on an outer surface of the 410 stainless steel rod and under a layer of insulation. Curve 1118 shows data for a thermocouple placed on an outer surface of the 410 stainless steel rod without a layer of insulation. A comparison of the curves shows that the temperature of the 304 stainless steel rod (curves 1112 and 1114) increased more rapidly than the temperature of the 410 stainless steel rod (curves 1116 and 1118). The temperature of the 304 stainless steel rod (curves 1112 and 1114) also reached a higher value than the temperature of the 410 stainless steel rod (curves 1116 and 1118). The temperature difference between the non-insulated section of the 410 stainless steel rod (curve 1118) and the insulated section of the 410 stainless steel rod (curve 1116) was less than the temperature difference between the non-insulated section of the 304 stainless steel rod (curve 1114) and the insulated section of the 304 stainless steel rod (curve 1112). The temperature of the 304 stainless steel rod was increasing at the termination of the experiment (curves 1112 and 1114) while the temperature of the 410 stainless steel rod had leveled out (curves 1116 and 1118). Thus, the 410 stainless steel rod (the temperature limited heater) provided better temperature control than the 304 stainless steel rod (the non-temperature limited heater) in the presence of varying thermal loads (due to the insulation).

A 6 foot temperature limited heater element was placed in a 6 foot 347H stainless steel canister. The heater element was connected to the canister in a series configuration. The heater element and canister were placed in an oven. The oven was used to raise the temperature of the heater element and the canister. At varying temperatures, a series of electrical currents were passed through the heater element and returned through the canister. The resistance of the heater element and the power factor of the heater element were determined from measurements during passing of the electrical currents.

FIG. 181 depicts experimentally measured electrical resistance (mΩ) versus temperature (° C.) at several currents for a temperature limited heater with a copper core, a carbon steel ferromagnetic conductor, and a 347H stainless steel support member. The ferromagnetic conductor was a low-carbon steel with a Curie temperature of 770° C. The ferromagnetic conductor was sandwiched between the copper core and the 347H support member. The copper core had a diameter of 0.5". The ferromagnetic conductor had an outside diameter of 0.765". The support member had an outside diameter of 1.05". The canister was a 3" Schedule 160 347H stainless steel canister.

Data 1120 depicts electrical resistance versus temperature for 300 A at 60 Hz AC applied current. Data 1122 depicts resistance versus temperature for 400 A at 60 Hz AC applied current. Data 1124 depicts resistance versus temperature for 500 A at 60 Hz AC applied current. Curve 1126 depicts resistance versus temperature for 10 A DC applied current. The resistance versus temperature data indicates that the AC resistance of the temperature limited heater linearly increased up to a temperature near the Curie temperature of the ferromagnetic conductor. Near the Curie temperature, the AC resistance decreased rapidly until the AC resistance equaled the DC resistance above the Curie temperature. The linear dependence of the AC resistance below the Curie temperature at least partially reflects the linear dependence of the AC resistance of 347H at these temperatures. Thus, the linear dependence of the AC resistance below the Curie temperature indicates that the majority of the current is flowing through the 347H support member at these temperatures.

FIG. 182 depicts experimentally measured electrical resistance (mΩ) versus temperature (° C.) data at several currents for a temperature limited heater with a copper core, a iron-cobalt ferromagnetic conductor, and a 347H stainless steel support member. The iron-cobalt ferromagnetic conductor was an iron-cobalt conductor with 6% cobalt by weight and a Curie temperature of 834° C. The ferromagnetic conductor was sandwiched between the copper core and the 347H support member. The copper core had a diameter of 0.465". The ferromagnetic conductor had an outside diameter of 0.765". The support member had an outside diameter of 1.05". The canister was a 3" Schedule 160 347H stainless steel canister.

Data 1128 depicts resistance versus temperature for 100 A at 60 Hz AC applied current. Data 1130 depicts resistance versus temperature for 400 A at 60 Hz AC applied current. Curve 1132 depicts resistance versus temperature for 10 A DC. The AC resistance of this temperature limited heater turned down at a higher temperature than the previous temperature limited heater. This was due to the added cobalt increasing the Curie temperature of the ferromagnetic conductor. The AC resistance was substantially the same as the AC resistance of a tube of 347H steel having the dimensions of the support member. This indicates that the majority of the current is flowing through the 347H support member at these temperatures. The resistance curves in FIG. 182 are generally the same shape as the resistance curves in FIG. 181.

FIG. 183 depicts experimentally measured power factor (y-axis) versus temperature (° C.) at two AC currents for the temperature limited heater with the copper core, the iron-cobalt ferromagnetic conductor, and the 347H stainless steel support member. Curve 1134 depicts power factor versus temperature for 100 A at 60 Hz AC applied current. Curve 1136 depicts power factor versus temperature for 400 A at 60 Hz AC applied current. The power factor was close to unity (1) except for the region around the Curie temperature. In the region around the Curie temperature, the non-linear magnetic properties and a larger portion of the current flowing through the ferromagnetic conductor produce inductive effects and distortion in the heater that lowers the power factor. FIG. 183 shows that the minimum value of the power factor for this heater remained above 0.85 at all temperatures in the experiment. Because only portions of the temperature limited heater used to heat a subsurface formation may be at the Curie temperature at any given point in time and the power factor for these portions does not go below 0.85 during use, the power factor for the entire temperature limited heater would remain above 0.85 (for example, above 0.9 or above 0.95) during use.

From the data in the experiments for the temperature limited heater with the copper core, the iron-cobalt ferromagnetic conductor, and the 347H stainless steel support member, the turndown ratio (y-axis) was calculated as a function of the maximum power (W/m) delivered by the temperature limited heater. The results of these calculations are depicted in FIG. 184. The curve in FIG. 184 shows that the turndown ratio (y-axis) remains above 2 for heater powers up to approximately 2000 W/m. This curve is used to determine the ability of a heater to effectively provide heat output in a sustainable manner. A temperature limited heater with the curve similar to the curve in FIG. 184 would be able to provide sufficient heat output while maintaining temperature limiting properties that inhibit the heater from overheating or malfunctioning.

A theoretical model has been used to predict the experimental results. The theoretical model is based on an analytical solution for the AC resistance of a composite conductor. The composite conductor has a thin layer of ferromagnetic material, with a relative magnetic permeability $\mu_2/\mu_0 \gg 1$, sandwiched between two non-ferromagnetic materials, whose relative magnetic permeabilities, $\mu_1/\mu_0$ and $\mu_3/\mu_0$, are close to unity and within which skin effects are negligible. An assumption in the model is that the ferromagnetic material is treated as linear. In addition, the way in which the relative magnetic permeability, $\mu_2/\mu_0$, is extracted from magnetic data for use in the model is far from rigorous.

In the theoretical model, the three conductors, from innermost to outermost, have radii a<b<c with electrical conductivities $\sigma_1$, $\sigma_2$, and $\sigma_3$, respectively. The electric and magnetic fields everywhere are of the harmonic form:

Electric Fields:

$$E_1(r,t) = E_{S1}(r)e^{j\omega t}; r<a; \tag{7}$$

$$E_2(r,t) = E_{S2}(r)e^{j\omega t}; a<r<b; \text{ and} \tag{8}$$

$$E_3(r,t) = E_{S3}(r)e^{j\omega t}; b<r<c. \tag{9}$$

Magnetic Fields:

$$H_1(r,t) = H_{S1}(r)e^{j\omega t}; r<a; \tag{10}$$

$$H_2(r,t) = H_{S2}(r)e^{j\omega t}; a<r<b; \text{ and} \tag{11}$$

$$H_3(r,t) = H_{S3}(r)e^{j\omega t}; b<r<c. \tag{12}$$

The boundary conditions satisfied at the interfaces are:

$$E_{S1}(a) = E_{S2}(a); H_{S1}(a) = H_{S2}(a); \text{ and} \tag{13}$$

$$E_{S2}(b) = E_{S3}(b); H_{S2}(b) = H_{S3}(b). \tag{14}$$

Current flows uniformly in the non-Curie conductors, so that:

$$H_{S1}(a) = J_{S1}(a)(a/2) = \tfrac{1}{2} a\sigma_1 E_{S1}(a); \text{ and} \tag{15}$$

$$I - 2\pi b H_{S3}(b) = \pi(c^2 - b^2) J_{S3}(b) = \pi(c^2 - b^2)\sigma_3 E_{S3}(b). \tag{16}$$

I denotes the total current flowing through the composite conductor sample. EQNS. 13 and 14 are used to express EQNS. 15 and 16 in terms of boundary conditions pertaining to material 2 (the ferromagnetic material). This yields:

$$H_{S2}(a) = \frac{1}{2} a\sigma_1 E_{S2}(a); \text{ and} \tag{17}$$

$$I = 2\pi b H_{S2}(b) + \pi(c^2 - b^2)\sigma_3 E_{S2}(b). \tag{18}$$

$E_{S2}(r)$ satisfies the equation:

$$\frac{1}{r}\frac{d}{dr}\left(r\frac{dE_{S2}}{dr}\right) - C^2 E_{S2} = 0, \tag{19}$$

with $$C^2 = j\omega\mu_2\sigma_2. \tag{20}$$

Using the fact that:

$$H_{S2}(r) = \frac{j}{\mu_2\omega}\frac{dE_{S2}}{dr}; \tag{21}$$

the boundary conditions in EQNS. 17 and 18 are expressed in terms of $E_{S2}$ and its derivatives as follows:

$$\left.\frac{j}{\mu_2\omega}\frac{dE_{S2}}{dr}\right|_a = \frac{1}{2} a\sigma_1 E_{S2}(a); \text{ and} \tag{22}$$

$$I = 2\pi b \left.\frac{j}{\mu_2\omega}\frac{dE_{S2}}{dr}\right|_b + \pi(c^2 - b^2)\sigma_3 E_{S2}(b). \tag{23}$$

The non-dimensional coordinate, $\chi$, is introduced via the equation:

$$r = \frac{1}{2}(a+b)\left\{1 + \frac{b-a}{a+b}\chi\right\}. \tag{24}$$

$\chi$ is $-1$ for $r=a$, and $\chi$ is 1 for $r=b$. EQN. 19 is written in terms of $\chi$ as:

$$(1+\beta\chi)^{-1}\frac{d}{d\chi}\left\{(1+\beta\chi)\frac{dE_{S2}}{d\chi}\right\} - \alpha^2\chi = 0, \tag{25}$$

with $$\alpha = \frac{1}{2}(b-a)C; \text{ and} \tag{26}$$

$$\beta = (b-a)/(b+a). \tag{27}$$

$\alpha$ can be expressed as:

$$\alpha = \alpha_R(1-i), \tag{28}$$

with $$\alpha_R^2 = \frac{1}{8}(b-a)^2\mu_2\sigma_2\omega = \frac{1}{4}(b-a)^2/\delta^2. \tag{29}$$

EQNS. 22 and 23 are expressed as:

$$\left.\frac{d}{d\chi}\right|_{-1} E_a = -j\gamma_a E_a; \text{ and} \tag{30}$$

$$\left.\frac{d}{d\chi}\right|_{1} E_b = j\gamma_b E_b - j\tilde{I}. \tag{31}$$

In EQNS. 30 and 31, the short-hand notation $E_a$ and $E_b$ is used for $E_{S2}(a)$ and $E_{S2}(b)$, respectively, and the dimensionless parameters $\gamma_a$ and $\gamma_b$ and normalized current $\tilde{I}$ have been introduced. These quantities are given by:

$$\gamma_a = \tfrac{1}{4}a(b-a)\omega\mu_2\sigma_1; \gamma_b = \tfrac{1}{2}(c^2-b^2)(b-a)\omega\mu_2\sigma_3/b; \text{ and} \tag{32}$$

$$\tilde{I} = \tfrac{1}{2}(b-a)\omega\mu_2 I/(2\pi b). \tag{33}$$

EQN. 32 can be expressed in terms of dimensionless parameters by using EQN. 29. The results are:

$$\gamma_a = 2(\sigma_1/\sigma_2)a\alpha_R^2/(b-a); \gamma_b = 4(\sigma_3/\sigma_2)(c^2-b^2)\alpha_R^2/\{b(b-a)\}). \tag{34}$$

An alternative way of writing EQN. 34 is:

$$\gamma_a = (\sigma_1/\sigma_2)a\alpha_R^2/\delta; \gamma_b = 2(\sigma_3/\sigma_2)(c^2-b^2)\alpha_R/(\delta b). \tag{35}$$

The mean power per unit length generated in the material is given by:

$$P = \frac{1}{2}\left\{\sigma_1 \pi a^2 |E_a|^2 + 2\pi\sigma_2 \int_a^b dr r |E_{S2}(r)|^2 + \sigma_3 \pi (c^2 - b^2)|E_b|^2\right\} \quad (36)$$

$$= \frac{1}{2}\left\{\sigma_1 \pi a^2 |E_a|^2 + \frac{1}{2}\pi(b^2 - a^2)\sigma_2 \int_{-1}^{1} d\chi\{1 + \beta\chi\}|E_{S2}(r)|^2 + \sigma_3 \pi (c^2 - b^2)|E_b|^2\right\}.$$

The AC resistance is then:

$$R_{AC} = P/(\tfrac{1}{2}|I|^2). \quad (37)$$

To obtain an approximate solution of EQN. 25, β, is assumed to be small enough to be neglected in EQN. 25. This assumption holds if the thickness of the ferromagnetic material (material 2) is much less than its mean radius. The general solution then takes the form:

$$E_{S2} = A e^{\alpha\chi} + B e^{-\alpha\chi}. \quad (38)$$

Then:

$$E_a = A e^{-\alpha} + B e^{\alpha}; \text{ and} \quad (39)$$

$$E_b = A e^{\alpha} + B e^{-\alpha}. \quad (40)$$

Substituting EQNS. 38-40 into EQNS. 30 and 31 yields the following set of equations for A and B:

$$\alpha(A e^{-\alpha} - B e^{\alpha}) = -j\gamma_a(A e^{-\alpha} + B e^{\alpha}); \text{ and} \quad (41)$$

$$\alpha(A e^{\alpha} - B e^{-\alpha}) = j\gamma_b(A e^{\alpha} + B e^{-\alpha}) - j\tilde{I}. \quad (42)$$

Rearranging EQN. 41 obtains an expression for B in terms of A:

$$B = \frac{\alpha + j\gamma_a}{\alpha - j\gamma_a} e^{-2\alpha} A. \quad (43)$$

This may be written as:

$$B = \frac{\alpha_R - i\gamma_a^+}{\alpha_R + i\gamma_a^-} e^{-2\alpha_R + 2i\alpha_R} A, \quad (44)$$

with $$\gamma_a^\pm = \gamma_a \pm \alpha_R. \quad (45)$$

If $$A = |A|\exp(i\phi_A) \quad (46)$$

and everything is referred back to the phase of A, then:

$$\phi_A = 0. \quad (47)$$

From EQN. 44:

$$B = |B|\exp(i\phi_B), \text{ with} \quad (48)$$

$$|B| = (\Gamma_+/\Gamma_-)\exp(-2\alpha_R)|A|; \text{ and} \quad (49)$$

$$\phi_B = 2\alpha_R - \phi_+ - \phi_-; \text{ where} \quad (50)$$

$$\Gamma_\pm = \{\alpha_R^2 + (\gamma_a^\pm)^2\}^{0.5}; \text{ and} \quad (51)$$

$$\phi_\pm = \tan^{-1}\{\phi_\pm/\alpha_R\}. \quad (52)$$

Then:

$$E_a = |A|\exp(-\alpha_R + i\alpha_R) + |B|\exp\{\alpha_R + i(\phi_B - \alpha_R)\}; \text{ and} \quad (53)$$

$$E_b = |A|\exp(\alpha_R - i\alpha_R) + |B|\exp\{-\alpha_R + i(\phi_B + \alpha_R)\}. \quad (54)$$

Hence:

$$Re[E_a] = |A|\exp(-\alpha_R)\cos(\alpha_R) + |B|\exp(\alpha_R)\cos(\phi_B - \alpha_R); \quad (55A)$$

$$Im[E_a] = |A|\exp(-\alpha_R)\sin(\alpha_R) + |B|\exp(\alpha_R)\sin(\phi_B - \alpha_R); \quad (55B)$$

$$Re[E_b] = |A|\exp(\alpha_R)\cos(\alpha_R) + |B|\exp(-\alpha_R)\cos(\phi_B + \alpha_R); \text{ and} \quad (55C)$$

$$Im[E_a] = |A|\exp(\alpha_R)\sin(\alpha_R) + |B|\exp(-\alpha_R)\sin(\phi_B + \alpha_R). \quad (55D)$$

The ratio of absolute values of currents flowing through the center and outer conductors is then given by:

$$\frac{|I_1|}{|I_3|} = \frac{a^2 \sigma_1}{(c^2 - b^2)\sigma_3}\sqrt{\frac{Re^2[E_a] + Im^2[E_a]}{Re^2[E_b] + Im^2[E_b]}}. \quad (56)$$

The total current flowing through the center conductor is given by:

$$I_2 = \sigma_2 \pi (b^2 - a^2)(A + B)\sin h(\alpha)/\alpha. \quad (57)$$

Now:

$$\sin h(\alpha)/\alpha = (1 + i)\{\sin h(\alpha_R)\cos(\alpha_R) - i\cos h(\alpha_R)\sin(\alpha_R)\}/(2\alpha_R) = (S^+ + S^- i), \text{ with} \quad (58)$$

$$S^\pm = \{\sin h(\alpha_R)\cos(\alpha_R) \pm \cos h(\alpha_R)\sin(\alpha_R)\}/(4\alpha_R). \quad (59)$$

Hence:

$$Re[I_2] = \sigma_2 \pi (b^2 - a^2)\{\{|A| + |B|\cos(\phi_B)\}S^+ - |B|\sin(\phi_B)S^-\}; \text{ and} \quad (60)$$

$$Im[I_2] = \sigma_2 \pi (b^2 - a^2)\{\{|A| + |B|\cos(\phi_B)\}S^- + |B|\sin(\phi_B)S^+\}. \quad (61)$$

Root-mean-square current is therefore given by:

$$I_{rms}^2 = \frac{1}{2}\{(Re[I_1] + Re[I_2] + Re[I_3])^2 + (Im[I_1] + Im[I_2] + Im[I_3])^2\}. \quad (62)$$

Furthermore, EQNS. 40-42 are used to evaluate the second term on the right-hand side of EQN. 29 (neglecting the term in β). The result is:

$$P = \frac{1}{2}\{\sigma_1 \pi a^2 |E_a|^2 + \pi(c^2 - b^2)\sigma_3 |E_b|^2 + \pi(b^2 - a^2)\sigma_2 L(|A|^2 + |B|^2)\sinh(2\alpha_R)/(2\alpha_R) + 2|A||B|\sin(\phi_B + 2\alpha_R)/(\phi_B + 2\alpha_R)]\}. \quad (63)$$

Dividing EQN. 63 by EQN. 62 yields an expression for the AC resistance (cf. EQN. 37).

Given values for the dimensions a, b and c, and $\sigma_1$, $\sigma_2$ and $\sigma_3$, which are known functions of temperature, and assuming a value for the relative magnetic permeability of the ferromagnetic material (material 2), or equivalently, the skin depth δ, A=1 can be set and the AC resistance per unit length $R_{AC}$ can be calculated. The ratio of the root-mean square current flowing through the inner conductor (material 1) and the ferromagnetic material (material 2) to the total can also be calculated. For a given total RMS current, then, the RMS current flowing through materials 1 and 2 can be calculated, which gives the magnetic field at the surface of material 2. Using magnetic data for material 2, a value for $\mu_2/\mu_0$ can be deduced and hence a value for $\delta$ can be deduced. Plotting this skin depth against the original skin depth produces a pair of curves that cross at the true $\delta$.

Magnetic data was obtained for carbon steel as a ferromagnetic material. B versus H curves, and hence relative permeabilities, were obtained from the magnetic data at various temperatures up to 1100° F. and magnetic fields up to 200 Oe (oersteds). A correlation was found that fitted the data well through the maximum permeability and beyond. FIG. 185 depicts examples of relative magnetic permeability (y-axis) versus magnetic field (Oe) for both the found correlations and raw data for carbon steel. Data 1138 is raw data for carbon steel at 400° F. Data 1140 is raw data for carbon steel at 1000° F. Curve 1142 is the found correlation for carbon steel at 400° F. Curve 1144 is the found correlation for carbon steel at 1000° F.

For the dimensions and materials of the copper/carbon steel/347H heater element in the experiments above, the theoretical calculations described above were carried out to calculate magnetic field at the outer surface of the carbon steel as a function of skin depth. Results of the theoretical calculations were presented on the same plot as skin depth versus magnetic field from the correlations applied to the magnetic data from FIG. 185. The theoretical calculations and correlations were made for four temperatures (200° F., 500° F., 800° F., and 1100° F.) and five total root-mean-square (RMS) currents (100 A, 200 A, 300 A, 400 A, and 500 A).

FIG. 186 shows the resulting plots of skin depth (in) versus magnetic field (Oe) for all four temperatures and 400 A current. Curve 1146 is the correlation from magnetic data at 200° F. Curve 1148 is the correlation from magnetic data at 500° F. Curve 1150 is the correlation from magnetic data at 800° F. Curve 1152 is the correlation from magnetic data at 1100° F. Curve 1154 is the theoretical calculation at the outer surface of the carbon steel as a function of skin depth at 200° F. Curve 1156 is the theoretical calculation at the outer surface of the carbon steel as a function of skin depth at 500° F. Curve 1158 is the theoretical calculation at the outer surface of the carbon steel as a function of skin depth at 800° F. Curve 1160 is the theoretical calculation at the outer surface of the carbon steel as a function of skin depth at 1100° F.

The skin depths obtained from the intersections of the same temperature curves in FIG. 186 were input into the equations described above and the AC resistance per unit length was calculated. The total AC resistance of the entire heater, including that of the canister, was subsequently calculated. A comparison between the experimental and numerical (calculated) results is shown in FIG. 187 for currents of 300 A (experimental data 1162 and numerical curve 1164), 400 A (experimental data 1166 and numerical curve 1168), and 500 A (experimental data 1170 and numerical curve 1172). Though the numerical results exhibit a steeper trend than the experimental results, the theoretical model captures the close bunching of the experimental data, and the overall values are quite reasonable given the assumptions involved in the theoretical model. For example, one assumption involved the use of a permeability derived from a quasistatic B-H curve to treat a dynamic system.

One feature of the theoretical model describing the flow of alternating current in the three-part temperature limited heater is that the AC resistance does not fall off monotonically with increasing skin depth. FIG. 188 shows the AC resistance (mΩ) per foot of the heater element as a function of skin depth (in.) at 1100° F. calculated from the theoretical model. The AC resistance may be maximized by selecting the skin depth that is at the peak of the non-monotonical portion of the resistance versus skin depth profile (for example, at about 0.23 in. in FIG. 188).

FIG. 189 shows the power generated per unit length (W/ft) in each heater component (curve 1174 (copper core), curve 1176 (carbon steel), curve 1178 (347H outer layer), and curve 1180 (total)) versus skin depth (in.). As expected, the power dissipation in the 347H falls off while the power dissipation in the copper core increases as the skin depth increases. The maximum power dissipation in the carbon steel occurs at the skin depth of about 0.23 inches and is expected to correspond to the minimum in the power factor, as shown in FIG. 183. The current density in the carbon steel behaves like a damped wave of wavelength $\lambda = 2\pi\delta$ and the effect of this wavelength on the boundary conditions at the copper/carbon steel and carbon steel/347H interface may be behind the structure in FIG. 188. For example, the local minimum in AC resistance is close to the value at which the thickness of the carbon steel layer corresponds to $\lambda/4$.

Formulae may be developed that describe the shapes of the AC resistance versus temperature profiles of temperature limited heaters for use in simulating the performance of the heaters in a particular embodiment. The data in FIGS. 181 and 182 show that the resistances initially rise linearly, then drop off increasingly steeply towards the DC lines. The resistance versus temperature profile of each heater can be described by:

$$R_{AC} = A_{AC} + B_{AC}T; T \ll T_C; \text{ and} \quad (64)$$

$$R_{AC} = R_{DC} = A_{DC} + B_{DC}T; T \gg T_C. \quad (65)$$

Note that $A_{DC}$ and $B_{DC}$ are independent of current, while $A_{AC}$ and $B_{AC}$ depend on the current. Choosing as a form crossing over between EQNS. 64 and 65 results in the following expression for $R_{AC}$:

$$R_{AC} = \frac{1}{2}\{1 + \tanh\{\alpha(T_0 - T)\}\}\{A_{AC} + B_{AC}T\} + \quad (66)$$
$$\frac{1}{2}\{1 - \tanh\{\alpha(T_0 - T)\}\}\{A_{DC} + B_{DC}T\} T \leq T_0; \text{ and}$$

$$R_{AC} = \frac{1}{2}\{1 + \tanh\{\beta(T_0 - T)\}\}\{A_{AC} + B_{AC}T\} +$$
$$\frac{1}{2}\{1 - \tanh\{\beta(T_0 - T)\}\}\{A_{DC} + B_{DC}T\} T \geq T_0.$$

Since $A_{AC}$ and $B_{AC}$ are functions of current, then:

$$A_{AC} = A_{AC}^{(0)} + A_{AC}^{(1)}I; B_{AC} = B_{AC}^{(0)} + B_{AC}^{(1)}I. \quad (67)$$

The parameter $\alpha$ is also a function of current, and exhibits the quadratic dependence:

$$\alpha = \alpha_0 + \alpha_1 I + \alpha_2 I^2. \quad (68)$$

The parameters $\beta$, $T_0$, as well as $A_{DC}$ and $B_{DC}$ are independent of current. Values of the parameters for the copper/carbon steel/347H heaters in the above experiments are listed in TABLE 2.

TABLE 2

| Parameter | Unit | copper/carbon steel/347H |
|---|---|---|
| $A_{DC}$ | mΩ | 0.6783 |
| $B_{DC}$ | mΩ/° F. | 6.53 × 10$^{-4}$ |
| $A_{AC}^{(0)}$ | mΩ | 3.6358 |
| $A_{AC}^{(1)}$ | mΩ/A | −1.247 × 10$^{-3}$ |
| $B_{AC}^{(0)}$ | mΩ/° F. | 2.3575 × 10$^{-3}$ |
| $B_{AC}^{(1)}$ | mΩ/(° F. A) | −2.28 × 10$^{-7}$ |
| $\alpha_0$ | 1/° F. | 0.2 |

TABLE 2-continued

| Parameter | Unit | copper/carbon steel/347H |
|---|---|---|
| $\alpha_1$ | 1/(° F. A) | $-7.9 \times 10^{-4}$ |
| $\alpha_2$ | 1/(° F. A$^2$) | $8 \times 10^{-7}$ |
| $\beta$ | 1/° F. | 0.017 |
| $T_0$ | ° F. | 1350 |

Figure 190A:
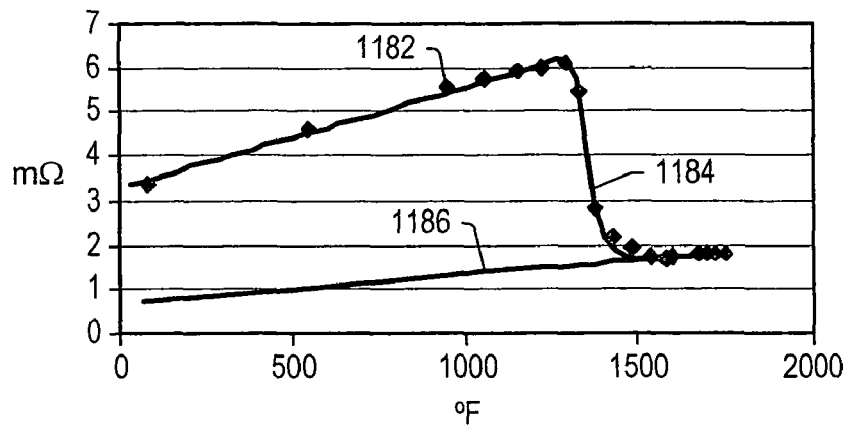
Figure 190B:
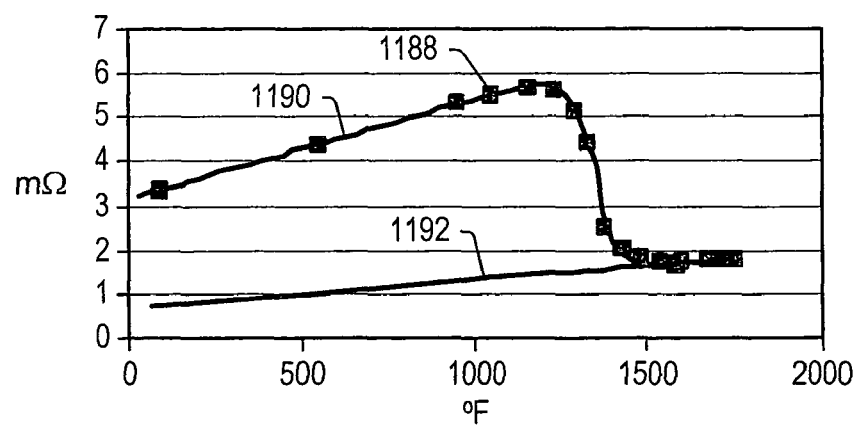
Figure 190C:
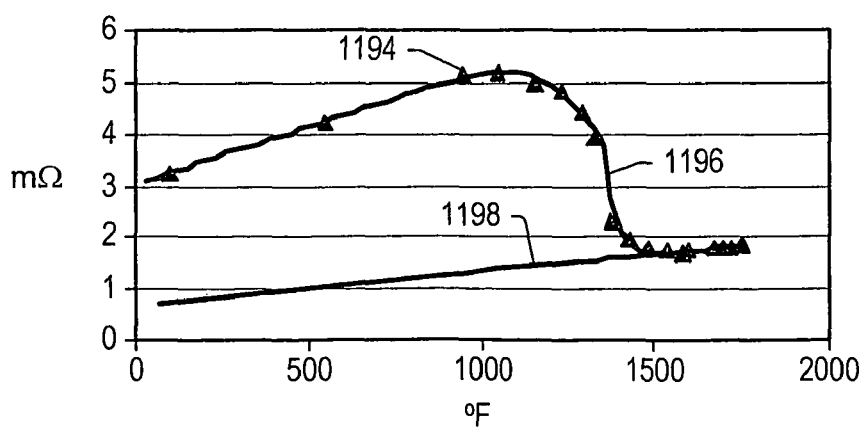

FIGS. 190 A-C compare the results of the theoretical calculations in EQNS. 66-68 with the experimental data at 300 A (FIG. 190A), 400 A (FIG. 190B) and 500 A (FIG. 190C). FIG. 190A depicts electrical resistance (mΩ) versus temperature (° F.) at 300 A. Data 1182 is the experimental data at 300 A. Curve 1184 is the theoretical calculation at 300 A. Curve 1186 is a plot of resistance versus temperature at 10 A DC. FIG. 190B depicts electrical resistance (mΩ) versus temperature (° F.) at 400 A. Data 1188 is the experimental data at 400 A. Curve 1190 is the theoretical calculation at 400 A. Curve 1192 is a plot of resistance versus temperature at 10 A DC. FIG. 190C depicts electrical resistance (mΩ) versus temperature (° F.) at 500 A. Data 1194 is the experimental data at 500 A. Curve 1196 is the theoretical calculation at 500 A. Curve 1198 is a plot of resistance versus temperature at 10 A DC. Note that, to obtain the resistance per foot, for example, in simulation work, the resistances given by the theoretical calculations must be divided by six.

A numerical simulation (FLUENT available from Fluent USA, Lebanon, N.H., U.S.A.) was used to compare operation of temperature limited heaters with three turndown ratios. The simulation was done for heaters in an oil shale formation (Green River oil shale). Simulation conditions were:

61 m length conductor-in-conduit Curie heaters (center conductor (2.54 cm diameter), conduit outer diameter 7.3 cm)

downhole heater test field richness profile for an oil shale formation 16.5 cm (6.5 inch) diameter wellbores at 9.14 m spacing between wellbores on triangular spacing 200 hours power ramp-up time to 820 watts/m initial heat injection rate constant current operation after ramp up Curie temperature of 720.6° C. for heater formation will swell and touch the heater canisters for oil shale richnesses at least 0.14 L/kg (35 gals/ton)

FIG. 191 displays temperature (° C.) of a center conductor of a conductor-in-conduit heater as a function of formation depth (m) for a temperature limited heater with a turndown ratio of 2:1. Curves 1200-1222 depict temperature profiles in the formation at various times ranging from 8 days after the start of heating to 675 days after the start of heating (1200: 8 days, 1202: 50 days, 1204: 91 days, 1206: 133 days, 1208: 216 days, 1210: 300 days, 1212: 383 days, 1214: 466 days, 1216: 550 days, 1218: 591 days, 1220: 633 days, 1222: 675 days). At a turndown ratio of 2:1, the Curie temperature of 720.6° C. was exceeded after 466 days in the richest oil shale layers. FIG. 192 shows the corresponding heater heat flux (W/m) through the formation for a turndown ratio of 2:1 along with the oil shale richness (l/kg) profile (curve 1224). Curves 1226-1258 show the heat flux profiles at various times from 8 days after the start of heating to 633 days after the start of heating (1226: 8 days; 1228: 50 days; 1230: 91 days; 1232: 133 days; 1234: 175 days; 1236: 216 days; 1238: 258 days; 1240: 300 days; 1232: 341 days; 1244: 383 days; 1246: 425 days; 1248: 466 days; 1250: 508 days; 1252: 550 days; 1254: 591 days; 1256: 633 days; 1258: 675 days). At a turndown ratio of 2:1, the center conductor temperature exceeded the Curie temperature in the richest oil shale layers.

FIG. 193 displays heater temperature (° C.) as a function of formation depth (m) for a turndown ratio of 3:1. Curves 1260-1282 show temperature profiles through the formation at various times ranging from 12 days after the start of heating to 703 days after the start of heating (1260: 12 days; 1262: 33 days; 1264: 62 days; 1266: 102 days; 1268: 146 days; 1270: 205 days; 1272: 271 days; 1274: 354 days; 1276: 467 days; 1278: 605 days; 1280: 662 days; 1282: 703 days). At a turndown ratio of 3:1, the Curie temperature was approached after 703 days. FIG. 194 shows the corresponding heater heat flux (W/m) through the formation for a turndown ratio of 3:1 along with the oil shale richness (l/kg) profile (curve 1284). Curves 1286-1306 show the heat flux profiles at various times from 12 days after the start of heating to 605 days after the start of heating (1286: 12 days, 1288: 32 days, 1290: 62 days, 1292: 102 days, 1294: 146 days, 1296: 205 days, 1298: 271 days, 1300: 354 days, 1302: 467 days, 1304: 605 days, 1306: 749 days). The center conductor temperature never exceeded the Curie temperature for the turndown ratio of 3:1. The center conductor temperature also showed a relatively flat temperature profile for the 3:1 turndown ratio.

FIG. 195 shows heater temperature (° C.) as a function of formation depth (m) for a turndown ratio of 4:1. Curves 1308-1328 show temperature profiles through the formation at various times ranging from 12 days after the start of heating to 467 days after the start of heating (1308: 12 days; 1310: 33 days; 1312: 62 days; 1314: 102 days; 1316: 147 days; 1318: 205 days; 1320: 272 days; 1322: 354 days; 1324: 467 days; 1326: 606 days, 1328: 678 days). At a turndown ratio of 4:1, the Curie temperature was not exceeded even after 678 days. The center conductor temperature never exceeded the Curie temperature for the turndown ratio of 4:1. The center conductor showed a temperature profile for the 4:1 turndown ratio that was somewhat flatter than the temperature profile for the 3:1 turndown ratio. These simulations show that the heater temperature stays at or below the Curie temperature for a longer time at higher turndown ratios. For this oil shale richness profile, a turndown ratio of at least 3:1 may be desirable.

Simulations have been performed to compare the use of temperature limited heaters and non-temperature limited heaters in an oil shale formation. Simulation data was produced for conductor-in-conduit heaters placed in 16.5 cm (6.5 inch) diameter wellbores with 12.2 m (40 feet) spacing between heaters using a formation simulator (for example, STARS) and a near wellbore simulator (for example, ABAQUS from ABAQUS, Inc., Providence, R.I., U.S.A.). Standard conductor-in-conduit heaters included 304 stainless steel conductors and conduits. Temperature limited conductor-in-conduit heaters included a metal with a Curie temperature of 760° C. for conductors and conduits. Results from the simulations are depicted in FIGS. 196-198.

FIG. 196 depicts heater temperature (° C.) at the conductor of a conductor-in-conduit heater versus depth (m) of the heater in the formation for a simulation after 20,000 hours of operation. Heater power was set at 820 watts/meter until 760° C. was reached, and the power was reduced to inhibit overheating. Curve 1330 depicts the conductor temperature for standard conductor-in-conduit heaters. Curve 1330 shows that a large variance in conductor temperature and a significant number of hot spots developed along the length of the conductor. The temperature of the conductor had a minimum value of 490° C. Curve 1332 depicts conductor temperature for temperature limited conductor-in-conduit heaters. As shown in FIG. 196, temperature distribution along the length of the conductor was more controlled for the temperature limited heaters. In addition, the operating temperature of the conductor was 730° C. for the temperature limited heaters. Thus, more heat input would be provided to the formation for a similar heater power using temperature limited heaters.

FIG. 197 depicts heater heat flux (W/m) versus time (yrs) for the heaters used in the simulation for heating oil shale. Curve 1334 depicts heat flux for standard conductor-in-conduit heaters. Curve 1336 depicts heat flux for temperature limited conductor-in-conduit heaters. As shown in FIG. 197, heat flux for the temperature limited heaters was maintained at a higher value for a longer period of time than heat flux for standard heaters. The higher heat flux may provide more uniform and faster heating of the formation.

FIG. 198 depicts cumulative heat input (kJ/m) (kilojoules per meter) versus time (yrs) for the heaters used in the simulation for heating oil shale. Curve 1338 depicts cumulative heat input for standard conductor-in-conduit heaters. Curve 1340 depicts cumulative heat input for temperature limited conductor-in-conduit heaters. As shown in FIG. 198, cumulative heat input for the temperature limited heaters increased faster than cumulative heat input for standard heaters. The faster accumulation of heat in the formation using temperature limited heaters may decrease the time needed for retorting the formation. Onset of retorting of the oil shale formation may begin around an average cumulative heat input of $1.1 \times 10^8$ kJ/meter. This value of cumulative heat input is reached around 5 years for temperature limited heaters and between 9 and 10 years for standard heaters.

FIG. 199 depicts experimental calculations of weight percentages of ferrite and austenite phases versus temperature for iron alloy TC3 (0.1% by weight carbon, 5% by weight cobalt, 12% by weight chromium, 0.5% by weight manganese, 0.5% by weight silicon). Curve 1344 depicts weight percentage of the ferrite phase. Curve 1346 depicts weight percentage of the austenite phase. The arrow points to the Curie temperature of the alloy. As shown in FIG. 199, the phase transformation is close to the Curie temperature but does not overlap with the Curie temperature for this alloy.

FIG. 200 depicts experimental calculations of weight percentages of ferrite and austenite phases versus temperature for iron alloy FM-4 (0.1% by weight carbon, 5% by weight cobalt, 0.5% by weight manganese, 0.5% by weight silicon). Curve 1348 depicts weight percentage of the ferrite phase. Curve 1350 depicts weight percentage of the austenite phase. The arrow points to the Curie temperature of the alloy. As shown in FIG. 200, the phase transformation broadens without chromium in the alloy and the phase transformation overlaps with the Curie temperature for this alloy.

FIG. 201 depicts the Curie temperature (solid horizontal bars) and phase transformation temperature range (slashed vertical bars) for several iron alloys. Column 1352 is for FM-2 iron-cobalt alloy. Column 1354 is for FM-4 iron-cobalt alloy. Column 1356 is for FM-6 iron-cobalt alloy. Column 1358 is for FM-8 iron-cobalt alloy. Column 1360 is for TC1 410 stainless steel alloy with cobalt. Column 1362 is for TC2 410 stainless steel alloy with cobalt. Column 1364 is for TC3 410 stainless steel alloy with cobalt. Column 1366 is for TC4 410 stainless steel alloy with cobalt. Column 1368 is for TC5 410 stainless steel alloy with cobalt. As shown in FIG. 201, the iron-cobalt alloys (FM-2, FM-4, FM-6, FM-8) have large phase transformation temperature ranges that overlap with the Curie temperature. The 410 stainless steel alloys with cobalt (TC1, TC2, TC3, TC4, TC5) have small phase transformation temperature ranges. The phase transformation temperature ranges for TC1, TC2, and TC3 are above the Curie temperature. The phase transformation temperature range for TC4 is below the Curie temperature. Thus, a temperature limited heater using TC4 may self-limit at a temperature below the Curie temperature of the TC4.

FIGS. 202-205 depict the effect of alloy addition to iron-cobalt alloys. FIGS. 202 and 203 depict the effect of carbon addition to an iron-cobalt alloy. FIGS. 204 and 205 depict the effect of titanium addition to an iron-cobalt alloy.

FIG. 202 depicts experimental calculations of weight percentages of ferrite and austenite phases versus temperature for an iron-cobalt alloy with 5.63% by weight cobalt and 0.4% by weight manganese. Curve 1370 depicts weight percentage of the ferrite phase. Curve 1372 depicts weight percentage of the austenite phase. The arrow points to the Curie temperature of the alloy. As shown in FIG. 202, the phase transformation is close to the Curie temperature but does not overlap with the Curie temperature for this alloy.

FIG. 203 depicts experimental calculations of weight percentages of ferrite and austenite phases versus temperature for an iron-cobalt alloy with 5.63% by weight cobalt, 0.4% by weight manganese, and 0.01% carbon. Curve 1374 depicts weight percentage of the ferrite phase. Curve 1376 depicts weight percentage of the austenite phase. The arrow points to the Curie temperature of the alloy. As shown in FIGS. 202 and 203, the phase transformation broadens with the addition of carbon to the alloy with the onset of the phase transformation shifting to a lower temperature. Thus, carbon can be added to an iron alloy to lower the onset temperature and broaden the temperature range of the phase transformation.

FIG. 204 depicts experimental calculations of weight percentages of ferrite and austenite phases versus temperature for an iron-cobalt alloy with 5.63% by weight cobalt, 0.4% by weight manganese, and 0.085% carbon. Curve 1378 depicts weight percentage of the ferrite phase. Curve 1380 depicts weight percentage of the austenite phase. The arrow points to the Curie temperature of the alloy. As shown in FIG. 204, the phase transformation overlaps with the Curie temperature.

FIG. 205 depicts experimental calculations of weight percentages of ferrite and austenite phases versus temperature for an iron-cobalt alloy with 5.63% by weight cobalt, 0.4% by weight manganese, 0.085% carbon, and 0.4% titanium. Curve 1382 depicts weight percentage of the ferrite phase. Curve 1384 depicts weight percentage of the austenite phase. The arrow points to the Curie temperature of the alloy. As shown in FIGS. 204 and 205, the phase transformation narrows with the addition of titanium to the alloy with the onset of the phase transformation shifting to a higher temperature. Thus, titanium can be added to an iron alloy to raise the onset temperature and narrow the temperature range of the phase transformation.

Calculations may be made to determine the effect of a thermally conductive fluid in an annulus of a temperature limited heater. The equations below (EQNS. 69-79) are used to relate a heater center rod temperature in a heated section to a conduit temperature adjacent to the heater center rod. In this example, the heater center rod is a 347H stainless steel tube with outer radius b. The conduit is made of 347H stainless steel and has inner radius R. The center heater rod and the conduit are at uniform temperatures $T_H$ and $T_C$, respectively. $T_C$ is maintained constant and a constant heat rate, Q, per unit length is supplied to the center heater rod. $T_H$ is the value at which the rate of heat per unit length transferred to the conduit by conduction and radiation balances the rate of heat generated, Q. Conduction across a gap between the center heater rod and inner surface of the conduit is assumed to take place in parallel with radiation across the gap. For simplicity, radiation across the gap is assumed to be radiation across a vacuum. The equations are thus:

$$Q = Q_C + Q_R; \quad (69)$$

where $Q_C$ represents the conductive component and $Q_R$ represents the radiative component of the heat flux across the gap. Denoting the inner radius of the conduit by R, conductive heat transport satisfies the equation:

$$Q_C = -2\pi r k_g \frac{dT}{dr}; b \le r \le R; \quad (70)$$

subject to the boundary conditions:

$$T(b) = T_H; T(R) = T_C. \quad (71)$$

The thermal conductivity of the gas in the gap, $k_g$, is well described by the equation:

$$k_g = a_g + b_g T \quad (72)$$

Substituting EQN. 72 into EQN. 70 and integrating subject to the boundary conditions in EQN. 71 gives:

$$\frac{Q_C}{2\pi} \ln(R/b) = k_g^{(eff)}(T_H - T_C); \quad (73)$$

with $$k_g^{(eff)} = a_g + \frac{1}{2} b_g (T_H + T_C). \quad (74)$$

The rate of radiative heat transport across the gap per unit length, $Q_R$, is given by:

$$Q_R = 2\pi\sigma b \in_R \in_{bR} \{T_H^4 - T_C^4\}; \quad (75)$$

where $$\in_{bR} = \in_b / \{\in_R + (b/R)\in_b(1-\in_R)\}. \quad (76)$$

In EQNS. 75 and 76, $\in_b$ and $\in_R$ denote the emissivities of the center heater rod and inner surface of the conduit, respectively, and σ is the Stefan-Boltzmann constant.

Substituting EQNS. 73 and 75 back into EQN. 69, and rearranging gives:

$$\frac{Q}{2\pi} = \frac{k_g^{eff}(T_H - T_C)}{\ln(R/b)} + \sigma b \in_R \in_{bR} \{T_H^4 - T_C^4\}. \quad (77)$$

To solve EQN. 77, t is denoted as the ratio of radiative to conductive heat flux across the gap:

$$t = \frac{\sigma b \in_R \in_{bR} \{T_H^2 + T_C^2\}\{T_H + T_C\}\ln(R/b)}{k_g^{eff}}. \quad (78)$$

Then EQN. 77 can be written in the form:

$$\frac{Q}{2\pi} = \frac{k_g^{eff}(T_H - T_C)}{\ln(R/b)} \{1 + t\}. \quad (79)$$

EQNS. 79 and 77 are solved iteratively for $T_H$ given Q and $T_C$. The numerical values of the parameters σ, $a_g$, and $b_g$ are listed in TABLE 3. Heater dimensions are given in TABLE 4. The emissivities $\in_S$ and $\in_a$ may be taken to be in the range 0.4-0.8.

TABLE 3

Material Parameters Used in the Calculations

| | Parameter | | | | |
|---|---|---|---|---|---|
| | σ | $a_g$ (air) | $b_g$ (air) | $a_g$ (He) | $b_g$ (He) |
| Unit | $Wm^{-2}K^{-4}$ | $Wm^{-1}K^{-1}$ | $Wm^{-1}K^{-2}$ | $Wm^{-1}K^{-1}$ | $Wm^{-1}K^{-2}$ |
| Value | $5.67 \times 10^{-8}$ | 0.01274 | $5.493 \times 10^{-5}$ | 0.07522 | $2.741 \times 10^{-4}$ |

TABLE 4

Set of Heater Dimensions

| Dimension | Inches | Meters |
|---|---|---|
| Heater rod outer radius b | ½ × 0.75 | $9.525 \times 10^{-3}$ |
| Conduit inner radius R | ½ × 1.771 | $2.249 \times 10^{-2}$ |

FIG. 206 shows heater rod temperature (° C.) as a function of the power (W/m) generated within the heater rod for a base case in which both the heater rod and conduit emissivities were 0.8, and a low emissivity case in which the heater rod emissivity was lowered to 0.4. The conduit temperature was set at 260° C. Cases in which the annular space is filled with air and with helium are compared in FIG. 206. Plot 1342 is for the base case in air. Plot 1386 is for the base case in helium. Plot 1388 is for the low emissivity case in air. Plot 1410 is for the low emissivity case in helium. FIGS. 207-213 repeat the same cases for conduit temperatures of 315° C. to 649° C. inclusive, with incremental steps of 55° C. in each figure. Note that the temperature scale in FIGS. 211-213 is offset by 111° C. with respect to the scale in FIGS. 206-210. FIGS. 206-213 show that helium in the annular space, which has a higher thermal conductivity than air, reduces the rod temperature for similar power generation.

FIG. 214 shows a plot of center heater rod (with 0.8 emissivity) temperature (vertical axis) versus conduit temperature (horizontal axis) for various heater powers with air or helium in the annulus. FIG. 215 shows a plot of center heater rod (with 0.4 emissivity) temperature (vertical axis) versus conduit temperature (horizontal axis) for various heater powers with air or helium in the annulus. Plots 1412 are for air and a heater power of 500 W/m. Plots 1414 are for air and a heater power of 833 W/m. Plots 1416 are for air and a heater power of 1167 W/m. Plots 1418 are for helium and a heater power of 500 W/m. Plots 1420 are for helium and a heater power of 833 W/m. Plots 1422 are for helium and a heater power of 1167 W/m. FIGS. 214 and 215 show that helium in the annular space, as compared to air in the annulus, reduces temperature difference between the heater and the canister.

FIG. 216 depicts spark gap breakdown voltages (V) versus pressure (atm) at different temperatures for a conductor-in-conduit heater with air in the annulus. FIG. 217 depicts spark gap breakdown voltages (V) versus pressure (atm) at different temperatures for a conductor-in-conduit heater with helium in the annulus. FIGS. 216 and 217 show breakdown voltages for a conductor-in-conduit heater with a 2.5 cm diameter center conductor and a 7.6 cm gap to the inner radius of the conduit. Plot 1424 is for a temperature of 300 K. Plot 1426 is for a temperature of 700 K. Plot 1428 is for a temperature of 1050 K. 480 V RMS is shown as a typical applied voltage. FIGS. 216 and 217 show that helium has a spark gap breakdown voltage smaller than the spark gap breakdown voltage for air at 1 atm. Thus, the pressure of helium may need to be increased to achieve spark gap breakdown voltages on the order of breakdown voltages for air.

FIG. 218 depicts leakage current (mA) versus voltage (V) for alumina and silicon nitride centralizers at selected temperatures. Leakage current was measured between a conductor and a conduit of a 0.91 m conductor-in-conduit section with two centralizers. The conductor-in-conduit was placed horizontally in a furnace. Plot 1430 depicts data for alumina centralizers at a temperature of 760° C. Plot 1432 depicts data for alumina centralizers at a temperature of 815° C. Plot 1434 depicts data for gas pressure sintered reaction bonded silicon nitride centralizers at a temperature of 760° C. Plot 1436 depicts data for gas pressure sintered reaction bonded silicon nitride at a temperature of 871° C. FIG. 218 shows that the leakage current of alumina increases substantially from 760° C. to 815° C. while the leakage current of gas pressure sintered reaction bonded silicon nitride remains relatively low from 760° C. to 871° C.

FIG. 219 depicts leakage current (mA) versus temperature (° F.) for two different types of silicon nitride. Plot 1438 depicts leakage current versus temperature for highly polished, gas pressure sintered reaction bonded silicon nitride. Plot 1440 depicts leakage current versus temperature for doped densified silicon nitride. FIG. 219 shows the improved leakage current versus temperature characteristics of gas pressure sintered reaction bonded silicon nitride versus doped silicon nitride.

Using silicon nitride centralizers allows for smaller diameter and higher temperature heaters. A smaller gap is needed between a conductor and a conduit because of the excellent electrical characteristics of the silicon nitride. Silicon nitride centralizers may allow higher operating voltages (for example, up to at least 1500 V, 2000 V, 2500 V, or 15 kV) to be used in heaters due to the electrical characteristics of the silicon nitride. Operating at higher voltages allows longer length heaters to be utilized (for example, lengths up to at least 500 m, 1000 m, or 1500 m at 2500 V). In some embodiments, boron nitride is used as a material for centralizers or other electrical insulators. Boron nitride is a better thermal conductor and has better electrical properties than silicon nitride. Boron nitride does not absorb water readily (boron nitride is substantially non-hygroscopic). Boron nitride is available in at least a hexagonal form and a face centered cubic form. A hexagonal crystalline formation of boron nitride has several desired properties, including, but not limited to, a high thermal conductivity and a low friction coefficient.

FIG. 220 depicts projected corrosion rates (metal loss per year) over a one-year period for several metals in a sulfidation atmosphere. The metals were exposed to a gaseous mixture containing about 1% by volume COS, about 32% by volume CO and about 67% volume $CO_2$ at about 538° C. (1000° F.), at about 649° C. (1200° C.), at about 760° C. (1400° F.), and at about 871° C. (about 1600° F.) for 384 hours. The resulting data was extrapolated to a one-year time period. The experimental conditions simulates in-situ sub-surface formation sulfidation conditions of 10% $H_2$ by volume, 10% $H_2S$ by volume and 25% $H_2O$ by volume at 870° C. Curve 1442 depicts 625 stainless steel. Curve 1444 depicts CF8C+ stainless steel. Curve 1446 depicts data for 410 stainless steel. Curve 1448 depicts 20 25 Nb stainless steel. Curve 1450 depicts 253 MA stainless steel. Curve 1452 depicts 347H stainless steel. Curve 1454 depicts 446 stainless steel. 410 stainless steel exhibits a decrease in corrosion at temperatures between 500° C. and 650° C.

In some embodiments, cobalt may be added to 410 stainless steel to decrease the rate of corrosion at elevated temperatures (for example, temperatures greater than 1200° F.) relative to untreated 410 stainless steel. Addition of cobalt to 410 stainless steel may enhance the strength of the stainless steel at high temperatures (for example, temperatures greater than 1200° F., greater than 1400° F., greater than 1500° F., or greater than 1600° F.) and/or change the magnetic characteristics of the metal. FIG. 221 depicts projected corrosion rates (metal loss per year) for 410 stainless steel and 410 stainless steel containing various amounts of cobalt in a sulfidation atmosphere. The metals were exposed to the same conditions as the metals in FIG. 221. Bar 1456 depicts data for 410 stainless steel. Bar 1458 depicts data for 410 stainless steel with 2.5% cobalt by weight. Bar 1460 depicts data for 410 stainless steel with 5% cobalt by weight. Bar 1462 depicts data for 410 stainless steel with 10% cobalt by weight. As the amount of cobalt in the 410 stainless steel increases, the corrosion rate in a sulfidation atmosphere decreases relative to non-cobalt containing 410 stainless steel in a temperature range of about 800° C. to about 880° C.

A STARS simulation (Computer Modelling Group, LTD., Calgary, Alberta, Canada) determined heating properties using temperature limited heaters with varying power outputs. FIG. 222 depicts an example of richness of an oil shale formation (gal/ton) versus depth (ft). Upper portions of the formation (above about 1210 feet) tend to have a leaner richness, lower water-filled porosity, and/or less dawsonite than deeper portions of the formation. For the simulation, a heater similar to the heater depicted in FIG. 90 was used. Portion 728 had a length of 368 feet above the dashed line shown in FIG. 222 and portion 726 had a length of 587 feet below the dashed line.

In the first example, the temperature limited heater had constant thermal properties along the entire length of the heater. The heater included a 0.565" diameter copper core with a carbon steel conductor (Curie temperature of 1418° F., pure iron with outside diameter of 0.825") surrounding the copper core. The outer conductor was 347H stainless steel surrounding the carbon steel conductor with an outside diameter of 1.2". The resistance per foot (mil/ft) versus temperature (° F.) profile of the heater is shown in FIG. 223. FIG. 224 depicts average temperature in the formation (° F.) versus time (days) as determined by the simulation for the first example. Curve 1470 depicts average temperature versus time for the top portion of the formation. Curve 1472 depicts average temperature versus time for the entire formation. Curve 1474 depicts average temperature versus time for the bottom portion of the formation. As shown, the average temperature in the bottom portion of the formation lagged behind the average temperature in the top portion of the formation and the entire formation. The top portion of the formation reached an average temperature of 644° F. in 1584 days. The bottom portion of the formation reached an average temperature of 644° F. in 1922 days. Thus, the bottom portion lagged behind the top portion by almost a year to reach an average temperature near a pyrolysis temperature.

In the second example, portion 728 of the temperature limited heater had the same properties used in the first example. Portion 726 of the heater was altered to have a Curie temperature of 1550° F. by the addition of cobalt to the iron conductor. FIG. 225 depicts resistance per foot (mΩ/ft) versus temperature (° F.) for the second heater example. Curve 1476 depicts the resistance profile for the top portion (portion 728). Curve 1478 depicts the resistance profile for the bottom portion (portion 726). FIG. 226 depicts average temperature in the formation (° F.) versus time (days) as determined by the simulation for the second example. Curve 1480 depicts average temperature versus time for the top portion of the formation. Curve 1482 depicts average temperature versus time for the entire formation. Curve 1484 depicts average temperature versus time for the bottom portion of the formation. As shown, the average temperature in the bottom portion of the formation lagged behind the average temperature in the top portion of the formation and the entire formation. The top portion of the formation reached an average temperature of 644° F. in 1574 days. The bottom portion of the formation reached an average temperature of 644° F. in 1701 days. Thus, the bottom portion still lagged behind the top portion to reach an average temperature near a pyrolysis temperature but the time lag was less than the time lag in the first example.

FIG. 227 depicts net heater energy input (Btu) versus time (days) for the second example. Curve 1486 depicts net heater energy input for the bottom portion. Curve 1488 depicts net heater input for the top portion. The net heater energy input to reach a temperature of 644° F. for the bottom portion was $2.35 \times 10^{10}$ Btu. The net heater energy input to reach a temperature of 644° F. for the top portion was $1.32 \times 10^{10}$ Btu. Thus, it took 12% more power to reach the desired temperature in the bottom portion.

FIG. 228 depicts power injection per foot (W/ft) versus time (days) for the second example. Curve 1490 depicts power injection rate for the bottom portion. Curve 1492 depicts power injection rate for the top portion. The power injection rate for the bottom portion was about 6% more than the power injection rate for the top portion. Thus, either reducing the power output of the top portion and/or increasing the power output of the bottom portion to a total of about 6% should provide approximately similar heating rates in the top and bottom portions.

In the third example, dimensions of the top portion (portion 728) were altered to provide less power output. Portion 728 was adjusted to have a copper core with an outside diameter of 0.545", a carbon steel conductor with an outside diameter of 0.700" surrounding the copper core, and an outer conductor of 347H stainless steel with an outside diameter of 1.2" surrounding the carbon steel conductor. The bottom portion (portion 726) had the same properties as the heater in the second example. FIG. 229 depicts resistance per foot (mΩ/ft) versus temperature (° F.) for the third heater example. Curve 1494 depicts the resistance profile for the top portion (portion 728). Curve 1496 depicts the resistance profile of the top portion in the second example. Curve 1498 depicts the resistance profile for the bottom portion (portion 726). FIG. 230 depicts average temperature in the formation (° F.) versus time (days) as determined by the simulation for the third example. Curve 1502 depicts average temperature versus time for the top portion of the formation. Curve 1500 depicts average temperature versus time for the bottom portion of the formation. As shown, the average temperature in the bottom portion of the formation was approximately the same as the average temperature in the top portion of the formation, especially after a time of about 1000 days. The top portion of the formation reached an average temperature of 644° F. in 1642 days. The bottom portion of the formation reached an average temperature of 644° F. in 1649 days. Thus, the bottom portion reached an average temperature near a pyrolysis temperature only 5 days later than the top portion.

FIG. 231 depicts cumulative energy injection (Btu) versus time (days) for each of the three heater examples. Curve 1508 depicts cumulative energy injection for the first heater example. Curve 1506 depicts cumulative energy injection for the second heater example. Curve 1504 depicts cumulative energy injection for the third heater example. The second and third heater examples have nearly identical cumulative energy injections. The first heater example had a cumulative energy injection about 7% higher to reach an average temperature of 644° F. in the bottom portion.

FIGS. 222-231 depict results for heaters with a 40 foot spacing between heaters in a triangular heating pattern. FIG. 232 depicts average temperature (° F.) versus time (days) for the third heater example with a 30 foot spacing between heaters in the formation as determined by the simulation. Curve 1510 depicts average temperature versus time for the top portion of the formation. Curve 1512 depicts average temperature versus time for the bottom portion of the formation. The curves in FIG. 232 still tracked with approximately equal heating rates in the top and bottom portions. The time to reach an average temperature in the portions was reduced. The top portion of the formation reached an average temperature of 644° F. in 903 days. The bottom portion of the formation reached an average temperature of 644° F. in 884 days. Thus, the reduced heater spacing decreases the time needed to reach an average selected temperature in the formation.

As a fourth example, the STARS simulation was used to determine heating properties of temperature limited heaters with varying power outputs when using the temperature limited heaters in the heater configuration and pattern depicted in FIGS. 124 and 126. The heater pattern had a 30 foot heater spacing. Portion 728 had a length of 368 feet and portion 726 had a length of 587 feet as in the previous examples. Portion 728 included a solid 410 stainless steel conductor with an outside diameter of 1.25". Portion 726 included a solid 410 stainless steel conductor with 9% by weight cobalt added. The Curie temperature of portion 726 is 230° F. higher than the Curie temperature of portion 728.

FIG. 233 depicts average temperature (° F.) versus time (days) for the fourth heater example using the heater configuration and pattern depicted in FIGS. 124 and 126 as determined by the simulation. Curve 1514 depicts average temperature versus time for the top portion of the formation. Curve 1516 depicts average temperature versus time for the bottom portion of the formation. The curves in FIG. 233 show approximately equal heating rates in the top and bottom portions. The top portion of the formation reached a temperature of 644° F. in 859 days. The bottom portion of the formation reached a temperature of 644° F. in 880 days. In this heater configuration and heater pattern, the top portion of the formation reached a selected temperature at about the same time as a bottom portion of the formation.

In some in situ conversion embodiments, a downhole gas turbine is used to provide a portion of the electricity for an electric heater. The exhaust from the gas turbine may heat the formation. The heater may be a temperature limited heater in a horizontal section of a U-shaped well. In some embodiments, the substantially horizontal section of the U-shaped well is over 1000 m long, over 1300 m long, over 1600 m long, or over 1900 m long.

FIG. 234 depicts a schematic representation of a heating system with a downhole gas turbine. Gas turbine 1520 is placed at or near the transition between overburden 382 and hydrocarbon layer 380. Gas turbine 1520 may include electrical generator 1522 and turbine gas combustor 1524. Inlet leg 1526 to gas turbine 1520 may have a relatively large diameter. The diameter may be 0.3 m, 0.4 m, 0.5 m or greater. Oxidant line 1528 and fuel line 1530 supply gas turbine 1520. In some embodiments, fuel line 1530 is placed within oxidant line 1528, or the oxidant line is placed in the fuel line. In some embodiments, the oxidant line is positioned adjacent to the fuel line. In some embodiments, inlet oxidant and fuel are used to cool gas turbine 1520. Oxidant may be, but is not limited to, air, oxygen, or oxygen enriched air.

Electricity provided by electrical generator 1522 is directed to temperature limited heater 1532 through lead-in conductors 1534. Lead-in conductors 1534 may be insulated conductors. If electrical generator 1522 is not able to supply enough electricity to temperature limited heater 1532 to heat hydrocarbon layer 380 to a desired temperature, additional electricity may be supplied to the temperature limited heater through a conductor placed in inlet leg 1522 and electrically coupled to the temperature limited heater.

Exhaust gas from gas turbine 1524 passes through tubular 1536 to outlet 1538. In an embodiment, the tubular is 4" stainless steel pipe placed in a 6" wellbore. The exhaust gases heat an initial section of hydrocarbon layer 380 before the gases become too cool to heat the hydrocarbon layer to the desired temperature. Temperature limited heater 1532 begins a selected distance from gas turbine 1520. The distance may be 200 m, 150 m, 100 m, or less. Heat provided to the portion of the formation from gas turbine 1520 to temperature limited heater 1532 may come from the exhaust gases passing through tubular 1536. Temperature limited heater 1532, which is at least partially supplied with electricity generated by gas turbine 1520, heats hydrocarbon layer 380 and the exhaust gases from the gas turbine. Temperature limited heater 1532 may be an insulated conductor heater with a self-limiting temperature of about 760° C. In some embodiments, temperature limited heater 1532 is placed in tubular 1536. In other embodiments, the temperature limited heater is on the outside of the tubular. Temperature limited heater 1532 may end at a selected horizontal distance from the outlet 1538 of the temperature limited heater. The distance may be 200 m, 150 m, 100 m, or less. The exhaust gases heated by temperature limited heater 1532 transfer heat to hydrocarbon layer 380 before passing through overburden 382 to outlet 1538.

Inlets and outlets of the U-shaped wells for heating a portion of the formation may be placed in alternating directions in adjacent wells. Alternating inlets and outlets of the U-shaped wells may allow for uniform heating of the hydrocarbon layer of the formation.

In some embodiments, a portion of oxidant for gas turbine 1520 is routed to the gas turbine from outlet 1538 of an adjacent U-shaped well. The portion of oxidant may be sent to the gas turbine through a separate line. Using oxidant from the exit of the adjacent well may allow some of the oxidant and/or heat from the exiting exhaust gases to be recovered and utilized. The separate exhaust gas line to the gas turbine may transfer heat to the main oxidant line and/or fuel line to the gas turbine.

Compressors and partial expanders may be located at the surface. Compressed fuel lines and oxidant lines extend to gas turbine 1520. Generators, burners, and expanders of the gas turbine may be located at or near the transition between the overburden and the hydrocarbon layer that is to be heated. Locating equipment in this manner may reduce the complexity of the downhole equipment, and reduce pressure drops for the oxidant going down the wellbore and the combustion gases going through the heater sections and back to the surface. The surface expander for a first well can expand gases from an adjacent well outlet since the adjacent well outlet is physically closer to the inlet of the first well than is the outlet of the first well. Moving compressed fuel and compressed oxidant down to the gas turbine may result in less pressure drop as compared to having cool fuel and oxidant travel down to the gas turbine. Placing gas turbine 1520 at or near the transition between overburden 382 and hydrocarbon layer 380 allows exhaust gas from the gas turbine to heat portions of the formation that are to be pyrolyzed. Placing the gas turbine 1520 at or near the transition between overburden 382 and hydrocarbon layer 380 may eliminate or reduce the amount of insulation needed between the overburden and inlet leg 1526. In some embodiments, tapered insulation may be applied at the exit of gas turbine 1520 to reduce excess heating of the formation near the gas turbine.

In some in situ conversion process embodiments, a circulation system is used to heat the formation. The circulation system may be a closed loop circulation system. FIG. 235 depicts a schematic representation of a system for heating a formation using a circulation system. The system may be used to heat hydrocarbons that are relatively deep in the ground and that are in formations that are relatively large in extent. In some embodiments, the hydrocarbons may be 100 m, 200 m, 300 m or more below the surface. The circulation system may also be used to heat hydrocarbons that are not as deep in the ground. The hydrocarbons may be in formations that extend lengthwise up to 500 m, 750 m, 1000 m, or more. The circulation system may become economically viable in formations where the length of the hydrocarbon containing formation to be treated is long compared to the thickness of the overburden. The ratio of the hydrocarbon formation extent to be heated by heaters to the overburden thickness may be at least 3, at least 5, or at least 10. The heaters of the circulation system may be positioned relative to adjacent heaters so that superposition of heat between heaters of the circulation system allows the temperature of the formation to be raised at least above the boiling point of aqueous formation fluid in the formation.

In some embodiments, heaters 534 may be formed in the formation by drilling a first wellbore and then drilling a second wellbore that connects with the first wellbore. Piping may be positioned in the U-shaped wellbore to form U-shaped heater 534. Heaters 534 are connected to heat transfer fluid circulation system 1540 by piping. Gas at high pressure may be used as the heat transfer fluid in the closed loop circulation system. In some embodiments, the heat transfer fluid is carbon dioxide. Carbon dioxide is chemically stable at the required temperatures and pressures and has a relatively high molecular weight that results in a high volumetric heat capacity. Other fluids such as steam, air, helium and/or nitrogen may also be used. The pressure of the heat transfer fluid entering the formation may be 3000 kPa or higher. The use of high pressure heat transfer fluid allows the heat transfer fluid to have a greater density, and therefore a greater capacity to transfer heat. Also, the pressure drop across the heaters is less for a system where the heat transfer fluid enters the heaters at a first pressure for a given mass flow rate than when the heat transfer fluid enters the heaters at a second pressure at the same mass flow rate when the first pressure is greater than the second pressure.

Heat transfer fluid circulation system 1540 may include heat supply 1542, first heat exchanger 1544, second heat exchanger 1546, and compressor 1548. Heat supply 1542 heats the heat transfer fluid to a high temperature. Heat supply 1542 may be a furnace, solar collector, reactor, fuel cell exhaust heat, or other high temperature source able to supply heat to the heat transfer fluid. In the embodiment depicted in FIG. 235, heat supply 1542 is a furnace that heats the heat transfer fluid to a temperature in a range from about 700° C. to about 920° C., from about 770° C. to about 870° C., or from about 800° C. to about 850° C. In an embodiment, heat supply 1542 heats the heat transfer fluid to a temperature of about 820° C. The heat transfer fluid flows from heat supply 1542 to heaters 534. Heat transfers from heaters 534 to formation 444 adjacent to the heaters. The temperature of the heat transfer fluid exiting formation 444 may be in a range from about 350° C. to about 580° C., from about 400° C. to about 530° C., or from about 450° C. to about 500° C. In an embodiment, the temperature of the heat transfer fluid exiting formation 444 is about 480° C. The metallurgy of the piping used to form heat transfer fluid circulation system 1540 may be varied to significantly reduce costs of the piping. High temperature steel may be used from heat supply 1542 to a point where the temperature is sufficiently low so that less expensive steel can be used from that point to first heat exchanger 1544. Several different steel grades may be used to form the piping of heat transfer fluid circulation system 1540.

Heat transfer fluid from heat supply 1542 of heat transfer fluid circulation system 1540 passes through overburden 382 of formation 444 to hydrocarbon layer 380. Portions of heaters 534 extending through overburden 382 may be insulated. In some embodiments, the insulation or part of the insulation is a polyimide insulating material. Inlet portions of heaters 534 in hydrocarbon layer 380 may have tapering insulation to reduce overheating of the hydrocarbon layer near the inlet of the heater into the hydrocarbon layer.

In some embodiments, the diameter of the pipe in overburden 382 may be smaller than the diameter of pipe through hydrocarbon layer 380. The smaller diameter pipe through overburden 382 may allow for less heat transfer to the overburden. Reducing the amount of heat transfer to overburden 382 reduces the amount of cooling of the heat transfer fluid supplied to pipe adjacent to hydrocarbon layer 380. The increased heat transfer in the smaller diameter pipe due to increased velocity of heat transfer fluid through the small diameter pipe is offset by the smaller surface area of the smaller diameter pipe and the decrease in residence time of the heat transfer fluid in the smaller diameter pipe.

After exiting formation 444, the heat transfer fluid passes through first heat exchanger 1544 and second heat exchanger 1546 to compressor 1548. First heat exchanger 1544 transfers heat between heat transfer fluid exiting formation 444 and heat transfer fluid exiting compressor 1548 to raise the temperature of the heat transfer fluid that enters heat supply 1542 and reduce the temperature of the fluid exiting formation 444. Second heat exchanger 1546 further reduces the temperature of the heat transfer fluid before the heat transfer fluid enters compressor 1548.

FIG. 236 depicts a plan view of an embodiment of wellbore openings in the formation that is to be heated using the circulation system. Heat transfer fluid entries 1550 into formation 444 alternate with heat transfer fluid exits 1552. Alternating heat transfer fluid entries 1550 with heat transfer fluid exits 1552 may allow for more uniform heating of the hydrocarbons in formation 444.

The circulation system may be used to heat a portion of the formation. Production wells in the formation are used to remove produced fluids. After production from the formation has ended, the circulation system may be used to recover heat from the formation. Heat transfer fluid may be circulated through heaters 534 after heat supply 1542 (depicted in FIG. 235) is disconnected from the circulation system. The heat transfer fluid may be a different heat transfer fluid than the heat transfer fluid used to heat the formation. Heat transfers from the heated formation to the heat transfer fluid. The heat transfer fluid may be used to heat another portion of the formation or the heat transfer fluid may be used for other purposes. In some embodiments, water is introduced into heaters 534 to produce steam. In some embodiments, low temperature steam is introduced into heaters 534 so that the passage of the steam through the heaters increases the temperature of the steam. Other heat transfer fluids including natural or synthetic oils, such as Syltherm oil (Dow Corning Corporation (Midland, Mich., U.S.A.), may be used instead of steam or water.

In some embodiments, the circulation system may be used in conjunction with electrical heating. In some embodiments, at least a portion of the pipe in the U-shaped wellbores adjacent to portions of the formation that are to be heated is made of a ferromagnetic material. For example, the piping adjacent to a layer or layers of the formation to be heated is made of a 9% to 13% chromium steel, such as 410 stainless steel. The pipe may be a temperature limited heater when time varying electric current is applied to the piping. The time varying electric current may resistively heat the piping, which heats the formation. In some embodiments, direct electric current may be used to resistively heat the piping, which heats the formation.

In some embodiments, the circulation system is used to heat the formation to a first temperature, and electrical energy is used to maintain the temperature of the formation and/or heat the formation to higher temperatures. The first temperature may be sufficient to vaporize aqueous formation fluid in the formation. The first temperature may be at most about 200° C., at most about 300° C., at most about 350° C., or at most about 400° C. Using the circulation system to heat the formation to the first temperature allows the formation to be dry when electricity is used to heat the formation. Heating the dry formation may minimize electrical current leakage into the formation.

In some embodiments, the circulation system and electrical heating may be used to heat the formation to a first temperature. The formation may be maintained, or the temperature of the formation may be increased from the first temperature, using the circulation system and/or electrical heating. In some embodiments, the formation may be raised to the first temperature using electrical heating, and the temperature may be maintained and/or increased using the circulation system. Economic factors, available electricity, availability of fuel for heating the heat transfer fluid, and other factors may be used to determine when electrical heating and/or circulation system heating are to be used.

In certain embodiments, the portion of heater 534 in hydrocarbon layer 380 is coupled to lead-in conductors. Lead-in conductors may be located in overburden 382. Lead-in conductors may electrically couple the portion of heater 534 in hydrocarbon layer 380 to one or more wellheads at the surface. Electrical isolators may be located at a junction of the portion of heater 534 in hydrocarbon layer 380 with portions of heater 534 in overburden 382 so that the portions of the heater in the overburden are electrically isolated from the portion of the heater in the hydrocarbon layer. In some embodiments, the lead-in conductors are placed inside of the pipe of the closed loop circulation system. In some embodiments, the lead-in conductors are positioned outside of the pipe of the closed loop circulation system. In some embodiments, the lead-in conductors are insulated conductors with mineral insulation, such as magnesium oxide. The lead-in conductors may include highly electrically conductive materials such as copper or aluminum to reduce heat losses in overburden 382 during electrical heating.

In certain embodiments, the portions of heater 534 in overburden 382 may be used as lead-in conductors. The portions of heater 534 in overburden 382 may be electrically coupled to the portion of heater 534 in hydrocarbon layer 380. In some embodiments, one or more electrically conducting materials (such as copper or aluminum) are coupled (for example, cladded or welded) to the portions of heater 534 in overburden 382 to reduce the electrical resistance of the portions of the heater in the overburden. Reducing the electrical resistance of the portions of heater 534 in overburden 382 reduces heat losses in the overburden during electrical heating.

In some embodiments, the portion of heater 534 in hydrocarbon layer 380 is a temperature limited heater with a self-limiting temperature between about 600° C. and about 1000° C. The portion of heater 534 in hydrocarbon layer 380 may be a 9% to 13% chromium stainless steel. For example, portion of heater 534 in hydrocarbon layer 380 may be 410 stainless steel. Time-varying current may be applied to the portion of heater 534 in hydrocarbon layer 380 so that the heater operates as a temperature limited heater.

FIG. 237 depicts a side view representation of an embodiment of a system for heating a portion of a formation using a circulated fluid system and/or electrical heating. Wellheads 418 of heaters 534 may be coupled to heat transfer fluid circulation system 1540 by piping. Wellheads 418 may also be coupled to electrical power supply system 1554. In some embodiments, heat transfer fluid circulation system 1540 is disconnected from the heaters when electrical power is used to heat the formation. In some embodiments, electrical power supply system 1554 is disconnected from the heaters when heat transfer fluid circulation system 1540 is used to heat the formation.

Electrical power supply system 1554 may include transformer 900 and cables 894, 896. In certain embodiments, cables 894, 896 are capable of carrying high currents with low losses. For example, cables 894, 896 may be thick copper or aluminum conductors. The cables may also have thick insulation layers. In some embodiments, cable 894 and/or cable 896 may be superconducting cables. The superconducting cables may be cooled by liquid nitrogen. Superconducting cables are available from Superpower, Inc. (Schenectady, N.Y., U.S.A.). Superconducting cables may minimize power loss and/or reduce the size of the cables needed to couple transformer 900 to the heaters.

Alternative energy sources may be used to supply electricity for subsurface electric heaters. Alternative energy sources include, but are not limited to, wind, off-peak power, hydroelectric power, geothermal, solar, and tidal wave action. Some of these alternative energy sources provide intermittent, time-variable power, or power-variable power. To provide power for subsurface electric heaters, power provided by these alternative energy sources may be conditioned to produce power with appropriate operating parameters (for example, voltage, frequency, and/or current) for the subsurface heaters.

FIG. 238 illustrates a schematic of an embodiment using wind to generate electricity for subsurface heaters. The generated electrical power may be used to power other equipment used to treat a subsurface formation such as, but not limited to, pumps, computers, or other electrical equipment. In certain embodiments, windmill 1560 is used to generate electricity to power heaters 534. Windmill 1560 may represent one or more windmills in a wind farm. The windmills convert wind to a usable mechanical form of motion. In some embodiments, the wind farm may include advanced windmills as suggested by the National Renewable Energy Laboratory (Golden, Colo., U.S.A.). In some embodiments, windmill 1560 includes other intermittent, time-variable, or power-variable power sources.

In some embodiments, gas turbine 1562 is used to generate electricity to power heaters 534. Windmill 1560 and/or gas turbine 1562 may be coupled to transformer 1564. Transformer 1564 may convert power from windmill 1560 and/or gas turbine 1562 into electrical power with appropriate operating parameters for heaters 534 (for example, AC or DC power with appropriate voltage, current, and/or frequency may be generated by the transformer).

In certain embodiments, tap controller 1566 is coupled to transformer 1564, control system 1568 and heaters 534. Tap controller 1566 may monitor and control transformer 1564 to maintain a constant voltage to heaters 534, regardless of the load of the heaters. Tap controller 1566 may control power output in a range from 5 MVA (megavolt amps) to 500 MVA, from 10 MVA to 400 MVA, or from 20 MVA to 300 MVA. As an example, during operation, an overload of voltage may be sent from transformer 1564. Tap controller 1566 may distribute the excess load to other heaters and/or other equipment in need of power. In some embodiments, tap controller 1566 may store the excess load for future use.

Control system 1568 may control tap controller 1566. Control system 1568 may be, for example, a computer controller or an analog logic system. Control system 1568 may use data supplied from power sensors 1570 to generate predictive algorithms and/or control tap controller 1566. For example, data may be an amount of power generated from windmill 1560, gas turbine 1562, and/or transformer 1564. Data may also include an amount of resistive load of heaters 534.

Automatic voltage regulation for resistive load of a heater maintains the life of the heaters and/or allows constant heat output from the heaters to a subsurface formation. Adjusting the load demands instead of adjusting the power source allows enhanced control of power supplied to heaters and/or other equipment that requires electricity. Power supplied to heaters 534 may be controlled within selected limits (for example, a power supplied and/or controlled to a heater within 1%, 5%, 10%, or 20% of power required by the heater). Control of power supplied from alternative energy sources may allow output of prime power at its rating, allow energy produced (for example, from an intermittent source, a subsurface formation, or a hydroelectric source) to be stored and used later, and/or allow use of power generated by intermittent power sources to be used as a constant source of energy.

Some hydrocarbon containing formations, such as oil shale formations, may include nahcolite, trona, dawsonite, and/or other minerals within the formation. In some embodiments, nahcolite is contained in unleached portions of the formation. Unleached portions of the formation are parts of the formation where minerals are not removed by groundwater in the formation. For example, in the Piceance basin in Colorado, unleached oil shale is found below a depth of about 500 m below grade. Deep unleached oil shale formations in the Piceance basin center tend to be relatively rich in hydrocarbons. For example, about 0.10 liters to about 0.15 liters of oil per kilogram (L/kg) of oil shale may be producible from an unleached oil shale formation.

Nahcolite is a mineral that includes sodium bicarbonate ($NaHCO_3$). Nahcolite may be found in formations in the Green River lakebeds in Colorado, U.S.A. In some embodiments, at least about 5 weight %, at least about 10 weight %, or at least about 20 weight % nahcolite may be present in the formation. Dawsonite is a mineral that includes sodium aluminum carbonate ($NaAl(CO_3)(OH)_2$). Dawsonite is typically present in the formation at weight percents greater than about 2 weight % or, in some embodiments, greater than about 5 weight %. Nahcolite and/or dawsonite may dissociate at temperatures used in the in situ conversion process. The dissociation is strongly endothermic and may produce large amounts of carbon dioxide.

Nahcolite and/or dawsonite may be solution mined prior to, during, and/or following treatment of the formation in situ to avoid dissociation reactions and/or to obtain desired chemical compounds. In certain embodiments, hot water or steam is used to dissolve nahcolite in situ to form an aqueous sodium bicarbonate solution before the in situ conversion process is used to process hydrocarbons in the formation. Nahcolite may form sodium ions ($Na^+$) and bicarbonate ions ($HCO_3^-$) in aqueous solution. The solution may be produced from the formation through production wells, thus avoiding dissociation reactions during the in situ conversion process. In some embodiments, dawsonite is thermally decomposed to alumina during the in situ conversion process for treating hydrocarbons in the formation. The alumina is solution mined after completion of the in situ conversion process.

Formations that include nahcolite and/or dawsonite may be treated using the in situ conversion process. A perimeter barrier may be formed around the portion of the formation to be treated. The perimeter barrier may inhibit migration of water into the treatment area. During solution mining and/or the in situ conversion process, the perimeter barrier may inhibit migration of dissolved minerals and formation fluid from the treatment area. During initial heating, a portion of the formation to be treated may be raised to a temperature below the dissociation temperature of the nahcolite. The first temperature may be at most about 90° C., or in some embodiments, at most about 80° C. The first temperature may be any temperature that increases the solvation rate of nahcolite in water, but is also below a temperature at which nahcolite dissociates (above about 95° C. at atmospheric pressure).

A first fluid may be injected into the heated portion. The first fluid may include water, brine, steam, or other fluids that form a solution with nahcolite and/or dawsonite. The first fluid may be at an increased temperature, for example, about 90° C., about 95° C., or about 100° C. The increased temperature may be similar to the first temperature of the portion of the formation.

In some embodiments, the first fluid is injected at an increased temperature into a portion of the formation that has not been heated by heat sources. The increased temperature may be a temperature below a boiling point of the first fluid, for example, about 90° C. for water. Providing the first fluid at an increased temperature increases a temperature of a portion of the formation. In certain embodiments, additional heat may be provided from one or more heat sources in the formation after the first fluid is injected.

In other embodiments, the first fluid is or includes steam. The steam may be produced by forming steam in a previously heated portion of the formation (for example by passing water through conduits that have been used to heat the formation), by heat exchange with fluids produced from the formation, and/or by generating steam in standard steam production facilities.

In some embodiments, heat from a hot previously treated portion of the formation is used to heat water, brine, and/or steam used for solution mining a new portion of the formation. Heat transfer fluid may be introduced into the hot previously treated portion of the formation. The heat transfer fluid may be water, steam, carbon dioxide, or other fluids. Heat may transfer from the hot formation to the heat transfer fluid. The heat transfer fluid is produced from the formation through production wells. The heat transfer fluid is sent to a heat exchanger. The heat exchanger may heat water, brine, and/or steam used as the first fluid to solution mine the new portion of the formation. The heat transfer fluid may be reintroduced into the heated portion of the formation to produce additional hot heat transfer fluid. In some embodiments, heat transfer fluid produced from the formation is treated to remove hydrocarbons or other materials before being reintroduced into the formation as part of a remediation process of the heated portion of the formation.

Steam injected for solution mining may have a temperature below the pyrolysis temperature of hydrocarbons in the formation. Injected steam may be at a temperature below 250° C., below 300° C., or below 400° C. The injected steam may be at a temperature of at least 150° C., at least 135° C., or at least 125° C. Injecting steam at pyrolysis temperatures may cause problems as hydrocarbons pyrolyze and hydrocarbon fines mix with the steam. The mixture of fines and steam may reduce permeability and/or cause plugging of production wells and the formation. Thus, the injected steam temperature is selected to inhibit plugging of the formation and/or wells in the formation. The temperature of the injected steam may be varied during the solution mining process. As the solution mining progresses and the nahcolite being solution mined is farther away from the injection point, the steam temperature may be increased so that steam and/or water that reaches the nahcolite to be solution mined is at an elevated temperature below the dissociation temperature of the nahcolite.

A second fluid may be produced from the formation following injection of the first fluid into the formation. The second fluid may include products of the injected first fluid in the formation. For example, the second fluid may include carbonic acid or other hydrated carbonate compounds formed from the dissolution of nahcolite in the first fluid. The second fluid may also include minerals and/or metals. The minerals and/or metals may include sodium, aluminum, phosphorus, and other elements. Producing the second fluid from the formation may reduce the amount of energy required to heat the formation by removing mass and by removing minerals that would otherwise undergo endothermic reactions.

Solution mining the formation before the in situ conversion process allows initial heating of the formation to be provided by heat transfer from the first fluid used during solution mining. Solution mining nahcolite or other minerals that decompose or dissociate by means of endothermic reactions before the in situ conversion process avoids having energy supplied to heat the formation being used to support these endothermic reactions. Solution mining allows for production of minerals with commercial value. Removing nahcolite or other minerals before the in situ conversion process removes mass from the formation. Thus, less mass is present in the formation that needs to be heated to higher temperatures and heating the formation to higher temperatures may be achieved more quickly and/or more efficiently. Removing mass from the formation also may increase the permeability of the formation. Increasing the permeability may reduce the number of production wells needed for the in situ conversion process. In certain embodiments, solution mining before the in situ conversion process reduces the time delay between startup of heating of the formation and production of hydrocarbons by two years or more.

FIG. 239 depicts an embodiment for solution mining the formation. Barrier 454 (for example, a frozen barrier or a grout barrier) may be formed around a perimeter of treatment area 424 of the formation. The footprint defined by the barrier may have any desired shape such as circular, square, rectangular, polygonal, or irregular shape. Barrier 454 may be any barrier formed to inhibit the flow of fluid into or out of treatment area 424. For example, barrier 454 may include one or more freeze wells that inhibit water flow through the barrier. Barrier 454 may be formed using one or more barrier wells 200. Formation of barrier 454 may be monitored using monitor wells 462 and/or by monitoring devices placed in barrier wells 200.

Water inside treatment area 424 may be pumped out of the treatment area through injection wells 916 and/or production wells 206. In certain embodiments, injection wells 916 are used as production wells 206 and vice versa (the wells are used as both an injection well and a production well). Water may be pumped out until a production rate of water is low or stops.

Heat may be provided to treatment area 424 through heater wells 502. In some embodiments, treatment area 424 is heated to a temperature from about 90° C. to about 120° C. (for example, a temperature of about 90° C., 95° C., 100° C., 110° C., or 120° C.). In certain embodiments, heat is provided to treatment area 424 from the first fluid injected into the formation. The first fluid may be injected at a temperature from about 90° C. to about 120° C. (for example, a temperature of about 90° C., 95° C., 100° C., 110° C., or 120° C.). In some embodiments, heater wells 502 are installed in treatment area 424 after the treatment area is solution mined. In some embodiments, some heat is provided from heaters placed in injection wells 916 and/or production wells 206. A temperature of treatment area 424 may be monitored using temperature measurement devices placed in monitoring wells 494 and/or temperature measurement devices in injection wells 916, production wells 206, and/or heater wells 502.

The first fluid is injected through one or more injection wells 916. In some embodiments, the first fluid is hot water. The first fluid may mix and/or combine with non-hydrocarbon material that is soluble in the first fluid, such as nahcolite, to produce a second fluid. The second fluid may be removed from the treatment area through injection wells 916, production wells 206, and/or heater wells 502. Injection wells 916, production wells 206, and/or heater wells 502 may be heated during removal of the second fluid. Heating one or more wells during removal of the second fluid may maintain the temperature of the fluid during removal of the fluid from the treatment area above a desired value. After producing a majority of the soluble non-hydrocarbon material from treatment area 424, solution remaining within the treatment area may be removed from the treatment area through injection wells 916, production wells 206, and/or heater wells 502. Removing the soluble non-hydrocarbon material may produce a relatively high permeability treatment area 424.

Hydrocarbons within treatment area 424 may be pyrolyzed and/or produced using the in situ conversion process following removal of the soluble non-hydrocarbon materials. The relatively high permeability treatment area allows for easy movement of hydrocarbon fluids in the formation during in situ conversion processing. The relatively high permeability treatment area provides an enhanced collection area for pyrolyzed and mobilized fluids in the formation. During the in situ conversion process, heat may be provided to treatment area 424 through heater wells 502. A mixture of hydrocarbons may be produced from the formation through production wells 206 and/or heater wells 502. In certain embodiments, injection wells 916 are used as either production wells and/or heater wells during the in situ conversion process.

In some embodiments, a controlled amount of oxidant (for example, air and/or oxygen) is provided to treatment area 424 at or near heater wells 502 when a temperature in the formation is above a temperature sufficient to support oxidation of hydrocarbons. At such a temperature, the oxidant reacts with the hydrocarbons to provide heat in addition to heat provided by electrical heaters in heater wells 502. The controlled amount of oxidant may facilitate oxidation of hydrocarbons in the formation to provide additional heat for pyrolyzing hydrocarbons in the formation. The oxidant may more easily flow through treatment area 424 because of the increased permeability of the treatment area after removal of the non-hydrocarbon materials. The oxidant may be provided in a controlled manner to control the heating of the formation. The amount of oxidant provided is controlled so that uncontrolled heating of the formation is avoided.

Following the in situ conversion process, treatment area 424 may be cooled by introducing water to produce steam from the hot portion of the formation. Introduction of water to produce steam may vaporize some hydrocarbons remaining in the formation. Water may be injected through injection wells 916. The injected water may cool the formation. The remaining hydrocarbons and generated steam may be produced through production wells 206 and/or heater wells 502. Treatment area 424 may be cooled to a temperature near the boiling point of water. The steam produced from the formation may be used to heat a first fluid used to solution mine another portion of the formation.

Treatment area 424 may be further cooled to a temperature at which water will condense in the formation. Water and/or solvent may be introduced into and be removed from the treatment area. Removing the condensed water and/or solvent from treatment area 424 may remove any additional soluble material remaining in the treatment area. The water and/or solvent may entrain non-soluble fluid present in the formation. Fluid may be pumped out of treatment area 424 through production well 206 and/or heater wells 502. The injection and removal of water and/or solvent may be repeated until a desired water quality within treatment area 424 is achieved. Water quality may be measured at injection wells 916, heater wells 502, and/or production wells 206. The water quality may substantially match or exceed the water quality of treatment area 424 prior to treatment.

In some embodiments, treatment area 424 may include a leached zone located above an unleached zone. The leached zone may have been leached naturally and/or by a separate leaching process. In certain embodiments, the unleached zone may be at a depth of at least about 500 m. A thickness of the unleached zone may be between about 100 m and about 500 m. However, the depth and thickness of the unleached zone may vary depending on, for example, a location of treatment area 424 and/or the type of formation. In certain embodiments, the first fluid is injected into the unleached zone below the leached zone. Heat may also be provided into the unleached zone.

In certain embodiments, a section of a formation may be left untreated by solution mining and/or unleached. The unleached section may be proximate a selected section of the formation that has been leached and/or solution mined by providing the first fluid as described above. The unleached section may inhibit the flow of water into the selected section. In some embodiments, more than one unleached section may be proximate a selected section.

Nahcolite may be present in the formation in layers or beds. In certain embodiments, solution mining layered or bedded nahcolite from the formation causes vertical shifting in the formation. FIG. 240 depicts an embodiment of a formation with nahcolite layers in the formation (before solution mining nahcolite from the formation). Hydrocarbon layers 380A have substantially no nahcolite and hydrocarbon layers 380B have nahcolite. FIG. 241 depicts the formation of FIG. 240 after the nahcolite has been solution mined. Layers 380B have collapsed due to the removal of the nahcolite from the layers. The collapsing of layers 380B causes compaction of the layers and vertical shifting of the formation. The richness of layers 380B is increased after compaction of the layers. In addition, the permeability of layers 380B may remain relatively high after compaction due to removal of the nahcolite. Heater wells may be placed in the formation after removal of nahcolite and the subsequent vertical shifting. Forming heater wellbores and/or installing heaters in the formation after the vertical shifting protects the heaters from being damaged due to the vertical shifting.

In certain embodiments, removing nahcolite from the formation interconnects two or more wells in the formation. Removing nahcolite from zones in the formation may increase the permeability in the zones. Some zones may have more nahcolite than others and become more permeable as the nahcolite is removed. At a certain time, zones with the increased permeability may interconnect two or more wells (for example, injection wells or production wells) in the formation.

FIG. 242 depicts an embodiment of two injection wells interconnected by a zone that has been solution mined to remove nahcolite from the zone. Injection wells 916 are used to solution mine hydrocarbon layer 380, which contains nahcolite. During the initial portion of the solution mining process, injection wells 916 are used to inject water and/or other fluids, and to produce dissolved nahcolite fluids from the formation. Each injection well 916 is used to inject water and produce fluid from a near wellbore region as the permeability of hydrocarbon layer is not sufficient to allow fluid to flow between the injection wells. In certain embodiments, zone 1572 has more nahcolite than other portions of hydrocarbon layer 380. With increased nahcolite removal from zone 1572, the permeability of the zone may increase. The permeability increases from the wellbores outwards as nahcolite is removed from zone 1572. At some point during solution mining of the formation, the permeability of zone 1572 increases to allow injection wells 916 to become interconnected such that fluid will flow between the wells. At this time, one injection well 916 may be used to inject water while the other injection well 916 is used to produce fluids from the formation in a continuous process. Injecting in one well and producing from a second well may be more economical and more efficient in removing nahcolite, as compared to injecting and producing through the same well. In some embodiments, additional wells may be drilled into zone 1572 and/or hydrocarbon layer 380 in addition to injection wells 916. The additional wells may be used to circulate additional water and/or to produce fluids from the formation. The wells may later be used as heater wells and/or production wells for the in situ conversion process treatment of hydrocarbon layer 380.

In some embodiments, the second fluid produced from the formation during solution mining is used to produce sodium bicarbonate. Sodium bicarbonate may be used in the food and pharmaceutical industries, in leather tanning, in fire retardation, in wastewater treatment, and in flue gas treatment (flue gas desulphurization and hydrogen chloride reduction). The second fluid may be kept pressurized and at an elevated temperature when removed from the formation. The second fluid may be cooled in a crystallizer to precipitate sodium bicarbonate.

In some embodiments, the second fluid produced from the formation during solution mining is used to produce sodium carbonate. Sodium carbonate may be used in the manufacture of glass, in the manufacture of detergents, in water purification, polymer production, tanning, paper manufacturing, effluent neutralization, metal refining, sugar extraction, and/or cement manufacturing. The second fluid removed from the formation may be heated in a treatment facility to form sodium carbonate (soda ash) and/or sodium carbonate brine. Heating sodium bicarbonate will form sodium carbonate according to the equation:

$$2NaHCO_3 \rightarrow Na_2CO_3 + CO_2 + H_2O. \tag{80}$$

In certain embodiments, the heat for heating the sodium bicarbonate is provided using heat from the formation. For example, a heat exchanger that uses steam produced from the water introduced into the hot formation may be used to heat the second fluid to dissociation temperatures of the sodium bicarbonate. In some embodiments, the second fluid is circulated through the formation to utilize heat in the formation for further reaction. Steam and/or hot water may also be added to facilitate circulation. In some embodiments, the second fluid is circulated through conduits previously used to heat the formation.

In some embodiments, higher temperatures are used in the formation (for example, above about 120° C., above about 130° C., above about 150° C., or below about 250° C.) during solution mining of nahcolite. The first fluid is introduced into the formation under pressure sufficient to inhibit sodium bicarbonate from dissociating to produce carbon dioxide. The pressure in the formation may be maintained at sufficiently high pressures to inhibit such nahcolite dissociation but below pressures that would result in fracturing the formation. In addition, the pressure in the formation may be maintained high enough to inhibit steam formation if hot water is being introduced in the formation. In some embodiments, a portion of the nahcolite may begin to decompose in situ. In such cases, nahcolite is removed from the formation as soda ash. If soda ash is produced from solution mining of nahcolite, the soda ash may be transported to a separate facility for treatment. The soda ash may be transported through a pipeline to the separate facility.

As described above, in certain embodiments, following removal of nahcolite from the formation, the formation is treated using the in situ conversion process to produce formation fluids from the formation. If dawsonite is present in the formation, dawsonite within the heated portion of the formation decomposes during heating of the formation to pyrolysis temperature. Dawsonite typically decomposes at temperatures above 270° C. according to the reaction:

$$2NaAl(OH)_2CO_3 \rightarrow Na_2CO_3 + Al_2O_3 + 2H_2O + CO_2. \tag{81}$$

In certain embodiments, alumina formed by dawsonite decomposition is solution mined using a chelating agent. The chelating agent may be injected through injection wells, production wells, and/or heater wells used for solution mining nahcolite and/or the in situ conversion process (for example, injection wells 916, production wells 206, and/or heater wells 502 depicted in FIG. 239). The chelating agent may be an aqueous acid. In certain embodiments, the chelating agent is EDTA (ethylenediaminetetraacetic acid). Other examples of possible chelating agents include, but are not limited to, ethylenediamine, porphyrins, dimercaprol, nitrilotriacetic acid, diethylenetriaminepentaacetic acid, phosphoric acids, acetic acid, acetoxy benzoic acids, nicotinic acid, pyruvic acid, citric acid, tartaric acid, malonic acid, imidizole, ascorbic acid, phenols, hydroxy ketones, sebacic acid, and boric acid. The mixture of chelating agent and alumina may be produced through production wells or other wells used for solution mining and/or the in situ conversion process (for example, injection wells 916, production wells 206, and/or heater wells 502, which are depicted in FIG. 239). The alumina may be separated from the chelating agent in a treatment facility. The recovered chelating agent may be recirculated back to the formation to solution mine more alumina.

In some embodiments, alumina within the formation may be solution mined using a basic fluid after the in situ conversion process. Basic fluids include, but are not limited to, sodium hydroxide, ammonia, magnesium hydroxide, magnesium carbonate, sodium carbonate, potassium carbonate, pyridine, and amines. In an embodiment, sodium carbonate brine, such as 0.5 Normal $Na_2CO_3$, is used to solution mine alumina. Sodium carbonate brine may be obtained from solution mining nahcolite from the formation. Obtaining the basic fluid by solution mining the nahcolite may significantly reduce costs associated with obtaining the basic fluid. The basic fluid may be injected into the formation through a heater well and/or an injection well. The basic fluid may combine with alumina to form an alumina solution that is removed from the formation. The alumina solution may be removed through a heater well, injection well, or production well.

Alumina may be extracted from the alumina solution in a treatment facility. In an embodiment, carbon dioxide is bubbled through the alumina solution to precipitate the alumina from the basic fluid. Carbon dioxide may be obtained from dissociation of nahcolite, from the in situ conversion process, or from decomposition of the dawsonite during the in situ conversion process.

In certain embodiments, a formation may include portions that are significantly rich in either nahcolite or dawsonite only. For example, a formation may contain significant amounts of nahcolite (for example, at least about 20 weight %, at least about 30 weight %, or at least about 40 weight %) in a depocenter of the formation. The depocenter may contain only about 5 weight % or less dawsonite on average. However, in bottom layers of the formation, a weight percent of dawsonite may be about 10 weight % or even as high as about 25 weight %. In such formations, it may be advantageous to solution mine for nahcolite only in nahcolite-rich areas, such as the depocenter, and solution mine for dawsonite only in the dawsonite-rich areas, such as the bottom layers. This selective solution mining may significantly reduce fluid costs, heating costs, and/or equipment costs associated with operating the solution mining process.

In certain formations, dawsonite composition varies between layers in the formation. For example, some layers of the formation may have dawsonite and some layers may not. In certain embodiments, more heat is provided to layers with more dawsonite than to layers with less dawsonite. Tailoring heat input to provide more heat to certain dawsonite layers more uniformly heats the formation as the reaction to decompose dawsonite absorbs some of the heat intended for pyrolyzing hydrocarbons. FIG. 243 depicts an embodiment for heating a formation with dawsonite in the formation. Hydrocarbon layer 380 may be cored to assess the dawsonite composition of the hydrocarbon layer. The mineral composition may be assessed using, for example, FTIR (Fourier transform infrared spectroscopy) or x-ray diffraction. Assessing the core composition may also assess the nahcolite composition of the core. After assessing the dawsonite composition, heater 880 may be placed in wellbore 910. Heater 880 includes sections to provide more heat to hydrocarbon layers with more dawsonite in the layers (hydrocarbon layers 380D). Hydrocarbon layers with less dawsonite (hydrocarbon layers 380C) are provided with less heat by heater 880. Heat output of heater 880 may be tailored by, for example, adjusting the resistance of the heater along the length of the heater. In one embodiment, heater 880 is a temperature limited heater, described herein, that has a higher temperature limit (for example, higher Curie temperature) in sections proximate layers 380D as compared to the temperature limit (Curie temperature) of sections proximate layers 380C. The resistance of heater 880 may also be adjusted by altering the resistive conducting materials along the length of the heater to supply a higher energy input (watts per meter) adjacent to dawsonite rich layers.

Solution mining dawsonite and nahcolite may be relatively simple processes that produce aluminum and soda ash from the formation. In some embodiments, hydrocarbons produced from the formation using the in situ conversion process may be fuel for a power plant that produces direct current (DC) electricity at or near the site of the in situ conversion operation. The produced DC electricity may be used on the site to produce aluminum metal from the alumina using the Hall process. Aluminum metal may be produced from the alumina by melting the alumina in a treatment facility on the site. Generating the DC electricity at the site may save on costs associated with using hydrotreaters, pipelines, or other treatment facilities associated with transporting and/or treating hydrocarbons produced from the formation using the in situ conversion process.

In some embodiments, a perimeter barrier may be formed around the portion of the formation to be treated. The perimeter barrier may inhibit migration of formation fluid into or out of the treatment area. The perimeter barrier may be a frozen barrier and/or a grout barrier. After formation of the perimeter barrier, the treatment area may be processed to produce desired products.

Formations that include non-hydrocarbon materials may be treated to remove and/or dissolve a portion of the non-hydrocarbon materials from a section of the formation before hydrocarbons are produced from the section. In some embodiments, the non-hydrocarbon materials are removed by solution mining. Removing a portion of the non-hydrocarbon materials may reduce the carbon dioxide generation sources present in the formation. Removing a portion of the non-hydrocarbon materials may increase the porosity and/or permeability of the section of the formation. Removing a portion of the non-hydrocarbon materials may result in a raised temperature in the section of the formation.

After solution mining, some of the wells in the treatment may be converted to heater wells, injection wells, and/or production wells. In some embodiments, additional wells are formed in the treatment area. The wells may be heater wells, injection wells, and/or production wells. Logging techniques may be employed to assess the physical characteristics, including any vertical shifting resulting from the solution mining, and/or the composition of material in the formation. Packing, baffles or other techniques may be used to inhibit formation fluid from entering the heater wells. The heater wells may be activated to heat the formation to a temperature sufficient to support combustion.

One or more production wells may be positioned in permeable sections of the treatment area. Production wells may be horizontally and/or vertically oriented. For example, production wells may be positioned in areas of the formation that have a permeability of greater than 5 darcy or 10 darcy. In some embodiments, production wells may be positioned near a perimeter barrier. A production well may allow water and production fluids to be removed from the formation. Positioning the production well near a perimeter barrier enhances the flow of fluids from the warmer zones of the formation to the cooler zones.

FIG. 244 depicts an embodiment of a process for treating a hydrocarbon containing formation with a combustion front. Barrier 454 (for example, a frozen barrier or a grout barrier) may be formed around a perimeter of treatment area 424 of the formation. The footprint defined by the barrier may have any desired shape such as circular, square, rectangular, polygonal, or irregular shape. Barrier 454 may be formed using one or more barrier wells 200. The barrier may be any barrier formed to inhibit the flow of fluid into or out of treatment area 424. In some embodiments, barrier 454 may be a double barrier.

Heat may be provided to treatment area 424 through heaters positioned in injection wells 916. In some embodiments, the heaters in injection wells 916 heat formation adjacent to the injections wells to temperatures sufficient to support combustion. Heaters in injection wells 916 may raise the formation near the injection wells to temperatures from about 90° C. to about 120° C. or higher (for example, a temperature of about 90° C., 95° C., 100° C., 110° C., or 120° C.).

Injection wells 916 may be used to introduce a combustion fuel, an oxidant, steam and/or a heat transfer fluid into treatment area 424, either before, during, or after heat is provided to the treatment area 424 from heaters. In some embodiments, injection wells 916 are in communication with each other to allow the introduced fluid to flow from one well to another. Injection wells 916 may be located at positions that are relatively far away from perimeter barrier 454. Introduced fluid may cause combustion of hydrocarbons in treatment area 424. Heat from the combustion may heat treatment area 424 and mobilize fluids toward production wells 206.

A temperature of treatment area 424 may be monitored using temperature measurement devices placed in monitoring wells and/or temperature measurement devices in injection wells 916, production wells 206, and/or heater wells.

In some embodiments, a controlled amount of oxidant (for example, air and/or oxygen) is provided in injection wells 916 to advance a heat front towards production wells 206. The amount of oxidant is controlled to limit the advancement rate of the heat front and to limit the temperature of the heat front. The advancing heat front may pyrolyze hydrocarbons. The high permeability in the formation allows the pyrolyzed hydrocarbons to spread in the formation towards production wells without being overtaken by the advancing heat front.

Vaporized formation fluid and/or gas formed during the combustion process may be removed through gas wells 1574 and/or injection well 916. Venting of gases through the gas wells and/or the injection well may force the combustion front in a desired direction.

In some embodiments, the formation may be heated to a temperature sufficient temperature to cause pyrolysis of the formation fluid by the steam and/or heat transfer fluid. The steam and/or heat transfer fluid may be heated to temperatures of about 300° C., about 400° C., about 500° C., or about 600° C. In certain embodiments, the steam and/or heat transfer fluid may be co-injected with the fuel and/or oxidant.

FIG. 245 depicts a representation of a cross-sectional view of an embodiment for treating a hydrocarbon containing formation with a combustion front. As the combustion front is initiated and/or fueled through injection well 916, formation fluid near periphery 1576 of the combustion front becomes mobile and flow towards production well 206 located proximate barrier 454. Combustion products and noncondensable formation fluid may be removed from the formation through gas wells 1574. Condensable formation fluid may be produced through production well 206. In some embodiments, production well 206 is located below injection well 916. Production well 206 may be about, or above 1 m, 5 m, to 10 m below injection well 916. Production well 206 may include a perforated liner that allows hydrocarbons to flow into the production well.

Carbon dioxide and/or hydrogen sulfide may be produced during in situ conversion processes and during many conventional production processes. Removal of hydrogen sulfide from produced formation fluid may reduce the toxicity and/or strong odor in the produced formation fluid, thus making the formation fluid more acceptable for transportation and/or processing. Removing carbon dioxide and/or hydrogen sulfide from produced formation fluids may reduce capital costs associated with removing the fluids and reduce or eliminate the need for certain surface facilities (for example, a Claus plant or Scot gas treater). Since carbon dioxide has a low heating value, removal of carbon dioxide from formation fluids may increase the heat capacity of a gas stream separated from the formation fluid.

Net release of carbon dioxide to the atmosphere and/or hydrogen sulfide conversion to sulfur from an in situ conversion process for hydrocarbons may be reduced by utilizing the produced carbon dioxide and/or by storing carbon dioxide and/or hydrogen sulfide within the formation or within another formation. In certain embodiments, carbon dioxide and/or hydrogen sulfide is stored in a deep saline, porous formation. The carbon dioxide and/or hydrogen sulfide may promote mineralization within the formation. In certain embodiments, carbon dioxide is stored at a depth in the formation such that the carbon dioxide is introduced in the formation in a supercritical state. The depths of outlets of insertion wells used to introduce carbon dioxide and/or hydrogen sulfide in the formation may be 900 m or more below the surface.

Injection of carbon dioxide and/or hydrogen sulfide into a non-producing formation or using the carbon dioxide and/or hydrogen sulfide as a flood fluid is described by Caroll in "Physical Properties Relevant to Acid Gas Injection," Presented at the 14th International Gas Convention Venezuelan Gas Processors Association on May 10-12, 2000 in Caracas, Venezuela; "Phase Equilibria Relevant to Acid Gas Injection: Part 1—Non-Aqueoues Phase Behaviour Journal of Canadian Petroleum Technology, 2002, Vol. 41 No. 6, pp. 1-6; and "Phase Equilibria Relevant to Acid Gas Injection: Part 2—Aqueoues Phase Behaviour Journal of Canadian Petroleum Technology, 2002, Vol. 41, No. 7, pp. 1-5, all of which are incorporated by reference as if fully set forth herein.

During production of formation fluids from a subsurface formation, carbonic acid may be produced from the reaction of carbon dioxide with water. Portions of wells made of certain materials, such as carbon steel, may start to deteriorate (e.g., corrode) in the presence of the carbonic acid. To inhibit corrosion due to carbonic acid, basic solutions and/or solvents may be introduced in the wellbore to neutralize and/or dissolve the carbonic acid.

In some embodiments, hydrogen sulfide is introduced into one or more wellbores in a subsurface formation. Introduction of the hydrogen sulfide may be performed at pressures below the lithostatic pressure of the subsurface formation to inhibit fracturing the formation. The injected hydrogen sulfide may form a sulfide layer on metal surfaces of the well. Formation of a sulfide layer may inhibit corrosion of the metal surfaces of the well by carbonic acid.

In certain embodiments, an electrical insulator (for example, a centralizer, an insulating layer, the electrical insulator in an insulated conductor heater, or any other electrical insulator described herein) includes a material that is fired or cured when heated in the subsurface. The material may develop desired dielectric or other electrical properties and/or physical properties after the material is fired or cured in a wellbore in the formation. The material may be fired or cured when a heater is turned on in the wellbore and the heater heats the material to its firing or curing temperature.

An example of such a material is a ceramic tape available from Composite Development Technology, Inc. (Lafayette, Colo., U.S.A.). The ceramic tape is flexible before it is fired. The ceramic tape obtains its dielectric properties after firing.

After firing, the ceramic tape is a hard-ceramic with good dielectric properties suitable for subsurface electrical heating.

In an embodiment, the ceramic tape is wrapped around an electrical conductor (for example, the conductor of a temperature limited heater). Electrical current may be applied to the electrical conductor to heat the heater and fire the ceramic tape. In some embodiments, the ceramic tape is pre-fired before installation of a heater. The ceramic tape may be pre-fired using, for example, a hot gas gun.

Before firing, the ceramic tape is flexible and easy to install in a variety of applications. In certain embodiments, the ceramic tape is used between centralizers in a conductor-in-conduit heater. The ceramic tape may inhibit shorting of the conductor and conduit if the centralizers fail (for example, if the centralizers buckle and fail). In certain embodiments, the ceramic tape is used as the centralizers in a conductor-in-conduit heater. In some embodiments, the ceramic tape is used as the electrical insulator in an insulated conductor heater. In some embodiments, the ceramic tape is used as the electrical insulator in splices between sections of heaters. In some embodiments, the ceramic tape is used to electrically insulate the legs of a three-phase heater. The three legs of the three-phase heater may be enclosed in one sheath with the ceramic tape separating the legs of the heater.

In this patent, certain U.S. patents, U.S. patent applications, and other materials (for example, articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. In addition, it is to be understood that features described herein independently may, in certain embodiments, be combined.

What is claimed is:

1. A method for heating a subsurface formation, comprising:
    applying an electrical current to an elongated heater such that the heater provides an electrically resistive heat output, wherein the elongated heater comprises two or more portions along the length of the heater that have different power outputs, at least one portion of the elongated heater comprising at least one temperature limited portion with at least one selected temperature at which the portion provides a reduced heat output;
    providing heat to the formation with the different power outputs such that the heater heats one or more portions of the formation at one or more selected heating rates; and
    allowing the heat to transfer to a section of the formation.

2. The method of claim 1, further comprising providing time-varying electrical current to the elongated heater such that the heater operates as a temperature limited heater.

3. The method of claim 1, further comprising providing heat to the formation with the different power outputs such that at least two of the portions of the formation reach a selected temperature at approximately the same time.

4. The method of claim 1, wherein the subsurface formation comprises hydrocarbons, the method further comprising allowing the heat to transfer to the formation such that at least some hydrocarbons are pyrolyzed in the formation.

5. The method of claim 1, further comprising producing a fluid from the formation.

6. The method of claim 5, wherein the fluid comprises hydrocarbons.

7. The method of claim 6, further comprising producing transportation fuel from at least a portion of the hydrocarbons.

8. The method of claim 1, wherein the elongated heater is at least 30 m in length.

9. The method of claim 1, wherein two or more portions of the elongated heater comprise different mechanical properties such that the heater has sufficient mechanical strength to support the weight of the heater at the operating temperature of the heater.

10. The method of claim 1, wherein at least one temperature limited portion of the elongated heater comprises:
    a ferromagnetic conductor; and
    an outer electrical conductor electrically coupled to the ferromagnetic conductor, the outer electrical conductor at least partially surrounding the ferromagnetic conductor, wherein the outer electrical conductor provides a majority of a resistive heat output of the heater at temperatures up to approximately the selected temperature of the ferromagnetic conductor.

11. The method of claim 1, wherein the portions of the elongated heater comprise temperature limited heaters with different selected temperatures.

12. The method of claim 1, wherein the portions of the elongated heater comprise different electrical resistivities.

13. The method of claim 1, further comprising varying dimensions of the portions of the elongated heater to provide the different power outputs.

14. The method of claim 1, further comprising varying materials in the portions of the heater to provide the different power outputs.

15. The method of claim 1, wherein the portions of the formation comprise different thermal properties and/or different richnesses.

16. The method of claim 1, further comprising heating at least two of the portions of the formation such that the portions reach a selected temperature at approximately the same time.

* * * * *